(12) United States Patent
Manoharan et al.

(10) Patent No.: US 8,975,389 B2
(45) Date of Patent: Mar. 10, 2015

(54) NUCLEIC ACID CHEMICAL MODIFICATIONS

(75) Inventors: Muthiah Manoharan, Cambridge, MA (US); Kallanthottathil G. Rajeev, Cambridge, MA (US); Alexander V. Kelin, Cambridge, MA (US); Sudhakar Rao Takkellapati, Cambridge, MA (US); Shigeo Matsuda, Cambridge, MA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 697 days.

(21) Appl. No.: 13/203,927

(22) PCT Filed: Mar. 2, 2010

(86) PCT No.: PCT/US2010/025966
§ 371 (c)(1),
(2), (4) Date: Nov. 30, 2011

(87) PCT Pub. No.: WO2010/101951
PCT Pub. Date: Sep. 10, 2010

(65) Prior Publication Data
US 2012/0071641 A1    Mar. 22, 2012

Related U.S. Application Data

(60) Provisional application No. 61/244,665, filed on Sep. 22, 2009, provisional application No. 61/226,017, filed on Jul. 16, 2009, provisional application No. 61/223,683, filed on Jul. 7, 2009, provisional application No. 61/156,864, filed on Mar. 2, 2009.

(51) Int. Cl.
*C07H 21/02* (2006.01)
*C07H 21/04* (2006.01)
*C07H 19/04* (2006.01)
*C07H 19/10* (2006.01)
*C07H 19/073* (2006.01)
*C07H 19/173* (2006.01)
*C07H 19/20* (2006.01)

(52) U.S. Cl.
CPC ............. *C07H 19/10* (2013.01); *C07H 19/073* (2013.01); *C07H 19/173* (2013.01); *C07H 19/20* (2013.01)
USPC ......................... 536/23.1; 536/26.7; 536/26.8

(58) Field of Classification Search
CPC .... C07H 19/073; C07H 19/20; C07H 19/173; C07H 19/10
See application file for complete search history.

(56) References Cited

U.S. PATENT DOCUMENTS

| | | | | |
|---|---|---|---|---|
| 5,898,031 A | * | 4/1999 | Crooke | 435/91.3 |
| 6,107,094 A | * | 8/2000 | Crooke | 435/455 |
| 6,534,639 B1 | * | 3/2003 | Manoharan et al. | 536/23.1 |
| 6,593,466 B1 | * | 7/2003 | Manoharan et al. | 536/26.7 |
| 6,670,468 B1 | * | 12/2003 | Cuenoud et al. | 536/25.3 |
| 6,914,148 B2 | * | 7/2005 | Manoharan et al. | 558/70 |
| 7,695,902 B2 | * | 4/2010 | Crooke | 435/6.12 |
| 2004/0033973 A1 | | 2/2004 | Manoharan et al. | |
| 2007/0054279 A1 | | 3/2007 | Manoharan et al. | |

FOREIGN PATENT DOCUMENTS

| | | |
|---|---|---|
| EP | 2143726 A1 | 1/2010 |
| WO | 2006038865 A1 | 4/2006 |
| WO | 2008141248 A2 | 11/2008 |

OTHER PUBLICATIONS

Griffey, Richard H. et al., "2'-O-Aminopropyl Ribonucleotides: A Zwitterionic Modification That Enhances the Exonuclease Resistance and Biological Activity of Antisense", J. Med. Chem 39:5100-5109 (1996).
Jawalekar, Anup M. et al., "Conjugation of Nucleosides and Oligonucleotides by [3 +2] Cycloaddition", J. Org. Chem 73:287-290 (2008).
Prakash, Thazha P. et al., "2'-O-[2-(Amino)-2-oxoethyl] Oligonucleotides", Organic Letters 5(4):403-406 (2003).
Prakash, Thazha P. et al., "2'-Modified Oligonucleotides for Antisense Therapeutics", Current Topics in Medicinal Chemistry 7:641-649 (2007).

* cited by examiner

*Primary Examiner* — Lawrence E Crane
(74) *Attorney, Agent, or Firm* — Jeffrey N. Townes; LeClairRyan

(57) ABSTRACT

The present invention provides nucleosides of formula (1) and oligonucleotides comprising at least one nucleoside of formula (2): Another aspect of the invention relates to a method of inhibiting the expression of a gene in cell, the method comprising (a) contacting an oligonucleotide of the invention with the cell; and (b) maintaining the cell from step (a) for a time sufficient to obtain degradation of the mRNA of the target gene.

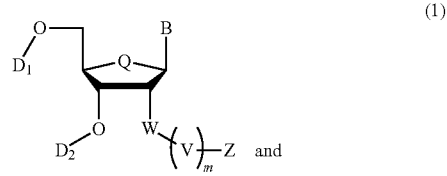

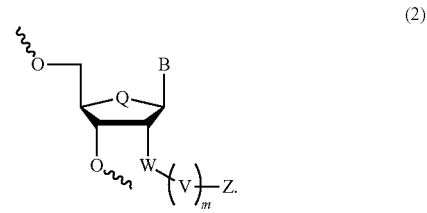

23 Claims, No Drawings

SEQUENCE LISTING

```
<160> NUMBER OF SEQ ID NOS: 109

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: misc_feature
<222> LOCATION: (1)..(10)
<223> OTHER INFORMATION: This sequence may encompass 4 to 10 nucleotides

<400> SEQUENCE: 1
tttttttttt                                                              10

<210> SEQ ID NO 2
<211> LENGTH: 29
<212> TYPE: PRT
<213> ORGANISM: Unknown
<220> FEATURE:
<223> OTHER INFORMATION: Description of Unknown: GALA endosomolytic
      ligand peptide

<400> SEQUENCE: 2

Ala Ala Leu Glu Ala Leu Ala Glu Ala Leu Glu Ala Leu Ala Glu Ala
1               5                   10                  15

Leu Glu Ala Leu Ala Glu Ala Ala Ala Ala Gly Gly Cys
                20                  25

<210> SEQ ID NO 3
<211> LENGTH: 30
<212> TYPE: PRT
<213> ORGANISM: Unknown
<220> FEATURE:
<223> OTHER INFORMATION: Description of Unknown: EALA endosomolytic
      ligand peptide

<400> SEQUENCE: 3

Ala Ala Leu Ala Glu Ala Leu Ala Glu Ala Leu Ala Glu Ala Leu Ala
1               5                   10                  15

Glu Ala Leu Ala Glu Ala Leu Ala Ala Ala Ala Gly Gly Cys
                20                  25                  30

<210> SEQ ID NO 4
<211> LENGTH: 15
<212> TYPE: PRT
<213> ORGANISM: Unknown
<220> FEATURE:
<223> OTHER INFORMATION: Description of Unknown: EALA endosomolytic
      ligand peptide

<400> SEQUENCE: 4

Ala Leu Glu Ala Leu Ala Glu Ala Leu Glu Ala Leu Ala Glu Ala
1               5                   10                  15

<210> SEQ ID NO 5
<211> LENGTH: 22
<212> TYPE: PRT
<213> ORGANISM: Unknown
<220> FEATURE:
<223> OTHER INFORMATION: Description of Unknown: INF-7 endosomolytic
      ligand peptide

<400> SEQUENCE: 5

Gly Leu Phe Glu Ala Ile Glu Gly Phe Ile Glu Asn Gly Trp Glu Gly
1               5                   10                  15

Met Ile Trp Asp Tyr Gly
                20

<210> SEQ ID NO 6
<211> LENGTH: 23
<212> TYPE: PRT
<213> ORGANISM: Unknown
```

```
<220> FEATURE:
<223> OTHER INFORMATION: Description of Unknown: Inf HA-2 endosomolytic
      ligand peptide

<400> SEQUENCE: 6

Gly Leu Phe Gly Ala Ile Ala Gly Phe Ile Glu Asn Gly Trp Glu Gly
1               5                   10                  15

Met Ile Asp Gly Trp Tyr Gly
            20

<210> SEQ ID NO 7
<211> LENGTH: 24
<212> TYPE: PRT
<213> ORGANISM: Unknown
<220> FEATURE:
<223> OTHER INFORMATION: Description of Unknown: diINF-7 endosomolytic
      ligand peptide

<400> SEQUENCE: 7

Gly Leu Phe Glu Ala Ile Glu Gly Phe Ile Glu Asn Gly Trp Glu Gly
1               5                   10                  15

Met Ile Asp Gly Trp Tyr Gly Cys
            20

<210> SEQ ID NO 8
<211> LENGTH: 22
<212> TYPE: PRT
<213> ORGANISM: Unknown
<220> FEATURE:
<223> OTHER INFORMATION: Description of Unknown: dINF3 endosomolytic
      ligand peptide

<400> SEQUENCE: 8

Gly Leu Phe Glu Ala Ile Glu Gly Phe Ile Glu Asn Gly Trp Glu Gly
1               5                   10                  15

Met Ile Asp Gly Gly Cys
            20

<210> SEQ ID NO 9
<211> LENGTH: 35
<212> TYPE: PRT
<213> ORGANISM: Unknown
<220> FEATURE:
<223> OTHER INFORMATION: Description of Unknown: GLF endosomolytic
      ligand peptide

<400> SEQUENCE: 9

Gly Leu Phe Gly Ala Leu Ala Glu Ala Leu Ala Glu Ala Leu Ala Glu
1               5                   10                  15

His Leu Ala Glu Ala Leu Ala Glu Ala Leu Glu Ala Leu Ala Ala Gly
            20                  25                  30

Gly Ser Cys
        35

<210> SEQ ID NO 10
<211> LENGTH: 34
<212> TYPE: PRT
<213> ORGANISM: Unknown
<220> FEATURE:
<223> OTHER INFORMATION: Description of Unknown: GALA-INF3 endosomolytic
      ligand peptide

<400> SEQUENCE: 10

Gly Leu Phe Glu Ala Ile Glu Gly Phe Ile Glu Asn Gly Trp Glu Gly
1               5                   10                  15
```

```
Leu Ala Glu Ala Leu Ala Glu Ala Leu Glu Ala Leu Ala Ala Gly Gly
            20                  25                  30

Ser Cys

<210> SEQ ID NO 11
<211> LENGTH: 21
<212> TYPE: PRT
<213> ORGANISM: Unknown
<220> FEATURE:
<223> OTHER INFORMATION: Description of Unknown: INF-5 endosomolytic
      ligand peptide
<220> FEATURE:
<221> NAME/KEY: MOD_RES
<222> LOCATION: (17)..(17)
<223> OTHER INFORMATION: Norleucine

<400> SEQUENCE: 11

Gly Leu Phe Glu Ala Ile Glu Gly Phe Ile Glu Asn Gly Trp Glu Gly
1               5                   10                  15

Leu Ile Asp Gly Lys
            20

<210> SEQ ID NO 12
<211> LENGTH: 20
<212> TYPE: PRT
<213> ORGANISM: Unknown
<220> FEATURE:
<223> OTHER INFORMATION: Description of Unknown: INF-5 endosomolytic
      ligand peptide
<220> FEATURE:
<221> NAME/KEY: MOD_RES
<222> LOCATION: (17)..(17)
<223> OTHER INFORMATION: Norleucine

<400> SEQUENCE: 12

Gly Leu Phe Glu Ala Ile Glu Gly Phe Ile Glu Asn Gly Trp Glu Gly
1               5                   10                  15

Leu Ile Asp Gly
            20

<210> SEQ ID NO 13
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Leu Phe Glu Ala Leu Leu Glu Leu Leu Glu Ser Leu Trp Glu Leu
1               5                   10                  15

Leu Leu Glu Ala
            20

<210> SEQ ID NO 14
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Leu Phe Lys Ala Leu Leu Lys Leu Leu Lys Ser Leu Trp Lys Leu
1               5                   10                  15
```

Leu Leu Lys Ala
        20

<210> SEQ ID NO 15
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Leu Phe Arg Ala Leu Leu Arg Leu Leu Arg Ser Leu Trp Arg Leu
1               5                   10                  15

Leu Leu Arg Ala
        20

<210> SEQ ID NO 16
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
        20                  25                  30

<210> SEQ ID NO 17
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Leu Phe Phe Glu Ala Ile Ala Glu Phe Ile Glu Gly Gly Trp Glu
1               5                   10                  15

Gly Leu Ile Glu Gly Cys
        20

<210> SEQ ID NO 18
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Ile Gly Ala Val Leu Lys Val Leu Thr Thr Gly Leu Pro Ala Leu
1               5                   10                  15

Ile Ser Trp Ile Lys Arg Lys Arg Gln Gln
        20                  25

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 19

His His His His His Trp Tyr Gly
1               5

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Cys His Lys Lys Lys Lys Lys Lys His Cys
1               5                   10

<210> SEQ ID NO 21
<211> LENGTH: 16
<212> TYPE: PRT
<213> ORGANISM: Unknown
<220> FEATURE:
<223> OTHER INFORMATION: Description of Unknown: Penetratin cell
      permeation peptide

<400> SEQUENCE: 21

Arg Gln Ile Lys Ile Trp Phe Gln Asn Arg Arg Met Lys Trp Lys Lys
1               5                   10                  15

<210> SEQ ID NO 22
<211> LENGTH: 14
<212> TYPE: PRT
<213> ORGANISM: Human immunodeficiency virus

<400> SEQUENCE: 22

Gly Arg Lys Lys Arg Arg Gln Arg Arg Pro Pro Gln Cys
1               5                   10

<210> SEQ ID NO 23
<211> LENGTH: 27
<212> TYPE: PRT
<213> ORGANISM: Unknown
<220> FEATURE:
<223> OTHER INFORMATION: Description of Unknown: Signal sequence-based
      cell permeation peptide

<400> SEQUENCE: 23

Gly Ala Leu Phe Leu Gly Trp Leu Gly Ala Ala Gly Ser Thr Met Gly
1               5                   10                  15

Ala Trp Ser Gln Pro Lys Lys Lys Arg Lys Val
            20                  25

<210> SEQ ID NO 24
<211> LENGTH: 18
<212> TYPE: PRT
<213> ORGANISM: Unknown
<220> FEATURE:
<223> OTHER INFORMATION: Description of Unknown: PVEC cell permeation
      peptide

<400> SEQUENCE: 24

Leu Leu Ile Ile Leu Arg Arg Arg Ile Arg Lys Gln Ala His Ala His
1               5                   10                  15

Ser Lys
```

```
<210> SEQ ID NO 25
<211> LENGTH: 26
<212> TYPE: PRT
<213> ORGANISM: Unknown
<220> FEATURE:
<223> OTHER INFORMATION: Description of Unknown: Transportan cell
      permeation peptide

<400> SEQUENCE: 25

Gly Trp Thr Leu Asn Ser Ala Gly Tyr Leu Leu Lys Ile Asn Leu Lys
1               5                   10                  15

Ala Leu Ala Ala Leu Ala Lys Lys Ile Leu
            20                  25

<210> SEQ ID NO 26
<211> LENGTH: 18
<212> TYPE: PRT
<213> ORGANISM: Unknown
<220> FEATURE:
<223> OTHER INFORMATION: Description of Unknown: Amphiphilic model cell
      permeation peptide

<400> SEQUENCE: 26

Lys Leu Ala Leu Lys Leu Ala Leu Lys Ala Leu Lys Ala Ala Leu Lys
1               5                   10                  15

Leu Ala

<210> SEQ ID NO 27
<211> LENGTH: 9
<212> TYPE: PRT
<213> ORGANISM: Unknown
<220> FEATURE:
<223> OTHER INFORMATION: Description of Unknown: Arg9 cell permeation
      peptide

<400> SEQUENCE: 27

Arg Arg Arg Arg Arg Arg Arg Arg Arg
1               5

<210> SEQ ID NO 28
<211> LENGTH: 10
<212> TYPE: PRT
<213> ORGANISM: Unknown
<220> FEATURE:
<223> OTHER INFORMATION: Description of Unknown: Bacterial cell wall
      permeation peptide

<400> SEQUENCE: 28

Lys Phe Phe Lys Phe Phe Lys Phe Phe Lys
1               5                   10

<210> SEQ ID NO 29
<211> LENGTH: 37
<212> TYPE: PRT
<213> ORGANISM: Unknown
<220> FEATURE:
<223> OTHER INFORMATION: Description of Unknown: LL-37 cell permeation
      peptide

<400> SEQUENCE: 29

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
        35
```

<210> SEQ ID NO 30
<211> LENGTH: 31
<212> TYPE: PRT
<213> ORGANISM: Unknown
<220> FEATURE:
<223> OTHER INFORMATION: Description of Unknown: Cecropin P1 cell
      permeation peptide

<400> SEQUENCE: 30

Ser Trp Leu Ser Lys Thr Ala Lys Lys Leu Glu Asn Ser Ala Lys Lys
1               5                   10                  15

Arg Ile Ser Glu Gly Ile Ala Ile Ala Ile Gln Gly Gly Pro Arg
            20                  25                  30

<210> SEQ ID NO 31
<211> LENGTH: 30
<212> TYPE: PRT
<213> ORGANISM: Unknown
<220> FEATURE:
<223> OTHER INFORMATION: Description of Unknown: Alpha-defensin cell
      permeation peptide

<400> SEQUENCE: 31

Ala Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30

<210> SEQ ID NO 32
<211> LENGTH: 36
<212> TYPE: PRT
<213> ORGANISM: Unknown
<220> FEATURE:
<223> OTHER INFORMATION: Description of Unknown: Beta-defensin cell
      permeation peptide

<400> SEQUENCE: 32

Asp His Tyr Asn Cys Val Ser Ser Gly Gly Gln Cys Leu Tyr Ser Ala
1               5                   10                  15

Cys Pro Ile Phe Thr Lys Ile Gln Gly Thr Cys Tyr Arg Gly Lys Ala
            20                  25                  30

Lys Cys Cys Lys
35

<210> SEQ ID NO 33
<211> LENGTH: 12
<212> TYPE: PRT
<213> ORGANISM: Unknown
<220> FEATURE:
<223> OTHER INFORMATION: Description of Unknown: Bactenecin cell permeation peptide

<400> SEQUENCE: 33

Arg Lys Cys Arg Ile Val Val Ile Arg Val Cys Arg
1 5 10

<210> SEQ ID NO 34
<211> LENGTH: 42
<212> TYPE: PRT
<213> ORGANISM: Unknown
<220> FEATURE:
<223> OTHER INFORMATION: Description of Unknown: PR-39 cell permeation peptide

<400> SEQUENCE: 34

```
Arg Arg Arg Pro Arg Pro Pro Tyr Leu Pro Arg Pro Arg Pro Pro
1               5                   10                  15

Phe Phe Pro Pro Arg Leu Pro Pro Arg Ile Pro Pro Gly Phe Pro Pro
            20                  25                  30

Arg Phe Pro Pro Arg Phe Pro Gly Lys Arg
        35                  40
```

<210> SEQ ID NO 35
<211> LENGTH: 13
<212> TYPE: PRT
<213> ORGANISM: Unknown
<220> FEATURE:
<223> OTHER INFORMATION: Description of Unknown: Indolicidin cell
      permeation peptide

<400> SEQUENCE: 35

```
Ile Leu Pro Trp Lys Trp Pro Trp Trp Pro Trp Arg Arg
1               5                   10
```

<210> SEQ ID NO 36
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

```
Ala Ala Val Ala Leu Leu Pro Ala Val Leu Leu Ala Leu Leu Ala Pro
1               5                   10                  15
```

<210> SEQ ID NO 37
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

```
Ala Ala Leu Leu Pro Val Leu Leu Ala Ala Pro
1               5                   10
```

<210> SEQ ID NO 38
<211> LENGTH: 13
<212> TYPE: PRT
<213> ORGANISM: Human immunodeficiency virus

<400> SEQUENCE: 38

```
Gly Arg Lys Lys Arg Arg Gln Arg Arg Arg Pro Pro Gln
1               5                   10
```

<210> SEQ ID NO 39
<211> LENGTH: 16
<212> TYPE: PRT
<213> ORGANISM: Drosophila sp.

<400> SEQUENCE: 39

```
Arg Gln Ile Lys Ile Trp Phe Gln Asn Arg Arg Met Lys Trp Lys Lys
1               5                   10                  15
```

<210> SEQ ID NO 40
<211> LENGTH: 21
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: Aeo4

<400> SEQUENCE: 40
uugucucugg uccuuacuua a                                              21

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: Aeo4
<220> FEATURE:
<221> NAME/KEY: modified_base
<222> LOCATION: (20)..(21)
<223> OTHER INFORMATION: Aeo4

<400> SEQUENCE: 41
augucucugg uccuuacuua a                                              21

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: Teo4
<220> FEATURE:
<221> NAME/KEY: modified_base
<222> LOCATION: (20)..(21)
<223> OTHER INFORMATION: Aeo4

<400> SEQUENCE: 42
tugucucugg uccuuacuua a                                              21

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (19)..(20)
<223> OTHER INFORMATION: Aeo
```

<400> SEQUENCE: 43
ugucucuggu ccuuacuuaa                                          20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (19)..(20)
<223> OTHER INFORMATION: Aeo

<400> SEQUENCE: 44
ugucucuggu ccuuacuuaa                                          20

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: Aeo

<400> SEQUENCE: 45
uugucucugg uccuuacuua a                                        21

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: Aeo

<400> SEQUENCE: 46
uugucucugg uccuuacuua a                                        21

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 47
aaguaaggac cagagacaat t                                        21

```
<210> SEQ ID NO 48
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
aaguaaggac cagagacaa                                                      19

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 49
aaguaaggac cagagacaat t                                                   21

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: Teo4
<220> FEATURE:
<221> NAME/KEY: modified_base
<222> LOCATION: (20)..(21)
<223> OTHER INFORMATION: Aeo

<400> SEQUENCE: 50
tugucucugg uccuuacuua a                                                   21

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: Teo4
<220> FEATURE:
<221> NAME/KEY: modified_base
<222> LOCATION: (20)..(21)
<223> OTHER INFORMATION: Aeo

<400> SEQUENCE: 51
tugucucugg uccuuacuua a                                                   21
```

```
<210> SEQ ID NO 52
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
uugucucugg uccuuacuua a                                              21

<210> SEQ ID NO 53
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
uugucucugg uccuuacuua a                                              21

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: Aeo

<400> SEQUENCE: 54
uugucucugg uccuuacuua a                                              21

<210> SEQ ID NO 55
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (21)..(22)
<223> OTHER INFORMATION: Aeo

<400> SEQUENCE: 55
tuugucucug guccuuacuu aa                                             22

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
```

<223> OTHER INFORMATION: Aeo

<400> SEQUENCE: 56
uugucucugg uccuuacuua a                                              21

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: Aeo

<400> SEQUENCE: 57
uugucucugg uccuuacuua a                                              21

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: Aeo

<400> SEQUENCE: 58
uugucucugg uccuuacuua a                                              21

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: Aeo

<400> SEQUENCE: 59
uugucucugg uccuuacuua a                                              21

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base

```
<222> LOCATION: (20)..(21)
<223> OTHER INFORMATION: Aea

<400> SEQUENCE: 60
uugucucugg uccuuacuua a                                              21

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: Tea
<220> FEATURE:
<221> NAME/KEY: modified_base
<222> LOCATION: (20)..(21)
<223> OTHER INFORMATION: Aea

<400> SEQUENCE: 61
tugucucugg uccuuacuua a                                              21

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: Tea
<220> FEATURE:
<221> NAME/KEY: modified_base
<222> LOCATION: (20)..(21)
<223> OTHER INFORMATION: Aeo

<400> SEQUENCE: 62
tugucucugg uccuuacuua a                                              21

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: Abasic DNA (2-hydroxymethyl-tetrahydropyrane-3-
      phosphate) nucleotide
<220> FEATURE:
<221> NAME/KEY: modified_base
<222> LOCATION: (20)..(21)
<223> OTHER INFORMATION: Aeo

<400> SEQUENCE: 63
nugucucugg uccuuacuua a                                              21
```

```
<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: Abasic DNA (2-hydroxymethyl-tetrahydropyrane-3-
      phosphate) nucleotide
<220> FEATURE:
<221> NAME/KEY: modified_base
<222> LOCATION: (20)..(21)
<223> OTHER INFORMATION: Aeo

<400> SEQUENCE: 64
nugucucugg uccuuacuua a                                              21

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: Teo1

<400> SEQUENCE: 65
ucgaaguacu cagcguaagt t                                              21

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (10)..(10)
<223> OTHER INFORMATION: Teo1

<400> SEQUENCE: 66
ucgaaguact cagcguaagt t                                              21

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
```

```
<222> LOCATION: (1)..(1)
<223> OTHER INFORMATION: Teo1

<400> SEQUENCE: 67
tcgaaguacu cagcguaagt t                                              21

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (7)..(7)
<223> OTHER INFORMATION: Teo1

<400> SEQUENCE: 68
ucgaagtacu cagcguaagt t                                              21

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: Teo2

<400> SEQUENCE: 69
ucgaaguacu cagcguaagt t                                              21

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (10)..(10)
<223> OTHER INFORMATION: Teo2

<400> SEQUENCE: 70
ucgaaguact cagcguaagt t                                              21

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
```

<221> NAME/KEY: modified_base
<222> LOCATION: (1)..(1)
<223> OTHER INFORMATION: Teo2

<400> SEQUENCE: 71
tcgaaguacu cagcguaagt t                                              21

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (7)..(7)
<223> OTHER INFORMATION: Teo2

<400> SEQUENCE: 72
ucgaagtacu cagcguaagt t                                              21

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: Teo3

<400> SEQUENCE: 73
ucgaaguacu cagcguaagt t                                              21

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (10)..(10)
<223> OTHER INFORMATION: Teo3

<400> SEQUENCE: 74
ucgaaguact cagcguaagt t                                              21

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<220> FEATURE:
<221> NAME/KEY: modified_base
<222> LOCATION: (1)..(1)
<223> OTHER INFORMATION: Teo3

<400> SEQUENCE: 75
tcgaaguacu cagcguaagt t                                              21

<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (7)..(7)
<223> OTHER INFORMATION: Teo3

<400> SEQUENCE: 76
ucgaagtacu cagcguaagt t                                              21

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: Teo4

<400> SEQUENCE: 77
ucgaaguacu cagcguaagt t                                              21

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (10)..(10)
<223> OTHER INFORMATION: Teo4

<400> SEQUENCE: 78
ucgaaguact cagcguaagt t                                              21

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

```
                        Synthetic oligonucleotide
<220> FEATURE:
<221> NAME/KEY: modified_base
<222> LOCATION: (1)..(1)
<223> OTHER INFORMATION: Teo4

<400> SEQUENCE: 79
tcgaaguacu cagcguaagt t                                              21

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (7)..(7)
<223> OTHER INFORMATION: Teo4

<400> SEQUENCE: 80
ucgaagtacu cagcguaagt t                                              21

<210> SEQ ID NO 81
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: Teo5

<400> SEQUENCE: 81
ucgaaguacu cagcguaagt t                                              21

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (10)..(10)
<223> OTHER INFORMATION: Teo5

<400> SEQUENCE: 82
ucgaaguact cagcguaagt t                                              21

<210> SEQ ID NO 83
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: Teo5

<400> SEQUENCE: 83
tcgaaguacu cagcguaagt t                                               21

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (7)..(7)
<223> OTHER INFORMATION: Teo5

<400> SEQUENCE: 84
ucgaagtacu cagcguaagt t                                               21

<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: Teo6

<400> SEQUENCE: 85
ucgaaguacu cagcguaagt t                                               21

<210> SEQ ID NO 86
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (10)..(10)
<223> OTHER INFORMATION: Teo6

<400> SEQUENCE: 86
ucgaaguact cagcguaagt t                                               21

<210> SEQ ID NO 87
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: Teo6

<400> SEQUENCE: 87
tcgaaguacu cagcguaagt t                                          21

<210> SEQ ID NO 88
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (7)..(7)
<223> OTHER INFORMATION: Teo6

<400> SEQUENCE: 88
ucgaagtacu cagcguaagt t                                          21

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: Teo7

<400> SEQUENCE: 89
ucgaaguacu cagcguaagt t                                          21

<210> SEQ ID NO 90
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (10)..(10)
<223> OTHER INFORMATION: Teo7

<400> SEQUENCE: 90
ucgaaguact cagcguaagt t                                          21

<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
        oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: Teo7

<400> SEQUENCE: 91
tcgaaguacu cagcguaagt t                                              21

<210> SEQ ID NO 92
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (7)..(7)
<223> OTHER INFORMATION: Teo7

<400> SEQUENCE: 92
ucgaagtacu cagcguaagt t                                              21

<210> SEQ ID NO 93
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: Teo8

<400> SEQUENCE: 93
ucgaaguacu cagcguaagt t                                              21

<210> SEQ ID NO 94
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (10)..(10)
<223> OTHER INFORMATION: Teo8

<400> SEQUENCE: 94
ucgaaguact cagcguaagt t                                              21

<210> SEQ ID NO 95
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: Teo8

<400> SEQUENCE: 95
tcgaaguacu cagcguaagt t                                              21

<210> SEQ ID NO 96
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (7)..(7)
<223> OTHER INFORMATION: Teo8

<400> SEQUENCE: 96
ucgaagtacu cagcguaagt t                                              21

<210> SEQ ID NO 97
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: Teo

<400> SEQUENCE: 97
ucgaaguacu cagcguaagt t                                              21

<210> SEQ ID NO 98
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (10)..(10)
<223> OTHER INFORMATION: Teo

<400> SEQUENCE: 98
ucgaaguact cagcguaagt t                                              21

<210> SEQ ID NO 99
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: Teo

<400> SEQUENCE: 99
tcgaaguacu cagcguaagt t                                             21

<210> SEQ ID NO 100
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (7)..(7)
<223> OTHER INFORMATION: Teo

<400> SEQUENCE: 100
ucgaagtacu cagcguaagt t                                             21

<210> SEQ ID NO 101
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: Teo

<400> SEQUENCE: 101
ucgaaguacu cagcguaagt t                                             21

<210> SEQ ID NO 102
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: Teo1

<400> SEQUENCE: 102
ucgaaguacu cagcguaagt t                                             21

<210> SEQ ID NO 103
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: Teo2

<400> SEQUENCE: 103
ucgaaguacu cagcguaagt t                                              21

<210> SEQ ID NO 104
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: Teo3

<400> SEQUENCE: 104
ucgaaguacu cagcguaagt t                                              21

<210> SEQ ID NO 105
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: Teo4

<400> SEQUENCE: 105
ucgaaguacu cagcguaagt t                                              21

<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: Teo5

<400> SEQUENCE: 106
ucgaaguacu cagcguaagt t                                              21

<210> SEQ ID NO 107
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: Teo6

<400> SEQUENCE: 107
ucgaaguacu cagcguaagt t                                              21

<210> SEQ ID NO 108
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: Teo7

<400> SEQUENCE: 108
ucgaaguacu cagcguaagt t                                              21

<210> SEQ ID NO 109
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: Teo8

<400> SEQUENCE: 109
ucgaaguacu cagcguaagt t                                              21
```

NUCLEIC ACID CHEMICAL MODIFICATIONS

PRIORITY CLAIM

This application claims benefit of priority to PCT Application No. PCT/US2010/025966, filed Mar. 2, 2010, which claims benefit of priority to U.S. Provisional Application No. 61/156,864, filed Mar. 2, 2009; U.S. Provisional Application No. 61/223,683, filed Jul. 7, 2009; U.S. Provisional Application No. 61/226,017, filed Jul. 16, 2009; and U.S. Provisional Application No. 61/244,665, filed Sep. 22, 2009, all of which are herein incorporated by reference in their entirety.

TECHNICAL FIELD

Provided herein are modified nucleosides and oligonucleotides prepared therefrom. More particularly, the 2'-sugar modified nucleosides and analogs in combination with natural and high affinity nucleobase modifications.

BACKGROUND

Oligonucleotides and their analogs have been developed for various uses in molecular biology, including use as probes, primers, linkers, adapters, and gene fragments. In a number of these applications, the oligonucleotides specifically hybridize to a target nucleic acid sequence. Hybridization is the sequence specific hydrogen bonding of oligonucleotides via Watson-Crick and/or Hoogsteen base pairs to RNA or DNA. The bases of such base pairs are said to be complementary to one another.

Double-stranded RNA molecules (dsRNA) can block gene expression by virtue of a highly conserved regulatory mechanism known as RNA interference (RNAi). Briefly, the RNA III Dicer enzyme processes dsRNA into small interfering RNA (also sometimes called short interfering RNA or siRNA) of approximately 22 nucleotides. One strand of the siRNA (the "antisense strand") then serves as a guide sequence to induce cleavage of messenger RNAs (mRNAs) including a nucleotide sequence which is at least partially complementary to the sequence of the antisense strand by an RNA-induced silencing complex, RISC. The antisense strand is not cleaved or otherwise degraded in this process, and the RISC including the antisense strand can subsequently affect the cleavage of further mRNAs.

It is desirable that oligonucleotides be able to be synthesized to have customized properties that are tailored for desired uses. Thus a number of chemical modifications have been introduced into oligonucleotides to increase their usefulness in diagnostics as research reagents and as therapeutic entities. (Chemically modified oligonucleotides include, for example, pseudouridine derivatives and lipid-containing oligonucleotides, as discussed below.) Such modifications include those designed to increase binding to a target strand (i.e., increase their melting temperatures, $T_m$), to assist in identification of the oligonucleotide or an oligonucleotide-target complex, to increase cell penetration, to stabilize against nucleases and other enzymes that degrade or interfere with the structure or activity of the oligonucleotides, to provide a mode of disruption (a terminating event) once sequence-specifically bound to a target, and to improve the pharmacokinetic properties of the oligonucleotide.

Even given the advances that have already been made in the art, there remains an ongoing need for new modifications designed to, for example, increase binding to a target strand (i.e., increase their melting temperatures, $T_m$), to assist in identification of the oligonucleotide or an oligonucleotide-target complex, to increase cell penetration, to stabilize against nucleases and other enzymes that degrade or interfere with the structure or activity of the oligonucleotides, to provide a mode of disruption (a terminating event) once sequence-specifically bound to a target, and to improve the pharmacokinetic properties of the oligonucleotide.

SUMMARY

In one aspect, the present invention provides an oligonucleotide comprising at least one modified nucleoside of formula (2), (4), (6), (8) or (10), optionally in combination with a natural base (and derivatives thereof) or modified nucleobase. The modified base includes high affinity modification such as G-clamp and analogs, phenoxazines and analogs, and bi- and tricyclic non-natural nucleoside bases. The invention further provides modified oligonucleotides with 3', 5' or both 3' and 5' terminal phosphate or phosphate mimics. The phosphate or phosphate mimics includes α- and/or β-configuration with respect to the sugar ring or combinations thereof. The phosphate or phosphate mimics include but not limited to: natural phosphate, phosphorothioate, phosphorodithioate, borano phosphate, borano thiophospahte, phosphonate, halogen substituted phosphoantes, phosphoramidates, phosphodiester, phosphotriester, thiophosphodiester, thiophosphotriester, diphosphates and triphosphates. The invention also provides sugar-modified purine dimers at 3' and 5'-terminals (i.e. 5'/3'-GG, AA, AG, GA, GI, IA etc.), where the purine bases are natural or chemically modified preferably at 2, 6, 7, and 8 positions; $N^2$ and $N^6$ exocyclic amine positions of the base or combinations thereof. The nucleoside at position 1 (5'-end) may contain a 2' and/or 4'-sugar modified natural and modified nucleobase, purine or pyrimidine nucleobase mimics or combinations thereof. The modified oligonucleotides may be single stranded siRNA (ss siRNA), double stranded siRNA (ds siRNA), micro RNA, antimicroRNA, aptamer, antisense oligonucleotide, immunostiumulatory oligonucleotide, RNAa activator or U1 adaptor, containing a motif selected from the modifications described herein and combinations of modifications thereof. The modified oligonucleotide may be one of the strands or constitute both strands of a double-stranded siRNA. In one occurrence the modified oligonucleotide is the guide or antisense strand and in another occurrence the modified oligonucleotide is the sense or passenger strand; or in another occurrence both the strands of ds siRNA bear modified oligoncleotides.

DETAILED DESCRIPTION

In one embodiment, the invention provides nucleosides of formula (1), or isomers thereof:

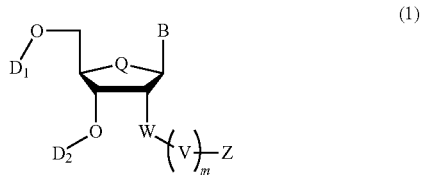

where one of $D_1$ and $D_2$ is H, hydroxyl protecting group and the other of $D_1$ and $D_2$ is H, a hydroxyl protecting group, solid support or a reactive phosphorus group; m is 1 to 15; B is selected from hydrogen, aliphatic, substituted aliphatic, natural nucleobase, modified nucleobase and universal nucleobase; Q is selected from O, S, $NR_{10}$, $CH_2$; W is absent, O, S or NR'; V is straight- or branched-, substituted or unsubstituted alkyl, substituted or unsubstituted alkenyl, substituted or unsubstituted alkynyl, of which one or more methylenes can be interrupted by O, S, S(O), $SO_2$, N(R'), C(O), N(R')C(O)O, OC(O)NR', CH(Z), phosphorus containing linkage, aryl, heteroaryl, heterocyclic, or cycloalkyl, where R' is hydrogen, acyl, aliphatic or substituted aliphatic; Z is selected from $OR_{10}$, $COR_{10}$, $CO_2R_{10}$,

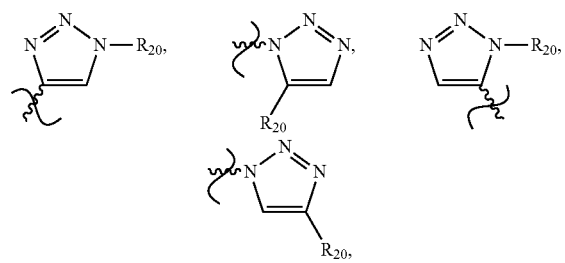

$NR_{20}R_{30}$, $CONR_{20}R_{30}$, $CON(H)NR_{20}R_{30}$, $ONR_{20}R_{30}$, $CON(H)N=CR_{40}R_{50}$, $N(R_{20})C(=NR_{30})NR_{20}R_{30}$, $N(R_{20})C(O)NR_{20}R_{30}$, $N(R_{20})C(S)NR_{20}R_{30}$, $OC(O)NR_{20}R_{30}$, $SC(O)NR_{20}R_{30}$, $N(R_{20})C(S)OR_{10}$, $N(R_{20})C(O)OR_{10}$, $N(R_{20})C(O)SR_{10}$, $N(R_{20})N=CR_{40}R_{50}$, $ON=CR_{40}R_{50}$, $SO_2R_{10}$, $SOR_{10}$, $SR_{10}$ and substituted or unsubstituted heterocyclic, where $R_{20}$, $R_{30}$, $R_{40}$ and $R_{50}$ for each occurrence are independently selected from is hydrogen, acyl, aliphatic or substituted aliphatic, aryl, heteroaryl, heterocyclic, $OR_{10}$, $COR_{10}$, $CO_2R_{10}$, $NR_{10}R_{10}'$; $R_{20}$ and $R_{30}$ can be taken together to form a heterocyclic ring; $R_{10}$ and $R_{10}'$ are independently hydrogen, aliphatic, substituted aliphatic, aryl, heteroaryl, or heterocyclic; provided that when W is O and Z is $OR_{10}$, V is not an unsubstituted-alkylene or an unsubstituted alkoxylene.

When a chiral center (or centers) is (are) present on the 2'-substituent on nucleoside formula (1), the stereochemistry represents for pure enantiomers (R or S), pure diasteromers (for e.g., RS, RR, SR and SS), meso, and mixtures of enantiomers (racemic) and diastereomers.

In one embodiment, the invention provides oligonucleotides comprising at least one nucleoside of formula (2), or isomers thereof:

(2)

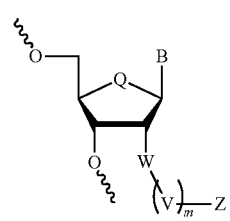

where m is 1 to 15; B is selected from hydrogen, aliphatic, substituted aliphatic, natural nucleobase, modified nucleobase and universal nucleobase; Q is selected from O, S, $NR_{10}$, $CH_2$; W is absent, O, S or NR'; V is straight- or branched-, substituted or unsubstituted alkyl, substituted or unsubstituted alkenyl, substituted or unsubstituted alkynyl, of which one or more methylenes can be interrupted by O, S, S(O), $SO_2$, N(R'), C(O), N(R')C(O)O, OC(O)NR', CH(Z), phosphorus containing linkage, aryl, heteroaryl, heterocyclic, or cycloalkyl, where R' is hydrogen, acyl, aliphatic or substituted aliphatic; Z is selected from $OR_{10}$, $COR_{10}$, $CO_2R_{10}$,

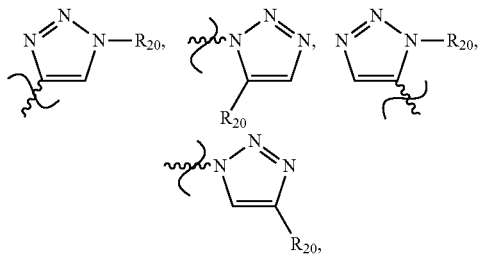

$NR_{20}R_{30}$, $CONR_{20}R_{30}$, $CON(H)NR_{20}R_{30}$, $ONR_{20}R_{30}$, $CON(H)N=CR_{40}R_{50}$, $N(R_{20})C(=NR_{30})NR_{20}R_{30}$, $N(R_{20})C(O)NR_{20}R_{30}$, $N(R_{20})C(S)NR_{20}R_{30}$, $OC(O)NR_{20}R_{30}$, $SC(O)NR_{20}R_{30}$, $N(R_{20})C(S)OR_{10}$, $N(R_{20})C(O)OR_{10}$, $N(R_{20})C(O)SR_{10}$, $N(R_{20})N=CR_{40}R_{50}$, $ON=CR_{40}R_{50}$, $SO_2R_{10}$, $SOR_{10}$, $SR_{10}$ and substituted or unsubstituted heterocyclic, where $R_{20}$, $R_{30}$, $R_{40}$ and $R_{50}$ for each occurrence are independently selected from is hydrogen, acyl, aliphatic or substituted aliphatic, aryl, heteroaryl, heterocyclic, $OR_{10}$, $COR_{10}$, $CO_2R_{10}$, $NR_{10}R_{10}'$; $R_{20}$ and $R_{30}$ can be taken together to form a heterocyclic ring; $R_{10}$ and $R_{10}'$ are independently hydrogen, aliphatic, substituted aliphatic, aryl, heteroaryl, or heterocyclic; provided that when W is O and Z is $OR_{10}$, V is not an unsubstituted-alkylene or an unsubstituted alkoxylene. When a chiral center (or centers) is (are) present on the 2'-substituent on nucleoside formula (2), the stereochemistry represents for pure enantiomers (R or S), pure diasteromers (for e.g., RS, RR, SR and SS), meso, and mixtures of enantiomers (racemic) and diastereomers at different ratio.

In one embodiment, the invention oligonucleotides comprising at least one nucleoside of formula (3), and isomers thereof, (3)

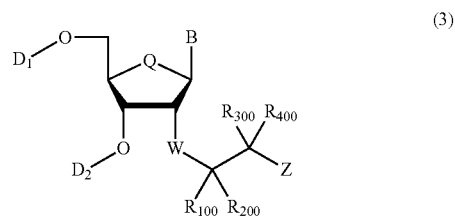

where one of $D_1$ and $D_2$ is H, hydroxyl protecting group and the other of $D_1$ and $D_2$ is H, a hydroxyl protecting group, solid support or a reactive phosphorus group; B is selected from hydrogen, aliphatic, substituted aliphatic, natural nucleobase, modified nucleobase and universal base; Q is selected from O, S, $NR_{10}$, $CH_2$; W is absent, O, S or NR'; $R_{100}$-$R_{400}$ are each independently selected from hydrogen, aliphatic, substituted aliphatic, aryl, halogen, heteroaryl, heterocyclic, or $R_{300}$ and $R_{400}$ can be taken together with the atom they attached to form a carbonyl, thiocarbonyl, $=NR_{20}$, $=N-NR_{20}R_{30}$, or $=N-NR_{20}C(O)R_{10}$; Z is selected from $OR_{10}$, $COR_{10}$, $CO_2R_{10}$,

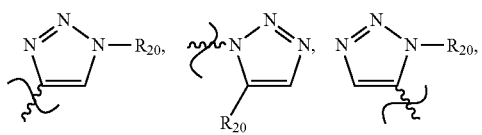

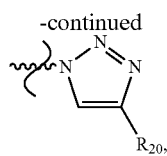

$NR_{20}R_{30}$, $CONR_{20}R_{30}$, $CON(H)NR_{20}R_{30}$, $ONR_{20}R_{30}$, $CON(H)N=CR_{40}R_{50}$, $N(R_{20})C(=NR_{30})NR_{20}R_{30}$, $N(R_{20})C(O)NR_{20}R_{30}$, $N(R_{20})C(S)NR_{20}R_{30}$, $OC(O)NR_{20}R_{30}$, $SC(O)NR_{20}R_{30}$, $N(R_{20})C(S)OR_{10}$, $N(R_{20})C(O)OR_{10}$, $N(R_{20})C(O)SR_{10}$, $N(R_{20})N=CR_{40}R_{50}$, $ON=CR_{40}R_{50}$, $SO_2R_{10}$, $SOR_{10}$, $SR_{10}$ and substituted or unsubstituted heterocyclic, where $R_{20}$, $R_{30}$, $R_{40}$ and $R_{50}$ are independently selected from is hydrogen, acyl, aliphatic or substituted aliphatic, aryl, heteroaryl, heterocyclic, $OR_{10}$, $COR_{10}$, $CO_2R_{10}$, $NR_{10}R_{10}'$; $R_{20}$ and $R_{30}$ can be taken together to form a heterocyclic ring; $R_{10}$ and $R_{10}'$ are independently hydrogen, aliphatic, substituted aliphatic, aryl, heteroaryl, or heterocyclic. When $R_{100}$ is not $R_{200}$ and $R_{300}$ is same as $R_{400}$ or vice versa, the formula (3) independently represent pure R and S enantiomers and mixture of these enantiomers at different ratio. When $R_{100}$, $R_{200}$, $R_{300}$ and $R_{400}$ are different, the formula (3) independently represent pure diastereomers and mixture of these diastereomers at different ratio.

In one embodiment, the invention oligonucleotides comprising at least one nucleoside of formula (4), and isomers thereof, (3)

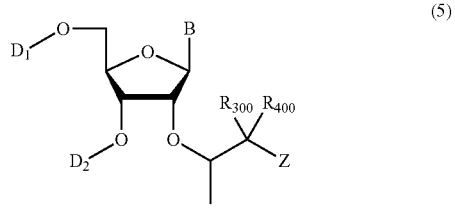

where B is selected from hydrogen, aliphatic, substituted aliphatic, natural nucleobase, modified nucleobase and universal base; Q is selected from O, S, $NR_{10}$, $CH_2$; W is absent, O, S or NR'; $R_{100}$-$R_{400}$ are each independently selected from hydrogen, aliphatic, substituted aliphatic, aryl, halogen, heteroaryl, heterocyclic, or $R_{300}$ and $R_{400}$ can be taken together with the atom they attached to form a carbonyl, thiocarbonyl, $=NR_{20}$, $=N-NR_{20}R_{30}$, or $=N-NR_{20}C(O)R_{10}$; Z is selected from $OR_{10}$, $COR_{10}$, $CO_2R_{10}$,

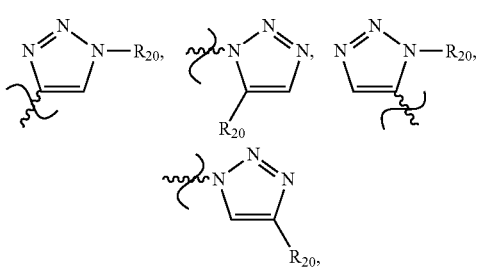

$NR_{20}R_{30}$, $CONR_{20}R_{30}$, $CON(H)NR_{20}R_{30}$, $ONR_{20}R_{30}$, $CON(H)N=CR_{40}R_{50}$, $N(R_{20})C(=NR_{30})NR_{20}R_{30}$, $N(R_{20})C(O)NR_{20}R_{30}$, $N(R_{20})C(S)NR_{20}R_{30}$, $OC(O)NR_{20}R_{30}$, $SC(O)NR_{20}R_{30}$, $N(R_{20})C(S)OR_{10}$, $N(R_{20})C(O)OR_{10}$, $N(R_{20})C(O)SR_{10}$, $N(R_{20})N=CR_{40}R_{50}$, $ON=CR_{40}R_{50}$, $SO_2R_{10}$, $SOR_{10}$, $SR_{10}$ and substituted or unsubstituted heterocyclic, where $R_{20}$, $R_{30}$, $R_{40}$ and $R_{50}$ are independently selected from is hydrogen, acyl, aliphatic or substituted aliphatic, aryl, heteroaryl, heterocyclic, $OR_{10}$, $COR_{10}$, $CO_2R_{10}$, $NR_{10}R_{10}'$; $R_{20}$ and $R_{30}$ can be taken together to form a heterocyclic ring; $R_{10}$ and $R_{10}'$ are independently hydrogen, aliphatic, substituted aliphatic, aryl, heteroaryl, or heterocyclic. When $R_{100}$ is not $R_{200}$ and $R_{300}$ is same as $R_{400}$ or vice versa, the formula (4) independently represent pure R and S enantiomers and mixture of these enantiomers at different ratio. When $R_{100}$, $R_{200}$, $R_{300}$ and $R_{400}$ are different, the formula (4) independently represent pure diastereomers and mixture of these diasgtereomers at different ratio.

In one embodiment, the invention oligonucleotides comprising at least one nucleoside of formula (5), and isomers thereof:

(5)

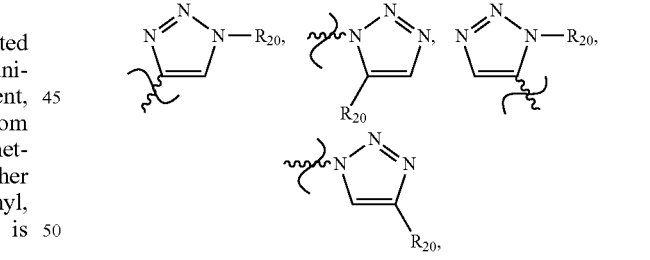

where one of $D_1$ and $D_2$ is H, hydroxyl protecting group and the other of $D_1$ and $D_2$ is H, a hydroxyl protecting group, solid support or a reactive phosphorus group; B is selected from hydrogen, aliphatic, substituted aliphatic, natural nucleobase, modified nucleobase and universal base; $R_{300}$ and $R_{400}$ are each independently selected from hydrogen, aliphatic, substituted aliphatic, aryl, halogen, heteroaryl, heterocyclic, or $R_{300}$ and $R_{400}$ can be taken together with the atom they attached to form a carbonyl, thiocarbonyl, $=NR_{20}$, $=N-NR_{20}R_{30}$, or $=N-NR_{20}C(O)R_{10}$; Z is selected from $OR_{10}$, $COR_{10}$, $CO_2R_{10}$, $NR_{20}R_{30}$, $CONR_{20}R_{30}$, $CON(H)NR_{20}R_{30}$, $ONR_{20}R_{30}$, $CON(H)N=CR_{40}R_{50}$, $N(R_{20})C(=NR_{30})NR_{20}R_{30}$, $N(R_{20})C(O)NR_{20}R_{30}$, $N(R_{20})C(S)NR_{20}R_{30}$, $OC(O)NR_{20}R_{30}$, $SC(O)NR_{20}R_{30}$, $N(R_{20})C(S)OR_{10}$, $N(R_{20})C(O)OR_{10}$, $N(R_{20})C(O)SR_{10}$, $N(R_{20})N=CR_{40}R_{50}$, $ON=CR_{40}R_{50}$, $SO_2R_{10}$, $SOR_{10}$, $SR_{10}$ and substituted or unsubstituted heterocyclic, where $R_{20}$, $R_{30}$, $R_{40}$ and $R_{50}$ for each occurrence are independently selected from is hydrogen, acyl, aliphatic or substituted aliphatic, aryl, heteroaryl, heterocyclic, $OR_{10}$, $COR_{10}$, $CO_2R_{10}$, $NR_{10}R_{10}'$; $R_{20}$ and $R_{30}$ can be taken together to form a heterocyclic ring; $R_{10}$ and $R_{10}'$ are independently hydrogen, aliphatic, substituted aliphatic, aryl, heteroaryl, or heterocyclic. When $R_{300}$ and $R_{400}$ are H, the formula (5) independently represent pure R and S enantiomers and mixture of these enantiomers at different ratio In one embodiment, the invention oligonucleotides comprising at least one nucleoside of formula (6), and isomers thereof,

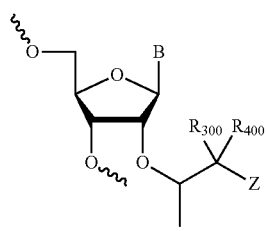

(6)

where B is selected from hydrogen, aliphatic, substituted aliphatic, natural nucleobase, modified nucleobase and universal base; $R_{300}$ and $R_{400}$ are each independently selected from hydrogen, aliphatic, substituted aliphatic, aryl, halogen, heteroaryl, heterocyclic, or $R_{300}$ and $R_{400}$ can be taken together with the atom they attached to form a carbonyl, thiocarbonyl, $=NR_{20}$, $=N-NR_{20}R_{30}$, or $=N-NR_{20}C(O)R_{10}$; Z is selected from $OR_{10}$, $COR_{10}$, $CO_2R_{10}$,

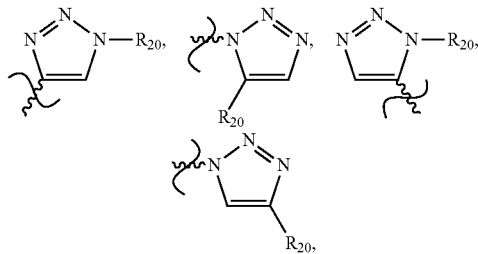

$NR_{20}R_{30}$, $CONR_{20}R_{30}$, $CON(H)NR_{20}R_{30}$, $ONR_{20}R_{30}$, $CON(H)N=CR_{40}R_{50}$, $N(R_{20})C(=NR_{30})NR_{20}R_{30}$, $N(R_{20})C(O)NR_{20}R_{30}$, $N(R_{20})C(S)NR_{20}R_{30}$, $OC(O)NR_{20}R_{30}$, $SC(O)NR_{20}R_{30}$, $N(R_{20})C(S)OR_{10}$, $N(R_{20})C(O)OR_{10}$, $N(R_{20})C(O)SR_{10}$, $N(R_{20})N=CR_{40}R_{50}$, $ON=CR_{40}R_{50}$, $SO_2R_{10}$, $SOR_{10}$, $SR_{10}$ and substituted or unsubstituted heterocyclic, where $R_{20}$, $R_{30}$, $R_{40}$ and $R_{50}$ for each occurrence are independently selected from is hydrogen, acyl, aliphatic or substituted aliphatic, aryl, heteroaryl, heterocyclic, $OR_{10}$, $COR_{10}$, $CO_2R_{10}$, $NR_{10}R_{10}'$; $R_{20}$ and $R_{30}$ can be taken together to form a heterocyclic ring; $R_{10}$ and $R_{10}'$ are independently hydrogen, aliphatic, substituted aliphatic, aryl, heteroaryl, or heterocyclic. When $R_{300}$ and $R_{400}$ are H, the formula (6) independently represent pure R and S enantiomers and mixture of these enantiomers at different ratio.

In one embodiment, the invention oligonucleotides comprising at least one nucleoside of formula (7),

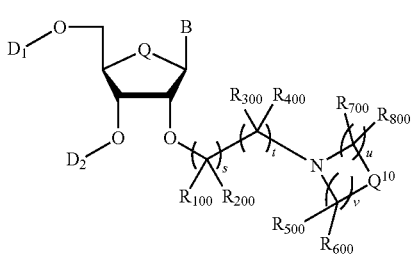

(7)

where one of $D_1$ and $D_2$ is H, hydroxyl protecting group and the other of $D_1$ and $D_2$ is H, a hydroxyl protecting group, solid support or a reactive phosphorus group; B is selected from hydrogen, aliphatic, substituted aliphatic, natural nucleobase, modified nucleobase and universal base; $R_{100}$-$R_{800}$ are each independently selected from hydrogen, aliphatic, substituted aliphatic, aryl, halogen, heteroaryl, heterocyclic, or either $R_{100}$ and $R_{200}$ or $R_{300}$ and $R_{400}$ can be taken together with the atom they attached to form a carbonyl, thiocarbonyl, $=NR_{20}$, $=N-NR_{20}R_{30}$, or $=N-NR_{20}C(O)R_{10}$ or $=NR_{20}$; $Q^{10}$ is O, S, NR$_{20}$, where $R_{20}$ is selected from hydrogen, acyl, aliphatic or substituted aliphatic, aryl, heteroaryl, heterocyclic, $OR_{10}$, $COR_{10}$, $CO_2R_{10}$,

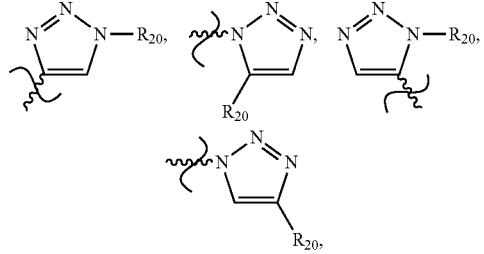

$NR_{10}R_{10}'$; $R_{20}$ and $R_{30}$ can be taken together to form a heterocyclic ring; $R_{10}$ and $R_{10}'$ are independently hydrogen, aliphatic, substituted aliphatic, aryl, heteroaryl, or heterocyclic. where $R_{20}$ is independently selected from is hydrogen, acyl, aliphatic or substituted aliphatic, aryl, heteroaryl, or heterocyclic; s and t independently for each occurrence 0, 1, 2, 3, 4, 5 or 6 provided that both s and t are not 0 in one occurrence; u and v independently in each occurrence is 0, 1, 2, 3, 4, 5 or 6 provided that both u and v are not 0 in one occurrence.

When u is 1 or 2, at least one of $R_{700}$ and $R_{800}$ can be taken together with the atom they attached to form a carbonyl, thiocarbonyl or $=NR^{20}$. When u is 2 or more, at least two of $R_{700}$ and $R_{800}$ can be taken together with the atom they attached to form a carbonyl, thiocarbonyl or $=NR_{20}$. The carbonyl, thiocarbonyl or $=NR^{20}$ is preferably linked to N or $Q^{10}$ of the ring. Similarly when v is 1 or 2 at least one of $R_{700}$ and $R_{800}$ can be taken together with the atom they attached to form a carbonyl, thiocarbonyl or $=NR^{20}$ When u is 2 or more, at least two of $R_{700}$ and $R_{800}$ can be taken together with the atom they attached to form a carbonyl, thiocarbonyl or $=NR^{20}$. The carbonyl, thiocarbonyl or $=NR^{20}$ preferably linked to N or $Q^{10}$ of the ring.

In one embodiment, the invention oligonucleotides comprising at least one nucleoside of formula (8),

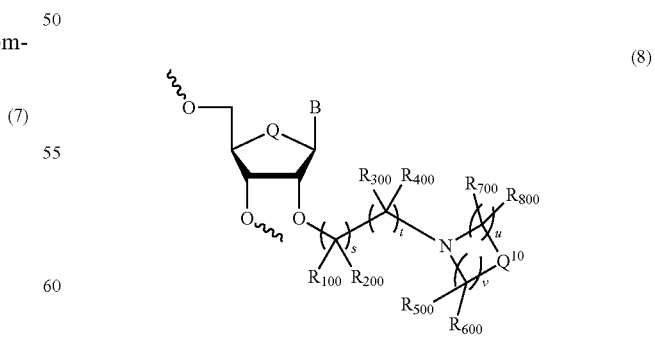

(8)

where B is selected from hydrogen, aliphatic, substituted aliphatic, natural nucleobase, modified nucleobase and universal base; $R_{100}$-$R_{800}$ are each independently selected from hydrogen, aliphatic, substituted aliphatic, aryl, halogen, heteroaryl, heterocyclic, or either $R_{100}$ and $R_{200}$ or $R_{300}$ and $R_{400}$ can be taken together with the atom they attached to form a carbonyl, thiocarbonyl, =$NR_{20}$, =N—$NR_{20}R_{30}$, or =N—$NR_{20}C(O)R_{10}$ or =$NR_{20}$; $Q^{10}$ is O, S, $NR_{20}$, where $R_{20}$ is selected from hydrogen, acyl, aliphatic or substituted aliphatic, aryl, heteroaryl, heterocyclic, $OR_{10}$, $COR_{10}$, $CO_2R_{10}$,

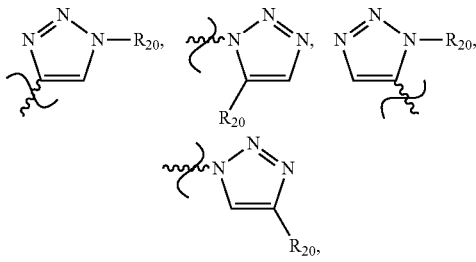

$NR_{10}R_{10}'$; $R_{20}$ and $R_{30}$ can be taken together to form a heterocyclic ring; $R_{10}$ and $R_{10}'$ are independently hydrogen, aliphatic, substituted aliphatic, aryl, heteroaryl, or heterocyclic. where $R_{20}$ is independently selected from is hydrogen, acyl, aliphatic or substituted aliphatic, aryl, heteroaryl, or heterocyclic; s and t independently for each occurrence 0, 1, 2, 3, 4, 5 or 6 provided that both s and t are not 0 in one occurrence; u and v independently in each occurrence is 0, 1, 2, 3, 4, 5 or 6 provided that both u and v are not 0 in one occurrence.

When u is 1 or 2, at least one of $R_{700}$ and $R_{800}$ can be taken together with the atom they attached to form a carbonyl, thiocarbonyl or =$NR^{20}$. When u is 2 or more, at least two of $R_{700}$ and $R_{800}$ can be taken together with the atom they attached to form a carbonyl, thiocarbonyl or =$NR_{20}$. The carbonyl, thiocarbonyl or =$NR^{20}$ preferably linked to N or $Q^{10}$ of the ring. Similarly when v is 1 or 2 at least one of $R_{700}$ and $R_{800}$ can be taken together with the atom they attached to form a carbonyl, thiocarbonyl or =$NR^{20}$ When u is 2 or more, at least two of $R_{700}$ and $R_{800}$ can be taken together with the atom they attached to form a carbonyl, thiocarbonyl or =$NR^{20}$. The carbonyl, thiocarbonyl or =$NR^{20}$ preferably linked to N or $Q^{10}$ of the ring.

In one embodiment, the invention oligonucleotides comprising at least one nucleoside of formula (9),

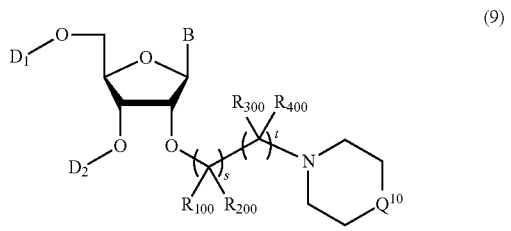

(9)

where B is selected from hydrogen, aliphatic, substituted aliphatic, natural nucleobase, modified nucleobase and universal base; $R_{100}$-$R_{400}$ are each independently selected from hydrogen, aliphatic, substituted aliphatic, aryl, halogen, heteroaryl, heterocyclic, or either $R_{100}$ and $R_{200}$ or $R_{300}$ and $R_{400}$ can be taken together with the atom they attached to form a carbonyl, thiocarbonyl, =$NR_{20}$, =N—$NR_{20}R_{30}$, or =N—$NR_{20}C(O)R_{10}$ or =$NR_{20}$; $Q^{10}$ is O, S, $NR_{20}$, where $R_{20}$ is selected from hydrogen, acyl, aliphatic or substituted aliphatic, aryl, heteroaryl, heterocyclic, $OR_{10}$, $COR_{10}$, $CO_2R_{10}$, $NR_{10}R_{10}'$; $R_{20}$ and $R_{30}$ can be taken together to form a heterocyclic ring; $R_{10}$ and $R_{10}'$ are independently hydrogen, aliphatic, substituted aliphatic, aryl, heteroaryl, or heterocyclic, where $R_{20}$ is independently selected from is hydrogen, acyl, aliphatic or substituted aliphatic, aryl, heteroaryl, or heterocyclic; s and t independently for each occurrence 0, 1, 2, 3, 4, 5 or 6 provided that both s and t are not 0 in one occurrence.

In one embodiment, the invention oligonucleotides comprising at least one nucleoside of formula (10),

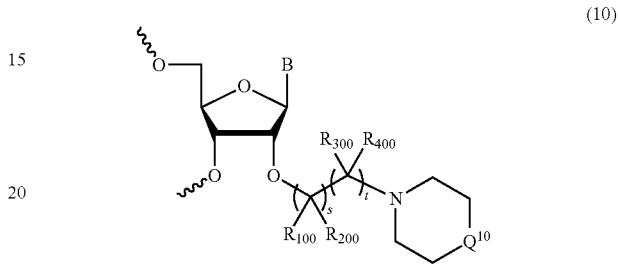

(10)

where B is selected from hydrogen, aliphatic, substituted aliphatic, natural nucleobase, modified nucleobase and universal base; $R_{100}$-$R_{400}$ are each independently selected from hydrogen, aliphatic, substituted aliphatic, aryl, halogen, heteroaryl, heterocyclic, or either $R_{100}$ and $R_{200}$ or $R_{300}$ and $R_{400}$ can be taken together with the atom they attached to form a carbonyl, thiocarbonyl, =$NR_{20}$, =N—$NR_{20}R_{30}$, or =N—$NR_{20}C(O)R_{10}$ or =$NR_{20}$; $Q^{10}$ is O, S, $NR_{20}$, where $R_{20}$ is selected from hydrogen, acyl, aliphatic or substituted aliphatic, aryl, heteroaryl, heterocyclic, $OR_{10}$, $COR_{10}$, $CO_2R_{10}$, $NR_{10}R_{10}'$; $R_{20}$ and $R_{30}$ can be taken together to form a heterocyclic ring; $R_{10}$ and $R_{10}'$ are independently hydrogen, aliphatic, substituted aliphatic, aryl, heteroaryl, or heterocyclic. where $R_{20}$ is independently selected from is hydrogen, acyl, aliphatic or substituted aliphatic, aryl, heteroaryl, or heterocyclic; s and t independently for each occurrence 0, 1, 2, 3, 4, 5 or 6 provided that both n and m are not 0 in one occurrence; s and t independently in each occurrence is 0, 1, 2, 3, 4, 5 or 6 provided that both s and t are not 0 in one occurrence.

In one embodiment, the invention provides nucleosides of formula (11), or isomers thereof:

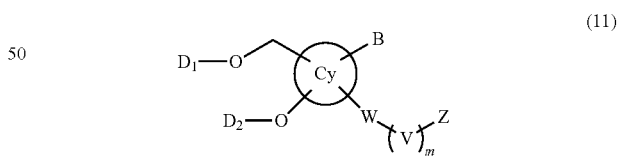

(11)

wherein

is a 3, 4, 5, 6, 7 or 8 heterocyclic or cycloalkyl ring; one of $D_1$ and $D_2$ is H, hydroxyl protecting group and the other is of $D_1$ and $D_2$ is H, a hydroxyl protecting group or a reactive phosphorus group; m is 1 to 15; B is selected from hydrogen, aliphatic, substituted aliphatic, natural nucleobase, modified nucleobase and universal nucleobase; W is absent, O, S or NR'; V is straight- or branched-, substituted or unsubstituted alkyl, substituted or unsubstituted alkenyl, substituted or unsubstituted alkynyl, of which one or more methylenes can be interrupted by O, S, S(O), SO$_2$, N(R'), C(O), substituted or unsubstituted aryl, substituted or unsubstituted heteroaryl, substituted or unsubstituted heterocyclic, substituted or unsubstituted cycloalkyl, where R' is hydrogen, acyl, aliphatic or substituted aliphatic; Z is selected from OR$_{10}$, COR$_{10}$), CO$_2$R$_{10}$, NR$_{20}$R$_{30}$, CONR$_{20}$R$_{30}$, CON(H)NR$_{20}$R$_{30}$, ONR$_{20}$R$_{30}$, CON(H)N=CR$_{40}$R$_{50}$, N(R$_{20}$)C(=NR$_{30}$) NR$_{20}$R$_{30}$, N(R$_{20}$)C(O)NR$_{20}$R$_{30}$, N(R$_{20}$)C(S)NR$_{20}$R$_{30}$, OC(O)NR$_{20}$R$_{30}$, SC(O)NR$_{20}$R$_{30}$, N(R$_{20}$)C(S)OR$_{10}$, N(R$_{20}$)C(O)OR$_{10}$, N(R$_{20}$)C(O)SR$_{10}$, N(R$_{20}$)N=CR$_{40}$R$_{50}$, ON=CR$_{40}$R$_{50}$, SO$_2$R$_{10}$, SOR$_{10}$, SR$_{10}$ and substituted or unsubstituted heterocyclic, where R$_{20}$, R$_{30}$, R$_{40}$ and R$_{50}$ for each occurrence are independently selected from is hydrogen, acyl, aliphatic or substituted aliphatic, aryl, heteroaryl, heterocyclic, OR$_{10}$, COR$_{10}$, CO$_2$R$_{10}$, NR$_{10}$R$_{10}$'; R$_{20}$ and R$_{30}$ can be taken together to form a heterocyclic ring; R$_{10}$ and R$_{10}$' are independently hydrogen, aliphatic, substituted aliphatic, aryl, heteroaryl, or heterocyclic; provided that when W is O and Z is OR$_{10}$, V is not an unsubstituted-alkylene or an unsubstituted alkoxylene. When chiral a center (or centers) is (are) present on the 2'-substituent on nucleoside formula (11), the stereochemistry represents for pure enantiomers (R or S), pure diasteromers (for e.g., RS, RR, SR and SS), meso, and mixtures of enantiomers (racemic) and diastereomers.

In one embodiment, the invention oligonucleotides comprising at least one nucleoside of formula (12), or isomers thereof:

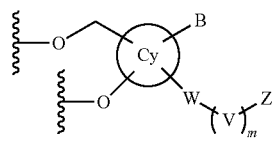

(12)

wherein

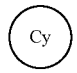

is a 3, 4, 5, 6, 7 or 8 heterocyclic or cycloalkyl ring; m is 1 to 15; B is selected from hydrogen, aliphatic, substituted aliphatic, natural nucleobase, modified nucleobase and universal nucleobase; W is absent, O, S or NR'; V is straight- or branched-, substituted or unsubstituted alkyl, substituted or unsubstituted alkenyl, substituted or unsubstituted alkynyl, of which one or more methylenes can be interrupted by O, S, S(O), SO$_2$, N(R'), C(O), substituted or unsubstituted aryl, substituted or unsubstituted heteroaryl, substituted or unsubstituted heterocyclic, substituted or unsubstituted cycloalkyl, where R' is hydrogen, acyl, aliphatic or substituted aliphatic; Z is selected from OR$_{10}$, COR$_{10}$, CO$_2$R$_{10}$, NR$_{20}$R$_{30}$, CONR$_{20}$R$_{30}$, CON(H)NR$_{20}$R$_{30}$, ONR$_{20}$R$_{30}$, CON(H) N=CR$_{40}$R$_{50}$, N(R$_{20}$)C(=NR$_{30}$)NR$_{20}$R$_{30}$, N(R$_{20}$)C(O) NR$_{20}$R$_{30}$, N(R$_{20}$)C(S)NR$_{20}$R$_{30}$, OC(O)NR$_{20}$R$_{30}$, SC(O) NR$_{20}$R$_{30}$, N(R$_{20}$)C(S)OR$_{10}$, N(R$_{20}$)C(O)OR$_{10}$, N(R$_{20}$)C(O) SR$_{10}$, N(R$_{20}$)N=CR$_{40}$R$_{50}$, ON=CR$_{40}$R$_{50}$, SO$_2$R$_{10}$, SOR$_{10}$, SR$_{10}$ and substituted or unsubstituted heterocyclic, where R$_{20}$, R$_{30}$, R$_{40}$ and R$_{50}$ for each occurrence are independently selected from is hydrogen, acyl, aliphatic or substituted aliphatic, aryl, heteroaryl, heterocyclic, OR$_{10}$, COR$_{10}$, CO$_2$R$_{10}$, NR$_{10}$R$_{10}$'; R$_{20}$ and R$_{30}$ can be taken together to form a heterocyclic ring; R$_{10}$ and R$_{10}$' are independently hydrogen, aliphatic, substituted aliphatic, aryl, heteroaryl, or heterocyclic; provided that when W is O and Z is OR$_{10}$, V is not an unsubstituted-alkylene or an unsubstituted alkoxylene. When chiral a center (or centers) is (are) present on the 2'-substituent on nucleoside formula (12), the stereochemistry represents for pure enantiomers (R or S), pure diasteromers (for e.g., RS, RR, SR and SS), meso, and mixtures of enantiomers (racemic) and diastereomers at different ratio.

In one embodiment, the invention provides nucleosides of formula (13), or isomers thereof:

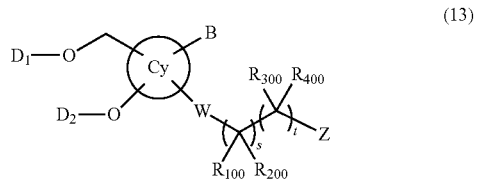

(13)

wherein

is a 3, 4, 5, 6, 7 or 8 heterocyclic or cycloalkyl ring; one of D$_1$ and D$_2$ is H, hydroxyl protecting group and the other is of D$_1$ and D$_2$ is H, a hydroxyl protecting group or a reactive phosphorus group; B is selected from hydrogen, aliphatic, substituted aliphatic, natural nucleobase, modified nucleobase and universal base; W is absent, O, S or NR'; R$_{100}$-R$_{400}$ are each independently selected from hydrogen, aliphatic, substituted aliphatic, aryl, halogen, heteroaryl, heterocyclic, or R$_{300}$ and R$_{400}$ can be taken together with the atom they attached to form a carbonyl, thiocarbonyl, =NR$_{20}$, =N—NR$_{20}$R$_{30}$, or =N—NR$_{20}$C(O)R$_{10}$; Z is selected from OR$_{10}$, COR$_{10}$, CO$_2$R$_{10}$, NR$_{20}$R$_{30}$, CONR$_{20}$R$_{30}$, CON(H)NR$_{20}$R$_{30}$, ONR$_{20}$R$_{30}$, CON(H)N=CR$_{40}$R$_{50}$, N(R$_{20}$)C(=NR$_{30}$) NR$_{20}$R$_{30}$, N(R$_{20}$)C(O)NR$_{20}$R$_{30}$, N(R$_{20}$)C(S)NR$_{20}$R$_{30}$, OC(O)NR$_{20}$R$_{30}$, SC(O)NR$_{20}$R$_{30}$, N(R$_{20}$)C(S)OR$_{10}$, N(R$_{20}$) C(O)OR$_{10}$, N(R$_{20}$)C(O)SR$_{10}$, N(R$_{20}$)N=CR$_{40}$R$_{50}$, ON=CR$_{40}$R$_{50}$, SO$_2$R$_{10}$, SOR$_{10}$, SR$_{10}$ and substituted or unsubstituted heterocyclic, where R$_{20}$, R$_{30}$, R$_{40}$ and R$_{50}$ are independently selected from is hydrogen, acyl, aliphatic or substituted aliphatic, aryl, heteroaryl, heterocyclic, OR$_{10}$, COR$_{10}$, CO$_2$R$_{10}$, NR$_{10}$R$_{10}$'; R$_{20}$ and R$_{30}$ can be taken together to form a heterocyclic ring; R$_{10}$ and R$_{10}$' are independently hydrogen, aliphatic, substituted aliphatic, aryl, heteroaryl, or heterocyclic; s and t independently for each occurrence 0, 1, 2, 3, 4, 5 or 6 provided that both s and t are not 0 in one occurrence.

In one embodiment, the invention oligonucleotides comprising at least one nucleoside of formula (14) or isomers thereof:

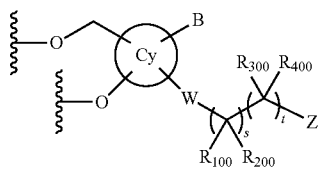

(14)

wherein

is a 3, 4, 5, 6, 7 or 8 heterocyclic or cycloalkyl ring; B is selected from hydrogen, aliphatic, substituted aliphatic, natural nucleobase, modified nucleobase and universal base; W is absent, O, S or NR'; $R_{100}$-$R_{400}$ are each independently selected from hydrogen, aliphatic, substituted aliphatic, aryl, halogen, heteroaryl, heterocyclic, or $R_{300}$ and $R_{400}$ can be taken together with the atom they attached to form a carbonyl, thiocarbonyl, $=NR_{20}$, $=N-NR_{20}R_{30}$, or $=N-NR_{20}C(O)R_{10}$; Z is selected from $OR_{10}$, $COR_{10}$, $CO_2R_{10}$, $NR_{20}R_{30}$, $CONR_{20}R_{30}$, $CON(H)NR_{20}R_{30}$, $ONR_{20}R_{30}$, $CON(H)N=CR_{40}R_{50}$, $N(R_{20})C(=NR_{30})NR_{20}R_{30}$, $N(R_{20})C(O)NR_{20}R_{30}$, $N(R_{20})C(S)NR_{20}R_{30}$, $OC(O)NR_{20}R_{30}$, $SC(O)NR_{20}R_{30}$, $N(R_{20})C(S)OR_{10}$, $N(R_{20})C(O)OR_{10}$, $N(R_{20})C(O)SR_{10}$, $N(R_{20})N=CR_{40}R_{50}$, $ON=CR_{40}R_{50}$, $SO_2R_{10}$, $SOR_{10}$, $SR_{10}$ and substituted or unsubstituted heterocyclic, where $R_{20}$, $R_{30}$, $R_{40}$ and $R_{50}$ are independently selected from is hydrogen, acyl, aliphatic or substituted aliphatic, aryl, heteroaryl, heterocyclic, $OR_{10}$, $COR_{10}$, $CO_2R_{10}$, $NR_{10}R_{10}'$; $R_{20}$ and $R_{30}$ can be taken together to form a heterocyclic ring; $R_{10}$ and $R_{10}'$ are independently hydrogen, aliphatic, substituted aliphatic, aryl, heteroaryl, or heterocyclic; and t independently for each occurrence 0, 1, 2, 3, 4, 5 or 6 provided that both s and t are not 0 in one occurrence.

In one embodiment, the invention provides nucleosides of formula (15), or isomers thereof:

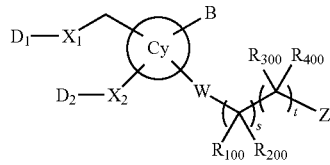

(15)

or isomers thereof, wherein

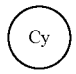

is a 3, 4, 5, 6, 7 or 8 heterocyclic or cycloalkyl ring; one of $D_1$ and $D_2$ is H, protecting group and the other is of $D_1$ and $D_2$ is H, a protecting group or a reactive phosphorus group; $X_1$ is S, NR', or $(CR_aR_b)_t$ wherein each $R_a$ and $R_b$ is, independently, H, F, $C_1$-$C_6$ haloalkyl, or $C_1$-$C_6$ alkyl, wherein t is 1 to 6; $X_2$ is O, S, or NR'; B is selected from hydrogen, aliphatic, substituted aliphatic, natural nucleobase, modified nucleobase and universal base; W is absent, O, S or NR'; $R_{100}$-$R_{400}$ are each independently selected from hydrogen, aliphatic, substituted aliphatic, aryl, halogen, heteroaryl, heterocyclic, or $R_{300}$ and $R_{400}$ can be taken together with the atom they attached to form a carbonyl, thiocarbonyl, $=NR_{20}$, $=N-NR_{20}R_{30}$, or $=N-NR_{20}C(O)R_{10}$; Z is selected from $OR_{10}$, $COR_{10}$, $CO_2R_{10}$, $NR_{20}R_{30}$, $CONR_{20}R_{30}$, $CON(H)NR_{20}R_{30}$, $ONR_{20}R_{30}$, $CON(H)N=CR_{40}R_{50}$, $N(R_{20})C(=NR_{30})NR_{20}R_{30}$, $N(R_{20})C(O)NR_{20}R_{30}$, $N(R_{20})C(S)NR_{20}R_{30}$, $OC(O)NR_{20}R_{30}$, $SC(O)NR_{20}R_{30}$, $N(R_{20})C(S)OR_{10}$, $N(R_{20})C(O)OR_{10}$, $N(R_{20})C(O)SR_{10}$, $N(R_{20})N=CR_{40}R_{50}$, $ON=CR_{40}R_{50}$, $SO_2R_{10}$, $SOR_{10}$, $SR_{10}$ and substituted or unsubstituted heterocyclic, where $R_{20}$, $R_{30}$, $R_{40}$ and $R_{50}$ are independently selected from is hydrogen, acyl, aliphatic or substituted aliphatic, aryl, heteroaryl, heterocyclic, $OR_{10}$, $COR_{10}$, $CO_2R_{10}$, $NR_{10}R_{10}'$; $R_{20}$ and $R_{30}$ can be taken together to form a heterocyclic ring; $R_{10}$ and $R_{10}'$ are independently hydrogen, aliphatic, substituted aliphatic, aryl, heteroaryl, or heterocyclic; and t independently for each occurrence 0, 1, 2, 3, 4, 5 or 6 provided that both s and t are not 0 in one occurrence.

In one embodiment, the invention oligonucleotides comprising at least one nucleoside of formula (16),

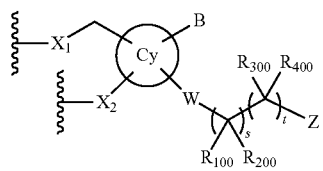

(16)

wherein is a 3, 4, 5, 6, 7 or 8 heterocyclic or cycloalkyl ring; $T_1$ and $T_2$ are each independently H, $C_1$-$C_9$ alkyl, $C_2$-$C_9$ alkenyl, $C_2$-$C_9$ alkynyl, substituted $C_1$-$C_9$ alkyl, substituted $C_1$-$C_9$ alkenyl and substituted $C_2$-$C_9$ alkynyl, provided that both $T_1$ and $T_2$ cannot be H; $X_1$ is O, S, NR', or $(CR_aR_b)_t$ wherein each $R_a$ and $R_b$ is, independently, H, F, $C_1$-$C_6$ haloalkyl, or $C_1$-$C_6$ alkyl, wherein t is 1 to 6; $X_2$ is O, S, or NR'; B is selected from hydrogen, aliphatic, substituted aliphatic, natural nucleobase, modified nucleobase and universal base; W is absent, O, S or NR'; $R_{100}$-$R_{400}$ are each independently selected from hydrogen, aliphatic, substituted aliphatic, aryl, heteroaryl, heterocyclic, or $R_{300}$ and $R_{400}$ can be taken together with the atom they attached to form a carbonyl, thiocarbonyl, $=NR_{20}$, $=N-NR_{20}R_{30}$, or $=N-NR_{20}C(O)R_{10}$; Z is selected from $OR_{10}$, $COR_{10}$, $CO_2R_{10}$, $NR_{20}R_{30}$, $CONR_{20}R_{30}$, $CON(H)NR_{20}R_{30}$, $ONR_{20}R_{30}$, $CON(H)N=CR_{40}R_{50}$, $N(R_{20})C(=NR_{30})NR_{20}R_{30}$, $N(R_{20})C(O)NR_{20}R_{30}$, $N(R_{20})C(S)NR_{20}R_{30}$, $OC(O)NR_{20}R_{30}$, $SC(O)NR_{20}R_{30}$, $N(R_{20})C(S)OR_{10}$, $N(R_{20})C(O)OR_{10}$, $N(R_{20})C(O)SR_{10}$, $N(R_{20})N=CR_{40}R_{50}$, $ON=CR_{40}R_{50}$, $SO_2R_{10}$, $SOR_{10}$, $SR_{10}$ and substituted or unsubstituted heterocyclic, where $R_{20}$, $R_{30}$, $R_{40}$ and $R_{50}$ are independently selected from is hydrogen, acyl, aliphatic or substituted aliphatic, aryl, heteroaryl, heterocyclic, $OR_{10}$, $COR_{10}$, $CO_2R_{10}$, $NR_{10}R_{10}'$; $R_{20}$ and $R_{30}$ can be taken together to form a heterocyclic ring; $R_{10}$ and $R_{10}'$ are independently hydrogen, aliphatic, substituted aliphatic, aryl, heteroaryl, or heterocyclic; s and t independently for each occurrence 0, 1, 2, 3, 4, 5 or 6 provided that both s and t are not 0 in one occurrence.

In one embodiment, the invention provides nucleosides of formula (17), or isomers thereof:

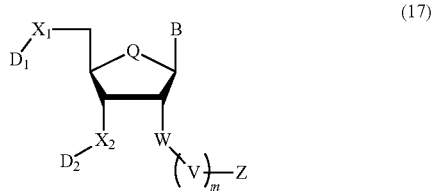

(17)

or isomers thereof, wherein one of $D_1$ and $D_2$ is H, protecting group and the other is of $D_1$ and $D_2$ is H, a protecting group or a reactive phosphorus group; $X_1$ is O, S, NR', or $(CR_aR_b)_t$, wherein each $R_a$ and $R_b$ is, independently, H, F, $C_1$-$C_6$ haloalkyl, or $C_1$-$C_6$ alkyl, wherein t is 1 to 6; $X_2$ is O, S, or NR'; m is 1 to 15; B is selected from hydrogen, aliphatic, substituted aliphatic, natural nucleobase, modified nucleobase and universal nucleobase; Q is selected from O, S, $NR_{10}$, $CH_2$; W is absent, O, S or NR'; V is straight- or branched-, substituted or unsubstituted alkyl, substituted or unsubstituted alkenyl, substituted or unsubstituted alkynyl, of which one or more methylenes can be interrupted by O, S, S(O), $SO_2$, N(R'), C(O), substituted or unsubstituted aryl, substituted or unsubstituted heteroaryl, substituted or unsubstituted heterocyclic, substituted or unsubstituted cycloalkyl, where R' is hydrogen, acyl, aliphatic or substituted aliphatic; Z is selected from $OR_{10}$, $COR_{10}$, $CO_2R_{10}$, $NR_{20}R_{30}$, $CONR_{20}R_{30}$, $CON(H)NR_{20}R_{30}$, $ONR_{20}R_{30}$, $CON(H)N=CR_{40}R_{50}$, $N(R_{20})C(=NR_{30})NR_{20}R_{30}$, $N(R_{20})C(O)NR_{20}R_{30}$, $N(R_{20})C(S)NR_{20}R_{30}$, $OC(O)NR_{20}R_{30}$, $SC(O)NR_{20}R_{30}$, $N(R_{20})C(S)OR_{10}$, $N(R_{20})C(O)OR_{10}$, $N(R_{20})C(O)SR_{10}$, $N(R_{20})N=CR_{40}R_{50}$, $ON=CR_{40}R_{50}$, $SO_2R_{10}$, $SOR_{10}$, $SR_{10}$ and substituted or unsubstituted heterocyclic, where $R_{20}$, $R_{30}$, $R_{40}$ and $R_{50}$ for each occurrence are independently selected from is hydrogen, acyl, aliphatic or substituted aliphatic, aryl, heteroaryl, heterocyclic, $OR_{10}$, $COR_{10}$, $CO_2R_{10}$, $NR_{10}R_{10}'$; $R_{20}$ and $R_{30}$ can be taken together to form a heterocyclic ring; $R_{10}$ and $R_{10}'$ are independently hydrogen, aliphatic, substituted aliphatic, aryl, heteroaryl, or heterocyclic; provided that when W is O and Z is $OR_{10}$, V is not an unsubstituted-alkylene or an unsubstituted alkoxylene.

In one embodiment, the invention provides oligonucleotides comprising at least one nucleoside of formula (18), or isomers thereof:

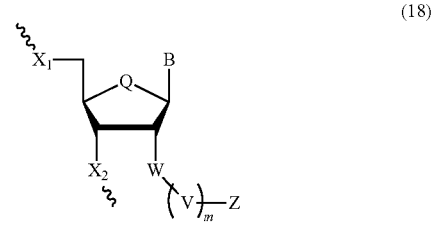

(18)

or isomers thereof, wherein m is 1 to 15; $X_1$ is O, S, NR', or $(CR_aR_b)_t$, wherein each $R_a$ and $R_b$ is, independently, H, F, $C_1$-$C_6$ haloalkyl, or $C_1$-$C_6$ alkyl, wherein t is 1 to 6; $X_2$ is O, S, or NR'; B is selected from hydrogen, aliphatic, substituted aliphatic, natural nucleobase, modified nucleobase and universal nucleobase; Q is selected from O, S, $NR_{10}$, $CH_2$; W is absent, O, S or NR'; V is straight- or branched-, substituted or unsubstituted alkyl, substituted or unsubstituted alkenyl, substituted or unsubstituted alkynyl, of which one or more methylenes can be interrupted by O, S, S(O), $SO_2$, N(R'), C(O), substituted or unsubstituted aryl, substituted or unsubstituted heteroaryl, substituted or unsubstituted heterocyclic, substituted or unsubstituted cycloalkyl, where R' is hydrogen, acyl, aliphatic or substituted aliphatic; Z is selected from $OR_{10}$, $COR_{10}$, $CO_2R_{10}$, $NR_{20}R_{30}$, $CONR_{20}R_{30}$, $CON(H)NR_{20}R_{30}$, $ONR_{20}R_{30}$, $CON(H)N=CR_{40}R_{50}$, $N(R_{20})C(=NR_{30})NR_{20}R_{30}$, $N(R_{20})C(O)NR_{20}R_{30}$, $N(R_{20})C(S)NR_{20}R_{30}$, $OC(O)NR_{20}R_{30}$, $SC(O)NR_{20}R_{30}$, $N(R_{20})C(S)OR_{10}$, $N(R_{20})$ $C(O)OR_{10}$, $N(R_{20})C(O)SR_{10}$, $N(R_{20})N=CR_{40}R_{50}$, $ON=CR_{40}R_{50}$, $SO_2R_{10}$, $SOR_{10}$, $SR_{10}$ and substituted or unsubstituted heterocyclic, where $R_{20}$, $R_{30}$, $R_{40}$ and $R_{50}$ for each occurrence are independently selected from is hydrogen, acyl, aliphatic or substituted aliphatic, aryl, heteroaryl, heterocyclic, $OR_{10}$, $COR_{10}$, $CO_2R_{10}$, $NR_{10}R_{10}'$; $R_{20}$ and $R_{30}$ can be taken together to form a heterocyclic ring; $R_{10}$ and $R_{10}'$ are independently hydrogen, aliphatic, substituted aliphatic, aryl, heteroaryl, or heterocyclic; provided that when W is O and Z is $OR_{10}$, V is not an unsubstituted-alkylene or an unsubstituted alkoxylene.

In one embodiment, the invention provides nucleosides of formula (19), or isomers thereof:

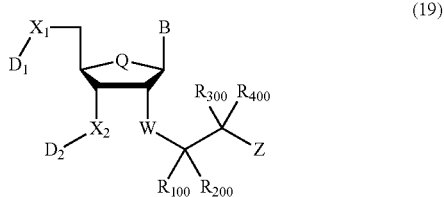

(19)

or isomers thereof, wherein one of $D_1$ and $D_2$ is H, protecting group and the other is of $D_1$ and $D_2$ is H, a protecting group or a reactive phosphorus group; $X_1$ is O, S, NR', or $(CR_aR_b)_t$, wherein each $R_a$ and $R_b$ is, independently, H, F, $C_1$-$C_6$ haloalkyl, or $C_1$-$C_6$ alkyl, wherein t is 1 to 6; $X_2$ is O, S, or NR'; B is selected from hydrogen, aliphatic, substituted aliphatic, natural nucleobase, modified nucleobase and universal base; Q is selected from O, S, $NR_{10}$, $CH_2$; W is absent, O, S or NR'; $R_{100}$-$R_{400}$ are each independently selected from hydrogen, aliphatic, substituted aliphatic, aryl, halogen, heteroaryl, heterocyclic, or $R_{300}$ and $R_{400}$ can be taken together with the atom they attached to form a carbonyl, thiocarbonyl, =$NR_{20}$, =N—$NR_{20}R_{30}$, or =N—$NR_{20}C(O)R_{10}$; Z is selected from $OR_{10}$, $COR_{10}$, $CO_2R_{10}$, $NR_{20}R_{30}$, $CONR_{20}R_{30}$, $CON(H)NR_{20}R_{30}$, $ONR_{20}R_{30}$, $CON(H)N=CR_{40}R_{50}$, $N(R_{20})C(=NR_{30})NR_{20}R_{30}$, $N(R_{20})C(O)NR_{20}R_{30}$, $N(R_{20})C(S)NR_{20}R_{30}$, $OC(O)NR_{20}R_{30}$, $SC(O)NR_{20}R_{30}$, $N(R_{20})C(S)OR_{10}$, $N(R_{20})C(O)OR_{10}$, $N(R_{20})C(O)SR_{10}$, $N(R_{20})N=CR_{40}R_{50}$, $ON=CR_{40}R_{50}$, $SO_2R_{10}$, $SOR_{10}$, $SR_{10}$ and substituted or unsubstituted heterocyclic, where $R_{20}$, $R_{30}$, $R_{40}$ and $R_{50}$ are independently selected from is hydrogen, acyl, aliphatic or substituted aliphatic, aryl, heteroaryl, heterocyclic, $OR_{10}$, $COR_{10}$, $CO_2R_{10}$, $NR_{10}R_{10}'$; $R_{20}$ and $R_{30}$ can be taken together to form a heterocyclic ring; $R_{10}$ and $R_{10}'$ are independently hydrogen, aliphatic, substituted aliphatic, aryl, heteroaryl, or heterocyclic.

In one embodiment, the invention oligonucleotides comprising at least one nucleoside of formula (20), and isomers thereof,

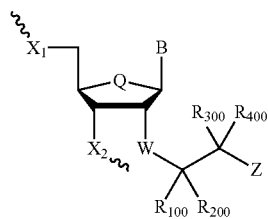

(20)

or isomers thereof, wherein $X_1$ is O, S, NR', or $(CR_aR_b)_t$ wherein each $R_a$ and $R_b$ is, independently, H, F, $C_1$-$C_6$ haloalkyl, or $C_1$-$C_6$ alkyl, wherein t is 1 to 6; $X_2$ is O, S, or NR'; B is selected from hydrogen, aliphatic, substituted aliphatic, natural nucleobase, modified nucleobase and universal base; Q is selected from O, S, $NR_{10}$, $CH_2$; W is absent, O, S or NR'; $R_{100}$-$R_{400}$ are each independently selected from hydrogen, aliphatic, substituted aliphatic, aryl, halogen, heteroaryl, heterocyclic, or $R_{300}$ and $R_{400}$ can be taken together with the atom they attached to form a carbonyl, thiocarbonyl, $=NR_{20}$, $=N-NR_{20}R_{30}$, or $=N-NR_{20}C(O)R_{10}$; Z is selected from $OR_{10}$, $COR_{10}$, $CO_2R_{10}$, $NR_{20}R_{30}$, $CONR_{20}R_{30}$, $CON(H)NR_{20}R_{30}$, $ONR_{20}R_{30}$, $CON(H)N=CR_{40}R_{50}$, $N(R_{20})C(=NR_{30})NR_{20}R_{30}$, $N(R_{20})C(O)NR_{20}R_{30}$, $N(R_{20})C(S)NR_{20}R_{30}$, $OC(O)NR_{20}R_{30}$, $SC(O)NR_{20}R_{30}$, $N(R_{20})C(S)OR_{10}$, $N(R_{20})C(O)OR_{10}$, $N(R_{20})C(O)SR_{10}$, $N(R_{20})N=CR_{40}R_{50}$, $ON=CR_{40}R_{50}$, $SO_2R_{10}$, $SOR_{10}$, $SR_{10}$ and substituted or unsubstituted heterocyclic, where $R_{20}$, $R_{30}$, $R_{40}$ and $R_{50}$ are independently selected from is hydrogen, acyl, aliphatic or substituted aliphatic, aryl, heteroaryl, heterocyclic, $OR_{10}$, $COR_{10}$, $CO_2R_{10}$, $NR_{10}R_{10}'$; $R_{20}$ and $R_{30}$ can be taken together to form a heterocyclic ring; $R_{10}$ and $R_{10}'$ are independently hydrogen, aliphatic, substituted aliphatic, aryl, heteroaryl, or heterocyclic.

In one embodiment, the invention oligonucleotides comprising at least one nucleoside of formula (21), and isomers thereof,

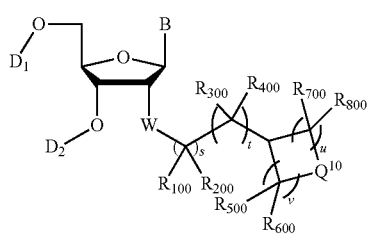

(21)

wherein:
one of $D_1$ and $D_2$ is H, or a hydroxyl protecting group and the other of $D_1$ and $D_2$ is H, a hydroxyl protecting group, or a reactive phosphorus group;
B is selected from the group consisting of hydrogen, unsubstituted or substituted aliphatic, a natural nucleobase, a modified nucleobase, and a universal base;
W is absent, O, S or NR', where R' is hydrogen, acyl, unsubstituted or substituted aliphatic;
$R_{100}$ and $R_{200}$ are each independently selected from the group consisting of hydrogen, unsubstituted or substituted aliphatic, aryl, halogen, heteroaryl, and heterocyclic; or $R_{100}$ and $R_{200}$ are taken together with the atom to which they are bound to form a carbonyl, thiocarbonyl, $=NR_{20}$, $=N-NR_{20}R_{30}$, $=N-NR_{20}C(O)R_{10}$ or $=NR_{20}$;

$R_{300}$ and $R_{400}$ are each independently selected from the group consisting of hydrogen, unsubstituted or substituted aliphatic, aryl, halogen, heteroaryl, and heterocyclic; or $R_{300}$ and $R_{400}$ are taken together with the atom to which they are bound to form a carbonyl, thiocarbonyl, $=NR_{20}$, $=N-NR_{20}R_{30}$, $=N-NR_{20}C(O)R_{10}$ or $=NR_{20}$;
$R_{500}$-$R_{800}$ are each independently selected from the group consisting of hydrogen, unsubstituted or substituted aliphatic, aryl, halogen, heteroaryl, and heterocyclic;
$Q^{10}$ is $CR_{10}R_{10}'$, O, S, or $NR_{20}$;
$R_{20}$ and $R_{30}$ are each independently selected from the group consisting of hydrogen, acyl, unsubstituted or substituted aliphatic, aryl, heteroaryl, heterocyclic, $OR_{10}$, $COR_{10}$, $CO_2R_{10}$,

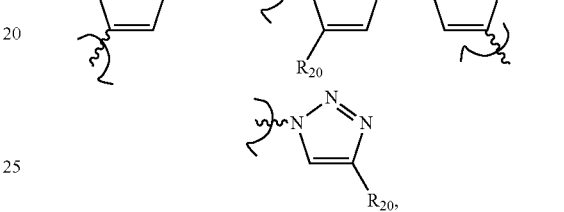

and $NR_{10}R_{10}'$; or $R_{20}$ and $R_{30}$ are taken together with the atom to which they are bound to form a heterocyclic ring;
$R_{10}$ and $R_{10}'$ are independently hydrogen, aliphatic, substituted aliphatic, aryl, heteroaryl, or heterocyclic;
s and t are independently for each occurrence 0, 1, 2, 3, 4, 5 or 6, provided that s and t are not both 0; and
u and v are independently for each occurrence 0, 1, 2, 3, 4, 5 or 6, provided that u and v are not both 0.

In one embodiment, the invention oligonucleotides comprising at least one nucleoside of formula (22), and isomers thereof,

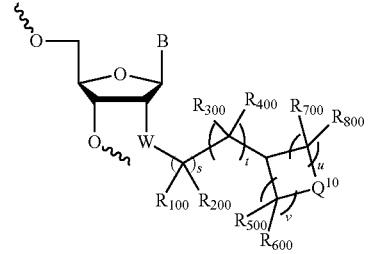

(22)

wherein:
B is selected from the group consisting of hydrogen, unsubstituted or substituted aliphatic, a natural nucleobase, a modified nucleobase, and a universal base;
W is absent, O, S or NR', where R' is hydrogen, acyl, unsubstituted or substituted aliphatic;
$R_{100}$ and $R_{200}$ are each independently selected from the group consisting of hydrogen, unsubstituted or substituted aliphatic, aryl, halogen, heteroaryl, and heterocyclic; or $R_{100}$ and $R_{200}$ are taken together with the atom to which they are bound to form a carbonyl, thiocarbonyl, $=NR_{20}$, $=N-NR_{20}R_{30}$, $=N-NR_{20}C(O)R_{10}$ or $=NR_{20}$;
$R_{300}$ and $R_{400}$ are each independently selected from the group consisting of hydrogen, unsubstituted or substituted aliphatic, aryl, halogen, heteroaryl, and heterocyclic; or $R_{300}$ and $R_{400}$ are taken together with the atom to which they are bound to form a carbonyl, thiocarbonyl, $=NR_{20}$, $=N-NR_{20}R_{30}$, $=N-NR_{20}C(O)R_{10}$ or $=NR_{20}$;

$R_{500}$-$R_{800}$ are each independently selected from the group consisting of hydrogen, unsubstituted or substituted aliphatic, aryl, halogen, heteroaryl, and heterocyclic;

$Q^{10}$ is $CR_{10}R_{10}'$, O, S, or $NR_{20}$;

$R_{20}$ and $R_{30}$ are each independently selected from the group consisting of hydrogen, acyl, unsubstituted or substituted aliphatic, aryl, heteroaryl, heterocyclic, $OR_{10}$, $COR_{10}$, $CO_2R_{10}$,

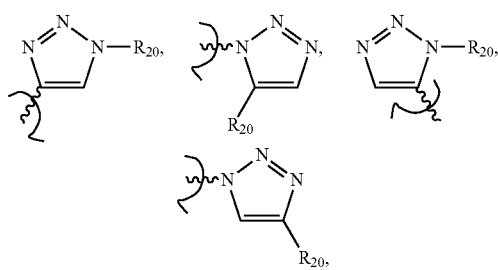

and $NR_{10}R_{10}'$; or $R_{20}$ and $R_{30}$ are taken together with the atom to which they are bound to form a heterocyclic ring;

$R_{10}$ and $R_{10}'$ are independently hydrogen, aliphatic, substituted aliphatic, aryl, heteroaryl, or heterocyclic;

s and t are independently for each occurrence 0, 1, 2, 3, 4, 5 or 6, provided that s and t are not both 0; and u and v are independently for each occurrence 0, 1, 2, 3, 4, 5 or 6, provided that u and v are not both 0.

In one embodiment, the invention oligonucleotides comprising at least one nucleoside of formula (23), and isomers thereof,

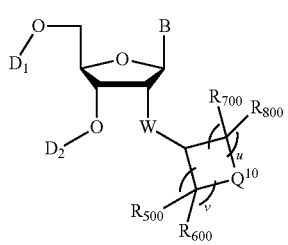
(23)

wherein:

one of $D_1$ and $D_2$ is H, or a hydroxyl protecting group and the other of $D_1$ and $D_2$ is H, a hydroxyl protecting group, or a reactive phosphorus group;

B is selected from the group consisting of hydrogen, unsubstituted or substituted aliphatic, a natural nucleobase, a modified nucleobase, and a universal base;

W is absent, O, S or NR', where R' is hydrogen, acyl, unsubstituted or substituted aliphatic;

$R_{500}$-$R_{800}$ are each independently selected from the group consisting of hydrogen, unsubstituted or substituted aliphatic, aryl, halogen, heteroaryl, and heterocyclic;

$Q^{10}$ is $CR_{10}R_{10}'$, O, S, or $NR_{20}$;

$R_{20}$ is selected from the group consisting of hydrogen, acyl, unsubstituted or substituted aliphatic, aryl, heteroaryl, heterocyclic, $OR_{10}$, $COR_{10}$, $CO_2R_{10}$,

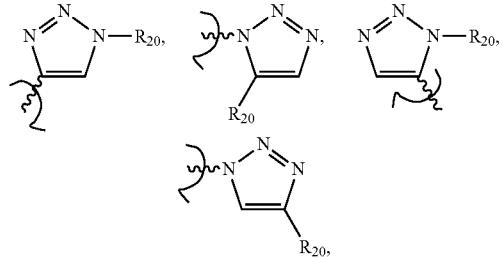

and $NR_{10}R_{10}'$;

$R_{10}$ and $R_{10}'$ are independently hydrogen, aliphatic, substituted aliphatic, aryl, heteroaryl, or heterocyclic; and u and v are independently for each occurrence 0, 1, 2, 3, 4, 5 or 6, provided that u and v are not both 0.

In one embodiment, the invention oligonucleotides comprising at least one nucleoside of formula (24), and isomers thereof,

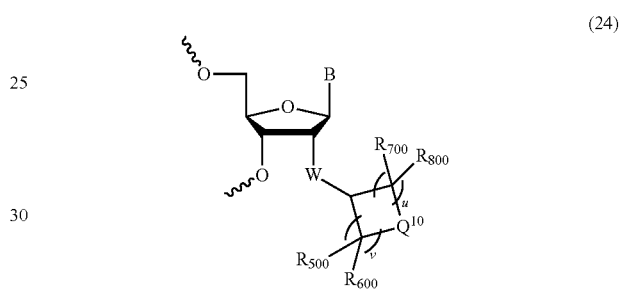
(24)

wherein:

B is selected from the group consisting of hydrogen, unsubstituted or substituted aliphatic, a natural nucleobase, a modified nucleobase, and a universal base;

W is absent, O, S or NR', where R' is hydrogen, acyl, unsubstituted or substituted aliphatic;

$R_{500}$-$R_{800}$ are each independently selected from the group consisting of hydrogen, unsubstituted or substituted aliphatic, aryl, halogen, heteroaryl, and heterocyclic;

$Q^{10}$ is $CR_{10}R_{10}'$, O, S, or $NR_{20}$;

$R_{20}$ is selected from the group consisting of hydrogen, acyl, unsubstituted or substituted aliphatic, aryl, heteroaryl, heterocyclic, $OR_{10}$, $COR_{10}$, $CO_2R_{10}$,

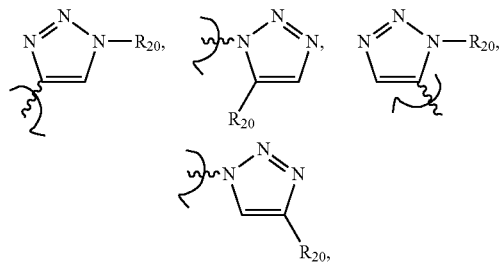

and $NR_{10}R_{10}'$;

$R_{10}$ and $R_{10}'$ are independently hydrogen, aliphatic, substituted aliphatic, aryl, heteroaryl, or heterocyclic; and u and v are independently for each occurrence 0, 1, 2, 3, 4, 5 or 6, provided that u and v are not both 0.

In one embodiment, the nucleosides provided herein are useful for modifying of oligonucleotides at one or more positions. Such modified oligonucleotides can be described as having a particular motif. In one embodiment, the motifs include without limitation, a gapped motif, a hemimer motif, a blockmer motif, a uniformly fully modified motif, a positionally modified motif and an alternating motif. In conjunction with these motifs a wide variety of internucleoside linkages can also be used including but not limited to phosphodiester and phosphorothioate internucleoside linkages which can be incorporated uniformly or in combinations. In one embodiment, altering the base sequence provides the targeting component for the oligonucleotides provided herein.

In one embodiment, one of $D_1$ or $D_2$ is a 4,4'-dimethoxytrityl protected hydroxyl group and the other $D_1$ or $D_2$ is a reactive phosphorus group comprising a diisopropylcyanoethoxy phosphoramidite group. See the Definitions section, below, for a description of a "reactive phosphorus group" and a "hydroxyl protecting group." In a preferred embodiment, $D_1$ is 4,4'-dimethoxytrityl protected hydroxyl group and $D_2$ comprises a diisopropylcyanoethoxy phosphoramidite group.

In one embodiment, B is uracil, 5-methyluracil, 5-methylcytosine, cytosine, 5-thiazolo-uracil, 5-thiazolo-cytosine, adenine, guanine or 2,6-diaminopurine, 6-oxopurine, pseudouridine, N1 substituted pseudouridine, xanthine, 2-aminopurine, or 7-deazapurine.

In one embodiment, each hydroxyl protecting group is, independently, acetyl, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, benzoyl, p-phenylbenzoyl, 2,6-dichlorobenzyl, diphenylmethyl, p-nitrobenzyl, triphenylmethyl (trityl), 4,4'-dimethoxytrityl, trimethylsilyl, triethylsilyl, t-butyldimethylsilyl, t-butyldiphenylsilyl, triphenylsilyl, triisopropylsilyl, benzoylformate, chloroacetyl, trichloroacetyl, trifluoroacetyl, pivaloyl, 9-fluorenylmethyl carbonate, mesylate, tosylate, triflate, trityl, monomethoxytrityl, dimethoxytrityl, trimethoxytrityl, 9-phenylxanthine-9-yl (Pixyl) or 9-(p-methoxyphenyl)xanthine-9-yl (MOX). In a preferred embodiment, each of the hydroxyl protecting groups is, independently, acetyl, benzyl, t-butyldimethylsilyl, t-butyldiphenylsilyl or 4,4'-dimethoxytrityl.

In one aspect of the invention, oligonucleotides containing 2'-O-alkylated sugar moieties for nucleic acid diagnostics and therapeutics, include one or more of the following nucleosides:

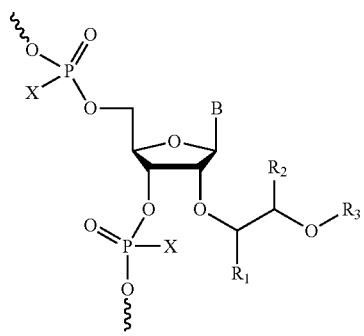

I

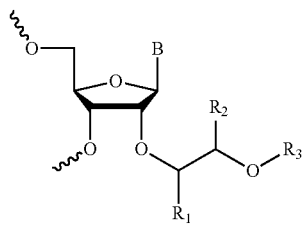

IA where $R_1$, $R_2$, $R_3$, $R_4$, $R_6$, $R_7$, $R_8$ and $R_9$ are independently selected form alkyl, aryl, cycloalkyl, heteroaryl, heterocylcoalkyl and acyl; B is optionally substituted natural or non-natural nucleobase or a universal nucleobase; Q and Y are independently selected from O, S, $CR'_2$, C(O), C(S), OC(O), N(R")C(O), OC(O)N(R"), N(R")C(O)O, ONR'(R"), CON(R")NR'(R") and NR", where R' is hydrogen, alkyl, aryl, cycloalkyl, heteroaryl, or heterocycloalkyl and R" is hydrogen, alkyl, aryl, cycloalkyl, heteroaryl, heterocycloalkyl or acyl; m, n and p are each independently 1 to 10.

Particular nucleosides of formulas I and IA include:
When $R_1$=Me, $R_2$ and $R_3$=Me
When $R_1$=Me, $R_2$=H and $R_3$=Me
When $R_1$=H, $R_2$ and $R_3$=Me
When $R_1$=Et, $R_2$ and $R_3$=Me
When $R_1$=Et, $R_2$=H and $R_3$=Me
When $R_1$=H, $R_2$ and $R_3$=Et
When $R_1$=$C_6H_5$, $R_2$=Me, and $R_3$=Me
When $R_1$=$C_6H_5$, $R_2$=H and $R_3$=Me
When $R_1$=$C_6H_5$, $R_2$=H and $R_3$=$C_6H_5$
When $R_1$=H, $R_2$=$C_6H_5$, and $R_3$=Me
When $R_1$=$CH_2N(R_4)(R_5)$, $R_2$=H, and $R_3$=OMe
When $R_1$=$CH_2N(R_4)(R_5)$, $R_2$=Me, and $R_3$=OMe
When $R_1$=H, $R_2$=$C_6H_5$, and $R_3$=Me
When $R_1$=H, $R_2$=$C_6H_5$, and $R_3$=$C_6H_5$ Oligonucleotides containing 2'-O-alkylated sugar moieties for nucleic acid diagnostics and therapeutics, also include one or more of the following nucleosides:

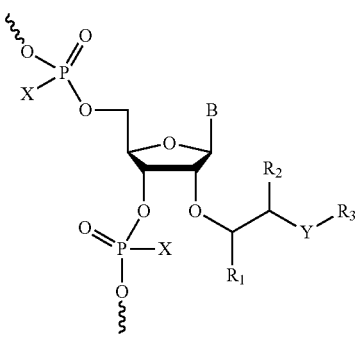

II

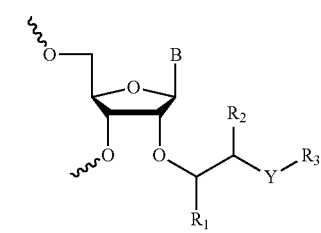

IIA

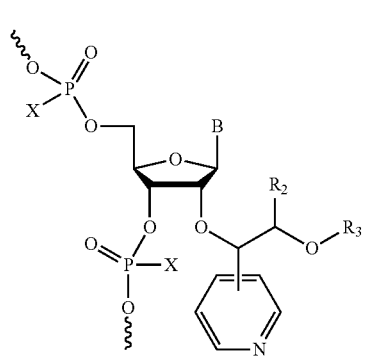
III
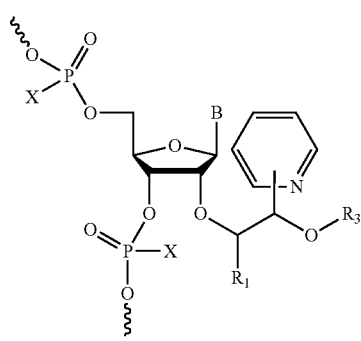
IV
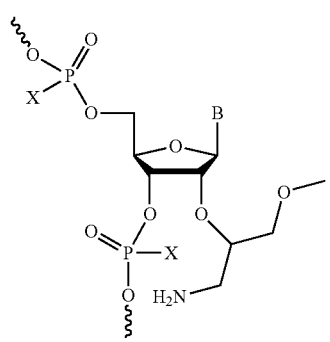
V
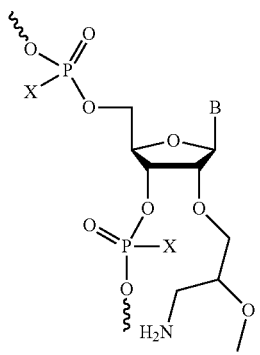
VI
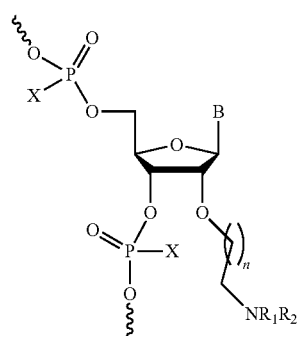
VII
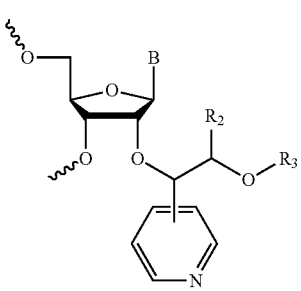
IIIA
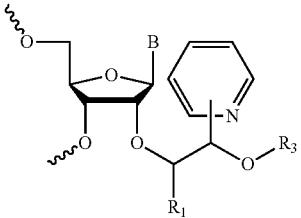
IVA
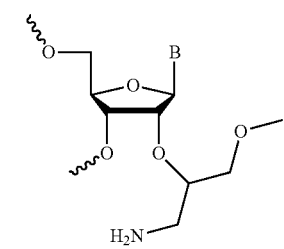
VA
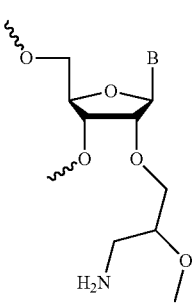
VIA -continued

VIIA

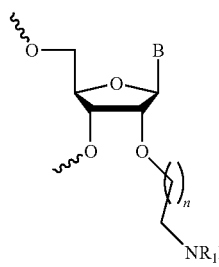

where $R_1$, $R_2$, $R_3$, $R_4$, $R_6$, $R_7$, $R_8$ and $R_9$ are independently selected form alkyl, aryl, cycloalkyl, heteroaryl, heterocylcoalkyl and acyl; B is optionally substituted natural or non-natural nucleobase or a universal nucleobase; Q and Y are independently selected from O, S, $CR'_2$, C(O), C(S), OC(O), N(R")C(O), OC(O)N(R"), N(R")C(O)O, ONR'(R"), CON(R")NR'(R") and NR", where R' is hydrogen, alkyl, aryl, cycloalkyl, heteroaryl, or heterocycloalkyl and R" is hydrogen, alkyl, aryl, cycloalkyl, heteroaryl, heterocycloalkyl or acyl; m, n and p are each independently 1 to 10.

Oligonucleotides containing 2'-O-alkylated ribose moieties: The alkyls are preferentially substituted at α- and/or β-positions and preferred choices are optically pure enantiomers, diastereomers and racemic mixtures of the substituted alkyls. The oligonucleotides may contain one or more of the following nucleosides:

XII

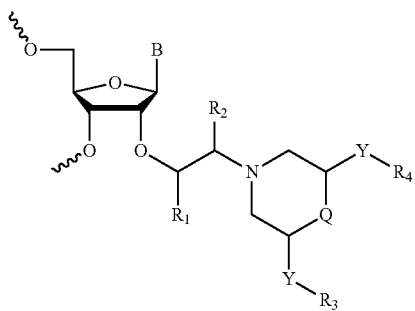

XI

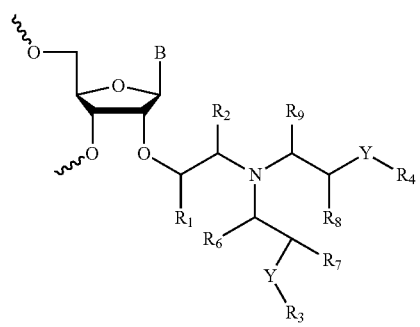

XIII

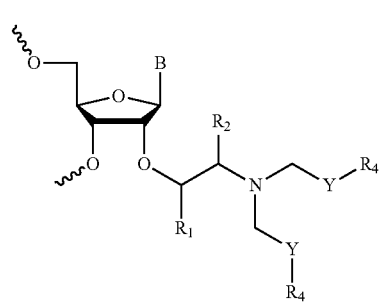

-continued

XIV

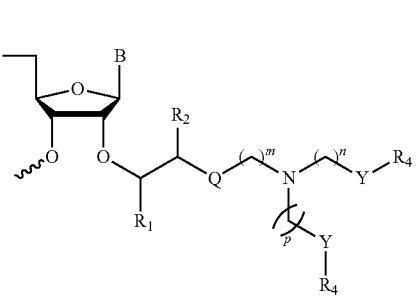

where $R_1$, $R_2$, $R_3$, $R_4$, $R_6$, $R_7$, $R_8$ and $R_9$ are independently selected form alkyl, aryl, cycloalkyl, heteroaryl, heterocylcoalkyl and acyl; B is optionally substituted natural or non-natural nucleobase or a universal nucleobase; Q and Y are independently selected from O, S, $CR'_2$, C(O), C(S), OC(O), N(R")C(O), OC(O)N(R"), N(R")C(O)O, ONR'(R"), CON(R")NR'(R") and NR", where R' is hydrogen, alkyl, aryl, cycloalkyl, heteroaryl, or heterocycloalkyl and R" is hydrogen, alkyl, aryl, cycloalkyl, heteroaryl, heterocycloalkyl or acyl; and m, n and p are each independently 1 to 10.

Representative nucleosides or embodiments according to the invention are those selected from the Table A below or its geometric isomers, enantiomers, diastereomers, and racemates thereof, where n is 1 to 10:

TABLE A

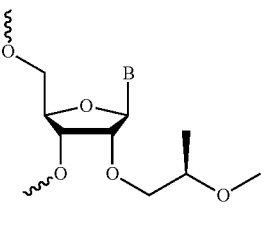

(2R)-2-MeMOE

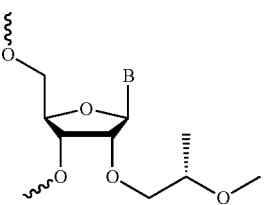

(2S)-2-MeMOE

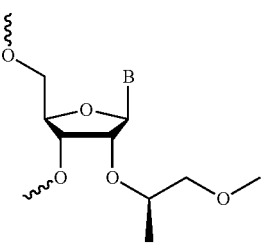

(1R)-1-MeMOE

TABLE A-continued
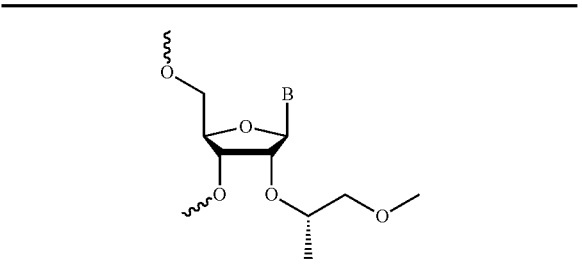
(1S)-1-MeMOE
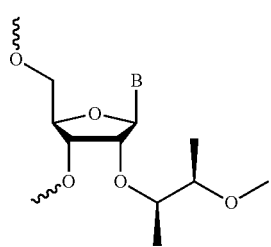
(1R,2R)-1,2-diMeMOE
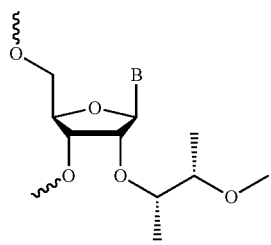
(1S,2S)-1,2-diMeMOE
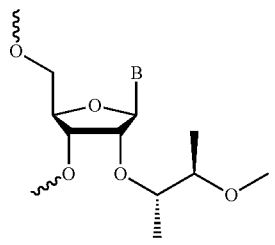
(1S,2R)-1,2-diMeMOE
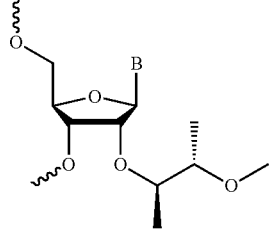
(1R,2S)-1,2-diMeMOE
TABLE A-continued
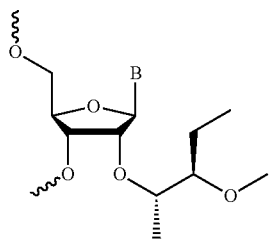
(1S,2R)-1-Me-2-EtMOE
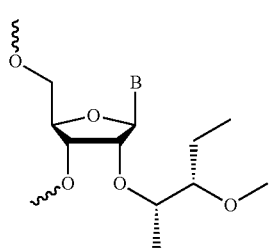
(1S,2S)-1-Me-2-EtMOE
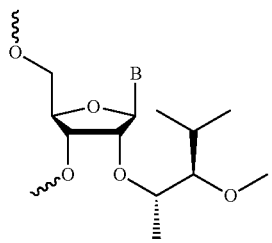
(1S,2R)-1-Me-2-isoPrMOE
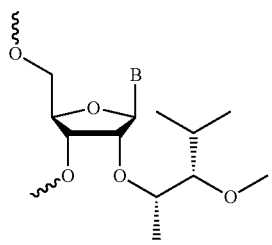
(1S,2S)-1-Me-2-isoPrMOE
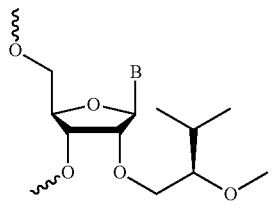
(2R)-2-isoPrMOE TABLE A-continued
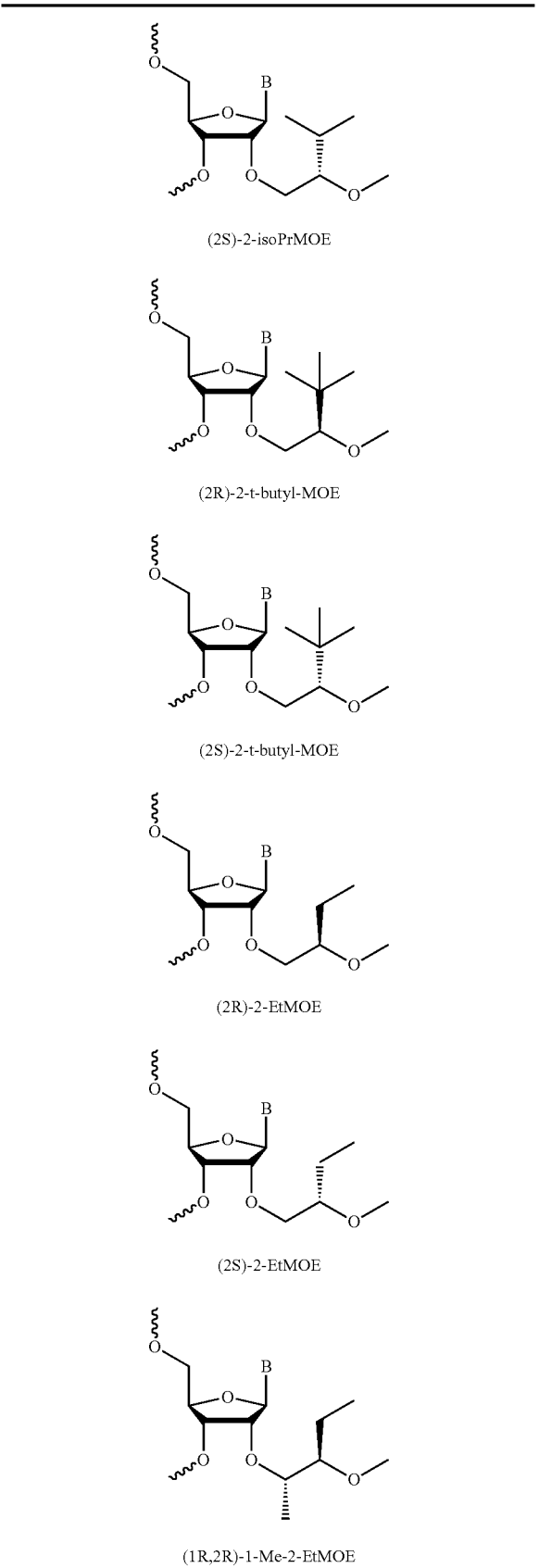
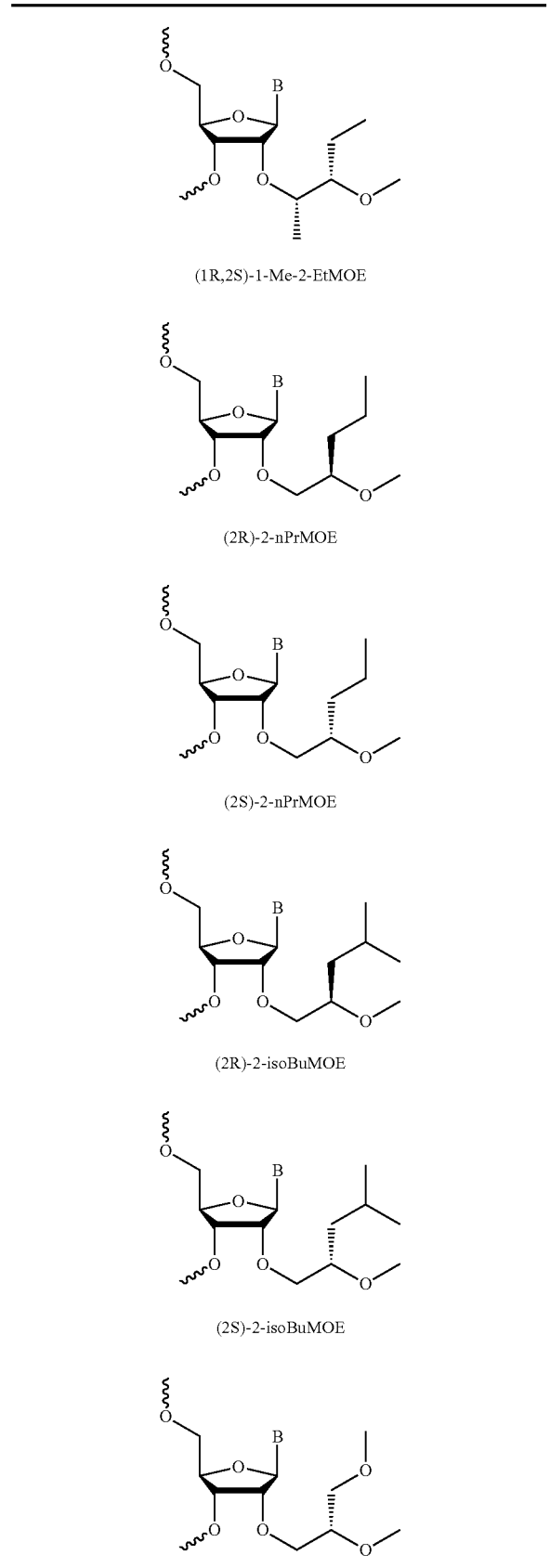

TABLE A-continued
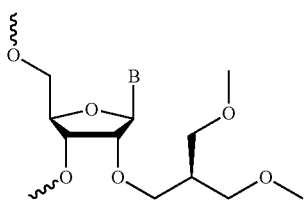
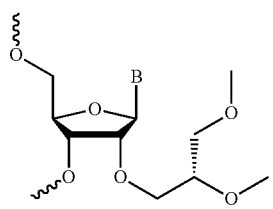
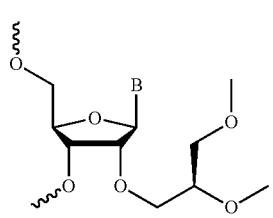
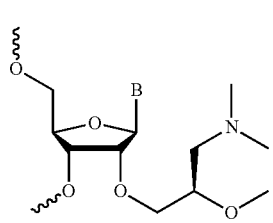
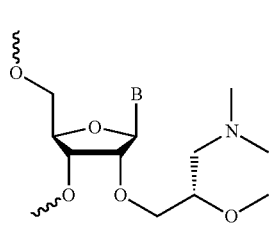
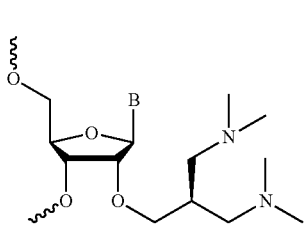
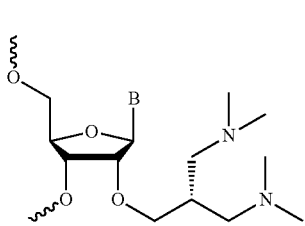
TABLE A-continued
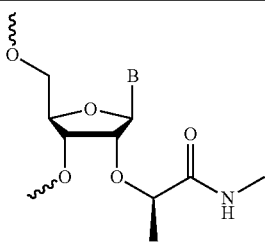
(1R)-1-MeNMA
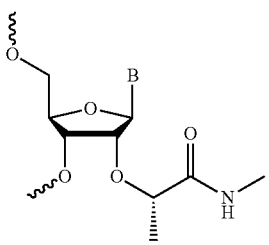
(1S)-1-MeNMA
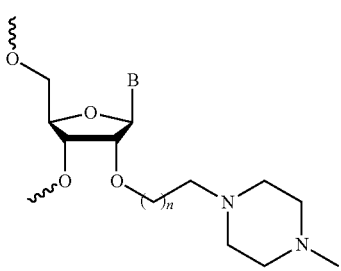
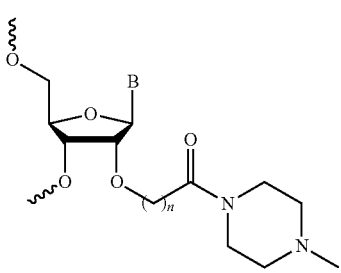
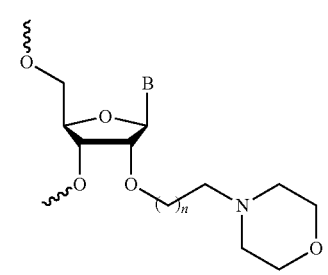
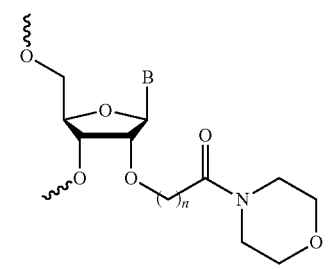

TABLE A-continued
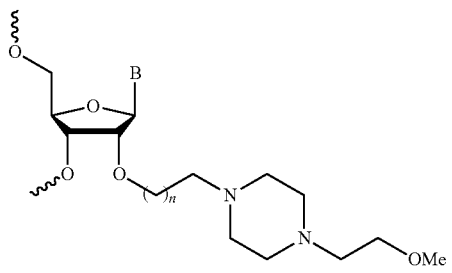
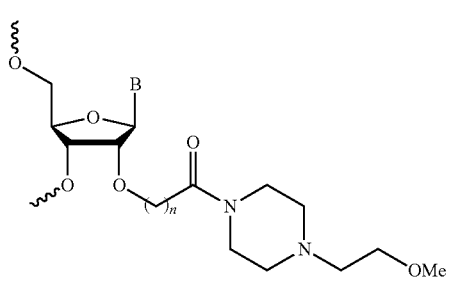
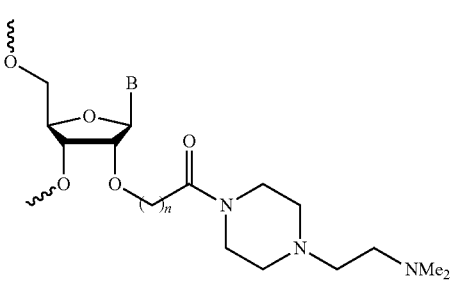
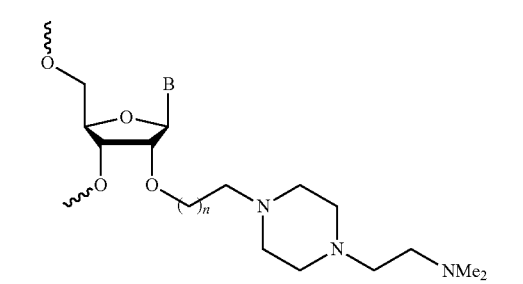
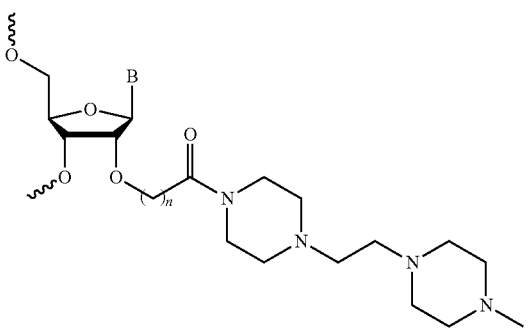
TABLE A-continued
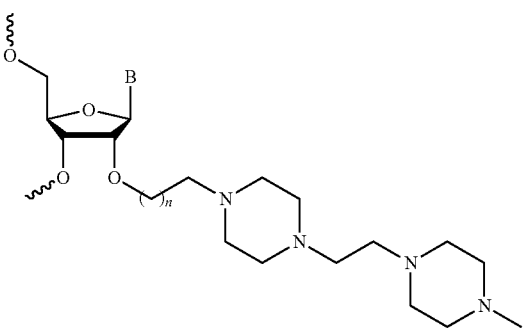
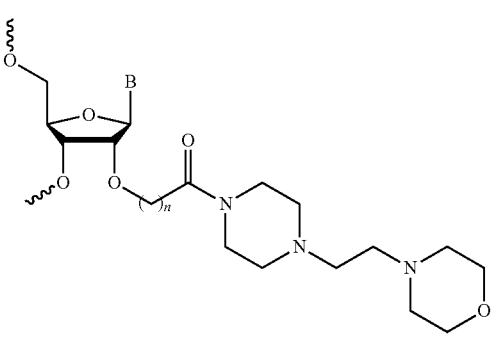
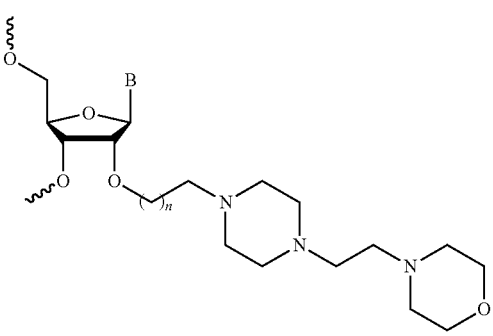
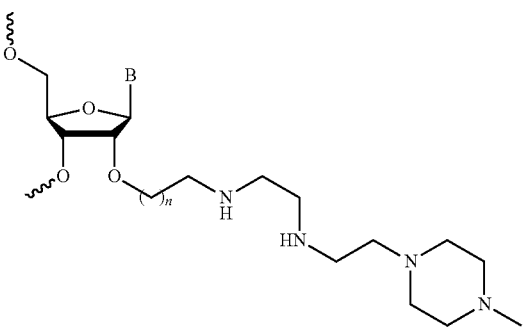
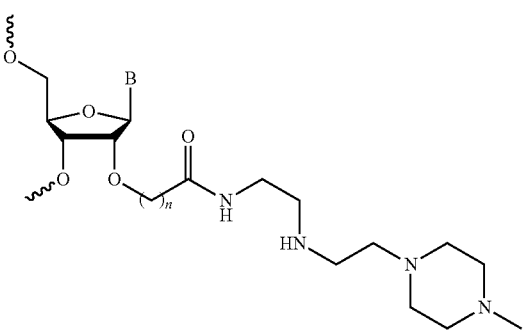

TABLE A-continued
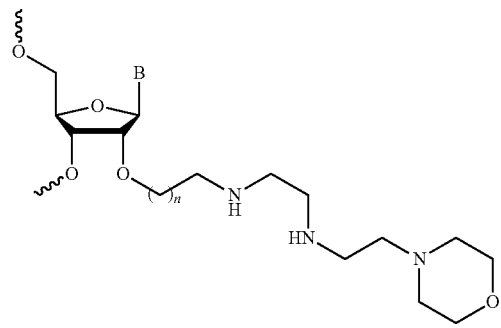
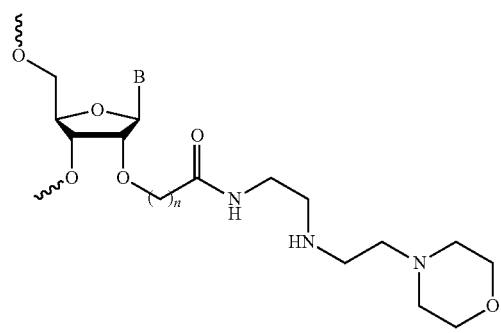
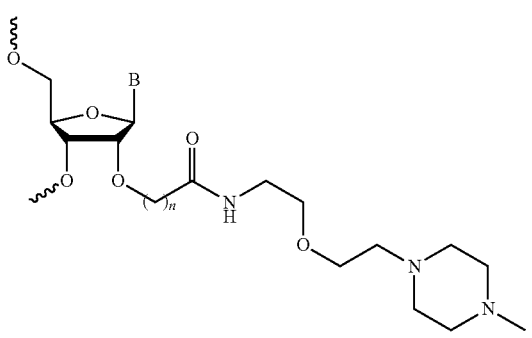
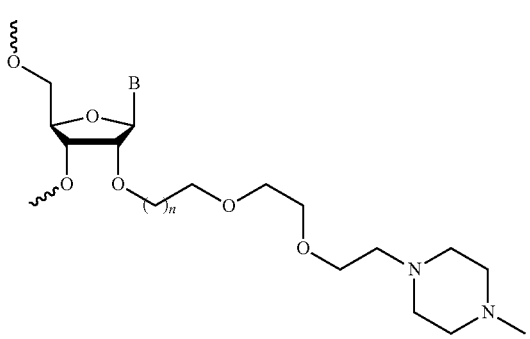
TABLE A-continued
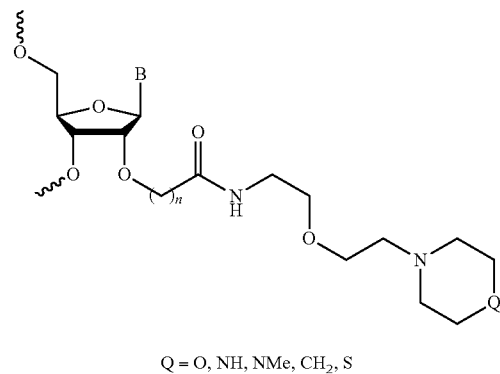
Q = O, NH, NMe, CH₂, S
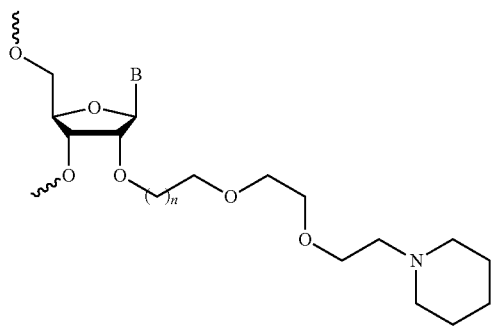
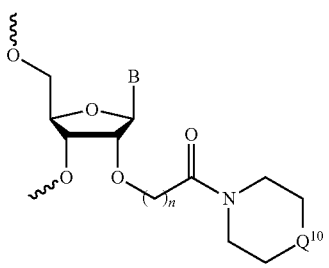
$Q^{10}$ = O, NH, NMe, CH₂, S
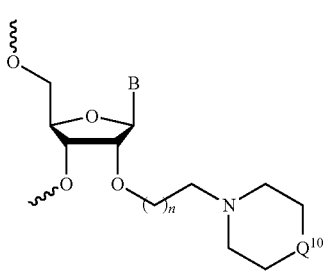
$Q^{10}$ = O, NH, NMe, CH₂, S
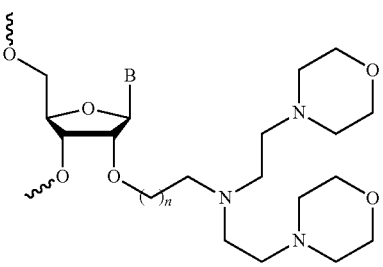

TABLE A-continued
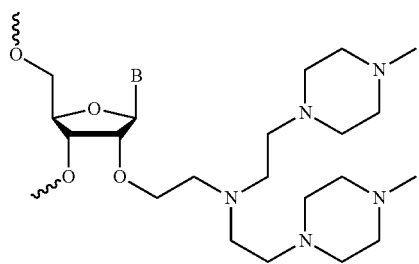
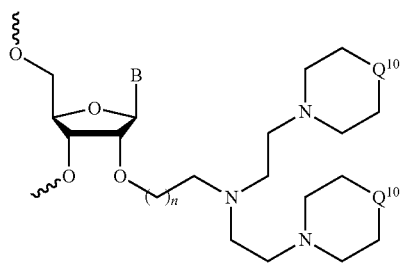
Q$^{10}$ = O, NH, NMe, CH$_2$, S
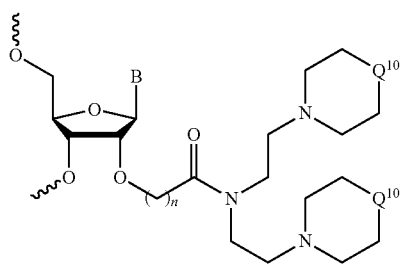
Q$^{10}$ = O, NH, NMe, CH$_2$, S
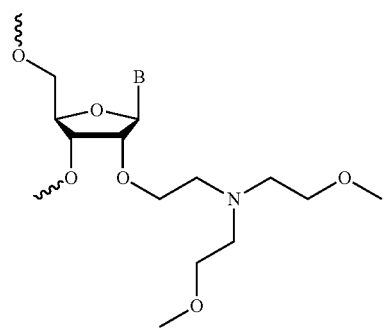
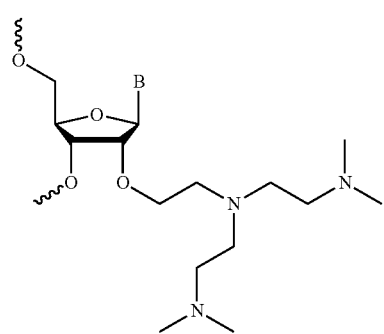
TABLE A-continued
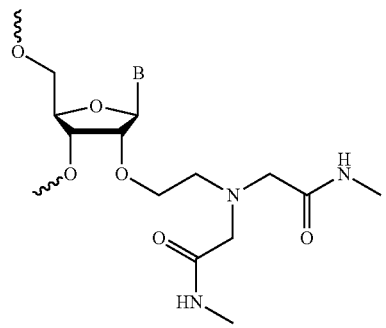
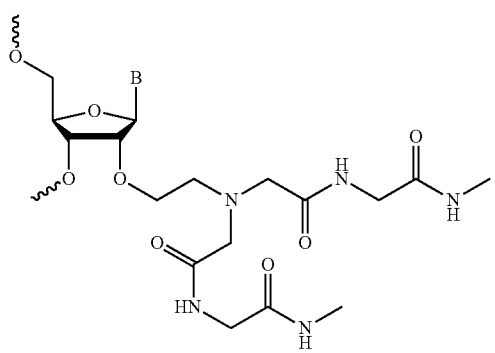
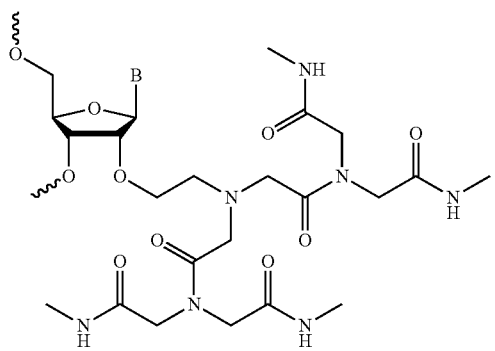
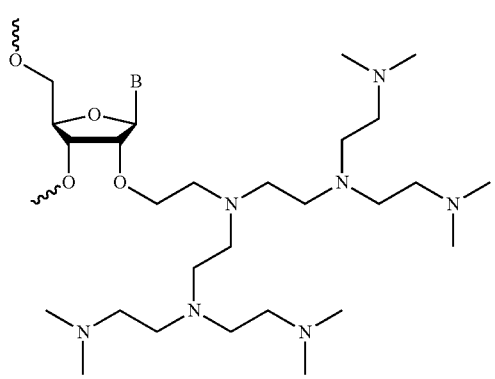

TABLE A-continued
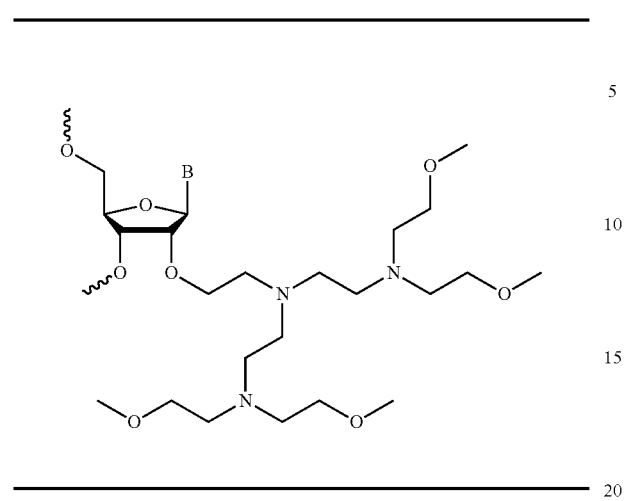
In one embodiment, oligonucleotides of the invention further comprising at least one nucleoside selected from:
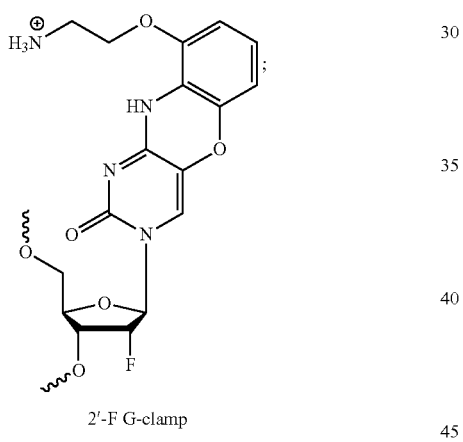
2'-F G-clamp
2'-F Phenylpyrrolocytosine (2'F-Phpc)
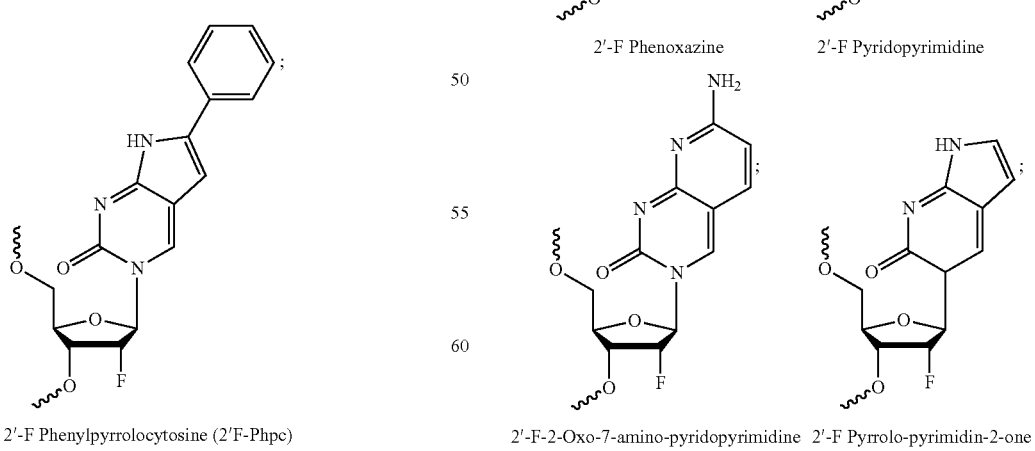
2'F- moPhpc
2'F- boPhpc
2'-F Phenoxazine  2'-F Pyridopyrimidine
2'-F-2-Oxo-7-amino-pyridopyrimidine  2'-F Pyrrolo-pyrimidin-2-one -continued

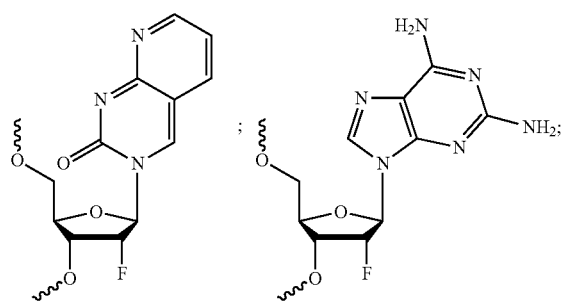

2'-F 2-Oxopyridopyrimidine    2'-F 2-Amino-A

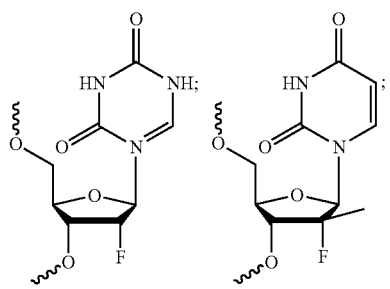

2'-F Pseudouridine    ara-2'-Me-2'-F U

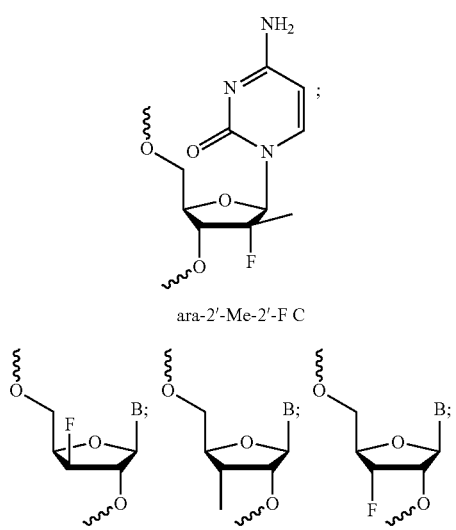

ara-2'-Me-2'-F C

2'-R G-clamp, where R is hydrogen, halogen, OH, O-alkyl, O-substituted alkyl

-continued

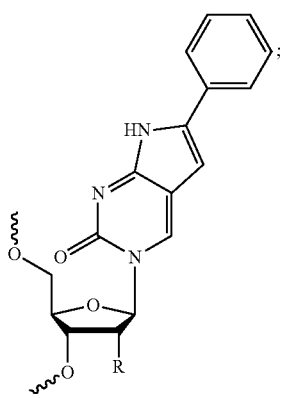

2'-R Phenylpyrrolocytosine (2'F-Phpc), where R is hydrogen, halogen, OH, O-alkyl, O-substituted alkyl

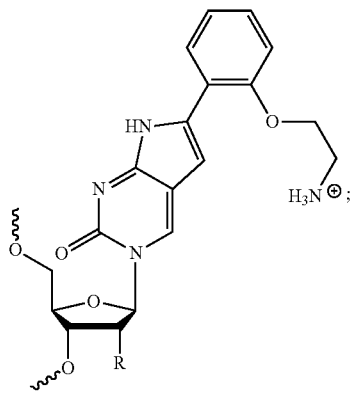

2'R- moPhpc where R is hydrogen, halogen, OH, O-alkyl, O-substituted alkyl

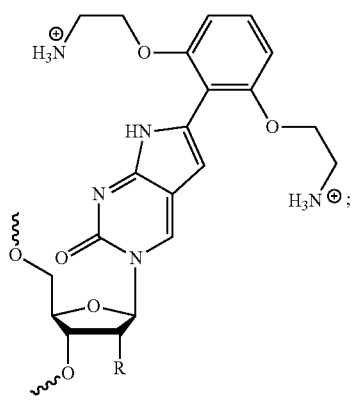

2'R- boPhpc, where R is hydrogen, halogen, OH, O-alkyl, O-substituted alkyl

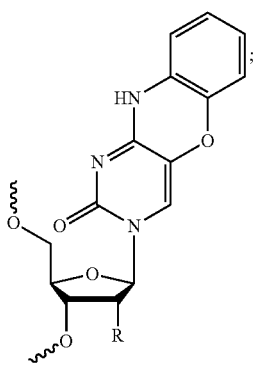

2′-R Phenoxazine, where R is hydrogen, halogen, OH, O-alkyl, O-substituted alkyl

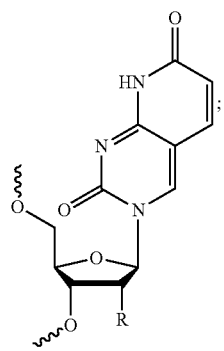

2′-R Pyridopyrimidine, where R is hydrogen halogen, OH, O-alkyl, O-substituted alkyl

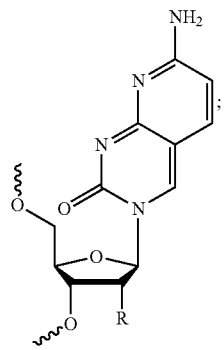

2′-R-2-Oxo-7-amino-pyridopyrimidine, where R is hydrogen, halogen, OH, O-alkyl, O-substituted alkyl

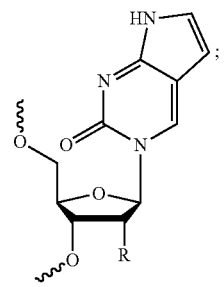

2′-R-Pyrrolo-pyrimidin-2-one, where R is hydrogen, halogen, OH, O-alky, O-substituted alkyl

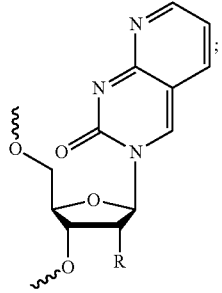

2′-R 2-Oxopyridopyrimidine, where R is hydrogen, halogen, OH, O-alkyl, O-substituted alkyl

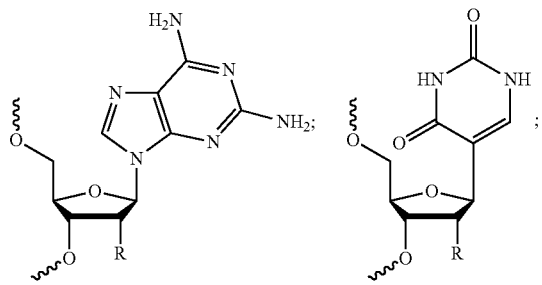

2′-R 2-Amino-A, where R is hydrogen, halogen, OH, O-alkyl, O-substituted alkyl

2′-R Pseudouridine, where R is hydrogen, halogen, OH, O-alky, O-substituted alkyl

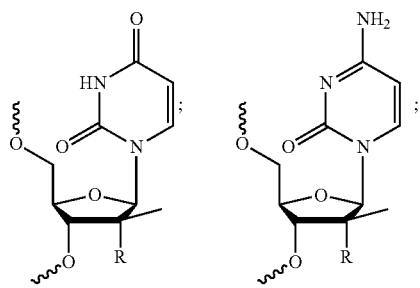

ara-2′-Me-R′-F U, where R is hydrogen, halogen, OH, O-alkyl, O-substituted alkyl ara-2′-Me-2′-R C, where R is hydrogen, halogen or OH, O-alkyl, O-substituted alkyl

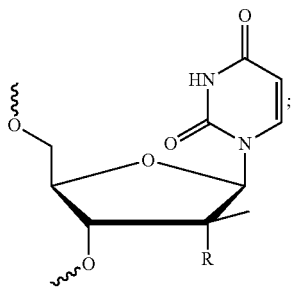

ara-2′-Me-R′-F U, where R is hydrogen, halogen, OH, O-alkyl, O-substituted alkyl -continued

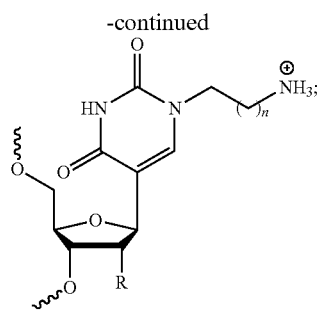

$N^1$-Aminoalkyl Pseudouridine, where R is hydrogen, halogen or OH, O-alkyl, O-substituted alkyl

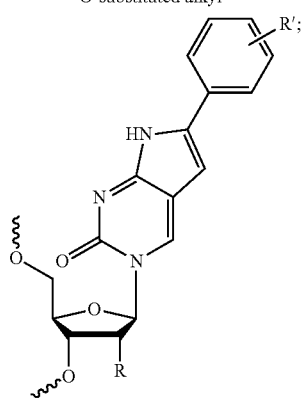

where R is hydrogen, halogen, OH, O-alkyl, O-substituted alkyl

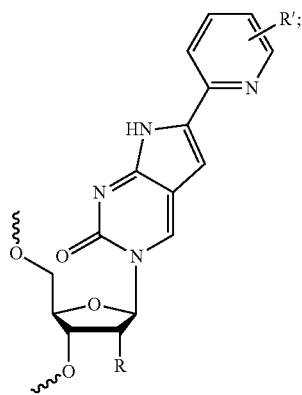

where R is hydrogen, halogen, OH, O-alkyl, O-substituted alkyl


where R is hydrogen, halogen, OH, O-alkyl, O-substituted alkyl

-continued

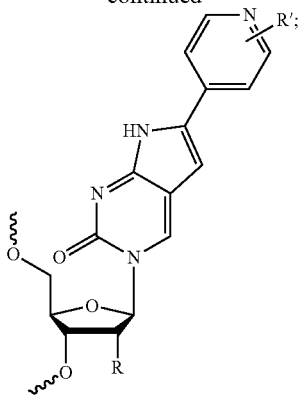

where R is hydrogen, halogen, OH, O-alkyl, O-substituted alkyl

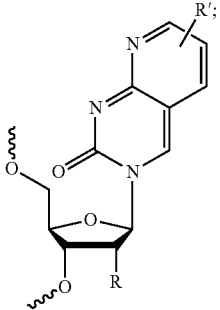

where R is hydrogen, halogen, OH, O-alkyl, O-substituted alkyl and combination thereof.

In one embodiment, the oligonucleotides of the invention comprise a 2' end or a 3'-end cap of formula (2a) or formula (2b), (2a)

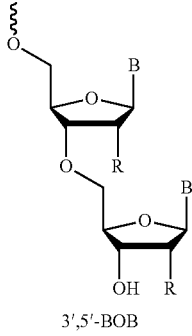

3',5'-BOB (2b)

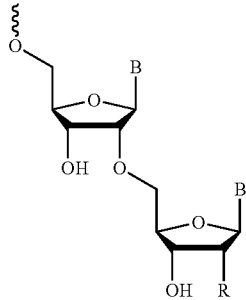

2',5'-BOB where B is hydrogen, a natural nucleobase, a modified nucleobase, or a universal base; R is hydrogen, halogen, OH, substituted or unsubstituted alkoxy, alkylthio, alkylamino, -D-aryl, —O-heteroaryl, or —O-heterocyclic. In one example, R is hydrogen, fluoro, OH, —O-alkyl, or —O-substituted alkyl.

In one embodiment, the oligonucleotides of the invention comprise a 2'-end or a 3'-end cap of formula (3a) or formula (3b):

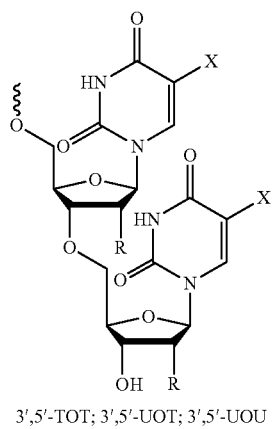

3',5'-TOT; 3',5'-UOT; 3',5'-UOU

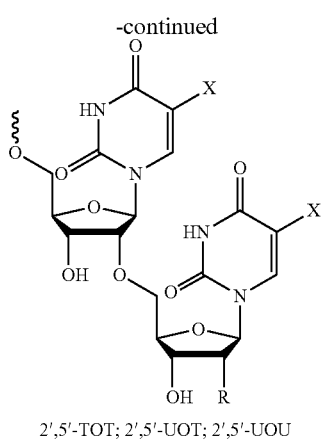

2',5'-TOT; 2',5'-UOT; 2',5'-UOU where X is hydrogen, substituted or unsubstituted alkyl, substituted or unsubstituted aryl, substituted or unsubstituted heteroaryl, or substituted or unsubstituted heterocyclic; R is hydrogen, halogen, OH, substituted or unsubstituted alkoxy, alkylthio, alkylamino, —O— aryl, —O-heteroaryl, or —O-heterocyclic. In one example, R is hydrogen, fluoro, OH, —O-alkyl, —O-substituted alkyl.

In one embodiment, the invention provides oliognucleotides prepared from at least one building block selected from the group consisting of:

| Building Block |
|---|

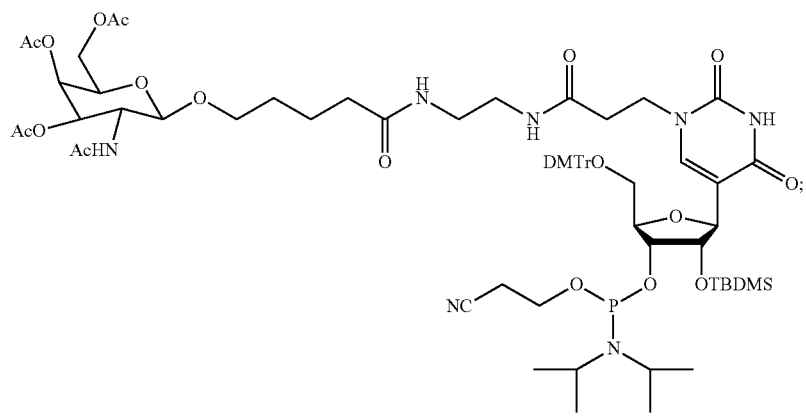

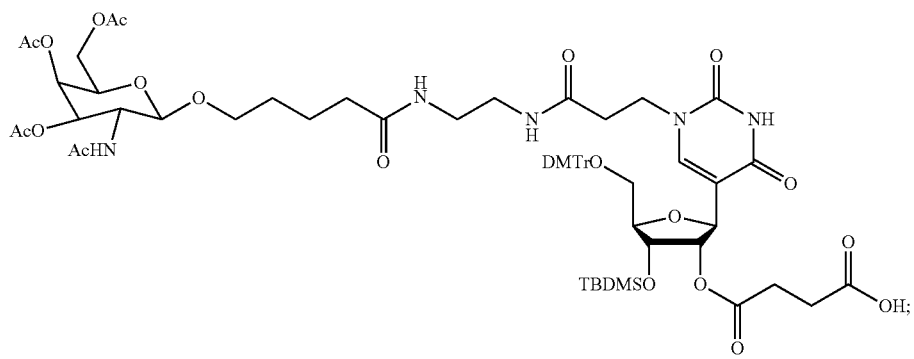

| Building Block |
|---|
| 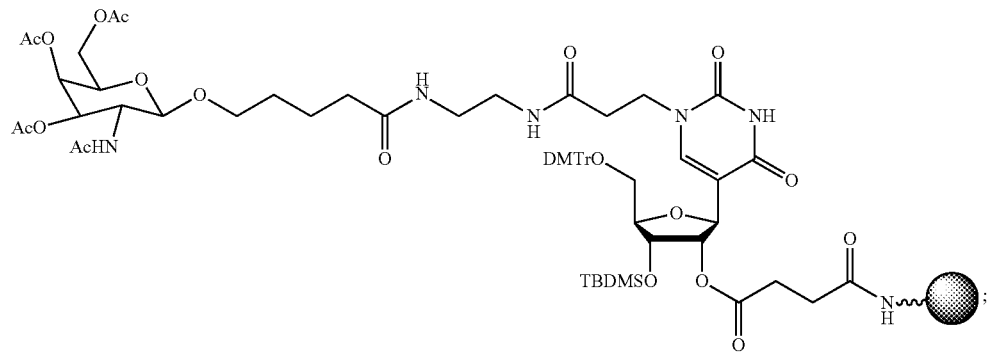 |
| 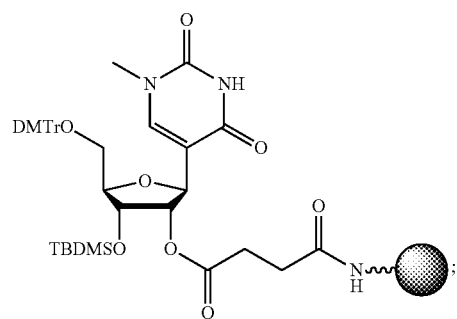 |
| 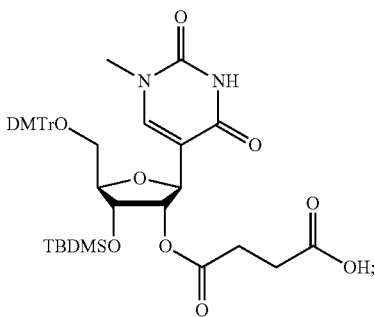 |
| 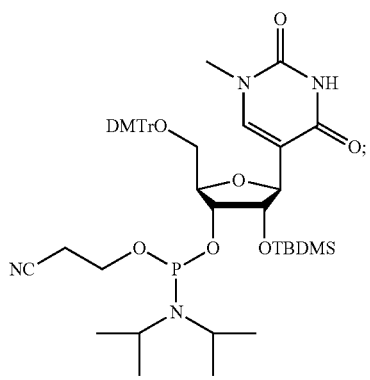 |

| Building Block |
|---|
| 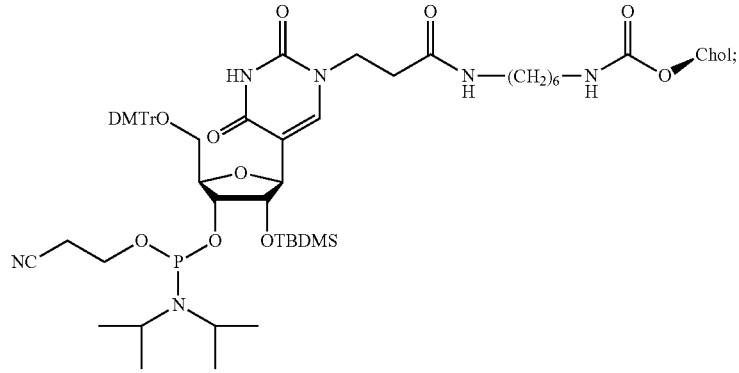 |
| 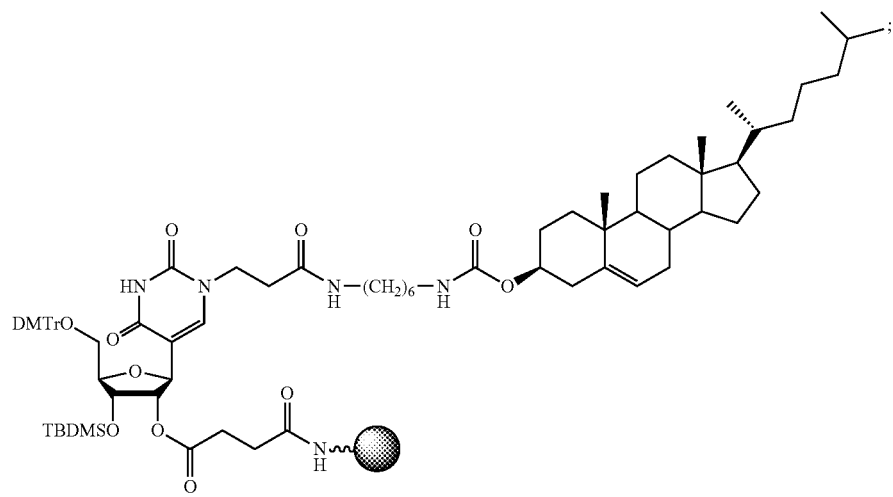 |
| 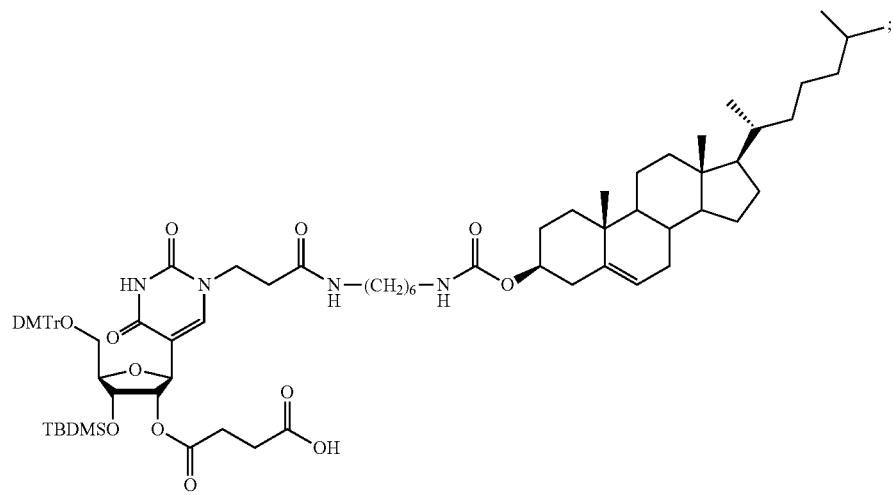 |

| Building Block |
|---|
| 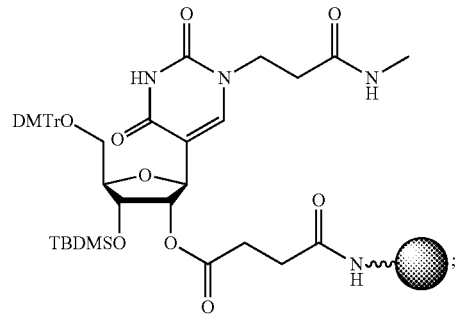 |
| 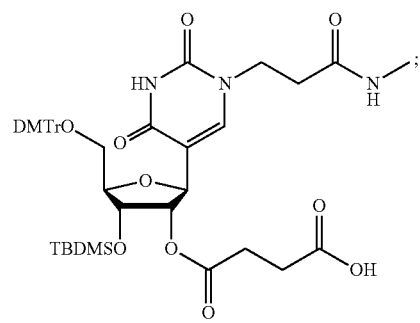 |
| 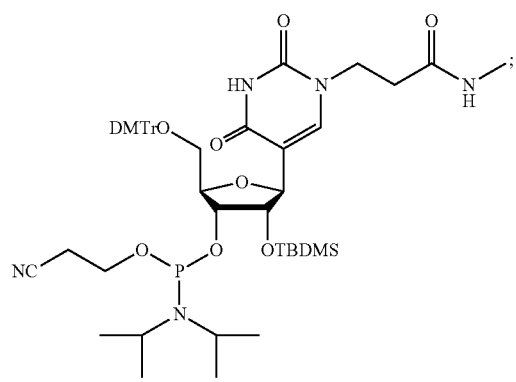 |
| 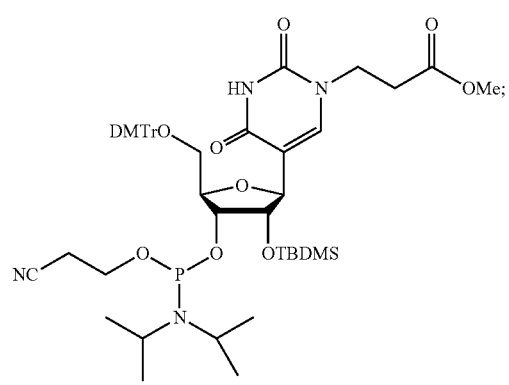 |

| Building Block |
|---|
| 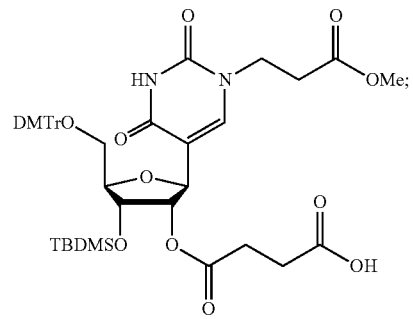 |
| 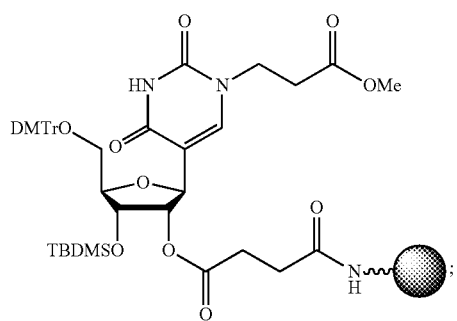 |
| 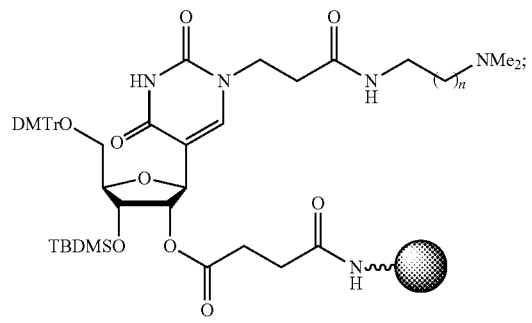<br>n = 1-9 |
| 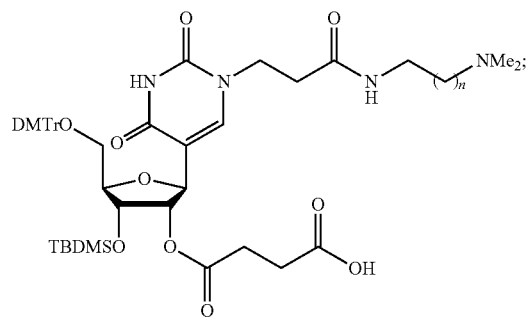<br>n = 1-9 |

| Building Block |
|---|
| 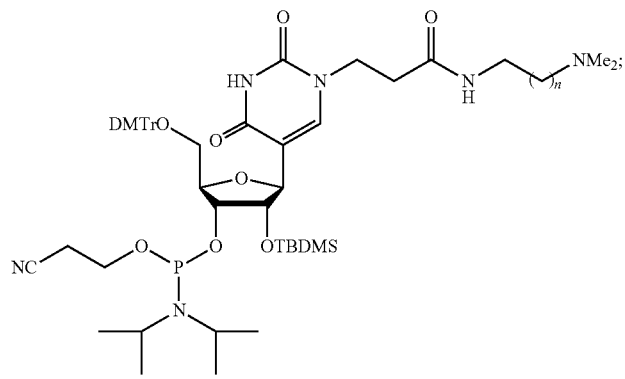
n = 1-9 |
| 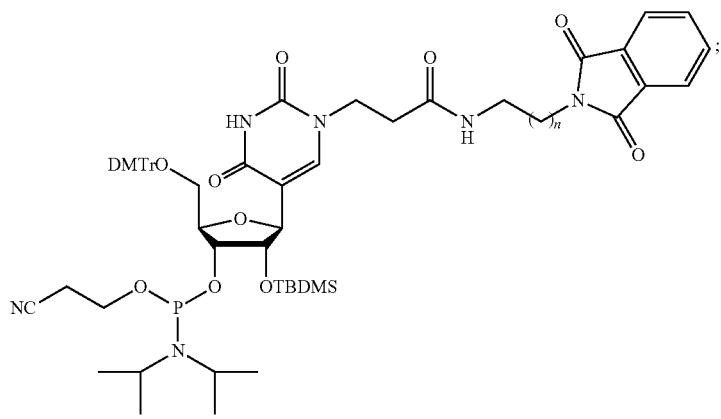
n = 1-9 |
| 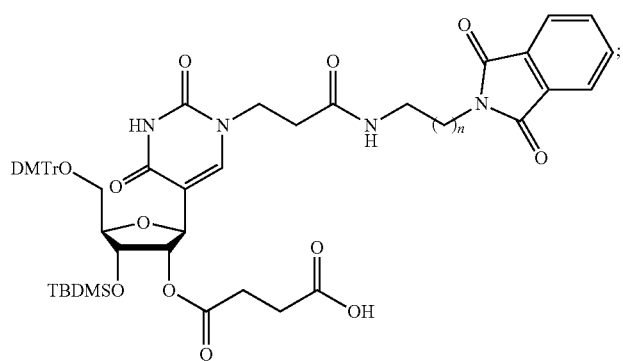
n = 1-9 |

| Building Block |
| --- |
| 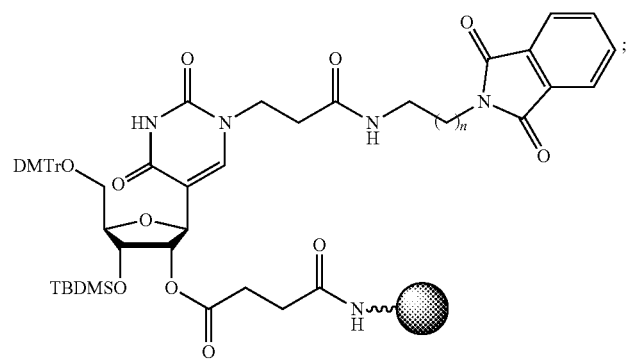
n = 1-9 |
| 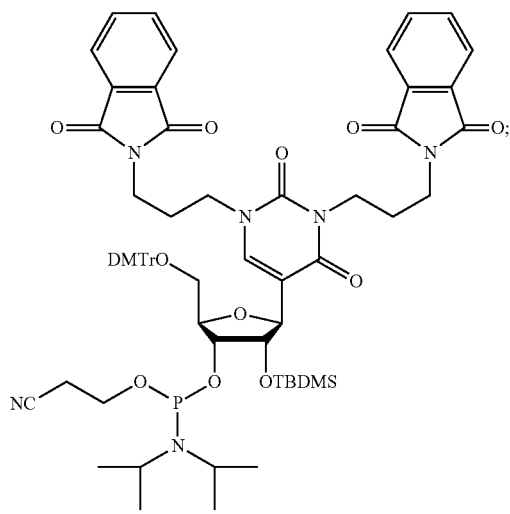 |
| 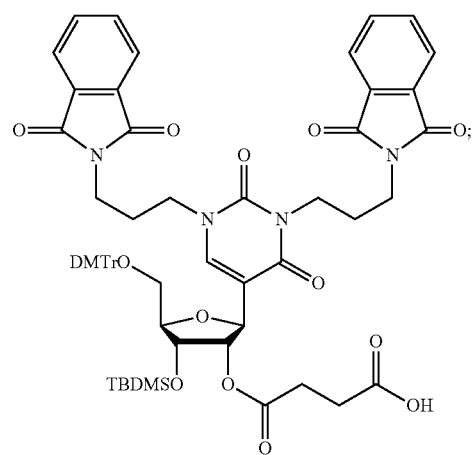 |

| Building Block |
|---|
| 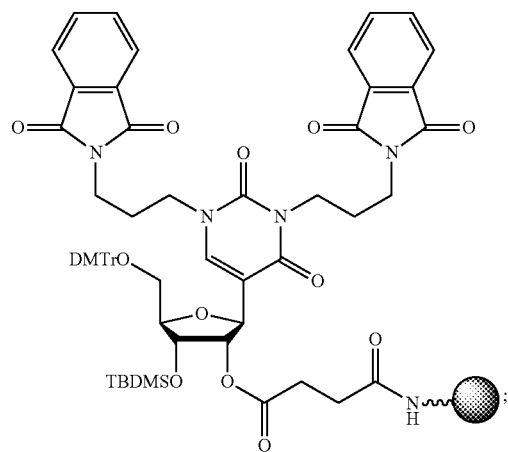 |
| 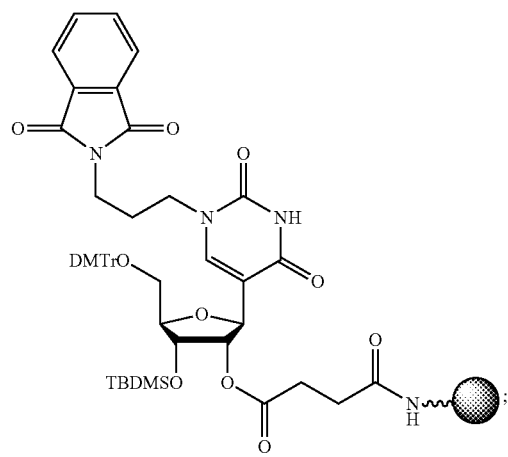 |
| 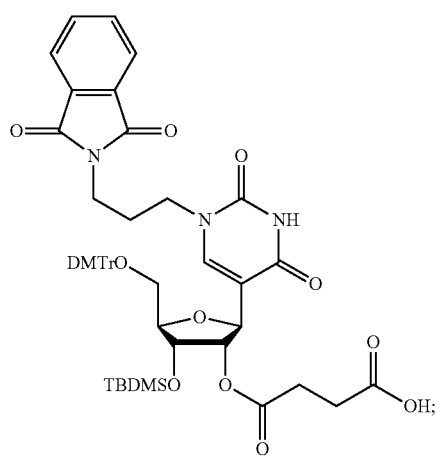 |

| Building Block |
| --- |
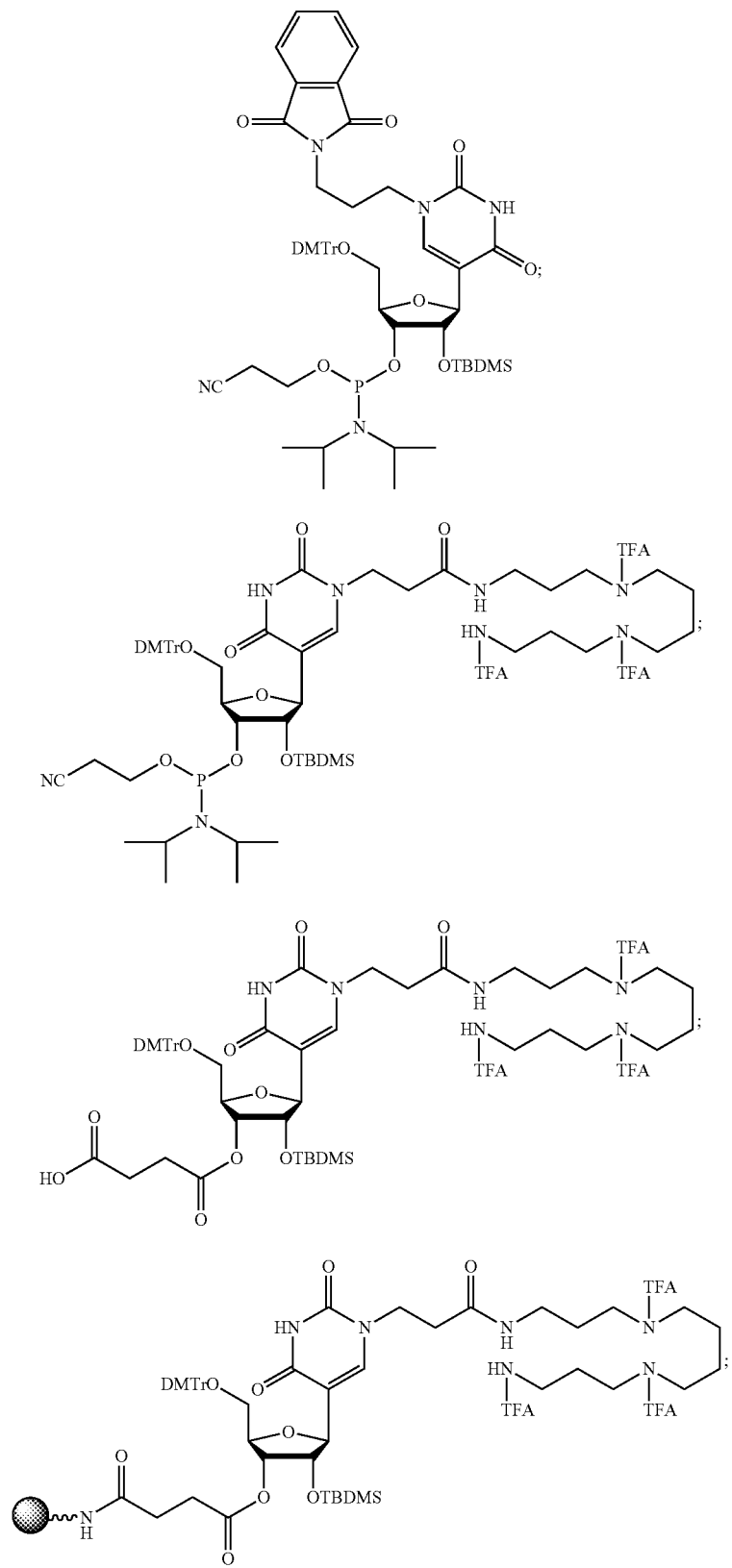

-continued

| Building Block |
|---|
| and combinations thereof; where  is a solid support. |

In one embodiment, oligonucleotides of the invention further comprise at least on 3'-F containing dinucleotide of formula (4):

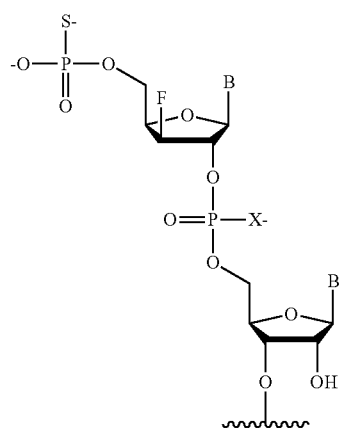

(4)

X = S, O

Nucleosides at the N-1 position have a 5'-phosphorothioate, or a 2'-5'-linkage between N1 and N2, with or without a 3'-F substitution. The synthesis of 3'-F amidites has been described recently. (Gunjal A D et al. Nucleic Acids Symposium series 52, 191-192, 2008).

In one embodiment, oligonucleotides of the invention further comprise a 3' exonuclease protection moiety prepared from the compound of formula (5) or (6):

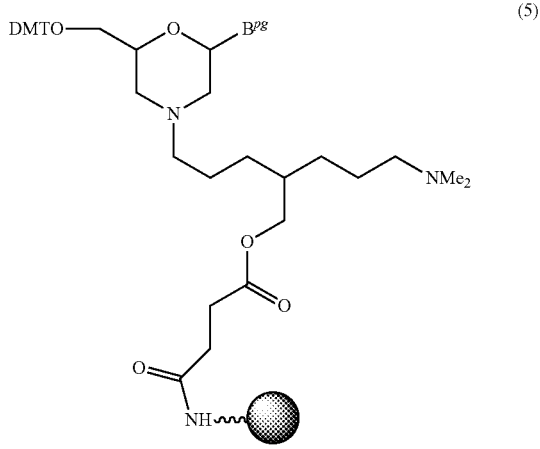

(5)

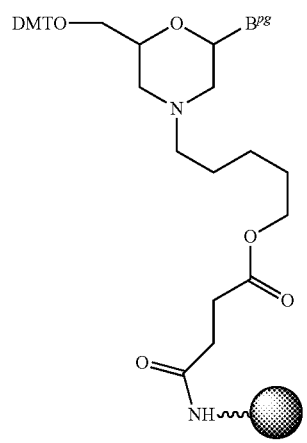

(6)

where $B^{pg}$ is hydrogen, an optionally protected natural nucleobase, an optionally protected modified nucleobase, and a universal base; and

is a solid support.

In one embodiment, oligonucleotides of the invention further comprise at least one nucleoside prepared from the monomer of formula (7), having one of the R groups listed below:

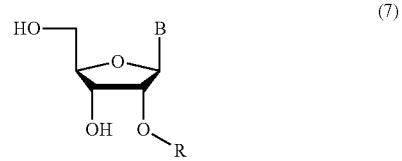

(7)

R

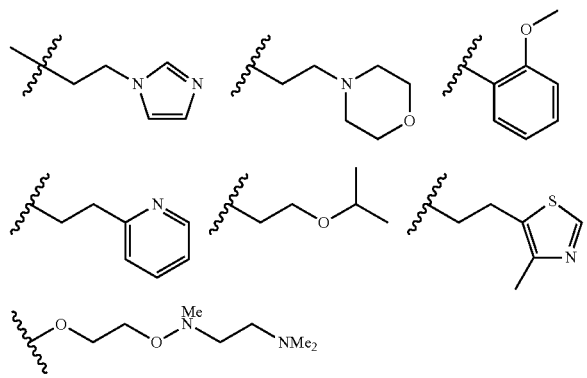

(DMAEM)AOE

In one embodiment, the oligonucleotides of the invention comprise at least one motif of formula (8). In one example the motif is present at the 3' end, 5' end, internucleotide or combinations thereof:

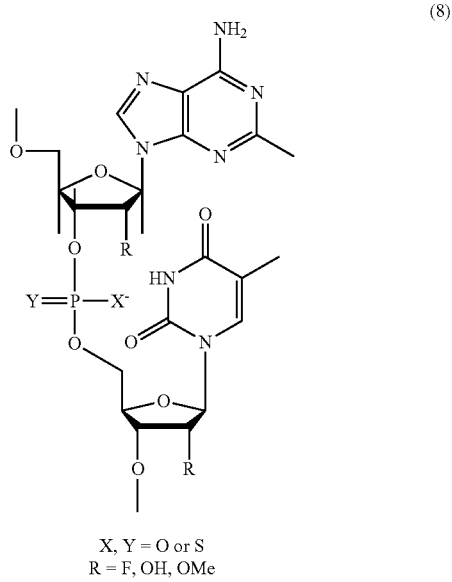

X, Y = O or S
R = F, OH, OMe

In one embodiment, the oligonucleotides of the invention comprise internucleoside linkages selected from phosphorus and non-phosphorus containing internucleoside. In one example, the phosphorus containing internucleoside includes, but not limited to, phosphodiester, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity where one or more internucleotide linkages is a 3' to 3', 5' to 5' or 2' to 2' linkage. Oligonucleotides having inverted polarity can comprise a single 3' to 3' linkage at the 3'-most inter-nucleotide linkage i.e. a single inverted nucleoside residue which may be abasic (the nucleobase is missing or has a hydroxyl group in place thereof). Various salts, mixed salts and free acid forms are also included. Representative U.S. patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, each of which is herein incorporated by reference.

In one embodiment, oligonucleotides of the invention comprise one or more internucleoside linkages that don't contain a phosphorus atom. Such oligonucleotides include, but are not limited to, those that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Representative U.S. patents that teach the preparation of the above non-phosphorus containing internucleoside linking group include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, each of which is herein incorporated by reference.

In one embodiment, oligonucleotides of the invention comprise one or more neutral internucleoside linkages that are non-ionic. Suitable neutral internucleoside linkages include, but are not limited to, phosphotriesters, methylphosphonates, MMI (3'-$CH_2$—N($CH_3$)—O-5'), amide-3 (3'-$CH_2$—C(=O)—N(H)-5'), amide-4 (3'-$CH_2$—N(H)—C(=O)-5'), formacetal (3'-O-$CH_2$—O-5'), and thioformacetal (3'-S—$CH_2$—O-5'); nonionic linkages containing siloxane (dialkylsiloxane), carboxylate ester, carboxamide, sulfide, sulfonate ester and/or amides (See for example: Carbohydrate Modifications in Antisense Research; Y. S. Sanghvi and P. D. Cook Eds. ACS Symposium Series 580; Chapters 3 and 4, (pp. 40-65)); and nonionic linkages containing mixed N, O, S and $CH_2$ component parts.

In one embodiment, the non-phosphodiester backbone linkage is selected from the group consisting of phosphorothioate, phosphorodithioate, alkyl-phosphonate and phosphoramidate backbone linkages.

In one aspect, the present invention provides an oligonucleotide comprising at least one modified nucleoside of formula (2), (4), (6), (8) or (10), optionally in combination with natural base and derivatives thereof, or modified nucleobase. The modified base preferably includes a high affinity modification, such as G-clamp and its analogs; phenoxazines and their analogs; and bi- and tricyclic non-natural nucleoside bases. The invention further provides modified oligonucleotides with 3', 5' or both 3' and 5' terminal phosphate or phosphate mimics. The phosphate or phosphate mimics includes α- and/or β-configuration with respect to the sugar ring or combinations thereof. The phosphate or phosphate mimics include but not limited to: natural phosphate, phosphorothioate, phosphorodithioate, borano phosphate, borano thiophospahte, phosphonate, halogen substituted phosphoantes, phosphoramidates, phosphodiester, phosphotriester, thiophosphodiester, thiophosphotriester, diphosphates and triphosphates. The invention also provides sugar-modified purine dimers at 3' and 5'-terminals (i.e. 5'/3'-GG, AA, AG, GA, GI, IA etc.), where the purine bases are natural or chemically modified, preferably at the 2, 6, 7, and 8 positions; $N^2$ and $N^6$ exocyclic amine positions of the base, or combinations thereof. The nucleoside at position 1 (5'-end) may contain a 2' and/or 4'-sugar modified natural and modified nucleobase, purine or pyrimidine nucleobase mimics or combinations thereof. The modified oligonucleotides may be single-stranded siRNA, double-stranded siRNA, microRNA, anti-microRNA, supermir, aptamer immunostimulatory, U1 adaptor, RNA activator or an antisense oligonucleotide containing a motif selected from the modifications described herein and combinations of modifications thereof. The modified oligonucleotide may be one of the strands or constitute for both strands of a double-stranded siRNA. In one occurrence, the modified oligonucleotide is the guide or antisense strand, and in another occurrence the modified oligonucleotide is sense or passenger strand of the double-stranded siRNA; or both the strands of ds siRNA bear modified oligoncleotides.

In one embodiment, the oligonucleotide comprises at least one ligand conjugate.

In one embodiment, the oligonucleotide comprises two or more ligand conjugates.

In one embodiment, the oligonucleotide is a double-stranded oligonucleotide.

In one embodiment, only one strand comprises the modified nucleoside.

In one embodiment, both strands comprise the modified nucleoside.

In one embodiment, the modified nucleoside is the same in the two strands.

In one embodiment, the modified nucleoside is different in the two strands.

In one embodiment, the oligonucleotide is a single-stranded oligonucleotide.

In one embodiment, the oligonucleotide has a hairpin structure.

In one embodiment, the oligonucleotide is an RNAi agent, an antisense, an antagomir, a microRNA, a pre-microRNA, an antimir, a ribozyme, RNA activator, U1 adaptor, immune stimulatory or an aptamer oligonucleotide.

In one embodiment, the RNAi agent is single stranded.

In one embodiment, the RNAi agent is double stranded and only the sense strand comprises the modified nucleoside.

In one embodiment, the RNAi agent is double stranded and only the antisense strand comprises the modified nucleoside.

In one embodiment, the RNAi agent is double-stranded and both the sense and the antisness strands comprise at least one modified nucleoside.

In one embodiment, the modified nucleoside is the same in both the sense and the antisness strands.

In one embodiment, the sense and the antisense strands comprise different modified nucleosides.

The nucleoside and oligonucleotides described herein contain one or more asymmetric centers and thus give rise to enantiomers, diastereomers, and other stereoisomeric forms that may be defined, in terms of absolute stereochemistry, as (R)- or (S)-, α or β, or as (D)- or (L)- such as for amino acids. Included herein are all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., Enantiomers, Racemates, and Resolutions (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion. In general, the term "oligomeric compound" refers to a contiguous sequence of linked monomelic subunits. In general each linked monomelic subunits is directly or indirectly attached to a heterocyclic base moiety but abasic sites are also possible. At least some and generally most if not essentially all of the heterocyclic bases in an oligomeric compound are capable of hybridizing to a nucleic acid molecule, normally a preselected RNA target. The term "oligomeric compound" therefore includes oligonucleotides, oligonucleotide analogs and oligonucleosides. It also includes polymers having a plurality of non-naturally occurring nucleoside mimetics and or nucleosides having sugar surrogate groups.

Oligonucleotides

In the context of this invention, the term "oligonucleotide" refers to a polymer or oligomer of nucleotide or nucleoside monomers consisting of naturally occurring bases, sugars and intersugar (backbone) linkages. The term "oligonucleotide" also includes polymers or oligomers comprising non-naturally occurring monomers, or portions thereof, which function similarly. Such modified or substituted oligonucleotides are often preferred over native forms because of properties such as, for example, enhanced cellular uptake and increased stability in the presence of nucleases.

The nucleic acids used herein can be single-stranded or double-stranded. A single stranded oligonucleotide may have double stranded regions and a double stranded oligonucleotide may have regions of single-stranded regions. Examples of double-stranded DNA include structural genes, genes including control and termination regions, and self-replicating systems such as viral or plasmid DNA. Examples of double-stranded RNA include siRNA and other RNA interference reagents. Single-stranded nucleic acids include, e.g., antisense oligonucleotides, ribozymes, microRNAs, aptamers, antagomirs, triplex-forming oligonucleotides and single-stranded RNAi agents.

Oligonucleotides of the present invention may be of various lengths. In particular embodiments, oligonucleotides may range from about 10 to 100 nucleotides in length. In various related embodiments, oligonucleotides, single-stranded, double-stranded, and triple-stranded, may range in length from about 10 to about 50 nucleotides, from about 20 to about 50 nucleotides, from about 15 to about 30 nucleotides, from about 20 to about 30 nucleotides in length.

The oligonucleotides of the invention may comprise any oligonucleotide modification described herein and below. In certain instances, it may be desirable to modify one or both strands of a dsRNA. In some cases, the two strands will include different modifications. Multiple different modifications can be included on each of the strands. The modifications on a given strand may differ from each other, and may also differ from the various modifications on other strands. For example, one strand may have a modification, e.g., a modification described herein, and a different strand may have a different modification, e.g., a different modification described herein. In other cases, one strand may have two or more different modifications, and the another strand may include a modification that differs from the at least two modifications on the other strand.

In one embodiment, oligonucleotides of the invention comprises 5' phosphorothioate or 5'-phosphorodithioate, nucleotides 1 and 2 having cationic modifications via C-5 position of pyrimidines, 2-Position of Purines, N2-G, G-clamp, 8-position of purines, 6-position of purines, internal nucleotides having a 2'-F sugar with base modifications (Pseudouridine, G-clamp, phenoxazine, pyridopyrimidines, gem2'-Me-up/2'-F-down), 3'-end with two purines with novel 2'-substituted MOE analogs, 5'-end nucleotides with novel 2'-substituted MOE analogs, 5'-end having a 3'-F and a 2'-5'-linkage, 4'-substituted nucleoside at the nucleotide 1 at 5'-end and the substituent is cationic, alkyl, alkoxyalkyl, thioether and the like, 4'-substitution at the 3'-end of the strand, and combinations thereof.

Double-Stranded Oligonucleotides

In one embodiment, the invention provides double-stranded ribonucleic acid (dsRNA) molecules for inhibiting the expression of the target gene (alone or in combination with a second dsRNA for inhibiting the expression of a second target gene) in a cell or mammal, where the dsRNA comprises an antisense strand comprising a region of complementarity which is complementary to at least a part of an mRNA formed in the expression of the target gene, and where the region of complementarity is less than 30 nucleotides in length, generally 19-24 nucleotides in length, and where the dsRNA, upon contact with a cell expressing the target gene, inhibits the expression of the target gene. The dsRNA comprises two RNA strands that are sufficiently complementary to hybridize to form a duplex structure. Generally, the duplex structure is between 15 and 30, more generally between 18 and 25, yet more generally between 19 and 24, and most generally between 19 and 21 base pairs in length. In one embodiment, longer dsRNAs of between 25 and 30 base pairs in length are preferred. In one embodiment, shorter dsRNAs of between 10 and 15 base pairs in length are preferred. In another embodiment, the dsRNA is at least 21 nucleotides long and includes a sense RNA strand and an antisense RNA strand, where the antisense RNA strand is 25 or fewer nucleotides in length, and the duplex region of the dsRNA is 18-25 nucleotides in length, e.g., 19-24 nucleotides in length.

In certain embodiments, the double-stranded region of a double-stranded oligonucleotide is equal to or at least, 10, 11, 12, 13, 14, 15, 16, 17, 18, 19, 20, 21, 22, 23, 23, 24, 25, 26, 27, 28, 29, or 30 nucleotide pairs in length.

In certain embodiments, the antisense strand of a double-stranded oligonucleotide is equal to or at least 14, 15, 16, 17, 18, 19, 20, 21, 22, 23, 23, 24, 25, 26, 27, 28, 29, or 30 nucleotides in length.

In certain embodiments, the sense strand of a double-stranded oligonucleotide is equal to or at least 10, 11, 12, 13, 14, 15, 16, 17, 18, 19, 20, 21, 22, 23, 23, 24, 25, 26, 27, 28, 29, or 30 nucleotides in length.

Similarly, the region of complementarity to the target sequence is between 15 and 30, more generally between 18 and 25, yet more generally between 19 and 24, and most generally between 19 and 21 nucleotides in length. The dsRNA of the invention may further comprise one or more single-stranded nucleotide overhang(s).

In a preferred embodiment, the target gene is a human target gene. In one embodiment, the target gene is selected from the group consisting of Factor VII, Eg5, PCSK9, TPX2, apoB, SAA, TTR, RSV, PDGF beta gene, Erb-B gene, Src gene, CRK gene, GRB2 gene, RAS gene, MEKK gene, JNK gene, RAF gene, Erk1/2 gene, PCNA(p21) gene, MYB gene, JUN gene, FOS gene, BCL-2 gene, Cyclin D gene, VEGF gene, EGFR gene, Cyclin A gene, Cyclin E gene, WNT-1 gene, beta-catenin gene, c-MET gene, PKC gene, NFKB gene, STAT3 gene, survivin gene, Her2/Neu gene, topoisomerase I gene, topoisomerase II alpha gene, p73 gene, p21(WAF1/CIP1) gene, p27(KIP1) gene, PPM1D gene, RAS gene, caveolin I gene, MIB I gene, MTAI gene, M68 gene, mutations in tumor suppressor genes, p53 tumor suppressor gene, and combinations thereof.

The skilled person is well aware that dsRNAs comprising a duplex structure of between 20 and 23, but specifically 21, base pairs have been hailed as particularly effective in inducing RNA interference (Elbashir et al., EMBO 2001, 20:6877-6888). However, others have found that shorter or longer dsRNAs can be effective as well. In the embodiments described above the dsRNAs of the invention can comprise at least one strand of a length of minimally 21 nt. It can be reasonably expected that shorter dsRNAs comprising a known sequence minus only a few nucleotides on one or both ends may be similarly effective as compared to the dsRNAs of the lengths described above. Hence, dsRNAs comprising a partial sequence of at least 15, 16, 17, 18, 19, 20, or more contiguous nucleotides, and differing in their ability to inhibit the expression of the target gene by not more than 5, 10, 15, 20, 25, or 30% inhibition from a dsRNA comprising the full sequence, are contemplated by the invention. Further dsRNAs that cleave within the target sequence can readily be made using the target gene sequence and the target sequence provided.

Double-stranded and single-stranded oligonucleotides that are effective in inducing RNA interference are also referred to as siRNA, RNAi agent and/or iRNA agent. These RNA interference inducing oligonucleotides associate with a cytoplasmic multi-protein complex known as RNAi-induced silencing complex (RISC). In certain embodiments, single-stranded and double stranded RNAi agents are sufficiently long that they can be cleaved by an endogenous molecule, e.g. by Dicer, to produce smaller oligonucleotides that can enter the RISC machinery and participate in RISC mediated cleavage of a target sequence, e.g. a target mRNA.

The present invention further includes RNAi agents that target within the sequence targeted by one of the agents of the present invention. As used herein a second RNAi agent is said to target within the sequence of a first RNAi agent if the second RNAi agent cleaves the message anywhere within the mRNA that is complementary to the antisense strand of the first RNAi agent. Such a second agent will generally consist of at least 15 contiguous nucleotides coupled to additional nucleotide sequences taken from the region contiguous to the selected sequence in the target gene.

The dsRNA of the invention may contain one or more mismatches to the target sequence. In a preferred embodiment, the dsRNA of the invention contains no more than 3 mismatches. If the antisense strand of the dsRNA contains mismatches to a target sequence, it is preferable that the area of mismatch not be located in the center of the region of complementarity. If the antisense strand of the dsRNA contains mismatches to the target sequence, it is preferable that the mismatch be restricted to 5 nucleotides from either end, for example 5, 4, 3, 2, or 1 nucleotide from either the 5' or 3' end of the region of complementarity. For example, for a 23 nucleotide dsRNA strand which is complementary to a region of the target gene, the dsRNA generally does not contain any mismatch within the central 13 nucleotides. The methods described within the invention can be used to determine whether a dsRNA containing a mismatch to a target sequence is effective in inhibiting the expression of the target gene. Consideration of the efficacy of dsRNAs with mismatches in inhibiting expression of the target gene is important, especially if the particular region of complementarity in the target gene is known to have polymorphic sequence variation within the population.

In certain embodiments, the sense-strand comprises a mismatch to the antisense strand. In certain embodiments, the mismatch is within 5 nucleotides from the end of the double stranded region, for example at positions 5, 4, 3, 2, or 1 from the end of the duplex region. Preferably, the mismatch is within 5 nucleotides from the end of the duplex corresponding to the 3'-end of the sense strand. In some embodiments, the mismatch is located in the target cleavage site region. In one embodiment, the sense strand comprises no more than 1, 2, 3, 4 or 5 mismatches to the antisense strand. In preferred embodiments, the sense strand comprises no more than 3 mismatches to the antisense strand.

In one embodiment, the sense strand comprises a nucleobase modification, e.g. an optionally substituted natural or non-natural nucleobase, a universal nucleobase, in the target cleavage site region.

In certain embodiments, the sense strand comprises an abasic nucleotide in the target cleavage site region.

The "target cleavage site" herein means the backbone linkage in the target gene, e.g. target mRNA, or the sense strand that is cleaved by the RISC mechanism by utilizing the iRNA agent. And the "target cleavage site region" comprises at least one or at least two nucleotides on both side of the cleavage site. For the sense strand, the target cleavage site is the backbone linkage in the sense strand that would get cleaved if the sense strand itself was the target to be cleaved by the RNAi mechanism. The target cleavage site can be determined using methods known in the art, for example the 5'-RACE assay as detailed in Soutschek et al., Nature (2004) 432, 173-178. As is well understood in the art, the cleavage site region for a conical double stranded RNAi agent comprising two 21-nucleotides long strands (wherein the strands form a double stranded region of 19 consecutive basepairs having 2-nucleotide single stranded overhangs at the 3'-ends), the cleavage site region corresponds to positions 9-12 from the 5'-end of the sense strand.

In one embodiment, at least one end of the dsRNA has a single-stranded nucleotide overhang of 1 to 4, generally 1 or 2 nucleotides. In certain embodiments, both ends of the double-stranded region have a single-stranded nucleotide overhang of 1 to 4, generally 1 or 2 nucleotides. As used herein, the term "overhang" refers to a double-stranded structure where at least one end of one strand is longer than the corresponding end of the other strand forming the double-stranded structure.

In some embodiments it is particularly preferred, e.g., to enhance stability, to include particular nucleobases in the single-stranded overhangs, or to include modified nucleotides or nucleotide surrogates, in single-strand overhangs. For example, it can be desirable to include purine nucleotides in overhangs. In some embodiments all or some of the bases in the single strand overhang will be modified, e.g., with a modification described herein. Modifications in the single-stranded overhangs can include any oligonucleotide modification described herein and below, e.g., the use of sugars with modifications at the 2' position, e.g., the use of deoxyribonucleotides, e.g., deoxythymidine, instead of ribonucleotides, and modifications in the phosphate group, e.g., phosphothioate modifications. Overhangs need not be homologous with the target sequence. In certain embodiments, the single strand overhangs are asymmetrically modified with a modification described herein, e.g. a first single-stand overhang comprises a modification that is not present in a second single-strand overhang.

In certain embodiments, the unpaired nucleotide adjacent to the terminal nucleotide base pair on the end of the double-stranded region is a purine.

In one embodiment, the single-stranded overhang has the sequence 5'-GCNN-3', where N is independently for each occurrence, A, G, C, U, dT, dU or absent. In certain embodiments, the single-stranded overhang has the sequence 5'-NN-3', wherein N is independently for each occurrence a modified or unmodified nucleotide described herein and below. dsRNAs having at least one nucleotide overhang have unexpectedly superior inhibitory properties than their blunt-ended counterparts. Without wishing to be bound by theory, presence of only one nucleotide overhang strengthens the interference activity of the dsRNA, without affecting its overall stability. dsRNA having only one overhang has proven particularly stable and effective in vivo, as well as in a variety of cells, cell culture mediums, blood, and serum. Generally, the single-stranded overhang is located at the 3'-terminal end of the antisense strand or, alternatively, at the 3'-terminal end of the sense strand. The dsRNA may also have a blunt end, generally located at the 5'-end of the antisense strand. Generally, the antisense strand of the dsRNA has a nucleotide overhang at the 3'-end, and the 5'-end is blunt.

In one embodiment, the antisense strand of the dsRNA has 1-10 nucleotides overhangs each at the 3' end and the 5' end over the sense strand. In one embodiment, the sense strand of the dsRNA has 1-10 nucleotides overhangs each at the 3' end and the 5' end over the antisense strand.

In certain embodiments, one strand has at least one stretch of 1-5 single-stranded nucleotides in the double-stranded region. In certain other embodiments, both strands have at least one stretch of 1-5 single-stranded nucleotides in the double stranded region. When both strands have a stretch of 1-5 single-stranded nucleotides in the double stranded region, such single-stranded nucleotides may be opposite to each other or they can be located such that the second strand has no single-stranded nucleotides opposite to the single-stranded oligonucleotides of the first strand and vice versa.

In certain embodiments, at least one strand of the double-stranded oligonucleotide has a ZXY structure, such as is described in PCT Application No. PCT/US2004/07070 filed on Mar. 8, 2004, contents of which are hereby incorporated in their entireties.

The dsRNAs of the invention may comprise any oligonucleotide modification described herein and below. In certain instances, it may be desirable to modify one or both strands of a dsRNA. In some cases, the two strands will include different modifications. Multiple different modifications can be included on each of the strands. The modifications on a given strand may differ from each other, and may also differ from the various modifications on other strands. For example, one strand may have a modification, e.g., a modification described herein, and a different strand may have a different modification, e.g., a different modification described herein. In other cases, one strand may have two or more different modifications, and the another strand may include a modification that differs from the at least two modifications on the other strand.

In one embodiment, the dsRNA is chemically modified to enhance stability. In one preferred embodiment, one or more of the nucleotides in the overhang is replaced with a nucleoside thiophosphate.

The present invention also includes dsRNA compounds which are chimeric compounds. "Chimeric" dsRNA compounds or "chimeras," in the context of this invention, are dsRNA compounds, particularly dsRNAs, which contain two or more chemically distinct regions, each made up of at least one monomer unit, i.e., a nucleotide in the case of an dsRNA compound. These dsRNAs typically contain at least one region where the dsRNA is modified so as to confer upon the dsRNA increased resistance to nuclease degradation, increased cellular uptake, and/or increased binding affinity for the target nucleic acid. An additional region of the dsRNA may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of dsRNA inhibition of gene expression.

The present invention also includes dsRNAs where the two strands are linked together. The two strands can be linked to each other at both ends, or at one end only. When the two strands are linked to each other at both ends, 5'-end of one strand is linked to the 3'-end of the second strand and vice versa. The two strands can be linked together by a polynucleotide linker such as $(dT)_n$; where n is 4-10 (SEQ ID NO: 1). When the two strands are linked to each other through a polynucleotide linker at one end only, the oligonucleotide forms a hairpin. The two strands can also be linked together by a non-nucleosidic linker, e.g. a linker described herein. It will be appreciated by one of skill in the art that any oligonucleotide chemical modifications or variations describe herein can be used in the polynucleotide linker.

Hairpin RNAi agents will have a duplex region equal to or at least 16, 17, 18, 19, 29, 21, 22, 23, 24, or 25 nucleotide pairs. The duplex region will may be equal to or less than 200, 100, or 50, in length. In one embodiment, ranges for the duplex region are 15-30, 17 to 23, 19 to 23, and 19 to 21 nucleotides pairs in length. The hairpin may have a single strand overhang or terminal unpaired region, in some embodiments at the 3', and in one embodiment on the antisense side of the hairpin. In one embodiment, the overhangs are 1-4 and more preferably 2-3 nucleotides in length.

The RNAi agents of the invention can target more than one RNA region. For example, an RNAi agent can include a first and second sequence that are sufficiently complementary to each other to hybridize. The first sequence can be complementary to a first target RNA region and the second sequence can be complementary to a second target RNA region. The first and second sequences of the RNAi agent can be on different RNA strands, and the mismatch between the first and second sequences can be less than 50%, 40%, 30%, 20%, 10%, 5%, or 1%. The first and second sequences of the RNAi agent can be on the same RNA strand, and in a related embodiment more than 50%, 60%, 70%, 80%, 90%, 95%, or 1% of the RNAi agent can be in bimolecular form. The first and second sequences of the RNAi agent can be fully complementary to each other.

RNAi agents of the invention can be used to target two or more RNA regions where the RNA regions differ from each other at 1, 2, 3, 4 or 5 positions. As used in this context, the phrase "differ from each other" refers to the RNA regions having different nucleotides at that position. In these cases the RNAi agent strand that is complementary to the RNA region to be targeted comprises universal nucleobases at positions complementary to where the RNA regions are different from each other. For example, the antisense strand of the double-stranded RNAi agent comprises universal nucleobases at positions complementary to where the RNA regions to be targeted do not match each other.

As used herein, a universal nucleobase is any modified, unmodified, naturally occurring or non-naturally occurring nucleobase that can base pair with all of the four naturally occurring nucleobases without substantially affecting the melting behavior, recognition by intracellular enzymes or activity of the oligonucleotide duplex. Some exemplary universal nucleobases include, but are not limited to, 2,4-difluorotoluene, nitropyrrolyl, nitroindolyl, 8-aza-7-deazaadenine, 4-fluoro-6-methylbenzimidazle, 4-methylbenzimidazle, 3-methyl isocarbostyrilyl, 5-methyl isocarbostyrilyl, 3-methyl-7-propynyl isocarbostyrilyl, 7-azaindolyl, 6-methyl-7-azaindolyl, imidizopyridinyl, 9-methyl-imidizopyridinyl, pyrrolopyrizinyl, isocarbostyrilyl, 7-propynyl isocarbostyrilyl, propynyl-7-azaindolyl, 2,4,5-trimethylphenyl, 4-methylinolyl, 4,6-dimethylindolyl, phenyl, napthalenyl, anthracenyl, phenanthracenyl, pyrenyl, stilbenzyl, tetracenyl, pentacenyl, and structural derivatives thereof.

The first target RNA region can be encoded by a first gene and the second target RNA region can encoded by a second gene, or the first and second target RNA regions can be different regions of an RNA from a single gene. The first and second sequences can differ by at least 1 nucleotide.

The first and second target RNA regions can be on transcripts encoded by first and second sequence variants, e.g., first and second alleles, of a gene. The sequence variants can be mutations, or polymorphisms, for example. The first target RNA region can include a nucleotide substitution, insertion, or deletion relative to the second target RNA region, or the second target RNA region can be a mutant or variant of the first target region.

The first and second target RNA regions can comprise viral or human RNA regions. The first and second target RNA regions can also be on variant transcripts of an oncogene or include different mutations of a tumor suppressor gene transcript. In addition, the first and second target RNA regions can correspond to hot-spots for genetic variation.

The double stranded oligonucleotides can be optimized for RNA interference by increasing the propensity of the duplex to disassociate or melt (decreasing the free energy of duplex association), in the region of the 5' end of the antisense strand This can be accomplished, e.g., by the inclusion of modifications or modified nucleosides which increase the propensity of the duplex to disassociate or melt in the region of the 5' end of the antisense strand. It can also be accomplished by inclusion of modifications or modified nucleosides or attachment of a ligand that increases the propensity of the duplex to disassociate of melt in the region of the 5' end of the antisense strand. While not wishing to be bound by theory, the effect may be due to promoting the effect of an enzyme such as helicase, for example, promoting the effect of the enzyme in the proximity of the 5' end of the antisense strand.

Modifications which increase the tendency of the 5' end of the antisense strand in the duplex to dissociate can be used alone or in combination with other modifications described herein, e.g., with modifications which decrease the tendency of the 3' end of the antisense in the duplex to dissociate. Likewise, modifications which decrease the tendency of the 3' end of the antisense in the duplex to dissociate can be used alone or in combination with other modifications described herein, e.g., with modifications which increase the tendency of the 5' end of the antisense in the duplex to dissociate.

Nucleic acid base pairs can be ranked on the basis of their propensity to promote dissociation or melting (e.g., on the free energy of association or dissociation of a particular pairing, the simplest approach is to examine the pairs on an individual pair basis, though next neighbor or similar analysis can also be used). In terms of promoting dissociation: A:U is preferred over G:C; G:U is preferred over G:C; I:C is preferred over G:C (I=inosine); mismatches, e.g., non-canonical or other than canonical pairings are preferred over canonical (A:T, A:U, G:C) pairings; pairings which include a universal base are preferred over canonical pairings.

It is preferred that pairings which decrease the propensity to form a duplex are used at 1 or more of the positions in the duplex at the 5' end of the antisense strand. The terminal pair (the most 5' pair in terms of the antisense strand), and the subsequent 4 base pairing positions (going in the 3' direction in terms of the antisense strand) in the duplex are preferred for placement of modifications to decrease the propensity to form a duplex. More preferred are placements in the terminal most pair and the subsequent 3, 2, or 1 base pairings. It is preferred that at least 1, and more preferably 2, 3, 4, or 5 of the base pairs from the 5'-end of antisense strand in the duplex be chosen independently from the group of: A:U, G:U, I:C, mismatched pairs, e.g., non-canonical or other than canonical pairings or pairings which include a universal base. In a preferred embodiment at least one, at least 2, or at least 3 base-pairs include a universal base.

Modifications or changes which promote dissociation are preferably made in the sense strand, though in some embodiments, such modifications/changes will be made in the antisense strand.

Nucleic acid base pairs can also be ranked on the basis of their propensity to promote stability and inhibit dissociation or melting (e.g., on the free energy of association or dissociation of a particular pairing, the simplest approach is to examine the pairs on an individual pair basis, though next neighbor or similar analysis can also be used). In terms of promoting duplex stability: G:C is preferred over A:U, Watson-Crick matches (A:T, A:U, G:C) are preferred over non-canonical or other than canonical pairings, analogs that increase stability are preferred over Watson-Crick matches (A:T, A:U, G:C), e.g. 2-amino-A:U is preferred over A:U, 2-thio U or 5 Me-thio-U:A, are preferred over U:A, G-clamp (an analog of C having 4 hydrogen bonds):G is preferred over C:G, guanadinium-G-clamp:G is preferred over C:G, psuedo uridine:A, is preferred over U:A, sugar modifications, e.g., 2' modifications, e.g., 2'-O-methyl (2'-OMe), 2'-F, locked nucleic acids, e.g., ENA and LNA, which enhance binding are preferred over non-modified moieties and can be present on one or both strands to enhance stability of the duplex.

It is preferred that pairings which increase the propensity to form a duplex are used at 1 or more of the positions in the duplex at the 3' end of the antisense strand. The terminal pair (the most 3' pair in terms of the antisense strand), and the subsequent 4 base pairing positions (going in the 5' direction in terms of the antisense strand) in the duplex are preferred for placement of modifications to decrease the propensity to form a duplex. More preferred are placements in the terminal most pair and the subsequent 3, 2, or 1 base pairings. It is preferred that at least 1, and more preferably 2, 3, 4, or 5 of the pairs of the recited regions be chosen independently from the group of: G:C, a pair having an analog that increases stability over Watson-Crick matches (A:T, A:U, G:C), 2-amino-A:U, 2-thio U or 5 Me-thio-U:A, G-clamp (an analog of C having 4 hydrogen bonds):G, guanadinium-G-clamp:G, psuedo uridine:A, a pair in which one or both subunits has a sugar modification, e.g., a 2' modification, e.g., 2'-OMe, 2'-F, ENA, or LNA, which enhance binding. In some embodiments, at least one, at least, at least 2, or at least 3, of the base pairs promote duplex stability.

In a preferred embodiment, at least one, at least 2, or at least 3, of the base pairs are a pair in which one or both subunits has a sugar modification, e.g., a 2' modification, e.g., 2'-O-Me (2'-O-methyl), 2'-O-MOE (2'-O-methoxyethyl), 2'-F, 2'-O-[2-(methylamino)-2-oxoethyl] (2'-O-NMA), 2'-S-methyl, 2'-O—CH$_2$-(4'-C) (LNA) and 2'-O—CH$_2$CH$_2$-(4'-C) (ENA), which enhances binding.

G-clamps and guanidinium G-clamps are discussed in the following references: Holmes and Gait, "The Synthesis of 2'-O-Methyl G-Clamp Containing Oligonucleotides and Their Inhibition of the HIV-1 Tat-TAR Interaction," Nucleosides, Nucleotides & Nucleic Acids, 22:1259-1262, 2003; Holmes et al., "Steric inhibition of human immunodeficiency virus type-1 Tat-dependent trans-activation in vitro and in cells by oligonucleotides containing 2'-O-methyl G-clamp ribonucleoside analogues," Nucleic Acids Research, 31:2759-2768, 2003; Wilds, et al., "Structural basis for recognition of guanosine by a synthetic tricyclic cytosine analogue: Guanidinium G-clamp," Helvetica Chimica Acta, 86:966-978, 2003; Rajeev, et al., "High-Affinity Peptide Nucleic Acid Oligomers Containing Tricyclic Cytosine Analogues," Organic Letters, 4:4395-4398, 2002; Ausin, et al., "Synthesis of Amino- and Guanidino-G-Clamp PNA Monomers," Organic Letters, 4:4073-4075, 2002; Maier et al., "Nuclease resistance of oligonucleotides containing the tricyclic cytosine analogues phenoxazine and 9-(2-aminoethoxy)-phenoxazine ("G-clamp") and origins of their nuclease resistance properties," Biochemistry, 41:1323-7, 2002; Flanagan, et al., "A cytosine analog that confers enhanced potency to antisense oligonucleotides," Proceedings Of The National Academy Of Sciences Of The United States Of America, 96:3513-8, 1999.

As is discussed above, an oligonucleotide can be modified to both decrease the stability of the antisense 5' end of the duplex and increase the stability of the antisense 3' end of the duplex. This can be effected by combining one or more of the stability decreasing modifications in the antisense 5' end of the duplex with one or more of the stability increasing modifications in the antisense 3' end of the duplex.

In certain embodiments, the terminal base pair of the double stranded region is a G-C base pair or four consecutive base pairs from the terminal end comprise at least two G-C base pairs. In further embodiments, each terminal end of the double stranded region comprises a G-C base pair at the terminal position or four consecutive base pairs from the terminal end comprise at least two G-C base pairs.

Single-Stranded Oligonucleotides

The single-stranded oligonucleotides of the present invention also comprise nucleotide sequence that is substantially complementary to a "sense" nucleic acid encoding a gene expression product, e.g., complementary to the coding strand of a double-stranded cDNA molecule or complementary to an RNA sequence, e.g., a pre-mRNA, mRNA, miRNA, or pre-miRNA. The region of complementarity is less than 30 nucleotides in length, and at least 15 nucleotides in length. Generally, the single stranded oligonucleotides are 10 to 25 nucleotides in length (e.g., 11, 12, 13, 14, 15, 16, 18, 19, 20, 21, 22, 23, or 24 nucleotides in length). In one embodiment the strand is 25-30 nucleotides. Single strands having less than 100% complementarity to the target mRNA, RNA or DNA are also embraced by the present invention. These single-stranded oligonucleotides are also referred to as antisense, antagomir and antimir oligonucleotides. In certain embodiments, the single-stranded oligonucleotide has a ZXY structure, such as is described in PCT Application No. PCT/US2004/07070, filed on Mar. 8, 2005.

The single-stranded oligonucleotide can hybridize to a complementary RNA, and prevent access of the translation machinery to the target RNA transcript, thereby preventing protein synthesis. The single-stranded oligonucleotide can also hybridize to a complementary RNA and the RNA target can be subsequently cleaved by an enzyme such as RNase H. Degradation of the target RNA prevents translation.

Single-stranded oligonucleotides, including those described and/or identified as single stranded siRNAs, microRNAs or mirs which may be used as targets or may serve as a template for the design of oligonucleotides of the invention are taught in, for example, Esau, et al. US Publication #20050261218 (U.S. Ser. No. 10/909,125) entitled "Oligonucleotides and compositions for use in modulation small non-coding RNAs" the entire contents of which is incorporated herein by reference. It will be appreciated by one of skill in the art that any oligonucleotide chemical modifications or variations describe herein also apply to single stranded oligonucleotides.

MicroRNAs (miRNAs or mirs) are a highly conserved class of small RNA molecules that are transcribed from DNA in the genomes of plants and animals, but are not translated into protein. Pre-microRNAs are processed into miRNAs. Processed microRNAs are single stranded ~17-25 nucleotide (nt) RNA molecules that become incorporated into the RNA-induced silencing complex (RISC) and have been identified as key regulators of development, cell proliferation, apoptosis and differentiation. They are believed to play a role in regulation of gene expression by binding to the 3'-untranslated region of specific mRNAs. RISC mediates down-regulation of gene expression through translational inhibition, transcript cleavage, or both. RISC is also implicated in transcriptional silencing in the nucleus of a wide range of eukaryotes.

The number of miRNA sequences identified to date is large and growing, illustrative examples of which can be found, for example, in: "*miRBase: microRNA sequences, targets and gene nomenclature*" Griffiths-Jones S, Grocock R J, van Dongen S, Bateman A, Enright A J. NAR, 2006, 34, Database Issue, D140-D144; "*The microRNA Registry*" Griffiths-Jones S, NAR, 2004, 32, Database Issue, D109-D111; and also on the worldwide web at http://microrna.dot.sanger.dot.ac.dot.uk/sequences/.

Antagomirs are RNA-like oligonucleotides that harbor various modifications for RNAse protection and pharmacologic properties, such as enhanced tissue and cellular uptake. They differ from normal RNA by, for example, complete 2'-O-methylation of sugar, phosphorothioate backbone and, for example, a cholesterol-moiety at 3'-end. Antagomirs may be used to efficiently silence endogenous miRNAs by forming duplexes comprising the antagomir and endogenous miRNA, thereby preventing miRNA-induced gene silencing. An example of antagomir-mediated miRNA silencing is the silencing of miR-122, described in Krutzfeldt et al, Nature, 2005, 438: 685-689, which is expressly incorporated by reference herein in its entirety. Antagomir RNAs may be synthesized using standard solid phase oligonucleotide synthesis protocols. See U.S. patent application Ser. Nos. 11/502,158 and 11/657,341 (the disclosure of each of which are incorporated herein by reference).

An antagomir can include ligand-conjugated monomer subunits and monomers for oligonucleotide synthesis. Exemplary monomers are described in U.S. application Ser. No. 10/916,185, filed on Aug. 10, 2004. An antagomir can have a ZXY structure, such as is described in PCT Application No. PCT/US2004/07070 filed on Mar. 8, 2004. An antagomir can be complexed with an amphipathic moiety. Exemplary amphipathic moieties for use with oligonucleotide agents are described in PCT Application No. PCT/US2004/07070, filed on Mar. 8, 2004.

Single stranded siRNAs (ss siRNAs) are known and are described in US publication US 2006/0166910 and hereby incorporated by herein by its entirety. A "single stranded siRNA" as used herein, is an RNAi agent which is made up of a single molecule. A single stranded RNAi agent may include a duplexed region, formed by intra-strand pairing, e.g., it may be, or include, a hairpin or pan-handle structure. Single strand RNAi agents may be antisense with regard to the target molecule.

A single strand RNAi agent may be sufficiently long that it can enter the RISC and participate in RISC mediated cleavage of a target mRNA. A single strand RNAi agent is at least 14, and in other embodiments at least 15, at least 20, at least 25, at least 29, at least 35, at least 40, or at least 50 nucleotides in length. In certain embodiments, it is less than 200, 100, or 60 nucleotides in length. In certain embodiments single strand RNAi agents are 5' phosphorylated or include a phosphoryl analog at the 5' prime terminus. In one embodiment, the single-stranded oligonucleotide inhibits the expression of a target gene via RISC mediated cleavage of the target sequence.

Preferably, the single-stranded RNA molecule has a length from 15-29 nucleotides. The RNA-strand may have a 3' hydroxyl group. In some cases, however, it may be preferable to modify the 3' end to make it resistant against 3' to 5' exonucleases. Tolerated 3'-modifications are for example terminal 2'-deoxy nucleotides, 3' phosphate, 2',3'-cyclic phosphate, C3 (or C6, C7, C12) aminolinker, thiol linkers, carboxyl linkers, non-nucleotidic spacers (C3, C6, C9, C12, abasic, triethylene glycol, hexaethylene glycol), biotin, fluoresceine, etc. Single stranded siRNAs of the invention include at least one of the following motifs: 5' phosphorothioate or 5'-phosphorodithioate, nucleotides 1 and 2 having cationic modifications via C-5 position of pyrimidines, 2-Position of Purines, N2-G, G-clamp, 8-position of purines, 6-position of purines, internal nucleotides having a 2'-F sugar with base modifications (Pseudouridine, G-clamp, phenoxazine, pyridopyrimidines, gem2'-Me-up/2'-F-down, 2,6-diaminopurine, 2-aminopuriine), 3'-end with two purines with novel 2'-substituted MOE analogs, 5'-end nucleotides with novel 2'-substituted MOE analogs, 5'-end having a 3'-F and a 2'-5'-linkage, 4'-substituted nucleoside at the nucleotide 1 at 5'-end and the substituent is cationic, alkyl, alkoxyalkyl, thioether and the like, 4'-substitution at the 3'-end of the strand, and combinations thereof.

Ribozymes are oligonucleotides having specific catalytic domains that possess endonuclease activity (Kim and Cech, Proc Natl Acad Sci USA. 1987 December; 84(24):8788-92; Forster and Symons, Cell. 1987 Apr. 24; 49(2):211-20). At least six basic varieties of naturally-occurring enzymatic RNAs are known presently. In general, enzymatic nucleic acids act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Methods of producing a ribozyme targeted to any target sequence are known in the art. Ribozymes may be designed as described in Int. Pat. Appl. Publ. No. WO 93/23569 and Int. Pat. Appl. Publ. No. WO 94/02595, each specifically incorporated herein by reference, and synthesized to be tested in vitro and in vivo, as described therein.

Aptamers are nucleic acid or peptide molecules that bind to a particular molecule of interest with high affinity and specificity (Tuerk and Gold, Science 249:505 (1990); Ellington and Szostak, Nature 346:818 (1990)). DNA or RNA aptamers have been successfully produced which bind many different entities from large proteins to small organic molecules. See Eaton, Curr. Opin. Chem. Biol. 1:10-16 (1997), Famulok, Curr. Opin. Struct. Biol. 9:324-9 (1999), and Hermann and Patel, Science 287:820-5 (2000). Aptamers may be RNA or DNA based. Generally, aptamers are engineered through repeated rounds of in vitro selection or equivalently, SELEX (systematic evolution of ligands by exponential enrichment)

to bind to various molecular targets such as small molecules, proteins, nucleic acids, and even cells, tissues and organisms. The aptamer may be prepared by any known method, including synthetic, recombinant, and purification methods, and may be used alone or in combination with other aptamers specific for the same target. Further, as described more fully herein, the term "aptamer" specifically includes "secondary aptamers" containing a consensus sequence derived from comparing two or more known aptamers to a given target.

Immunostimulatory Oligonucleotides

Nucleic acids of the present invention may be immunostimulatory, including immunostimulatory oligonucleotides (single- or double-stranded) capable of inducing an immune response when administered to a subject, which may be a mammal or other patient. The immune response may be an innate or an adaptive immune response. The immune system is divided into a more innate immune system, and acquired adaptive immune system of vertebrates, the latter of which is further divided into humoral cellular components. In particular embodiments, the immune response may be mucosal.

Immunostimulatory nucleic acids are considered to be non-sequence specific when it is not required that they specifically bind to and reduce the expression of a target polynucleotide in order to provoke an immune response. Thus, certain immunostimulatory nucleic acids may comprise a sequence corresponding to a region of a naturally occurring gene or mRNA, but they may still be considered non-sequence specific immunostimulatory nucleic acids.

In one embodiment, the immunostimulatory nucleic acid or oligonucleotide comprises at least one CpG dinucleotide. The oligonucleotide or CpG dinucleotide may be unmethylated or methylated. In another embodiment, the immunostimulatory nucleic acid comprises at least one CpG dinucleotide having a methylated cytosine. In one embodiment, the nucleic acid comprises a single CpG dinucleotide, wherein the cytosine in said CpG dinucleotide is methylated. Methods of immune stimulation using single stranded oligonucleotides and immune stimulatory oligonucleotides.

The immunostimulatory nucleic acid or oligonucleotide comprises capable of inducing an anti-viral or an antibacterial response, in particular, the induction of type I IFN, IL-18 and/or IL-1β by modulating RIG-I.

RNA Activator

Recent studies have found that dsRNA can also activate gene expression, a mechanism that has been termed "small RNA-induced gene activation" or RNAa. See for example Li, L. C. et al. *Proc Natl Acad Sci USA*. (2006), 103(46):17337-42 and Li L. C. (2008). "Small RNA-Mediated Gene Activation". RNA and the Regulation of Gene Expression: A Hidden Layer of Complexity. Caister Academic Press. ISBN 978-1-904455-25-7. It has been shown that dsRNAs targeting gene promoters induce potent transcriptional activation of associated genes. Endogenous miRNA that cause RNAa has also been found in humans. Check E. Nature (2007). 448 (7156): 855-858.

Another surprising observation is that gene activation by RNAa is long-lasting. Induction of gene expression has been seen to last for over ten days. The prolonged effect of RNAa could be attributed to epigenetic changes at dsRNA target sites.

miRNA Mimics miRNA mimics represent a class of molecules that can be used to imitate the gene modulating activity of one or more miRNAs. Thus, the term "microRNA mimic" refers to synthetic non-coding RNAs (i.e. the miRNA is not obtained by purification from a source of the endogenous miRNA) that are capable of entering the RNAi pathway and regulating gene expression. miRNA mimics can be designed as mature molecules (e.g. single stranded) or mimic precursors (e.g., pri- or pre-miRNAs).

In one design, miRNA mimics are double stranded molecules (e.g., with a duplex region of between about 16 and about 31 nucleotides in length) and contain one or more sequences that have identity with the mature strand of a given miRNA.

Modifications can comprise 2' modifications (including 2'-O methyl modifications and 2' F modifications) on one or both strands of the molecule and internucleotide modifications (e.g. phorphorthioate modifications) that enhance nucleic acid stability and/or specificity. In addition, miRNA mimics can include overhangs. The overhangs can consist of 1-6 nucleotides on either the 3' or 5' end of either strand and can be modified to enhance stability or functionality.

In one embodiment, a miRNA mimic comprises a duplex region of between 16 and 31 nucleotides and one or more of the following chemical modification patterns: the sense strand contains 2'-O-methyl modifications of nucleotides 1 and 2 (counting from the 5' end of the sense oligonucleotide), and all of the Cs and Us; the antisense strand modifications can comprise 2' F modification of all of the Cs and Us, phosphorylation of the 5' end of the oligonucleotide, and stabilized internucleotide linkages associated with a 2 nucleotide 3' overhang.

Supermirs

A supermir refers to an oligonucleotide, e.g., single stranded, double stranded or partially double stranded, which has a nucleotide sequence that is substantially identical to an miRNA and that is antisense with respect to its target. This term includes oligonucleotides which comprise at least one non-naturally-occurring portion which functions similarly. In a preferred embodiment, the supermir does not include a sense strand, and in another preferred embodiment, the supermir does not self-hybridize to a significant extent. An supermir featured in the invention can have secondary structure, but it is substantially single-stranded under physiological conditions. An supermir that is substantially single-stranded is single-stranded to the extent that less than about 50% (e.g., less than about 40%, 30%, 20%, 10%, or 5%) of the supermir is duplexed with itself. The supermir can include a hairpin segment, e.g., sequence, preferably at the 3' end can self hybridize and form a duplex region, e.g., a duplex region of at least 1, 2, 3, or 4 and preferably less than 8, 7, 6, or 5 nucleotides, e.g., 5 nucleotides. The duplexed region can be connected by a linker, e.g., a nucleotide linker, e.g., 3, 4, 5, or 6 dTs, e.g., modified dTs. In another embodiment the supermir is duplexed with a shorter oligo, e.g., of 5, 6, 7, 8, 9, or 10 nucleotides in length, e.g., at one or both of the 3' and 5' end or at one end and in the non-terminal or middle of the supermir.

Antimirs or miRNA Inhibitors

The terms "antimir" "microRNA inhibitor", "miR inhibitor", or "inhibitor" are synonymous and refer to oligonucleotides or modified oligonucleotides that interfere with the activity of specific miRNAs. Inhibitors can adopt a variety of configurations including single stranded, double stranded (RNA/RNA or RNA/DNA duplexes), and hairpin designs, in general, microRNA inhibitors comprise one or more sequences or portions of sequences that are complementary or partially complementary with the mature strand (or strands) of the miRNA to be targeted, in addition, the miRNA inhibitor may also comprise additional sequences located 5' and 3' to the sequence that is the reverse complement of the mature miRNA. The additional sequences may be the reverse complements of the sequences that are adjacent to the mature miRNA in the pri-miRNA from which the mature miRNA is derived, or the additional sequences may be arbitrary sequences (having a mixture of A, G, C, U, or dT). In some embodiments, one or both of the additional sequences are arbitrary sequences capable of forming hairpins. Thus, in some embodiments, the sequence that is the reverse complement of the miRNA is flanked on the 5' side and on the 3' side by hairpin structures. MicroRNA inhibitors, when double stranded, may include mismatches between nucleotides on opposite strands. Furthermore, microRNA inhibitors may be linked to conjugate moieties in order to facilitate uptake of the inhibitor into a cell.

MicroRNA inhibitors, including hairpin miRNA inhibitors, are described in detail in Vermeulen et al., "Double-Stranded Regions Are Essential Design Components Of Potent Inhibitors of RISC Function," RNA 13: 723-730 (2007) and in WO2007/095387 and WO 2008/036825 each of which is incorporated herein by reference in its entirety. A person of ordinary skill in the art can select a sequence from the database for a desired miRNA and design an inhibitor useful for the methods disclosed herein.

Other Oligonucleotides

Because transcription factors recognize their relatively short binding sequences, even in the absence of surrounding genomic DNA, short oligonucleotides bearing the consensus binding sequence of a specific transcription factor can be used as tools for manipulating gene expression in living cells. This strategy involves the intracellular delivery of such "decoy oligonucleotides", which are then recognized and bound by the target factor. Occupation of the transcription factor's DNA-binding site by the decoy renders the transcription factor incapable of subsequently binding to the promoter regions of target genes. Decoys can be used as therapeutic agents, either to inhibit the expression of genes that are activated by a transcription factor, or to upregulate genes that are suppressed by the binding of a transcription factor. Examples of the utilization of decoy oligonucleotides may be found in Mann et al., J. Clin. Invest., 2000, 106: 1071-1075, which is expressly incorporated by reference herein, in its entirety.

U1 adaptor inhibit polyA sites and are bifunctional oligonucleotides with a target domain complementary to a site in the target gene's terminal exon and a 'U1 domain' that binds to the U1 smaller nuclear RNA component of the U1 snRNP (Goraczniak, et al., 2008, Nature Biotechnology, 27(3), 257-263, which is expressly incorporated by reference herein, in its entirety). U1 snRNP is a ribonucleoprotein complex that functions primarily to direct early steps in spliceosome formation by binding to the pre-mRNA exon-intron boundary (Brown and Simpson, 1998, Annu Rev Plant Physiol Plant Mol Biol 49:77-95). Nucleotides 2-11 of the 5' end of U1 snRNA base pair bind with the 5' ss of the pre mRNA. In one embodiment, oligonucleotides of the invention are U1 adaptors. In one embodiment, the U1 adaptor can be administered in combination with at least one other iRNA agent.

Oligonucleotide Modifications

Unmodified oligonucleotides may be less than optimal in some applications, e.g., unmodified oligonucleotides can be prone to degradation by e.g., cellular nucleases. Nucleases can hydrolyze nucleic acid phosphodiester bonds. However, chemical modifications to one or more of the above oligonucleotide components can confer improved properties, and, e.g., can render oligonucleotides more stable to nucleases.

Modified nucleic acids and nucleotide surrogates can include one or more of:

(i) alteration, e.g., replacement, of one or both of the non-linking phosphate oxygens and/or of one or more of the linking phosphate oxygens in the phosphodiester backbone linkage.

(ii) alteration, e.g., replacement, of a constituent of the ribose sugar, e.g., of the 2' hydroxyl on the ribose sugar;

(iii) wholesale replacement of the phosphate moiety with "dephospho" linkers;

(iv) modification or replacement of a naturally occurring base with a non-natural base;

(v) replacement or modification of the ribose-phosphate backbone;

(vi) modification of the 3' end or 5' end of the oligonucleotide, e.g., removal, modification or replacement of a terminal phosphate group or conjugation of a moiety, e.g., a fluorescently labeled moiety, to either the 3" or 5' end of oligonucleotide; and (vii) modification of the sugar (e.g., six membered rings).

The terms replacement, modification, alteration, and the like, as used in this context, do not imply any process limitation, e.g., modification does not mean that one must start with a reference or naturally occurring ribonucleic acid and modify it to produce a modified ribonucleic acid bur rather modified simply indicates a difference from a naturally occurring molecule.

As oligonucleotides are polymers of subunits or monomers, many of the modifications described herein can occur at a position which is repeated within an oligonucleotide, e.g., a modification of a nucleobase, a sugar, a phosphate moiety, or the non-bridging oxygen of a phosphate moiety. It is not necessary for all positions in a given oligonucleotide to be uniformly modified, and in fact more than one of the aforementioned modifications may be incorporated in a single oligonucleotide or even at a single nucleoside within an oligonucleotide.

In some cases the modification will occur at all of the subject positions in the oligonucleotide but in many, and in fact in most cases it will not. By way of example, a modification may only occur at a 3' or 5' terminal position, may only occur in the internal region, may only occur in a terminal regions, e.g. at a position on a terminal nucleotide or in the last 2, 3, 4, 5, or 10 nucleotides of an oligonucleotide. A modification may occur in a double strand region, a single strand region, or in both. A modification may occur only in the double strand region of an oligonucleotide or may only occur in a single strand region of an oligonucleotide. E.g., a phosphorothioate modification at a non-bridging oxygen position may only occur at one or both termini, may only occur in a terminal regions, e.g., at a position on a terminal nucleotide or in the last 2, 3, 4, 5, or 10 nucleotides of a strand, or may occur in double strand and single strand regions, particularly at termini. The 5' end or ends can be phosphorylated.

A modification described herein may be the sole modification, or the sole type of modification included on multiple nucleotides, or a modification can be combined with one or more other modifications described herein. The modifications described herein can also be combined onto an oligonucleotide, e.g. different nucleotides of an oligonucleotide have different modifications described herein.

In some embodiments it is particularly preferred, e.g., to enhance stability, to include particular nucleobases in overhangs, or to include modified nucleotides or nucleotide surrogates, in single strand overhangs, e.g., in a 5' or 3' overhang, or in both. E.g., it can be desirable to include purine nucleotides in overhangs. In some embodiments all or some of the bases in a 3' or 5' overhang will be modified, e.g., with a modification described herein. Modifications can include, e.g., the use of modifications at the 2' OH group of the ribose sugar, e.g., the use of deoxyribonucleotides, e.g., deoxythymidine, instead of ribonucleotides, and modifications in the phosphate group, e.g., phosphothioate modifications. Overhangs need not be homologous with the target sequence.

Specific modifications are discussed in more detail below.
The Phosphate Group

The phosphate group is a negatively charged species. The charge is distributed equally over the two non-bridging oxygen atoms. However, the phosphate group can be modified by replacing one of the oxygens with a different substituent. One result of this modification to RNA phosphate backbones can be increased resistance of the oligoribonucleotide to nucleolytic breakdown. Thus while not wishing to be bound by theory, it can be desirable in some embodiments to introduce alterations which result in either an uncharged linker or a charged linker with unsymmetrical charge distribution.

Examples of modified phosphate groups include phosphorothioate, phosphoroselenates, borano phosphates, borano phosphate esters, hydrogen phosphonates, phosphoroamidates, alkyl or aryl phosphonates and phosphotriesters. In one embodiment, one of the non-bridging phosphate oxygen atoms in the phosphate backbone moiety can be replaced by any of the following: S, Se, $BR_3$ (R is hydrogen, alkyl, aryl), C (i.e. an alkyl group, an aryl group, etc. . . . ), H, $NR_2$ (R is hydrogen, alkyl, aryl), or OR (R is alkyl or aryl). The phosphorous atom in an unmodified phosphate group is achiral. However, replacement of one of the non-bridging oxygens with one of the above atoms or groups of atoms renders the phosphorous atom chiral; in other words a phosphorous atom in a phosphate group modified in this way is a stereogenic center. The stereogenic phosphorous atom can possess either the "R" configuration (herein Rp) or the "S" configuration (herein Sp).

Phosphorodithioates have both non-bridging oxygens replaced by sulfur. The phosphorus center in the phosphorodithioates is achiral which precludes the formation of oligoribonucleotides diastereomers. Thus, while not wishing to be bound by theory, modifications to both non-bridging oxygens, which eliminate the chiral center, e.g. phosphorodithioate formation, may be desirable in that they cannot produce diastereomer mixtures. Thus, the non-bridging oxygens can be independently any one of S, Se, B, C, H, N, or OR (R is alkyl or aryl).

The phosphate linker can also be modified by replacement of bridging oxygen, (i.e. oxygen that links the phosphate to the nucleoside), with nitrogen (bridged phosphoroamidates), sulfur (bridged phosphorothioates) and carbon (bridged methylenephosphonates). The replacement can occur at the either linking oxygen or at both the linking oxygens. When the bridging oxygen is the 3'-oxygen of a nucleoside, replacement with carbon is preferred. When the bridging oxygen is the 5'-oxygen of a nucleoside, replacement with nitrogen is preferred.
Replacement of the Phosphate Group The phosphate group can be replaced by non-phosphorus containing connectors, e.g., diphospho linkers. While not wishing to be bound by theory, it is believed that since the charged phosphodiester group is the reaction center in nucleolytic degradation, its replacement with neutral structural mimics should impart enhanced nuclease stability. Again, while not wishing to be bound by theory, it can be desirable, in some embodiment, to introduce alterations in which the charged phosphate group is replaced by a neutral moiety.

Examples of moieties which can replace the phosphate group include methyl phosphonate, hydroxylamino, siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino. Preferred replacements include the methylenecarbonylamino and methylenemethylimino groups.

Modified phosphate linkages where at least one of the oxygens linked to the phosphate has been replaced or the phosphate group has been replaced by a non-phosphorous group, are also referred to as "non-phosphodiester backbone linkage."
Replacement of Ribophosphate Backbone Oligonucleotide-mimicking scaffolds can also be constructed wherein the phosphate linker and ribose sugar are replaced by nuclease resistant nucleoside or nucleotide surrogates. While not wishing to be bound by theory, it is believed that the absence of a repetitively charged backbone diminishes binding to proteins that recognize polyanions (e.g. nucleases). Again, while not wishing to be bound by theory, it can be desirable in some embodiment, to introduce alterations in which the bases are tethered by a neutral surrogate backbone. Examples include the mophilino, cyclobutyl, pyrrolidine and peptide nucleic acid (PNA) nucleoside surrogates. A preferred surrogate is a PNA surrogate.
Sugar Modifications An oligonucleotide can include modification of all or some of the sugar groups of the nucleic acid. E.g., the 2' hydroxyl group (OH) can be modified or replaced with a number of different "oxy" or "deoxy" substituents. While not being bound by theory, enhanced stability is expected since the hydroxyl can no longer be deprotonated to form a 2'-alkoxide ion. The 2'-alkoxide can catalyze degradation by intramolecular nucleophilic attack on the linker phosphorus atom. Again, while not wishing to be bound by theory, it can be desirable to some embodiments to introduce alterations in which alkoxide formation at the 2' position is not possible.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), $O(CH_2CH_2O)_nCH_2CH_2OR$; "locked" nucleic acids, e.g., LNA in which the 2' hydroxyl is connected by a methylene bridge to the 4' carbon of the same ribose sugar and ENA in which the 2' hydroxyl is connected by an ethylene bridge to the 4' carbon of the same ribose sugar; G-AMINE (AMINE=$NH_2$; alkylamino, dialkylamino, heterocyclyl, arylamino, diaryl amino, heteroaryl amino, diheteroaryl amino, ethylene diamine, polyamino or aminoalkoxy) and $O(CH_2)_n$ AMINE, (e.g., AMINE=$NH_2$, alkylamino, dialkylamino, heterocyclyl, arylamino, diaryl amino, heteroaryl amino, diheteroaryl amino, ethylene diamine, polyamino or aminoalkoxy). It is noteworthy that oligonucleotides containing only the methoxyethyl group (MOE), ($OCH_2CH_2OCH_3$, a PEG derivative), exhibit nuclease stabilities comparable to those modified with the robust phosphorothioate modification.

"Deoxy" modifications include hydrogen (i.e. deoxyribose sugars, which are of particular relevance to the overhang portions of partially ds RNA); halo (e.g., fluoro); amino (e.g. $NH_2$, alkylamino, dialkylamino, heterocyclyl, arylamino, diaryl amino, heteroaryl amino, diheteroaryl amino, or amino acid); $NH(CH_2CH_2NH)_nCH_2CH_2$-AMINE (AMINE=$NH_2$, alkylamino, dialkylamino, heterocyclyl, arylamino, diaryl amino, heteroaryl amino, or diheteroaryl amino); NHC(O)R (R=alkyl, cycloalkyl, aryl, aralkyl, heteroaryl or sugar); cyano; mercapto; alkyl-thioalkyl; thioalkoxy; alkyl; cycloalkyl; aryl; alkenyl and alkynyl, which may be optionally substituted with e.g., an amino functionality.

The sugar group can also contain one or more carbons that possess the opposite stereochemical configuration than that of the corresponding carbon in ribose. Thus, an oligonucleotide can include nucleotides containing e.g., arabinose, as the sugar. The monomer can have an alpha linkage at the 1' position on the sugar, e.g., alpha-nucleosides. Oligonucleotides can also include "abasic" sugars, which lack a nucleobase at C-1'. These abasic sugars can also be further containing modifications at one or more of the constituent sugar atoms. Oligonucleotides can also contain one or more sugars that are in the L form, e.g. L-nucleosides.

Modification to the sugar group may also include replacement of the 4'-O with a sulfur, nitrogen or $CH_2$ group. Other modifications to the sugar group include deletion of the C2'

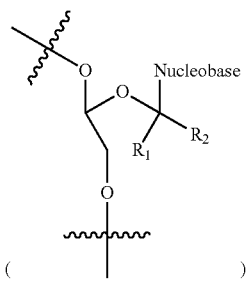

or deletion of 4'-O

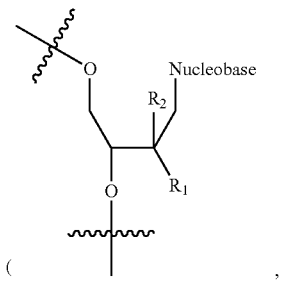

where $R_1$ and $R_2$ independently are H, halogen, $OR_3$, or alkyl; and $R_3$ is H, alkyl, cycloalkyl, aryl, aralkyl, heteroaryl or sugar).

Preferred substitutents are 2'-O-Me (2'-O-methyl), 2'-O-MOE (2'-O-methoxyethyl), 2'-F, 2'-O-[2-(methylamino)-2-oxoethyl] (2'-O-NMA), 2'-S-methyl, 2'-O—$CH_2$-(4'-C) (LNA), 2'-O—$CH_2CH_2$-(4'-C) (ENA), 2'-O-aminopropyl (2'-O-AP), 2'-O-dimethylaminoethyl (2'-O-DMAOE), 2'-O-dimethylaminopropyl (2'-O-DMAP), 2'-O—$CH_2CH_2N$ $(CH_2CH_2NMe_2)_2$ and 2'-O-dimethylaminoethyloxyethyl (2'-O-DMAEOE).

One or more nucleotides of an oligonucleotide may have L-sugar with modifications in place of the modified nucleoside in its entity pursuant to the invention described. The L-sugar has the same sugar and base modification or combinations thereof as in D-sugar. One or more nucleotides of an oligonucleotide having the L-sugar may have a 2'-5' linkage or inverted linkages, e.g. 3'-3', 5'-5',2'-2' or 2'-3' linkages. These linkages can be placed between two L-sugar moieties, between L- and D-sugars or between two D-sugars in an oligonucleotide bearing a modified L-nucleoside.

Terminal Modifications

The 3' and 5' ends of an oligonucleotide can be modified. Such modifications can be at the 3' end, 5' end or both ends of the molecule. They can include modification or replacement of an entire terminal phosphate or of one or more of the atoms of the phosphate group. E.g., the 3' and 5' ends of an oligonucleotide can be conjugated to other functional molecular entities such as labeling moieties, e.g., fluorophores (e.g., pyrene, TAMRA, fluorescein, Cy3 or Cy5 dyes) or protecting groups (based e.g., on sulfur, silicon, boron or ester). The functional molecular entities can be attached to the sugar through a phosphate group and/or a linker. The terminal atom of the linker can connect to or replace the linking atom of the phosphate group or the C-3' or C-5' O, N, S or C group of the sugar. Alternatively, the linker can connect to or replace the terminal atom of a nucleotide surrogate (e.g., PNAs).

When a linker/phosphate-functional molecular entity-linker/phosphate array is interposed between two strands of a dsRNA, this array can substitute for a hairpin RNA loop in a hairpin-type RNA agent.

Terminal modifications useful for modulating activity include modification of the 5' end with phosphate or phosphate analogs. E.g., in preferred embodiments antisense strands of dsRNAs, are 5' phosphorylated or include a phosphoryl analog at the 5' prime terminus. 5'-phosphate modifications include those which are compatible with RISC mediated gene silencing. Modifications at the 5'-terminal end can also be useful in stimulating or inhibiting the immune system of a subject. In certain embodiments, the 5'-end of the oligonucleotide comprises the modification

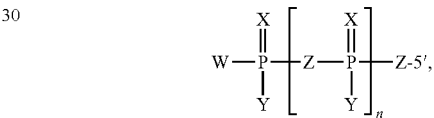

wherein W, X and Y are each independently selected from the group consisting of O, OR(R is hydrogen, alkyl, aryl), S, Se, $BR_3$ (R is hydrogen, alkyl, aryl), C (i.e. an alkyl group, an aryl group, etc. . . . ), H, $NR_2$ (R is hydrogen, alkyl, aryl), or OR (R is hydrogen, alkyl or aryl); Z is independently for each occurrence O, S, $CH_2$, or NR (R is hydrogen, alkyl, aryl); and n is 0-2.

Suitable modifications include: 5'-monophosphate $((HO)_2(O)P—O-5')$; 5'-diphosphate $((HO)_2(O)P—O—P(HO)(O)—O-5')$; 5'-triphosphate $((HO)_2(O)P—O—(HO)(O)P—O—P(HO)(O)—O-5')$; 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; $(HO)_2(S)P—O-5'$); 5'-monodithiophosphate (phosphorodithioate; (HO)(HS)(S)P—O-5'), 5'-phosphorothiolate $((HO)_2(O)P—S-5')$; any additional combination of oxygen/sulfur replaced monophosphate, diphosphate and triphosphates (e.g. 5'-alpha-thiotriphosphate, 5'-beta-thiotriphosphate, 5'-gamma-thiotriphosphate, etc.), 5'-phosphoramidates $((HO)_2(O)P—NH-5', (HO)(NH_2)(O)P—O-5')$, 5'-alkylphosphonates (R=alkyl=methyl, ethyl, isopropyl, propyl, etc., e.g. RP(OH)(O)—O-5'-, $(OH)_2(O)P-5'-CH_2—)$, 5'-alkyletherphosphonates (R=alkylether=methoxymethyl ($MeOCH_2—$), ethoxymethyl, etc., e.g. RP(OH)(O)—O-5'-); two or more phosphates or all phopshophate mimics described with separation by substituted or unsubstituted alkyl, alkenyl or alkynyl spacings: e.g., $((HO)2(X)P—O[—(CH_2)_a—O—P(X)(OH)—O]_b-5'$, $((HO)2(X)P—O[—(CH_2), P(X)(OH)—O]_b-5'$, $((HO)2(X)P—[—(CH_2)_a—O—P(X)(OH)—O]_b-5'$;

dialkyl terminal phosphates and phosphate mimics: HO[—(CH$_2$)$_a$—O—P(X)(OH)—O]$_b$-5', H$_2$N[—(CH$_2$)$_a$—O—P(X)(OH)—O]$_b$-5', H[—(CH$_2$)$_a$—O—P(X)(OH)—O]$_b$-5', Me$_2$N[—(CH$_2$)$_a$—O—P(X)(OH)—O]$_b$-5', HO[—(CH$_2$)$_a$—P(X)(OH)—O]$_b$-5', H$_2$N[—(CH$_2$)$_a$—P(X)(OH)—O]$_b$-5', H[—(CH$_2$)$_a$—P(X)(OH)—O]$_b$-5', Me$_2$N[—(CH$_2$)$_a$—P(X)(OH)—O]$_b$-5' Other embodiments include replacement of oxygen/sulfur with BH$_3$, BH$_3^-$ and/or Se. In one occurrence, at terminals of the oligonucleotides, the phosphate and phosphoate mimics described are β to the sugar moiety and in another occurrence the phosphate and phosphate mimics are α to the sugar moiety; or in another occurrence both α and β phosphate bearing moieties are simultaneously present.

In another embodiment, the phosphate groups described above are placed at the 3'-end of the oligonucleotide, for example at the 2' and/or the 3' position of the 3'-nucleoside sugar.

In one embodiment, the configuration of phosphate or phosphate mimics at 5' terminal is β to the sugar moiety.

In another embodiment, the configuration of phosphate or phosphate mimics at 5' terminal is α to the sugar moiety.

In one embodiment, the configuration of phosphate or phosphate mimics at 3' terminal is β to the sugar moiety.

In another embodiment, the configuration of phosphate or phosphate mimics at 3' terminal is α to the sugar moiety.

In one embodiment both α and β phosphate or phosphate mimics are simultaneously present at the terminals Terminal modifications can also be useful for monitoring distribution, and in such cases the preferred groups to be added include fluorophores, e.g., fluorscein or an Alexa dye, e.g., Alexa 488. Terminal modifications can also be useful for enhancing uptake, useful modifications for this include cholesterol. Terminal modifications can also be useful for cross-linking an RNA agent to another moiety; modifications useful for this include mitomycin C, psoralen and derivatives thereof.

Nucleobases

Adenine, guanine, cytosine and uracil are the most common bases found in RNA. These bases can be modified or replaced to provide RNA's having improved properties. For example, nuclease resistant oligoribonucleotides can be prepared with these bases or with synthetic and natural nucleobases (e.g., inosine, thymine, xanthine, hypoxanthine, nubularine, isoguanisine, or tubercidine) and any one of the above modifications. Alternatively, substituted or modified analogs of any of the above bases and "universal bases" can be employed. Examples include 2-(halo)adenine, 2-(alkyl)adenine, 2-(propyl)adenine, 2-(amino)adenine, 2-(aminoalkyll) adenine, 2-(aminopropyl)adenine, 2-(methylthio)-N$^6$-(isopentenyl)adenine, 6-(alkyl)adenine, 6-(methyl)adenine, 7-(deaza)adenine, 8-(alkenyl)adenine, 8-(alkyl)adenine, 8-(alkynyl)adenine, 8-(amino)adenine, 8-(halo)adenine, 8-(hydroxyl)adenine, 8-(thioalkyl)adenine, 8-(thiol)adenine, N$^6$-(isopentyl)adenine, N$^6$-(methyl)adenine, N$^6$,N$^6$-(dimethyl)adenine, 2-(alkyl)guanine, 2-(propyl)guanine, 6-(alkyl)guanine, 6-(methyl)guanine, 7-(alkyl)guanine, 7-(methyl)guanine, 7-(deaza)guanine, 8-(alkyl)guanine, 8-(alkenyl)guanine, 8-(alkynyl)guanine, 8-(amino)guanine, 8-(halo)guanine, 8-(hydroxyl)guanine, 8-(thioalkyl)guanine, 8-(thiol)guanine, N-(methyl)guanine, 2-(thio)cytosine, 3-(deaza)-5-(aza)cytosine, 3-(alkyl)cytosine, 3-(methyl)cytosine, 5-(alkyl)cytosine, 5-(alkynyl)cytosine, 5-(halo)cytosine, 5-(methyl)cytosine, 5-(propynyl)cytosine, 5-(propynyl)cytosine, 5-(trifluoromethyl)cytosine, 6-(azo)cytosine, N$^4$-(acetyl)cytosine, 3-(3-amino-3-carboxypropyl)uracil, 2-(thio)uracil, 5-(methyl)-2-(thio)uracil, 5-(methylaminomethyl)-2-(thio)uracil, 4-(thio)uracil, 5-(methyl)-4-(thio) uracil, 5-(methylaminomethyl)-4-(thio)uracil, 5-(methyl)-2,4-(dithio)uracil, 5-(methylaminomethyl)-2,4-(dithio)uracil, 5-(2-aminopropyl)uracil, 5-(alkyl)uracil, 5-(alkynyl)uracil, 5-(allylamino)uracil, 5-(aminoallyl)uracil, 5-(aminoalkyl) uracil, 5-(guanidiniumalkyl)uracil, 5-(1,3-diazole-1-alkyl) uracil, 5-(cyanoalkyl)uracil, 5-(dialkylaminoalkyl)uracil, 5-(dimethylaminoalkyl)uracil, 5-(halo)uracil, 5-(methoxy) uracil, uracil-5-oxyacetic acid, 5-(methoxycarbonylmethyl)-2-(thio)uracil, 5-(methoxycarbonyl-methyl)uracil, 5-(propynyl)uracil, 5-(propynyl)uracil, 5-(trifluoromethyl)uracil, 6-(azo)uracil, dihydrouracil, N$^3$-(methyl)uracil, 5-uracil (i.e., pseudouracil), 2-(thio)pseudouracil, 4-(thio)pseudouracil, 2,4-(dithio)psuedouracil, 5-(alkyl)pseudouracil, 5-(methyl) pseudouracil, 5-(alkyl)-2-(thio)pseudouracil, 5-(methyl)-2-(thio)pseudouracil, 5-(alkyl)-4-(thio)pseudouracil, 5-(methyl)-4-(thio)pseudouracil, 5-(alkyl)-2,4-(dithio) pseudouracil, 5-(methyl)-2,4-(dithio)pseudouracil, 1-substituted pseudouracil, 1-substituted 2(thio)-pseudouracil, 1-substituted 4-(thio)pseudouracil, 1-substituted 2,4-(dithio)pseudouracil, 1-(aminocarbonylethylenyl)-pseudouracil, 1-(aminocarbonylethylenyl)-2(thio)-pseudouracil, 1-(aminocarbonylethylenyl)-4-(thio)pseudouracil, 1-(aminocarbonylethylenyl)-2,4-(dithio)pseudouracil, 1-(aminoalkylaminocarbonylethylenyl)-pseudouracil, 1-(aminoalkylamino-carbonylethylenyl)-2(thio)-pseudouracil, 1-(aminoalkylaminocarbonylethylenyl)-4-(thio)pseudouracil, 1-(aminoalkylaminocarbonylethylenyl)-2,4-(dithio) pseudouracil, 1,3-(diaza)-2-(oxo)-phenoxazin-1-yl, 1-(aza)-2-(thio)-3-(aza)-phenoxazin-1-yl, 1,3-(diaza)-2-(oxo)-phenthiazin-1-yl, 1-(aza)-2-(thio)-3-(aza)-phenthiazin-1-yl, 7-substituted 1,3-(diaza)-2-(oxo)-phenoxazin-1-yl, 7-substituted 1-(aza)-2-(thio)-3-(aza)-phenoxazin-1-yl, 7-substituted 1,3-(diaza)-2-(oxo)-phenthiazin-1-yl, 7-substituted 1-(aza)-2-(thio)-3-(aza)-phenthiazin-1-yl, 7-(aminoalkylhydroxy)-1,3-(diaza)-2-(oxo)-phenoxazin-1-yl, 7-(aminoalkylhydroxy)-1-(aza)-2-(thio)-3-(aza)-phenoxazin-1-yl, 7-(aminoalkylhydroxy)-1,3-(diaza)-2-(oxo)-phenthiazin-1-yl, 7-(aminoalkylhydroxy)-1-(aza)-2-(thio)-3-(aza)-phenthiazin-1-yl, 7-(guanidiniumalkylhydroxy)-1,3-(diaza)-2-(oxo)-phenoxazin-1-yl, 7-(guanidiniumalkylhydroxy)-1-(aza)-2-(thio)-3-(aza)-phenoxazin-1-yl, 7-(guanidiniumalkyl-hydroxy)-1,3-(diaza)-2-(oxo)-phenthiazin-1-yl, 7-(guanidiniumalkylhydroxy)-1-(aza)-2-(thio)-3-(aza)-phenthiazin-1-yl, 1,3,5-(triaza)-2,6-(dioxa)-naphthalene, inosine, xanthine, hypoxanthine, nubularine, tubercidine, isoguanisine, inosinyl, 2-aza-inosinyl, 7-deaza-inosinyl, nitroimidazolyl, nitropyrazolyl, nitrobenzimidazolyl, nitroindazolyl, aminoindolyl, pyrrolopyrimidinyl, 3-(methyl)isocarbostyrilyl, 5-(methyl)isocarbostyrilyl, 3-(methyl)-7-(propynyl)isocarbostyrilyl, 7-(aza)indolyl, 6-(methyl)-7-(aza)indolyl, imidizopyridinyl, 9-(methyl)-imidizopyridinyl, pyrrolopyrizinyl, isocarbostyrilyl, 7-(propynyl)isocarbostyrilyl, propynyl-7-(aza)indolyl, 2,4,5-(trimethyl)phenyl, 4-(methyl)indolyl, 4,6-(dimethyl)indolyl, phenyl, napthalenyl, anthracenyl, phenanthracenyl, pyrenyl, stilbenzyl, tetracenyl, pentacenyl, difluorotolyl, 4-(fluoro)-6-(methyl)benzimidazole, 4-(methyl)benzimidazole, 6-(azo) thymine, 2-pyridinone, 5-nitroindole, 3-nitropyrrole, 6-(aza) pyrimidine, 2-(amino)purine, 2,6-(diamino)purine, 5-substituted pyrimidines, N$^2$-substituted purines, N$^6$-substituted purines, O$^6$-substituted purines, substituted 1,2,4-triazoles, or any O-alkylated or N-alkylated derivatives thereof;

Further purines and pyrimidines include those disclosed in U.S. Pat. No. 3,687,808, hereby incorporated by reference, those disclosed in International Application No. PCT/US09/038,425, filed Mar. 26, 2009, hereby incorporated by reference, those disclosed in the Concise Encyclopedia Of Polymer Science And Engineering, pages 858-859, Kroschwitz, J. I., ed. John Wiley & Sons, 1990, and those disclosed by Englisch et al., Angewandte Chemie, International Edition, 1991, 30, 613.

Cationic Groups

Modifications to oligonucleotides can also include attachment of one or more cationic groups to the sugar, base, and/or the phosphorus atom of a phosphate or modified phosphate backbone moiety. A cationic group can be attached to any atom capable of substitution on a natural, unusual or universal base. A preferred position is one that does not interfere with hybridization, i.e., does not interfere with the hydrogen bonding interactions needed for base pairing. A cationic group can be attached e.g., through the C2' position of a sugar or analogous position in a cyclic or acyclic sugar surrogate. Cationic groups can include e.g., protonated amino groups, derived from e.g., O-AMINE (AMINE=$NH_2$; alkylamino, dialkylamino, heterocyclyl, arylamino, diaryl amino, heteroaryl amino, or diheteroaryl amino, ethylene diamine, polyamino); aminoalkoxy, e.g., $O(CH_2)_n$AMINE, (e.g., AMINE=$NH_2$; alkylamino, dialkylamino, heterocyclyl, arylamino, diaryl amino, heteroaryl amino, or diheteroaryl amino, ethylene diamine, polyamino); amino (e.g. $NH_2$; alkylamino, dialkylamino, heterocyclyl, arylamino, diaryl amino, heteroaryl amino, diheteroaryl amino, or amino acid); or $NH(CH_2CH_2NH)_nCH_2CH_2$-AMINE (AMINE=$NH_2$; alkylamino, dialkylamino, heterocyclyl, arylamino, diaryl amino, heteroaryl amino, or diheteroaryl amino).

End-Caps for Exonuclease Protection

Placement within an Oligonucleotide

Some modifications may preferably be included on an oligonucleotide at a particular location, e.g., at an internal position of a strand, or on the 5' or 3' end of an oligonucleotide. A preferred location of a modification on an oligonucleotide, may confer preferred properties on the agent. For example, preferred locations of particular modifications may confer optimum gene silencing properties, or increased resistance to endonuclease or exonuclease activity.

One or more nucleotides of an oligonucleotide may have a 5'-5', 3'-3',3'-2', 2'-5',2'-3' or a 2'-2' linkage, preferably a 2'-5' linkage. In certain embodiments, the last nucleotide on the terminal end is linked via an inverted linkages, e.g. 3'-3', 5'-5', 2'-2' or 2'-3' linkage to the rest of the oligonucleotide.

An oligonucleotide may comprise at least one 5'-pyrimidine-purine-3' (5'-PyPU-3') dinucleotide motif wherein the pyrimidine ribose sugar is modified at the 2'-position. In certain embodiments, the pyrimidine ribose sugar is replaced by a non ribose moiety, e.g., a six membered ring. In certain other embodiments, the oligonucleotide comprises at least one 5'-pyrimidine-purine-3' (5'-PyPu-3') dinucleotide wherein the ribose sugar of the pyrimidine is modified with a modification chosen independently from a group consisting of 2'-H, 2'-O-Me (2'-O-methyl), 2'-O-MOE (2'-O-methoxyethyl), 2'-F, 2'-O-[2-(methylamino)-2-oxoethyl](2'-O-NMA), 2'-S-methyl, 2'-O—$CH_2$-(4'-C) (LNA) and 2'-O—$CH_2CH_2$-(4'-C) (ENA). In one embodiment, the 5'-most pyrimidines in all occurrences of sequence motif 5'-pyrimidine-purine-3' (5'-PyPu-3') dinucleotide in the oligonucleotide comprise a sugar 2'-modification.

In certain embodiments, the oligonucleotide comprises at least one 5'-PyPu-3' dinucleotide motif where the C5 position of the pyrimidine is conjugated with a stabilizing moiety, e.g., a cationic group. In one embodiment, pyrimidines in all 5'-PyPu-3' dinucleotide motif comprise a stabilizing moiety at the C5 position.

In certain embodiments, the oligonucleotide comprises at least one 5'-PyPu-3' dinucleotide motif where the $N^2$, $N^6$, and/or $C^8$ position of the purine is conjugated with a stabilizing moiety, e.g., a cationic group. In one embodiment, purines in all 5'-PyPu-3' dinucleotide motifs comprise a stabilizing moiety at the $N^2$, $N^6$, and/or $C^8$ position.

In certain embodiments, both the pyrimidine and purine in the 5'-PyPu-3' dinucleotide motif are conjugated with stabilizing groups.

In certain embodiments, the internucleotide linkage between 3'- of a pyrimidine and 5'- of a purine is a non-phosphodiester linkage described herein.

In certain embodiments, the both the pyrimidine and the purine in a 5'-PyPu-3' dinucleotide motif are unmodified and the internucleotide linkage between them is a non-phosphodiester linkage described herein.

In certain embodiments, both the pyrimidine and the purine in a 5'-PyPu-3' dinucleotide motif comprise unmodified sugars, e.g., 2'-OH and at least one of them comprises a nucleobase modification. In one embodiment, both the pyrimidine and the purine in a 5'-PyPu-3' dinucleotide motif comprise unmodified sugars, e.g., 2'-OH and both of them comprise a nucleobase modification.

In certain embodiments, the oligonucleotide comprises at least one 5'-PyPu-3'-dinucleotide motif where the pyrimide comprises a modification at the 2'-position, the internucleotide linkage is a non-phosphodiester linkage and at least one of the pyrimidine and the purine comprises a nucleobase modification. In one embodiment, the pyrimined comprises the nucleobase modification. In another embodiment, the purine comprises the nucleobase modification. In yet another embodiment, both the pyrimidine and the purine comprise the nucleobase modification.

In certain embodiments, the oligonucleotide comprises at least one 5'-PyPu-3'-dinucleotide motif where the purine comprises a modification at the 2'-position, the internucleotide linkage is a non-phosphodiester linkage and at least one of the pyrimidine and the purine comprises a nucleobase modification. In one embodiment, the pyrimined comprises the nucleobase modification. In another embodiment, the purine comprises the nucleobase modification. In yet another embodiment, both the pyrimidine and the purine comprise the nucleobase modification.

In one embodiment, the single stranded siRNA (ss siRNA) and double stranded siRNA (ds siRNA) of the invention comprises a motif selected from the group consisting of:
(a) 2'-modified uridines in all occurrences of the sequence motif 5'-uridine-adenosine-3' (5'-UA-3'),
(b) 2'-modified uridines in all occurrences of the sequence motif 5'-uridine-guanosine-3' (5'-UG-3'),
(c) 2'-modified cytidines in all occurrences of the sequence motif 5'-cytidine-adenosine-3' (5'-CA-3'),
(d) 2'-modified cytidines in all occurrences of the sequence motif 5'-cytidine-Guanosine-3' (5'-CA-3'),
(e) 2'-modified 5'-most uridines in all occurrences of the sequence motif 5'-uridine-uridine-3' (5'-UU-3'),
(f) 2'-modified 5'-most cytidines in all occurrences of the sequence motif 5'-cytidine-cytidine-3' (5'-CC-3'),
(g) 2'-modified cytidines in all occurrences of the sequence motif 5'-cytidine-uridine-3' (5'-CU-3'),
(h) 2'-modified uridines in all occurrences of the sequence motif 5'-uridine-cytidine-3' (5'-UC-3'), and
(h) combinations thereof;

and wherein siRNA comprises at least one modification at internucleotide linkage, nucleobase and/or 2' sugar modification. Examples of the non-phosphodiester modification includes, but not limited to phosphorothioate, phosphorodithioate, phosphotriesters, aminoalkylphosphotriesters, methyl and other alkyl phosphonates, selenophosphates, phosphoramidates and boranophosphates. Examples of the nucleobase modifications include, but not limited to: C-5 pyrimidine with an alkyl group or aminoalkyls and other cationic groups such as guanidinium and amidine functionalities, SH or OH, $N^2$- and $N^6$- of purines with an alkyl group or aminoalkyls and other cationic groups such as guanidinium and amidine functionalities or SH and OH, G-clamps, guanidinium G-clamps, and pseudouridine known in the art or G-clamps and pseudourines provided herein in. Examples of 2' modifications includes those know in the art, as well as ones disclosed herein. In one example, when there is a 2' OH moiety present in the said motif, at least either internucleotide linkage or nucleobase or both must be modified. In another example, 2'-position of the sugar of the 3'-most nucleoside is modified but not of the 5'-most nucleoside and vice versa, then at least either the internucleotide linkage or nucleobase of the 5'-most or 3'-most or both the nucleobase of the motif or both internucleotide linkage and nucleobase must be modified. In another example, both nucleoside in the motif bear unmodified ribo-sugar (i.e., 2'-OH on both nucleoside), then at least either the internucleotide linkage or nucleobase of the 5'-most or 3'-most or both the nucleobase, or both internucleotide linkage and at least one of the nucleobases of the motif must be modified. The preferred nucleobase modification bears a cationic amino group connected via an appropriate alkyl, alkenyl or a tether with an amide linkages.

A double-stranded oligonucleotide may include at least one 5'-uridine-adenine-3' (5'-UA-3') dinucleotide wherein the uridine is a 2'-modified nucleotide, or a terminal 5'-uridine-guanine-3' (5'-UG-3') dinucleotide, wherein the 5'-uridine is a 2'-modified nucleotide, or a terminal 5'-cytidine-adenine-3' (5'-CA-3') dinucleotide, wherein the 5'-cytidine is a 2'-modified nucleotide, or a terminal 5'-uridine-uridine-3' (5'-UU-3') dinucleotide, wherein the 5'-uridine is a 2'-modified nucleotide, or a terminal 5'-cytidine-cytidine-3' (5'-CC-3') dinucleotide, wherein the 5'-cytidine is a 2'-modified nucleotide, or a terminal 5'-cytidine-uridine-3' (5'-CU-3') dinucleotide, wherein the 5'-cytidine is a 2'-modified nucleotide, or a terminal 5'-uridine-cytidine-3' (5'-UC-3') dinucleotide, wherein the 5'-uridine is a 2'-modified nucleotide. Double-stranded oligonucleotides including these modifications are particularly stabilized against endonuclease activity.

Modifications and monomers described herein may be used to asymmetrically modified a double-stranded oligonucleotide. An asymmetrically modified double-stranded oligonucleotide is one in which one strand has a modification which is not present on the other strand. As such, an asymmetrical modification is a modification found on one strand but not on the other strand. Any modification, e.g., any modification described herein, can be present as an asymmetrical modification. An asymmetrical modification can confer any of the desired properties associated with a modification, e.g., those properties discussed herein. For example, an asymmetrical modification can confer resistance to degradation, an alteration in half life; target the oligonucleotide to a particular target, e.g., to a particular tissue; modulate, e.g., increase or decrease, the affinity of a strand for its complement or target sequence; or hinder or promote modification of a terminal moiety, e.g., modification by a kinase or other enzymes involved in the RISC mechanism pathway. The designation of a modification as having one property does not mean that it has no other property, e.g., a modification referred to as one which promotes stabilization might also enhance targeting. Asymmetrical modifications can include those in which only one strand is modified as well as those in which both are modified.

When the two strands of double-stranded oligonucleotide are linked together, e.g. a hairpin or a dumbbell, the two strands of the double stranded region may also be strands forming asymmetrically modified. For example, first strand of the double-stranded region comprises at least one asymmetric modification that is not present in the second strand of the double stranded region or vice versa.

While not wishing to be bound by theory or any particular mechanistic model, it is believed that asymmetrical modification allows a double-stranded RNAi agent to be optimized in view of the different or "asymmetrical" functions of the sense and antisense strands. For example, both strands can be modified to increase nuclease resistance, however, since some changes can inhibit RISC activity, these changes can be chosen for the sense stand. In addition, since some modifications, e.g., a ligand, can add large bulky groups that, e.g., can interfere with the cleavage activity of the RISC complex, such modifications are preferably placed on the sense strand. Thus, ligands, especially bulky ones (e.g. cholesterol), are preferentially added to the sense strand. The ligand may be present at either (or both) the 5' or 3' end of the sense strand of a RNAi agent.

Each strand can include one or more asymmetrical modifications. By way of example: one strand can include a first asymmetrical modification which confers a first property on the oligonucleotide and the other strand can have a second asymmetrical modification which confers a second property on the oligonucleotide. For example, one strand, e.g., the sense strand can have a modification which targets the oligonucleotide to a tissue, and the other strand, e.g., the antisense strand, has a modification which promotes hybridization with the target gene sequence.

In some embodiments both strands can be modified to optimize the same property, e.g., to increase resistance to nucleolytic degradation, but different modifications are chosen for the sense and the antisense strands, because the modifications affect other properties as well.

Multiple asymmetric modifications can be introduced into either or both of the sense and antisense strand. A strand can have at least 1, 2, 3, 4, 5, 6, 7, 8, or more modifications and all or substantially all of the monomers, e.g., nucleotides of a strand can be asymmetrically modified.

In certain embodiments, the asymmetric modifications are chosen so that only one of the two strands of double-stranded RNAi agent is effective in inducing RNAi. Inhibiting the induction of RNAi by one strand may reduce the off target effects due to cleavage of a target sequence by that strand.

General References

The oligoribonucleotides and oligoribonucleosides used in accordance with this invention may be synthesized with solid phase synthesis, see for example "Oligonucleotide synthesis, a practical approach", Ed. M. J. Gait, IRL Press, 1984; "Oligonucleotides and Analogues, A Practical Approach", Ed. F. Eckstein, IRL Press, 1991 (especially Chapter 1, Modern machine-aided methods of oligodeoxyribonucleotide synthesis, Chapter 2, Oligoribonucleotide synthesis, Chapter 3,2'-O-Methyloligoribonucleotide- s: synthesis and applications, Chapter 4, Phosphorothioate oligonucleotides, Chapter 5, Synthesis of oligonucleotide phosphorodithioates, Chapter 6, Synthesis of oligo-2'-deoxyribonucleoside methylphosphonates, and. Chapter 7, Oligodeoxynucleotides containing modified bases. Other particularly useful synthetic procedures, reagents, blocking groups and reaction conditions are described in Martin, P., *Helv. Chim. Acta*, 1995, 78, 486-504; Beaucage, S. L. and Iyer, R. P., *Tetrahedron,* 1992, 48, 2223-2311 and Beaucage, S. L. and Iyer, R. P., *Tetrahedron,* 1993, 49, 6123-6194, or references referred to therein. Modification described in WO 00/44895, WO01/75164, or WO02/44321 can be used herein. The disclosure of all publications, patents, and published patent applications listed herein are hereby incorporated by reference.

Phosphate Group References

The preparation of phosphinate oligoribonucleotides is described in U.S. Pat. No. 5,508,270. The preparation of alkyl phosphonate oligoribonucleotides is described in U.S. Pat. No. 4,469,863. The preparation of phosphoramidite oligoribonucleotides is described in U.S. Pat. Nos. 5,256,775 and 5,366,878. The preparation of phosphotriester oligoribonucleotides is described in U.S. Pat. No. 5,023,243. The preparation of borano phosphate oligoribonucleotide is described in U.S. Pat. Nos. 5,130,302 and 5,177,198. The preparation of 3'-Deoxy-3'-amino phosphoramidate oligoribonucleotides is described in U.S. Pat. No. 5,476,925. 3'-Deoxy-3'-methylenephosphonate oligoribonucleotides is described in An, H, et al. *J. Org. Chem.* 2001, 66, 2789-2801. Preparation of sulfur bridged nucleotides is described in Sproat et al. *Nucleosides Nucleotides* 1988, 7,651 and Crosstick et al. *Tetrahedron Lett.* 1989, 30, 4693.

Sugar Group References

Modifications to the 2' modifications can be found in Verma, S. et al. *Annu. Rev. Biochem.* 1998, 67, 99-134 and all references therein. Specific modifications to the ribose can be found in the following references: 2'-fluoro (Kawasaki et. al., *J. Med. Chem.,* 1993, 36, 831-841), 2'-MOE (Martin, P. *Helv. Chim. Acta* 1996, 79, 1930-1938), "LNA" (Wengel, J. *Acc. Chem. Res.* 1999, 32, 301-310).

Replacement of the Phosphate Group References

Methylenemethylimino linked oligoribonucleosides, also identified herein as MMI linked oligoribonucleosides, methylenedimethylhydrazo linked oligoribonucleosides, also identified herein as MDH linked oligoribonucleosides, and methylenecarbonylamino linked oligonucleosides, also identified herein as amide-3 linked oligoribonucleosides, and methyleneaminocarbonyl linked oligonucleosides, also identified herein as amide-4 linked oligoribonucleosides as well as mixed backbone compounds having, as for instance, alternating MMI and PO or PS linkages can be prepared as is described in U.S. Pat. Nos. 5,378,825, 5,386,023, 5,489,677 and in published PCT applications PCT/US92/04294 and PCT/US92/04305 (published as WO 92/20822 WO and 92/20823, respectively). Formacetal and thioformacetal linked oligoribonucleosides can be prepared as is described in U.S. Pat. Nos. 5,264,562 and 5,264,564. Ethylene oxide linked oligoribonucleosides can be prepared as is described in U.S. Pat. No. 5,223,618. Siloxane replacements are described in Cormier, J. F. et al. *Nucleic Acids Res.* 1988, 16, 4583. Carbonate replacements are described in Tittensor, J. R. *J. Chem. Soc. C* 1971, 1933. Carboxymethyl replacements are described in Edge, M. D. et al. *J. Chem. Soc. Perkin Trans.* 1 1972, 1991. Carbamate replacements are described in Stirchak, E. P. Nucleic Acids Res. 1989, 17, 6129.

Replacement of the Phosphate-Ribose Backbone References

Cyclobutyl sugar surrogate compounds can be prepared as is described in U.S. Pat. No. 5,359,044. Pyrrolidine sugar surrogate can be prepared as is described in U.S. Pat. No. 5,519,134. Morpholino sugar surrogates can be prepared as is described in U.S. Pat. Nos. 5,142,047 and 5,235,033, and other related patent disclosures. Peptide Nucleic Acids (PNAs) are known per se and can be prepared in accordance with any of the various procedures referred to in Peptide Nucleic Acids (PNA): Synthesis, Properties and Potential Applications, Bioorganic & Medicinal Chemistry, 1996, 4, 5-23. They may also be prepared in accordance with U.S. Pat. No. 5,539,083.

Terminal Modification References

Terminal modifications are described in Manoharan, M. et al. *Antisense and Nucleic Acid Drug Development* 12, 103-128 (2002) and references therein.

Bases References

N-2 substituted purine nucleoside amidites can be prepared as is described in U.S. Pat. No. 5,459,255. 3-Deaza purine nucleoside amidites can be prepared as is described in U.S. Pat. No. 5,457,191. 5,6-Substituted pyrimidine nucleoside amidites can be prepared as is described in U.S. Pat. No. 5,614,617. 5-Propynyl pyrimidine nucleoside amidites can be prepared as is described in U.S. Pat. No. 5,484,908. Additional references are disclosed in the above section on base modifications Oligonucleotide Production The oligonucleotide compounds of the invention can be prepared using solution-phase or solid-phase organic synthesis. Organic synthesis offers the advantage that the oligonucleotide strands comprising non-natural or modified nucleotides can be easily prepared. Any other means for such synthesis known in the art may additionally or alternatively be employed. It is also known to use similar techniques to prepare other oligonucleotides, such as the phosphorothioates, phosphorodithioates and alkylated derivatives. The double-stranded oligonucleotide compounds of the invention may be prepared using a two-step procedure. First, the individual strands of the double-stranded molecule are prepared separately. Then, the component strands are annealed.

Regardless of the method of synthesis, the oligonucleotide can be prepared in a solution (e.g., an aqueous and/or organic solution) that is appropriate for formulation. For example, the oligonucleotide preparation can be precipitated and redissolved in pure double-distilled water, and lyophilized. The dried oligonucleotide can then be resuspended in a solution appropriate for the intended formulation process.

Teachings regarding the synthesis of particular modified oligonucleotides may be found in the following U.S. patents or pending patent applications: U.S. Pat. Nos. 5,138,045 and 5,218,105, drawn to polyamine conjugated oligonucleotides; U.S. Pat. No. 5,212,295, drawn to monomers for the preparation of oligonucleotides having chiral phosphorus linkages; U.S. Pat. Nos. 5,378,825 and 5,541,307, drawn to oligonucleotides having modified backbones; U.S. Pat. No. 5,386,023, drawn to backbone-modified oligonucleotides and the preparation thereof through reductive coupling; U.S. Pat. No. 5,457,191, drawn to modified nucleobases based on the 3-deazapurine ring system and methods of synthesis thereof; U.S. Pat. No. 5,459,255, drawn to modified nucleobases based on N-2 substituted purines; U.S. Pat. No. 5,521,302, drawn to processes for preparing oligonucleotides having chiral phosphorus linkages; U.S. Pat. No. 5,539,082, drawn to peptide nucleic acids; U.S. Pat. No. 5,554,746, drawn to oligonucleotides having .beta.-lactam backbones; U.S. Pat. No. 5,571,902, drawn to methods and materials for the synthesis of oligonucleotides; U.S. Pat. No. 5,578,718, drawn to nucleosides having alkylthio groups, wherein such groups may be used as linkers to other moieties attached at any of a variety of positions of the nucleoside; U.S. Pat. Nos. 5,587,361 and 5,599,797, drawn to oligonucleotides having phosphorothioate linkages of high chiral purity; U.S. Pat. No. 5,506,351, drawn to processes for the preparation of 2'-O-alkyl guanosine and related compounds, including 2,6-diaminopurine compounds; U.S. Pat. No. 5,587,469, drawn to oligonucleotides having N-2 substituted purines; U.S. Pat. No. 5,587,470, drawn to oligonucleotides having 3-deazapurines; U.S. Pat. No. 5,223,168, and U.S. Pat. No. 5,608,046, both drawn to conjugated 4'-desmethyl nucleoside analogs; U.S.

Pat. Nos. 5,602,240, and 5,610,289, drawn to backbone-modified oligonucleotide analogs; and U.S. Pat. Nos. 6,262,241, and 5,459,255, drawn to, inter alia, methods of synthesizing 2'-fluoro-oligonucleotides.

Ligands

A wide variety of entities can be coupled to the oligonucleotides of the present invention. Ligands can include naturally occurring molecules, or be recombinant or synthetic molecules. Preferred moieties are ligands, which are coupled, preferably covalently, either directly or indirectly via an intervening tether.

In preferred embodiments, a ligand alters the distribution, targeting or lifetime of the molecule into which it is incorporated. In preferred embodiments a ligand provides an enhanced affinity for a selected target, e.g., molecule, cell or cell type, compartment, e.g., a cellular or organ compartment, tissue, organ or region of the body, as, e.g., compared to a species absent such a ligand. Ligands providing enhanced affinity for a selected target are also termed targeting ligands.

Some ligands can have endosomolytic properties. The endosomolytic ligands promote the lysis of the endosome and/or transport of the composition of the invention, or its components, from cellular compartments such as the endosome, lysosome, endoplasmic reticulum (ER), golgi apparatus, microtubule, peroxisome, or other vesicular bodies within the cell, to the cytoplasm of the cell. The endosomolytic ligand may be a polyanionic peptide or peptidomimetic which shows pH-dependent membrane activity and fusogenicity. In one embodiment, the endosomolytic ligand assumes its active conformation at endosomal pH. The "active" conformation is that conformation in which the endosomolytic ligand promotes lysis of the endosome and/or transport of the composition of the invention, or its components, from the endosome to the cytoplasm of the cell. Exemplary endosomolytic ligands include the GALA peptide (Subbarao et al., Biochemistry, 1987, 26: 2964-2972), the EALA peptide (Vogel et al., J. Am. Chem. Soc., 1996, 118: 1581-1586), and their derivatives (Turk et al., Biochem. Biophys. Acta, 2002, 1559: 56-68). In one embodiment, the endosomolytic component may contain a chemical group (e.g., an amino acid) which will undergo a change in charge or protonation in response to a change in pH. The endosomolytic component may be linear or branched. Exemplary primary sequences of peptide based endosomolytic ligands are shown in Table 1.

TABLE 1

List of peptides with endosomolytic activity.

| Name | Sequence (N to C) | SEQ ID NO: | Ref. |
|---|---|---|---|
| GALA | AALEALAEALEALAEALEALAEAAAAGGC | 2 | 1 |
| EALA | AALAEALAEALAEALAEALAEALAAAAGGC | 3 | 2 |
|  | ALEALAEALEALAEA | 4 | 3 |
| INF-7 | GLFEAIEGFIENGWEGMIWDYG | 5 | 4 |
| Inf HA-2 | GLFGAIAGFIENGWEGMIDGWYG | 6 | 5 |
| diINF-7 | GLF EAI EGFI ENGW EGMI DGWYGC | 7 | 5 |
|  | GLF EAI EGFI ENGW EGMI DGWYGC | 7 |  |
| diINF3 | GLF EAI EGFI ENGW EGMI DGGC | 8 | 6 |
|  | GLF EAI EGFI ENGW EGMI DGGC | 8 |  |
| GLF | GLFGALAEALAEALAEHLAEALAEALEALAAGGSC | 9 | 6 |
| GALA-INF3 | GLFEAIEGFIENGWEGLAEALAEALEALAAGGSC | 10 | 6 |
| INF-5 | GLF EAI EGFI ENGW EGnI DG K | 11 | 4 |
|  | GLF EAI EGFI ENGW EGnI DG | 12 |  | n, norleucine

References
1. Subbarao et al., Biochemistry, 1987, 26: 2964-2972.
2. Vogel et al., J. Am. Chem. Soc., 1996, 118: 1581-1586
3. Turk, M. J., Reddy, J. A. et al. (2002). Characterization of a novel pH-sensitive peptide that enhances drug release from folate-targeted liposomes at endosomal pHs. Biochim. Biophys. Acta 1559, 56-68.
4. Plank, C. Oberhauser, B. Mechtler, K. Koch, C. Wagner, E. (1994). The influence of endosome-disruptive peptides on gene transfer using synthetic virus-like gene transfer systems, J. Biol. Chem. 269 12918-12924.
5. Mastrobattista, E., Koning, G. A. et al. (2002). Functional characterization of an endosome-disruptive peptide and its application in cytosolic delivery of immunoliposome-entrapped proteins. J. Biol. Chem. 277, 27135-43.
6. Oberhauser, B., Plank, C. et al. (1995). Enhancing endosomal exit of nucleic acids using pH-sensitive viral fusion peptides. Deliv. Strategies Antisense Oligonucleotide Ther. 247-66.

Other exemplary endosmolytioc/fusogenic peptides include GLFEALLELLESLWELLLEA (SEQ ID NO: 13) (JTS-1), GLFKALLKLLKSLWKLLLKA (SEQ ID NO: 14) (ppTG1), GLFRALLRLLRSLWRLLLRA (SEQ ID NO: 15) (ppTG20), WEAKLAKALAKALAKHLAKALAKALKA-CEA (SEQ ID NO: 16) (KALA), GLFFEAIAEFIEGGWEG-LIEGC (SEQ ID NO: 17) (HA), GIGAVLKVLTTGLPAL-ISWIKRKRQQ (SEQ ID NO: 18) (Melittin), and histidine rich peptides $H_5WYG$ (SEQ ID NO: 19) and $CHK_6HC$ (SEQ ID NO: 20).

Without wishing to be bound by theory, endosomolytic/fusogenic lipids fuse with and consequently destabilize a membrane. Fusogenic lipids usually have small head groups and unsaturated acyl chains. Exemplary fusogenic lipids include, but are not limited to, 1,2-dileoyl-sn-3-phosphoethanolamine (DOPE), phosphatidylethanolamine (POPE), palmitoyloleoylphosphatidylcholine (POPC), (6Z,9Z,28Z,31Z)-heptatriaconta-6,9,28,31-tetraen-19-ol (Di-Lin), N-methyl(2,2-di((9Z,12Z)-octadeca-9,12-dienyl)-1,3-dioxolan-4-yl)methanamine (DLin-k-DMA) and N-methyl-2-(2,2-di((9Z,12Z)-octadeca-9,12-dienyl)-1,3-dioxolan-4-yl) ethanamine (XTC).

Synthetic polymers with endosomolytic activity amenable to the present invention are described in United States Patent Application Publications Nos. 2009/0048410; 2009/0023890; 2008/0287630; 2008/0287628; 2008/0281044; 2008/0281041; 2008/0269450; 2007/0105804; 20070036865; and 2004/0198687, contents of which are hereby incorporated by reference in their entirety.

Ligands can improve transport, hybridization, and specificity properties and may also improve nuclease resistance of the resultant natural or modified oligoribonucleotide, or a polymeric molecule comprising any combination of monomers described herein and/or natural or modified ribonucleotides.

Ligands in general can include therapeutic modifiers, e.g., for enhancing uptake; diagnostic compounds or reporter groups e.g., for monitoring distribution; cross-linking agents; and nuclease-resistance conferring moieties. General examples include lipids, steroids, vitamins, sugars, proteins, peptides, polyamines, and peptide mimics.

Ligands can include a naturally occurring substance, such as a protein (e.g., human serum albumin (HSA), low-density lipoprotein (LDL), high-density lipoprotein (HDL), or globulin); an carbohydrate (e.g., a dextran, pullulan, chitin, chitosan, inulin, cyclodextrin or hyaluronic acid); or a lipid. The ligand may also be a recombinant or synthetic molecule, such as a synthetic polymer, e.g., a synthetic polyamino acid, an oligonucleotide (e.g. an aptamer). Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-gulucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, an RGD peptide, an RGD peptide mimetic or an aptamer. Table 2 shows some examples of targeting ligands and their associated receptors.

TABLE 2

Targeting Ligands and their associated receptors

| Liver Cells | Ligand | Receptor |
|---|---|---|
| 1) Parenchymal Cell (PC) (Hepatocytes) | Galactose | ASGP-R (Asiologlycoprotein receptor) |
|  | Gal NAc (n-acetyl-galactosamine) | ASPG-R Gal NAc Receptor |
|  | Lactose |  |
|  | Asialofetuin | ASPG-r |
| 2) Sinusoidal Endothelial Cell (SEC) | Hyaluronan | Hyaluronan receptor |
|  | Procollagen | Procollagen receptor |
|  | Negatively charged molecules | Scavenger receptors |
|  | Mannose | Mannose receptors |
|  | N-acetyl Glucosamine | Scavenger receptors |
|  | Immunoglobulins | Fc Receptor |
|  | LPS | CD14 Receptor |
|  | Insulin | Receptor mediated transcytosis |
|  | Transferrin | Receptor mediated transcytosis |
|  | Albumins | Non-specific |
|  | Sugar-Albumin conjugates |  |
|  | Mannose-6-phosphate | Mannose-6-phosphate receptor |
| 3) Kupffer Cell (KC) | Mannose | Mannose receptors |
|  | Fucose | Fucose receptors |
|  | Albumins | Non-specific |
|  | Mannose-albumin conjugates |  |

Other examples of ligands include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g, cholesterol, cholic acid, adamantane acetic acid, 1-pyrene butyric acid, dihydrotestosterone, 1,3-Bis-O (hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-gulucosamine multivalent mannose, multivalent fucose, or aptamers. The ligand can be, for example, a lipopolysaccharide, an activator of p38 MAP kinase, or an activator of NF-κB.

The ligand can be a substance, e.g, a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

The ligand can increase the uptake of the oligonucleotide into the cell by activating an inflammatory response, for example. Exemplary ligands that would have such an effect include tumor necrosis factor alpha (TNFalpha), interleukin-1 beta, or gamma interferon.

In one aspect, the ligand is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In a preferred embodiment, the lipid based ligand binds HSA. Preferably, it binds HSA with a sufficient affinity such that the conjugate will be preferably distributed to a non-kidney tissue. However, it is preferred that the affinity not be so strong that the HSA-ligand binding cannot be reversed.

In another preferred embodiment, the lipid based ligand binds HSA weakly or not at all, such that the conjugate will be preferably distributed to the kidney. Other moieties that target to kidney cells can also be used in place of or in addition to the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by cancer cells. Also included are HAS, low density lipoprotein (LDL) and high-density lipoprotein (HDL).

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The peptide or peptidomimetic moiety can be about 5-50 amino acids long, e.g., about 5, 10, 15, 20, 25, 30, 35, 40, 45, or 50 amino acids long (see Table 3, for example).

TABLE 3

Exemplary Cell Permeation Peptides.

| Cell Permeation Peptide | Amino acid Sequence | SEQ ID NO: | Reference |
| --- | --- | --- | --- |
| Penetratin | RQIKIWFQNRRMKWKK | 21 | Derossi et al., J. Biol. Chem. 269: 10444, 1994 |
| Tat fragment (48-60) | GRKKRRQRRRPPQC | 22 | Vives et al., J. Biol. Chem., 272: 16010, 1997 |
| Signal Sequence-based peptide | GALFLGWLGAAGSTMGAWSQPKKKRKV | 23 | Chaloin et al., Biochem. Biophys. Res. Commun., 243: 601, 1998 |
| PVEC | LLIILRRRIRKQAHAHSK | 24 | Elmquist et al., Exp. Cell Res., 269: 237, 2001 |
| Transportan | GWTLNSAGYLLKINLKALAALAKKIL | 25 | Pooga et al., FASEB J., 12: 67, 1998 |
| Amphiphilic model peptide | KLALKLALKALKAALKLA | 26 | Oehlke et al., Mol. Ther., 2: 339, 2000 |
| Arg$_9$ | RRRRRRRRR | 27 | Mitchell et al., J. Pept. Res., 56: 318, 2000 |
| Bacterial cell wall permeating | KFFKFFKFFK | 28 | |
| LL-37 | LLGDFFRKSKEKIGKEFKRIVQRIKDFLRNLVPRTES | 29 | |
| Cecropin P1 | SWLSKTAKKLENSAKKRISEGIAIAIQGGPR | 30 | |
| a-defensin | ACYCRIPACIAGERRYGTCIYQGRLWAFCC | 31 | |
| b-defensin | DHYNCVSSGGQCLYSACPIFTKIQGTC | 32 | |

TABLE 3-continued

Exemplary Cell Permeation Peptides.

| Cell Permeation Peptide | Amino acid Sequence | SEQ ID NO: | Reference |
|---|---|---|---|
| | YRGKAKCCK | | |
| Bactenecin | RKCRIVVIRVCR | 33 | |
| PR-39 | RRRPRPPYLPRPRPPPFFPPRLPPRIPPGF PPRFPPRFPGKR-NH2 | 34 | |
| Indolicidin | ILPWKWPWWPWRR-NH2 | 35 | |

A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVLLALLAP (SEQ ID NO: 36). An RFGF analogue (e.g., amino acid sequence AALLPVLLAAP (SEQ ID NO: 37)) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ (SEQ ID NO: 38)) and the Drosophila Antennapedia protein (RQIKIWFQNRRMKWKK (SEQ ID NO: 39)) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-84, 1991). Preferably the peptide or peptidomimetic tethered to an iRNA agent via an incorporated monomer unit is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

An RGD peptide moiety can be used to target a tumor cell, such as an endothelial tumor cell or a breast cancer tumor cell (Zitzmann et al., Cancer Res., 62:5139-43, 2002). An RGD peptide can facilitate targeting of an iRNA agent to tumors of a variety of other tissues, including the lung, kidney, spleen, or liver (Aoki et al., Cancer Gene Therapy 8:783-787, 2001). Preferably, the RGD peptide will facilitate targeting of an iRNA agent to the kidney. The RGD peptide can be linear or cyclic, and can be modified, e.g., glycosylated or methylated to facilitate targeting to specific tissues. For example, a glycosylated RGD peptide can deliver an iRNA agent to a tumor cell expressing $\alpha_v\beta_3$ (Haubner et al., Jour. Nucl. Med., 42:326-336, 2001).

Peptides that target markers enriched in proliferating cells can be used. E.g., RGD containing peptides and peptidomimetics can target cancer cells, in particular cells that exhibit an integrin receptor. Thus, one could use RGD peptides, cyclic peptides containing RGD, RGD peptides that include D-amino acids, as well as synthetic RGD mimics. In addition to RGD, one can use other moieties that target the integrin ligand. Generally, such ligands can be used to control proliferating cells and angiogeneis. Preferred conjugates of this type ligands that targets PECAM-1, VEGF, or other cancer gene, e.g., a cancer gene described herein.

A "cell permeation peptide" is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003).

In one embodiment, a targeting peptide can be an amphipathic α-helical peptide. Exemplary amphipathic α-helical peptides include, but are not limited to, cecropins, lycotoxins, paradaxins, buforin, CPF, bombinin-like peptide (BLP), cathelicidins, ceratotoxins, S. clava peptides, hagfish intestinal antimicrobial peptides (HFIAPs), magainines, brevinins-2, dermaseptins, melittins, pleurocidin, $H_2A$ peptides, Xenopus peptides, esculentinis-1, and caerins. A number of factors will preferably be considered to maintain the integrity of helix stability. For example, a maximum number of helix stabilization residues will be utilized (e.g., leu, ala, or lys), and a minimum number helix destabilization residues will be utilized (e.g., proline, or cyclic monomeric units. The capping residue will be considered (for example Gly is an exemplary N-capping residue and/or C-terminal amidation can be used to provide an extra H-bond to stabilize the helix. Formation of salt bridges between residues with opposite charges, separated by i±3, or i±4 positions can provide stability. For example, cationic residues such as lysine, arginine, homo-arginine, ornithine or histidine can form salt bridges with the anionic residues glutamate or aspartate.

Peptide and peptidomimetic ligands include those having naturally occurring or modified peptides, e.g., D or L peptides; α, β, or γ peptides; N-methyl peptides; azapeptides; peptides having one or more amide, i.e., peptide, linkages replaced with one or more urea, thiourea, carbamate, or sulfonyl urea linkages; or cyclic peptides.

The targeting ligand can be any ligand that is capable of targeting a specific receptor. Examples are: folate, GalNAc, galactose, mannose, mannose-6P, clusters of sugars such as GalNAc cluster, mannose cluster, galactose cluster, or an apatamer. A cluster is a combination of two or more sugar units. Such sugar units may be linked to each other through glycosisidc linkages or linked to a scaffold molecule.

A number of folate and folate analogs amenable to the present invention as ligands are described in U.S. Pat. Nos.

2,816,110; 51410,104; 5,552,545; 6,335,434 and 7,128,893, contents which are herein incorporated in their entireties by reference.

The targeting ligands also include integrin receptor ligands, Chemokine receptor ligands, transferrin, biotin, serotonin receptor ligands, PSMA, endothelin, GCPII, somatostatin, LDL and HDL ligands. The ligands can also be based on nucleic acid, e.g., an aptamer. The aptamer can be unmodified or have any combination of modifications disclosed herein.

Endosomal release agents include imidazoles, poly or oligoimidazoles, PEIs, peptides, fusogenic peptides, polycarboxylates, polyacations, masked oligo or poly cations or anions, acetals, polyacetals, ketals/polyketyals, orthoesters, polymers with masked or unmasked cationic or anionic charges, dendrimers with masked or unmasked cationic or anionic charges.

PK modulator stands for pharmacokinetic modulator and refers to molecules which can modulate the pharmacokinetics of a molecule to which they are conjugated. PK modulator include lipophiles, bile acids, steroids, phospholipid analogues, peptides, protein binding agents, PEG, vitamins etc. Exemplary PK modulator include, but are not limited to, cholesterol, fatty acids, cholic acid, lithocholic acid, dialkylglycerides, diacylglyceride, phospholipids, sphingolipids, naproxen, ibuprofen, vitamin E, biotin etc. Oligonucleotides that comprise a number of phosphorothioate linkages are also known to bind to serum protein, thus short oligonucleotides, e.g. oligonucleotides of about 5 bases, 10 bases, 15 bases or 20 bases, comprising multiple of phosphorothioate linkages in the backbone are also amenable to the present invention as ligands (e.g. as PK modulating ligands).

In addition, aptamers that bind serum components (e.g. serum proteins) are also amenable to the present invention as PK modulating ligands.

Other ligand conjugates amenable to the invention are described in copending applications U.S. Ser. No. 10/916,185, filed Aug. 10, 2004; U.S. Ser. No. 10/946,873, filed Sep. 21, 2004; U.S. Ser. No. 10/833,934, filed Aug. 3, 2007; U.S. Ser. No. 11/115,989 filed Apr. 27, 2005 and U.S. Ser. No. 11/944,227 filed Nov. 21, 2007, U.S. Ser. No. 10/985,426, filed Nov. 9, 2004; U.S. Ser. No. 11/119,533, filed Apr. 29, 2005; U.S. Ser. No. 11/197,753, filed Aug. 4, 2005; U.S. Ser. No. 12/328,528, filed Dec. 4, 2008; and U.S. Ser. No. 12/328,537, filed Dec. 4, 2008, contents which are herein incorporated in their entireties for all purposes. Ligands and ligand conjugated monomers amenable to the invention are also described in International Application Nos. PCT/US04/001461, filed Jan. 21, 2004; PCT/US04/010586, filed Apr. 5, 2004; PCT/US04/011255, filed Apr. 9, 2005; PCT/US05/014472, filed Apr. 27, 2005; PCT/US05/015305, filed Apr. 29, 2005; PCT/US05/027722, filed Aug. 4, 2005; PCT/US08/061,289, filed Apr. 23, 2008; PCT/US08/071,576, filed Jul. 30, 2008; PCT/US08/085,574, filed Dec. 4, 2008 and PCT/US09/40274, filed Apr. 10, 2009, which are incorporated by reference in their entireties for all purposes.

When two or more ligands are present, the ligands can all have same properties, all have different properties or some ligands have the same properties while others have different properties. For example, a ligand can have targeting properties, have endosomolytic activity or have PK modulating properties. In a preferred embodiment, all the ligands have different properties.

Ligands can be coupled to the oligonucleotides at various places, for example, 3'-end, 5'-end, and/or at an internal position. In preferred embodiments, the ligand is attached to the oligonucleotides via an intervening tether, e.g. a carrier described herein. The ligand or tethered ligand may be present on a monomer when the monomer is incorporated into the growing strand. Such monomers are also referred to as carrier monomers herein. The carrier monomer is a cyclic group or acyclic group; preferably, the cyclic group is selected from pyrrolidinyl, pyrazolinyl, pyrazolidinyl, imidazolinyl, imidazolidinyl, piperidinyl, piperazinyl, [1,3]-dioxolane, oxazolidinyl, isoxazolidinyl, morpholinyl, thiazolidinyl, isothiazolidinyl, quinoxalinyl, pyridazinonyl, tetrahydrofuryl and decalin; preferably, the acyclic group is selected from serinol backbone or diethanolamine backbone. In certain embodiments, the ligand is conjugated with a nucleoside monomer before incorporation of such nucleoside to the oligonucleotide.

In some embodiments, the ligand may be incorporated via coupling to a "precursor" monomer after the "precursor" monomer has been incorporated into the growing strand. For example, a monomer having, e.g., an amino-terminated tether (i.e., having no associated ligand), e.g., monomer-$(CH_2)_n$NH$_2$ may be incorporated into a growing oligonucleotide strand. In a subsequent operation, i.e., after incorporation of the precursor monomer into the strand, a ligand having an electrophilic group, e.g., a pentafluorophenyl ester or aldehyde group, can subsequently be attached to the precursor monomer by coupling the electrophilic group of the ligand with the terminal nucleophilic group of the precursor monomer's tether.

In another example, a monomer having a chemical group suitable for taking part in Click Chemistry reaction may be incorporated e.g., an azide or alkyne terminated tether/linker. In a subsequent operation, i.e., after incorporation of the precursor monomer into the strand, a ligand having complementary chemical group, e.g. an alkyne or azide can be attached to the precursor monomer by coupling the alkyne and the azide together.

For double-stranded oligonucleotides, ligands can be attached to one or both strands. In some embodiments, a double-stranded iRNA agent contains a ligand conjugated to the sense strand. In other embodiments, a double-stranded iRNA agent contains a ligand conjugated to the antisense strand.

In some embodiments, ligand can be conjugated to nucleobases, sugar moieties, or internucleosidic linkages of nucleic acid molecules. Conjugation to purine nucleobases or derivatives thereof can occur at any position including, endocyclic and exocyclic atoms. In some embodiments, the 2-, 6-, 7-, or 8-positions of a purine nucleobase are attached to a conjugate moiety. Conjugation to pyrimidine nucleobases or derivatives thereof can also occur at any position. In some embodiments, the 2-, 5-, and 6-positions of a pyrimidine nucleobase can be substituted with a conjugate moiety. Conjugation to sugar moieties of nucleosides can occur at any carbon atom. Example carbon atoms of a sugar moiety that can be attached to a conjugate moiety include the 2', 3', and 5' carbon atoms. The 1' position can also be attached to a conjugate moiety, such as in an abasic residue. Internucleosidic linkages can also bear conjugate moieties. For phosphorus-containing linkages (e.g., phosphodiester, phosphorothioate, phosphorodithiotate, phosphoroamidate, and the like), the conjugate moiety can be attached directly to the phosphorus atom or to an O, N, or S atom bound to the phosphorus atom. For amine- or amide-containing internucleosidic linkages (e.g., PNA), the conjugate moiety can be attached to the nitrogen atom of the amine or amide or to an adjacent carbon atom.

There are numerous methods for preparing conjugates of oligonucleotides. Generally, an oligomeric compound is attached to a conjugate moiety by contacting a reactive group (e.g., OH, SH, amine, carboxyl, aldehyde, and the like) on the oligomeric compound with a reactive group on the conjugate moiety. In some embodiments, one reactive group is electrophilic and the other is nucleophilic.

For example, an electrophilic group can be a carbonyl-containing functionality and a nucleophilic group can be an amine or thiol. Methods for conjugation of nucleic acids and related oligonucleotides with and without linking groups are well described in the literature such as, for example, in Manoharan in Antisense Research and Applications, Crooke and LeBleu, eds., CRC Press, Boca Raton, Fla., 1993, Chapter 17, which is incorporated herein by reference in its entirety.

Representative United States patents that teach the preparation of oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,149,782; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928; 5,672,662; 5,688,941; 5,714,166; 6,153,737; 6,172,208; 6,300,319; 6,335,434; 6,335,437; 6,395,437; 6,444,806; 6,486,308; 6,525,031; 6,528,631; 6,559,279; each of which is herein incorporated by reference.

Linkers

In one embodiment, the covalent linkages between the oligonucleotide and other components, e.g. a ligand or a ligand carrying monomer may be mediated by a linker. This linker may be cleavable or non-cleavable, depending on the application. In one embodiment, a cleavable linker may be used to release the nucleic acid after transport to the desired target. The intended nature of the conjugation or coupling interaction, or the desired biological effect, will determine the choice of linker group.

The term "linker" means an organic moiety that connects two parts of a compound. Linkers typically comprise a direct bond or an atom such as oxygen or sulfur, a unit such as $NR^1$, $C(O)$, $C(O)NH$, $SO$, $SO_2$, $SO_2NH$ or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylheterocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, where one or more methylenes can be interrupted or terminated by O, S, S(O), $SO_2$, $N(R^1)_2$, C(O), cleavable linking group, substituted or unsubstituted aryl, substituted or unsubstituted heteroaryl, substituted or unsubstituted heterocyclic; where $R^1$ is hydrogen, acyl, aliphatic or substituted aliphatic.

In one embodiment, the linker is —[(P-Q-R)$_q$—X—(P'-Q'-R')$_{q'}$]$_{q''}$-T-, wherein:

P, R, T, P' and R' are each independently for each occurrence absent, CO, NH, O, S, OC(O), NHC(O), $CH_2$, $CH_2NH$, $CH_2O$; $NHCH(R^a)C(O)$, —C(O)—CH(R$^a$)—NH—, C(O)-(optionally substituted alkyl)-NH—, CH=N—O,

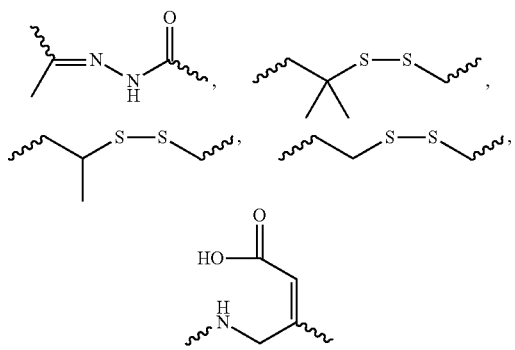

or heterocyclyl;

Q and Q' are each independently for each occurrence absent, —(CH$_2$)$_n$—, —C(R$^{100}$)(R$^{200}$)(CH$_2$)$_n$—, —(CH$_2$)$_n$C(R$^{100}$)(R$^{200}$)—, —(CH$_2$CH$_2$O)$_m$CH$_2$CH$_2$—, or —(CH$_2$CH$_2$O)$_m$CH$_2$CH$_2$NH—;

X is absent or a cleavable linking group;

$R^a$ is H or an amino acid side chain;

$R^{100}$ and $R^{200}$ are each independently for each occurrence H, CH$_3$, OH, SH or N(R$^X$)$_2$;

$R^X$ is independently for each occurrence H, methyl, ethyl, propyl, isopropyl, butyl or benzyl;

q, q' and q" are each independently for each occurrence 0-20 and wherein the repeating unit can be the same or different;

n is independently for each occurrence 1-20; and m is independently for each occurrence 0-50.

In one embodiment, the linker comprises at least one cleavable linking group.

In one embodiment, the linker is a branched linker. The branchpoint of the branched linker may be at least trivalent, but may be a tetravalent, pentavalent or hexavalent atom, or a group presenting such multiple valencies. In one embodiment, the branchpoint is, —N, —N(Q)-C, —O—C, —S—C, —SS—C, —C(O)N(Q)-C, —OC(O)N(Q)-C, —N(Q)C(O)—C, or —N(Q)C(O)O—C; wherein Q is independently for each occurrence H or optionally substituted alkyl. In other embodiment, the branchpoint is glycerol or a glycerol derivative.

Cleavable Linking Groups

A cleavable linking group is one which is sufficiently stable outside the cell, but which upon entry into a target cell is cleaved to release the two parts the linker is holding together. In a preferred embodiment, the cleavable linking group is cleaved at least 10 times or more, preferably at least 100 times faster in the target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred pH, thereby releasing the cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. For example, liver targeting ligands can be linked to the cationic lipids through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It may be useful to make initial evaluations in cell-free or culture conditions and to confirm by further evaluations in whole animals. In preferred embodiments, useful candidate compounds are cleaved at least 2, 4, 10 or 100 times faster in the cell (or under in vitro conditions selected to mimic intracellular conditions) as compared to blood or serum (or under in vitro conditions selected to mimic extracellular conditions).

Redox Cleavable Linking Groups

One class of cleavable linking groups are redox cleavable linking groups that are cleaved upon reduction or oxidation. An example of reductively cleavable linking group is a disulphide linking group (—S—S—). To determine if a candidate cleavable linking group is a suitable "reductively cleavable linking group," or for example is suitable for use with a particular iRNA moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In a preferred embodiment, candidate compounds are cleaved by at most 10% in the blood. In preferred embodiments, useful candidate compounds are degraded at least 2, 4, 10 or 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

Phosphate-Based Cleavable Linking Groups

Phosphate-based cleavable linking groups are cleaved by agents that degrade or hydrolyze the phosphate group. An example of an agent that cleaves phosphate groups in cells are enzymes such as phosphatases in cells. Examples of phosphate-based linking groups are —O—P(O)(ORk)-O—, —O—P(S)(ORk)-O—, —O—P(S)(SRk)-O—, —S—P(O)(ORk)-O—, —O—P(O)(ORk)-S—, —S—P(O)(ORk)-S—, —O—P(S)(ORk)-S—, —S—P(S)(ORk)-O—, —O—P(O)(Rk)-O—, —O—P(S)(Rk)-O—, —S—P(O)(Rk)-O—, —S—P(S)(Rk)-O—, —S—P(O)(Rk)-S—, —O—P(S)(Rk)-S—, where Rk is a metal counter ion, H or optionally substituted alkyl. Preferred counter ions are alkali metal or transition metal ions with an overall charge of +1. Preferred embodiments are —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, —O—P(S)(H)—S—. A preferred embodiment is —O—P(O)(OH)—O—. These candidates can be evaluated using methods analogous to those described above.

Acid Cleavable Linking Groups

Acid cleavable linking groups are linking groups that are cleaved under acidic conditions. In preferred embodiments acid cleavable linking groups are cleaved in an acidic environment with a pH of about 6.5 or lower (e.g., about 6.0, 5.5, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C=NN—, C(O)O, or —OC(O). A preferred embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

Ester-Based Linking Groups

Ester-based cleavable linking groups are cleaved by enzymes such as esterases and amidases in cells. Examples of ester-based cleavable linking groups include but are not limited to esters of alkylene, alkenylene and alkynylene groups. Ester cleavable linking groups have the general formula —C(O)O—, or —OC(O)—. These candidates can be evaluated using methods analogous to those described above.

Peptide-Based Cleaving Groups

Peptide-based cleavable linking groups are cleaved by enzymes such as peptidases and proteases in cells. Peptide-based cleavable linking groups are peptide bonds formed between amino acids to yield oligopeptides (e.g., dipeptides, tripeptides etc.) and polypeptides. Peptide-based cleavable groups do not include the amide group (—C(O)NH—). The amide group can be formed between any alkylene, alkenylene or alkynelene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide-based cleavable linking groups have the general formula —NHCHR$^A$C(O)NH-CHR$^B$C(O)—, where R$^A$ and R$^B$ are the R groups of the two adjacent amino acids. These candidates can be evaluated using methods analogous to those described above.

Formulations

For ease of exposition the formulations, compositions and methods in this section are discussed largely with regard to RNAi agents. It may be understood, however, that these formulations, compositions and methods can be practiced with other oligonucleotides of the invention, e.g., antisense, antagomir, aptamer and ribozyme, and such practice is within the invention.

A formulated RNAi composition can assume a variety of states. In some examples, the composition is at least partially crystalline, uniformly crystalline, and/or anhydrous (e.g., less than 80, 50, 30, 20, or 10% water). In another example, the RNAi is in an aqueous phase, e.g., in a solution that includes water.

The aqueous phase or the crystalline compositions can, e.g., be incorporated into a delivery vehicle, e.g., a liposome (particularly for the aqueous phase) or a particle (e.g., a microparticle as can be appropriate for a crystalline composition). Generally, the RNAi composition is formulated in a manner that is compatible with the intended method of administration.

In particular embodiments, the composition is prepared by at least one of the following methods: spray drying, lyophilization, vacuum drying, evaporation, fluid bed drying, or a combination of these techniques; or sonication with a lipid, freeze-drying, condensation and other self-assembly.

An RNAi preparation can be formulated in combination with another agent, e.g., another therapeutic agent or an agent that stabilizes the RNAi agent, e.g., a protein that complex with RNAi agent to form an iRNP. Still other agents include chelators, e.g., EDTA (e.g., to remove divalent cations such as $Mg^{2+}$), salts, RNAse inhibitors (e.g., a broad specificity RNAse inhibitor such as RNAsin) and so forth.

In one embodiment, the RNAi preparation includes another RNAi agent, e.g., a second RNAi that can mediated RNAi with respect to a second gene, or with respect to the same gene. Still other preparation can include at least 3, 5, ten, twenty, fifty, or a hundred or more different RNAi species. Such RNAi agents can mediate RNAi with respect to a similar number of different genes.

In one embodiment, the RNAi preparation includes at least a second therapeutic agent (e.g., an agent other than RNA or DNA). For example, an RNAi composition for the treatment of a viral disease, e.g., HIV, might include a known antiviral agent (e.g., a protease inhibitor or reverse transcriptase inhibitor). In another example, an RNAi agent composition for the treatment of a cancer might further comprise a chemotherapeutic agent.

Exemplary formulations are discussed below:

Liposomes

The oligonucleotides of the invention, e.g. antisense, antagomir, aptamer, ribozyme and RNAi agent can be formulated in liposomes. As used herein, a liposome is a structure having lipid-containing membranes enclosing an aqueous interior. Liposomes may have one or more lipid membranes. Liposomes may be characterized by membrane type and by size. Small unilamellar vesicles (SUVs) have a single membrane and typically range between 0.02 and 0.05 µm in diameter; large unilamellar vesicles (LUVS) are typically larger than 0.05 µm. Oligolamellar large vesicles and multilamellar vesicles have multiple, usually concentric, membrane layers and are typically larger than 0.1 µm. Liposomes with several nonconcentric membranes, i.e., several smaller vesicles contained within a larger vesicle, are termed multivesicular vesicles.

Liposomes may further include one or more additional lipids and/or other components such as cholesterol. Other lipids may be included in the liposome compositions for a variety of purposes, such as to prevent lipid oxidation, to stabilize the bilayer, to reduce aggregation during formation or to attach ligands onto the liposome surface. Any of a number of lipids may be present, including amphipathic, neutral, cationic, and anionic lipids. Such lipids can be used alone or in combination.

Additional components that may be present in a liposomes include bilayer stabilizing components such as polyamide oligomers (see, e.g., U.S. Pat. No. 6,320,017), peptides, proteins, detergents, lipid-derivatives, such as PEG conjugated to phosphatidylethanolamine, PEG conjugated to phosphatidic acid, PEG conjugated to ceramides (see, U.S. Pat. No. 5,885,613), PEG conjugated dialkylamines and PEG conjugated 1,2-diacyloxypropan-3-amines.

Liposome can include components selected to reduce aggregation of lipid particles during formation, which may result from steric stabilization of particles which prevents charge-induced aggregation during formation. Suitable components that reduce aggregation include, but are not limited to, polyethylene glycol (PEG)-modified lipids, monosialoganglioside Gm1, and polyamide oligomers ("PAO") such as (described in U.S. Pat. No. 6,320,017). Exemplary suitable PEG-modified lipids include, but are not limited to, PEG-modified phosphatidylethanolamine and phosphatidic acid, PEG-ceramide conjugates (e.g., PEG-CerC14 or PEG-CerC20), PEG-modified dialkylamines and PEG-modified 1,2-diacyloxypropan-3-amines. Particularly preferred are PEG-modified diacylglycerols and dialkylglycerols. Other compounds with uncharged, hydrophilic, steric-barrier moieties, which prevent aggregation during formation, like PEG, Gm1, or ATTA, can also be coupled to lipids to reduce aggregation during formation. ATTA-lipids are described, e.g., in U.S. Pat. No. 6,320,017, and PEG-lipid conjugates are described, e.g., in U.S. Pat. Nos. 5,820,873, 5,534,499 and 5,885,613. Typically, the concentration of the lipid component selected to reduce aggregation is about 1 to 15% (by mole percent of lipids). It should be noted that aggregation preventing compounds do not necessarily require lipid conjugation to function properly. Free PEG or free ATTA in solution may be sufficient to prevent aggregation. If the liposomes are stable after formulation, the PEG or ATTA can be dialyzed away before administration to a subject.

Neutral lipids, when present in the liposome composition, can be any of a number of lipid species which exist either in an uncharged or neutral zwitterionic form at physiological pH. Such lipids include, for example diacylphosphatidylcholine, diacylphosphatidylethanolamine, ceramide, sphingomyelin, dihydrosphingomyelin, cephalin, and cerebrosides. The selection of neutral lipids for use in liposomes described herein is generally guided by consideration of, e.g., liposome size and stability of the liposomes in the bloodstream. Preferably, the neutral lipid component is a lipid having two acyl groups, (i.e., diacylphosphatidylcholine and diacylphosphatidylethanolamine). Lipids having a variety of acyl chain groups of varying chain length and degree of saturation are available or may be isolated or synthesized by well-known techniques. In one group of embodiments, lipids containing saturated fatty acids with carbon chain lengths in the range of $C_{14}$ to $C_{22}$ are preferred. In another group of embodiments, lipids with mono or diunsaturated fatty acids with carbon chain lengths in the range of $C_{14}$ to $C_{22}$ are used. Additionally, lipids having mixtures of saturated and unsaturated fatty acid chains can be used. Preferably, the neutral lipids used in the present invention are DOPE, DSPC, POPC, DMPC, DPPC or any related phosphatidylcholine. The neutral lipids useful in the present invention may also be composed of sphingomyelin, dihydrosphingomyeline, or phospholipids with other head groups, such as serine and inositol.

The sterol component of the lipid mixture, when present, can be any of those sterols conventionally used in the field of liposome, lipid vesicle or lipid particle preparation. A preferred sterol is cholesterol.

Cationic lipids, when present in the liposome composition, can be any of a number of lipid species which carry a net positive charge at about physiological pH. Such lipids include, but are not limited to, N,N-dioleyl-N,N-dimethylammonium chloride ("DODAC"); N-(2,3-dioleyloxy)propyl-N, N—N-triethylammonium chloride ("DOTMA"); N,N-distearyl-N,N-dimethylammonium bromide ("DDAB"); N-(2, 3-dioleoyloxy)propyl)-N,N,N-trimethylammonium chloride ("DOTAP"); 1,2-Dioleyloxy-3-trimethylaminopropane chloride salt ("DOTAP.Cl"); 3β-(N—(N',N'-dimethylaminoethane)-carbamoyl)cholesterol ("DC-Chol"), N-(1-(2,3-dioleyloxy)propyl)-N-2-(sperminecarboxamido)ethyl)-N,N-dimethylammonium trifluoracetate ("DOSPA"), dioctadecylamidoglycyl carboxyspermine ("DOGS"), 1,2-dileoyl-sn-3-phosphoethanolamine ("DOPE"), 1,2-dioleoyl-3-dimethylammonium propane ("DODAP"), N, N-dimethyl-2,3-dioleyloxy)propylamine ("DODMA"), N-(1,2-dimyristyloxyprop-3-yl)-N,N-dimethyl-N-hydroxyethyl ammonium bromide ("DMRIE"), 5-carboxyspermylglycine diocaoleyamide ("DOGS"), and dipalmitoylphosphatidylethanolamine 5-carboxyspermyl-amide ("DPPES"). Additionally, a number of commercial preparations of cationic lipids can be used, such as, e.g., LIPOFECTIN (including DOTMA and DOPE, available from GIBCO/BRL), and LIPOFECTAMINE (comprising DOSPA and DOPE, available from GIBCO/BRL). Other cationic lipids suitable for lipid particle formation are described in WO98/39359, WO96/37194. Other cationic lipids suitable for liposome formation are described in U.S. Provisional applications No. 61/018,616 (filed Jan. 2, 2008), No. 61/039,748 (filed Mar. 26, 2008), No. 61/047,087 (filed Apr. 22, 2008) and No. 61/051,528 (filed May 21, 2008), all of which are incorporated by reference in their entireties for all purposes.

Anionic lipids, when present in the liposome composition, can be any of a number of lipid species which carry a net negative charge at about physiological pH. Such lipids include, but are not limited to, phosphatidylglycerol, cardiolipin, diacylphosphatidylserine, diacylphosphatidic acid, N-dodecanoyl phosphatidylethanoloamine, N-succinyl phosphatidylethanolamine, N-glutaryl phosphatidylethanolamine, lysylphosphatidylglycerol, and other anionic modifying groups joined to neutral lipids.

"Amphipathic lipids" refer to any suitable material, wherein the hydrophobic portion of the lipid material orients into a hydrophobic phase, while the hydrophilic portion orients toward the aqueous phase. Such compounds include, but are not limited to, phospholipids, aminolipids, and sphingolipids. Representative phospholipids include sphingomyelin, phosphatidylcholine, phosphatidylethanolamine, phosphatidylserine, phosphatidylinositol, phosphatidic acid, palmitoyloleoyl phosphatdylcholine, lysophosphatidylcholine, lysophosphatidylethanoloamine, dipalmitoylphosphatidylcholine, dioleoylphosphatidylcholine, distearoylphosphatidylcholine, or dilinoleoylphosphatidylcholine. Other phosphorus-lacking compounds, such as sphingolipids, glycosphingolipid families, diacylglycerols, and β-acyloxyacids, can also be used. Additionally, such amphipathic lipids can be readily mixed with other lipids, such as triglycerides and sterols.

Also suitable for inclusion in the liposome compostions of the present invention are programmable fusion lipids. Liposomes containing programmable fusion lipids have little tendency to fuse with cell membranes and deliver their payload until a given signal event occurs. This allows the liposome to distribute more evenly after injection into an organism or disease site before it starts fusing with cells. The signal event can be, for example, a change in pH, temperature, ionic environment, or time. In the latter case, a fusion delaying or "cloaking" component, such as an ATTA-lipid conjugate or a PEG-lipid conjugate, can simply exchange out of the liposome membrane over time. By the time the liposome is suitably distributed in the body, it has lost sufficient cloaking agent so as to be fusogenic. With other signal events, it is desirable to choose a signal that is associated with the disease site or target cell, such as increased temperature at a site of inflammation.

A liposome can also include a targeting moiety, e.g., a targeting moiety that is specific to a cell type or tissue. Targeting of liposomes with a surface coating of hydrophilic polymer chains, such as polyethylene glycol (PEG) chains, for targeting has been proposed (Allen, et al., *Biochimica et Biophysica Acta* 1237: 99-108 (1995); DeFrees, et al., *Journal of the American Chemistry Society* 118: 6101-6104 (1996); Blume, et al., *Biochimica et Biophysica Acta* 1149: 180-184 (1993); Klibanov, et al., *Journal of Liposome Research* 2: 321-334 (1992); U.S. Pat. No. 5,013,556; Zalipsky, *Bioconjugate Chemistry* 4: 296-299 (1993); Zalipsky, *FEBS Letters* 353: 71-74 (1994); Zalipsky, in Stealth Liposomes Chapter 9 (Lasic and Martin, Eds) CRC Press, Boca Raton Fla. (1995). Other targeting moieties, such as ligands, cell surface receptors, glycoproteins, vitamins (e.g., riboflavin), aptamers and monoclonal antibodies, can also be used. The targeting moieties can include the entire protein or fragments thereof. Targeting mechanisms generally require that the targeting agents be positioned on the surface of the liposome in such a manner that the targeting moiety is available for interaction with the target, for example, a cell surface receptor.

In one approach, a targeting moiety, such as receptor binding ligand, for targeting the liposome is linked to the lipids forming the liposome. In another approach, the targeting moiety is attached to the distal ends of the PEG chains forming the hydrophilic polymer coating (Klibanov, et al., *Journal of Liposome Research* 2: 321-334 (1992); Kirpotin et al., *FEBS Letters* 388: 115-118 (1996)). A variety of different targeting agents and methods are known and available in the art, including those described, e.g., in Sapra, P. and Allen, T M, *Prog. Lipid Res.* 42(5):439-62 (2003); and Abra, R M et al., *J. Liposome Res.* 12:1-3, (2002). Other lipids conjugated with targeting moieties are described in U.S. provisional application No. 61/127,751 (filed May 14, 2008) and PCT application #PCT/US2007/080331 (filed Oct. 3, 2007), all of which are incorporated by reference in their entireties for all purposes.

A liposome composition of the invention can be prepared by a variety of methods that are known in the art. See e.g., U.S. Pat. No. 4,235,871, U.S. Pat. No. 4,897,355 and U.S. Pat. No. 5,171,678; published PCT applications WO 96/14057 and WO 96/37194; Felgner, P. L. et al., *Proc. Natl. Acad. Sci.*, USA (1987) 8:7413-7417, Bangham, et al. *M. Mol. Biol.* (1965) 23:238, Olson, et al. *Biochim. Biophys.*

*Acta* (1979) 557:9, Szoka, et al. *Proc. Natl. Acad. Sci.* (1978) 75: 4194, Mayhew, et al. *Biochim. Biophys. Acta* (1984) 775: 169, Kim, et al. *Biochim. Biophys. Acta* (1983) 728:339, and Fukunaga, et al. *Endocrinol*. (1984) 115:757.

For example, a liposome composition of the invention can be prepared by first dissolving the lipid components of a liposome in a detergent so that micelles are formed with the lipid component. The detergent can have a high critical micelle concentration and maybe nonionic. Exemplary detergents include, but are not limited to, cholate, CHAPS, octyl-glucoside, deoxycholate and lauroyl sarcosine. The RNAi agent preparation e.g., an emulsion, is then added to the micelles that include the lipid components. After condensation, the detergent is removed, e.g., by dialysis, to yield a liposome containing the RNAi agent. If necessary a carrier compound that assists in condensation can be added during the condensation reaction, e.g., by controlled addition. For example, the carrier compound can be a polymer other than a nucleic acid (e.g., spermine or spermidine). To favor condensation, pH of the mixture can also be adjusted.

In another example, liposomes of the present invention may be prepared by diffusing a lipid derivatized with a hydrophilic polymer into preformed liposome, such as by exposing preformed liposomes to micelles composed of lipid-grafted polymers, at lipid concentrations corresponding to the final mole percent of derivatized lipid which is desired in the liposome. Liposomes containing a hydrophilic polymer can also be formed by homogenization, lipid-field hydration, or extrusion techniques, as are known in the art.

In another exemplary formulation procedure, the RNAi agent is first dispersed by sonication in a lysophosphatidylcholine or other low CMC surfactant (including polymer grafted lipids). The resulting micellar suspension of RNAi agent is then used to rehydrate a dried lipid sample that contains a suitable mole percent of polymer-grafted lipid, or cholesterol. The lipid and active agent suspension is then formed into liposomes using extrusion techniques as are known in the art, and the resulting liposomes separated from the unencapsulated solution by standard column separation.

In one aspect of the present invention, the liposomes are prepared to have substantially homogeneous sizes in a selected size range. One effective sizing method involves extruding an aqueous suspension of the liposomes through a series of polycarbonate membranes having a selected uniform pore size; the pore size of the membrane will correspond roughly with the largest sizes of liposomes produced by extrusion through that membrane. See e.g., U.S. Pat. No. 4,737,323.

Other suitable formulations for RNAi agents are described in PCT application # PCT/US2007/080331 (filed Oct. 3, 2007) and U.S. Provisional applications No. 61/018,616 (filed Jan. 2, 2008), No. 61/039,748 (filed Mar. 26, 2008), No. 61/047,087 (filed Apr. 22, 2008) and No. 61/051,528 (filed May 21, 2008), No. 61/113,179 (filed Nov. 10, 2008) all of which are incorporated by reference in their entireties for all purposes.

Micelles and Other Membranous Formulations

Recently, the pharmaceutical industry introduced microemulsification technology to improve bioavailability of some lipophilic (water insoluble) pharmaceutical agents. Examples include Trimetrine (Dordunoo, S. K., et al., Drug Development and Industrial Pharmacy, 17(12), 1685-1713, 1991 and REV 5901 (Sheen, P. C., et al., J Pharm Sci 80(7), 712-714, 1991). Among other things, microemulsification provides enhanced bioavailability by preferentially directing absorption to the lymphatic system instead of the circulatory system, which thereby bypasses the liver, and prevents destruction of the compounds in the hepatobiliary circulation.

In one aspect of invention, the formulations contain micelles formed from a compound of the present invention and at least one amphiphilic carrier, in which the micelles have an average diameter of less than about 100 nm. More preferred embodiments provide micelles having an average diameter less than about 50 nm, and even more preferred embodiments provide micelles having an average diameter less than about 30 nm, or even less than about 20 nm.

As defined herein, "micelles" are a particular type of molecular assembly in which amphipathic molecules are arranged in a spherical structure such that all hydrophobic portions on the molecules are directed inward, leaving the hydrophilic portions in contact with the surrounding aqueous phase. The converse arrangement exists if the environment is hydrophobic.

While all suitable amphiphilic carriers are contemplated, the presently preferred carriers are generally those that have Generally-Recognized-as-Safe (GRAS) status, and that can both solubilize the compound of the present invention and microemulsify it at a later stage when the solution comes into a contact with a complex water phase (such as one found in human gastrointestinal tract). Usually, amphiphilic ingredients that satisfy these requirements have HLB (hydrophilic to lipophilic balance) values of 2-20, and their structures contain straight chain aliphatic radicals in the range of C-6 to C-20. Examples are polyethylene-glycolized fatty glycerides and polyethylene glycols.

Exemplary amphiphilic carriers include, but are not limited to, lecithin, hyaluronic acid, pharmaceutically acceptable salts of hyaluronic acid, glycolic acid, lactic acid, chamomile extract, cucumber extract, oleic acid, linoleic acid, linolenic acid, monoolein, monooleates, monolaurates, borage oil, evening of primrose oil, menthol, trihydroxy oxo cholanyl glycine and pharmaceutically acceptable salts thereof, glycerin, polyglycerin, lysine, polylysine, triolein, polyoxyethylene ethers and analogues thereof, polidocanol alkyl ethers and analogues thereof, chenodeoxycholate, deoxycholate, and mixtures thereof.

Particularly preferred amphiphilic carriers are saturated and monounsaturated polyethyleneglycolyzed fatty acid glycerides, such as those obtained from fully or partially hydrogenated various vegetable oils. Such oils may advantageously consist of tri-, di- and mono-fatty acid glycerides and di- and mono-polyethyleneglycol esters of the corresponding fatty acids, with a particularly preferred fatty acid composition including capric acid 4-10, capric acid 3-9, lauric acid 40-50, myristic acid 14-24, palmitic acid 4-14 and stearic acid 5-15%. Another useful class of amphiphilic carriers includes partially esterified sorbitan and/or sorbitol, with saturated or mono-unsaturated fatty acids (SPAN-series) or corresponding ethoxylated analogs (TWEEN-series).

Commercially available amphiphilic carriers are particularly contemplated, including Gelucire-series, Labrafil, Labrasol, or Lauroglycol (all manufactured and distributed by Gattefosse Corporation, Saint Priest, France), PEG-mono-oleate, PEG-di-oleate, PEG-mono-laurate and di-laurate, Lecithin, Polysorbate 80, etc (produced and distributed by a number of companies in USA and worldwide).

Mixed micelle formulation suitable for delivery through transdermal membranes may be prepared by mixing an aqueous solution of the RNAi composition, an alkali metal $C_8$ to $C_{22}$ alkyl sulphate, and an amphiphilic carrier. The amphiphilic carrier may be added at the same time or after addition of the alkali metal alkyl sulphate. Mixed micelles will form with substantially any kind of mixing of the ingredients but vigorous mixing in order to provide smaller size micelles.

In one method a first micelle composition is prepared which contains the RNAi composition and at least the alkali metal alkyl sulphate. The first micelle composition is then mixed with at least three amphiphilic carriers to form a mixed micelle composition. In another method, the micelle composition is prepared by mixing the RNAi composition, the alkali metal alkyl sulphate and at least one of the amphiphilic carriers, followed by addition of the remaining micelle amphiphilic carriers, with vigorous mixing.

Phenol and/or m-cresol may be added to the mixed micelle composition to stabilize the formulation and protect against bacterial growth. Alternatively, phenol and/or m-cresol may be added with the amphiphilic carriers. An isotonic agent such as glycerin may also be added after formation of the mixed micelle composition.

For delivery of the micelle formulation as a spray, the formulation can be put into an aerosol dispenser and the dispenser is charged with a propellant, such as hydrogen-containing chlorofluorocarbons, hydrogen-containing fluorocarbons, dimethyl ether, diethyl ether and HFA 134a (1,1,1,2 tetrafluoroethane).

Emulsions

The oligonucleotides of the present invention may be prepared and formulated as emulsions. Emulsions are typically heterogenous systems of one liquid dispersed in another in the form of droplets (Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising two immiscible liquid phases intimately mixed and dispersed with each other. In general, emulsions may be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions may contain additional components in addition to the dispersed phases, and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials is also included in emulsion formulations and contributes to the properties of emulsions. These include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of ease of formulation, as well as efficacy from an absorption and bioavailability standpoint (Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of FLiPs are formulated as microemulsions. A microemulsion may be defined as a system of water, oil and amphiphile which is a single optically isotropic and thermodynamically stable liquid solution (Rosoff, in Pharmaceutical Dosage Forms, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington's Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in Pharmaceutical Dosage Forms, Lieberman, Rieger and Banker (Eds.), 1988, Marcel Dekker, Inc., New York, N.Y., volume 1, p. 245; Block, in Pharmaceutical Dosage Forms, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., Pharmaceutical Research, 1994, 11, 1385-1390; Ritschel, Meth. Find. Exp. Clin. Pharmacol., 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., Pharmaceutical Research, 1994, 11, 1385; Ho et al., J. Pharm. Sci., 1996, 85, 138-143). Often microemulsions may form spontaneously when their components are brought together at ambient temperature. This may be particularly advantageous when formulating thermolabile drugs, peptides or dsRNAs. Microemulsions have also been effective in the transdermal delivery of active components in both cosmetic and pharmaceutical applications. It is expected that the microemulsion compositions and formulations of the present invention will facilitate the increased systemic absorption of dsRNAs and nucleic acids from the gastrointestinal tract, as well as improve the local cellular uptake of dsRNAs and nucleic acids.

Microemulsions of the present invention may also contain additional components and additives such as sorbitan monostearate (Grill 3), Labrasol, and penetration enhancers to improve the properties of the formulation and to enhance the absorption of the dsRNAs and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., Critical Reviews in Therapeutic Drug Carrier Systems, 1991, p. 92). Each of these classes has been discussed above.

Lipid Particles

It has been shown that cholesterol-conjugated sRNA is bind to HDL and LDL lipoprotein particles which mediate cellular uptake upon binding to their respective receptors. Both high-density lipoproteins (HDL) and low density lipoproteins (LDL) play a critical role in cholesterol transport. HDL directs sRNAi delivery into liver, gut, kidney and steroidogenic organs, whereas LDL targets sRNAi primarily to liver (Wolfrum et al. Nature Biotechnology Vol. 25 (2007)). Thus in one aspect the invention provides formulated lipid particles (FLiPs) comprising (a) an oligonucleotide of the invention, e.g., antisense, antagomir, aptamer, ribozyme and an RNAi agent, where the oligonucleotide has been conjugated to a lipophile and (b) at least one lipid component, for example an emulsion, liposome, isolated lipoprotein, reconstituted lipoprotein or phospholipid, to which the conjugated oligonucleotide has been aggregated, admixed or associated.

The stoichiometry of oligonucleotide to the lipid component may be 1:1. Alternatively the stoichiometry may be 1:many, many:1 or many:many, where many is greater than 2.

The FLiP may comprise triacylglycerol, phospholipids, glycerol and one or several lipid-binding proteins aggregated, admixed or associated via a lipophilic linker molecule with a single- or double-stranded oligonucleotide, wherein the FLiP has an affinity to heart, lung and/or muscle tissue. Surprisingly, it has been found that due to one or several lipid-binding proteins in combination with the above mentioned lipids, the affinity to heart, lung and/or muscle tissue is very specific. These FLiPs may therefore serve as carrier for oligonucleotides. Due to their affinity to heart, lung and muscle cells, they may specifically transport the oligonucleotides to these tissues. Therefore, the FLiPs according to the present invention may be used for many severe heart, lung and muscle diseases, for example myocarditis, ischemic heart disease, myopathies, cardiomyopathies, metabolic diseases, rhabdomyosarcomas.

One suitable lipid component for FLiP is Intralipid. Intralipid® is a brand name for the first safe fat emulsion for human use. Intralipid® 20% (a 20% intravenous fat emulsion) is a sterile, non-pyrogenic fat emulsion prepared for intravenous administration as a source of calories and essential fatty acids. It is made up of 20% soybean oil, 1.2% egg yolk phospholipids, 2.25% glycerin, and water for injection. Intralipid® 10% is made up of 10% soybean oil, 1.2% egg yolk phospholipids, 2.25% glycerin, and water for injection. It is further within the present invention that other suitable oils, such as saflower oil, may serve to produce the lipid component of the FLiP.

In one embodiment of the invention is a FLiP comprising a lipid particle comprising 15-25% triacylglycerol, about 1-2% phospholipids and 2-3% glycerol, and one or several lipid-binding proteins.

In another embodiment of the invention the lipid particle comprises about 20% triacylglycerol, about 1.2% phospholipids and about 2.25% glycerol, which corresponds to the total composition of Intralipid, and one or several lipid-binding proteins.

Another suitable lipid component for FLiPs is lipoproteins, for example isolated lipoproteins or more preferably reconstituted lipoprotieins. Liporoteins are particles that contain both proteins and lipids. The lipids or their derivatives may be covalently or non-covalently bound to the proteins. Exemplary lipoproteins include chylomicrons, VLDL (Very Low Density Lipoproteins), IDL (Intermediate Density Lipoproteins), LDL (Low Density Lipoproteins) and HDL (High Density Lipoproteins).

Methods of producing reconstituted lipoproteins have been described in scientific literature, for example see A. Jones, Experimental Lung Res. 6, 255-270 (1984), U.S. Pat. Nos. 4,643,988 and 5,128,318, PCT publication WO87/02062, Canadian patent #2,138,925. Other methods of producing reconstituted lipoproteins, especially for apolipoproteins A-I, A-II, A-IV, apoC and apoE have been described in A. Jonas, Methods in Enzymology 128, 553-582 (1986) and G. Franceschini et al. J. Biol. Chem., 260(30), 16321-25 (1985).

The most frequently used lipid for reconstitution is phosphatidyl choline, extracted either from eggs or soybeans. Other phospholipids are also used, also lipids such as triglycerides or cholesterol. For reconstitution the lipids are first dissolved in an organic solvent, which is subsequently evaporated under nitrogen. In this method the lipid is bound in a thin film to a glass wall. Afterwards the apolipoproteins and a detergent, normally sodium cholate, are added and mixed. The added sodium cholate causes a dispersion of the lipid. After a suitable incubation period, the mixture is dialyzed against large quantities of buffer for a longer period of time; the sodium cholate is thereby removed for the most part, and at the same time lipids and apolipoproteins spontaneously form themselves into lipoproteins or so-called reconstituted lipoproteins. As alternatives to dialysis, hydrophobic adsorbents are available which can adsorb detergents (Bio-Beads SM-2, Bio Rad; Amberlite XAD-2, Rohm & Haas) (E. A. Bonomo, J. B. Swaney, J. Lipid Res., 29, 380-384 (1988)), or the detergent can be removed by means of gel chromatography (Sephadex G-25, Pharmacia). Lipoproteins can also be produced without detergents, for example through incubation of an aqueous suspension of a suitable lipid with apolipoproteins, the addition of lipid which was dissolved in an organic solvent, to apolipoproteins, with or without additional heating of this mixture, or through treatment of an apoA-I-lipid-mixture with ultrasound. With these methods, starting, for example, with apoA-I and phosphatidyl choline, disk-shaped particles can be obtained which correspond to lipoproteins in their nascent state. Normally, following the incubation, unbound apolipoproteins and free lipid are separated by means of centrifugation or gel chromatography in order to isolate the homogeneous, reconstituted lipoproteins particles.

Phospholipids used for reconstituted lipoproteins can be of natural origin, such as egg yolk or soybean phospholipids, or synthetic or semisynthetic origin. The phospholipids can be partially purified or fractionated to comprise pure fractions or mixtures of phosphatidyl cholines, phosphatidyl ethanolamines, phosphatidyl inositols, phosphatidic acids, phosphatidyl serines, sphingomyelin or phosphatidyl glycerols. According to specific embodiments of the present invention it is preferred to select phospholipids with defined fatty acid radicals, such as dimyristoyl phosphatidyl choline (DMPC), dioleoylphosphatidylethanolamine (DOPE), palmitoyloleoylphosphatidylcholine (POPC), egg phosphatidylcholine (EPC), distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), -phosphatidylethanolamine (POPE), dioleoyl-phosphatidylethanolamine 4-(N-maleimidomethyl)-cyclohexane-1-carboxylate (DOPE-mal), and combinations thereof, and the like phosphatidyl cholines with defined acyl groups selected from naturally occurring fatty acids, generally having 8 to 22 carbon atoms. According to a specific embodiment of the present invention phosphatidyl cholines having only saturated fatty acid residues between 14 and 18 carbon atoms are preferred, and of those dipalmitoyl phosphatidyl choline is especially preferred.

Other phospholipids suitable for reconstitution with lipoproteins include, e.g., phosphatidylcholine, phosphatidylglycerol, lecithin, b, g-dipalmitoyl-a-lecithin, sphingomyelin, phosphatidylserine, phosphatidic acid, N-(2,3-di(9-(Z)-octadecenyloxy))-prop-1-yl-N,N,N-trimethylammonium chloride, phosphatidylethanolamine, lysolecithin, lysophosphatidylethanolamine, phosphatidylinositol, cephalin, cardiolipin, cerebrosides, dicetylphosphate, dioleoylphosphatidylcholine, dipalmitoylphosphatidylcholine, dipalmitoylphosphatidylglycerol, dioleoylphosphatidylglycerol, palmitoyl-oleoyl-phosphatidylcholine, di-stearoyl-phosphatidylcholine, stearoyl-palmitoyl-phosphatidylcholine, di-palmitoyl-phosphatidylethanolamine, di-stearoyl-phosphatidylethanolamine, di-myrstoyl-phosphatidylserine, di-oleyl-phosphatidylcholine, and the like. Non-phosphorus containing lipids may also be used in the liposomes of the compositions of the present invention. These include, e.g., stearylamine, docecylamine, acetyl palmitate, fatty acid amides, and the like.

Besides the phospholipids, the lipoprotein may comprise, in various amounts at least one nonpolar component which can be selected among pharmaceutical acceptable oils (triglycerides) exemplified by the commonly employed vegetabilic oils such as soybean oil, safflower oil, olive oil, sesame oil, borage oil, castor oil and cottonseed oil or oils from other sources like mineral oils or marine oils including hydrogenated and/or fractionated triglycerides from such sources. Also medium chain triglycerides (MCT-oils, e.g. Miglyol®), and various synthetic or semisynthetic mono-, di- or triglycerides, such as the defined nonpolar lipids disclosed in WO 92/05571 may be used in the present invention as well as acetylated monoglycerides, or alkyl esters of fatty acids, such isopropyl myristate, ethyl oleate (see EP 0 353 267) or fatty acid alcohols, such as oleyl alcohol, cetyl alcohol or various nonpolar derivatives of cholesterol, such as cholesterol esters.

One or more complementary surface active agent can be added to the reconstituted lipoproteins, for example as complements to the characteristics of amphiphilic agent or to improve its lipid particle stabilizing capacity or enable an improved solubilization of the protein. Such complementary agents can be pharmaceutically acceptable non-ionic surfactants which preferably are alkylene oxide derivatives of an organic compound which contains one or more hydroxylic groups. For example ethoxylated and/or propoxylated alcohol or ester compounds or mixtures thereof are commonly available and are well known as such complements to those skilled in the art. Examples of such compounds are esters of sorbitol and fatty acids, such as sorbitan monopalmitate or sorbitan monopalmitate, oily sucrose esters, polyoxyethylene sorbitane fatty acid esters, polyoxyethylene sorbitol fatty acid esters, polyoxyethylene fatty acid esters, polyoxyethylene alkyl ethers, polyoxyethylene sterol ethers, polyoxyethylenepolypropoxy alkyl ethers, block polymers and cethyl ether, as well as polyoxyethylene castor oil or hydrogenated castor oil derivatives and polyglycerine fatty acid esters. Suitable nonionic surfactants, include, but are not limited to various grades of Pluronic®, Poloxamer®, Span®, Tween®, Polysorbate®, Tyloxapol®, Emulphor® or Cremophor® and the like. The complementary surface active agents may also be of an ionic nature, such as bile duct agents, cholic acid or deoxycholic their salts and derivatives or free fatty acids, such as oleic acid, linoleic acid and others. Other ionic surface active agents are found among cationic lipids like C10-C24: alkylamines or alkanolamine and cationic cholesterol esters.

In the final FLiP, the oligonucleotide component is aggregated, associated or admixed with the lipid components via a lipophilic moiety. This aggregation, association or admixture may be at the surface of the final FLiP formulation. Alternatively, some integration of any of a portion or all of the lipophilic moiety may occur, extending into the lipid particle. Any lipophilic linker molecule that is able to bind oligonucleotides to lipids can be chosen. Examples include pyrrolidine and hydroxyprolinol.

The process for making the lipid particles comprises the steps of:

a) mixing a lipid components with one or several lipophile (e.g. cholesterol) conjugated oligonucleotides that may be chemically modified;
b) fractionating this mixture;
c) selecting the fraction with particles of 30-50 nm, preferably of about 40 nm in size.

Alternatively, the FLiP can be made by first isolating the lipid particles comprising triacylglycerol, phospholipids, glycerol and one or several lipid-binding proteins and then mixing the isolated particles with >2-fold molar excess of lipophile (e.g. cholesterol) conjugated oligonucleotide. The steps of fractionating and selecting the particles are deleted by this alternative process for making the FLiPs.

Other pharmacologically acceptable components can be added to the FLiPs when desired, such as antioxidants (exemplified by alpha-tocopherol) and solubilization adjuvants (exemplified by benzylalcohol).

Release Modifiers

The release characteristics of a formulation of the present invention depend on the encapsulating material, the concentration of encapsulated drug, and the presence of release modifiers. For example, release can be manipulated to be pH dependent, for example, using a pH sensitive coating that releases only at a low pH, as in the stomach, or a higher pH, as in the intestine. An enteric coating can be used to prevent release from occurring until after passage through the stomach. Multiple coatings or mixtures of cyanamide encapsulated in different materials can be used to obtain an initial release in the stomach, followed by later release in the intestine. Release can also be manipulated by inclusion of salts or pore forming agents, which can increase water uptake or release of drug by diffusion from the capsule. Excipients which modify the solubility of the drug can also be used to control the release rate. Agents which enhance degradation of the matrix or release from the matrix can also be incorporated. They can be added to the drug, added as a separate phase (i.e., as particulates), or can be co-dissolved in the polymer phase depending on the compound. In all cases the amount should be between 0.1 and thirty percent (w/w polymer). Types of degradation enhancers include inorganic salts such as ammonium sulfate and ammonium chloride, organic acids such as citric acid, benzoic acid, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween® and Pluronic®. Pore forming agents which add microstructure to the matrices (i.e., water soluble compounds such as inorganic salts and sugars) are added as particulates. The range should be between one and thirty percent (w/w polymer).

Uptake can also be manipulated by altering residence time of the particles in the gut. This can be achieved, for example, by coating the particle with, or selecting as the encapsulating material, a mucosal adhesive polymer. Examples include most polymers with free carboxyl groups, such as chitosan, celluloses, and especially polyacrylates (as used herein, polyacrylates refers to polymers including acrylate groups and modified acrylate groups such as cyanoacrylates and methacrylates).

Polymers

Hydrophilic polymers suitable for use in the formulations of the present invention are those which are readily water-soluble, can be covalently attached to a vesicle-forming lipid, and which are tolerated in vivo without toxic effects (i.e., are biocompatible). Suitable polymers include polyethylene glycol (PEG), polylactic (also termed polylactide), polyglycolic acid (also termed polyglycolide), a polylactic-polyglycolic acid copolymer, and polyvinyl alcohol. Preferred polymers are those having a molecular weight of from about 100 or 120 daltons up to about 5,000 or 10,000 daltons, and more preferably from about 300 daltons to about 5,000 daltons. In a particularly preferred embodiment, the polymer is polyethyleneglycol having a molecular weight of from about 100 to about 5,000 daltons, and more preferably having a molecular weight of from about 300 to about 5,000 daltons. In a particularly preferred embodiment, the polymer is polyethyleneglycol of 750 daltons (PEG(750)). Polymers may also be defined by the number of monomers therein; a preferred embodiment of the present invention utilizes polymers of at least about three monomers, such PEG polymers consisting of three monomers (approximately 150 daltons).

Other hydrophilic polymers which may be suitable for use in the present invention include polyvinylpyrrolidone, polymethoxazoline, polyethyloxazoline, polyhydroxypropyl methacrylamide, polymethacrylamide, polydimethylacrylamide, and derivatized celluloses such as hydroxymethylcellulose or hydroxyethylcellulose.

In one embodiment, a formulation of the present invention comprises a biocompatible polymer selected from the group consisting of polyamides, polycarbonates, polyalkylenes, polymers of acrylic and methacrylic esters, polyvinyl polymers, polyglycolides, polysiloxanes, polyurethanes and copolymers thereof, celluloses, polypropylene, polyethylenes, polystyrene, polymers of lactic acid and glycolic acid, polyanhydrides, poly(ortho)esters, poly(butic acid), poly(valeric acid), poly(lactide-co-caprolactone), polysaccharides, proteins, polyhyaluronic acids, polycyanoacrylates, and blends, mixtures, or copolymers thereof.

Surfactants

The above discussed formulation may also include one or more surfactants. Surfactants find wide application in formulations such as emulsions (including microemulsions) and liposomes. The use of surfactants in drug products, formulations and in emulsions has been reviewed (Rieger, in "Pharmaceutical Dosage Forms," Marcel Dekker, Inc., New York, N.Y., 1988, p. 285). Surfactants may be classified into different classes based on the nature of the hydrophilic group: nonionic, anionic, cationic and amphoteric (Rieger, in Pharmaceutical Dosage Forms, Lieberman, Rieger and Banker (Eds.), 1988, Marcel Dekker, Inc., New York, N.Y., volume 1, p. 285).

Nonionic surfactants include, but are not limited to, nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

Anionic surfactants include, but are not limited to, carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

Cationic surfactants include, but are not limited to, quaternary ammonium salts and ethoxylated amines. The quaternary ammonium salts are the most used members of this class.

Amphoteric surfactants include, but are not limited to, acrylic acid derivatives, substituted alkylamides, N-alkylbetaines and phosphatides.

A surfactant may also be selected from any suitable aliphatic, cycloaliphatic or aromatic surfactant, including but not limited to biocompatible lysophosphatidylcholines (LPCs) of varying chain lengths (for example, from about C14 to about C20). Polymer-derivatized lipids such as PEG-lipids may also be utilized for micelle formation as they will act to inhibit micelle/membrane fusion, and as the addition of a polymer to surfactant molecules decreases the CMC of the surfactant and aids in micelle formation. Preferred are surfactants with CMCs in the micromolar range; higher CMC surfactants may be utilized to prepare micelles entrapped within liposomes of the present invention, however, micelle surfactant monomers could affect liposome bilayer stability and would be a factor in designing a liposome of a desired stability.

Penetration Enhancers

In one embodiment, the formulations of the present invention employ various penetration enhancers to affect the efficient delivery of RNAi agents to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Some exemplary formulations for oligonucleotides are described in International Application Nos. PCT/US07/079, 203, filed Sep. 21, 2007; PCT/US07/080,331, filed Oct. 3, 2007; U.S. patent application Ser. No. 12/123,922, filed May 28, 2008; U.S. Patent Application Publication Nos. 20060240093 and 20070135372 and U.S. Provisional Application Nos. 61/018,616, filed Jan. 2, 2008; 61/039,748, filed Mar. 26, 2008; 61/045,228, filed Apr. 15, 2008; 61/047,087, filed Apr. 22, 2008; and 61/051,528, filed May 21, 2008, contents of which are herein incorporated by reference in their entireties for all purposes.

Pharmaceutical Compositions

In another aspect, the present invention provides pharmaceutically acceptable compositions which comprise a therapeutically-effective amount of one or more of the oligonucleotides described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) lubricating agents, such as magnesium state, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; and (22) other non-toxic compatible substances employed in pharmaceutical formulations.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In one embodiment, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In one embodiment, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium.

Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Formulations for ocular administration can include mucomimetics such as hyaluronic acid, chondroitin sulfate, hydroxypropyl methylcellulose or poly (vinyl alcohol), preservatives such as sorbic acid, EDTA or benzylchronium chloride, and the usual quantities of diluents and/or carriers.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient, when used for the indicated analgesic effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms. Preferred dosing is one administration per day.

While it is possible for a compound of the present invention to be administered alone, it is preferable to administer the compound as a pharmaceutical formulation (composition).

The compounds according to the invention may be formulated for administration in any convenient way for use in human or veterinary medicine, by analogy with other pharmaceuticals.

In another aspect, the present invention provides pharmaceutically acceptable compositions which comprise a therapeutically-effective amount of one or more of the subject compounds, as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin, lungs, or mucous membranes; or (4) intravaginally or intrarectally, for example, as a pessary, cream or foam; (5) sublingually or buccally; (6) ocularly; (7) transdermally; or (8) nasally.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W.H. Freedman and CO., San Francisco, U.S.A., 1969 or "Livestock Feeds and Feeding" O and B books, Corvallis, Ore., U.S.A., 1977).

Methods of Use

One aspect of the present invention relates to a method of modulating the expression of a target gene in a cell. The method comprises: (a) providing a composition of the invention; (b) contacting a cell with the composition; and (c) allowing the cell to internalize the composition. The method can be performed in vitro, ex vivo or in vivo, e.g., to treat a subject identified as being in need of treatment by a composition of the invention.

In certain embodiments, the cell is a mammalian cell.

In yet another aspect, the invention provides a method for modulating the expression of the target gene in a mammal. The method comprises: administering a composition featured in the invention to the mammal such that expression of the target gene is modulated. The composition may be administered by any means known in the art including, but not limited to oral or parenteral routes, including intravenous, intramuscular, subcutaneous, transdermal, airway (aerosol), nasal, rectal, and topical (including buccal and sublingual) administration. In preferred embodiments, the compositions are administered by intravenous infusion or injection. Target genes include genes promoting unwanted cell proliferation, growth factor gene, growth factor receptor gene, genes expressing kinases, an adaptor protein gene, a gene encoding a G protein super family molecule, a gene encoding a transcription factor, a gene which mediates angiogenesis, a viral gene, a gene required for viral replication, a cellular gene which mediates viral function, a gene of a bacterial pathogen, a gene of an amoebic pathogen, a gene of a parasitic pathogen, a gene of a fungal pathogen, a gene which mediates an unwanted immune response, a gene which mediates the processing of pain, a gene which mediates a neurological disease, an allene gene found in cells characterized by loss of heterozygosity, or one allege gene of a polymorphic gene.

Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims.

The phrases "2'-modification" and "2'-modified nucleotide" refer to a nucleotide unit having a sugar moiety, for example a ribosyl moiety, that is modified at the 2'-position such that the hydroxyl group (2'-OH) is replaced by, for example, —F, —H, —CH$_3$, —CH$_2$CH$_3$, —OCH$_3$, —OCH$_2$CH$_3$, —OCH$_2$CH$_2$OMe, —OCH$_2$C(=O)NHMe, —OCH$_2$-(4'-C) (a so-called "LNA sugar modification"), or —OCH$_2$CH$_2$-(4'-C) (a so-called "ENA sugar modification"). For example, the phrases "2'-fluoro modification" and "2'-fluoro modified nucleotide" refer to a nucleotide unit having a sugar moiety, for example a ribosyl moiety, that is modified at the 2'-position such that the hydroxyl group (2'-OH) is replaced by a fluoro group (2'-F). U.S. Pat. Nos. 6,262,241, and 5,459,255 (both of which are incorporated by reference), are drawn to, inter alia, methods of synthesizing 2'-fluoro modified nucleotides and oligonucleotides.

The phrase "antisense strand" as used herein, refers to a polynucleotide that is substantially or 100% complementary to a target nucleic acid of interest. An antisense strand may comprise a polynucleotide that is RNA, DNA or chimeric RNA/DNA. For example, an antisense strand may be complementary, in whole or in part, to a molecule of messenger RNA, an RNA sequence that is not mRNA (e.g., tRNA, rRNA and hnRNA) or a sequence of DNA that is either coding or non-coding. The phrase "antisense strand" includes the antisense region of both polynucleotides that are formed from two separate strands, as well as unimolecular polynucleotides that are capable of forming hairpin structures. The terms "antisense strand" and "guide strand" are used interchangeably herein.

The phrase "sense strand" refers to a polynucleotide that has the same nucleotide sequence, in whole or in part, as a target nucleic acid such as a messenger RNA or a sequence of DNA. The sense strand is not incorporated into the functional riboprotein RISC. The terms "sense strand" and "passenger strand" are used interchangeably herein.

The term "duplex" includes a region of complementarity between two regions of two or more polynucleotides that comprise separate strands, such as a sense strand and an antisense strand, or between two regions of a single contiguous polynucleotide.

As used herein, "specifically hybridizable" and "complementary" refers to the ability of polynucleotides to form base pairs with one another. Base pairs are typically formed by hydrogen bonds between nucleotide units in antiparallel polynucleotide strands. Complementary polynucleotide strands can base pair in the Watson-Crick manner (e.g., a to t, a to u, c to g), or in any other manner that allows for the formation of stable duplexes. "Perfect complementarity" or 100% complementarity refers to the situation in which each nucleotide unit of one polynucleotide strand can hydrogen bond with each nucleotide unit of a second polynucleotide strand. Less than perfect complementarity refers to the situation in which some, but not all, nucleotide units of two strands can hydrogen bond with each other. "Substantial complementarity" refers to polynucleotide strands exhibiting 90% or greater complementarity, excluding regions of the polynucleotide strands, such as overhangs, that are selected so as to be noncomplementary. Specific binding requires a sufficient degree of complementarity to avoid non-specific binding of the oligomeric compound to non-target sequences under conditions in which specific binding is desired, i.e., under physiological conditions in the case of in vivo assays or therapeutic treatment, or in the case of in vitro assays, under conditions in which the assays are performed. The non-target sequences typically differ by at least 5 nucleotides.

The term "off-target" and the phrase "off-target effects" refer to any instance in which an RNAi agent against a given target causes an unintended affect by interacting either directly or indirectly with another mRNA sequence, a DNA sequence or a cellular protein or other moiety. For example, an "off-target effect" may occur when there is a simultaneous degradation of other transcripts due to partial homology or complementarity between that other transcript and the sense and/or antisense strand of a double-stranded RNAi agent.

The phrase "first 5' terminal nucleotide" includes first 5' terminal antisense nucleotides and first 5' terminal antisense nucleotides. "First 5' terminal antisense nucleotide" refers to the nucleotide of the antisense strand that is located at the 5' most position of that strand with respect to the bases of the antisense strand that have corresponding complementary bases on the sense strand. Thus, in a double stranded polynucleotide that is made of two separate strands, it refers to the 5' most base other than bases that are part of any 5' overhang on the antisense strand. When the first 5' terminal antisense nucleotide is part of a hairpin molecule, the term "terminal" refers to the 5' most relative position within the antisense region and thus is the 5" most nucleotide of the antisense region. The phrase "first 5" terminal sense nucleotide" is defined in reference to the sense nucleotide. In molecules comprising two separate strands, it refers to the nucleotide of the sense strand that is located at the 5' most position of that strand with respect to the bases of the sense strand that have corresponding complementary bases on the antisense strand. Thus, in a double stranded polynucleotide that is made of two separate strands, it is the 5' most base other than bases that are part of any 5' overhang on the sense strand.

In one embodiment, an siRNA compound is "sufficiently complementary" to a target RNA, e.g., a target mRNA, such that the siRNA compound silences production of protein encoded by the target mRNA. In another embodiment, the siRNA compound is "exactly complementary" to a target RNA, e.g., the target RNA and the siRNA compound anneal, for example to form a hybrid made exclusively of Watson-Crick base pairs in the region of exact complementarity. A "sufficiently complementary" target RNA can include an internal region (e.g., of at least 10 nucleotides) that is exactly complementary to a target RNA. Moreover, In one embodiment, the siRNA compound specifically discriminates a single-nucleotide difference. In this case, the siRNA compound only mediates RNAi if exact complementary is found in the region (e.g., within 7 nucleotides of) the single-nucleotide difference.

In one embodiment, oligonucleotides of the invention are prepared by connecting nucleosides with optionally protected phosphorus containing internucleoside linkages. Representative protecting groups for phosphorus containing internucleoside linkages such as phosphodiester and phosphorothioate linkages include β-cyanoethyl, diphenylsilylethyl, δ-cyanobutenyl, cyano p-xylyl (CPX), N-methyl-N-trifluoroacetyl ethyl (META), acetoxy phenoxy ethyl (APE) and butene-4-yl groups. See for example U.S. Pat. Nos. 4,725, 677 and Re. 34,069 (β-cyanoethyl); Beaucage, S. L. and Iyer, R. P., Tetrahedron, 49 No. 10, pp. 1925-1963 (1993); Beaucage, S. L. and Iyer, R. P., Tetrahedron, 49 No. 46, pp. 10441-10488 (1993); Beaucage, S. L. and Iyer, R. P., Tetrahedron, 48 No. 12, pp. 2223-2311 (1992).

In one embodiment, nucleosides having reactive phosphorus groups are provided that are useful for forming internucleoside linkages including for example phosphodiester and phosphorothioate internucleoside linkages. Such reactive phosphorus groups are known in the art and contain phosphorus atoms in $P^{III}$ or $P^V$ valence state including, but not limited to, phosphoramidite, H-phosphonate, phosphate triesters and phosphorus containing chiral auxiliaries. A preferred synthetic solid phase synthesis utilizes phosphoramidites ($P^{III}$ chemistry) as reactive phosphites. The intermediate phosphite compounds are subsequently oxidized to the Pv state using known methods to yield, in preferred embodiments, phosphodiester or phosphorothioate internucleotide linkages.

As used herein the term "internucleoside linkage" or "internucleoside linking group" is meant to include all manner of internucleoside linking groups known in the art including but not limited to, phosphorus containing internucleoside linking groups such as phosphodiester and phosphorothioate, non-phosphorus containing internucleoside linking groups such as formacetyl and methyl eneimino, and neutral non-ionic internucleoside linking groups such as amide-3 (3'-$CH_2$—C(=O)—N(H)-5'), amide-4 (3'-$CH_2$—N(H)—C(=O)-5').

As used herein the term "alternating motif" refers to a an oligonucleotide comprising a contiguous sequence of linked monomer subunits wherein the monomer subunits have two different types of sugar groups that alternate for essentially the entire sequence of the oligonucleotide. Oligonucleotides having an alternating motif can be described by the formula:

5'-A(-L-B-L-A)n(-L-B)nn-3' where A and B are monomelic subunits that have different sugar groups, each L is an internucleoside linking group, n is from about 4 to about 12 and nn is 0 or 1. This permits alternating oligonucleotides from about 9 to about 26 monomer subunits in length. This length range is not meant to be limiting as longer and shorter oligonucleotides are also amenable to the present invention. In one embodiment, one of A and B is a 2'-modified nucleoside as provided herein.

As used herein the term "uniformly fully modified motif" refers to an oligonucleotide comprising a contiguous sequence of linked monomer subunits that each have the same type of sugar group. In one embodiment, the uniformly fully modified motif includes a contiguous sequence of nucleosides of the invention. In one embodiment, one or both of the 3' and 5'-ends of the contiguous sequence of the nucleosides provided herein, comprise terminal groups such as one or more unmodified nucleosides.

As used herein the term "hemimer motif" refers to an oligonucleotide having a short contiguous sequence of monomer subunits having one type of sugar group located at the 5' or the 3' end wherein the remainder of the monomer subunits have a different type of sugar group. In general, a hemimer is an oligomeric compound of uniform sugar groups further comprising a short region (1, 2, 3, 4 or about 5 monomelic subunits) having uniform but different sugar groups and located on either the 3' or the 5' end of the oligomeric compound. In one embodiment, the hemimer motif comprises a contiguous sequence of from about 10 to about 28 monomer subunits of one type with from 1 to 5 or from 2 to about 5 monomer subunits of a second type located at one of the termini. In one embodiment, a hemimer is a contiguous sequence of from about 8 to about 20 β-D-2'-deoxyribonucleosides having from 1-12 contiguous nucleosides of the invention located at one of the termini. In one embodiment, a hemimer is a contiguous sequence of from about 8 to about 20 β-D-2'-deoxyribonucleosides having from 1-5 contiguous nucleosides of the invention located at one of the termini. In one embodiment, a hemimer is a contiguous sequence of from about 12 to about 18 β-D-2'-deoxyribo-nucleosides having from 1-3 contiguous nucleosides of the invention located at one of the termini. In one embodiment, a hemimer is a contiguous sequence of from about 10 to about 14 β-D-2'-deoxyribonucleosides having from 1-3 contiguous nucleosides of the invention located at one of the termini.

As used herein the term "blockmer motif" refers to an oligonucleotide comprising an otherwise contiguous sequence of monomer subunits wherein the sugar groups of each monomer subunit is the same except for an interrupting internal block of contiguous monomer subunits having a different type of sugar group. A blockmer overlaps somewhat with a gapmer in the definition but typically only the monomer subunits in the block have non-naturally occurring sugar groups in a blockmer and only the monomer subunits in the external regions have non-naturally occurring sugar groups in a gapmer with the remainder of monomer subunits in the blockmer or gapmer being β-D-2'-deoxyribonucleosides or β-D-ribonucleosides. In one embodiment, blockmer oligonucleotides are provided herein wherein all of the monomer subunits comprise non-naturally occurring sugar groups.

As used herein the term "positionally modified motif" is meant to include an otherwise contiguous sequence of monomer subunits having one type of sugar group that is interrupted with two or more regions of from 1 to about 5 contiguous monomer subunits having another type of sugar group. Each of the two or more regions of from 1 to about 5 contiguous monomer subunits are independently uniformly modified with respect to the type of sugar group. In one embodiment, each of the two or more regions have the same type of sugar group. In one embodiment, each of the two or more regions have a different type of sugar group. In one embodiment, positionally modified oligonucleotides are provided comprising a sequence of from 8 to 20 β-D-2'-deoxyribonucleosides that further includes two or three regions of from 2 to about 5 contiguous nucleosides of the invention. Positionally modified oligonucleotides are distinguished from gapped motifs, hemimer motifs, blockmer motifs and alternating motifs because the pattern of regional substitution defined by any positional motif does not fit into the definition provided herein for one of these other motifs. The term positionally modified oligomeric compound includes many different specific substitution patterns.

As used herein the term "gapmer" or "gapped oligomeric compound" refers to an oligomeric compound having two external regions or wings and an internal region or gap. The three regions form a contiguous sequence of monomer subunits with the sugar groups of the external regions being different than the sugar groups of the internal region and wherein the sugar group of each monomer subunit within a particular region is the same. When the sugar groups of the external regions are the same the gapmer is a symmetric gapmer and when the sugar group used in the 5'-external region is different from the sugar group used in the 3'-external region, the gapmer is an asymmetric gapmer. In one embodiment, the external regions are small (each independently 1, 2, 3, 4 or about 5 monomer subunits) and the monomer subunits comprise non-naturally occurring sugar groups with the internal region comprising β-D-2'-deoxyribonucleosides. In one embodiment, the external regions each, independently, comprise from 1 to about 5 monomer subunits having non-naturally occurring sugar groups and the internal region comprises from 6 to 18 unmodified nucleosides. The internal region or the gap generally comprises β-D-2'-deoxyribonucleosides but can comprise non-naturally occurring sugar groups.

In one embodiment, the gapped oligonucleotides comprise an internal region of β-D-2'-deoxyribonucleosides with one of the external regions comprising nucleosides of the invention. In one embodiment, the gapped oligonucleotide comprise an internal region of β-D-2'-deoxyribonucleosides with both of the external regions comprising nucleosides of the invention. In one embodiment, the gapped oligonucleotide comprise an internal region of β-D-2'-deoxyribonucleosides with both of the external regions comprising nucleosides of the invention. In one embodiment, gapped oligonucleotides are provided herein wherein all of the monomer subunits comprise non-naturally occurring sugar groups. In one embodiment, gapped oliogonucleotides are provided comprising one or two nucleosides of the invention at the 5'-end, two or three nucleosides of the invention at the 3'-end and an internal region of from 10 to 16 β-D-2'-deoxyribonucleosides. In one embodiment, gapped oligonucleotides are provided comprising one nucleoside of the invention at the 5'-end, two nucleosides of the invention at the 3'-end and an internal region of from 10 to 16 β-D-2'-deoxyribonucleosides. In one embodiment, gapped oligonucleotides are provided comprising two nucleosides of the invention at the 5'-end, two nucleosides of the invention at the 3'-end and an internal region of from 10 to 14 β-D-2'-deoxyribonucleosides. In one embodiment, gapped oligonucleotides are provided that are from about 10 to about 21 monomer subunits in length. In one embodiment, gapped oligonucleotides are provided that are from about 12 to about 16 monomer subunits in length. In one embodiment, gapped oligonucleotides are provided that are from about 12 to about 14 monomer subunits in length.

The phrase "pharmaceutically acceptable carrier or diluent" includes compositions that facilitate the introduction of nucleic acid therapeutics such as siRNA, dsRNA, dsDNA, shRNA, microRNA, antimicroRNA, antagomir, antimir, antisense, aptamer or dsRNA/DNA hybrids into a cell and includes but is not limited to solvents or dispersants, coatings, anti-infective agents, isotonic agents, and agents that mediate absorption time or release of the inventive polynucleotides and double stranded polynucleotides. The phrase "pharmaceutically acceptable" includes approval by a regulatory agency of a government, for example, the U.S. federal government, a non-U.S. government, or a U.S. state government, or inclusion in a listing in the U.S. Pharmacopeia or any other generally recognized pharmacopeia for use in animals, including in humans.

The terms "silence" and "inhibit the expression of" and related terms and phrases, refer to the at least partial suppression of the expression of a gene targeted by an siRNA or siNA, as manifested by a reduction of the amount of mRNA transcribed from the target gene which may be isolated from a first cell or group of cells in which the target gene is transcribed and which has or have been treated such that the expression of the target gene is inhibited, as compared to a second cell or group of cells substantially identical to the first cell or group of cells but which has or have not been so treated (i.e., control cells).

The term "halo" or "halogen" refers to any radical of fluorine, chlorine, bromine or iodine.

The term "aliphatic," as used herein, refers to a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation polyalkoxys, such as polyalkylene glycols, polyamines, and polyimines. Aliphatic groups as used herein may optionally include further substituent groups.

The term "acyl" refers to hydrogen, alkyl, partially saturated or fully saturated cycloalkyl, partially saturated or fully saturated heterocycle, aryl, and heteroaryl substituted carbonyl groups. For example, acyl includes groups such as (Ci-C6)alkanoyl (e.g., formyl, acetyl, propionyl, butyryl, valeryl, caproyl, t-butylacetyl, etc.), (C3-Ce)cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions. When indicated as being "optionally substituted", the acyl group may be unsubstituted or optionally substituted with one or more substituents (typically, one to three substituents) independently selected from the group of substituents listed below in the definition for "substituted" or the alkyl, cycloalkyl, heterocycle, aryl and heteroaryl portion of the acyl group may be substituted as described above in the preferred and more preferred list of substituents, respectively.

For simplicity, chemical moieties are defined and referred to throughout can be univalent chemical moieties (e.g., alkyl, aryl, etc.) or multivalent moieties under the appropriate structural circumstances clear to those skilled in the art. For example, an "alkyl" moiety can be referred to a monovalent radical (e.g. $CH_3-CH_2-$), or in other instances, a bivalent linking moiety can be "alkyl," in which case those skilled in the art will understand the alkyl to be a divalent radical (e.g., $-CH_2-CH_2-$), which is equivalent to the term "alkylene." Similarly, in circumstances in which divalent moieties are required and are stated as being "alkoxy", "alkylamino", "aryloxy", "alkylthio", "aryl", "heteroaryl", "heterocyclic", "alkyl" "alkenyl", "alkynyl", "aliphatic", or "cycloalkyl", those skilled in the art will understand that the terms alkoxy", "alkylamino", "aryloxy", "alkylthio", "aryl", "heteroaryl", "heterocyclic", "alkyl", "alkenyl", "alkynyl", "aliphatic", or "cycloalkyl" refer to the corresponding divalent moiety.

The term "alkyl" refers to saturated and unsaturated non-aromatic hydrocarbon chains that may be a straight chain or branched chain, containing the indicated number of carbon atoms (these include without limitation propyl, allyl, or propargyl), which may be optionally inserted with N, O, or S. For example, $C_1$-$C_{10}$ indicates that the group may have from 1 to 10 (inclusive) carbon atoms in it. The term "alkoxy" refers to an $-O$-alkyl radical. The term "alkylene" refers to a divalent alkyl (i.e., $-R-$). The term "alkylenedioxo" refers to a divalent species of the structure $-O-R-O-$, in which R represents an alkylene. The term "aminoalkyl" refers to an alkyl substituted with an amino. The term "mercapto" refers to an $-SH$ radical. The term "thioalkoxy" refers to an $-S$-alkyl radical.

The term "aryl" refers to a 6-carbon monocyclic or 10-carbon bicyclic aromatic ring system wherein 0, 1, 2, 3, or 4 atoms of each ring may be substituted by a substituent. Examples of aryl groups include phenyl, naphthyl and the like. The term "arylalkyl" or the term "aralkyl" refers to alkyl substituted with an aryl. The term "arylalkoxy" refers to an alkoxy substituted with aryl.

The term "cycloalkyl" as employed herein includes saturated and partially unsaturated cyclic hydrocarbon groups having 3 to 12 carbons, for example, 3 to 8 carbons, and, for example, 3 to 6 carbons, wherein the cycloalkyl group additionally may be optionally substituted. Cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, the heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Examples of heteroaryl groups include pyridyl, furyl or furanyl, imidazolyl, benzimidazolyl, pyrimidinyl, thiophenyl or thienyl, quinolinyl, indolyl, thiazolyl, and the like. The term "heteroarylalkyl" or the term "heteroaralkyl" refers to an alkyl substituted with a heteroaryl. The term "heteroarylalkoxy" refers to an alkoxy substituted with heteroaryl.

The term "heterocyclyl" or "heterocyclic" refers to a non-aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, the heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, morpholinyl, tetrahydrofuranyl, and the like.

The term "acyl" refers to an alkylcarbonyl, cycloalkylcarbonyl, arylcarbonyl, heterocyclylcarbonyl, or heteroarylcarbonyl substituent, any of which may be further substituted by substituents.

The term "substituents" refers to a group "substituted" on an alkyl, cycloalkyl, aryl, heterocyclyl, or heteroaryl group at any atom of that group. Suitable substituents include, without limitation, halo, hydroxy, oxo, nitro, haloalkyl, alkyl, alkaryl, aryl, aralkyl, alkoxy, aryloxy, amino, acylamino, alkylcarbamoyl, arylcarbamoyl, aminoalkyl, alkoxycarbonyl, carboxy, hydroxyalkyl, alkanesulfonyl, arenesulfonyl, alkanesulfonamido, arenesulfonamido, aralkylsulfonamido, alkylcarbonyl, acyloxy, cyano, ureido or conjugate groups.

In many cases, protecting groups are used during preparation of the compounds of the invention. As used herein, the term "protected" means that the indicated moiety has a protecting group appended thereon. In some preferred embodiments of the invention, compounds contain one or more protecting groups. A wide variety of protecting groups can be employed in the methods of the invention. In general, protecting groups render chemical functionalities inert to specific reaction conditions, and can be appended to and removed from such functionalities in a molecule without substantially damaging the remainder of the molecule.

Representative hydroxyl protecting groups, for example, are disclosed by Beaucage et al. (*Tetrahedron* 1992, 48, 2223-2311). Further hydroxyl protecting groups, as well as other representative protecting groups, are disclosed in Greene and Wuts, *Protective Groups in Organic Synthesis*, Chapter 2, 2d ed., John Wiley & Sons, New York, 1991, and *Oligonucleotides And Analogues A Practical Approach*, Ekstein, F. Ed., IRL Press, N.Y., 1991.

Examples of hydroxyl protecting groups include, but are not limited to, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, 2,6-dichlorobenzyl, diphenylmethyl, p,p'-dinitrobenzhydryl, p-nitrobenzyl, triphenylmethyl, trimethylsilyl, triethylsilyl, t-butyldimethylsilyl, t-butyldiphenylsilyl, triphenylsilyl, benzoylformate, acetate, chloroacetate, trichloroacetate, trifluoroacetate, pivaloate, benzoate, p-phenylbenzoate, 9-fluorenylmethyl carbonate, mesylate and tosylate.

Amino-protecting groups stable to acid treatment are selectively removed with base treatment, and are used to make reactive amino groups selectively available for substitution. Examples of such groups are the Fmoc (E. Atherton and R. C. Sheppard in *The Peptides*, S. Udenfriend, J. Meienhofer, Eds., Academic Press, Orlando, 1987, volume 9, p. 1) and various substituted sulfonylethyl carbamates exemplified by the Nsc group (Samukov et al., *Tetrahedron Lett.* 1994, 35, 7821; Verhart and Tesser, *Rec. Trav. Chim. Pays-Bas* 1987, 107, 621).

Additional amino-protecting groups include, but are not limited to, carbamate protecting groups, such as 2-trimethylsilylethoxycarbonyl (Teoc), 1-methyl-1-(4-biphenylyl) ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide protecting groups, such as formyl, acetyl, trihaloacetyl, benzoyl, and nitrophenylacetyl; sulfonamide protecting groups, such as 2-nitrobenzenesulfonyl; and imine and cyclic imide protecting groups, such as phthalimido and dithiasuccinoyl. Equivalents of these amino-protecting groups are also encompassed by the compounds and methods of the present invention.

Evaluation of Candidate RNAs

One can evaluate a candidate RNA agent, e.g., a modified RNA, for a selected property by exposing the agent or modified molecule and a control molecule to the appropriate conditions and evaluating for the presence of the selected property. For example, resistance to a degradent can be evaluated as follows. A candidate modified RNA (and a control molecule, usually the unmodified form) can be exposed to degradative conditions, e.g., exposed to a milieu, which includes a degradative agent, e.g., a nuclease. E.g., one can use a biological sample, e.g., one that is similar to a milieu, which might be encountered, in therapeutic use, e.g., blood or a cellular fraction, e.g., a cell-free homogenate or disrupted cells. The candidate and control could then be evaluated for resistance to degradation by any of a number of approaches. For example, the candidate and control could be labeled prior to exposure, with, e.g., a radioactive or enzymatic label, or a fluorescent label, such as Cy3 or Cy5. Control and modified RNA's can be incubated with the degradative agent, and optionally a control, e.g., an inactivated, e.g., heat inactivated, degradative agent. A physical parameter, e.g., size, of the modified and control molecules are then determined. They can be determined by a physical method, e.g., by polyacrylamide gel electrophoresis or a sizing column, to assess whether the molecule has maintained its original length, or assessed functionally. Alternatively, Northern blot analysis can be used to assay the length of an unlabeled modified molecule.

A functional assay can also be used to evaluate the candidate agent. A functional assay can be applied initially or after an earlier non-functional assay, (e.g., assay for resistance to degradation) to determine if the modification alters the ability of the molecule to silence gene expression. For example, a cell, e.g., a mammalian cell, such as a mouse or human cell, can be co-transfected with a plasmid expressing a fluorescent protein, e.g., GFP, and a candidate RNA agent homologous to the transcript encoding the fluorescent protein (see, e.g., WO 00/44914). For example, a modified dsiRNA homologous to the GFP mRNA can be assayed for the ability to inhibit GFP expression by monitoring for a decrease in cell fluorescence, as compared to a control cell, in which the transfection did not include the candidate dsiRNA, e.g., controls with no agent added and/or controls with a non-modified RNA added. Efficacy of the candidate agent on gene expression can be assessed by comparing cell fluorescence in the presence of the modified and unmodified dssiRNA compounds.

In an alternative functional assay, a candidate dssiRNA compound homologous to an endogenous mouse gene, for example, a maternally expressed gene, such as c-mos, can be injected into an immature mouse oocyte to assess the ability of the agent to inhibit gene expression in vivo (see, e.g., WO 01/36646). A phenotype of the oocyte, e.g., the ability to maintain arrest in metaphase II, can be monitored as an indicator that the agent is inhibiting expression. For example, cleavage of c-mos mRNA by a dssiRNA compound would cause the oocyte to exit metaphase arrest and initiate parthenogenetic development (Colledge et al. Nature 370: 65-68, 1994; Hashimoto et al. Nature, 370:68-71, 1994). The effect of the modified agent on target RNA levels can be verified by Northern blot to assay for a decrease in the level of target mRNA, or by Western blot to assay for a decrease in the level of target protein, as compared to a negative control. Controls can include cells in which with no agent is added.

Kits

In certain other aspects, the invention provides kits that include a suitable container containing a pharmaceutical formulation of an RNAi agent. In one embodiment the individual components of the pharmaceutical formulation may be provided in one container. Alternatively, it may be desirable to provide the components of the pharmaceutical formulation separately in two or more containers, e.g., one container for an RNAi agent preparation, and at least another for a carrier compound. The kit may be packaged in a number of different configurations such as one or more containers in a single box. The different components can be combined, e.g., according to instructions provided with the kit. The components can be combined according to a method described herein, e.g., to prepare and administer a pharmaceutical composition. The kit can also include a delivery device.

SYNTHETIC METHODS AND EXAMPLES

The compounds of the inventions may be prepared by any process known to be applicable to the preparation of chemically-related compounds. Suitable processes for making certain intermediates include, for example, those references listed below which are herein incorporated by reference.

Necessary starting materials may be obtained by standard procedures of organic chemistry. Alternatively necessary starting materials are obtainable by analogous procedures to those illustrated which are within the ordinary skill of a chemist. The compounds and processes of the present invention will be better understood in connection with the following representative synthetic schemes and examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

REFERENCES

Cook et al. Synthesis of 2'-O-substituted pyrimidine nucleosides via nucleophilic alkylation in preparation of substituted oligoribonucleotide duplexes. U.S. Pat. No. 5,760,202

Codington et al. Nucleosides. XVIII. Synthesis of 2'-fluorothymidine, 2' fluorodeoxyuridine, and other 2'-halo-2'-deoxy nucleosides. J. Org. Chem. 1964, 29, 558-64.

An et al. Synthesis of novel 3'-C-methylene thymidine and 5-methyluridine/cytidine H-phosphonates and phosphonamidites for new backbone modification of oligonucleotides. J. Org. Chem. 2001, 66, 2789.

Baker and Cowsert, Antisense oligonucleotide inhibition of human TNFR1 expression and its therapeutic uses U.S. Pat. No. 6,007,995.

Shi et al. Synthesis and in vitro anti-HCV activity of β-D- and L-2'-deoxy-2'-fluororibonucleosides. Nucleosides, Nucleotides & Nucleic Acids 2005, 24, 875.

Miraglia et al. Antisense modulation of mdm2 expression. US publication 2003203862.

Ross et al. Kilo-scale synthesis process for 2'-O-(2-methoxyethyl)-pyrimidine derivatives. Nucleosides, nucleotides & Nucleic acids, 2005, 24, 815.

Bhat et al. Modulation of human survivin expression by compounds comprising single and double-stranded oligonucleotides and uses for cancer therapy. WO 2005/002507.

Murakami et al. The mechanism of action of β-D-2'-deoxy-2'-fluoro-2'-C-methylcytidine involves a second metabolic pathway leading to β-D-2'-deoxy-2'-fluoro-2'-C-methyluridine 5'-triphosphate, a potent inhibitor of the hepatitis C virus RNA-dependent RNA polymerase. Antimicrobial Agents and Chemotherapy 2008, 52, 458.

Clark et al. Design, Synthesis, and Antiviral Activity of 2'-Deoxy-2'-fluoro-2'-C-methyl-cytidine, a Potent Inhibitor of Hepatitis C Virus Replication. J. Org. Chem. 2005, 48, 5504.

Benzaria et al. 2'-C-methyl branched pyrimidine ribonucleoside analogues: potent inhibitors of RNA virus replication. Antiviral Chemistry & Chemotherapy 2007, 18, 225.

Roberts et al. Preparation of nucleoside derivatives for treating hepatitis C virus infection WO 2003/093290.

Johansen et al. Compositions and methods for treatment of viral diseases. WO 2008/033466.

Clark et al. Design, Synthesis, and Antiviral Activity of 2'-Deoxy-2'-fluoro-2'-C-methyl-cytidine, a Potent Inhibitor of Hepatitis C Virus Replication. J. Org. Chem. 2005, 48, 5504.

Hong et al. Preparation of sugar modified nucleosides as antiviral agents. WO 2003/062255.

Damhan and Peng 2'-Deoxy-2'-fluoro-β-D-arabinonucleoside 5'-triphosphates and their use in enzymic nucleic acid synthesis. WO 2008/022469.

Watanabe, K. Role of modified nucleosides in the translation function of tRNAs from extreme thermophilic bacteria and animal mitochondria. Bull. Chem. Soc. Japan 2007, 80, 1253.

Baker et al. SiRNA having modified bases for binding to adenine and guanine and their use in gene modulation and disease treatment. WO 2004/044245.

Diop-Frimpong et al. Stabilizing contributions of sulfur-modified nucleotides: crystal structure of a DNA duplex with 2'-O-[2-(methoxy)ethyl]-2-thiothymidines. Nucleic Acids Res. 2005, 33, 5297.

Rajeev et al. 2'-Modified-2-thiothymidine Oligonucleotides. Organic Lett. 2003, 5, 3005.

Hardee and Dellamary Compositions and methods for the treatment of severe acute respiratory syndrome (SARS). WO 2005/020885.

Sochacka et al. Nucleosides. 153. Synthesis of 1-methyl-5-(3-azido-2,3-dideoxy-β-D-erythro-pentofuranosyl)uracil and 1-methyl-5-(3-azido-2,3-dideoxy-2-fluoro-β-D-arabinofuranosyl)uracil. The C-nucleoside isostere of 3'-azido-3'-deoxythymidine and its 2'-"up"-fluoro analog. J. Med. Chem. 1990, 33, 1995.

Mokany et al. Multicomponent nucleic acid enzymes and methods for their use. WO 2007/041774.

Ross et al. Synthesis and incorporation of 2'-O-methyl-pseudouridine into oligonucleotides. Nucleosides & Nucleotides, 1997), 16, 1547.

Wigler et al. Effects of 4-thiopseudouridine on the salvage of pseudouridine by Escherichia coli cells. J. Carbohydrates, Nucleosides, Nucleotides 1974, 1, 307.

Xia et al. Gene Silencing Activity of siRNAs with a Ribo-difluorotoluoyl Nucleotide. ACS Chem. Biol. 2006, 1, 176.

Manoharan et al. Single- and double-stranded oligonucleotides containing modified nucleobases for inhibition of gene expression and treatment of disease. US patent application publication 2006/035254.

Tuttle et al. Purine 2'-deoxy-2'-fluororibosides as antiinfluenza virus agents. J. Med. Chem. 1993, 36, 119.

Tisdale et al. Preparation of 2'-deoxy-2'-fluororibonucleosides as medicinal virucides. EP 417999.

Jin and Kim Pyrimidyl phosphonate antiviral compounds and methods of use. WO 2005/070901.

Ecker et al. Methods for identification of coronaviruses by PCR amplification of a RdRp orf-1b or nsp11 target region for diagnostic application. WO 2004/111187.

Lin and Matteucci Preparation of phenoxazin-1-yl oligodeoxyribonucleotides as enzyme and gene expression inhibitors. WO 99/24452.

Holmes et al. Steric inhibition of human immunodeficiency virus type-1 Tat-dependent trans-activation in vitro and in cells by oligonucleotides containing 2'-O-methyl G-clamp ribonucleoside analogues. *Ncleic Acids Research* 2003, 31, 2759.

Lin et al., Tricyclic 2'-Deoxycytidine Analogs: Syntheses and Incorporation into Oligodeoxynucleotides Which Have Enhanced Binding to Complementary RNA. *J. Am. Chem. Soc.*, 1995, 117, 3873.

Sandin et al., Synthesis and oligonucleotide incorporation of fluorescent cytosine analogue tC: a promising nucleic acid probe. *Nature Protocols,* 2007, 2, 615.

Lin et al., Tricyclic 2'-Deoxycytidine Analogs: Syntheses and Incorporation into Oligodeoxynucleotides Which Have Enhanced Binding to Complementary RNA. *J. Am. Chem. Soc.*, 1995, 117, 3873.

Alekseeva et al., Nucleosides with tricyclic aglycone. The ribonucleosides of condensed 1,2,4-triazine: synthesis and antiherpetic activity. *Biopolimeri i Klitina,* 2006, 22, 468.

Leydier et al. 4'-Thio-β-D-oligoribonucleotides: nuclease resistance and hydrogen bonding properties. *Nucleosides & Nucleotides* 1995, 14, 1027.

Bhat et al. Preparation of antisense 4'-thionucleosides-containing oligoribonucleotides duplexes for use in the RNA interference pathway of gene modulation. WO 2005/027962.

Yoshimura et al. A practical synthesis of 4'-thioribonucleosides. *Tetrahedron Letters,* 2006, 47, 591.

Hoshika et al. Synthesis and physical and physiological properties of 4'-thio-RNA: application to post-modification of RNA aptamer toward NF-κB. Nucleic Acids Res. 2004, 32, 3815.

Dande et al. Improving RNA Interference in Mammalian Cells by 4'-Thio-Modified Small Interfering RNA (siRNA): Effect on siRNA Activity and Nuclease Stability When Used in Combination with 2'-O-Alkyl Modifications. *J. Med. Chem.* 2006, 49, 1624

Hoshika et al. Synthesis and physical and physiological properties of 4'-thio-RNA: application to post-modification of RNA aptamer toward NF-κB. *Nucleic Acids Res.* 2004, 32, 3815.

Matsuda et al. Preparation of 4'-thionucleotide and oligonucleotides containing them. WO 2004/018494.

Inoue et al. Practical Synthesis of 2'-Deoxy-4'-thioribonucleosides: Substrates for the Synthesis of 4'-ThioDNA. *J. Org. Chem.* 2005, 70, 8597.

Takahashi et al. Synthesis and crystal structure of 2'-deoxy-2'-fluoro-4'-thioribonucleosides: substrates for the synthesis of novel modified RNAs. *Tetrahedron,* 2008, 64, 4313.

Scheme 1

Pseudouridine Functionalization
A. For post-synthetic conjugation

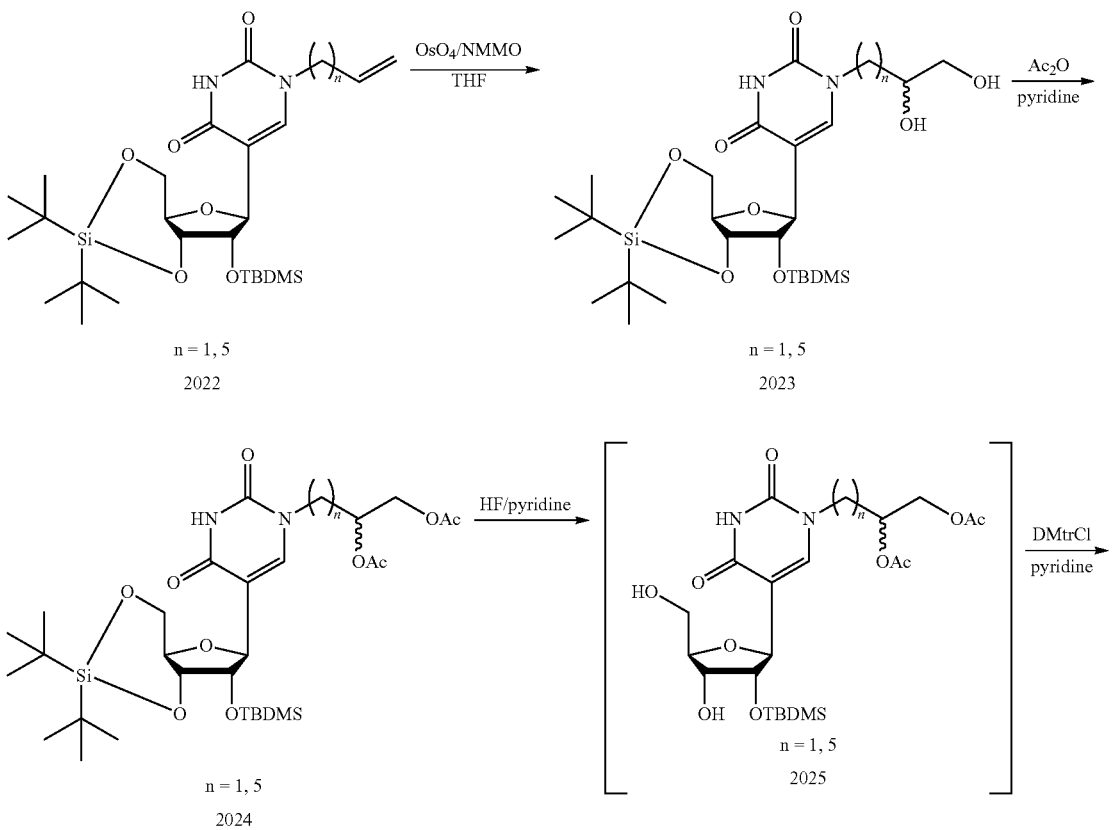

-continued
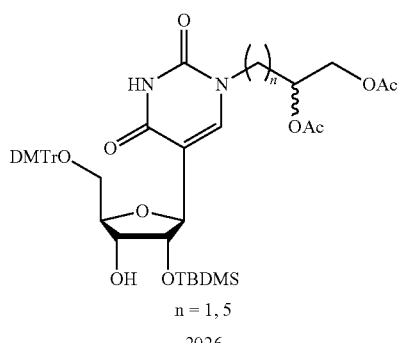
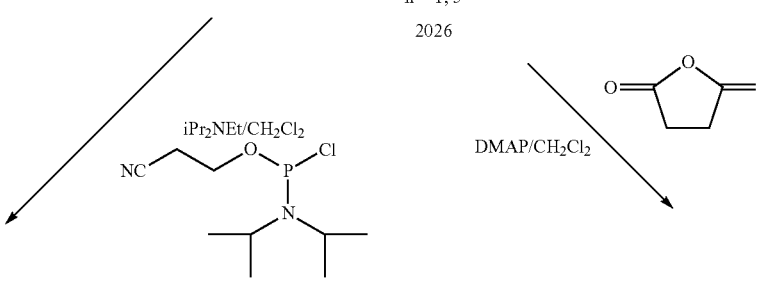
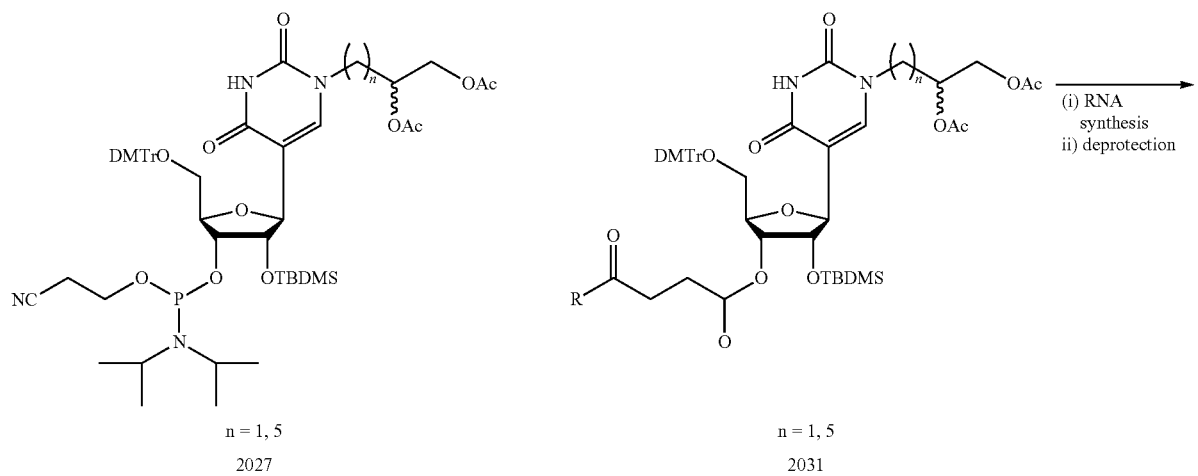
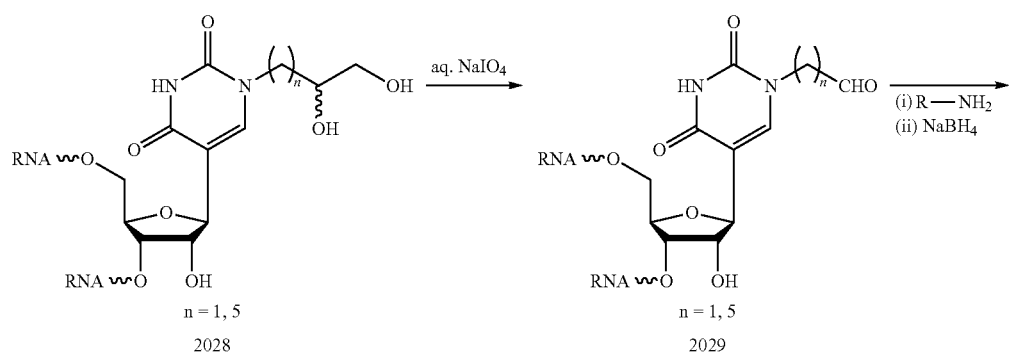

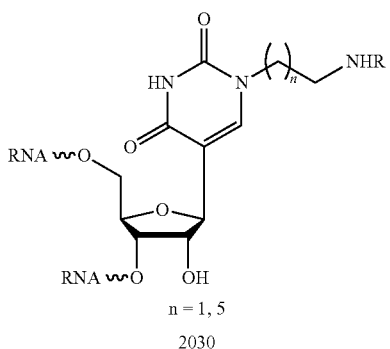
n = 1, 5
2030
Scheme 2 For conjugated building blocks
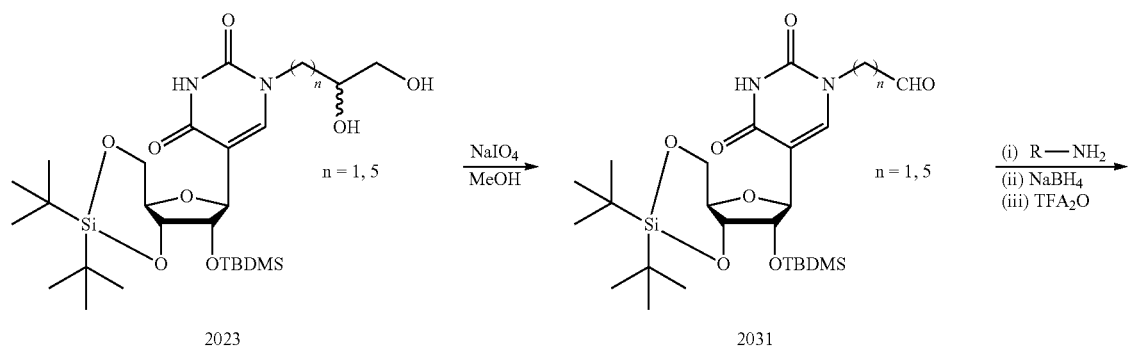
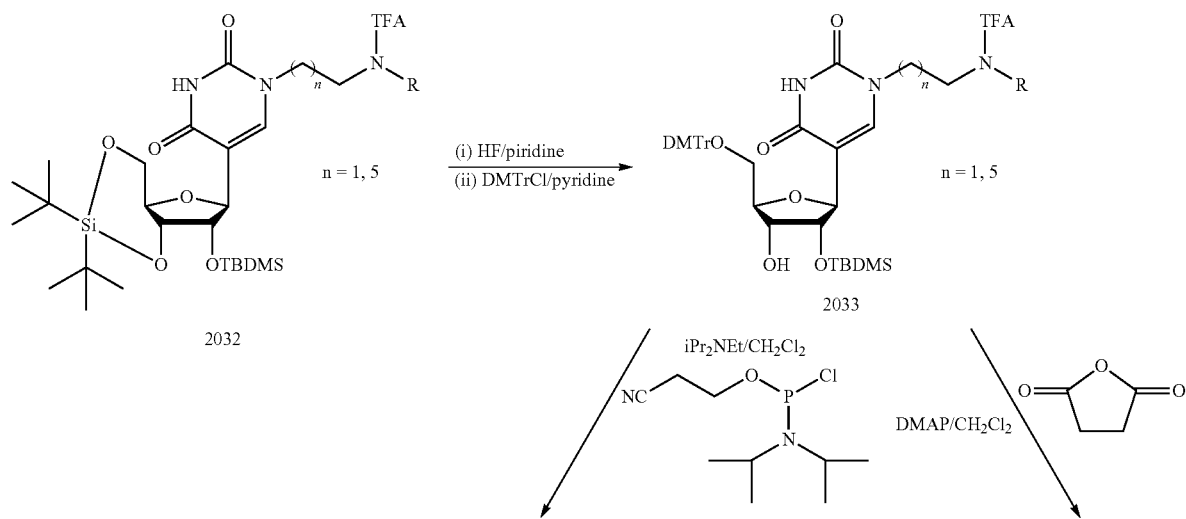

-continued
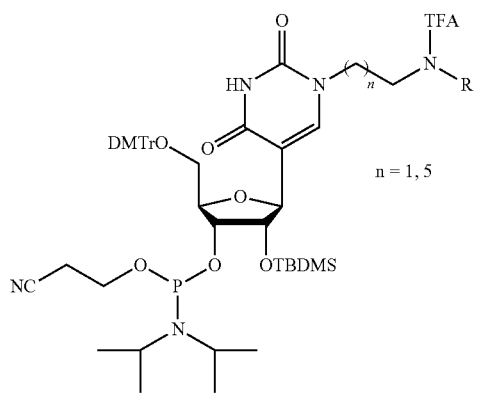
2034
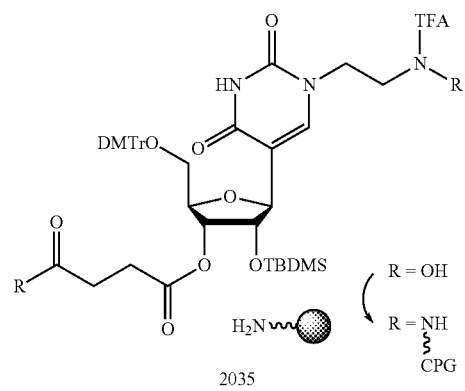
2035
Scheme 3
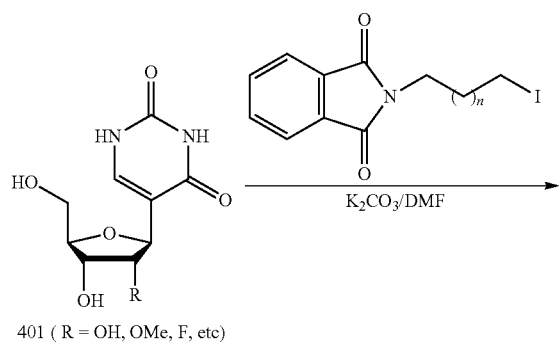
401 (R = OH, OMe, F, etc)
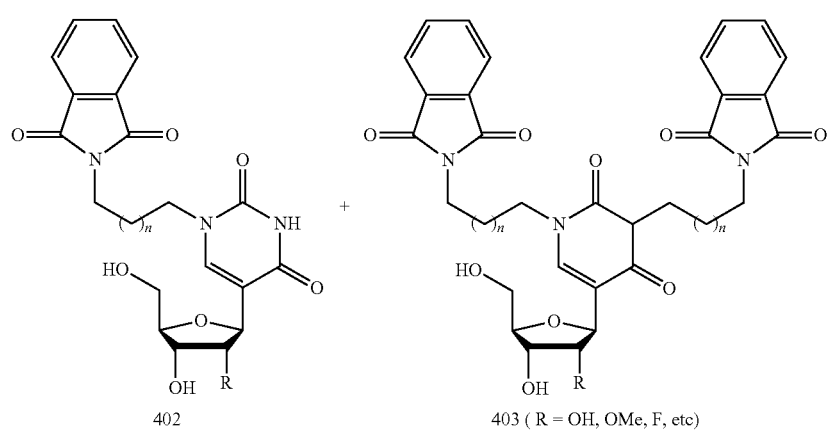
402
403 (R = OH, OMe, F, etc)
402 (R = OH) → (i) DMTrCl/pyridine (ii) TBDMSCl/AgNO₃/pyridine/THF -continued
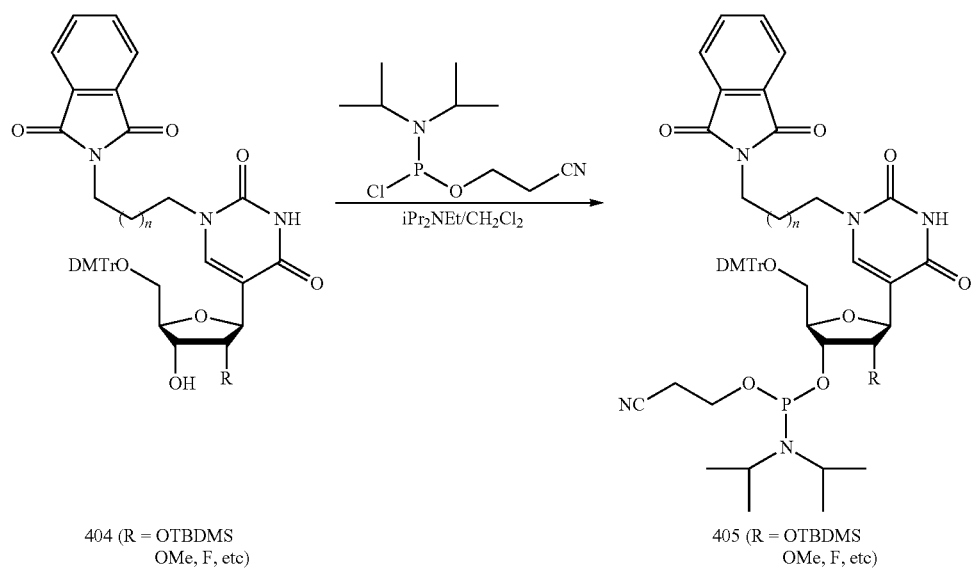
404 (R = OTBDMS, OMe, F, etc)
405 (R = OTBDMS, OMe, F, etc)
(I) succinic anhydride/DMAP/CH₂Cl₂
(ii) CPG-NH₂/HBTU/iPr₂NEt/DMF
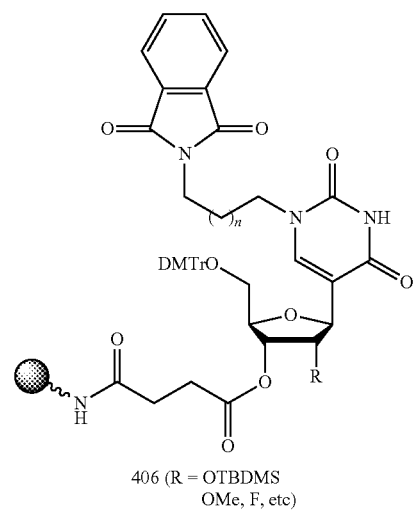
406 (R = OTBDMS, OMe, F, etc)
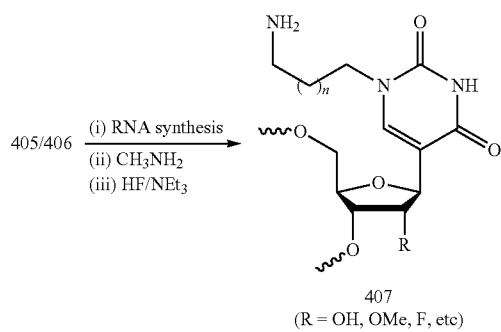
407 (R = OH, OMe, F, etc)

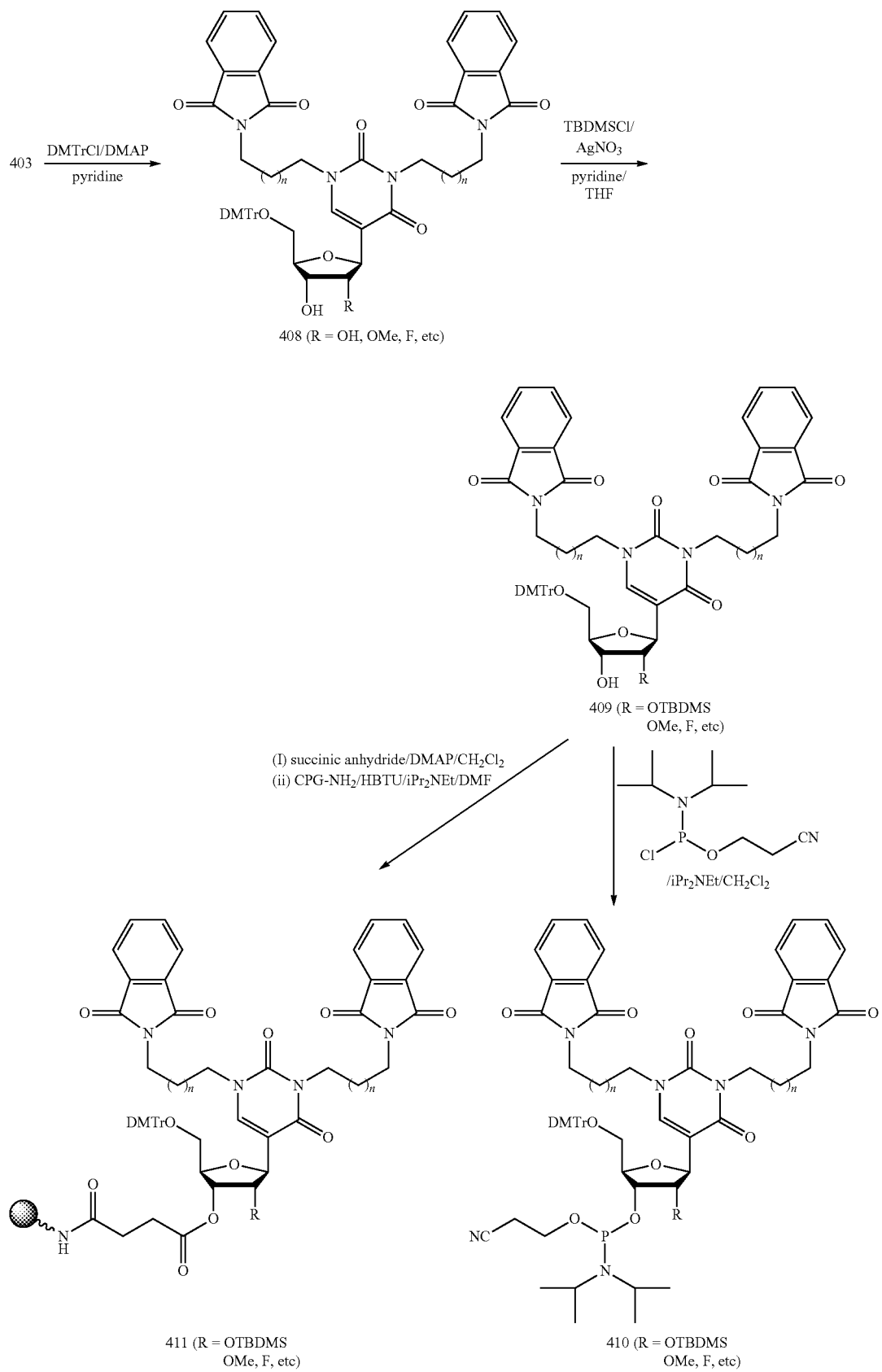

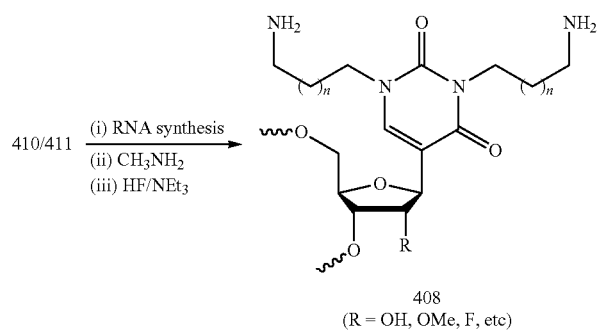
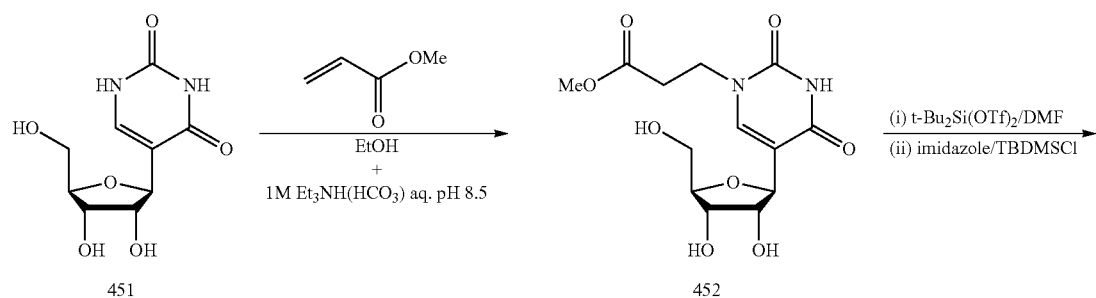
Scheme 4
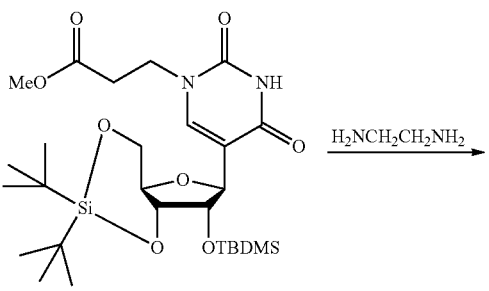
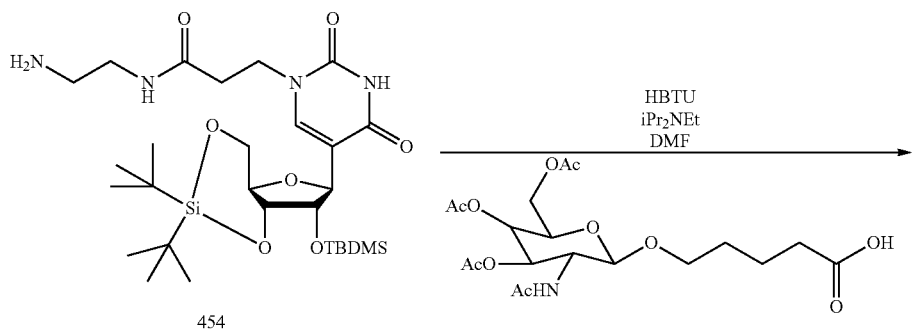

-continued
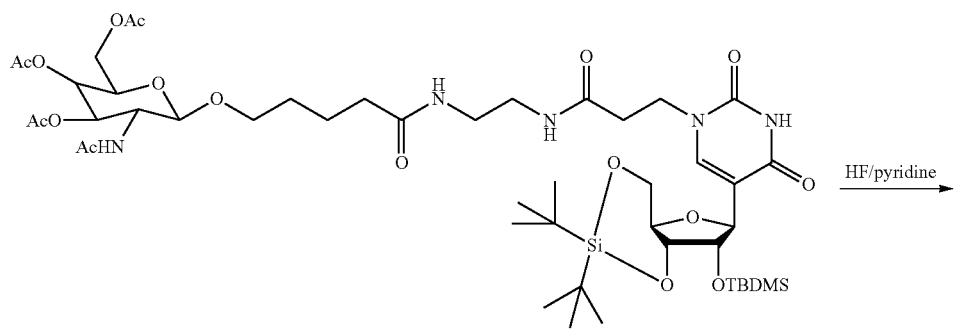
455
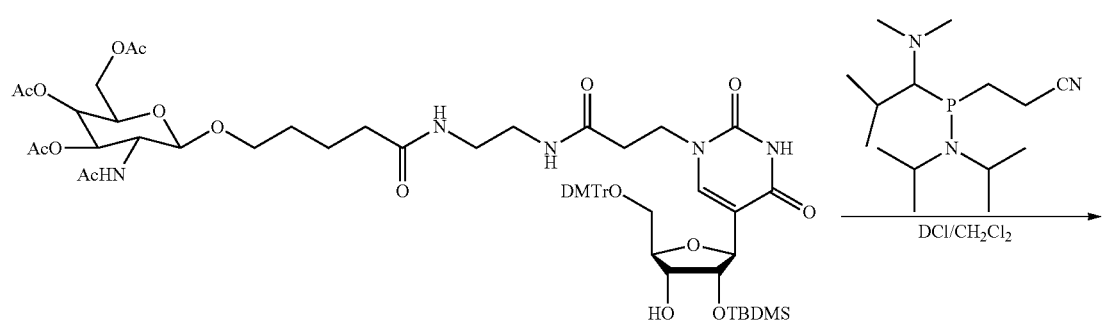
456
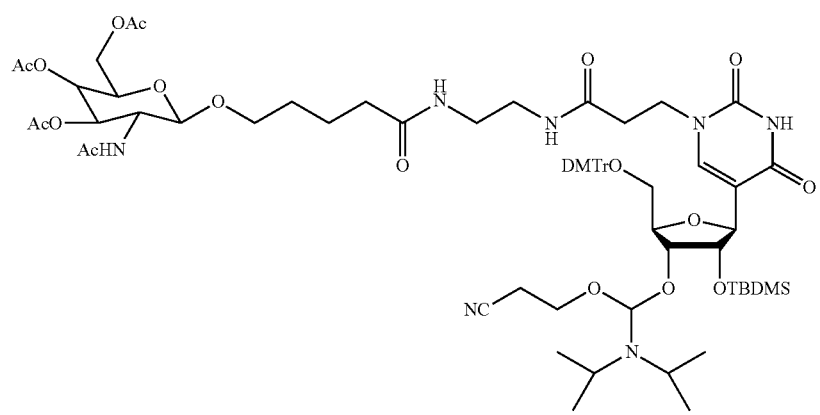
457
Scheme 5
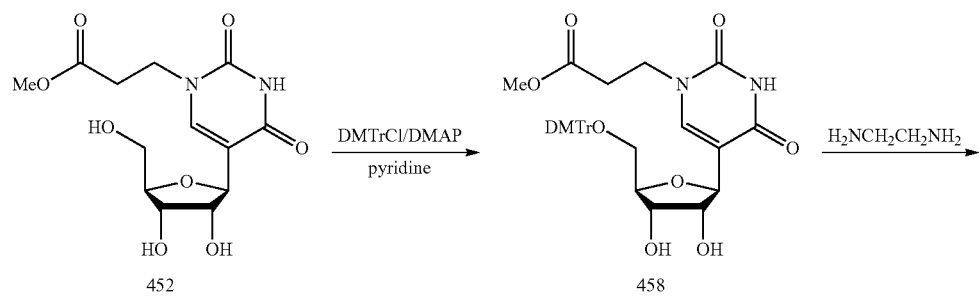
452    458

-continued
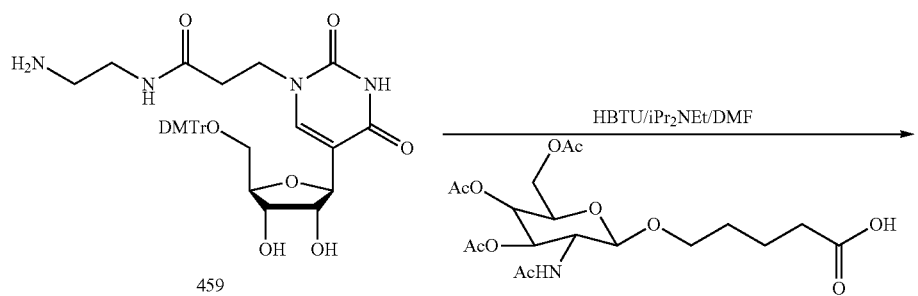
459
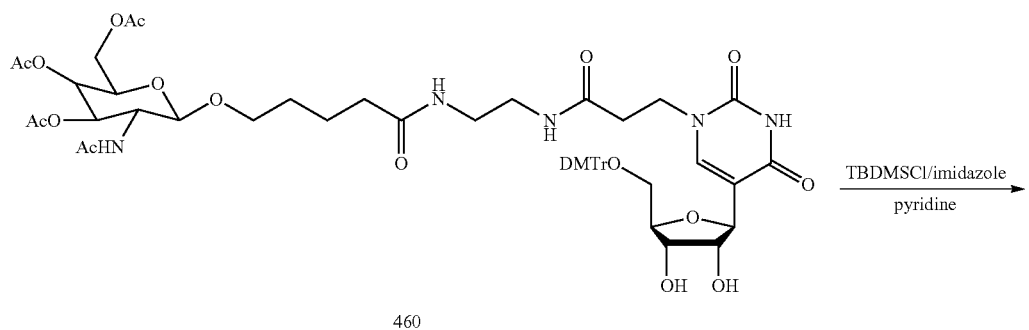
460
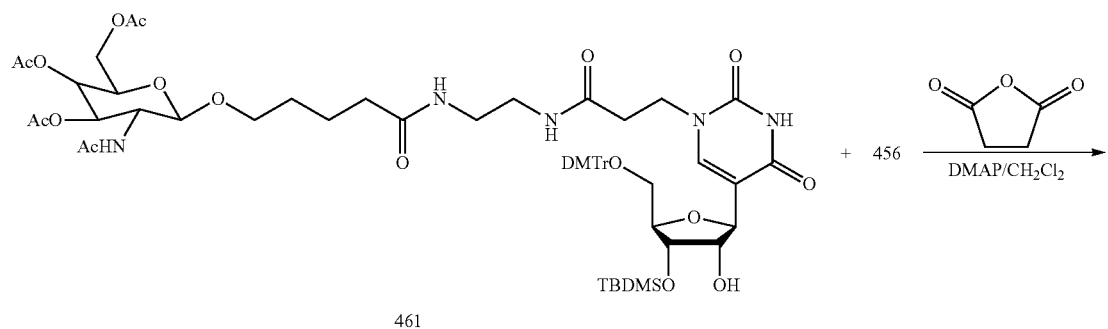
461
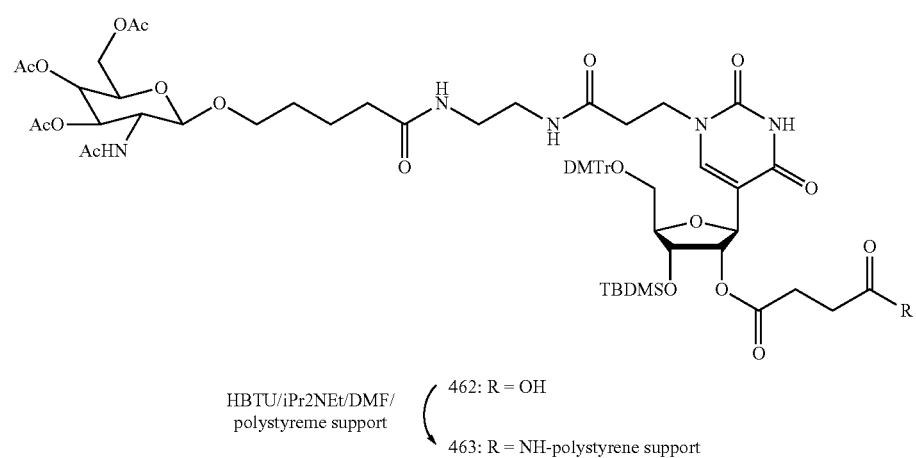
462: R = OH
463: R = NH-polystyrene support
HBTU/iPr2NEt/DMF/
polystyrene support Scheme 6. Pyridopyrimidine nucleosides.
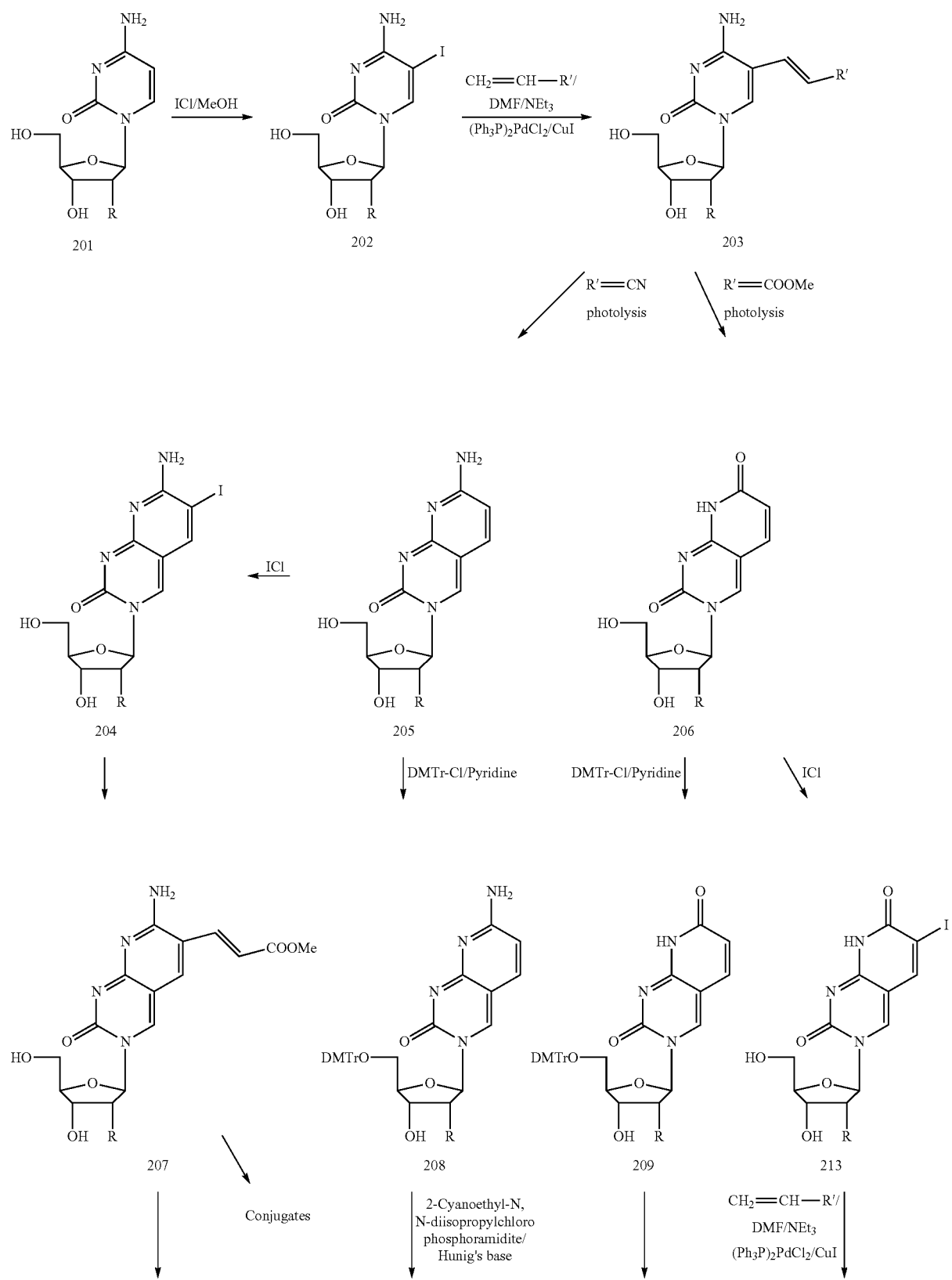

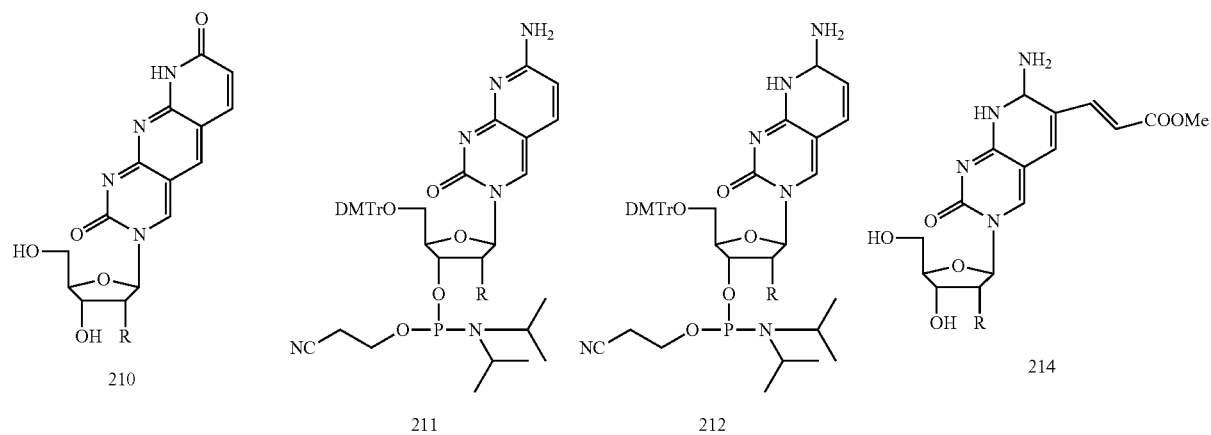
A. R = F
B. R = O-alkyl
C. R = O-aminoalkyl
Scheme 7.
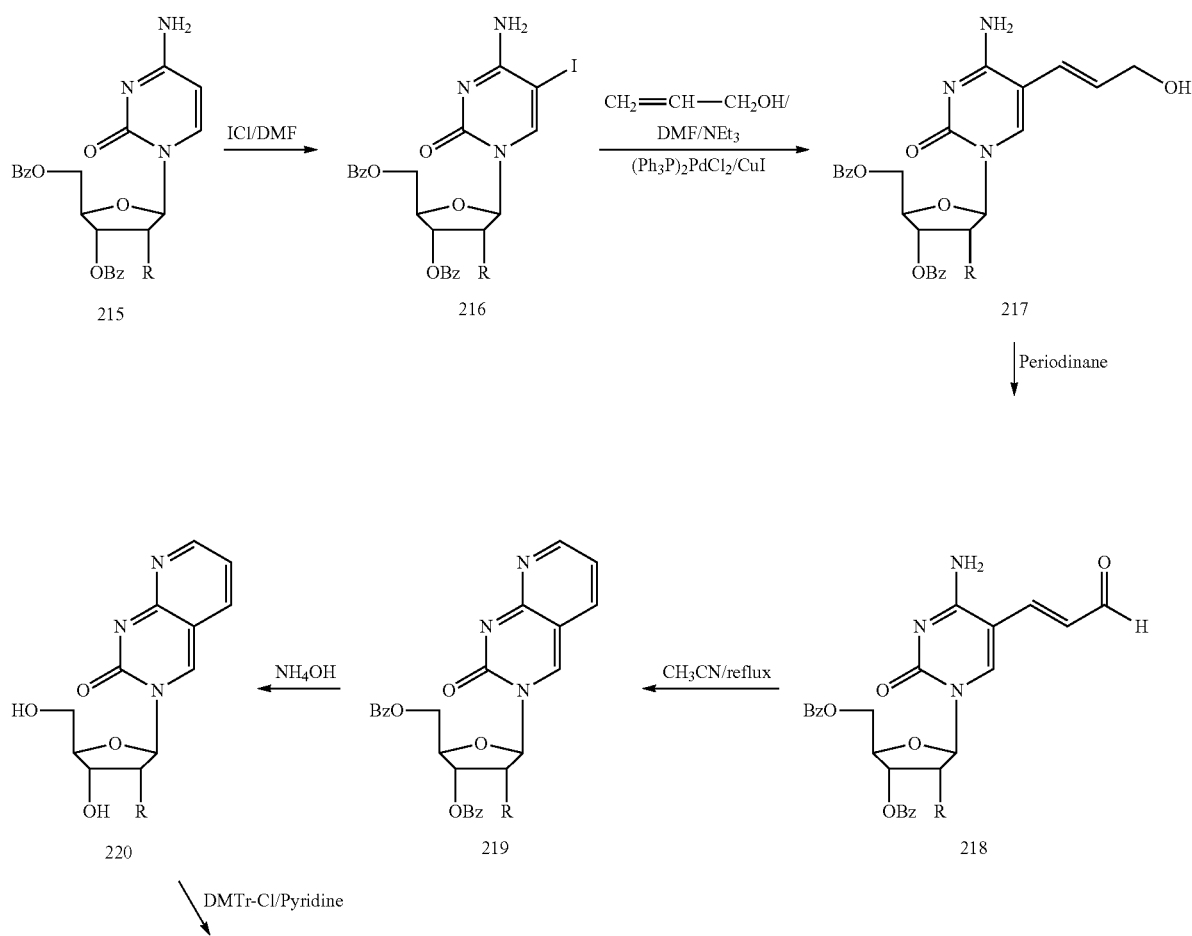

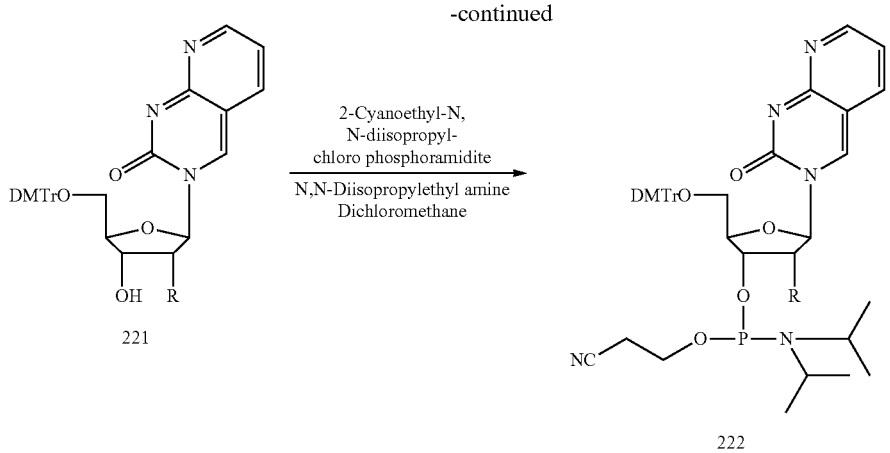
A. R = F
B. R = O-alkyl
C. R = O-aminoalkyl
Scheme 8-1
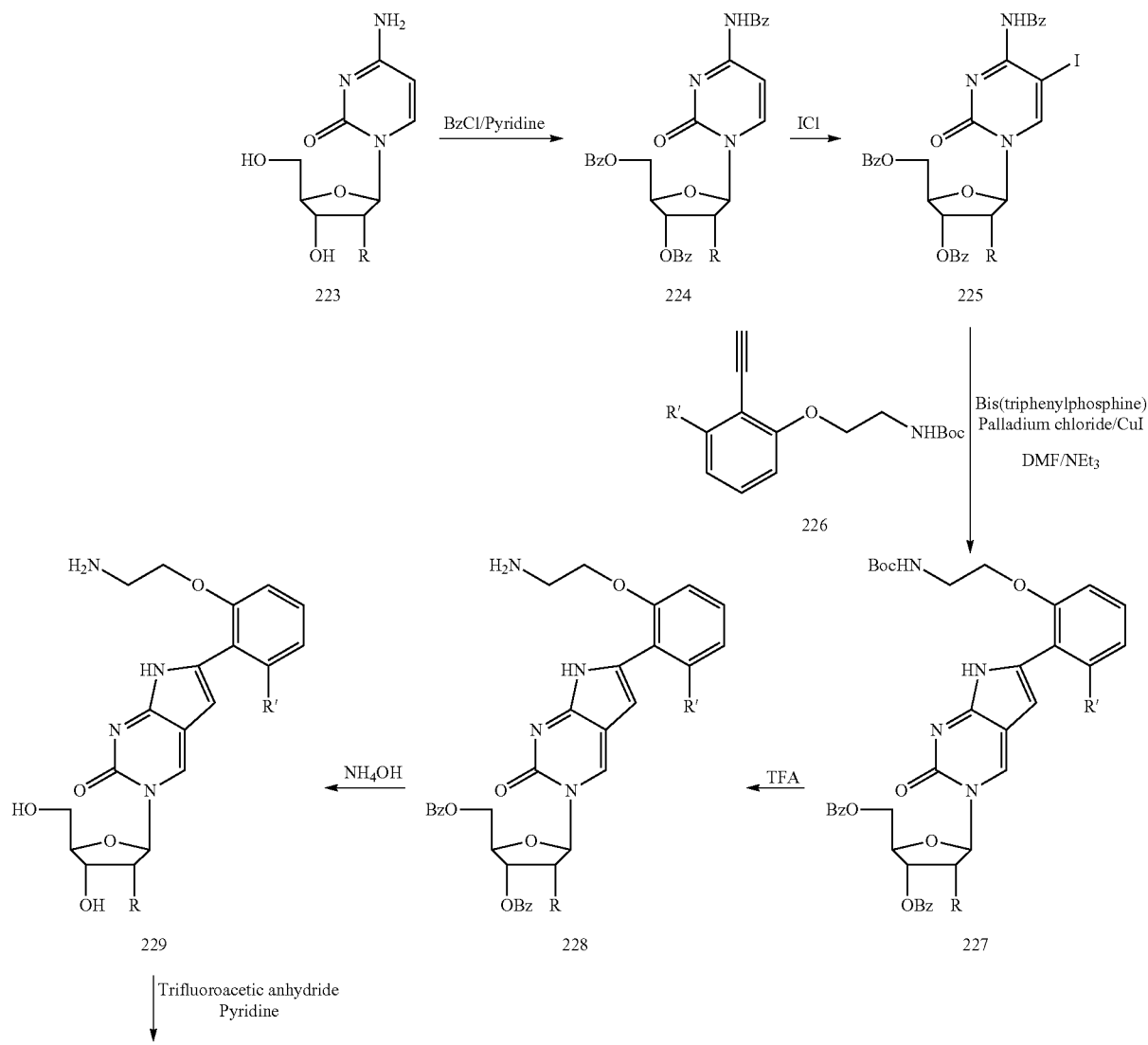

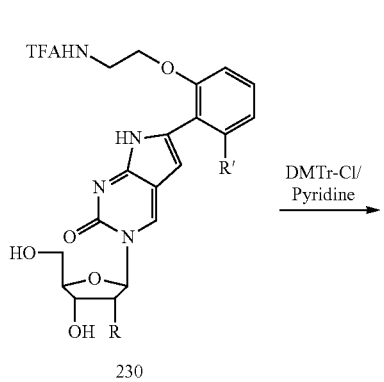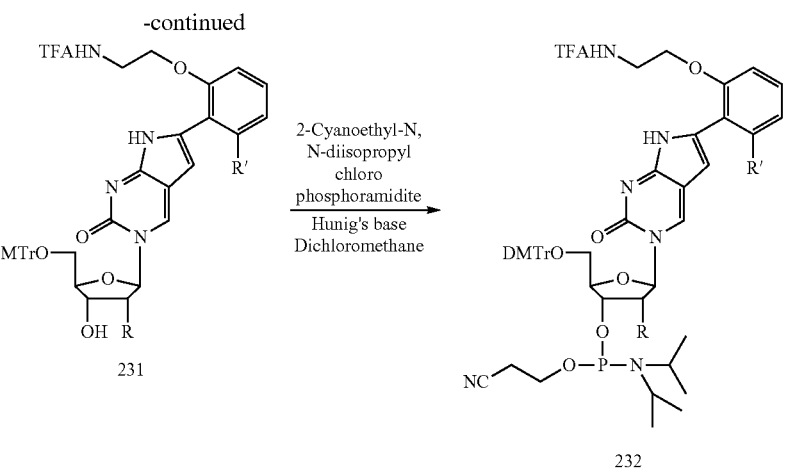
A. R = F, R' = H
B. R = O-alkyl, R' = H
C. R = O-aminoalkyl, R' = H
D. R = F, R' = OCH₂CH₂NHTFA
E. R = O-alkyl, R' = OCH₂CH₂NHTFA
F. R = O-aminoalkyl, R' = OCH₂CH₂NHTFA
Scheme 8-2
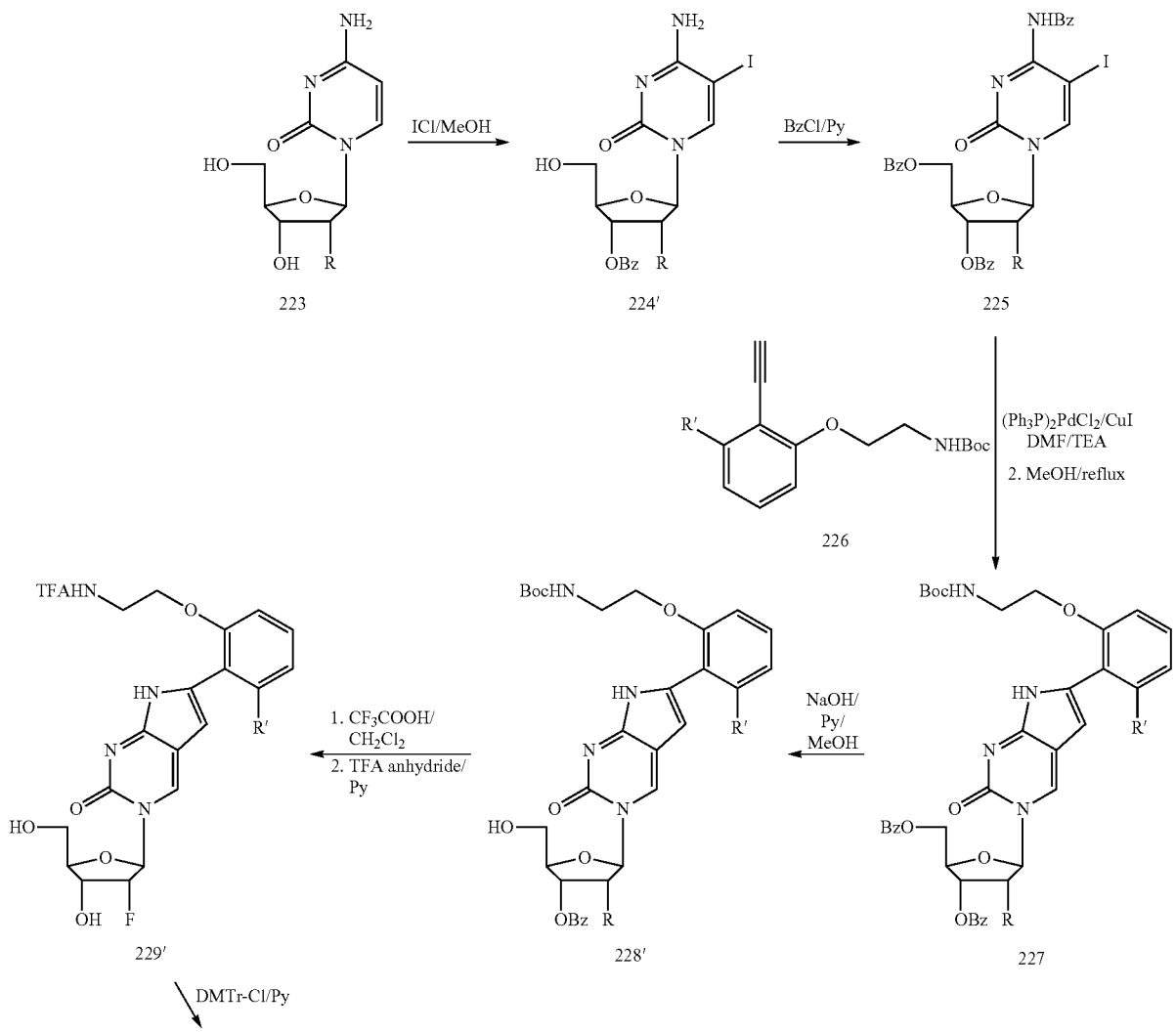

171
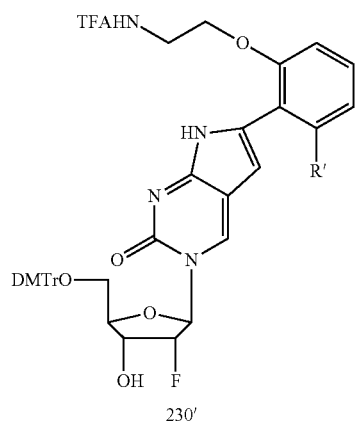
230'
A. R = F, R' = H
B. R = O-Alkyl, R' = H
C. R = O-aminoalkyl, R' = H
D. R = F, R' = OCH$_2$CH$_2$NHTFA
E. R = O-alkyl, R' = OCH$_2$CH$_2$NHTFA
F. R = O-aminoalkyl, R' = OCH$_2$CH$_2$NHTFA
172
-continued
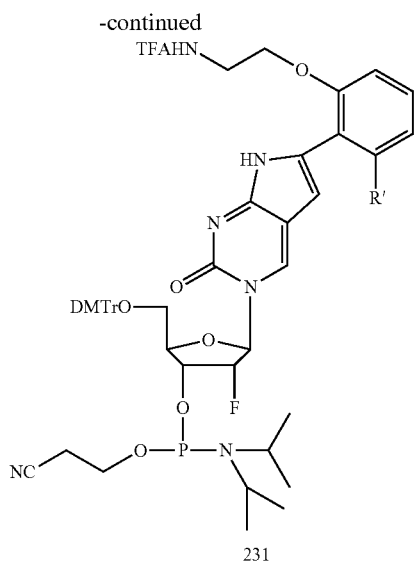
231
Scheme 9
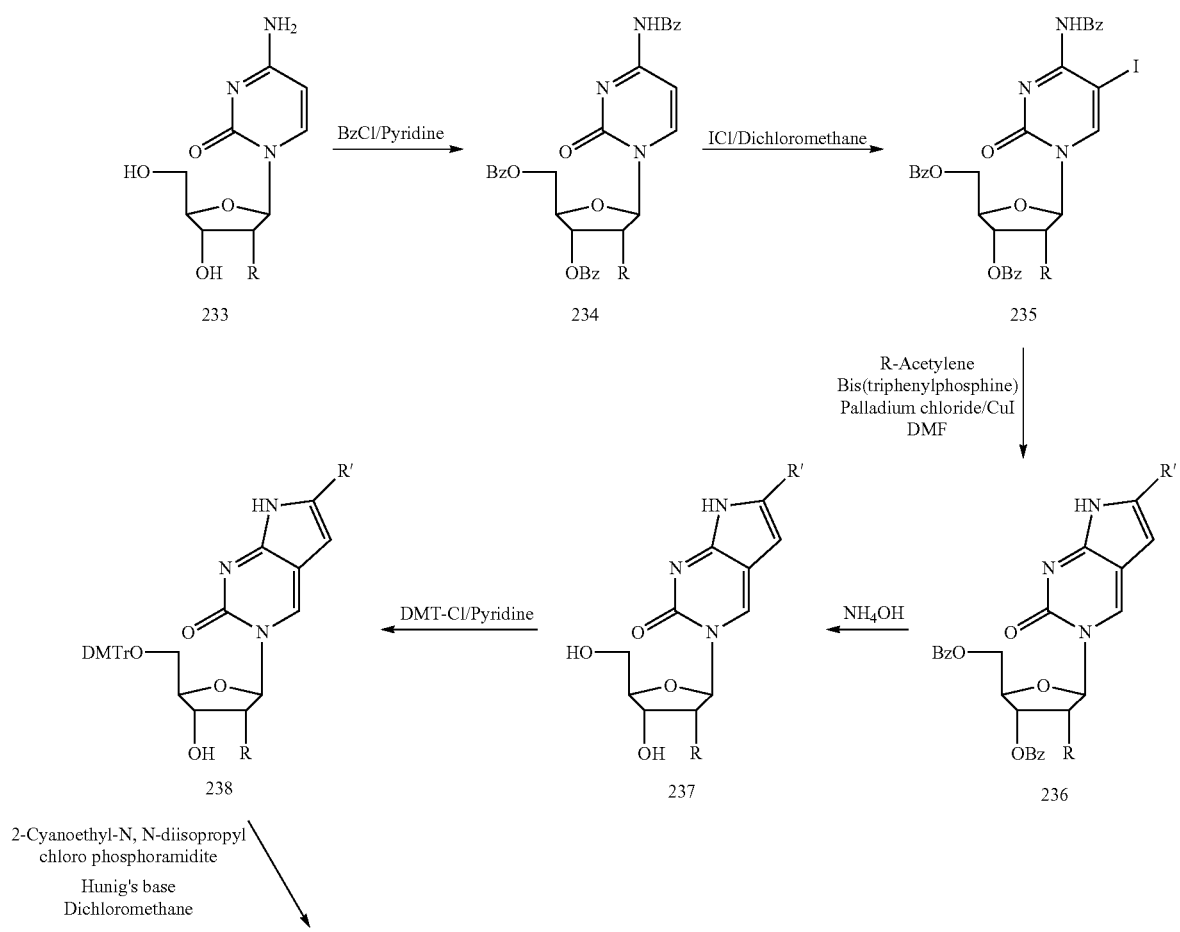

-continued

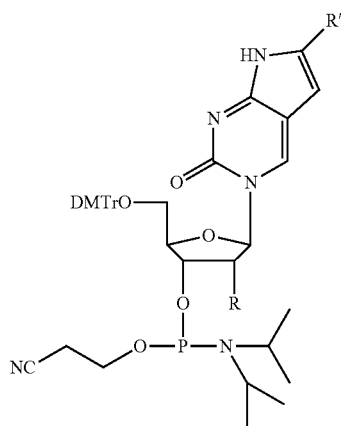
239

A. R = F, R' = H
B. R = F, R' = alkyl
C. R = F, R' = Phenyl or substituted phenyl
D. R = F, R' = pyridyl or substituted pyridyl
E. R = F, R' = heterocycle
F. R = O-alkyl, R' = H
G. R = O-alkyl, R' = alkyl
H. R = O-alkyl, R' = Phenyl or substituted phenyl
I. R = O-alkyl, R' = pyridyl or substituted pyridyl
J. R = O-alkyl, R' = heterocycle
K. R = O-aminoalkyl, R' = H
L. R = O-aminoalkyl, R' = alkyl
M. R = O-aminoalkyl, R' = Phenyl or substituted phenyl
N. R = O-aminoalkyl, R' = pyridyl or substituted pyridyl
O. R = O-aminoalkyl, R' = heterocycle Scheme 10

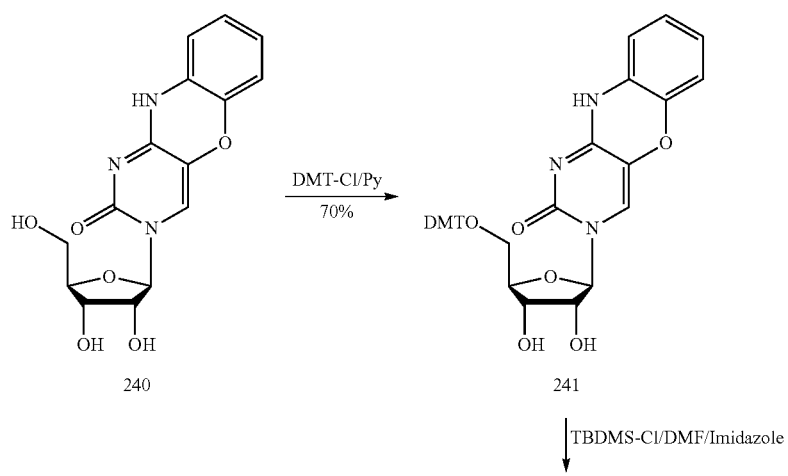

-continued
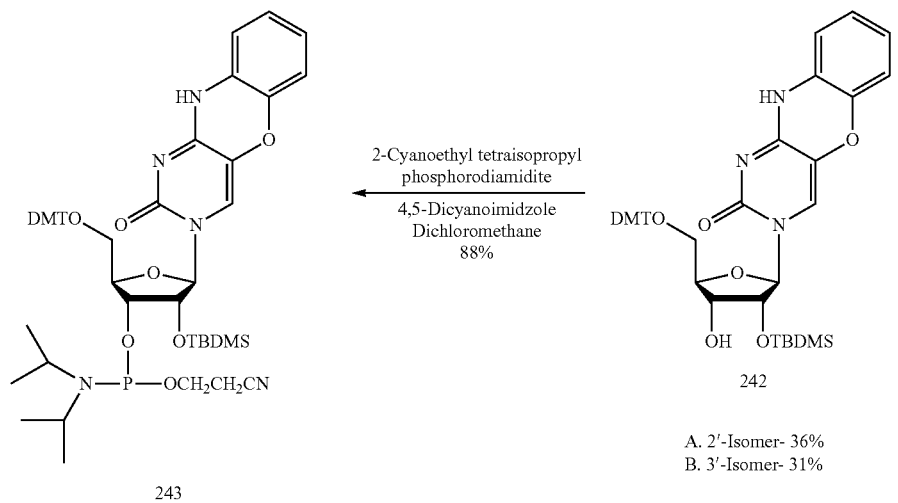
Scheme 11
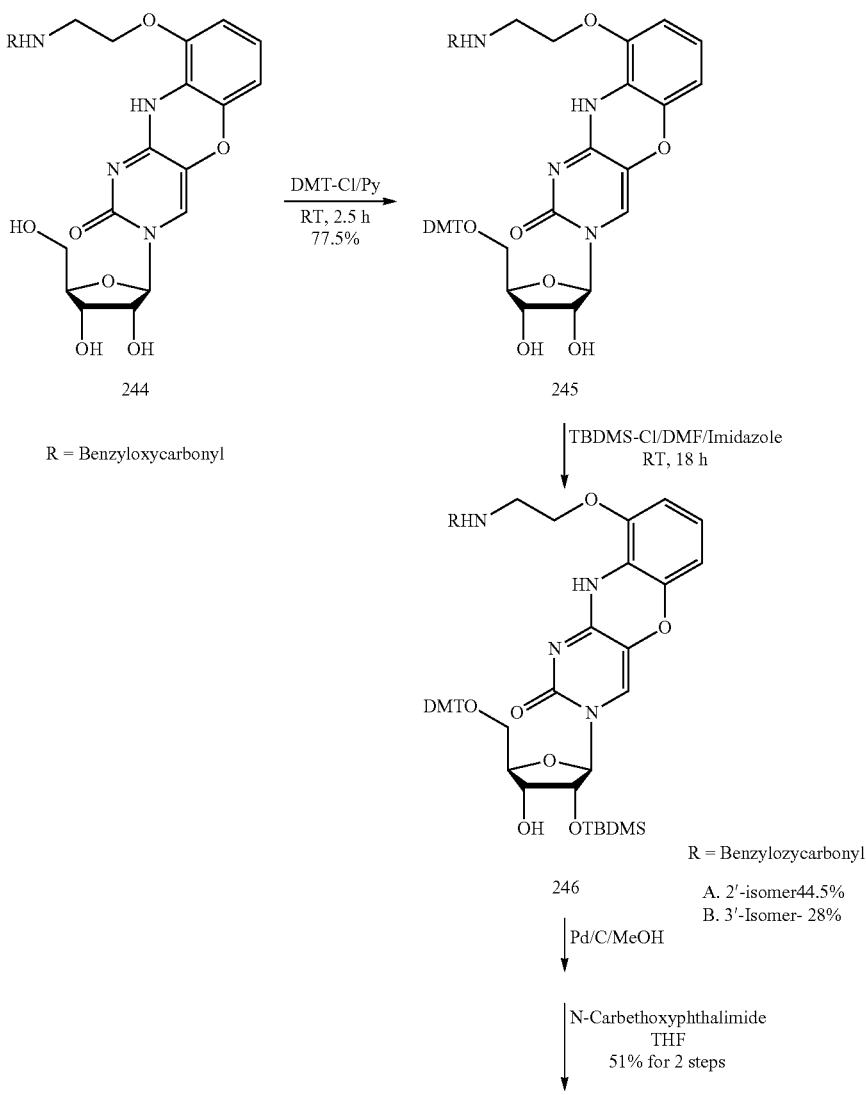

177
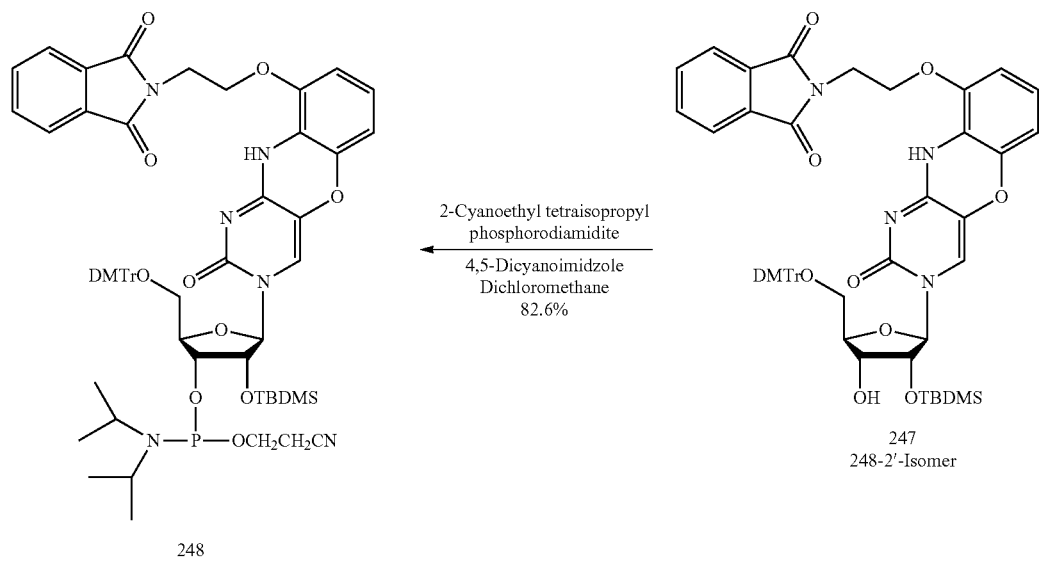
178
-continued
Scheme 12
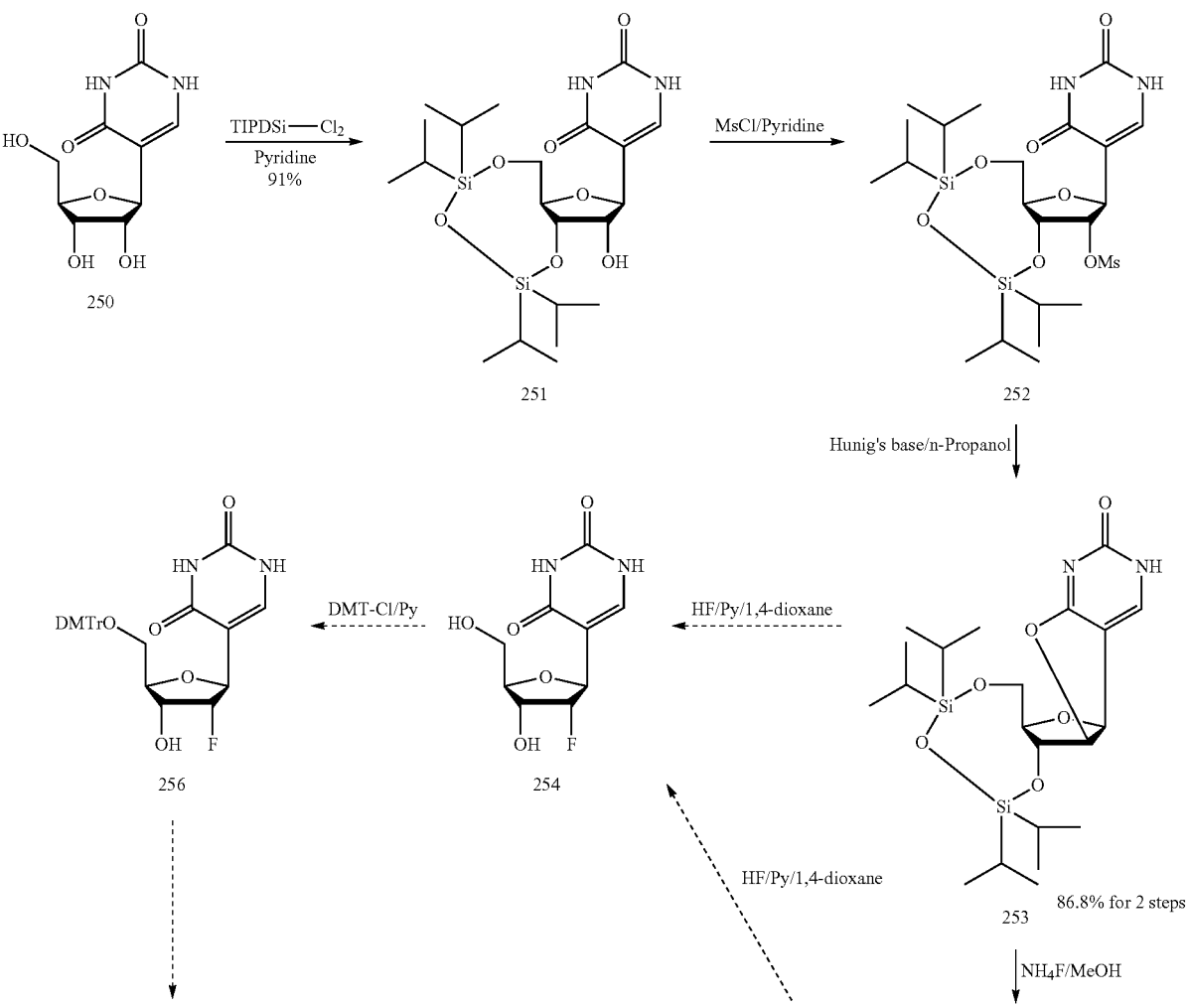

-continued
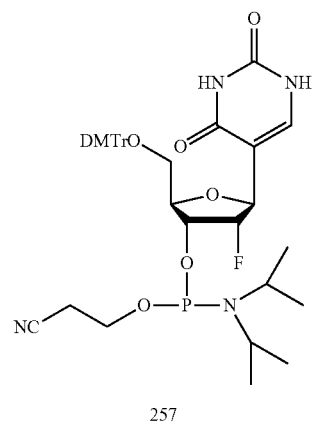
257
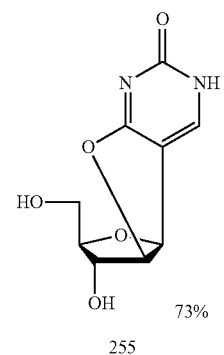
255  73%
Scheme 13
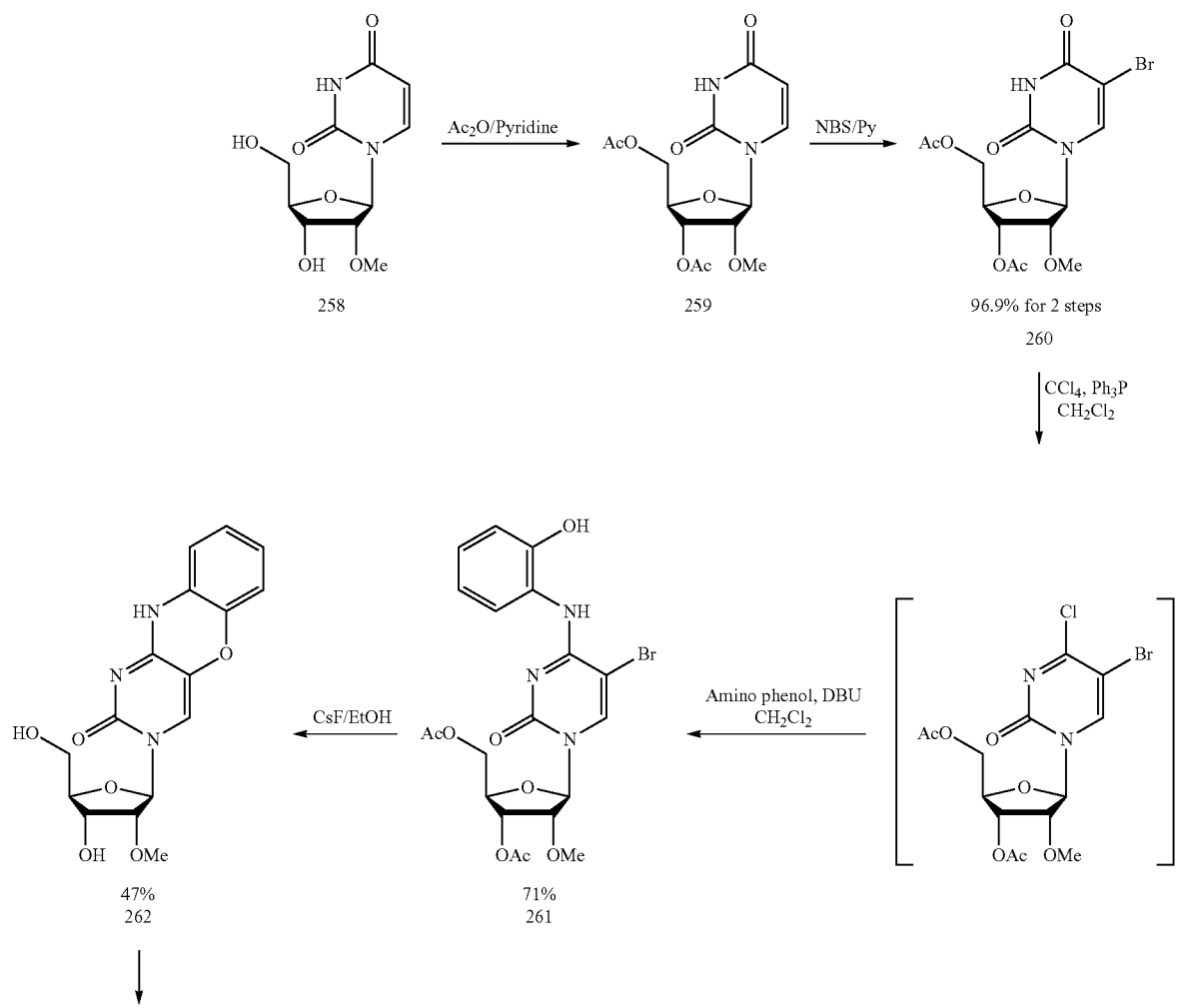

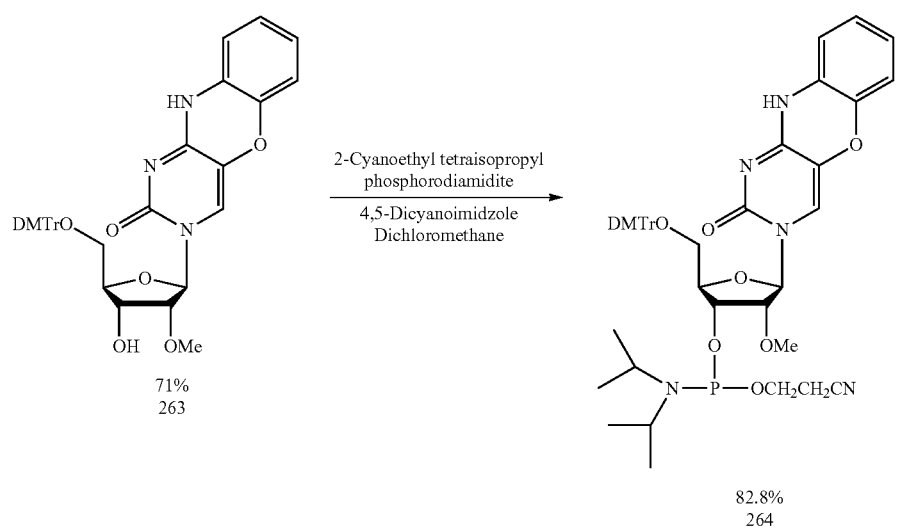
Scheme 14
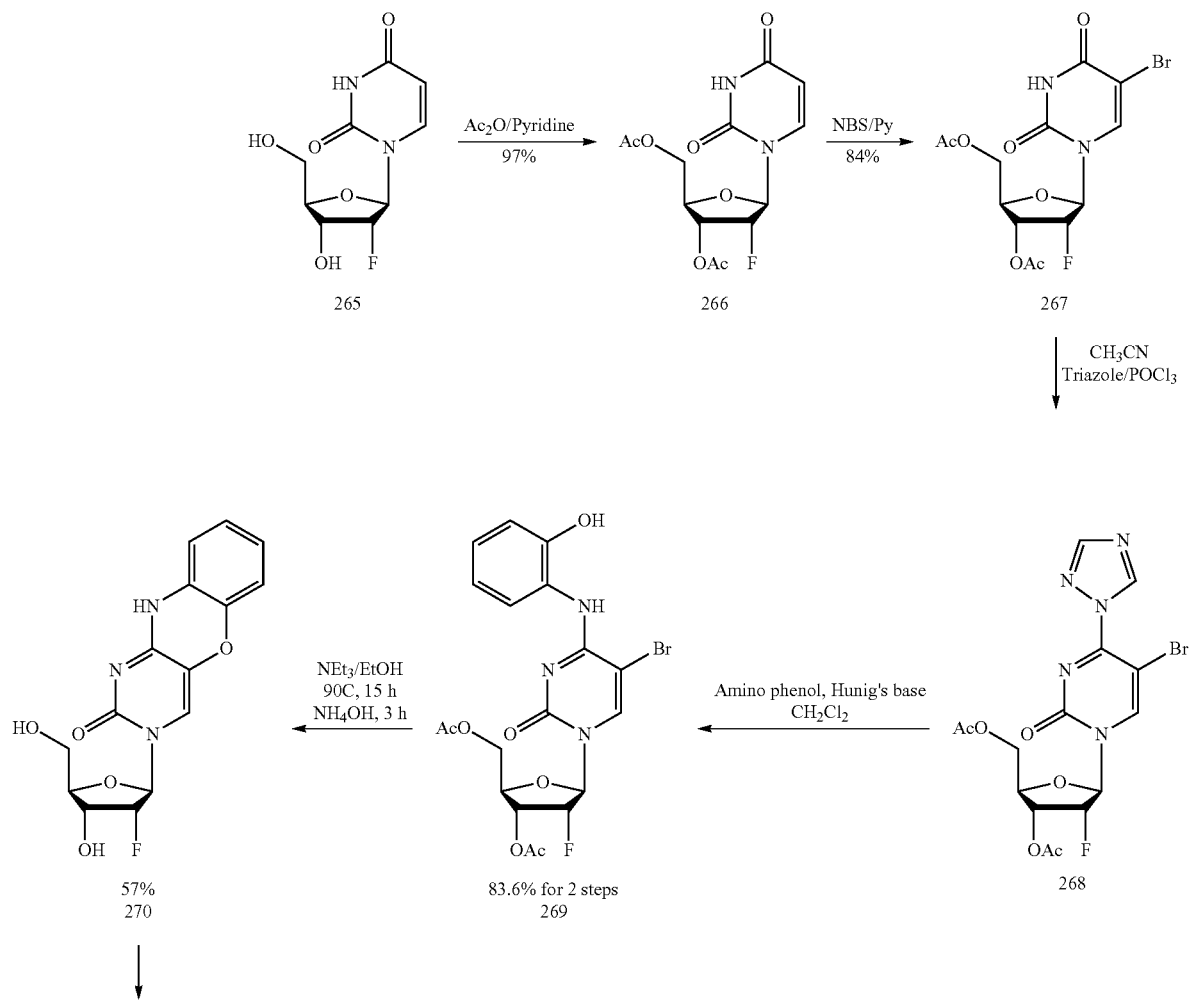

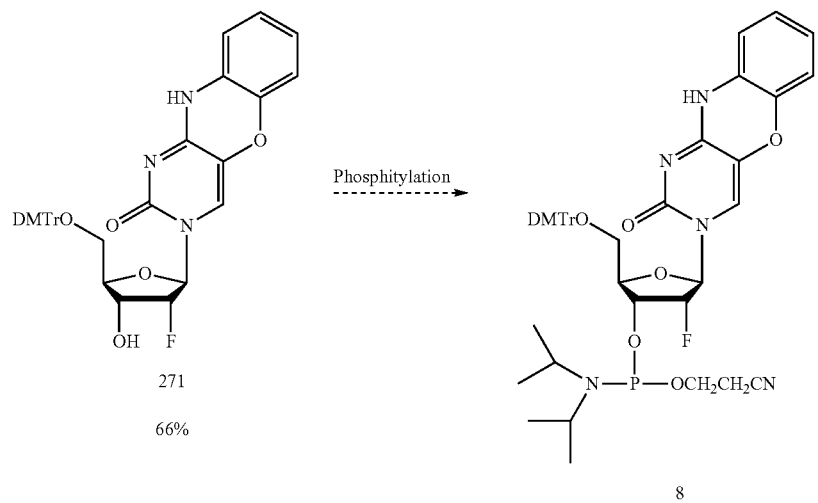
Scheme 15
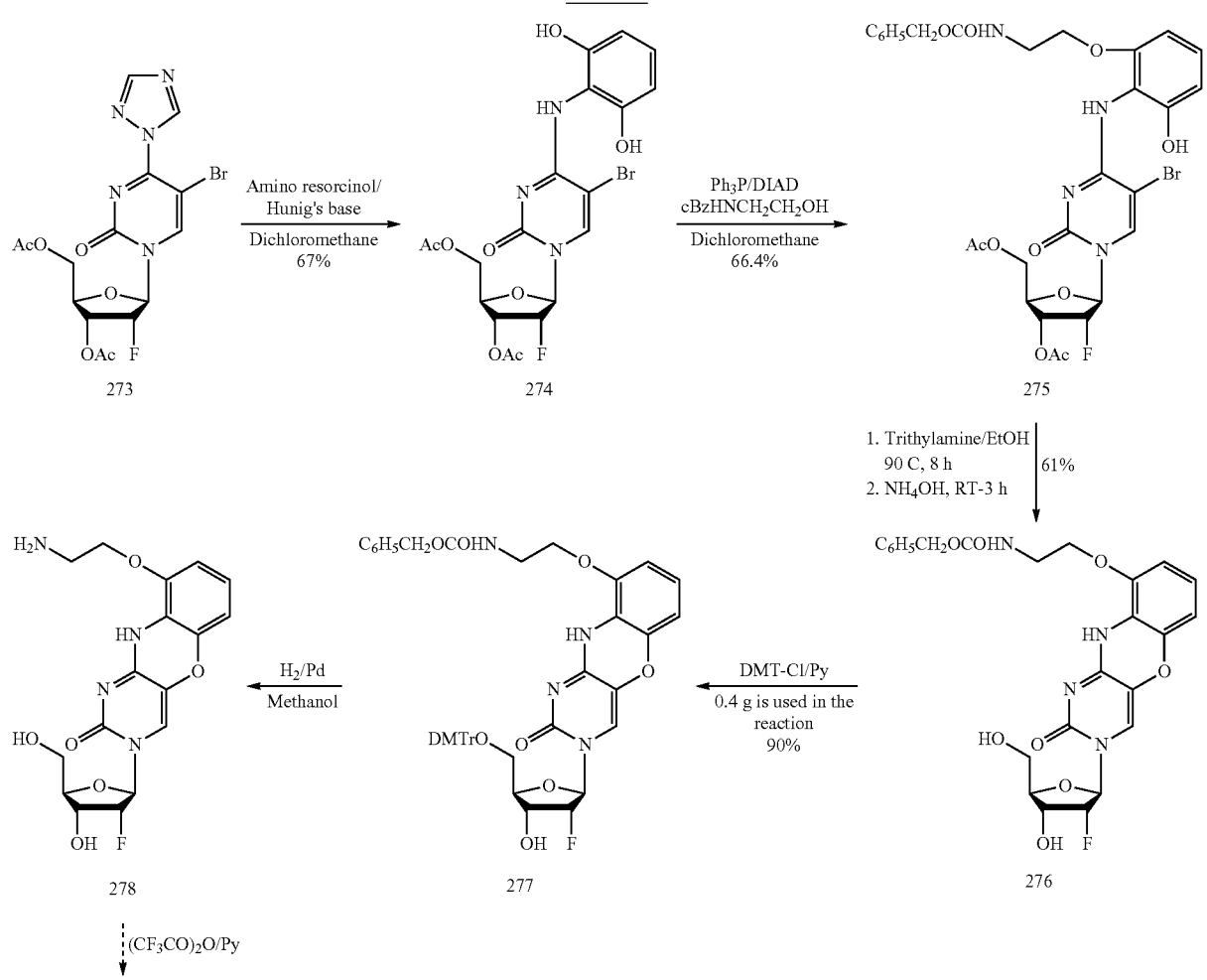

-continued
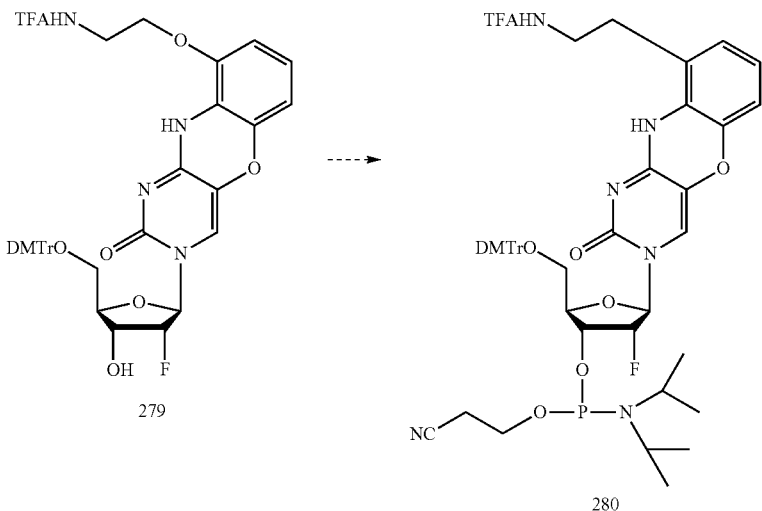
Scheme 16
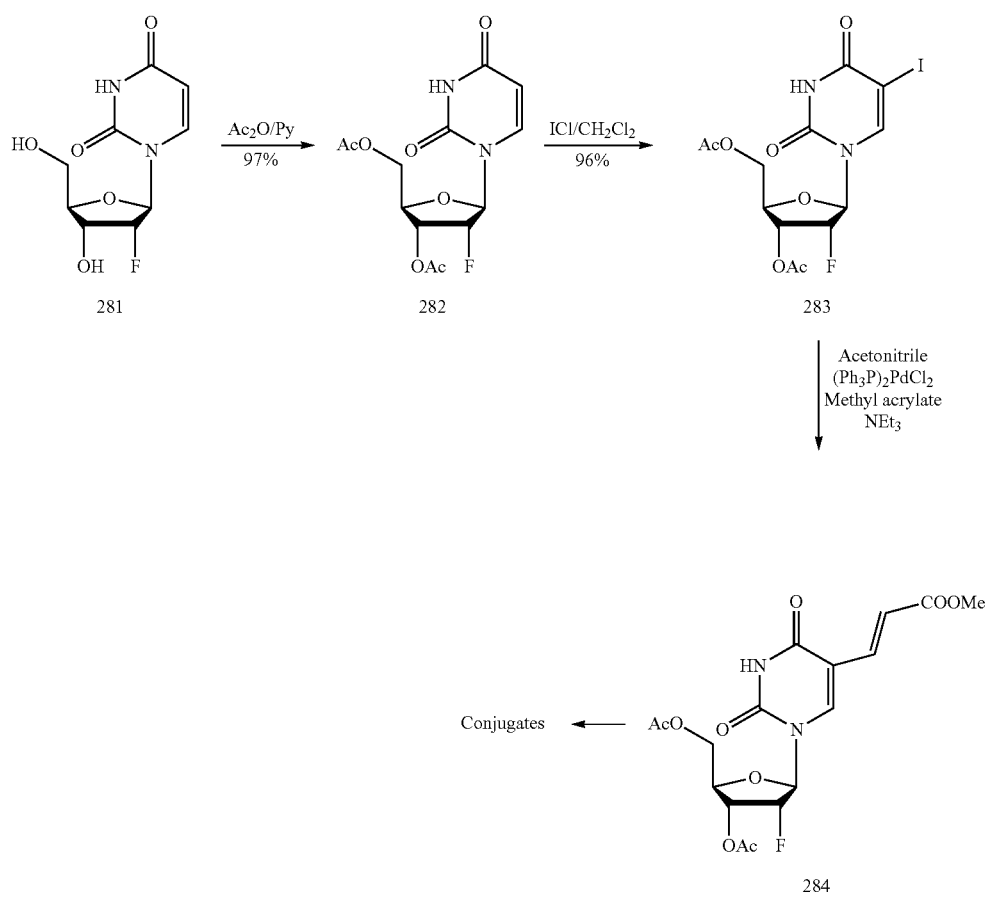

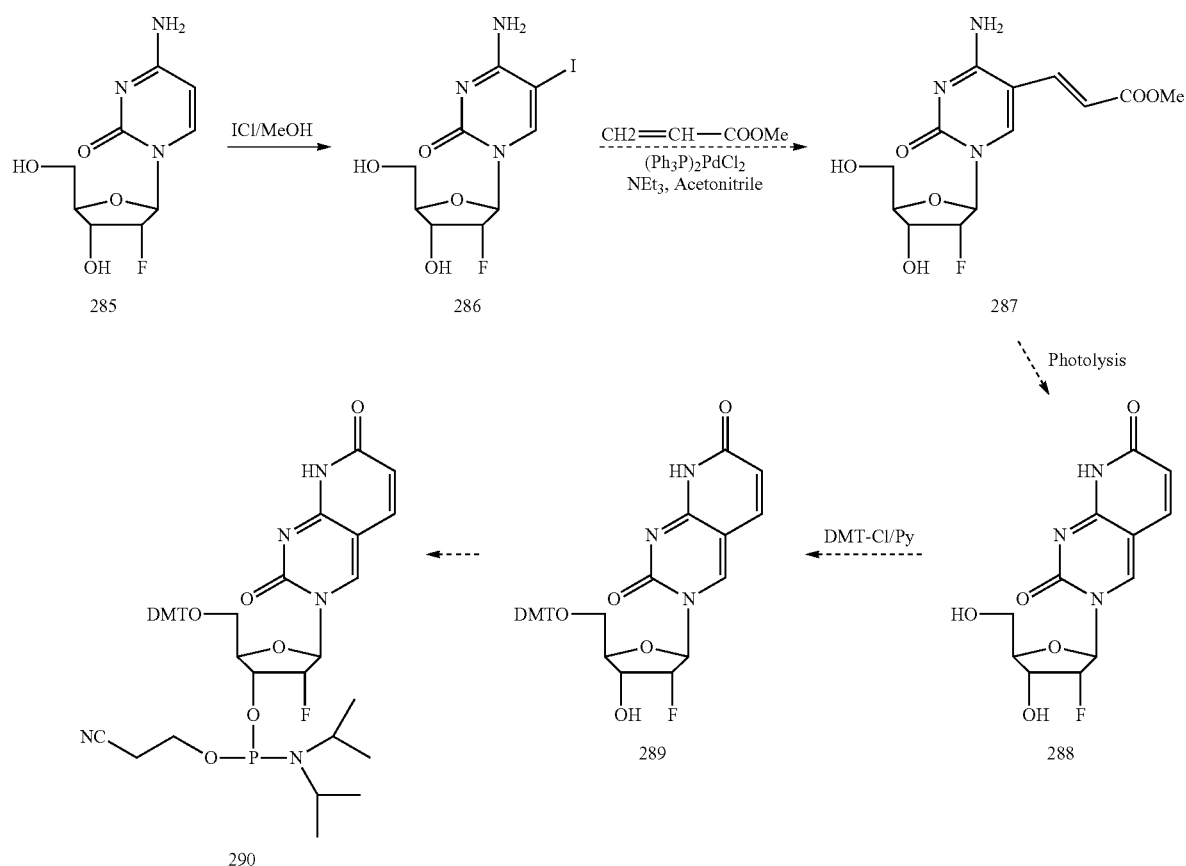
Scheme 17
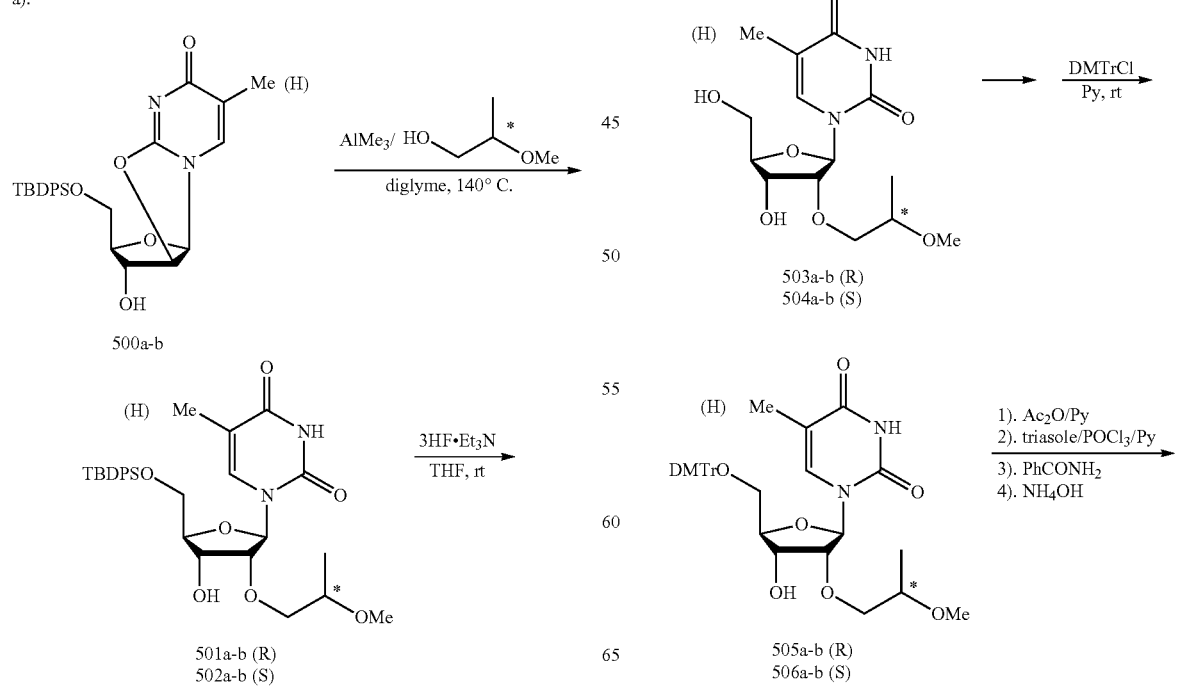
Scheme 18_2'-O-Alkyl Modifications

189
-continued
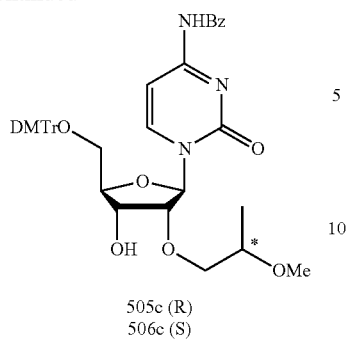
505c (R)
506c (S)
b).
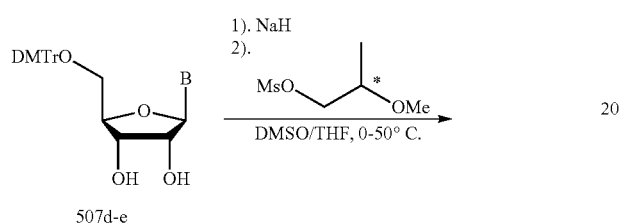
507d-e
505d-e (R)
506d-e (S)
c).
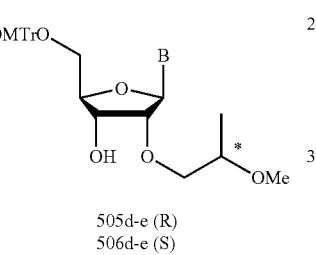
505a-e (R)
506a-e (S)
508a-e (R)
508a-e (S)
d).
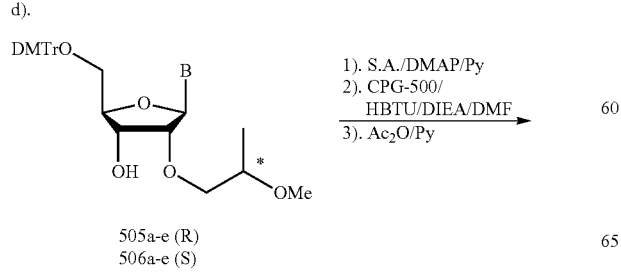
505a-e (R)
506a-e (S)
190
-continued
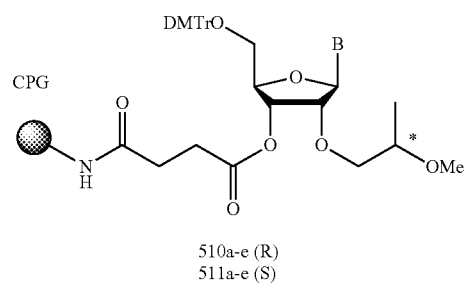
510a-e (R)
511a-e (S)
B: U T C$^{Bz}$ A$^{Bz}$ G$^{ibu}$
number: a b c d e
Scheme 19
a).
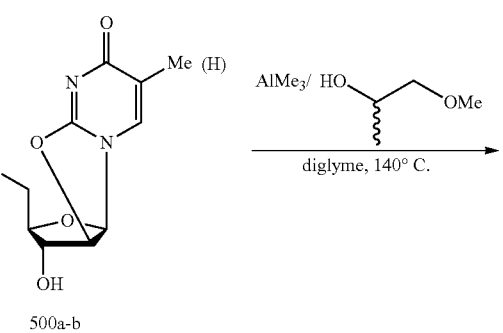
500a-b
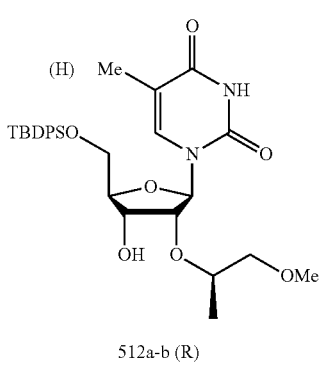
512a-b (R)
Separation
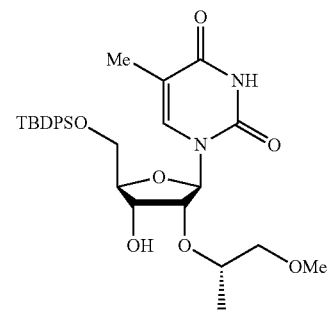
513a-b (S)

b).
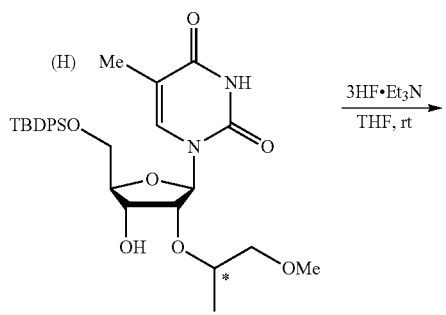
512a-b (R)
513a-b (S)
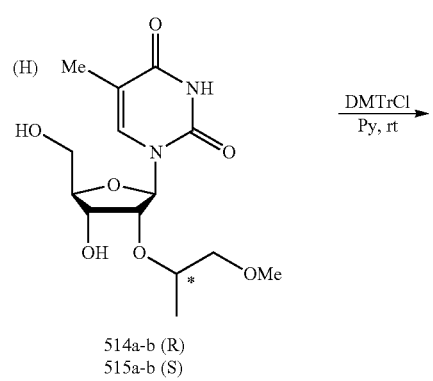
514a-b (R)
515a-b (S)
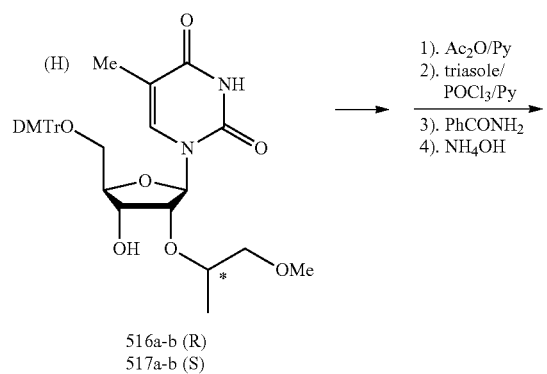
516a-b (R)
517a-b (S)
c).
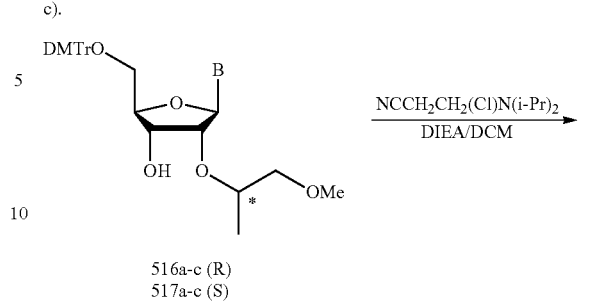
516a-c (R)
517a-c (S)
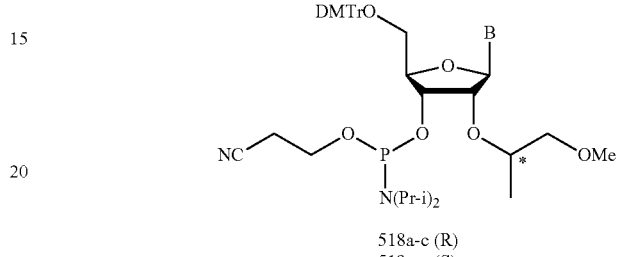
518a-c (R)
519a-c (S)
d).
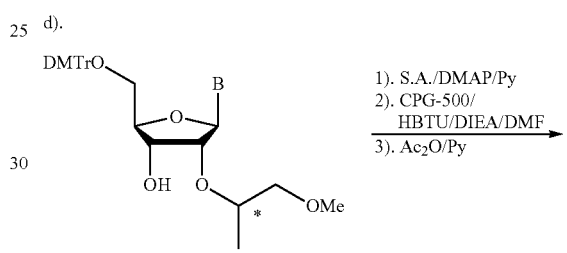
516a-c (R)
517a-c (S)
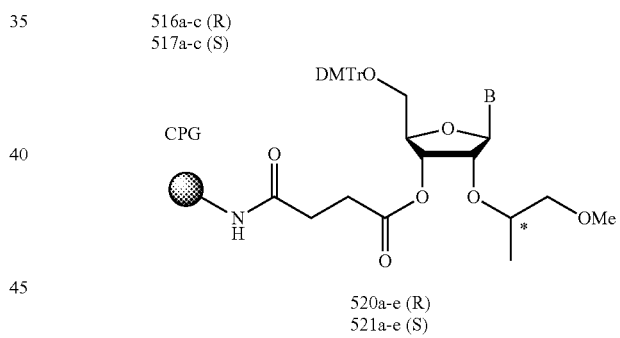
520a-e (R)
521a-e (S)
B: U T C$^{Bz}$ A$^{Bz}$ G$^{ibu}$
number: a b c d e
Scheme 20
a).
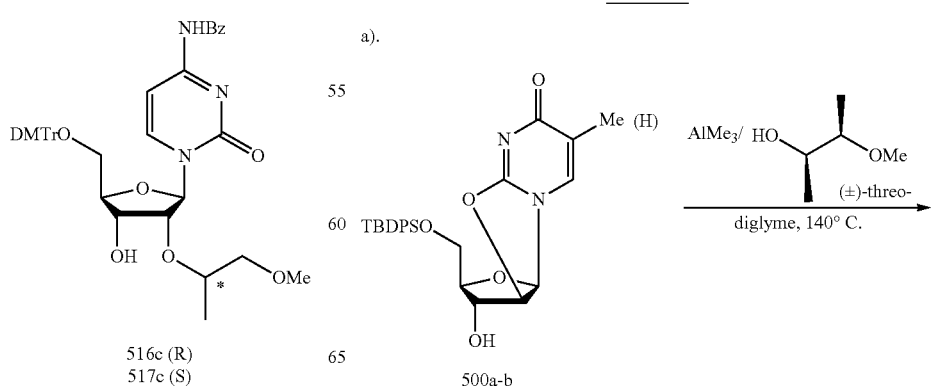
500a-b

193
-continued
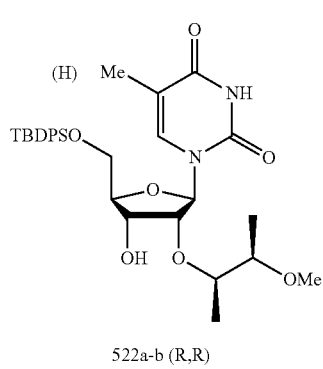
522a-b (R,R)
+
Separation
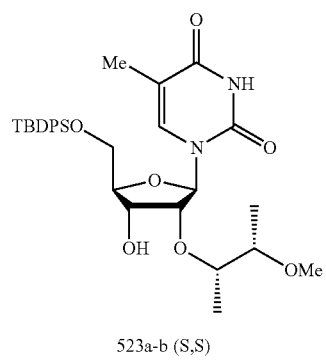
523a-b (S,S)
b).
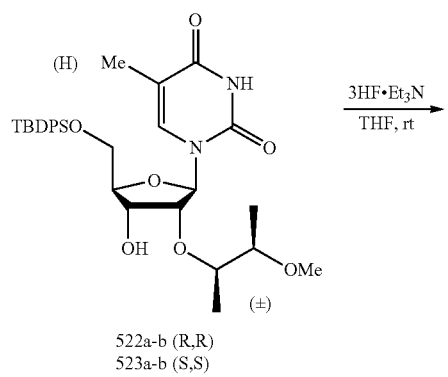
522a-b (R,R)
523a-b (S,S)
$\xrightarrow{\text{3HF·Et}_3\text{N}}{\text{THF, rt}}$
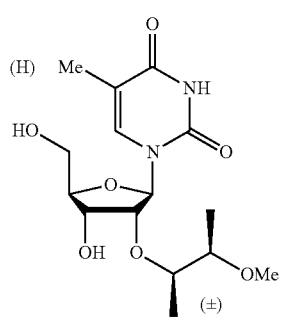
524a-b (R,R)
525a-b (S,S)
$\xrightarrow{\text{DMTrCl}}{\text{Py, rt}}$
194
-continued
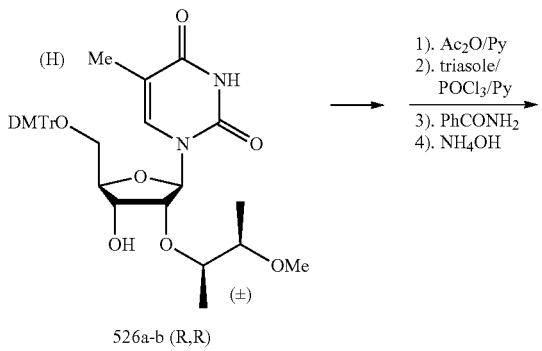
526a-b (R,R)
527a-b (S,S)
1). Ac₂O/Py
2). triasole/POCl₃/Py
3). PhCONH₂
4). NH₄OH
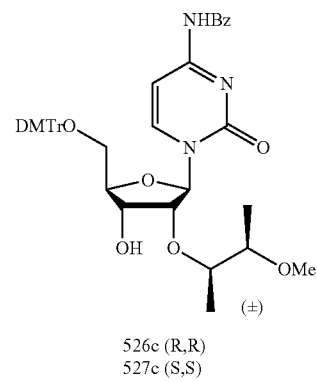
526c (R,R)
527c (S,S)
c).
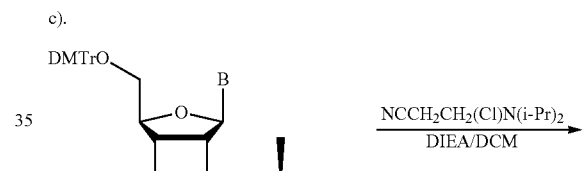
526a-c (R,R)
527a-c (S,S)
$\xrightarrow{\text{NCCH}_2\text{CH}_2(\text{Cl})\text{N(i-Pr)}_2}{\text{DIEA/DCM}}$
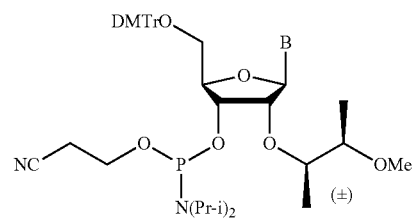
528a-c (R,R)
529a-c (S,S)
d).
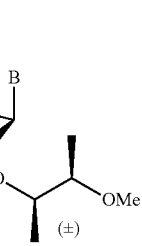
526a-c (R,R)
527a-c (S,S)
1). S.A./DMAP/Py
2). CPG-500/HBTU/DIEA/DMF
3). Ac₂O/Py

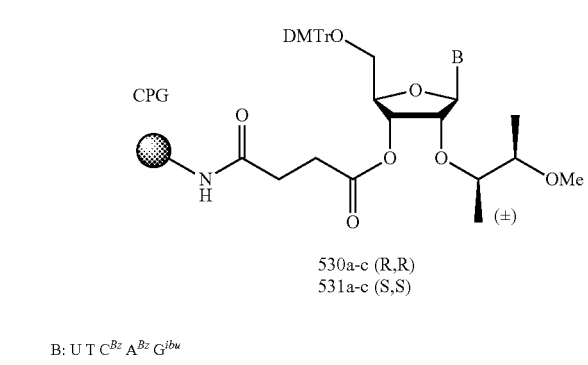
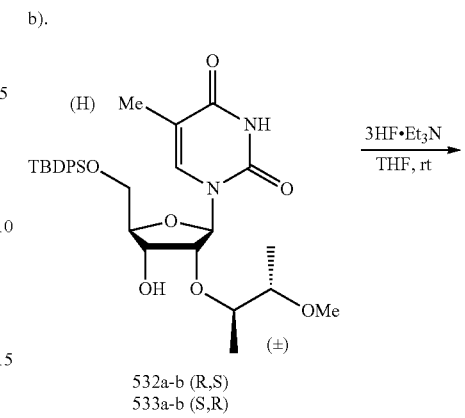
Scheme 21
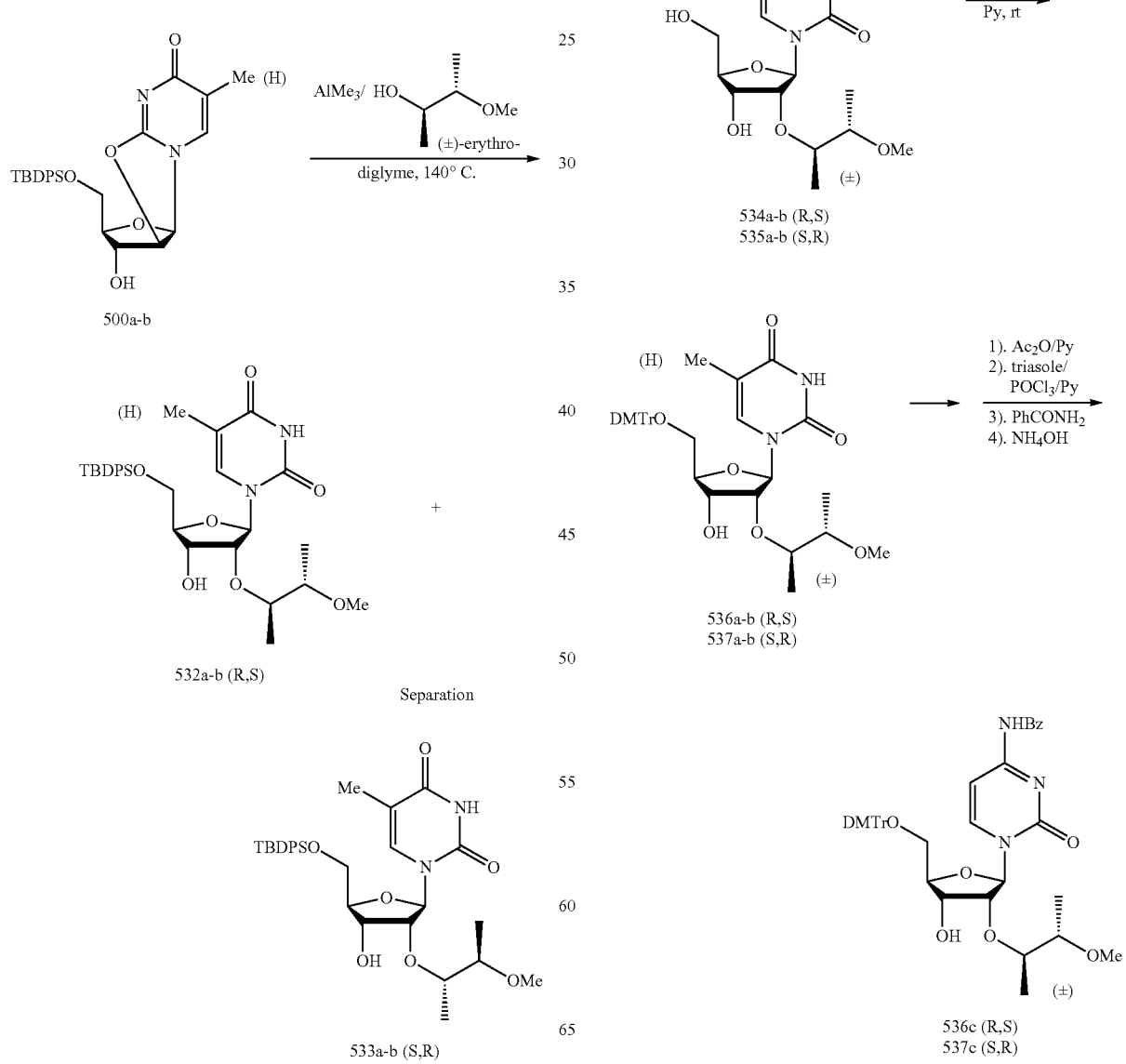

197
-continued
c).
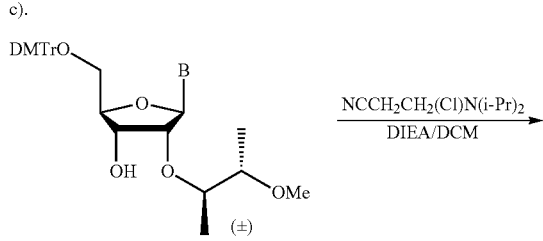
536a-c (R,S)
537a-c (S,R)
NCCH₂CH₂(Cl)N(i-Pr)₂
───────────────→
DIEA/DCM
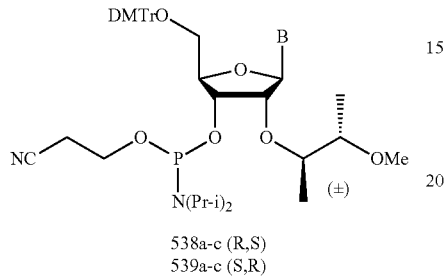
538a-c (R,S)
539a-c (S,R)
d).
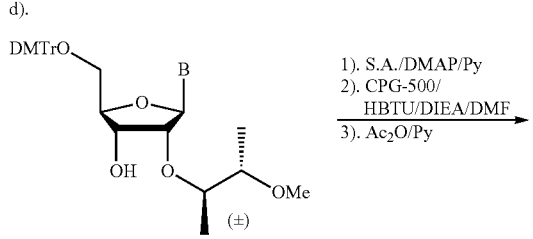
536a-c (R,S)
537a-c (S,R)
1). S.A./DMAP/Py
2). CPG-500/
   HBTU/DIEA/DMF
3). Ac₂O/Py
───────────────→
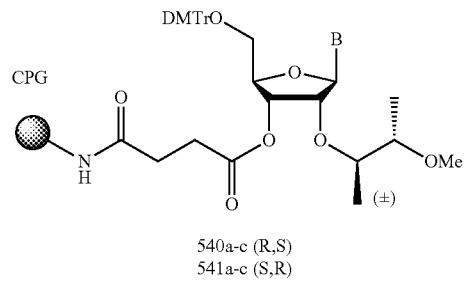
540a-c (R,S)
541a-c (S,R)
B: U T C^{Bz} A^{Bz} G^{ibu}
number: a b c d e
198
-continued
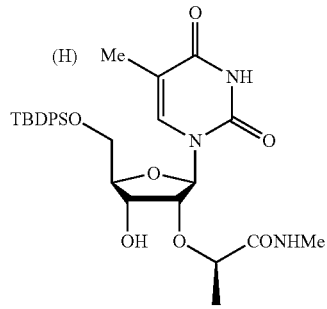
542a-b (R)
+
Separation
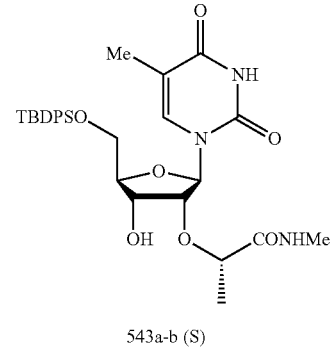
543a-b (S)
b).
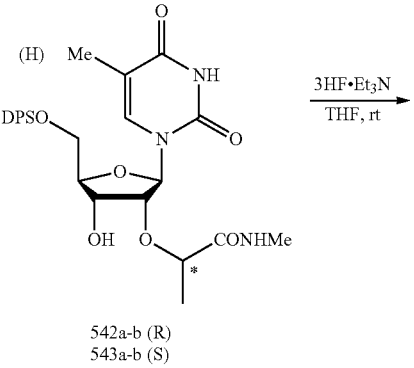
542a-b (R)
543a-b (S)
3HF·Et₃N
─────────→
THF, rt
Scheme 22
a).
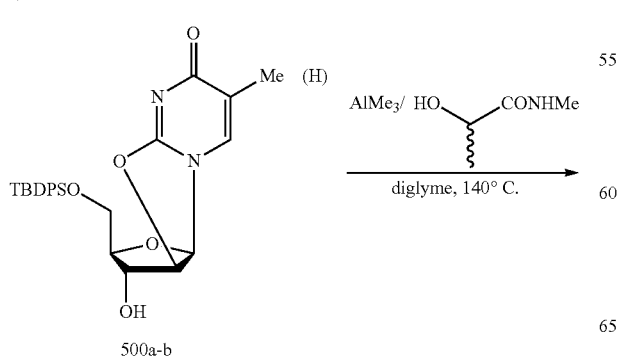
500a-b
AlMe₃/ HO⧸⧹CONHMe
──────────────────→
diglyme, 140° C.
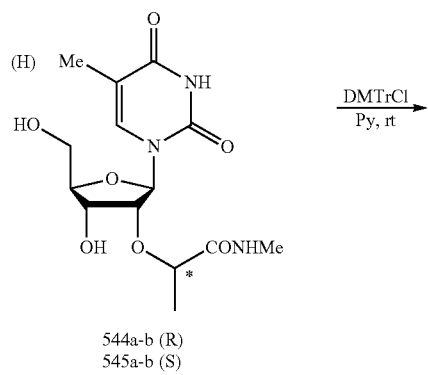
544a-b (R)
545a-b (S)
DMTrCl
────────→
Py, rt 199
-continued
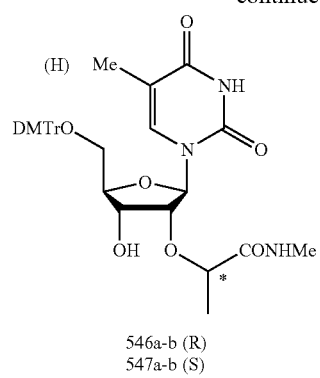
546a-b (R)
547a-b (S)
1). Ac₂O/Py
2). triasole/ POCl₃/Py
3). PhCONH₂
4). NH₄OH
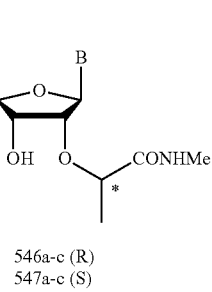
546c (R)
547c (S)
c).
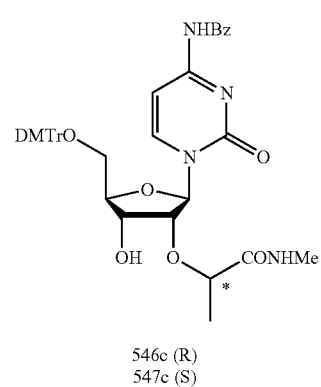
507d-e
1). NaH
2). Br—CH(CONHMe)—
DMSO/THF, 0-50° C.
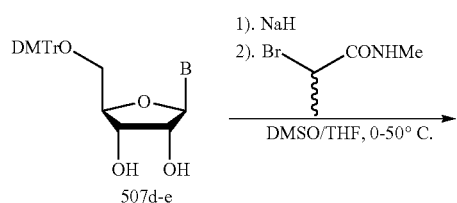
546d-e (R)
+ Separation
B: U T C$^{Bz}$ A$^{Bz}$ G$^{ibu}$
number: a b c d e
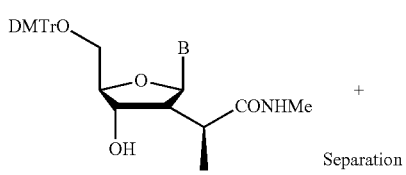
547d-e (S)
200
-continued
d).
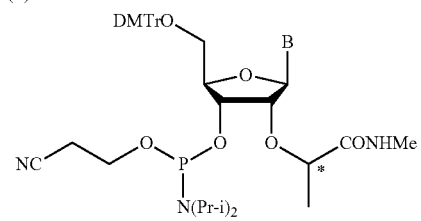
546a-c (R)
547a-c (S)
NCCH₂CH₂(Cl)N(i-Pr)₂
―――――――――――
DIEA/DCM
548a-c (R)
549a-c (S)
e).
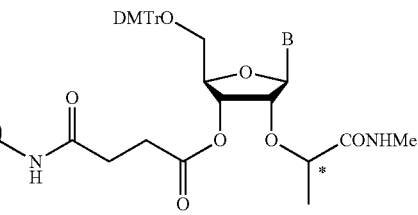
546a-c (R)
547a-c (S)
1). S.A./DMAP/Py
2). CPG-500/ HBTU/DIEA/DMF
3). Ac₂O/Py
550a-e (R)
551a-e (S)
Scheme 23
a).
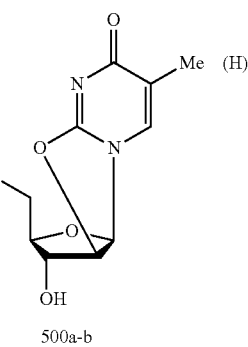
500a-b
+

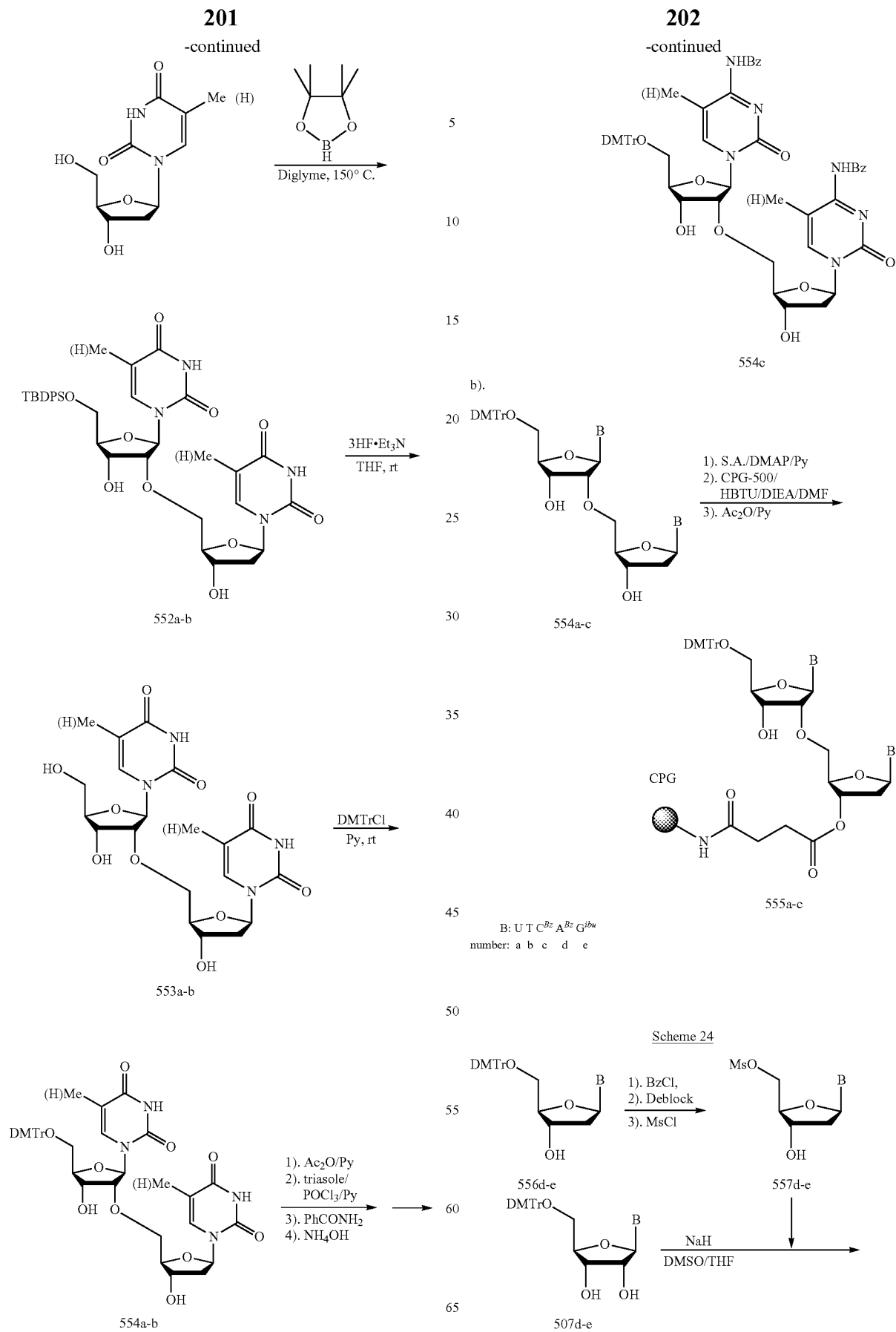

203
-continued
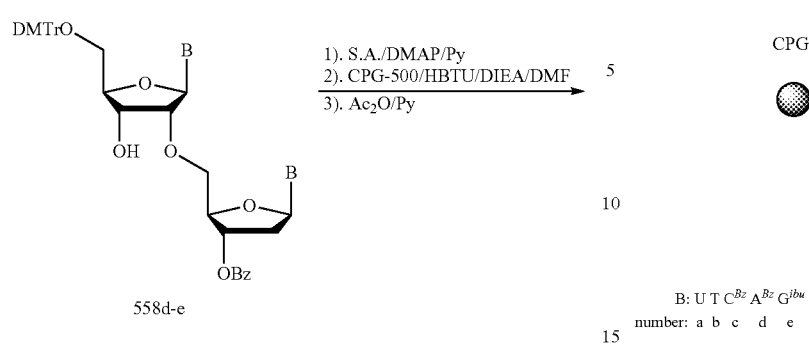
558d-e
204
-continued
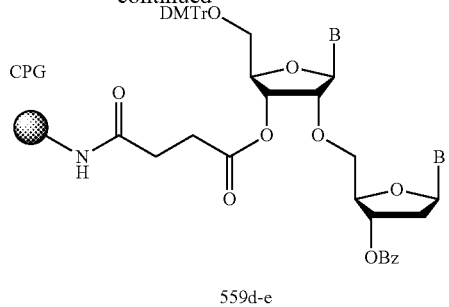
559d-e
B: U T C$^{Bz}$ A$^{Bz}$ G$^{ibu}$
number: a b c d e
Scheme 25
a).
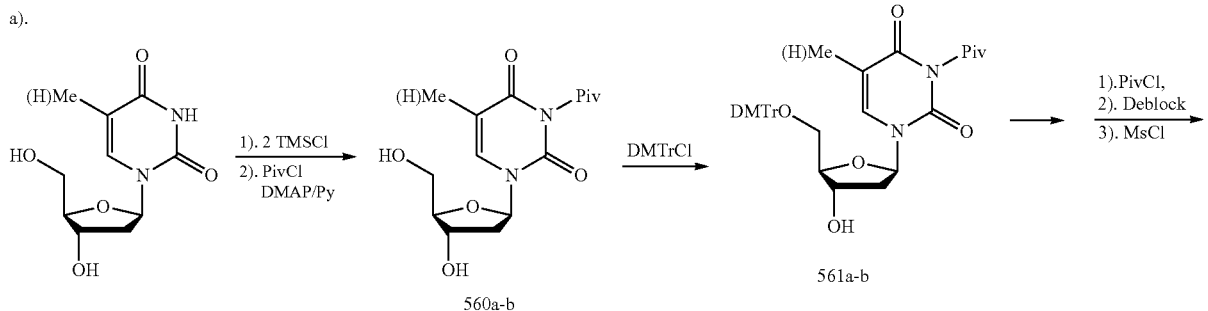
560a-b  561a-b
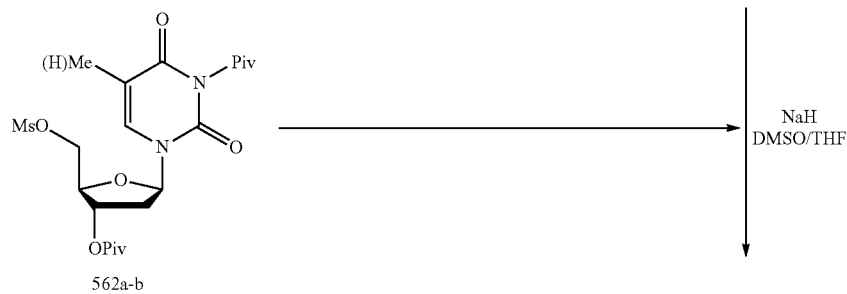
562a-b
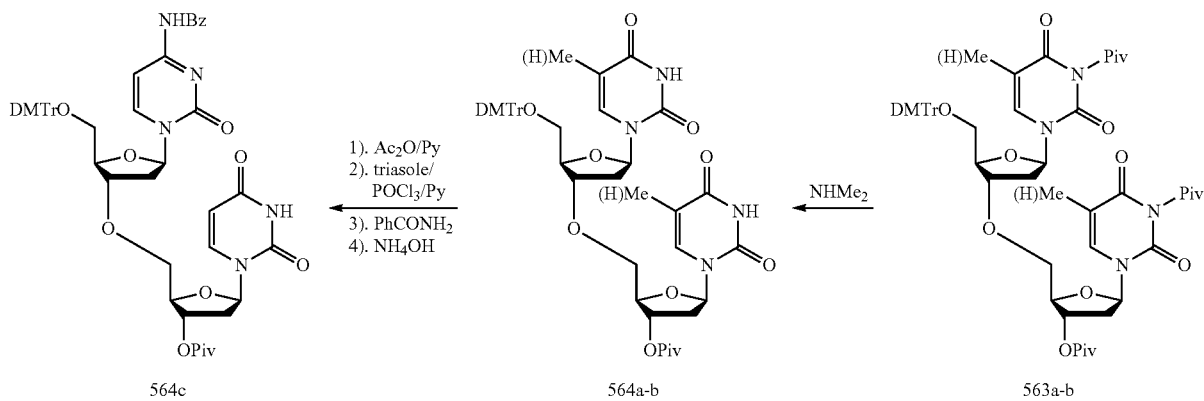
564c  564a-b  563a-b b).
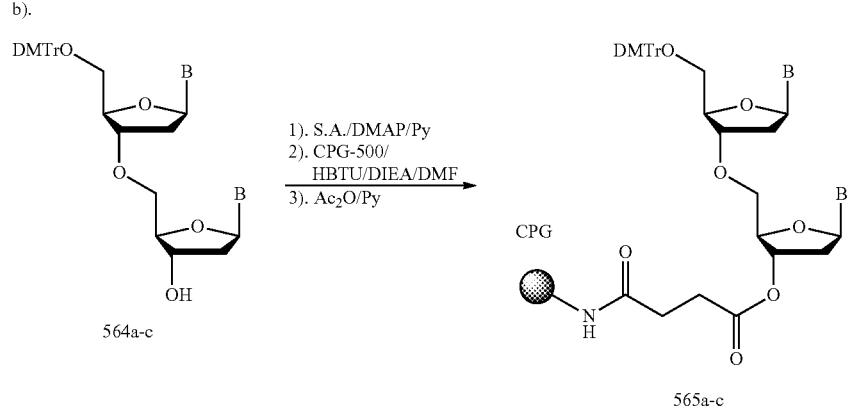
B: U T C$^{Bz}$ A$^{Bz}$ G$^{ibu}$
number: a b c d e
Scheme 26
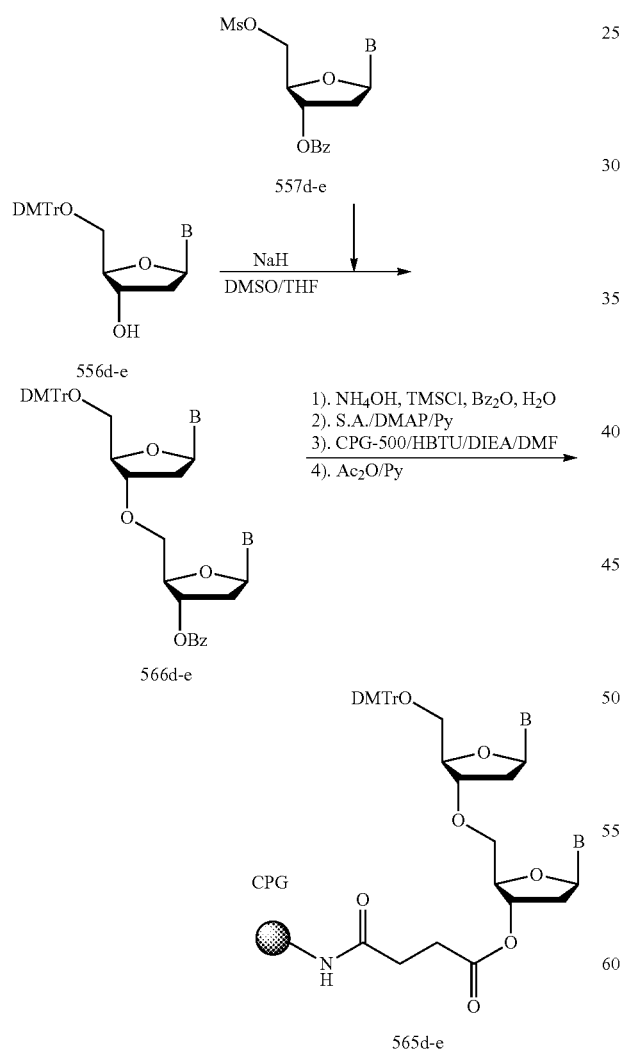
B: U T C$^{Bz}$ A$^{Bz}$ G$^{ibu}$
number: a b c d e
Scheme 27
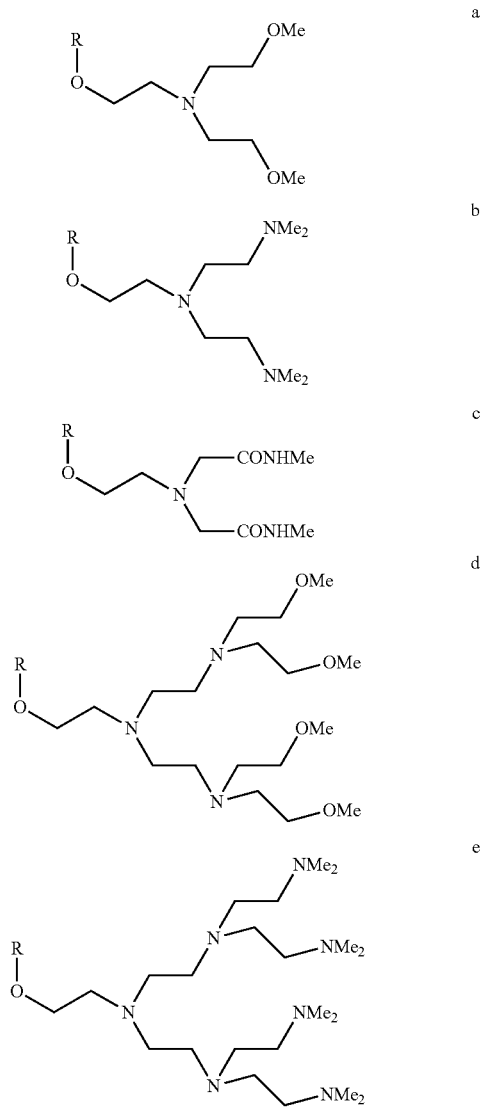

| | |
|---|---|
| 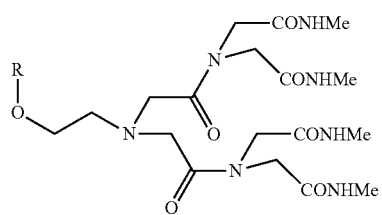 | f |
| 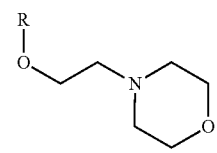 | g |
| 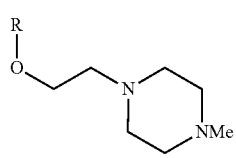 | h |
| 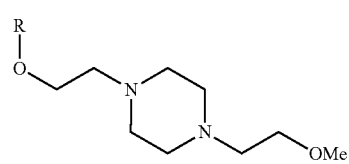 | i |
| 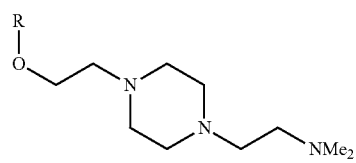 | j |
| 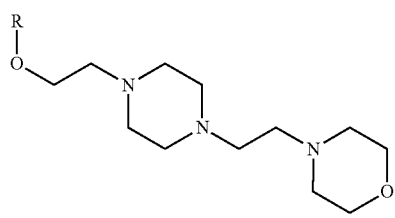 | k |
| 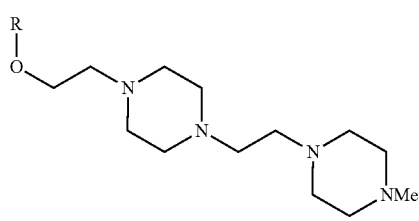 | l |
| 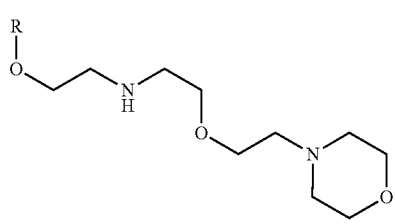 | m |
| | |
|---|---|
| 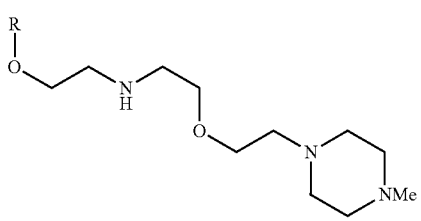 | n |
| 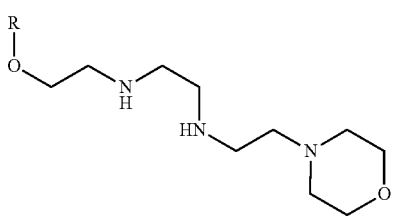 | o |
| 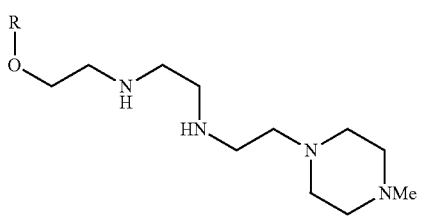 | p |
| 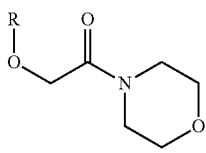 | q |
| 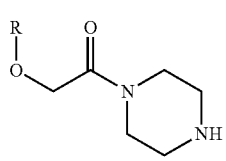 | r |
| 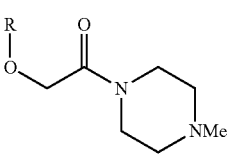 | s |
| 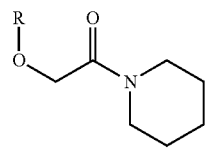 | t |
| 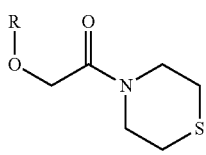 | u | v
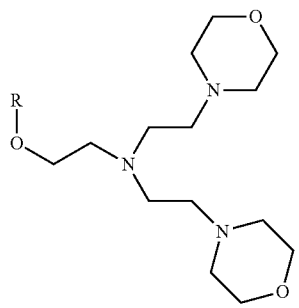
w
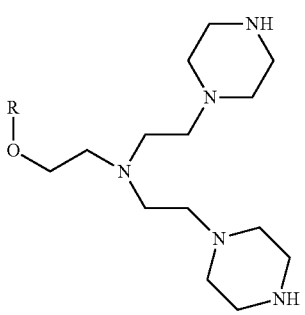
x
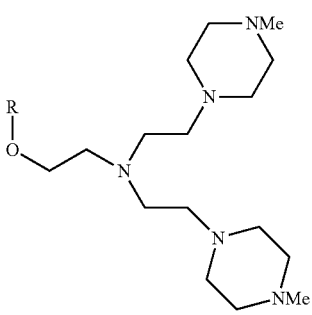
y
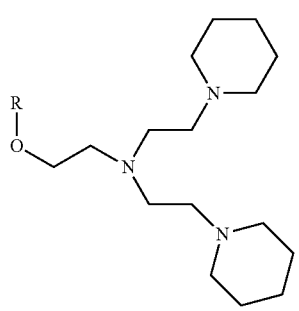
z
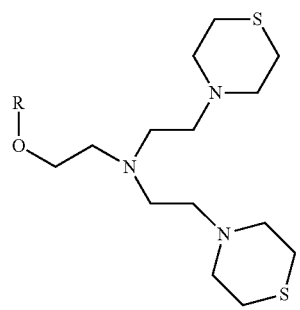
567: R = H
568: R = Ms
Synthesis of derivatives of U, C and A 2'-modified with amines and polyamines:
a).
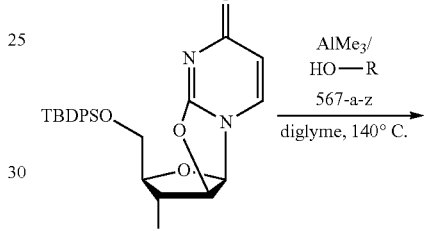
500a
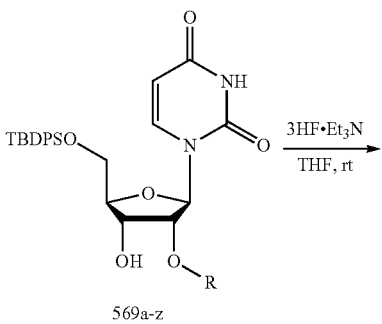
569a-z
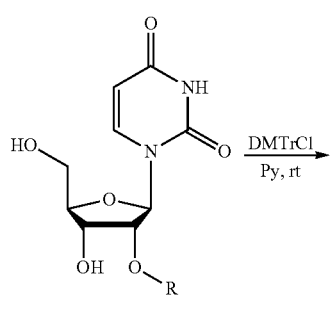
570a-z

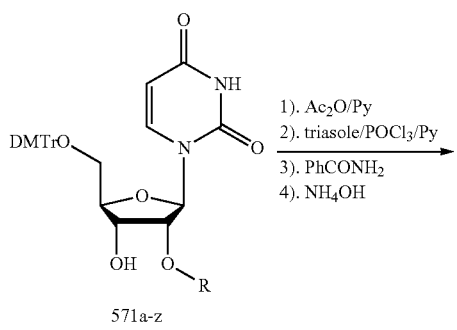
571a-z
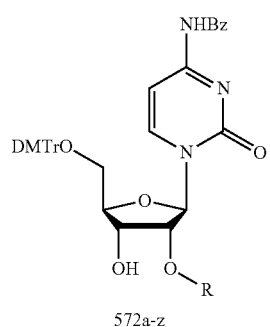
572a-z
b).
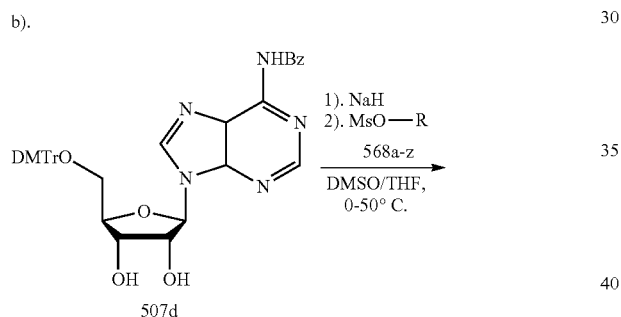
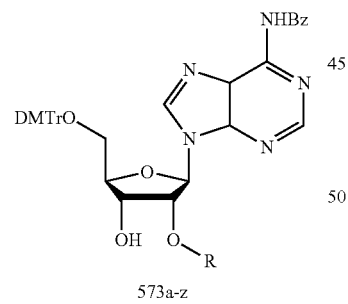
573a-z
c).
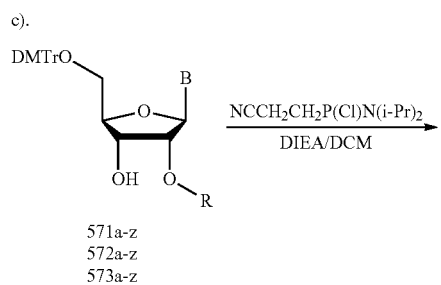
571a-z
572a-z
573a-z
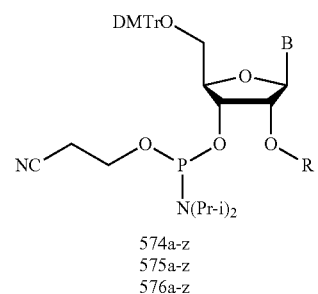
574a-z
575a-z
576a-z
d).
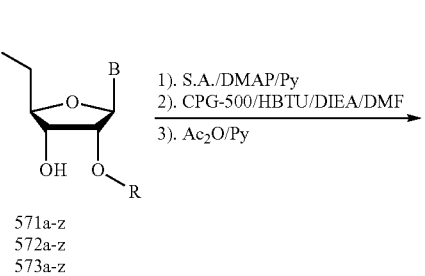
571a-z
572a-z
573a-z
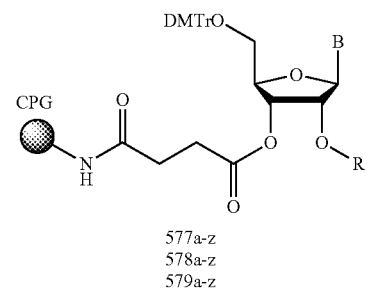
577a-z
578a-z
579a-z
Scheme 28: 2′ = 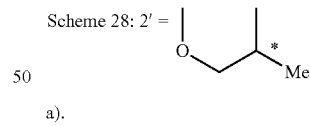
a).
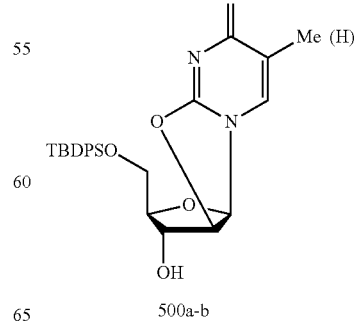
500a-b

213
-continued
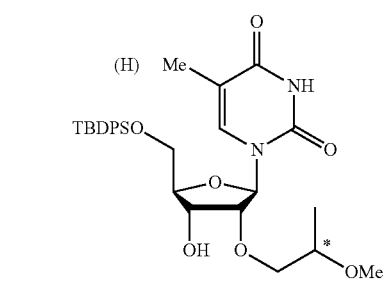
501a-b (R)
502a-b (S)
3HF·Et₃N / THF, rt
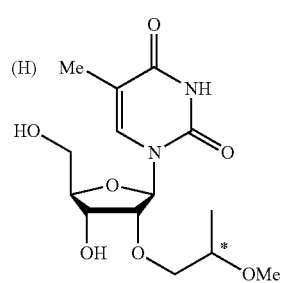
503a-b (R)
504a-b (S)
DMTrCl / Py, rt
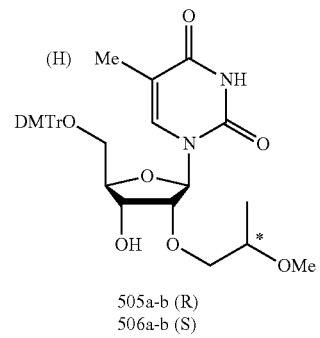
505a-b (R)
506a-b (S)
1). TMSCl/NMP/MeCN
2). p-nitrophenol/TFAA
3). NH₃/H₂O/dioxane
4). Ac₂O/DMF
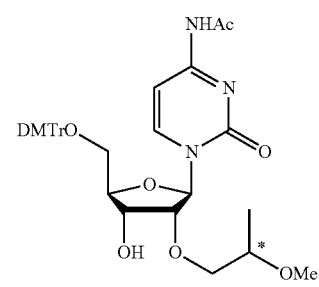
505′c (R)
506′c (S)
b).
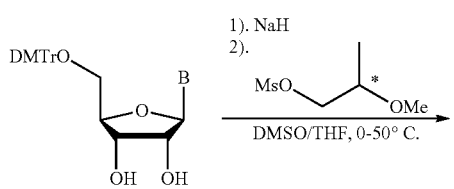
507d-e
1). NaH
2). MsO—CH(Me)—CH₂—OMe / DMSO/THF, 0–50° C.
214
-continued
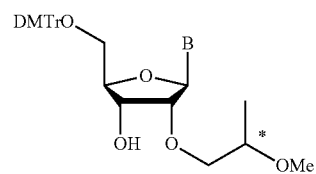
505d-e (R)
506d-e (S)
c).
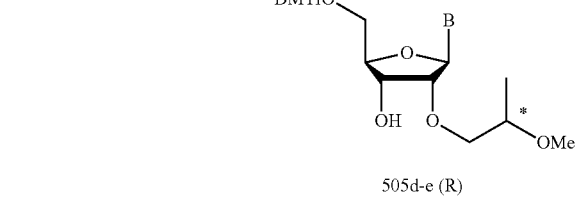
505a-c′, d-e (R)
506a-c′, d-e (S)
NCCH₂CH₂(Cl)N(i-Pr)₂ / DIEA/DCM
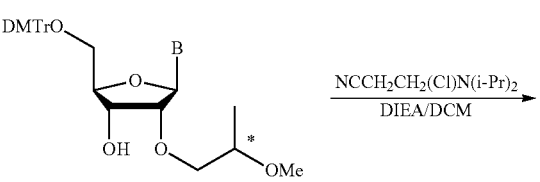
508a-c′, d-e (R)
509a-c′, d-e (S)
d).
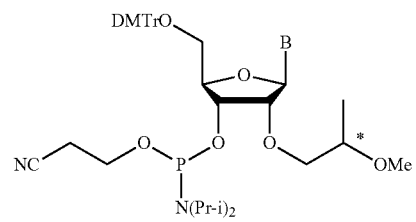
505a-c′, d-e (R)
506a-c′, d-e (S)
1). S.A./DMAP/Py
2). CPG-500/HBTU/DIEA/DMF
3). Ac₂O/Py
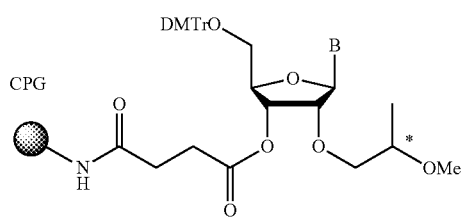
510a-c′, d-e (R)
511a-c′, d-e (S)
B: U T C$^{Bz}$ A$^{Bz}$ G$^{ibu}$
number: a b c d e Scheme 29: 2' = 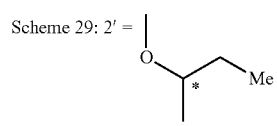
a).
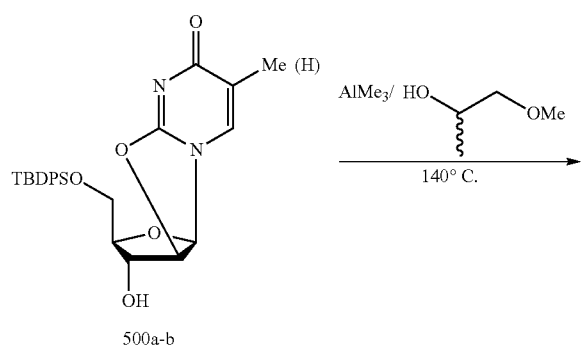
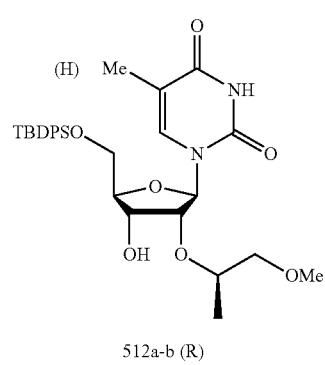
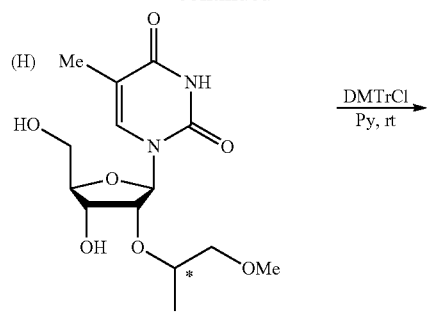
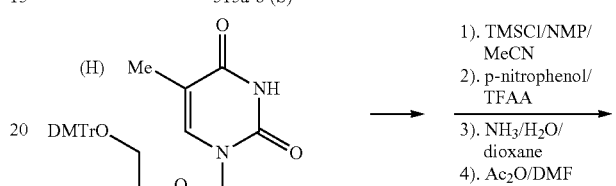
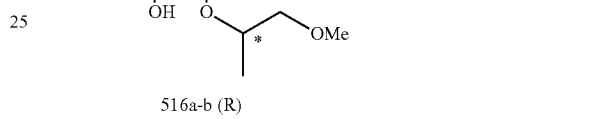
b).
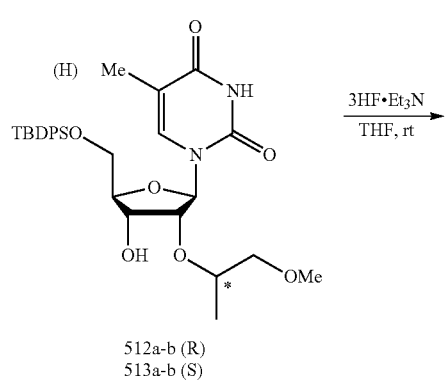
c).
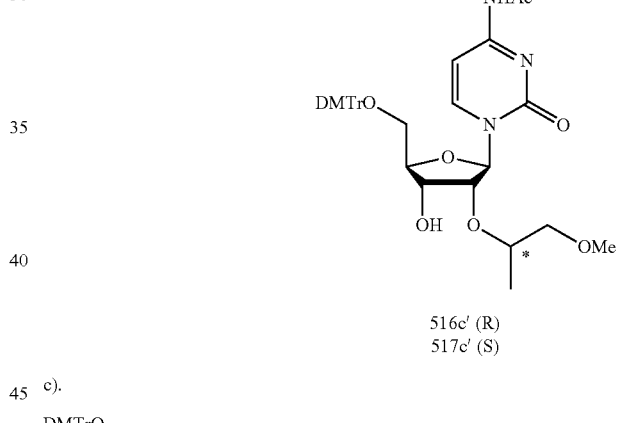
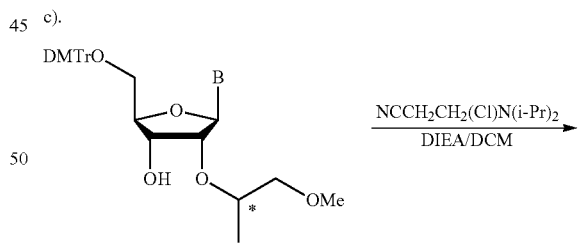
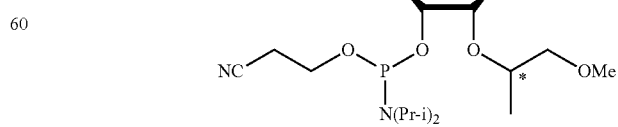

217
-continued
d).
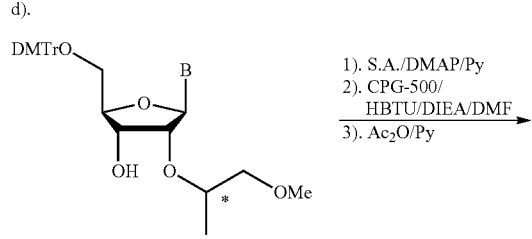
1). S.A./DMAP/Py
2). CPG-500/ HBTU/DIEA/DMF
3). Ac₂O/Py
516a-c' (R)
517a-c' (S)
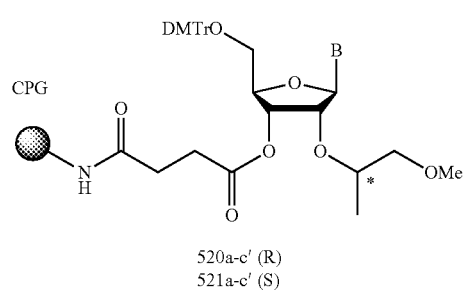
520a-c' (R)
521a-c' (S)
B: U T C^Bz A^Bz G^ibu
number: a b c d e
Scheme 30: 2' = 
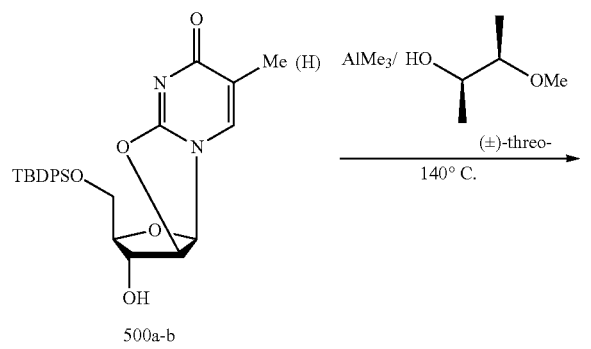
(±)-threo-
a).
500a-b
AlMe₃/ HO⟨⟩OMe
─────────────→
(±)-threo-
140° C.
522a-b (R,R)
+
Separation
218
-continued
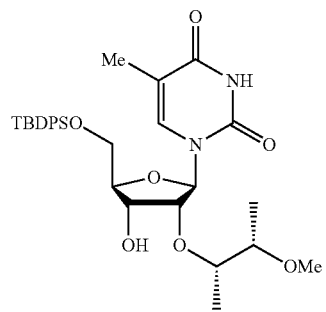
523a-b (S,S)
b).
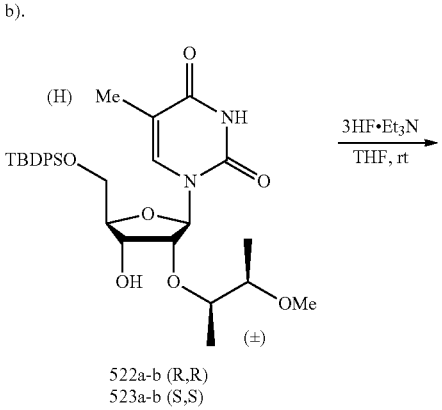
522a-b (R,R)
523a-b (S,S)
3HF·Et₃N
─────→
THF, rt
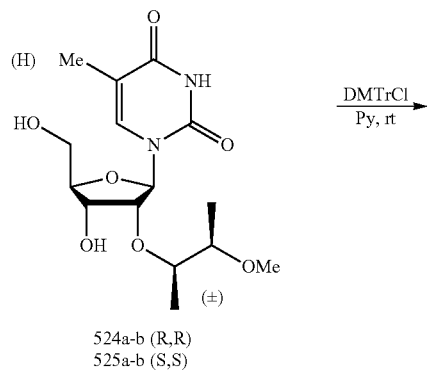
524a-b (R,R)
525a-b (S,S)
DMTrCl
─────→
Py, rt
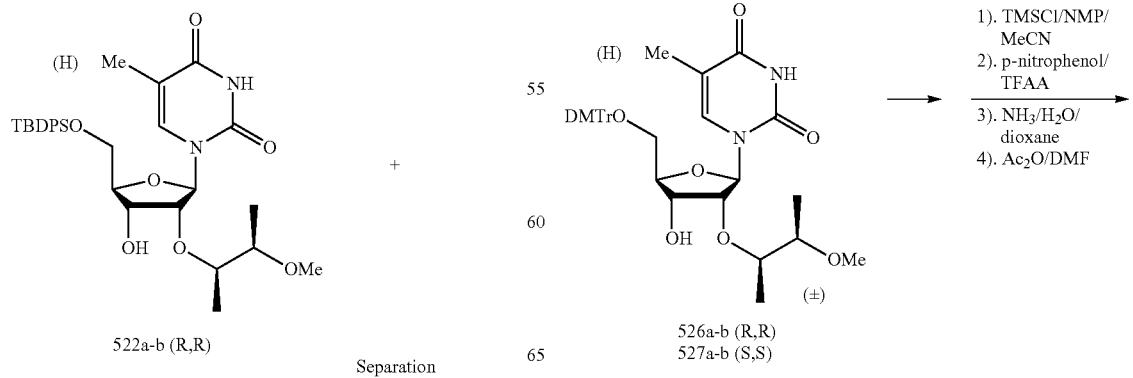
526a-b (R,R)
527a-b (S,S)
1). TMSCl/NMP/ MeCN
2). p-nitrophenol/ TFAA
3). NH₃/H₂O/ dioxane
4). Ac₂O/DMF

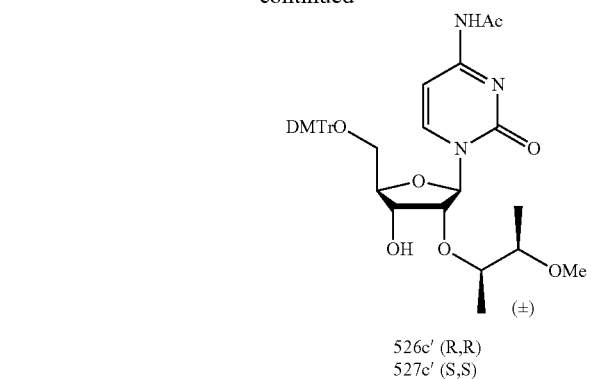
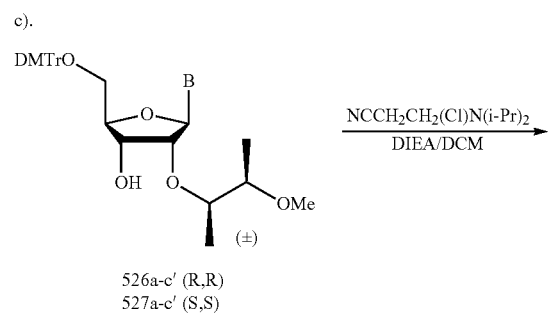
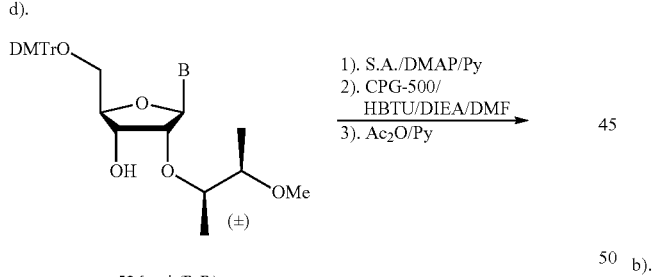
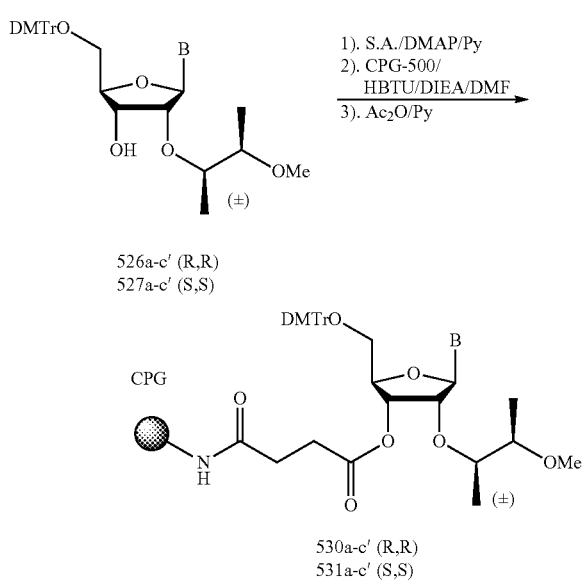
B: U T C$^{Bz}$ A$^{Bz}$ G$^{ibu}$
number: a b c d e
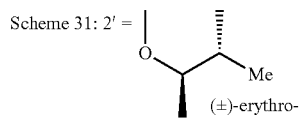
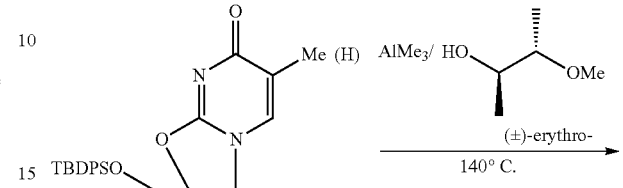
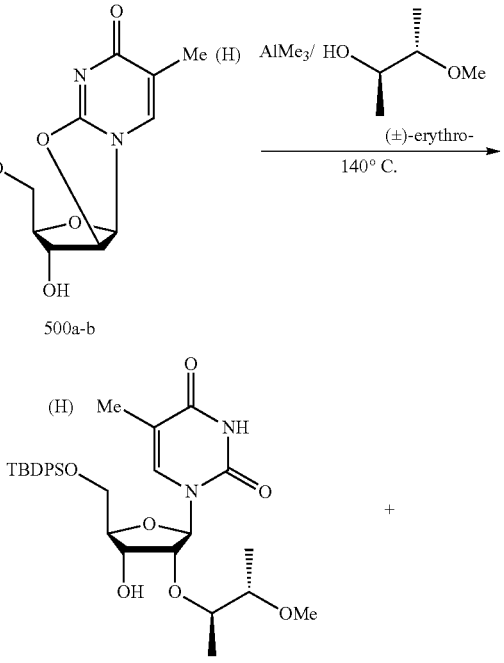

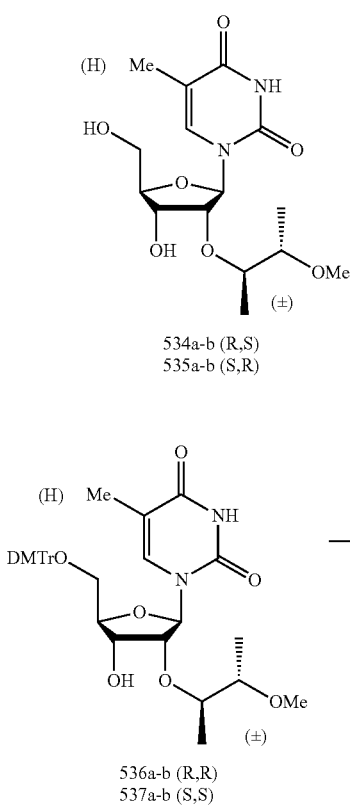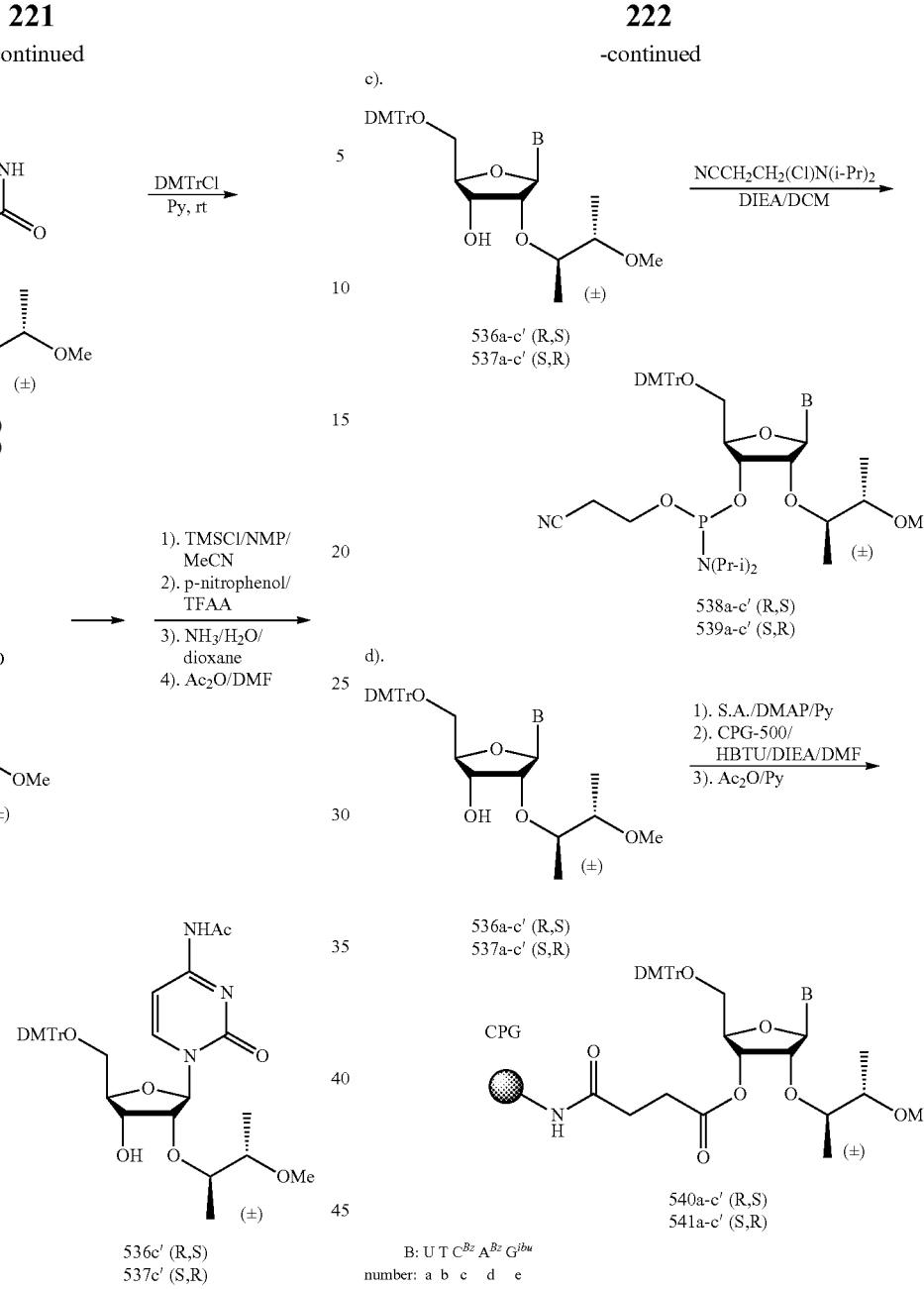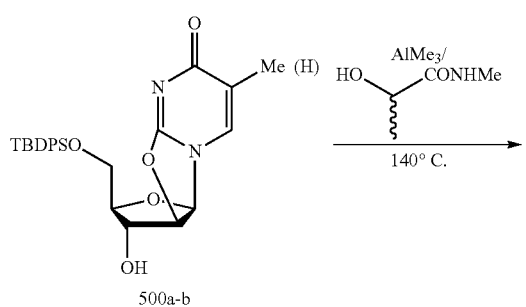
Scheme 32:
a).

-continued
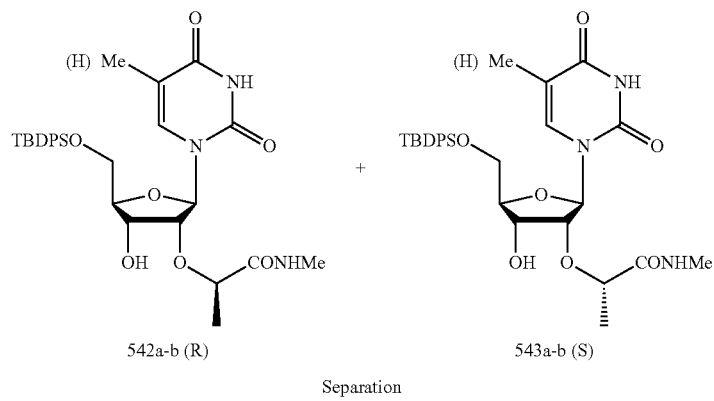
b).
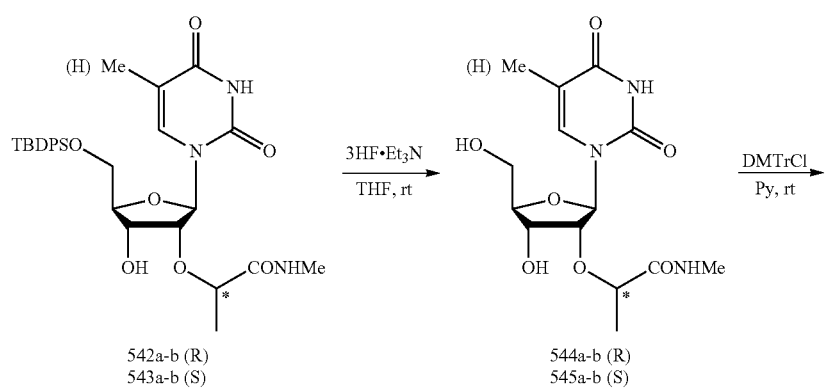
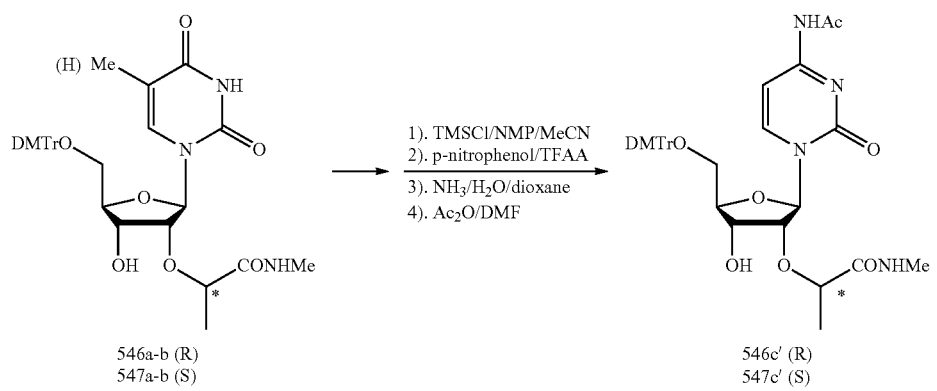
c).
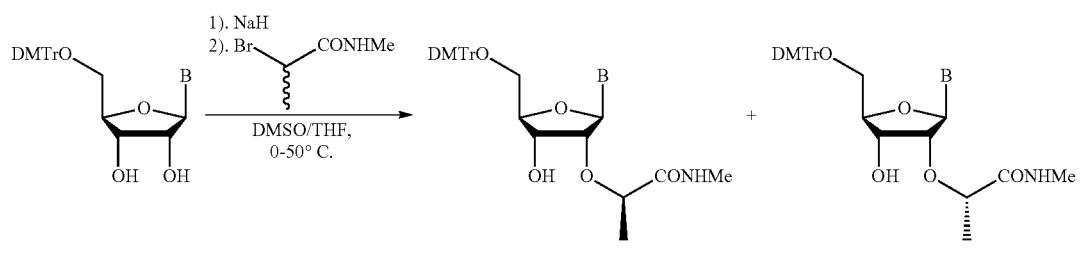
Separation

-continued
d).
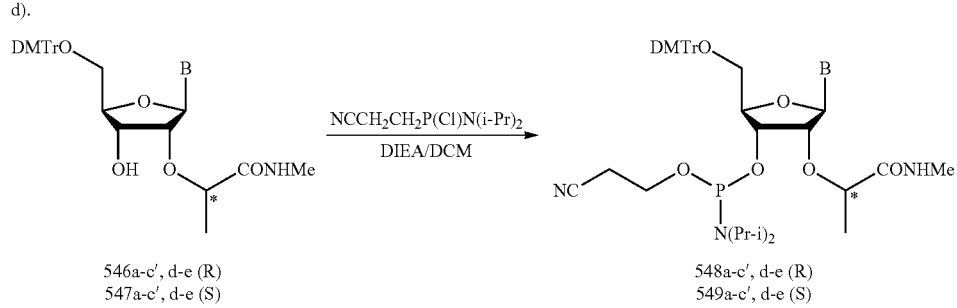
546a-c', d-e (R)
547a-c', d-e (S)
548a-c', d-e (R)
549a-c', d-e (S)
e).
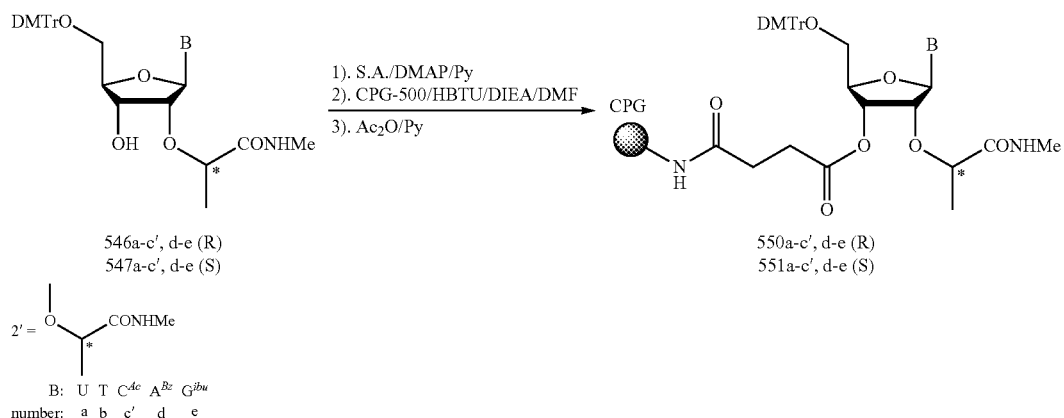
546a-c', d-e (R)
547a-c', d-e (S)
550a-c', d-e (R)
551a-c', d-e (S)
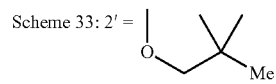
B: U T C^{Ac} A^{Bz} G^{ibu}
number: a b c' d e
Scheme 33: 2' =
a).
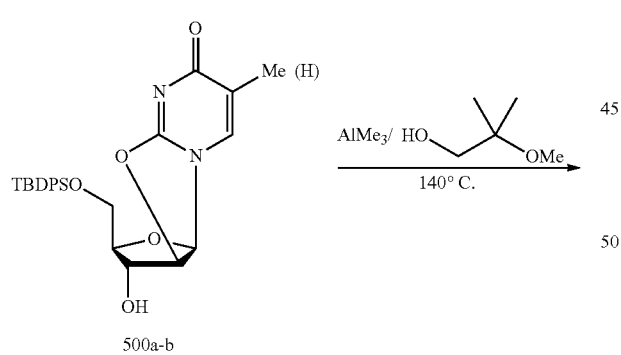
500a-b
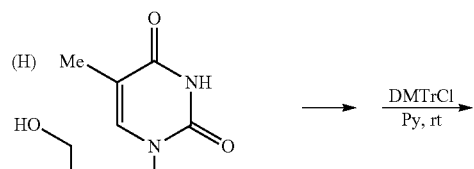
533a-b
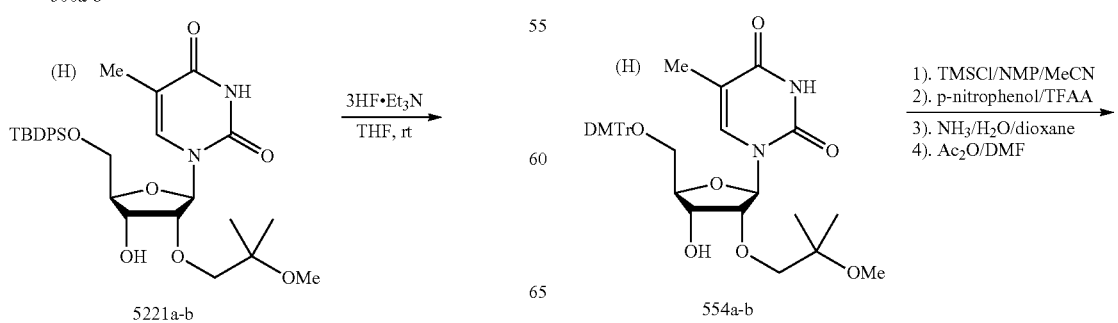
5221a-b
554a-b

227
-continued
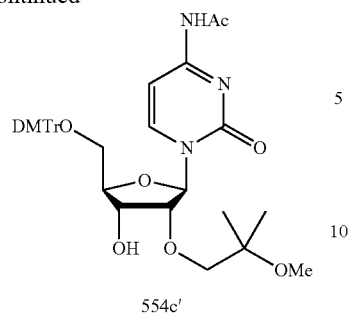
554c'
b).
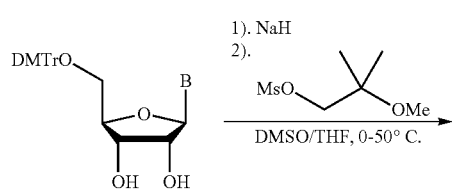
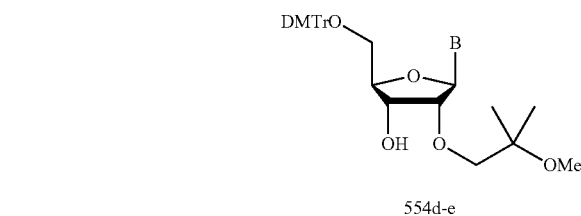
c).
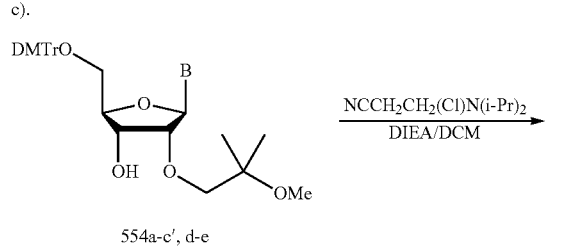
d).
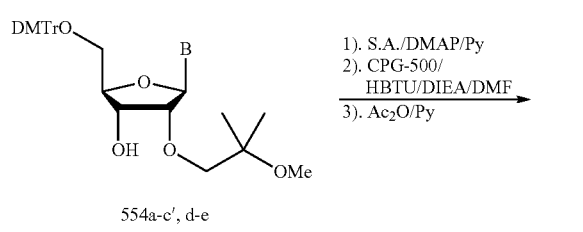
228
-continued
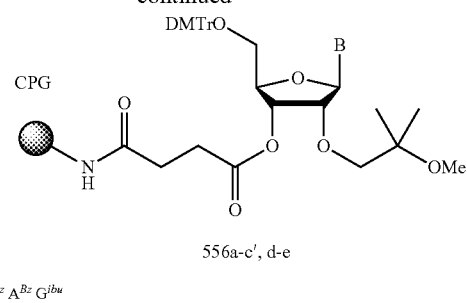
556a-c', d-e
B: U T C$^{Bz}$ A$^{Bz}$ G$^{ibu}$
number: a b c d e
Scheme 34: 2' = 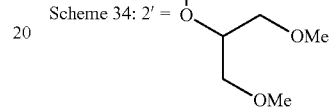
B: U T C$^{Ac}$ A$^{Bz}$ G$^{bu}$
number: a b c' d e
a).
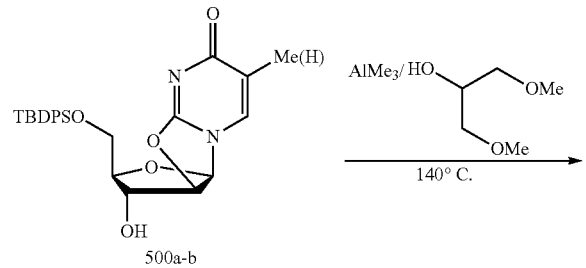
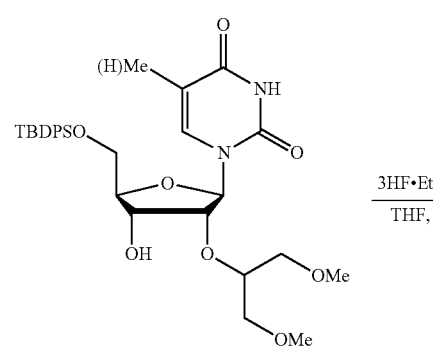
557a-b
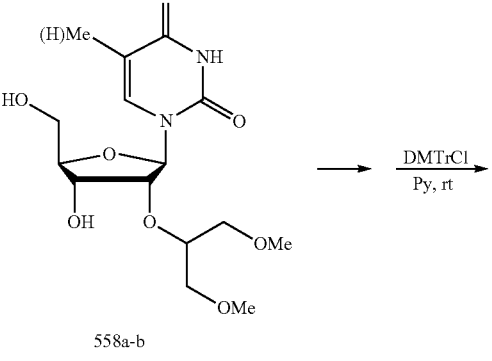
558a-b 229
-continued
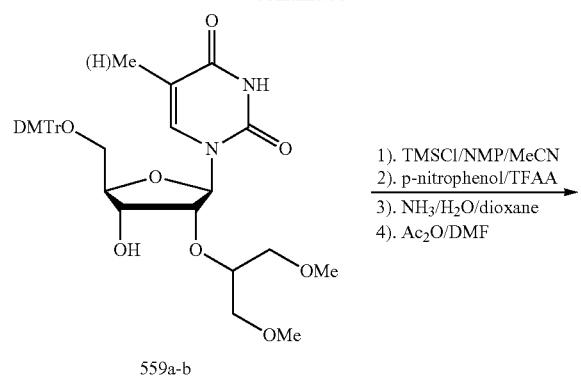
559a-b
1). TMSCl/NMP/MeCN
2). p-nitrophenol/TFAA
3). NH$_3$/H$_2$O/dioxane
4). Ac$_2$O/DMF
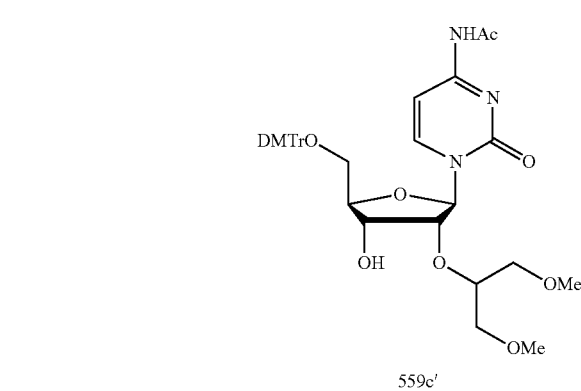
559c'
b).
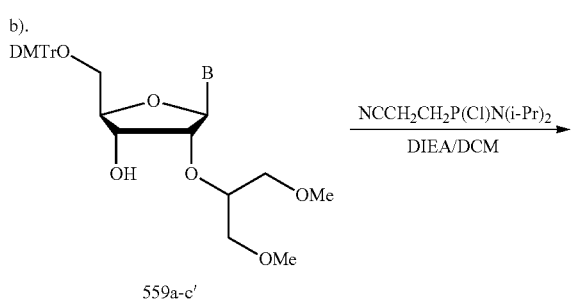
559a-c'
NCCH$_2$CH$_2$P(Cl)N(i-Pr)$_2$
DIEA/DCM
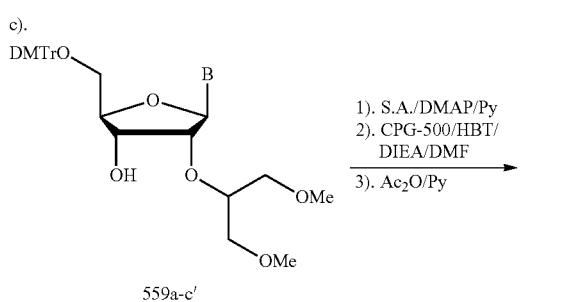
560a-c'
c).
559a-c'
1). S.A./DMAP/Py
2). CPG-500/HBT/DIEA/DMF
3). Ac$_2$O/Py
230
-continued
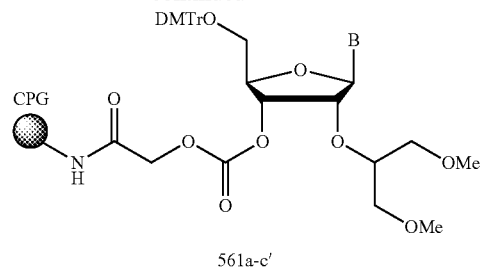
561a-c'
Scheme 35: 2' = 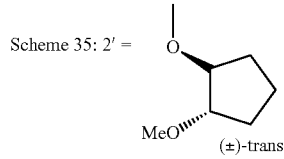
(±)-trans
B: U T C$^{Ac}$ A$^{Bz}$ G$^{bu}$
number: a b c' d e
a).
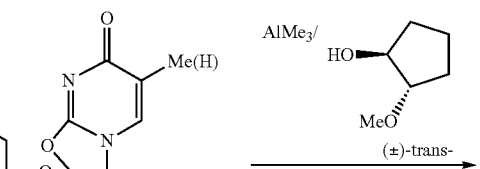
500a-b
AlMe$_3$/
(±)-trans-
140° C.
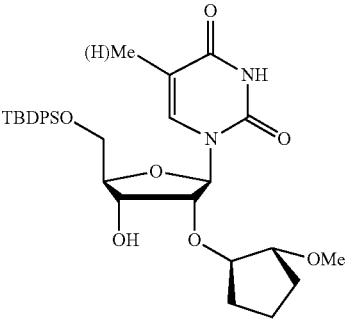
563a-b (R,R)
Seperation
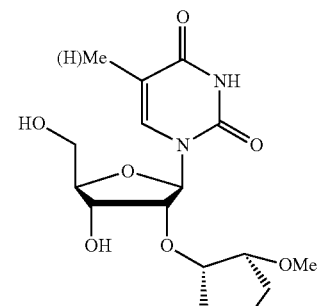
564a-b (S,S)

b).
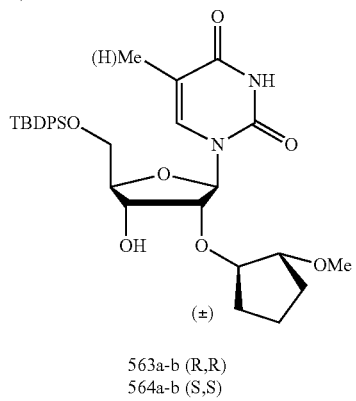
563a-b (R,R)
564a-b (S,S)
3HF·Et₃N / THF, rt →
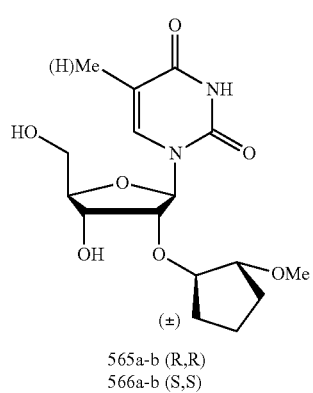
565a-b (R,R)
566a-b (S,S)
DMTrCl / Py, rt →
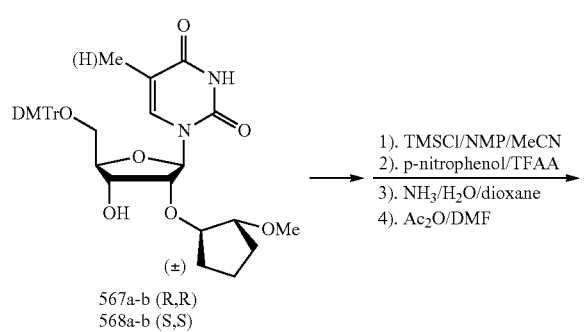
567a-b (R,R)
568a-b (S,S)
1). TMSCl/NMP/MeCN
2). p-nitrophenol/TFAA
3). NH₃/H₂O/dioxane
4). Ac₂O/DMF
→
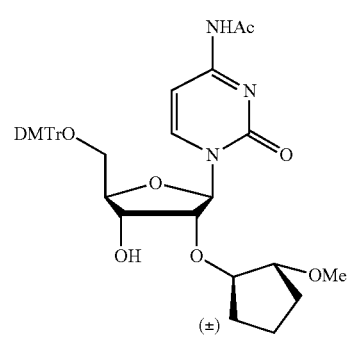
567c′ (R,R)
568c′ (S,S)
c).
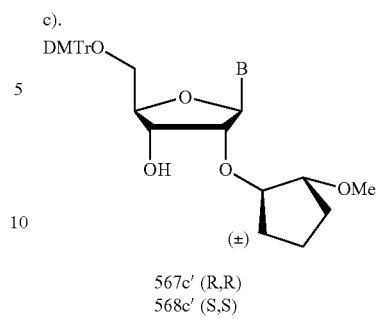
567c′ (R,R)
568c′ (S,S)
NCCH₂CH₂P(Cl)N(i-Pr)₂ / DIEA/DCM →
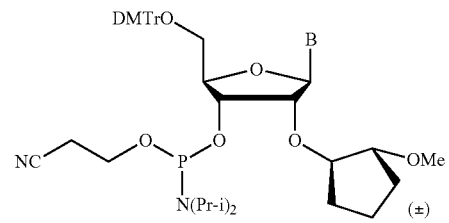
569a-c′ (R,R)
570a-c′ (S,S)
d).
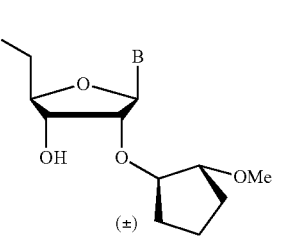
567a-c′ (R,R)
568a-c′ (S,S)
1). S.A./DMAP/Py
2). CPG-500/HBT/DIEA/DMF
3). Ac₂O/Py
→
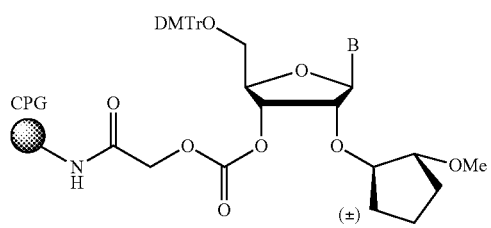
571a-c′ (R,R)
572a-c′ (S,S)
Scheme 36: 2′ = 
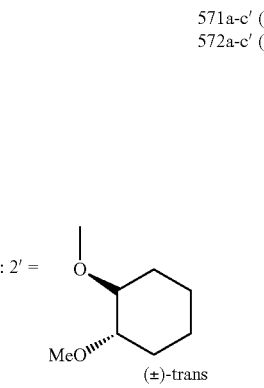
(±)-trans
B: U T C^{Ac} A^{Bz} G^{bu}
number: a b c′ d e

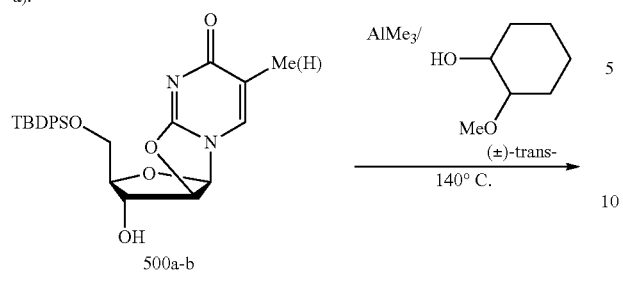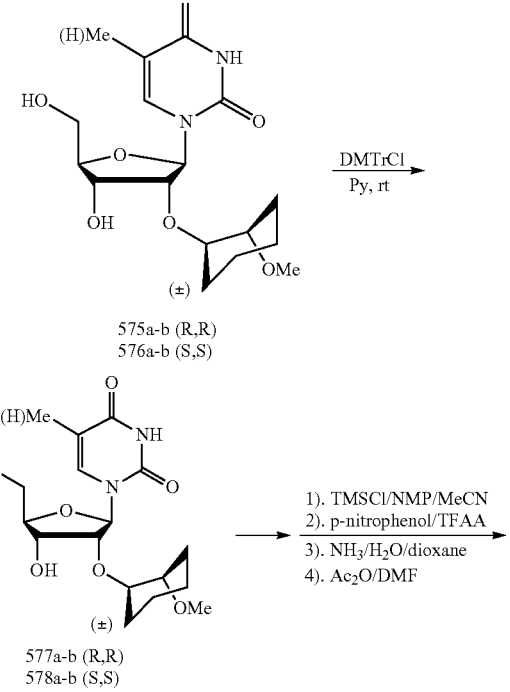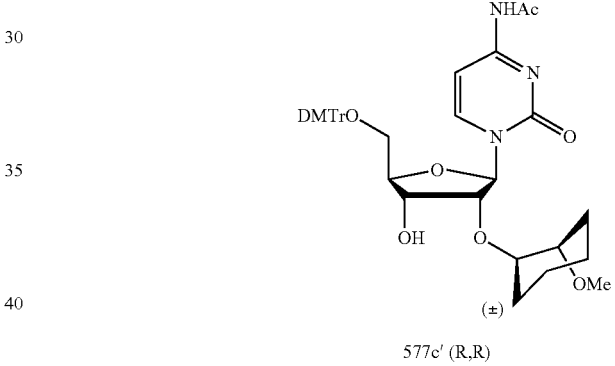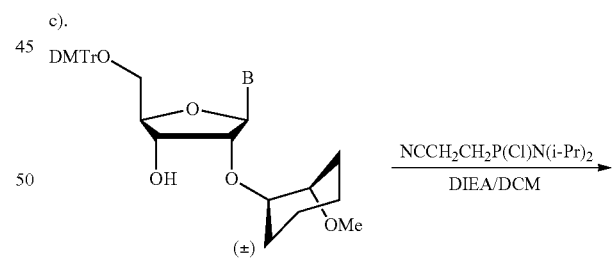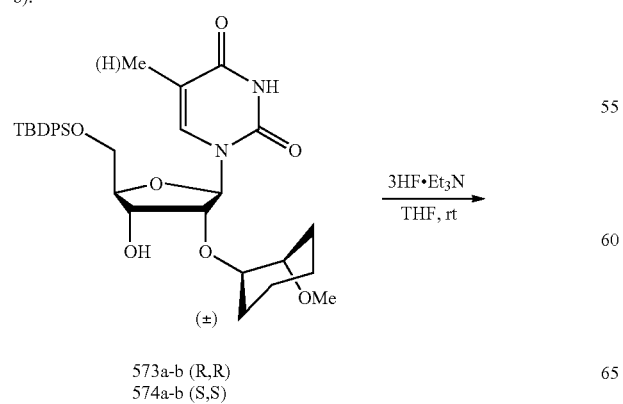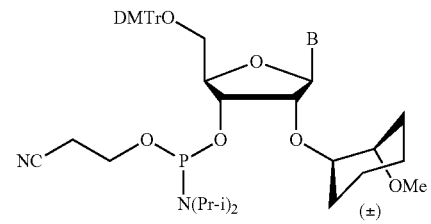

235
-continued
d).
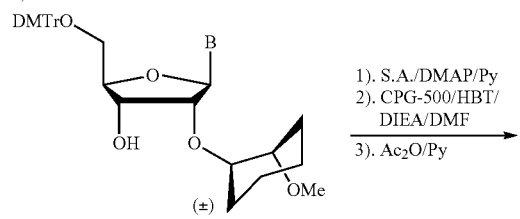
577a-c' (R,R)
578a-c' (S,S)
1). S.A./DMAP/Py
2). CPG-500/HBT/
    DIEA/DMF
3). Ac₂O/Py
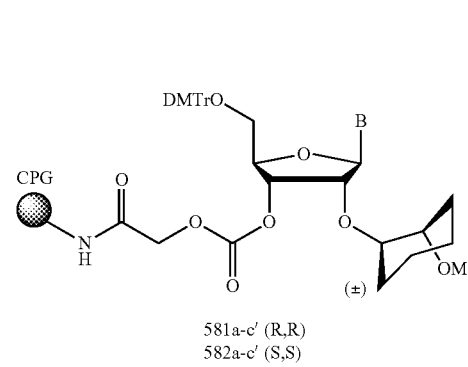
581a-c' (R,R)
582a-c' (S,S)
Scheme 37: 5', 2'-(O)-Dimers
a).
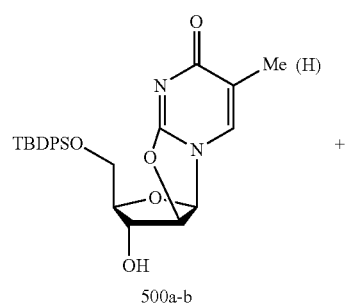
500a-b
+
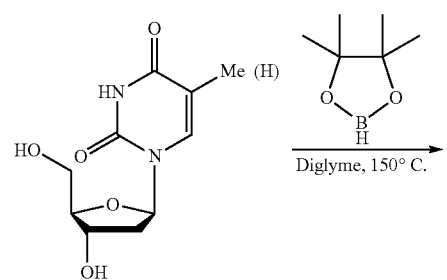
236
-continued
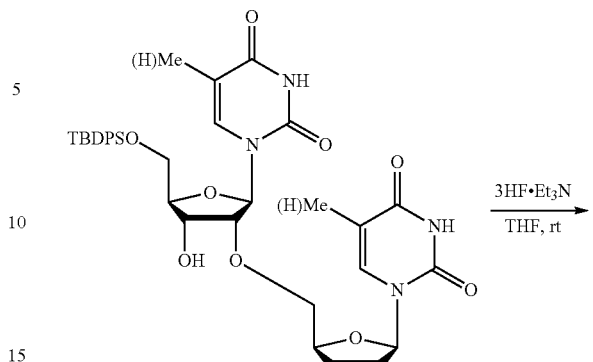
583a-b
3HF·Et₃N
—————→
THF, rt
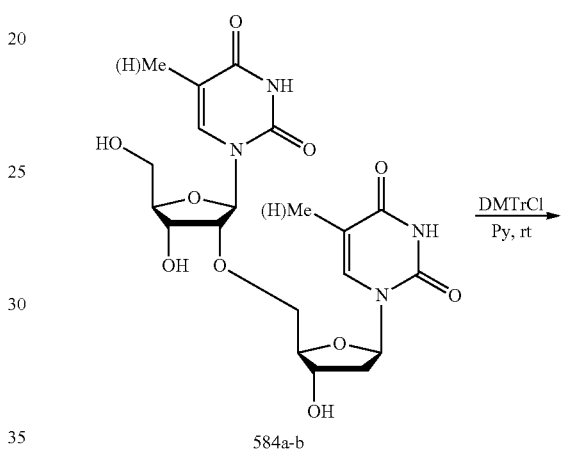
584a-b
DMTrCl
—————→
Py, rt
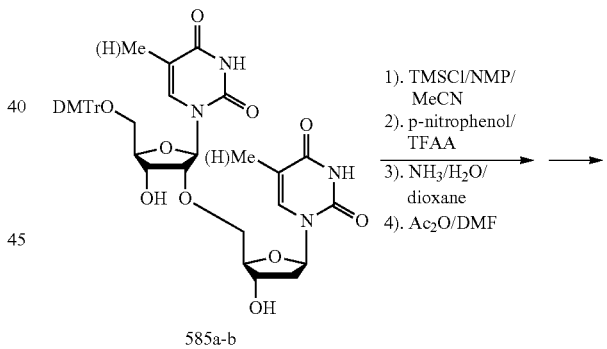
585a-b
1). TMSCl/NMP/
    MeCN
2). p-nitrophenol/
    TFAA
3). NH₃/H₂O/
    dioxane
4). Ac₂O/DMF
—————→
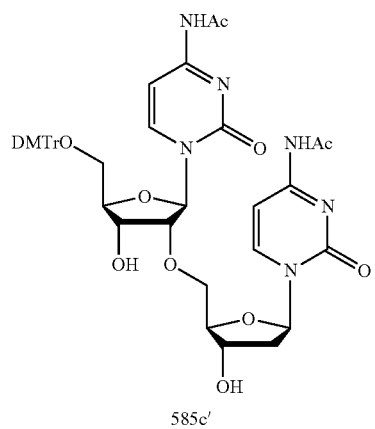
585c'

237
-continued
b).
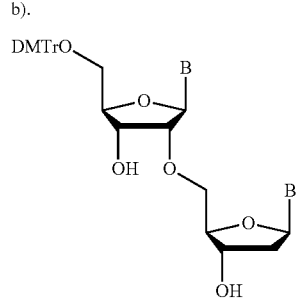
585a-c'
1). S.A./DMAP/Py
2). CPG-500/HBTU/DIEA/DMF
3). Ac₂O/Py
→
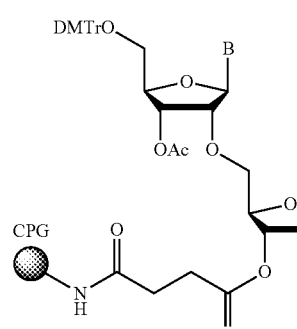
586a-c'
238
-continued
c).
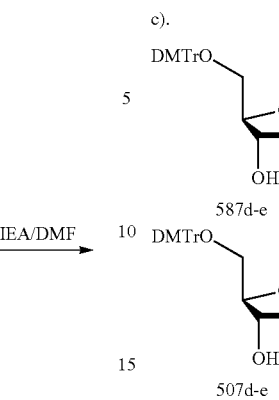
587d-e
1). TBSCl,
2). Deblock
3). MsCl
→
588d-e
507d-e
NaH
DMSO/THF
→
589d-e
1). S.A./DMAP/Py
2). CPG-500/HBTU/DIEA/DMF
3). Ac₂O/Py
→
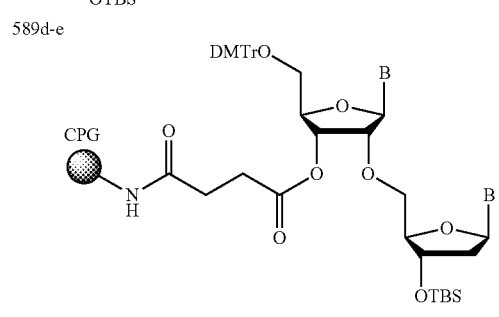
590d-e
B:      U   T   C$^{Ac}$   A$^{Bz}$   G$^{ibu}$
number: a   b   c'         d          e
Scheme 38: 5', 3'-(O)-Dimers
a).
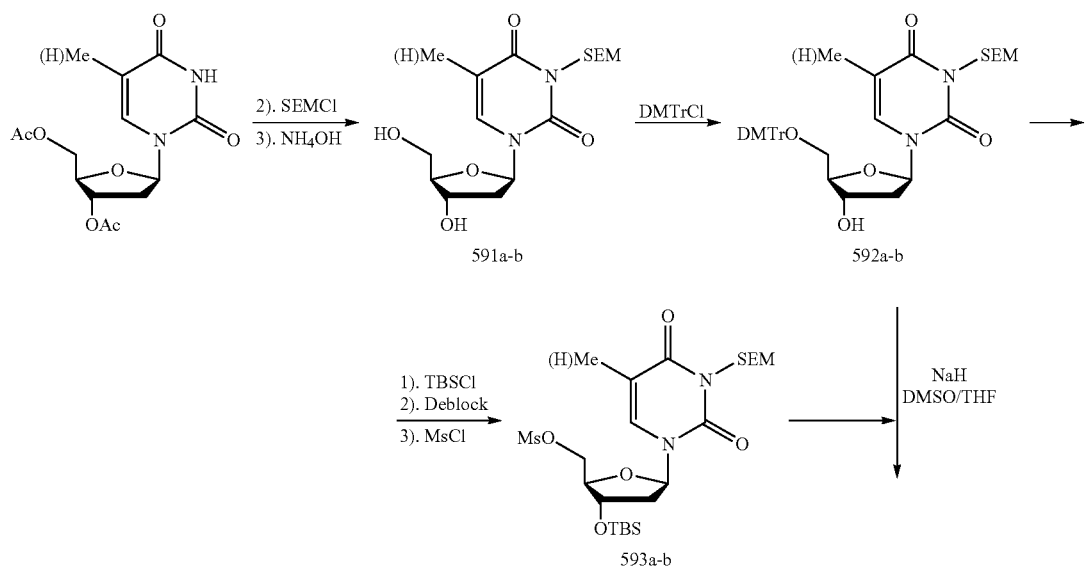

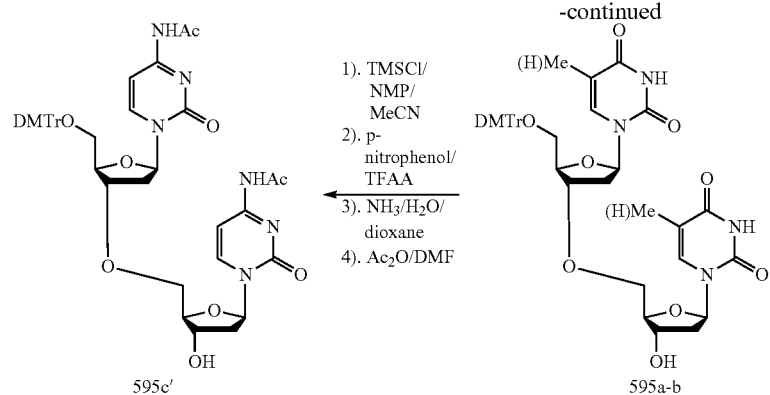
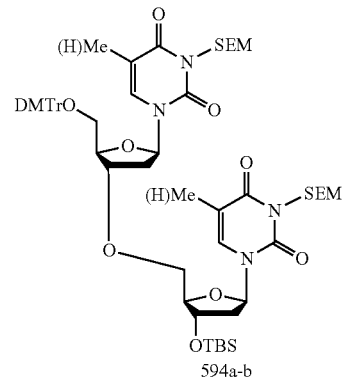
b).
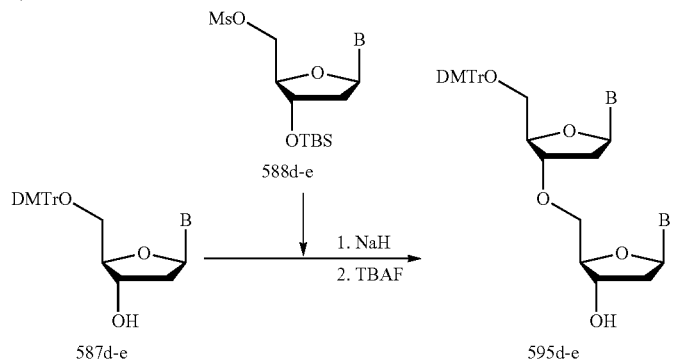
c).
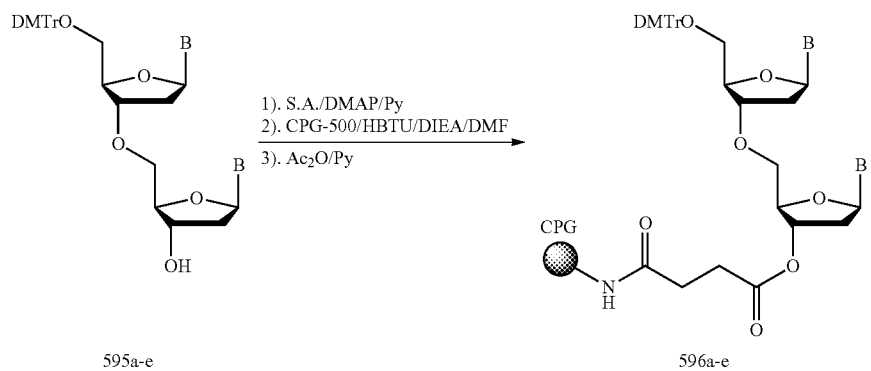
595a-e
B:   U   T   C$^{Ac}$   A$^{Bz}$   G$^{ibu}$
number: a   b   c′   d   e
Scheme 39:
Synthesis of derivatives of T, 5-Me-C and A 2′-modified with amines and polyamines:
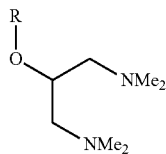
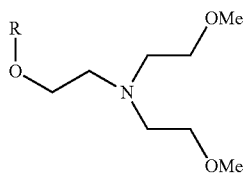
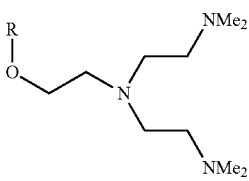

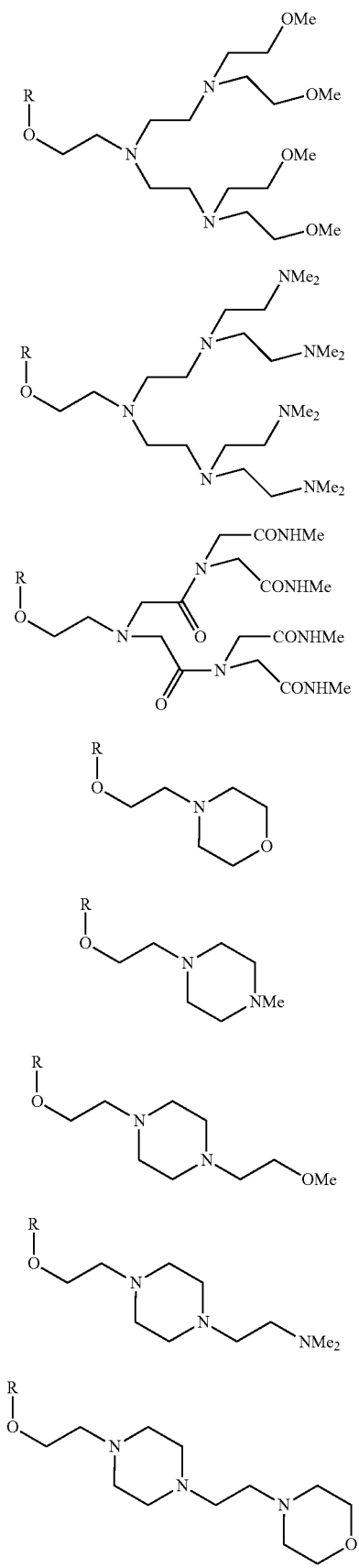
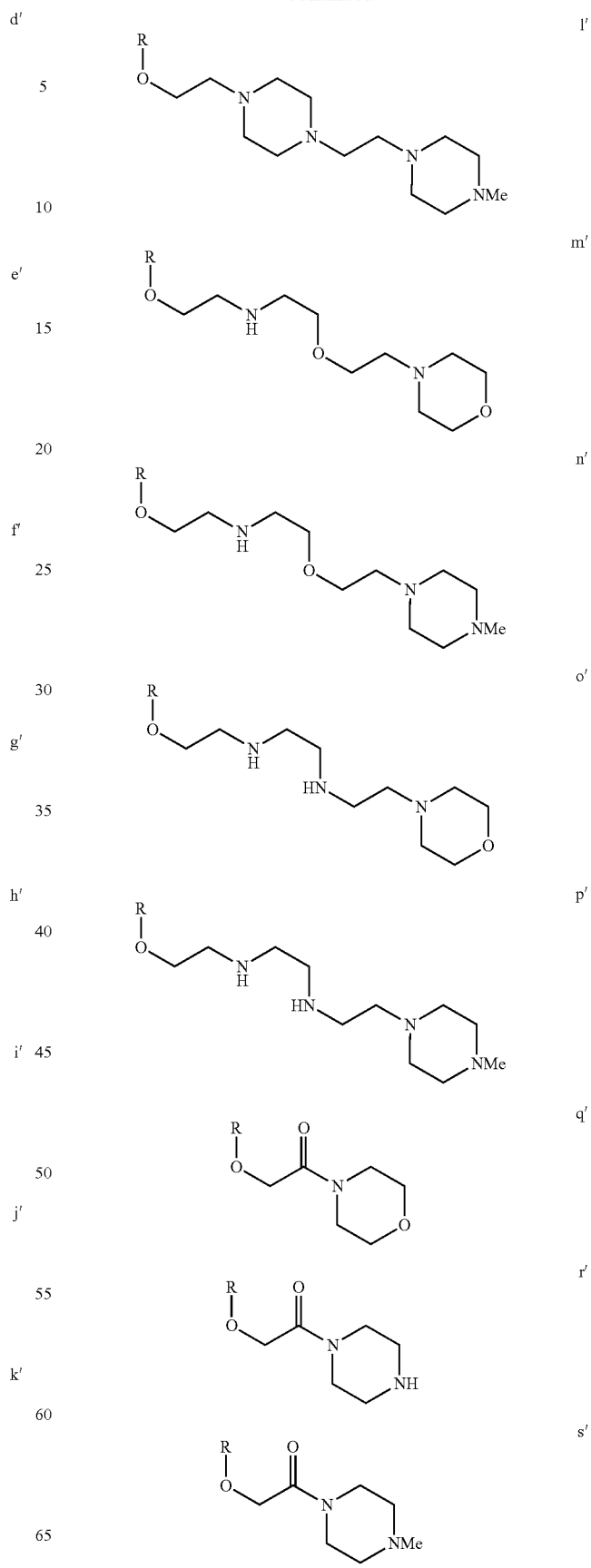

243
-continued
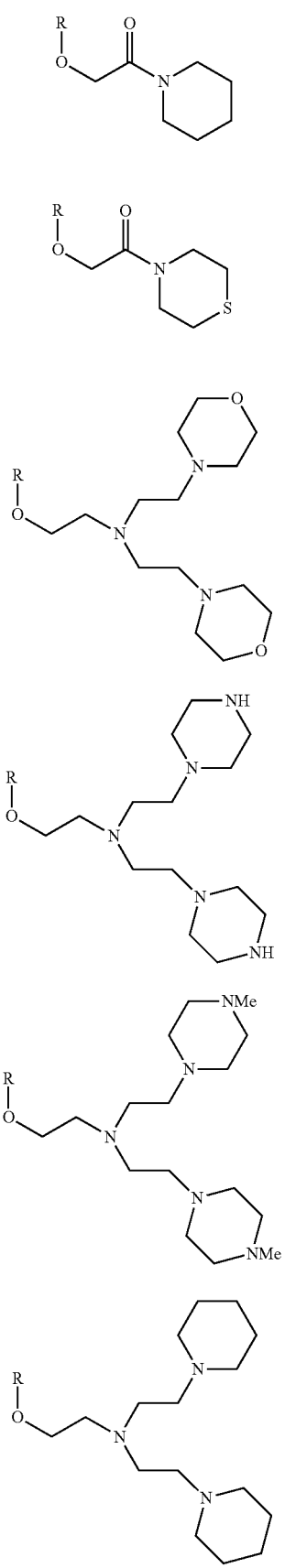
244
-continued
t'
z'
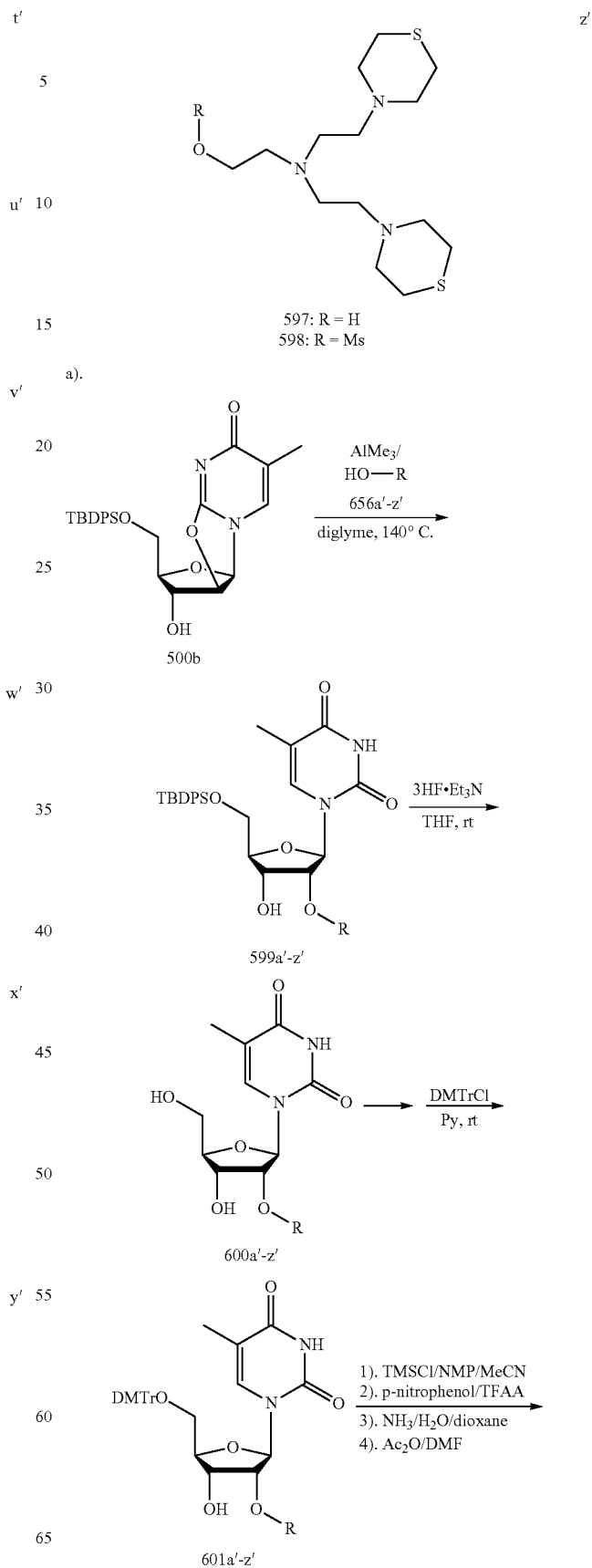
597: R = H
598: R = Ms
a).
v'
w'
x'
y'

-continued
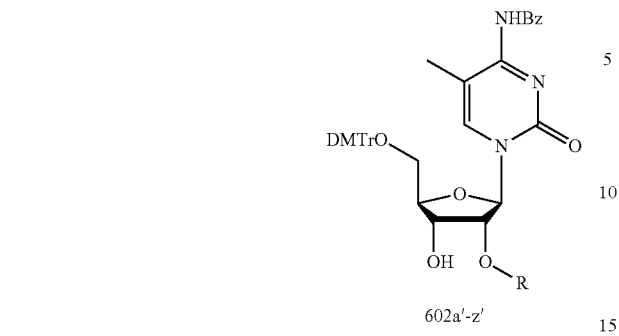
602a'-z'
b).
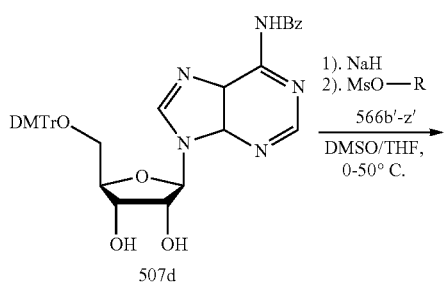
507d
1). NaH
2). MsO—R
566b'-z'
DMSO/THF,
0-50° C.
c).
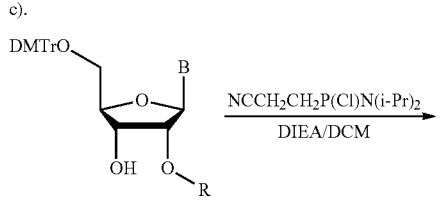
601a'-z'
602a'-z'
603a'-z'
NCCH₂CH₂P(Cl)N(i-Pr)₂
―――――――――――→
DIEA/DCM
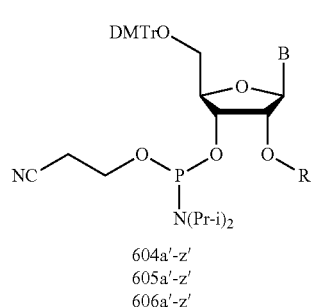
604a'-z'
605a'-z'
606a'-z'
-continued
d).
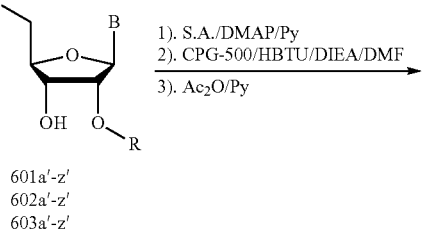
601a'-z'
602a'-z'
603a'-z'
1). S.A./DMAP/Py
2). CPG-500/HBTU/DIEA/DMF
3). Ac₂O/Py
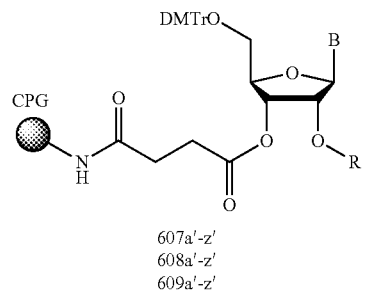
607a'-z'
608a'-z'
609a'-z'
Alternative synthesis of guanine derivatives:
505-506e, 546-547e, 554e, 589e, 595e.
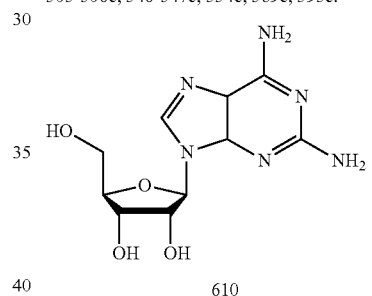
610
MsOR (or BrR)
―――――――――→
KOH/DMSO, rt
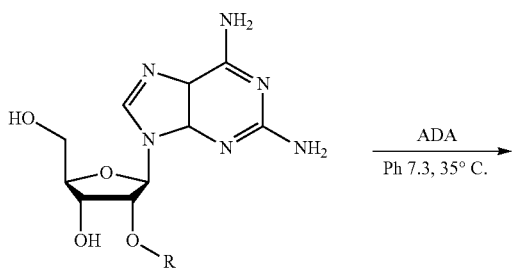
611
ADA
―――――→
Ph 7.3, 35° C.
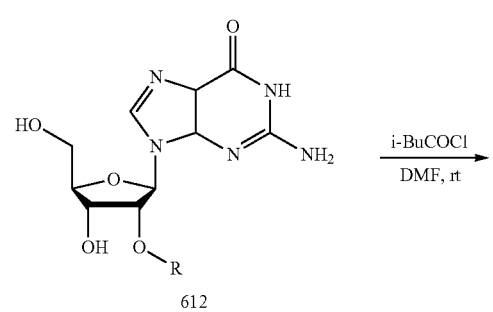
612
i-BuCOCl
―――――→
DMF, rt

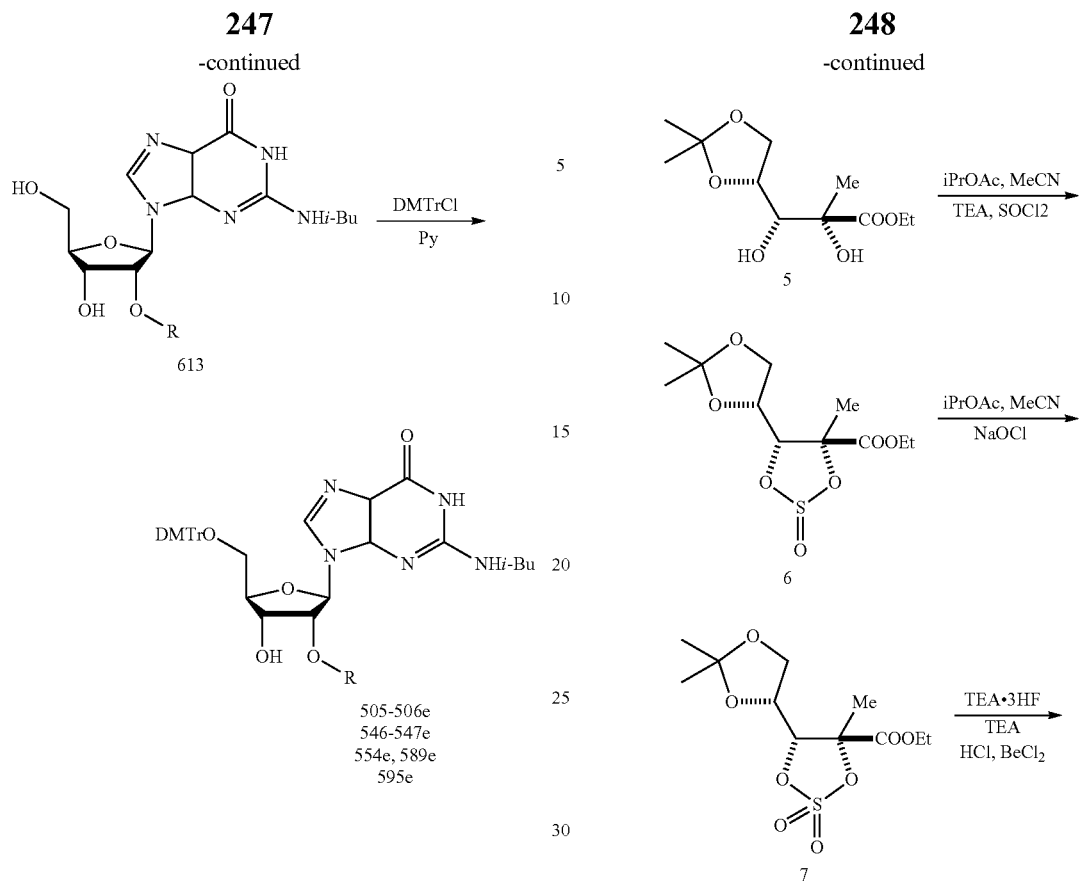
Scheme 40: Gem 2'-F/2'-Me U and C containing oligonucleotides
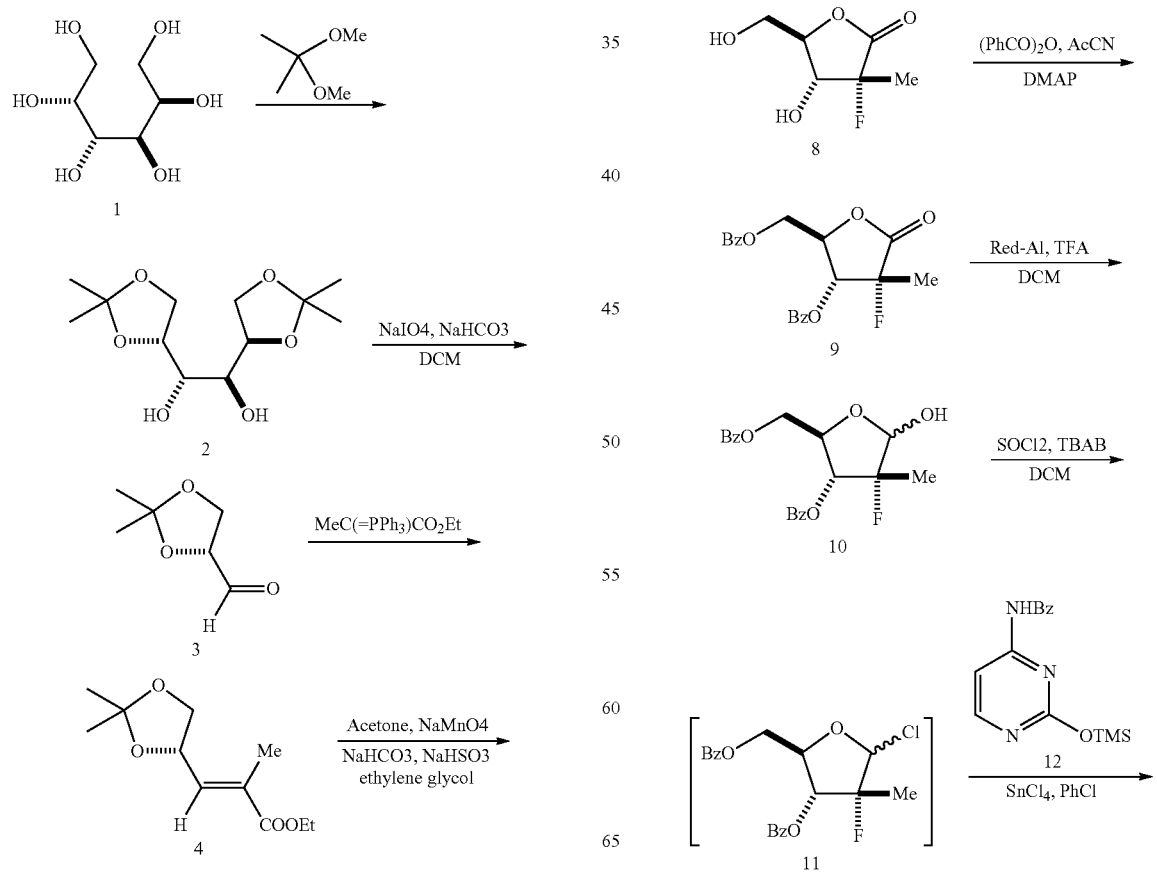

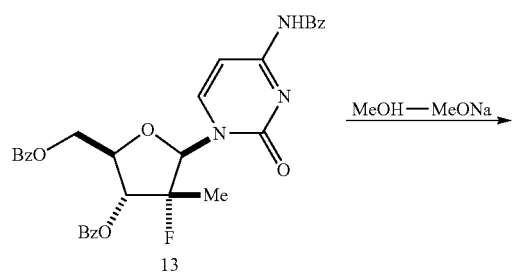
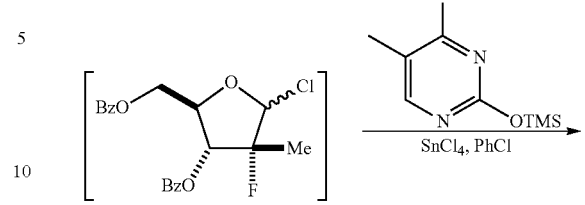
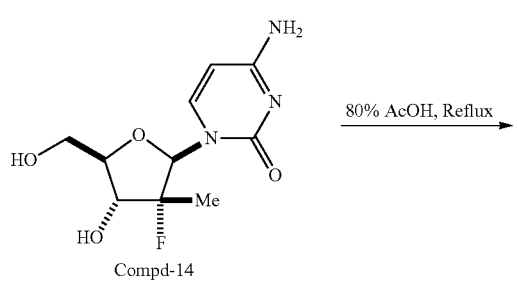
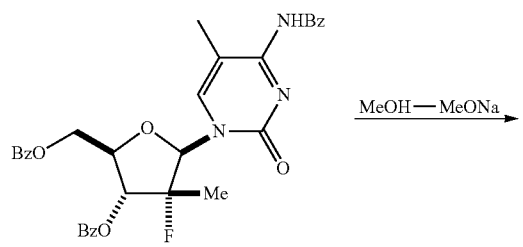
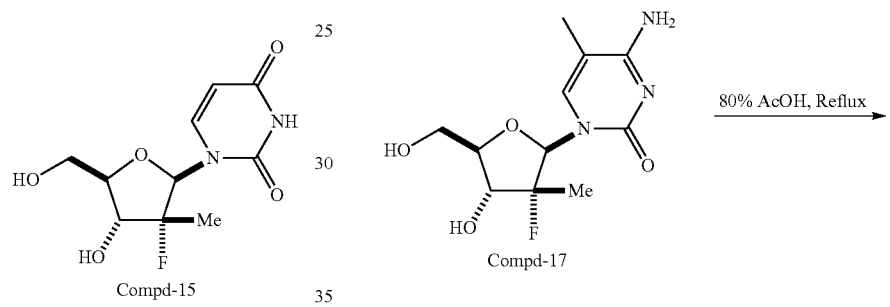
Scheme 41: Gem 2'-F/2'-Me containing 5-Me-U and 5-Me-C oligonucleotides
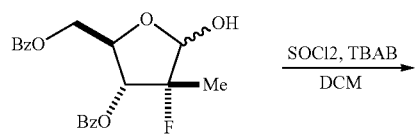
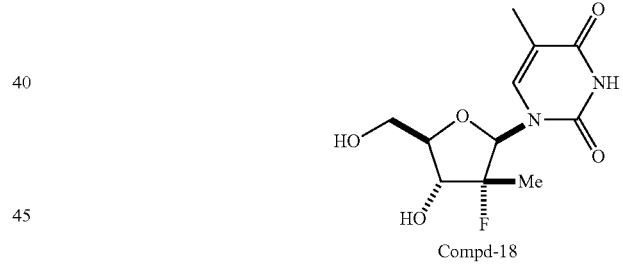
Scheme 42
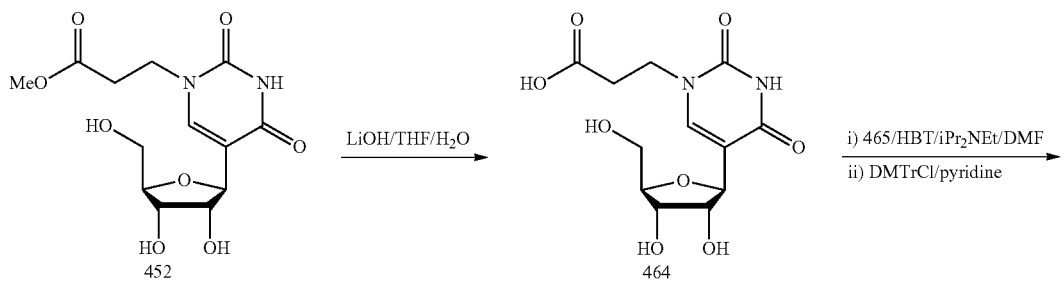

-continued
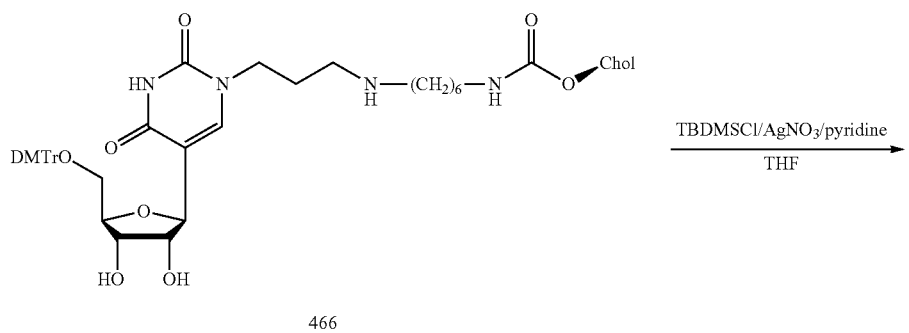
466
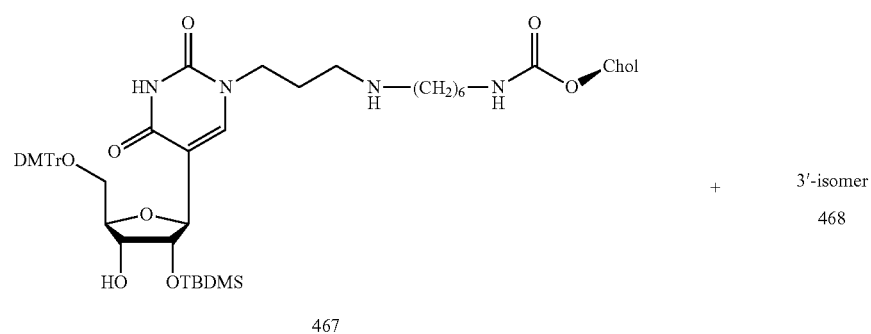
467
+ 3'-isomer
468
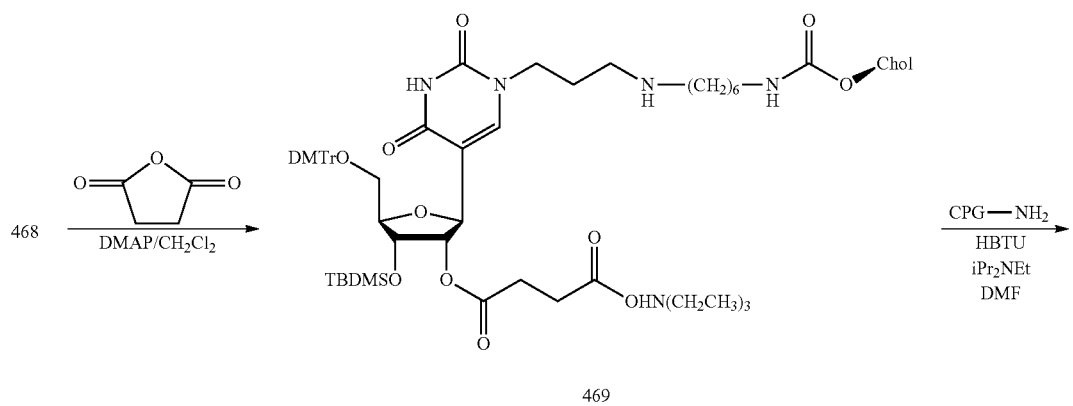
469
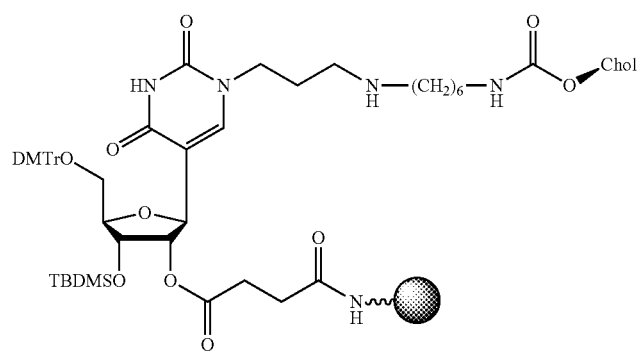
470

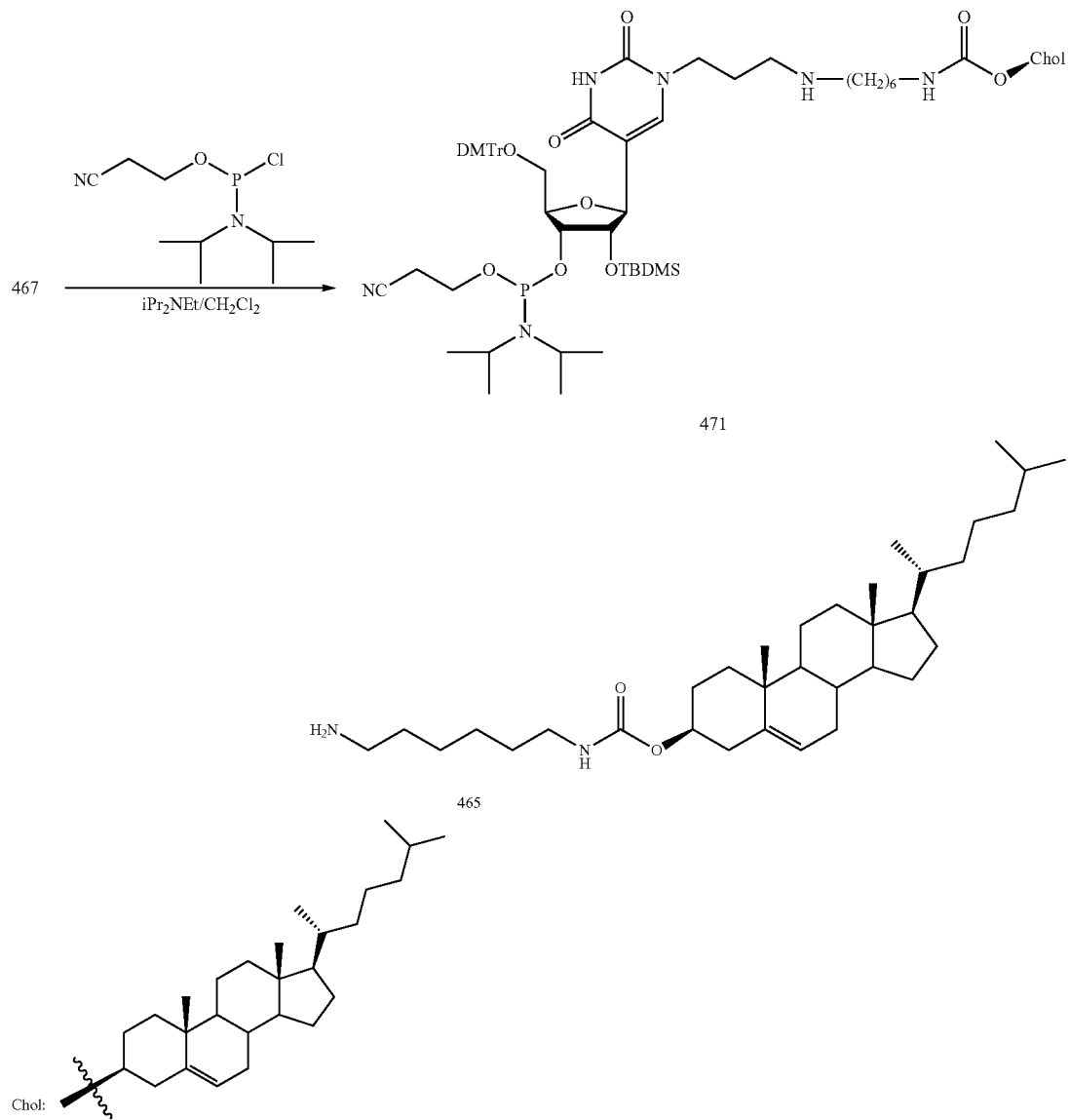
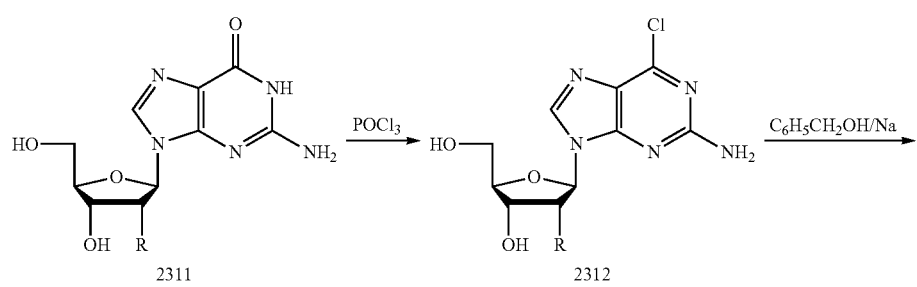
Scheem 43. 2'-Substituted-2-Fluoroinosine synthesis
R = H, OMe or F

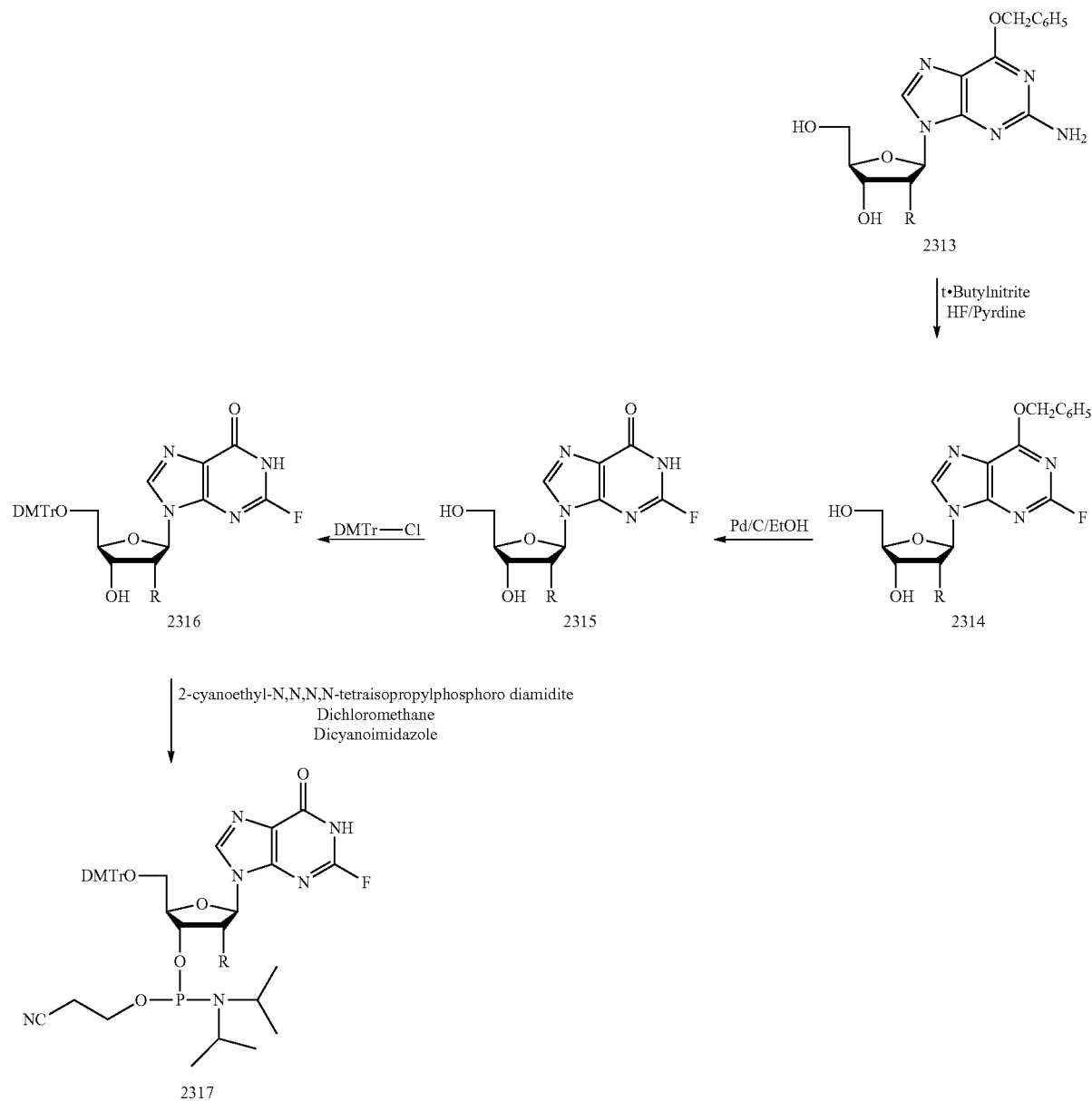
Scheme 44. Alternative synthesis of guanine derivatives: 505-506e, 546-547e, and 558e.
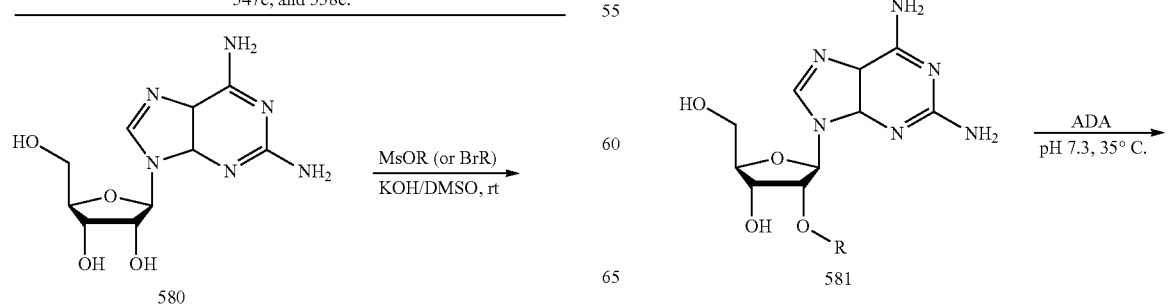

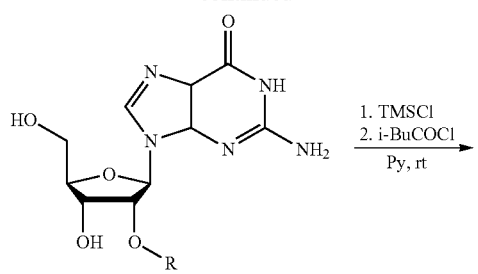

582

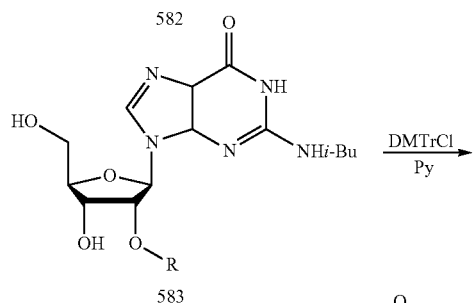

583

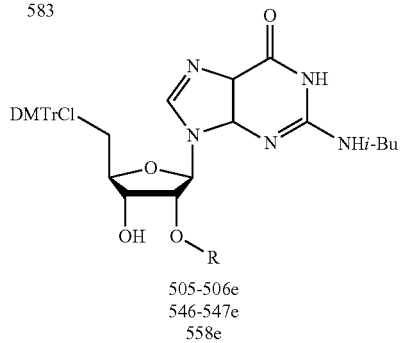

505-506e
546-547e
558e

Scheme 45. Postsynthetic N² derivatization of purines

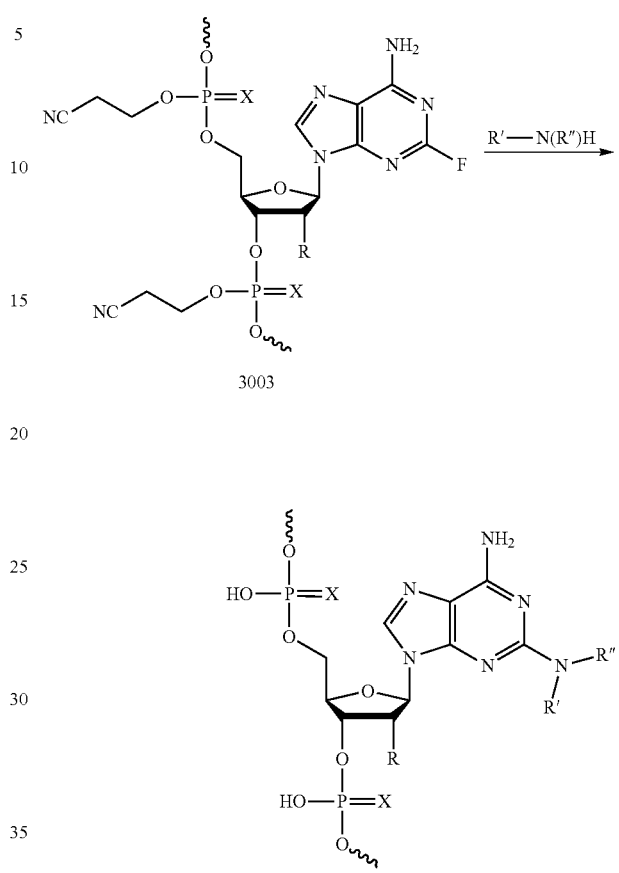

3001

3002

3003

3004

X = O, S, BH₃
R' = H, alkyl, alkenyl, alkynyl, aryl, ω-hyrdoxyalkyl, ω-hyrdoxyalkenyl, ω-hyrdoxyalkynyl, ω-aminoalkyl, ω-aminoalkenyl, ω-aminoalkynyl,
—[(CH₂)$_n$N(R″)]$_m$—H; —[(CH₂)$_n$O]$_m$—H,
—[(CH₂)$_p$O]$_q$—[(CH₂)$_r$N(R″)]$_s$—H; —[(CH₂)$_r$N(R″)]$_s$—[(CH₂)$_p$O]$_q$—H
or any other aliphatic, aromatic/heteroaormatic, cyclic or heterocyclic substituent
R″ = H, alkyl, alkenyl, alkynyl, aryl, ω-hyrdoxyalkyl, ω-hyrdoxyalkenyl, ω-hyrdoxyalkynyl, ω-aminoalkyl, ω-aminoalkenyl, ω-aminoalkynyl,
—[(CH₂)$_n$N(R′)]$_m$—H; —[(CH₂)$_n$O]$_m$—H,
—[(CH₂)$_p$O]$_q$—[(CH₂)$_r$N(R′)]$_s$—H; —[(CH₂)$_r$N(R′)]$_s$—[(CH₂)$_p$O]$_q$—H
or any other aliphatic, aromatic/heteroaormatic, cyclic or heterocyclic substituent Scheme 46-1

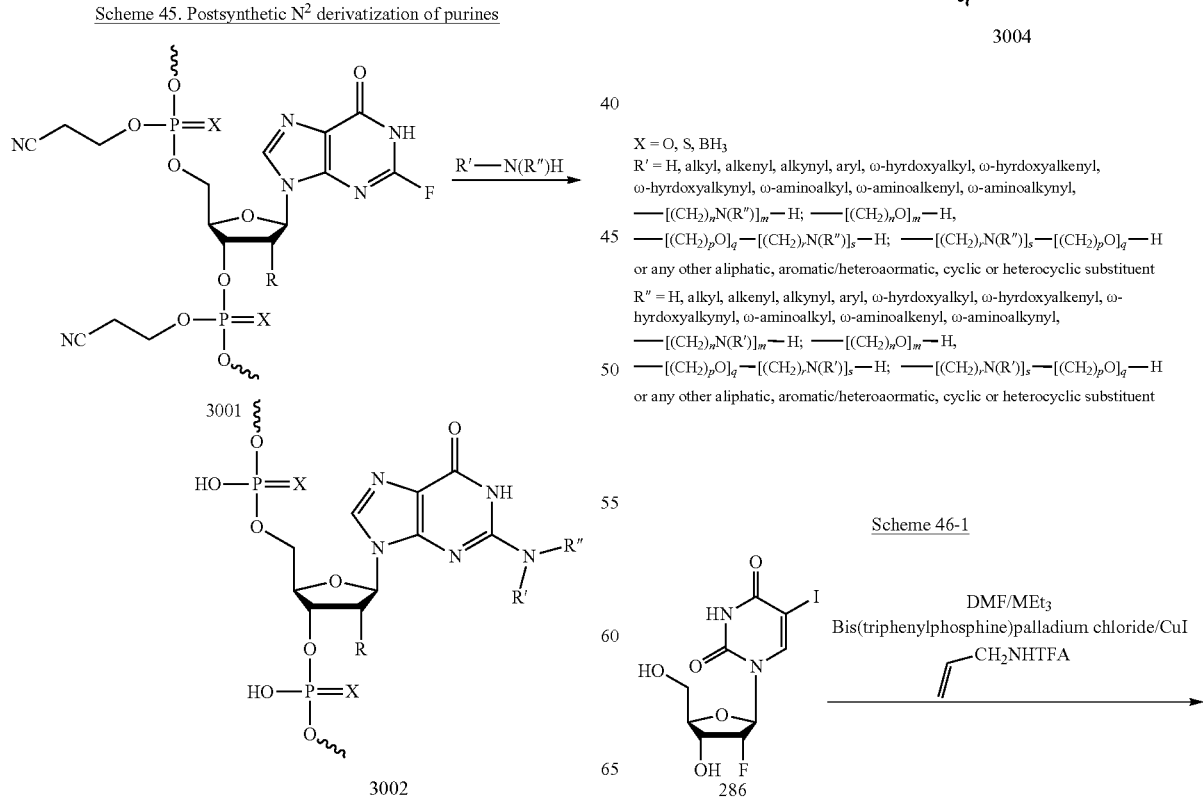

286

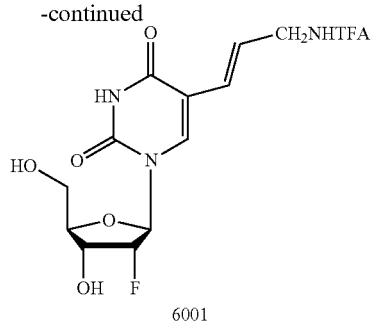
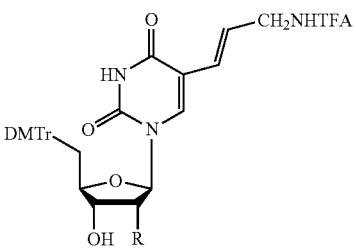
Scheme 46-2
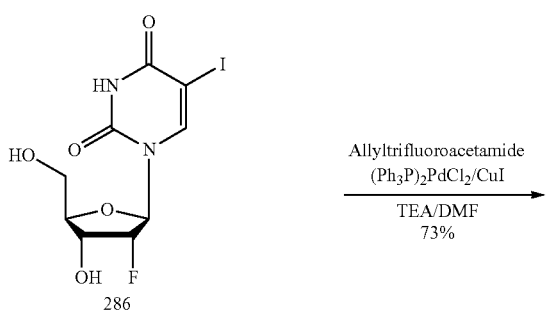
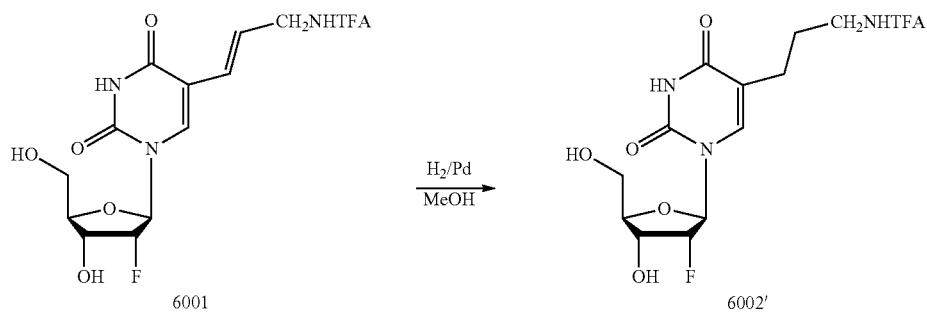
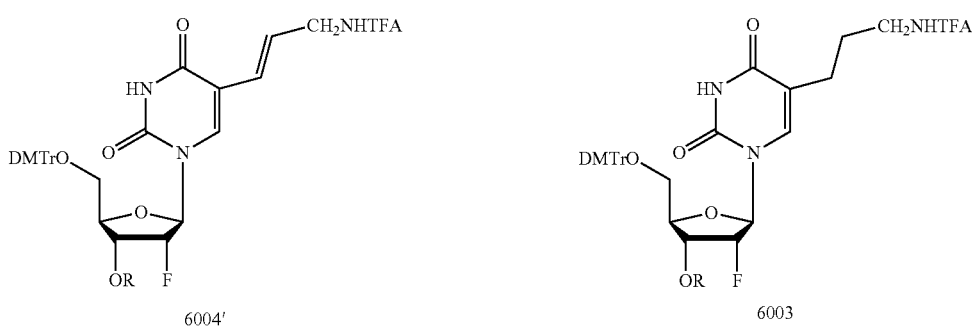
A. R = H
B. R = Cyanoethyl-amidite Scheme 47-1

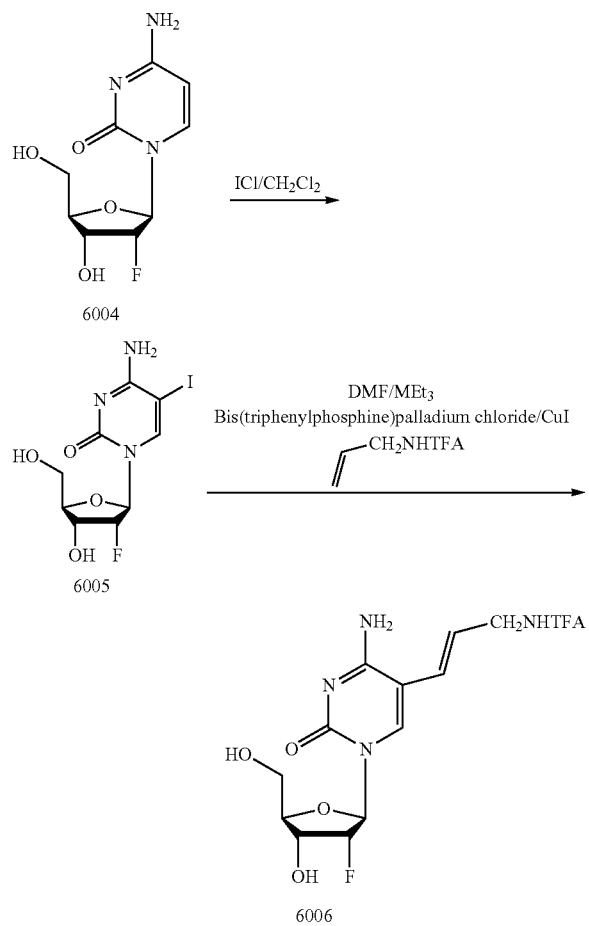

Scheme 47-2

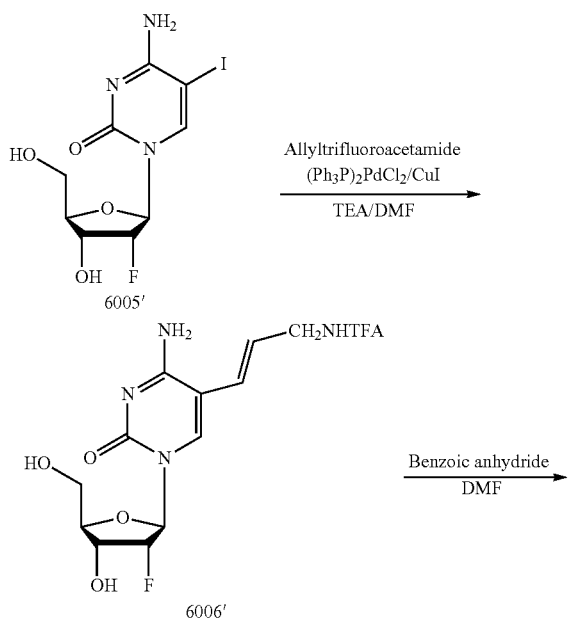

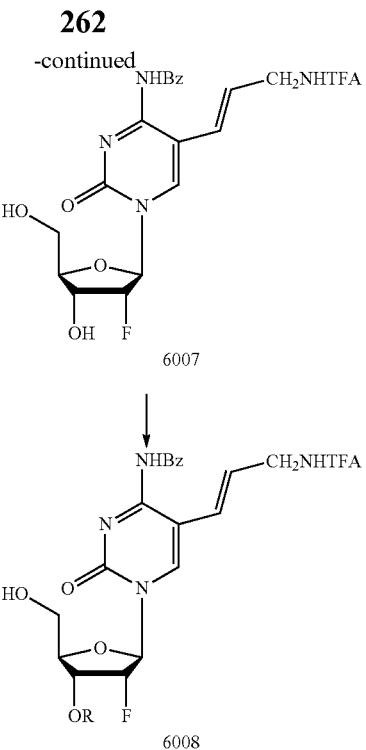

A. R = H
B. R = 2-cyanoethylamidite

EXAMPLES

The invention now being generally described, it will be more readily understood by reference to the following examples which are included merely for purposes of illustration of certain aspects and embodiments of the present invention, and are not intended to limit the invention.

Compounds from Scheme 3:
402 (R=OH, n=1)
403 (R=OH, n=1)

To a solution of 401 (R=OH, 9.0 g, 36.86 mmol) in DMF (500 mL), N-(3-iodopropyl)phthalimide (n=1, 12.95 g, 41.1 mmol) and $K_2CO_3$ (5.68 g, 41.1 mmol) were added. The reaction mixture was stirred at room temperature overnight, then heated at 50° C. for 3 h. After removing the solvent, the crude material was purified by silica gel column chromatography (10% MeOH in $CH_2Cl_2$) to give compound 402 (R=OH, n=1, 3.98 g, 9.23 mmol, 25%, $R_f$=0.26 with 10% MeOH in $CH_2Cl_2$) and compound 403 (R=OH, n=1, 8.34 g, 13.48 mmol, 37%, $R_f$=0.56 with 10% MeOH in $CH_2Cl_2$). 402 (R=OH, n=1): $^1$H NMR (DMSO-$d_6$, 400 MHz) δ 11.35 (s, 1H), 7.83-7.89 (m, 4H), 7.81 (s, 1H), 4.95 (d, J=5.2 Hz, 1H), 4.75-4.78 (m, 1H), 4.73 (d, J=6.0 Hz, 1H), 4.43 (d, J=4.4 Hz, 1H), 3.96 (q, J=5.0 Hz, 1H), 3.87 (q, J=5.6 Hz, 1H), 3.57-3.74 (m, 5H), 3.42-3.47 (m, 1H), 1.90-1.94 (m, 2H). $^{13}$C NMR (DMSO-$d_6$, 100 MHz) δ 167.8, 162.9, 150.4, 143.2, 134.3, 131.6, 122.9, 111.5, 83.3, 79.0, 73.5, 70.3, 61.1, 45.5, 34.8, 27.4. Molecular weight for $C_{20}H_{21}N_3NaO_8$ $(M+Na)^+$ Calc. 454.12. Found 454.1.

403 (R=OH, n=1): $^1$H NMR (DMSO-$d_6$, 400 MHz) δ 7.81-7.88 (m, 9H), 4.95 (d, J=4.8 Hz, 1H), 4.75-4.78 (m, 1H), 4.72 (d, J=6.0 Hz, 1H), 4.46 (d, J=3.6 Hz, 1H), 3.84-3.93 (m, 2H), 3.56-3.79 (m, 10H), 3.43-3.49 (m, 1H), 1.83-1.95 (m, 4H). $^{13}$C NMR (DMSO-$d_6$, 100 MHz) δ 167.8, 167.7, 161.4, 150.4, 141.4, 134.3, 134.2, 131.6, 131.5, 122.9, 111.1, 82.9, 79.3, 73.6, 70.0, 60.8, 46.5, 38.2, 35.3, 34.7, 27.1, 26.0. Molecular weight for $C_{31}H_{30}N_4NaO_{10}$ $(M+Na)^+$ Calc. 641.19. Found 641.0.

404 (R=OTBDMS, n=1)

402 (R=OH, n=1) is treated with DMTrCl in pyridine to give a 5'-O-DMTr protected nucleoside, which is selectively converted to the corresponding 2'-O-TBDMS analog 404 (R=OTBDMS, n=1) under the conditions of TBDMSCl/silver nitrate/pyridine in THF (ref. G. H. Hakimelahi, Z. A. Proba, and K. K. Ogilvie, *Tetrahedron Lett.*, 22, (1981), 5243).

404 (R=OTBDMS, n=1): $^1$H NMR (DMSO-$d_6$, 400 MHz) δ 11.36, 7.84 (s, 4H), 7.50 (s, 1H), 7.19-7.41 (m, 9H), 6.85-6.88 (m, 4H), 4.64 (d, J=6.0 Hz, 1H), 4.51 (d, J=2.8 Hz, 1H), 4.12 (t, J=3.4 Hz, 1H), 3.89-3.92 (m, 2H), 3.71 (s, 6H), 3.51-3.58 (m, 1H), 3.43 (t, J=6.8 Hz, 2H), 3.16-3.17 (m, 2H), 1.73-1.79 (m, 2H), 0.86 (s, 9H), 0.056 (s, 3H), 0.043 (s, 3H).

Molecular weight for $C_{47}H_{53}N_3NaO_{10}Si$ $(M+Na)^+$ Calc. 870.34. Found 870.2.

408 (R=OH, n=1)

To a solution of 403 (R=OH, n=1, 8.34 g, 13.48 mmol) in pyridine (140 mL), DMAP (329 mg, 2.70 mmol), DMTrCl (4.57 g, 13.48 mmol) were added. The reaction mixture was stirred overnight. After evaporation, the residue was extracted with $CH_2Cl_2$ and saturated $NaHCO_3$ aq., dried over anhydrous $Na_2SO_4$, and purified by silica gel column chromatography (2% MeOH in $CH_2Cl_2$, $R_f$=0.18) to give 408 (R=OH, n=1, 7.92 g, 8.60 mmol, 64%).

408 (R=OH, n=1): $^1$H NMR (MeOH-$d_4$, 400 MHz) δ 7.80-7.87 (m, 8H), 7.55 (s, 1H), 7.16-7.70 (m, 9H), 6.84-6.87 (m, 4H), 5.06 (d, J=4.4 Hz, 1H), 4.79 (d, J=6.4 Hz, 1H), 4.54 (d, J=2.4 Hz, 1H), 3.87-3.94 (m, 3H), 3.78 (t, J=7.4 Hz, 2H), 3.70 (s, 6H), 3.55-3.61 (m, 3H), 3.39-3.46 (m, 3H), 3.14-3.15 (m, 2H), 1.77-1.85 (m, 4H). $^{13}$C NMR (MeOH-$d_4$, 100 MHz) δ 167.7, 161.2, 157.9, 150.3, 144.8, 140.8, 135.6, 135.4, 134.3, 134.2, 131.5, 129.7, 129.6, 127.7, 126.5, 122.9, 113.0, 111.3, 85.2, 80.7, 80.2, 73.4, 70.7, 64.0, 54.9, 46.5, 38.2, 35.2, 34.7, 26.9, 26.0. Molecular weight for $C_{52}H_{48}N_4NaO_{12}$ $(M+Na)^+$ Calc. 943.32. Found 943.2.

409 (R=OTBDMS, n=1)

To a solution of 408 (R=OH, n=1, 7.92 g, 8.60 mmol) in THF (86 mL), pyridine (2.57 mL, 31.8 mmol), and $AgNO_3$ (1.75 g, 10.3 mmol) was added. After 15 min, TBDMSCl (1.30 g, 8.60 mmol) was added and the reaction mixture was stirred overnight under Ar gas. The reaction mixture was filtered through Celite, then extracted with $CH_2Cl_2$ and saturated $NaHCO_3$ aq., and dried over anhydrous $Na_2SO_4$. The crude was purified by silica gel column chromatography to give 409 (R=OTBDMS, 3.47 g, 3.36 mmol, 39%, $R_f$=0.30 developed with Hexane:EtOAc=3:2) and the corresponding 3'-O-TBDMS isomer (3.41 g, 3.29 mmol, 38%, $R_f$=0.20 developed with Hexane:EtOAc=3:2).

409 (R=OTBDMS, n=1): $^1$H NMR (MeOH-$d_4$, 400 MHz) δ 7.81-7.87 (m, 8H), 7.52 (s, 1H), 7.17-7.42 (m, 9H), 6.85-6.87 (m, 4H), 4.63-4.65 (m, 1H), 4.53 (d, J=2.8 Hz, 1H), 4.08 (t, J=3.4 Hz, 1H), 3.90-3.92 (m, 2H), 3.76-3.79 (m, 2H), 3.70 (s, 6H), 3.55-3.59 (m, 3H), 3.40-3.44 (m, 3H), 3.18-3.19 (m, 2H), 1.75-1.86 (m, 4H), 0.83 (s, 9H), 0.022 (s, 3H), 0.017 (s, 3H). $^{13}$C NMR (MeOH-$d_4$, 100 MHz) δ 167.7, 167.6, 161.0, 157.9, 150.3, 144.8, 140.8, 135.6, 135.3, 134.2, 131.5, 131.4, 129.7, 129.6, 127.6, 126.5, 122.8, 113.0, 111.0, 85.2, 80.7, 80.2, 75.7, 70.4, 63.8, 54.9, 46.4, 38.1, 35.2, 34.6, 26.9, 26.0, 25.7, 18.5, 17.8, −4.79, −4.96. Molecular weight for $C_{58}H_{62}N_4NaO_{12}Si$ $(M+Na)^+$ Calc. 1057.40. Found 1057.3.

405/410: Phosphitylation is carried out using 2-cyanoethyl N,N-diisopropylchlorophosphoramidite and $iPr_2NEt$ in $CH_2Cl_2$. Aqueous work-up followed by silica gel column chromatography gives the corresponding phosphoramidite.

406/411: Succination is carried out using succinic anhydride and DMAP in $CH_2Cl_2$. Silica gel column chromatography of the crude mixture gives the corresponding succinated compound.

407/412: Standard RNA synthesis with an automated RNA synthesizer using the building block 405/406, followed by cleavage and deprotection with aqueous alkaline solution such as $CH_3NH_2$ for base protection and subsequent treatment with fluorine-containing solution $HF/Et_3N$ in $THF/H_2O$ for 2'-O-TBDMS group, gives a modified RNA oligomer 407 containing a mono-alkylamino group.

A modified RNA oligomer 412 containing bis-alkylamino groups is prepared using the building block 410/411 in the same manner Compounds from Scheme 4:

Compound 452

To a solution of pseudouridine 451 (20 g, 81.9 mmol) in 1M triethylammoniumbicarbonate buffer (pH 8.5, 780 mL) and EtOH (940 mL), methyl acrylate (235 mL, 2.61 mol) was dropwisely added. The reaction mixture was stirred for 16 hours. After removal of the solvent, the crude material was purified by silica gel column chromatography (10% MeOH in $CH_2Cl_2$, $R_f$=0.23) to give compound 452 (26.6 g, 80.5 mmol, 98%).

$^1$H NMR (MeOH-$d_4$, 400 MHz) δ 7.77 (d, J=0.8 Hz, 1H), 4.58 (d, J=4.8 Hz, 1H), 4.15 (t, J=5.2 Hz, 1H), 4.05 (t, J=5.0 Hz, 1H), 3.98-4.02 (m, 2H), 3.91-3.94 (m, 1H), 3.80 (dd, J=12.0 Hz, 3.3 Hz, 1H), 3.67 (s, 3H), 3.66 (dd, J=12.0 Hz, 3.3 Hz, 1H), 2.73-2.77 (m, 2H). $^{13}$C NMR (CDCl$_3$, 100 MHz) δ 173.1, 165.4, 152.5, 145.8, 112.9, 85.6, 81.5, 75.6, 72.6, 63.3, 52.5, 46.2, 33.7. Molecular weight for $C_{13}H_{19}N_2O_8$ $(M+H)^+$ Calc. 330.11. Found 331.0.

Compound 453

To a solution of compound 452 (11.67 g, 35.3 mmol) in DMF (65 mL), di-tert-butylsilyl bis(trifluoromethanesulfonate) (15.46 mL, 42.4 mmol) was added dropwise under stirring at 0° C. The reaction mixture was kept stirring at 0° C. for 30 min and treated with imidazole (12.0 g, 176.5 mmol). The mixture was stirred at 0° C. for 10 min and then at room temperature for 30 min TBDMSCl (7.98 g, 53.0 mmol) was added and the reaction mixture was heated at 75° C. for 6 hours. The reaction mixture was extracted with $Et_2O$ and saturated $NaHCO_3$ aq., dried over anhydrous $Na_2SO_4$, and concentrated. The residue was purified by silica gel column chromatography (hexane:EtOAc=1:1, $R_f$=0.50) to give compound 453 (15.0 g, 25.6 mmol, 73%).

$^1$H NMR (DMSO-$d_6$, 400 MHz) δ 11.39 (s, 1H), 7.54 (s, 1H), 4.55 (s, 1H), 4.34-4.38 (m, 1H), 4.18 (d, J=4.4 Hz, 1H), 3.86-4.00 (m, 5H), 3.58 (s, 3H), 2.67 (t, J=6.6 Hz, 2H), 1.02 (s, 9H), 0.99 (s, 9H), 0.89 (s, 9H), 0.13 (s, 3H), 0.087 (s, 3H). Molecular weight for $C_{27}H_{49}N_2O_8Si_2$ $(M+H)^+$ Calc. 585.30. Found 585.2.

Compound 454

Compound 453 (1.24 g, 2.12 mmol) was treated with ethylenediamine (10 mL) at room temperature for 2 hours. Ethylenediamine was removed by evaporation and the residue was dried in vacuo. The crude was extracted with $CH_2Cl_2$ and saturated $NaHCO_3$ aq., dried over anhydrous $Na_2SO_4$, and concentrated to give 454 as a white solid (1.16 g, 1.89 mmol, 89%).

$^1$H NMR (MeOD-$d_4$, 400 MHz) δ 7.49 (s, 1H), 4.63 (s, 1H), 4.39-4.41 (m, 1H), 4.29 (d, J=3.6 Hz, 1H), 4.00-4.04 (m, 5H), 3.18-3.26 (m, 2H), 2.69 (t, J=6.2 Hz, 2H), 2.56-2.61 (m,

2H), 1.07 (s, 9H), 1.04 (s, 9H), 0.94 (s, 9H), 0.17 (s, 3H), 0.13 (s, 3H). Molecular weight for $C_{28}H_{53}N_4O_7Si_2$ (M+H)$^+$ Calc. 613.35. Found 613.2.

Compound 455

To a solution of GalNAc acid (930 mg, 2.08 mmol) in DMF (10 mL), HBTU (789 mg, 2.08 mmol) and iPr$_2$NEt (1.65 mL, 9.45 mmol) were added. After 10 min, compound 454 in DMF (15 mL) was added to the solution and stirred overnight. The reaction mixture was extracted with Et$_2$O and saturated NaHCO$_3$ aq. and dried over anhydrous Na$_2$SO$_4$. After evaporation, the crude was purified by silica gel column chromatography (10% MeOH in CH$_2$Cl$_2$, R$_f$=0.43) to give compound 455 (1.83 g, 1.76 mmol, 93%).

$^1$H NMR (DMSO-d$_6$, 400 MHz) δ 11.36 (s, 1H), 7.98 (s, 1H), 7.82 (d, J=9.2 Hz, 1H), 7.77, (s, 1H), 7.51 (s, 1H), 5.21 (d, J=3.6 Hz, 1H), 4.96 (dd, J=11.4 Hz, 3.4 Hz, 1H), 4.53 (s, 1H), 4.48 (d, J=8.4 Hz, 1H), 4.33-4.36 (m, 1H), 4.18 (d, J=4.4 Hz, 1H), 3.85-4.02 (m, 9H), 3.67-3.73 (m, 1H), 3.37-3.43 (m, 1H), 3.04 (s, 4H), 2.39-2.44 (m, 2H), 2.10 (s, 3H), 2.02-2.05 (m, 2H), 1.99 (s, 3H), 1.89 (s, 3H), 1.77 (s, 3H), 1.46-1.49 (m, 4H), 1.01 (s, 9H), 0.99 (s, 9H), 0.89 (s, 9H), 0.12 (s, 3H), 0.080 (s, 3H). $^{13}$C NMR (DMSO-d$_6$, 100 MHz) δ 172.0, 169.8, 169.7, 169.5, 169.2, 162.3, 150.3, 143.4, 110.6, 100.8, 83.4, 76.2, 74.7, 73.1, 70.3, 69.7, 68.5, 67.5, 66.6, 61.3, 54.9, 54.8, 49.3, 44.6, 38.3, 38.0, 34.9, 33.9, 28.5, 27.3, 26.7, 25.7, 25.6, 22.6, 22.0, 21.6, 20.4, 20.3, 19.8, 17.8, −4.5, −5.1. Molecular weight for $C_{47}H_{79}N_5NaO_{17}Si_2$ (M+Na)$^+$ Calc. 1064.49. Found 1064.2.

Compound 456

Hydrogen fluoride-pyridine (~70% HF, 0.165 mL, 6.34 mmol) was diluted in pyridine (2 mL) under cooling. The resulting solution was added to a solution of compound 455 in CH$_2$Cl$_2$ at 0° C. and the mixture was stirred at 0° C. for 2 hours. The reaction solution was diluted in CH$_2$Cl$_2$ and washed with saturated NaHCO$_3$ aq. and dried over anhydrous Na$_2$SO$_4$. After evaporation, the crude was dried in vacuo to give a white foam. To a solution of this material in pyridine (15 mL), DMTrCl (596 mg, 1.76 mmol) was added. The reaction mixture was stirred at room temperature for 4 hours and then evaporated. The residue was extracted with CH$_2$Cl$_2$ and saturated NaHCO$_3$ aq. and dried over anhydrous Na$_2$SO$_4$. The crude was purified by silica gel column chromatography (10% MeOH in CH$_2$Cl$_2$, R$_f$=0.57) to give compound 456 (1.65 g, 1.37 mmol, 78%).

$^1$H NMR (DMSO-d$_6$, 400 MHz) δ 11.33 (s, 1H), 7.92 (s, 1H), 7.81 (d, J=9.6 Hz, 1H), 7.75, (s, 1H), 7.42-7.44 (m, 3H), 7.19-7.32 (m, 7H), 6.87-6.90 (m, 4H), 5.21 (d, J=3.2 Hz, 1H), 4.96 (dd, J=11.4 Hz, 3.4 Hz, 1H), 4.63 (d, J=6.4 Hz, 1H), 4.53 (d, J=2.4 Hz, 1H), 4.48 (d, J=8.4 Hz, 1H), 4.02-4.07 (m, 4H), 3.81-3.91 (m, 3H), 3.73 (s, 6H), 3.68-3.70 (m, 2H), 3.53-3.63 (m, 1H), 3.23-3.40 (m, 2H), 3.02-3.14 (m, 5H), 2.32-2.35 (m, 2H), 2.10 (s, 3H), 2.00-2.04 (m, 2H), 1.99 (s, 3H), 1.89 (s, 3H), 1.76 (s, 3H), 1.44-1.47 (m, 4H), 0.87 (s, 9H), 0.064 (s, 3H), 0.041 (s, 3H). Molecular weight for $C_{60}H_{81}N_5NaO_{19}Si$ (M+Na)$^+$ Calc. 1226.52. Found 1226.4.

Compound 457

To a solution of compound 456 (1.86 g, 1.54 mmol) in CH$_2$Cl$_2$ (20 mL), 2-cyanoethyl N,N,N',N'-tetraisopropylphosphordiamidite (1.47 mL, 4.63 mmol) and 4,5-dicyanoimidazole (182 mg, 1.54 mmol) were added at 0° C. The reaction mixture was stirred at room temperature for 20 hours under argon atmosphere. The reaction mixture was diluted with CH$_2$Cl$_2$ (300 mL) and washed with saturated NaHCO$_3$ (100 mL). The organic layer was separate and dried over anhydrous Na$_2$SO$_4$. The filtrate was concentrated and the resulting crude material was purified by silica gel column chromatography (EtOAc then 0-3% MeOH in CH$_2$Cl$_2$) to give 457 (1.80 g, 1.28 mmol, 83%, R$_f$=0.43 developed by 10% MeOH in CH$_2$Cl$_2$).

$^1$H NMR (400 MHz, DMSO) δ 11.34 (s, 0.5H), 11.33 (s, 0.5H), 7.91 (s, 1H), 7.81 (d, J=9.2, 1H), 7.75 (s, 1H), 7.56 (s, 0.5H), 7.52 (s, 0.5H), 7.43 (t, J=8.2, 2H), 7.19-7.32 (m, 7H), 6.85-6.90 (m, 4H), 5.21 (s, 0.5H), 5.21 (s, 0.5H), 4.96 (dd, J=11.2, 3.4, 1H), 4.47-4.51 (m, 2H), 4.36-4.41 (m, 1H), 4.02-4.07 (m, 5H), 3.83-3.90 (m, 1H), 3.73 (s, 3H), 3.72 (s, 3H), 3.69-3.71 (m, 3H), 3.31-3.60 (m, xx H), 3.04-3.26 (m, 6H), 2.69-2.73 (m, 1H), 2.35 (t, J=6.3, 2H), 2.10 (s, 3H), 2.03 (m, 2H), 1.99 (s, 3H), 1.89 (s, 3H), 1.77 (s, 3H), 1.45-1.48 (m, 4H), 0.91-1.08 (m, 12H), 0.85 (s, 9H), 0.063 (s, 1.5H), 0.046 (s, 1.5H), 0.035 (3H). $^{31}$P NMR (DMSO-d$_6$, 162 MHz) δ 147.92, 147.70. Molecular weight for $C_{69}H_{98}N_7NaO_{20}PSi$ (M+Na)$^+$ Calc. 1426.63. Found 1426.5.

Compounds from Scheme 5:

Compound 458:

To a solution of 452 (21.5 g, 65.1 mmol) in pyridine (400 mL), DMAP (1.59 g, 13.0 mmol) and DMTrCl (22.1 g, 65.1 mmol) were added. The reaction mixture was stirred at room temperature for 6 hours and then evaporated. The residue was extracted with EtOAc and saturated NaHCO$_3$ aq., dried over anhydrous Na$_2$SO$_4$, and purified by silica gel column chromatography (5% MeOH in CH$_2$Cl$_2$, R$_f$=0.30) to give 458 (36.2 g, 57.2 mmol, 88%).

$^1$H NMR (DMSO-d$_6$, 400 MHz) δ 11.37 (s, 1H), 7.48 (s, 1H), 7.36 (d, J=8.0 Hz, 2H), 7.27-7.32 (m, 6H), 7.20-7.23 (m, 1H), 6.87-6.90 (m, 4H), 5.06 (d, J=4.8 Hz, 1H), 4.80 (d, J=6.4 Hz, 1H), 4.54 (d, J=2.8 Hz, 1H), 3.84-3.93 (m, 1H), 3.73 (s, 6H), 3.56-3.69 (m, 2H), 3.53 (s, 3H), 3.15-3.17 (m, 2H), 2.58 (t, J=6.6 Hz, 2H). $^{13}$C NMR (MeOH-d$_4$, 100 MHz) δ 172.7, 165.5, 160.2, 152.7, 146.4, 144.5, 137.4, 137.3, 131.5, 131.4, 129.6, 128.9, 128.0, 114.2, 114.0, 87.5, 83.0, 81.1, 76.2, 72.4, 64.7, 55.8, 52.4, 46.2, 33.5. Molecular weight for $C_{34}H_{36}N_2NaO_{10}$ (M+Na)$^+$ Calc. 655.23. Found 655.2.

Compound 459:

Compound 458 (13.9 g, 22.0 mmol) was treated with ethylenediamine (75 mL) at room temperature for 18 hours. Ethylenediamine was removed by evaporation and co-evaporated with toluene. The residue was extracted with CH$_2$Cl$_2$/MeOH (180 mL/20 mL) and H$_2$O (50 mL) and the organic layer was dried over anhydrous Na$_2$SO$_4$, and then concentrated. The crude was crystallized with Hexane and CH$_2$Cl$_2$ to give 459 as a pale yellow solid (11.7 g, 17.7 mmol, 80%).

$^1$H NMR (MeOD-d$_4$, 400 MHz) δ 7.57 (s, 1H), 7.21-7.48 (m, 9H), 6.86-6.88 (m, 4H), 4.71 (d, J=3.2 Hz, 1H), 4.02-4.17 (m, 3H), 3.79-3.82 (m, 1H), 3.78 (s, 6H), 3.31-3.36 (m, 3H), 3.15 (t, J=6.2 Hz, 2H), 2.63 (t, J=6.0 Hz, 2H), 2.41 (t, J=6.2 Hz, 2H). Molecular weight for $C_{35}H_{40}N_4NaO_9$ (M+H)$^+$ Calc. 683.27. Found 683.2.

Compound 460:

To a solution of GalNAc acid (5.60 g, 12.5 mmol) in DMF (50 mL), HBTU (4.70 g, 12.4 mmol) and iPr$_2$NEt (10.3 mL, 59.3 mmol) were added. After 10 min, compound 459 in DMF (50 mL) was added to the solution and stirred overnight. The reaction mixture was extracted with EtOAc and H$_2$O and dried over anhydrous Na$_2$SO$_4$. After evaporation, the crude was purified by silica gel column chromatography (10% MeOH in CH$_2$Cl$_2$, R$_f$=0.50) to give compound 460 (6.85 g, 6.28 mmol, 59%).

$^1$H NMR (DMSO-d$_6$, 400 MHz) δ 11.33 (s, 1H), 7.93 (s, 1H), 7.81 (d, J=9.2 Hz, 1H), 7.75, (s, 1H), 7.41-7.44 (m, 3H), 7.27-7.31 (m, 6H), 7.18-7.22 (m, 1H), 6.87-6.89 (m, 4H), 5.21 (d, J=3.2 Hz, 1H), 5.03 (d, J=4.8 Hz, 1H), 4.96 (dd, J=11.2 Hz, 3.6 Hz, 1H), 4.78 (d, J=6.4 Hz, 1H), 4.51 (d, J=2.8 Hz, 1H), 4.48 (d, J=8.4 Hz, 1H), 4.02 (m, 3H), 3.82-3.92 (m,

4H), 3.73 (s, 6H), 3.54-3.70 (m, 3H), 3.36-3.42 (m, 1H), 3.02-3.21 (m, 6H), 2.35 (t, J=6.6 Hz, 2H), 2.09 (s, 3H), 2.02 (t, J=7.0 Hz, 2H), 1.99 (s, 3H), 1.88 (s, 3H), 1.76 (s, 3H), 1.43-1.49 (m, 4H). $^{13}$C NMR (DMSO-$d_6$, 100 MHz) δ 172.0, 169.9, 169.8, 169.5, 169.4, 169.2, 162.6, 157.9, 150.3, 144.9, 143.2, 135.7, 135.6, 129.7, 127.7, 126.5, 113.0, 111.3, 100.9, 85.2, 80.7, 79.8, 73.5, 70.8, 70.4, 69.7, 68.5, 66.6, 64.1, 61.3, 54.9, 54.8, 49.3, 48.5, 44.8, 38.3, 38.1, 34.9, 33.9, 28.5, 22.7, 21.6, 20.4, 20.3. Molecular weight for $C_{54}H_{67}N_5NaO_{19}$ (M+Na)$^+$ Calc. 1112.43. Found 1112.2.

Compound 461:

To a solution of compound 460 (1.55 g, 1.42 mmol) in pyridine (10 mL), TBDMSCl (214 mg, 1.42 mmol) and imidazole (290 mg, 4.26 mmol) were added. The reaction mixture was stirred overnight. After evaporation, the residue was extracted with $CH_2Cl_2$ and saturated $NaHCO_3$ aq. and dried over anhydrous $Na_2SO_4$. The crude material was purified by silica gel column chromatography (5% MeOH in $CH_2Cl_2$, $R_f$=0.15) to give compound 461 (550 mg, 0.457 mmol, 32%) and its 2'-O-TBDMS isomer 456 (390 mg, 0.324 mmol, 23%).

$^1$H NMR (DMSO-$d_6$, 400 MHz) δ 11.32 (s, 1H), 7.94 (s, 1H), 7.82 (d, J=9.2 Hz, 1H), 7.75, (s, 1H), 7.54 (s, 1H), 7.40-7.41 (m, 2H), 7.21-7.32 (m, 7H), 6.87-6.89 (m, 4H), 5.21 (d, J=3.2 Hz, 1H), 4.96 (dd, J=11.2 Hz, 3.6 Hz, 1H), 4.73 (d, J=4.8 Hz, 1H), 4.47-4.49 (m, 2H), 3.95-4.02 (m, 5H), 3.83-3.88 (m, 2H), 3.72 (s, 6H), 3.68-3.71 (m, 3H), 3.38-3.41 (m, 1H), 3.03-3.19 (m, 6H), 2.39 (t, J=6.6 Hz, 2H), 2.10 (s, 3H), 2.02 (t, J=7.0 Hz, 2H), 1.99 (s, 3H), 1.89 (s, 3H), 1.77 (s, 3H), 1.45-1.50 (m, 4H), 0.74 (s, 9H), −0.034, (s, 3H), −0.11 (s, 3H).

Molecular weight for $C_{60}H_{81}N_5NaO_{19}Si$ (M+Na)$^+$ Calc. 1226.52. Found 1227.4.

Compound 462:

To a solution of compound 461 (2.28 g, 1.89 mmol) in $CH_2Cl_2$ (60 mL), DMAP (693 mg, 5.67 mmol) and succinic anhydride (378 mg, 3.78 mmol) were added. The reaction mixture was stirred overnight at room temperature. Silica gel column chromatography (10% MeOH/10% $Et_3N$ in $CH_2Cl_2$, $R_f$=0.44) of the crude mixture without aqueous work-up gave the compound 462 as the corresponding triethylammonium salt (2.50 g, 1.78 mmol, 94%).

$^1$H NMR (DMSO-$d_6$, 400 MHz) δ 8.42 (s, 1H), 8.18 (s, 1H), 8.05 (d, J=9.2 Hz, 1H), 7.71 (s, 1H), 7.48-7.50 (m, 2H), 7.29-7.40 (m, 7H), 6.95-6.97 (m, 4H), 5.28-5.30 (m, 2H), 5.07 (dd, J=11.2 Hz, 3.6 Hz, 1H), 4.70 (d, J=4.0 Hz, 1H), 4.60 (d, J=8.4 Hz, 1H), 4.37 (t, J=5.8 Hz, 1H), 4.09-4.13 (m, 3H), 3.91-3.97 (m, 2H), 3.81 (s, 6H), 3.78-3.85 (m, 3H), 3.42-3.49 (m, 2H), 3.27-3.30 (m, 1H), 3.10-3.16 (m, 5H), 2.43-2.53 (m, 5H), 2.18 (s, 3H), 2.12 (t, J=7.2 Hz, 2H), 2.07 (s, 3H), 1.97 (s, 3H), 1.85 (s, 3H), 1.52-1.57 (m, 4H), 0.79 (s, 9H), 0.00 (s, 3H), −0.075 (s, 3H). $^{13}$C NMR (DMSO-$d_6$, 100 MHz) δ 173.8, 172.2, 172.1, 171.5, 169.9, 169.6, 169.5, 169.3, 162.5, 158.1, 150.4, 144.7, 144.6, 135.5, 135.4, 129.7, 127.7, 126.6, 113.1, 109.5, 100.9, 85.6, 81.6, 77.5, 74.2, 71.0, 70.5, 69.8, 68.5, 66.7, 63.6, 61.4, 52.0, 49.3, 38.4, 38.2, 34.9, 34.0, 30.0, 29.5, 28.5, 25.8, 25.5, 25.4, 22.7, 21.6, 21.4, 20.5, 20.4, 17.5, 14.7, 7.1, −5.1, −5.4.

Molecular weight for $C_{64}H_{84}N_5O_{22}Si$ (M−H)$^−$ Calc. 1302.54. Found 1302.4.

Compound 463:

To a solution of compound 462 (98 mg, 0.07 mmol) in DMF (10 mL), HBTU (30 mg, 0.077 mmol), iPr$_2$NEt (0.061 mL, 0.35 mmol), and Aminomethyl Polystyrene Support (ARTVISION, considered as 70 μmmol/g, 1.10 g, 0.077 mmol) were successively added. The mixture was shaken for 24 hours, then filtered, washed with $CH_2Cl_2$, and dried in vacuo. The residual amino groups were capped by shaking for 1 hour with pyridine (15 mL), acetic anhydride (5 mL), and triethylamine (1 mL). After filtering, washing with $CH_2Cl_2$ (100 mL), then 50% MeOH/$CH_2Cl_2$ (100 mL), and drying in vacuo gave compound 463 (1.12 g).

Loading: 47 μmol/g.

Compounds from Scheme 6:

Synthesis of Compound 203B

A solution of compound 202 (5 mmol, this is prepared as described in the literature, J. shi, J. Du, T. Ma. K. W Pankiewicz, S. E. Patterson, P. M. Tharnish, T. M. McBrayer, L. J. Stuyver, M. J. Otto, C. K. Chu, R. F. Schinazi, K. a. Watanabe, Bioorg. Med. Chem., 2005, 13, 1641-1652) in DMF (30 mL) is degassed and purged with argon. To this solution acrylonitrile (20 mmol), triethyl amine (10 mmol) bis(triphenylphosphine)palladium chloride (0.5 mmol) and copper iodide (1 mmol) are added and the mixture is heated at 80 C for 18 h. The solvent is evaporated and the product is purified by silica gel column chromatography to give pure 203B.

Synthesis of Compound 205.

A solution of 203B (3 mmol) in water (150 mL) is irradiated at 300 nm using a high pressure mercury lamp for 30 min Water is evaporated to give compound 205.

Synthesis of Compound 208.

To a solution of compound 205 (3 mmol) in anhydrous pyridine (20 mL) is added DMTr-Cl (10 mmol) and the reaction mixture is stirred at room temperature for 3 h. The reaction mixture is diluted with dichloromethane and washed with saturated sodium bicarbonate solution. Organic layer is dried over sodium sulfate and evaporated and the residue is purified by silica gel column chromatography to give pure 208.

Synthesis of Compound 211.

Reaction of 208 (3 mmol) with 2-cyanoethyl-N,N-diisopropylchloro phosphoramidite (3.6 mmol) in dichloromethane (15 mL) in the presence of Hunig's base (12 mmol) for 30 min gives the phosphoramidite 211 which can be purified by short silica gel column chromatography to obtain the pure product.

Synthesis of Compound 204

To a solution of compound 205 (3 mmol) in DMF (20 mL) is added Iodine monochloride (6 mmol) and the mixture is heated at 90 C for 24 h. The solvent is evaporated and the residue is purified by silica gel column chromatography to give compound 204.

Synthesis of Compound 207.

In a similar manner as described for compound 203, reaction of 204 with methyl acrylate in anhydrous DMF in the presence of palladium catalyst and copper iodide gives 207.

Synthesis of Compound 210.

As described for the synthesis of 206, irradiation of 207 in water at 300 nm for 30 min gives compound 210.

Compounds from Scheme 7:

Synthesis of Compound 217

To a solution of compound 215 (5 mmol) in dry DMF (50 mL) is added iodine monochloride (10 mmol) and the mixture is heated at 70 C for 24 h. The solvent is evaporated and the residue is purified by silica gel column chromatography to give compound 216.

To a degassed solution of 216 in dry DMF (25 mL) is added triethyl amine (2 mL) allyl alcohol (20 mmol), bis(triphenylphosphine)palladium chloride (0.5 mmol) and copper iodide (1 mmol). The reaction flask is placed in an oil bath at 90 C for 18 h. The solvent was evaporated and the residue is purified by silica gel column chromatography to give 217.

Synthesis of Compound 218.

To a solution of compound 217 (3 mmol) in dichloromethane (30 mL) is added Des s-Martin periodinane (3 mmol). After 2 h at ambient temperature the mixture was diluted with dichloromethane and washed with saturated sodium bicarbonate solution. Organic layer was dried over sodium sulfate, evaporated and the residue is purified by silica gel column chromatography to give compound 218.

Synthesis Compound 219.

A solution of compound 218 (2 mmol) in dry acetonitrile (20 mL) is heated under reflux for 2 h. The solvent is evaporated under reduced pressure and the product is purified by silica gel column chromatography to give 219.

Synthesis of Compound 221.

A solution of compound 219 (2 mmol) in ammonium hydroxide (20 mL) is stirred at room temperature for 4 h. Ammonium hydroxide is evaporated to dryness. The residue is dried by co-evaporation with dry pyridine then redissolved in pyridine (20 mL) to which DMTr-Cl (2.6 mmol) is added and stirred at room temperature for 3 h. The reaction mixture is diluted with dichloromethane and washed with water. Organic layer is dried over sodium sulfate and evaporated. The residue is purified by silica gel column chromatography to give pure compound 221.

Synthesis of Compound 222.

In a similar manner as described for 211 phosphitylation of 221 gives phosphoramidite 222.

Compounds from Scheme 8-1:

Synthesis of Compound 225

2'-Fluoro-2'-deoxycytidine (223, R=F, 5 g) was suspended in anhydrous pyridine (175 mL) and the reaction flask was cooled in an ice bath. To this was added benzoyl chloride (12 mL) and the mixture was stirred at room temperature for 18 h. The reaction was quenched by the addition of water (15 ml). After 30 min the reaction mixture was diluted with dichloromethane (300 mL) and washed with saturated sodium bicarbonate solution (2×250 mL). Organic layer was dried (sodium sulfate) and evaporated. The residue was co-evaporated with toluene. The solid obtained was suspended in toluene and collected by filtration. The product was dried and used in the next reaction.

The benzoyl derivative 224 obtained as above was suspended in dichloromethane (200 mL). To this solution was added iodine monochloride (5.69 g, 35 mmol) and the mixture was heated under reflux for 12 h. The solvent was evaporated under reduced pressure and the product was purified using silica gel column chromatography.

Synthesis of Compound 227A.

To a solution of 225 (10 mmol) in dry DMF (50 mL) is added 226 (12 mmol, this is prepared as described in the literature, F. Wojciechowski and R. H. E. Hudson, J. Am. Chem. Soc., 2008, 130, 12574) and the solution is degassed and purged with argon. To this solution, triethylamine (20 mmol) bis(triphenylphosphine)palladium chloride (1 mmol), copper iodide (2 mmol) are added and the mixture is heated at 90 C for 24 h. Evaporation of the solvent and purification by silica gel column chromatography gives pure 227A.

Synthesis of Compound 229A.

Compound 227A (5 mmol) is treated with trifluoroacetic acid (25 ml) at room temperature for 3 h. Evaporation of trifluoroacetic acid gives compound 228A. Debenzolyation of compound 228A is accomplished by treating with ammonium hydroxide (10 mL) at room temperature for 6 h. Evaporation of ammonium hydroxide gives compound 229A.

Synthesis of Compound 231A.

The protection of amino functionality of compound 229A is accomplished by treating 229A (5 mmol) with trifluoroacetic anhydride (3 ml) in anhydrous pyridine (50 mL) at 0-5 C for 3 h. The reaction is quenched by the addition of methanol (0.5 mL) and after 15 min the reaction mixture is evaporated to dryness to give the amine protected compound 230. This on reaction with DMTr-Cl (1.3 eq) in anhydrous pyridine (50 mL) for 3 h followed workup and silica gel column chromatography gives pure 231A.

Synthesis of Compound 232 A.

Reaction of 231A (3 mmol) with 2-cyanoethyl-N,N-diisopropylchloro phosphoramidite (3.6 mmol) in dichloromethane (15 mL) in the presence of Hunig's base (12 mmol) for 30 min gives the phosphoramidite 232A which can be purified by short silica gel column chromatography to obtain the pure product.

Compounds from Scheme 8-2:

Synthesis of Compound 225A: To a suspension of 223A (10 g) in dry methanol (20 ml) was added ICl (10 g) and the mixture was heated under reflux for 20 h. The solvent was evaporated and the crude was purified by silica gel column chromatography using a gradient 0-25% methanol in dichloromethane to give 11.2 g of 224'A. To a cold solution of 224'A (1 g, 2.69 mmol) in dry pyridine (20 ml) was added benzoyl chloride (1.26 ml, 10.8 mmol) and the mixture was stirred at room temperature overnight. Reaction was quenched by the addition of water. The mixture was diluted with dichloromethane and washed with sat. sodium bicarbonate solution. Organic layer was evaporated and coevaporated with toluene. The residue was purified by silica gel column chromatography using a gradient 0-5% methanol in dichloromethane to give 1.6 g of 225A.

Synthesis of Compound 227A: A solution of 225A (4.2 g, 6.14 mmol) and 226 (2.3 g, 8.8 mmol) in anhydrous DMF (60 ml) and triethylamine (30 ml) was degassed by bubbling argon. To this solution Dichloro bis(triphenylphosphine)palladium (0.42 g) and copper iodide (0.23 g) were added and the mixture was heated at 48° C. for 18 h. The solvent was evaporated and the residue was dissolved in methanol (300 ml). The reaction mixture was heated under reflux for 18 h. The solvent was evaporated and the residue was purified by silica gel column chromatography. The product was eluted using a gradient of 0-5% methanol in dichloromethane. Evaporation of the appropriate fractions containing the product gave 3.8 g of 227A.

Synthesis of Compound 228'A: To a cold (ice bath) solution of 227A (3.8 g) in a mixture of pyridine (60 ml) and methanol (60 ml) was added 1 N NaOH (11 ml). After stirring the mixture at 0-5° C. for 1 h, the reaction was quenched by the addition of dilute HCl (1N, 11 ml). Methanol was evaporated and the solution was diluted with dichloromethane (250 ml) and washed with water (50 ml). Organic layer was dried over sodium sulfate and evaporated. The residue was co-evaporated with toluene and purified by silica gel column chromatography to give 1.8 g of 228'A. $^1$H NMR (400 MHz, DMSO) δ 11.47 (s, 1H), 8.71 (s, 1H), 7.78-7.66 (m, 1H), 7.38-7.25 (m, 1H), 7.11 (t, J=6.6, 2H), 7.00 (t, J=7.5, 1H), 6.76 (s, 1H), 6.04 (d, J=17.5, 1H), 5.57 (d, J=6.5, 1H), 5.29 (t, J=5.0, 1H), 4.93 (dd, J=52.9, 4.0, 1H), 4.22-4.05 (m, 3H), 3.97 (d, J=8.7, 1H), 3.94-3.82 (m, 1H), 3.75-3.62 (m, 1H), 3.38 (dd, J=11.1, 5.5, 2H), 1.34 (s, 9H). $^{19}$F NMR (376 MHz, DMSO) δ −203.50 (m). MS: Calcd: 505 Found: 504 (M−1)−.

Synthesis of Compound 229'A: A solution of compound 228'A (0.8 g) in 50% TFA-dichloromethane (20 ml) was stirred at 0° C. for 2 h. After this time the reaction mixture was evaporated. The residue was co-evaporated with toluene (25 ml) followed by anhydrous pyridine (20 ml). This was dissolved in dry pyridine (15 ml), the solution was cooled in an ice bath and trifluoroacetic anhydride (2 ml) was added. The reaction mixture was stirred at 0-5° C. for 2 h. Reaction was quenched by the addition of methanol, diluted with dichloromethane (150 ml) and washed with water (50 ml). Organic layer was dried over sodium sulfate and evaporated. The residue was co-evaporated with toluene (20 ml) and purified by silica gel column chromatography. The product was eluted using a gradient of 0-10% methanol in dichloromethane. Appropriate fractions containing the product were evaporated to give 0.4 g of pure 229'A.

Synthesis of Compound 230'A: To a solution of 229'A (0.4 g) in anhydrous pyridine was added 4,4'-DMT-Cl (0.4 g) and the mixture was stirred at room temperature for 5 h. The reaction mixture was diluted with dichloromethane (100 ml) and washed with water (50 ml). Organic layer was evaporated and the residue was co-evaporated with toluene. The product was purified using silica gel column chromatography using a gradient of 0-5% methanol in dichloromethane to give 0.36 g of $^1$H NMR (400 MHz, DMSO) δ 11.39 (s, 1H), 9.57 (t, J=5.3, 1H), 8.54 (s, 1H), 7.64-7.54 (m, 1H), 7.43 (d, J=7.5, 3H), 7.36-7.26 (m, 9H), 7.21 (t, J=7.2, 1H), 7.13 (d, J=8.3, 1H), 7.02 (t, J=7.6, 1H), 6.86 (dd, J=8.9, 7.4, 5H), 6.02 (d, J=18.6, 1H), 5.77-5.68 (m, 1H), 5.01 (dd, J=52.9, 3.9, 1H), 4.55-4.37 (m, 1H), 4.14 (dd, J=13.3, 7.4, 4H), 4.00 (q, J=7.1, 1H), 3.70-3.60 (m, 8H), 3.57-3.42 (m, 4H), 3.34 (d, J=11.1, 2H). $^{19}$F NMR (376 MHz, DMSO) δ −77.22 (s), −202.65 (m).

Synthesis of Compound 230'B (2'OMe PC-GClamp): In a similar manner as described for 230'A, compound 230'B was synthesized starting from Tri-benzoyl-2'-OMe-5-iodocytidine and 226. $^1$H NMR (400 MHz, DMSO) δ 11.35 (s, 1H), 9.56 (t, J=5.4, 1H), 8.57 (s, 1H), 7.64-7.54 (m, 1H), 7.43 (d, J=7.5, 2H), 7.38-7.26 (m, 8H), 7.21 (t, J=7.2, 1H), 7.13 (d, J=8.3, 1H), 7.02 (t, J=7.5, 1H), 6.86 (t, J=8.2, 4H), 5.94 (s, 1H), 5.87 (s, 1H), 5.22 (d, J=7.5, 1H), 4.32 (td, J=8.1, 5.1, 1H), 4.14 (t, J=5.5, 2H), 4.06 (d, J=7.5, 1H), 3.73 (d, J=4.8, 1H), 3.66 (s, 3H), 3.63 (s, 3H), 3.53 (s, 3H). $^{19}$F NMR (376 MHz, DMSO) δ −77.15 (s).

Synthesis of Compound 231: To a solution of 230' (1 mmol) in dichloromethane (10 ml) is added 2-cyanoethyl-tetraisopropylphosphoramidite (1.3 mmol) and dicyanoimidazole (0.9 mmol). The mixture is stirred at room temperature for 6 h, diluted with dichloromethane and washed with sodium bicarbonate solution. Organic layer is dried over sodium sulfate and evaporated. The residue is subjected to column chromatography to give compound 231.

Compounds from Scheme 10:

3-(5'-O-Dimethoxytrityl-β-D-ribofuranosyl)-1,3-diaza-2-oxophenoxazine (241) (Scheme 10): Phenoxazine nucleoside 240 (4.75 g, 14.25 mmol) (K-Y. Lin and M. Matteucci, J. Am. Chem. Soc. 1998, 120, 8531; S. C. Holmes, A. A. Arzumanov and M. J. Gait, Nucleic Acids Res., 2003, 31, 2759) was dried by coevaporation with dry pyridine (40 ml). Then it was suspended in dry pyridine (35 ml) and DMT-Cl (5.34 g, 15.76 mmol) was added. After 3 h the reaction mixture was diluted with dichloromethane (200 ml) and washed with water. Organic layer was dried over sodium sulfate and evaporated. The residue was coevaporated with toluene and purified by silica gel column chromatography. Product was eluted using a gradient of 0-5% methanol in dichloromethane. The appropriate fractions containing the pure product were pooled and evaporated to give 6.38 g (70.4%) of compound 241. $^1$H NMR (400 MHz, DMSO) δ 10.63 (s, 1H), 7.52-7.14 (m, 11H), 7.02-6.73 (m, 7H), 6.56-6.38 (m, 1H), 5.71 (d, J=4, 1H), 5.43 (d, J=8, 1H), 5.10 (d, J=8, 1H), 4.18-4.01 (m, 2H), 4.03-3.90 (m, 1H), 3.69, 3.70 (2 s, 6H), 3.32-3.28 (m, 1H), 3.23-3.10 (m, 1H).

Silylation of 3-(5'-O-Dimethoxytrityl-β-D-ribofuranosyl)-1,3-diaza-2-oxophenoxazine (242A, 242B)

To a solution of 241 (5.88 g, 9.27 mmol) in dry DMF (30 ml) were added imidazole (1.63 g, 24 mmol) followed by TBDMS-Cl (1.81 g, 12 mmol). After stirring the mixture at room temperature for 18 h, it was diluted with dichloromethane (150 ml) and washed with water (2×150 ml). Organic layer was dried over sodium sulfate and evaporated. The residue containing 2'-silylated and 3'-silylated products was chromatographed on a silica gel column. 2'-Isomer was eluted using a gradient of 10-25% ethyl acetate in dichloromethane. Finally 3'-isomer was eluted using 25-50% ethyl acetate in dichloromethane. The appropriate fractions containing pure products were collected and evaporated to give 2.5 g (36%) of 2'-isomer 242A and 2.1 g (30.2%) of 3'-isomer 242B. $^1$H NMR (400 MHz, DMSO) δ 10.65 (s, 1H), 7.94 (s, 1H), 7.59-7.14 (m, 10H), 7.01-6.68 (m, 6H), 6.44 (ddd, J=9.3, 7.9, 4.0, 1H), 5.69 (d, J=4, 1H), 5.07 (d, J=6.1, 1H), 4.29-4.15 (m, 1H), 4.11 (dd, J=11.1, 5.9, 1H), 4.05-3.94 (m, 1H), 3.70, 3.69 (2 s, 6H), 3.36 (dt, J=8.0, 4.1, 1H), 3.24-3.11 (m, 1H), 0.87 (s, 9H), 0.08, 0.09 2 s, 6H).

3-(5'-O-Dimethoxytrityl-2'-O-methyl-β-D-ribofuranosyl)-1,3-diaza-2-oxophenoxazine 3'-O-(2-cyanoethyl) N,N-diisopropylphosphoramidite (243): To a solution of DMT Phenoxazine nucleoside (1.12 g, 1.5 mmol) in dry dichloromethane (5 ml) were added 4,5-dicyanoimidazole (159 mg, 1.35 mmol) followed by 2-cyanoethyl-N,N,N',N''-tetraisopropylphosphorodiamidite (0.52 ml, 1.65 mmol) under an argon atmosphere. After stirring for 4 h at room temperature the reaction mixture was diluted with ethyl acetate (50 ml) and washed with sodium acetate solution (0.5 M, 200 ml) followed by sat. sodium chloride solution (125 ml). Organic layer was dried over sodium sulfate and evaporated. The residue was purified by short silica gel column chromatography and the product was eluted using a mixture of dichloromethane and ethyl acetate containing triethylamine. The appropriate fractions containing the product were collected and evaporated to give 1.25 g (88%) of pure 243. $^{31}$P NMR (162 MHz, CD$_3$CN) δ 149.20, 148.86.

Compounds from Scheme 11:

3-(5'-O-Dimethoxytrityl-β-D-ribofuranosyl)-9-(2-N-benzylcarbamyl-ethoxy)-1,3-diaza-2-oxophenoxazine (245) (Scheme 11): The sub (5 g, 9.5 mmol) was dried by coevaporation with dry pyridine (50 ml). Then it was dissolved in dry pyridine (35 ml) and DMT-Cl (3.8 g, 11.2 mmol) was added. After stirring at room temperature for 2.5 h, the reaction mixture was diluted with dichloromethane (150 ml) and washed with water (200 ml). Organic layer was dried over sodium sulfate and evaporated. The residue was coevaporated with toluene and purified by silica gel column chromatography. The product was eluted using a gradient of 0-5% methanol in dichloromethane. The fractions containing the pure product were pooled and evaporated to give 6.1 g (77.5%) of 245. $^1$H NMR (400 MHz, DMSO) δ 9.84 (s, 1H), 7.76 (s, 1H), 7.56-7.14 (m, 16H), 7.00-6.82 (m, 4H), 6.83 (s, 1H), 6.59 (d, J=8.2, 1H), 6.13 (dd, J=8.2, 0.8, 1H), 5.72 (d, J=3.5, 1H), 5.44 (d, J=5.2, 1H), 5.10 (d, J=6.2, 1H), 5.04 (s, 2H), 4.20-4.01 (m, 2H), 4.03-3.87 (m, 2H), 3.69, 3.70 (2 s, 6H), 3.42 (d, J=4.9, 2H), 3.35-3.29 (m, 1H), 3.24-3.11 (m, 1H).

Silylation of 3-(5'-O-Dimethoxytrityl-β-D-ribofuranosyl)-9-(2-N-benzylcarbamyl-ethoxy)-1,3-diaza-2-oxophenoxazine (246A, 246B). To a solution of 245 (5.85 g, 7.05 mmol) in dry DMF (30 ml) were added imidazole (1.19 g, 17.5 mmol) followed by TBDMS-Cl (1.13 g, 7.5 mmol). After stirring for 18 h, the reaction mixture was diluted with dichloromethane (150 ml) and washed with water (250 ml). Organic layer was dried over sodium sulfate and evaporated to give a foam containing 2'-silyl derivative, 3'-silyl derivative and bis silyl derivative. The mixture was chromatographed on a silica gel column and the pure products were eluted using a gradient of 5-60% ethyl acetate in dichloromethane. The pure fractions containing the product were evaporated to give 2.95 g (44.43%) of 2'-silyl derivate 246A and 1.86 g (28%) of 3'-silyl derivative 246B. $^1$H NMR $^1$H NMR (400 MHz, DMSO) δ 9.77 (s, 1H), 7.80 (s, 1H), 7.55-7.07 (m, 16H), 6.81 (dd, J=8.9, 5.8, 4H), 6.70 (t, J=8.3, 1H), 6.51 (d, J=8.1, 1H), 6.01 (d, J=7.5, 1H), 5.63 (d, J=3.6, 1H), 5.03-4.94 (m, 3H), 4.21-3.99 (m, 2H), 3.99-3.89 (m, 2H), 3.85 (d, J=4.6, 2H), 3.61, 3.63 (2 s, 6H), 3.47-3.22 (m, 2H), 3.09 (d, J=9.1, 1H), 2.80 (s, 1H), 2.65 (d, J=0.4, 1H), 0.78 (s, 9H), 0.00, 0.01 (2 s, 6H).

3-(5'-O-Dimethoxytrityl-2'-O-tert.butyldimethylsilyl-β-D-ribofuranosyl)-9-(2-N-phthalimido-ethoxy)-1,3-diaza-2-oxophenoxazine (247, 248):

To a solution of compound 246A (2.17 g) in dry methanol (60 ml) was added Pd/C (Degussa type, 240 mg, 10 wt % on carbon) and the mixture was stirred at room temperature under a positive pressure of hydrogen for 4 h. The reaction mixture was filtered and evaporated. The residue was dried in vaccuo for an hour and directly used in the next step.

To a solution of the compound obtained as above in dry THF (20 ml) were added N-carbethoxyphthalimide (0.52 g, 2.4 mmol) and 4-(dimethylamino)pyridine (0.293 g, 2.4 mmol). The mixture was stirred at room temperature overnight, diluted with dichloromethane (100 ml) and washed with water (50 ml). Organic layer was dried and evaporated. The residue containing 2' and 3' silyl isomers was chromatographed on a silica gel column and the pure isomers were eluted using a mixture of hexanes in ethyl acetate. The appropriate fractions containing the pure isomers were pooled and evaporated to give 1.1 g (51%) of 2'-isomer 247 and 0.6 g (27.8%) of 3'-isomer 248. $^1$H NMR (400 MHz, DMSO) δ 9.28 (brs, 1H), 7.92-7.69 (m, 4H), 7.44-7.29 (m, 3H), 7.31-7.19 (m, 7H), 7.13 (t, J=7.3, 1H), 6.89-6.77 (m, 4H), 6.68 (t, J=8.3, 1H), 6.55 (d, J=8.0, 1H), 5.99 (dd, J=8.2, 1.0, 1H), 5.61 (d, J=3.7, 1H), 4.97 (d, J=6.1, 1H), 4.18-3.83 (m, 7H), 3.61, 3.63 (2 s, 6H), 3.34-3.25 (m, 1H), 3.09 (d, J=9.0, 1H), 0.79 (m, 9H), 0.00, 0.01 (2 s, 6H).

3-(5'-O-Dimethoxytrityl-2'-O-tert.butyldimethylsilyl-β-D-ribofuranosyl)-9-(2-N-phthalimido-ethoxy)-1,3-diaza-2-oxophenoxazine 3'-O-(2-cyanoethyl) N,N,-diisopropylphosphoramidite (249):

To a solution of the nucleoside 247 (1 g, 1.06 mmol) in dry dichloromethane (10 ml) were added 3,4-dicyanoimidazole (0.112 g, 0.95 mmol) followed by 2-cyanoethyl-N,N,N',N'-tetraisopropylphosphorodiamidite (0.35 ml, 1.12 mmol) under an argon atmosphere. After stirring for 4 h an additional 0.12 ml of phosphitylating agent was added. Thirty minutes later the reaction mixture was diluted with ethyl acetate (75 ml) and washed with saturated sodium bicarbonate solution (150 ml). Organic layer was dried over sodium sulfate and evaporated. The residue was purified on a silica gel column. The product was eluted using a mixture of dichloromethane and ethyl acetate containing triethylamine. The fractions containing the pure product were pooled and evaporated to give 1 g (82.6%). $^{31}$P NMR (162 MHz, CD$_3$CN) δ 149.42, 148.77. Compounds in Scheme 12:

3',5'-O-(1,1,3,3-Tetraisopropyl-1,3-disiloxanediyl)-pseudouridine (251) (Scheme 12) Pseudouridine 250 (20 g, 82 mmol) was dried by coevaporation with dry pyridine (80 ml). The dried material was suspended in dry pyridine (150 ml) and the reaction flask was cooled in an ice bath. To this cold suspension 1,3-dichloro-1,1,3,3-tetraisopropyldisiloxane (30 g, 95 mmol) was added in about 5 min. The reaction flask was allowed to warm to room temperature slowly by leaving the flask in the ice bath. After stirring for 18 h the reaction mixture was diluted with dichloromethane (200 ml) and washed with 10% aqueous sodium bicarbonate solution (150 ml). Aq layer was extracted with dichloromethane (50 ml) and the combined organic layer was dried over sodium sulfate and evaporated. The residue was coevaporated with toluene and purified by silica gel column chromatography. The product was eluted using a gradient of 0-4% methanol in dichloromethane and the appropriate fractions containing the product were evaporated to give 39 g (97.8%) of a colorless foam.

2',4-Anhydro-3',5'-O-(1,1,3,3-tetraisopropyl-1,3-disiloxanediyl)-pseudouridine (253):The substrate 251 (38.29 g, 78.7 mmol) was dried by coevaporation with dry pyridine (80 ml). Then it was dissolved in dry pyridine (80 ml) and the reaction flask was cooled in an ice bath. To this cold solution, methanesulfonyl chloride (8 ml, mmol) was added in approximately 3 min. The resulting mixture was stirred for 18 h while allowing the reaction mixture to warm slowly to room temperature by leaving the reaction flask in the ice bath. The reaction was quenched by the addition of 3 ml of sat. sodium bicarbonate solution. After 30 min the reaction mixture was diluted with dichloromethane (200 ml) and washed with 10% sodium bicarbonate solution (150 ml). Organic layer was dried over sodium sulfate and evaporated. The residue was coevaporated with toluene and used in the next step without any further purification.

The product obtained as above was suspended in a mixture of n-propanol (300 ml) and N,N-diisopropylethyl amine (75 ml) and the mixture was heated at 120 C for 2 h. The clear solution obtained was allowed to cool to room temperature and kept at room temperature overnight. The crystallized product was collected by filtration after washing with a small amount of n-propanol it was dried at 40 C in vaccuo to give 32 g (86.8%) of pure 253. $^1$H NMR (400 MHz, DMSO) δ 7.98 (s, 1H), 5.36 (d, J=6.7, 1H), 5.27 (dd, J=6.7, 4.2, 1H), 4.25 (dd, J=8.8, 4.2, 1H), 3.88 (qd, J=13.0, 3.2, 2H), 3.70 (dt, J=8.8, 3.1, 1H), 1.18-0.86 (m, 28H). 2',4-Anhydropseudouridine (255): Silyl anhydro derivative 253 (20.5 g, 43.74 mmol) was suspended in methanol (250 ml) to which ammonium fluoride (6 g) was added and heated under reflux for 1 h. Solvent was evaporated and the product was purified by a short silica gel column chromatography. Product was eluted using a gradient of 0-20% methanol in dichloromethane. The fractions containing the product were collected and evaporated to give 7.23 g (73%) of 255. $^1$H NMR (400 MHz, DMSO) δ 11.30 (s, 1H), 7.91 (s, 1H), 5.66 (d, J=5.1, 1H), 5.29 (d, J=6.0, 1H), 5.04 (dd, J=6.0, 2.1, 1H), 4.70 (t, J=5.6, 1H), 4.06 (td, J=5.4, 2.1, 1H), 3.65 (dt, J=5.7, 4.6, 1H), 3.44-3.13 (m, 2H).

5'-O-Dimethoxytrityl-2'-fluoropseudouridine 3'-O-(2-cyanoethyl)N,N-diisopropylphosphoramidite (257). Compound 253 or 255 on treatment with HF/Pyridine in anhydrous dioxane at elevated temperature gives 2'-fluoropseudouridine 254 which can be converted to the corresponding 5'-dimethoxytrityl derivative 256, by treating with 1.25 equivalents 4,4'-dimethoxytrityl chloride in anhydrous pyridine. Compound 256 (1 mmol) on treatment with 2-cyanoethyl-N,N,N',N''-tetraisopropylphosphorodiamidite (1.2 mmol) in dichloromethane in the presence of 3,4-dicyanoimidazole (0.9 mmol), work up of the reaction followed by silica gel column chromatography gives the corresponding 3'-phposphoramidite 257. Alternatively this compound can also be prepared by treating with 2-cyanoethyl-N,N-diisopropylchloro phosphoramidite in dichloromethane in the presence of Hunig's base.

Compounds in Scheme 13:

5-Bromo-3',5'-diacetyl-2'-O-methyluridine (260) (Scheme 13). To a solution of 2'-O-methyluridine (25 g, 96.9 mmol) in dry pyridine (200 ml) was added acetic anhydride (50 ml, mmol) and the reaction mixture was stirred at room temperature for 18 h. The reaction was quenched by the addition of methanol (50 ml). After 30 min the solvent was evaporated. The residue was dissolved in dichloromethane (350 ml) and washed with saturated sodium bicarbonate solution (4×150 ml). Aqueous layer was extracted with dichloromethane (2×75 ml) and the combined organic layers was dried over sodium sulfate and evaporated. The residue was coevaporated with toluene and used directly in the next reaction without any further purification. To a solution of the compound obtained as above in dry pyridine (250 ml) was added N-bromosuccinimide (26.7 g, mmol) and mixture was stirred at room temperature for 20 h. The reaction mixture was diluted with dichloromethane (450 ml) and washed with saturated sodium bicarbonate solution (3×250 ml). Aqueous layer was extracted with dichloromethane (2×100 ml) and the combined organic layer was dried over sodium sulfate and evaporated. The residue was coevaporated with toluene and the product was purified by silica gel column chromatography. The product was eluted using a gradient of 0-2% methanol in dichloromethane. Appropriate fractions containing the pure product were pooled and evaporated to 39.5 g (96.9%) of 260. $^1$H NMR (400 MHz, DMSO) δ 11.95 (s, 1H), 8.11 (s, 1H), 5.78 (d, J=4.9, 1H), 5.17 (t, J=5.2, 1H), 4.36-4.15 (m, 4H), 3.30 (d, J=5.7, 4H), 2.08 (d, J=2.4, 6H).

5-Bromo-3',5'-diacetyl 2'-O-methyl-N$^4$-(2-hydroxyphenyl)cytidine (261): To a solution of 260 (13.3 g, 31.66 mmol) in dry dichloromethane (100 ml) and carbon tetrachloride (100 ml) was added triphenylphosphine (12.46 g, 47.5 mmol). The mixture was heated under reflux for 3 h. An additional 5.4 g of triphenylphosphine was added and the reaction continued overnight. The reaction mixture was allowed to cool to room temperature and diluted with 80 ml of dichloromethane. To this 2-aminophenol (8.73 g, 80 mmol) followed by DBU (11.96 ml, 80 mmol) were added and the mixture was stirred at room temperature overnight. The reaction mixture was diluted with dichloromethane (50 ml) and washed with 5% citric acid (450 ml) followed by water (100 ml). Organic layer was dried over sodium sulfate and evaporated. The residue was triturated with toluene followed by dichloromethane to give a solid which was collected by filtration. The solid was washed with a small amount of dichloromethane. The filtrate was directly loaded on a silica gel column and the product was eluted using a gradient of 02-% methanol in dichloromethane. The fractions containing the pure product were collected and evaporated to give a total yield of 11.5 g (71%) of 261. $^1$H NMR (400 MHz, DMSO) δ 10.20 (s, 1H), 8.45 (s, 1H), 8.16 (s, 1H), 8.08 (dd, J=8.0, 1.3, 1H), 7.20-6.71 (m, 3H), 5.85 (d, J=4.4, 1H), 5.15 (t, J=5.4, 1H), 4.38-4.13 (m, 4H), 3.32 (d, J=2.0, 6H), 2.09 (d, J=8.5, 6H).

3-(2'-O-Methyl-β-D-ribofuranosyl)-1,3-diaza-2-oxophenoxazine (262): To a suspension of 261 (3.5 g) in absolute ethanol (120 ml) was added cesium fluoride (10.2 g) and the mixture was heated under reflux for 24 h. The solvent was evaporated and the residue was purified by silica gel column chromatography. The product was eluted using a gradient of 0-10% methanol in dichloromethane in dichloromethane. The appropriate fractions containing the pure product were pooled and evaporated to give 1.2 g (47.2%) of 262. $^1$H NMR (400 MHz, DMSO) δ 10.35 (d, J=35.4, 1H), 9.97 (d, J=11.1, OH), 8.36 (d, J=7.5, OH), 7.46 (d, J=29.6, 1H), 6.68-6.45 (m, 4H), 5.55 (d, J=4.2, 1H), 4.98 (t, J=4.8, 1H), 4.82 (d, J=6.1, 1H), 3.83 (d, J=5.6, 1H), 3.60-3.52 (m, 1H), 3.50-3.38 (m, 2H), 3.32 (dd, J=4.5, 2.7, 1H), 3.07 (s, 6H).

3-(5'-O-Dimethoxytrityl-2'-O-methyl-β-D-ribofuranosyl)-1,3-diaza-2-oxophenoxazine (263): To a solution of the nucleoside (2.3 g) in dry pyridine (40 ml) was added DMT-Cl (2.56 g) and the mixture was stirred at room temperature for 3.5 h. The reaction mixture was diluted with dichloromethane (150 ml) and washed with water (100 ml). Organic layer was dried over sodium sulfate and evaporated. The residue was coevaporated with toluene and purified by silica gel column chromatography. The product was eluted using a gradient of 0-4% methanol in dichloromethane. Appropriate fractions containing the pure product were pooled and evaporated to give 3.05 g (71%) of 263. $^1$H NMR (400 MHz, DMSO) δ 10.65 (s, 1H), 7.60-7.18 (m, 10H), 7.03-6.75 (m, 6H), 6.47-6.43 (m, 1H), 5.85-5.67 (m, 1H), 5.18 (d, J=6.8, 1H), 4.22 (dd, J=12.0, 6.5, 1H), 3.96 (m, 1H), 3.77 (dd, J=4.7, 3.6, 1H), 3.70, 3.71 (2 s, 6H), 3.44 (s, 3H), 3.38-3.34 (m, 1H), 3.17 (d, J=8.9, 1H).

3-(5'-O-Dimethoxytrityl-2'-O-methyl-β-D-ribofuranosyl)-1,3-diaza-2-oxophenoxazine 3'-O-(2-cyanoethyl) N,N-diisopropylphosphoramidite (264): To a solution of 263 (1.2 g, 1.85 mmol) in dry dichloromethane (10 ml) were added dicyanoimidazole (207 mg, 1.75 mmol) followed by 2-cyanoethyl-N,N,N',N'-tetraisopropylphosphorodiamidite (0.72 ml, 2.3 mmol) under an argon atmosphere and the mixture was stirred at room temperature for 18 h. The reaction mixture was diluted with ethyl acetate (75 ml) and washed with saturated sodium bicarbonate (100 ml). Organic layer was dried over sodium sulfate and evaporated. The residue was purified by silica gel column chromatography and the product was eluted using a mixture of dichloromethane and ethyl acetate containing triethylamine. Appropriate fractions containing the product were pooled and evaporated. The solid obtained was dissolved in dichloromethane (5 ml) and the solution was added to rapidly stirred pentane (300 ml). The precipitated product was collected by filtration and dried to give 1.3 g (82.8%) of 264. $^{31}$P NMR (162 MHz, CD$_3$CN) δ 155.33, 154.90

Compounds in Scheme 14:

5-Bromo-3',5'-diacetyl-2'-fluoro-2'-deoxyuridine (267): To a suspension of 2'-fluoro-2'-deoxyuridine (24.6 g, 100 mmol) in dry pyridine (150 ml) was added acetic anhydride (37.78 ml, 400 mmol). After stirring the mixture at room temperature for 18 h, the reaction was quenched by the addition of methanol (20 ml). After 30 min the solvent was evaporated. To the residue dichloromethane (100 ml) was added and the colorless solid was collected by filtration. The solid product was washed with dichloromethane (150 ml) and dried to give 22 g of 266. The dichloromethane solution which contained some product was washed with sat. sodium bicarbonate solution (3×200 ml). Organic layer was dried over sodium sulfate and evaporated. The residue was coevaporated with toluene to give a colorless solid which was further dried to give a total of 32 g (97%) of 266.

The diacetyl derivative 266 obtained was suspended in dry pyridine (150 ml) to which N-bromosuccinimide (22 g, 123.6 mmol) was added and stirred at room temperature for 18 h. After evaporating the solvent the residue was dissolved in dichloromethane (350 ml) and washed with water (3×200 ml) followed by sat. sodium bicarbonate solution (150 ml). Organic layer was dried over sodium sulfate and evaporated. The residue was coevaporated with toluene and the crude product was purified by silica gel column chromatography using a gradient of 0-1.5% methanol in dichloromethane to give 33.3 g (84%) of 267.

5-Bromo-3',5'-diacetyl-N⁴-(2-hydroxyphenyl)-2'-fluoro-2'-deoxycytidine (269): To a suspension of triazole (50.34 g, 729 mmol) and phosphorus oxychloride (14.55 ml, 156 mmol) in dry acetonitrile (400 ml) was added triethylamine (97.2 ml, 697 mmol) slowly at 0 C (ice bath). After stirring for 20 min a solution of diacetyl-5-bromo-2'-fluoro-2'-deoxyuridine 267 (33 g, 80.65 mmol) in dry acetonitrile (150 ml) was added to the reaction flask. Ice bath was removed and the mixture was stirred at room temperature for 3 h. Excess triethylamine (70 ml) and water (30 ml) were added and stirred for 30 min. The solvent was evaporated to a residue and partitioned between dichloromethane and sodium bicarbonate solution. Aqueous layer was extracted with dichloromethane and the combined organic layer was dried over sodium sulfate. The solvent was evaporated to give a light yellow solid which was dried under high vacuum overnight to give the triazole derivative in quantitative yield and directly used in the next step without further purification.

To the triazole derivative 268 (22 g, 47.8 mmol) in dichloromethane (200 ml) was added aminophenol (13 g, 120 mmol) followed by Hunig's base (20.8 ml, 120 mmol). The reaction mixture was stirred at room temperature overnight, washed with 5% citric acid (4×350 ml). Aqueous layer was extracted with dichloromethane (100 ml) and the combined organic layer was dried over sodium sulfate and evaporated to give a foam. This was purified on a silica gel column using a gradient of 0-2% methanol in dichloromethane. The appropriate fractions containing the pure product were evaporated to give 20 g (83.6%) of 269. $^1$H NMR (400 MHz, DMSO) δ 10.21 (s, 1H), 8.45 (s, 1H), 8.22 (s, 1H), 8.05 (dd, J=8.0, 1.1, 1H), 7.01 (td, J=8.0, 1.5, 1H), 6.90 (dd, J=8.0, 1.2, 1H), 6.89-6.78 (m, 2H), 5.85 (dd, J=21.9, 1.1, 1H), 5.55-5.38 (m, 1H), 5.27 (s, 1H), 4.39-4.25 (m, 2H), 4.26-4.14 (m, 1H), 2.05, 2.08 (2 s, 6H).

3-(2'-Fluoro-2'-deoxy-β-D-ribofuranosyl)-1,3-diaza-2-oxophenoxazine (270): To a suspension of 3',5'-diacetyl-4 (hydroxyphenyl)-5-bromo-2'-fluoro-2'-deoxycytidine 269 (1.2 g, 2.4 mmol) in absolute alcohol (100 ml) was added triethylamine (20 ml) and the reaction flash was placed in an oil bath at 90 C for 18 h. The reaction mixture was allowed to cool to room temperature. To the cooled solution 100 ml of ammonium hydroxide was added and the mixture was stirred at room temperature for 3 h. The solvent was evaporated and the solid obtained was purified on a silica gel column using a gradient of 0-10% methanol in ethyl acetate. The appropriate fractions containing the pure product were evaporated to give 0.46 g (58%) of 270. $^1$H NMR (400 MHz, DMSO) δ 10.66 (s, 1H), 7.71 (s, 1H), 6.98-6.72 (m, 4H), 5.84 (dd, J=17.0, 1.2, 1H), 5.58 (d, J=6.3, 1H), 5.42-5.28 (m, 1H), 5.07-4.90 (m, 1H), 4.90 (s, 1H) 3.82 (dt, J=12.2, 11.5, 2H), 3.68-3.51 (m, 1H), 3.34 (s, 1H). $^{19}$F-NMR: −204.68

3-(5'-O-Dimethoxytrityl-2'-fluoro-2'-deoxy-β-D-ribofuranosyl)-1,3-diaza-2-oxophenoxazine (271): To a solution of 2'-fluorophenoxazine 270 (0.44 g, 1.3 mmol) in dry pyridine (20 ml) was added DMT-Cl (0.66 g, 1.95 mmol) and the reaction mixture was stirred at room temperature for 3 h. An additional 140 mg of DMT-Cl was added and after stirring for the 1.5 h, diluted with dichloromethane (100 ml) and washed with water (50 ml). Organic layer was dried over sodium sulfate and evaporated. The residue was purified by silica gel column chromatography using a gradient of 0-5% methanol in dichloromethane. The appropriate fractions containing the product was evaporated to give 0.55 g (66%) of 271. $^1$H NMR (400 MHz, DMSO) δ 10.66 (s, 1H), 7.49-7.16 (m, 10H), 6.84 (dddd, J=18.1, 9.2, 6.8, 3.1, 7H), 6.43 (dd, J=11.3, 10.1, 1H), 5.80 (d, J=18.9, 1H), 5.64 (d, J=6.9, 1H), 5.00 (dd, J=53.2, 4.3, 1H), 4.46-4.26 (m, 1H), 4.02 (dd, J=14.1, 7.0, 1H), 3.68, 3.70 (2 s, 6H), 3.41-3.20 (m, 2H).

3-(5'-O-Dimethoxytrityl-2'-fluoro-2'-deoxy-β-D-ribofuranosyl)-1,3-diaza-2-oxophenoxazine 3'-O-(2-cyanoethyl) N,N-diisopropylphosphoramidite (272): Compound 271 (1 mmol) on treatment with 2-cyanoethyl-N,N,N',N''-tetraisopropylphosphorodiamidite (1.2 mmol) in dichloromethane in the presence of 3,4-dicyanoimidazole (0.9 mmol), work up of the reaction followed by silica gel column chromatography gives the corresponding 3'-phposphoramidite 272. Alternatively this compound can also be prepared by treating with 2-cyanoethyl-N,N-diisopropylchloro phosphoramidite in dichloromethane in the presence of Hunig's base.

Compounds in Scheme 15:

5-Bromo-3',5'-diacetyl-N⁴-(2,6-dihydroxyphenyl)-2'-fluoro-2'-deoxycytidine (274) (Scheme 15): To a solution of triazolyl derivative 273 (9.2 g, 20 mmol) in dry dichloromethane (175 ml) was added amino resorcinol hydrochloride (4.5 g, 27.9 mmol) followed by Hunig's base (9 ml, 52 mmol). After stirring the mixture at room temperature for 18 h, diluted with dichloromethane (200 ml) and washed with 5% citric acid (2×250 ml). Organic layer was dried over sodium sulfate and evaporated. The crude product was purified by silica gel column chromatography using a gradient of 0-5% methanol in dichloromethane. The appropriate fractions containing the product were evaporated to give 6.88 g (66.7%) of 274.

5-Bromo-3',5'-diacetyl-N⁴-(2-(2-N-benzylcarbamyl-ethoxy)-6-hydroxyphenyl)-2'-fluoro-2'-deoxycytidine (275): To a solution of diacetyl-4-(dihydroxyphenyl)-5-bromo-2'-fluoro-2'-deoxycytidine (6.5 g, 12.6 mmol) in dry dichloromethane (175 ml) was added triphenylphosphine (4.98 g, 19 mmol) and benzyl-N-(2-hydroxyethyl)carbamate (3.12 g, 16 mmol). The reaction flask was cooled in an ice bath and diisopropylazodicarboxylate (3.68 ml, 19 mmol) was added in about 5 min. The reaction mixture was stirred overnight by allowing it to slowly warm to room temperature. The reaction mixture was diluted with dichloromethane and washed with water. Organic layer was dried and evaporated. The product was purified by silica gel column chromatography using a gradient of 0-5% methanol in dichloromethane. The appropriate fractions containing the product were evaporated to give 5.8 g (66.4%) of 275. $^1$H NMR (400 MHz, DMSO) δ 9.67 (s, 1H), 8.36 (s, 1H), 8.16 (s, 1H), 7.51-7.22 (m, 7H), 7.06 (t, J=8.3, 1H), 5.84 (d, J=21.1, 1H), 5.42 (dd, 1H), 5.22-5.32 (m, 1H), 4.99 (s, 2H), 4.43-4.15 (m, 3H), 3.98 (t, J=5.6, 2H), 3.44-3.22 (m, 2H), 2.05, 2.08 (2 s, 6H). MS: Calcd: 692.11, 694.11. Found: 691 (M−H), 693 (M−H).

3-(2'-Fluoro-2'-deoxy-β-D-ribofuranosyl)-9-(2-N-benzylcarbamyl-ethoxy)-1,3-diaza-2-oxophenoxazine (276): A solution of 275 (4.5 g, 6.49 mmol) in a mixture of absolute alcohol (400 ml) and triethylamine (80 ml) was heated in an oil bath at 90 C for 15. The mixture was allowed to cool to room temperature and ammonium hydroxide (200 ml) was added to the reaction flask. After stirring for 3 h, it was evaporated to dryness. The residue was coevaporated with ethanol followed by dichloromethane and purified by silica gel column chromatography using a gradient of 0-8% methanol in ethyl acetate to yield 2.1 g (61%) of pure product. $^1$H NMR (400 MHz, DMSO) δ 9.88 (s, 1H), 7.78 (d, J=11.5, 2H), 7.47-7.23 (m, 4H), 6.80 (t, J=8.3, 1H), 6.61 (d, J=8.3, 1H), 6.44 (d, J=8.2, 1H), 5.86 (d, J=17.0, 1H), 5.55 (s, 1H), 5.33 (s, 1H), 5.04 (s, 2H), 4.90 (dd, 1H), 4.14 (d, J=22.3, 1H), 3.92 (s, 2H), 3.86 (d, J=7.8, 1H), 3.78 (d, J=12.0, 1H), 3.60 (d, J=12.1, 2H), 3.41 (d, J=4.4, 2H). $^{19}$F-NMR: m, −204.51−−204.76

3-(5'-O-Dimethoxytrityl-2'-fluoro-2'-deoxy-β-D-ribofuranosyl)-9-(2-N-benzylcarbamyl-ethoxy)-1,3-diaza-2-oxophenoxazine (277): To a solution of 276 (0.4 g, 0.75 mmol) in dry pyridine (10 ml) was added DMT-Cl (338 mg, 1 mmol) and the mixture was stirred at room temperature for 4 h. The reaction mixture was diluted with dichloromethane (100 ml) and washed with water (50 ml). Organic layer was dried over sodium sulfate and evaporated. The residue was coevaporated with toluene and purified by silica gel column chromatography using a gradient of 0-5% methanol in dichloromethane to give 0.57 g (90.7%) of pure product. $^1$H NMR (400 MHz, DMSO) δ 9.90 (s, 1H), 7.77 (s, 1H), 7.55-7.26 (m, 14H), 7.21 (t, J=7.3, 1H), 6.88 (dd, J=8.8, 4.7, 4H), 6.77 (t, J=8.3, 1H), 6.59 (d, J=8.3, 1H), 6.09 (d, J=8.2, 1H), 5.81 (d, J=19.0, 1H), 5.65 (d, J=6.9, 1H), 5.04 (s, 2H), 4.99 (dd, 1H), 4.36 (dd, J=14.2, 10.0, 1H), 4.02 (d, J=5.7, 1H), 3.91 (t, J=4.5, 2H), 3.69 (s, 3H), 3.68 (s, 3H), 3.52-3.33 (m, 3H), 3.25 (d, J=10.0, 1H). $^{19}$F-NMR: m, −203.1.

3-(5'-O-Dimethoxytrityl-2'-fluoro-2'-deoxy-β-D-ribofuranosyl)-9-(2-N-trifluoroacetamido-ethoxy)-1,3-diaza-2-oxophenoxazine (278) To a solution of 277 (0.4 g, 0.48 mmol) in a mixture of methanol (25 ml) and triethylamine (2 ml) was added 10% palladium on carbon (75 mg, Degussa type) and the mixture was stirred under a positive pressure of H$_2$ for 4 h. The reaction mixture was filtered and evaporated. The residue was coevaporated with dry pyridine. The residue was dissolved in pyridine (6 ml) and the reaction flask was cooled in an ice bath. To this cold solution trifluoroacetic anhydride (0.6 ml) was added dropwise. After stirring the mixture for 3 h, diluted with dichloromethane and washed with water. Organic layer was dried over sodium sulfate and evaporated. The residue was coevaporated with toluene and purified by silica gel column chromatography using a gradient of 0-4% methanol in dichloromethane to give 0.21 g (55%) of pure 278. $^1$H NMR (400 MHz, DMSO) δ 9.88 (s, 1H), 9.73 (s, 1H), 7.55-7.17 (m, 10H), 6.88 (dd, J=8.8, 4.8, 4H), 6.78 (t, J=8.3, 1H), 6.59 (d, J=8.3, 1H), 6.10 (d, J=8.1, 1H), 5.81 (d, J=18.9, 1H), 5.66 (d, J=6.9, 1H), 5.12-4.88 (m, 1H), 4.47-4.29 (m, 1H), 4.00 (dd, J=9.6, 5.9, 2H), 3.68, 3.70 (2 s, 6H), 3.63 (d, J=4.4, 2H), 3.47-3.29 (m, 1H), 3.25 (d, J=10.2, 1H). $^{19}$F-NMR: s, −77.1; m, −203.1.

3-(5'-O-Dimethoxytrityl-2'-fluoro-2'-deoxy-β-D-ribofuranosyl)-9-(2-N-trifluoroacetamido-ethoxy)-1,3-diaza-2-oxophenoxazine 3'-O-(2-cyanoethyl) N,N-diisopropylphosphoramidite (279)

Compound 278 (1 mmol) on treatment with 2-cyanoethyl-N,N,N',N''-tetraisopropylphosphorodiamidite (1.2 mmol) in dichloromethane in the presence of 3,4-dicyanoimidazole (0.9 mmol), work up of the reaction followed by silica gel column chromatography gives the corresponding 3'-phposphoramidite 279. Alternatively this compound can also be prepared by treating with 2-cyanoethyl-N,N-diisopropylchloro phosphoramidite in dichloromethane in the presence of Hunig's base.

Compounds in Scheme 16:

3',5'-Diacetyl-5-iodo-2'-fluoro-2'-deoxyuridine (283, J. shi, J. Du, T. Ma. K. W. Pankiewicz, S. E. Patterson, P. M. Tharnish, T. M. McBrayer, L. J. Stuyver, M. J. Otto, C. K. Chu, R. F. Schinazi, K. a. Watanabe, Bioorg. Med. Chem., 2005, 13, 1641-1652) (Scheme 16):

To a solution of 2'-fluorouridine (2.46 g, 10 mmol) in anhydrous pyridine (15 ml) was added acetic anhydride (5.67 ml, 60 mmol) and the mixture was stirred at room temperature for 18 h. The reaction was quenched by the addition of methanol (5 ml) and after 30 min at room temperature the reaction mixture was diluted with dichloromethane (150 ml) and washed with sat. sodium bicarbonate solution (250 ml). Organic layer was dried over sodium sulfate and evaporated. The residue was coevaporated with toluene and dried on a high vacuum pump to give 3.23 g (97.9%) of 282 as a colorless foam.

To a solution of 282 (1.65 g, 5 mmol) in dichloromethane (50 ml) was added iodine monochloride (1.5 g, 9.24 mmol) and the mixture was heated under reflux for 5 h. The reaction mixture was allowed to cool to room temperature and washed with 5% sodium bisulfite solution (100 ml) followed by sat. sodium bicarbonate solution (200 ml). Organic layer was dried and evaporated to give 2.2 g (96%) of 283. $^1$H NMR (400 MHz, DMSO) δ 11.84 (s, 1H), 8.18 (s, 1H), 5.85 (dd, J=22.1, 1.5, 1H), 5.52 (ddd, J=52.5, 5.2, 1.7, 1H), 5.34-5.18 (m, 1H), 4.41-4.24 (m, 2H), 4.18 (dd, J=12.1, 5.2, 1H), 2.07, 2.10 (2 s, 6H). $^{19}$F-NMR: m, −200.75.

3',5'-Diacetyl-5-[2-(Methoxycarbonyl)ethenyl]-2'-fluoro-2'-deoxyuridine (284): To a solution of 283 (1.82 g, 4 mmol) in dry acetonitrile (50 ml) was added triethylamine (1.2 ml), methyl acrylate (0.54 ml, 6 mmol) and dichlorobis(triphenylphosphine)palladium(II) (35 mg) and the mixture was heated at 90 C for 18 h. The solvent was evaporated and the residue was purified by silica gel column chromatography to give 1.5 g (90.5%) of 284. $^1$H NMR (400 MHz, DMSO) δ 11.83 (s, 1H), 8.24 (s, 1H), 7.37 (d, J=15.8, 1H), 6.87 (d, J=15.9, 1H), 5.90 (d, J=20, 1H), 5.53 (ddd, J=52.3, 5.4, 1.5, 1H), 5.34-5.18 (m, 1H), 4.42-4.20 (m, 3H), 3.67 (s, 3H), 2.11 (s, 3H), 2.03 (s, 3H). $^{19}$F-NMR: m, −200.8.

Compounds in Scheme 17:

5-Iodo-2'-fluoro-2-deoxycytidine (286, J. shi, J. Du, T. Ma. K. W. Pankiewicz, S. E. Patterson, P. M. Tharnish, T. M. McBrayer, L. J. Stuyver, M. J. Otto, C. K. Chu, R. F. Schinazi, K. a. Watanabe, Bioorg. Med. Chem., 2005, 13, 1641-1652) (Scheme 17): To a suspension of 2'-Fluoro-2'-deoxycytidine (3.8 g, 15.45 mmol) in dry methanol (150 ml) was added iodine monochloride (5 g, 30.8 mmol) and the mixture was heated at 50 C for 7 h. The reaction mixture was allowed to cool to room temperature and the solvent was evaporated. The residue was triturated with dichloromethane to remove excess reagent and the crude product was purified by silica gel column chromatography.

5-[2-(Methoxycarbonyl)ethenyl]2'-Fluoro-2'-deoxycytidine (287): To a solution of 286 (0.75 g, 2 mmol) in a mixture of dry acetonitrile (6 ml) and DMF (24 ml) was added triethylamine (0.6 ml), methyl acrylate (0.27 ml, 3 mmol) and dichlorobis(triphenylphosphine)palladium(II) (50 mg) and the mixture was heated at 90 C for 26 h. The solvent was evaporated and the residue was purified by silica gel column chromatography to give 287. $^1$H NMR (400 MHz, DMSO) δ 8.67 (s, 1H), 7.58 (dd, J=16.2, 12.0, 3H), 6.24 (d, J=15.7, 1H), 5.88 (d, J=17.2, 1H), 5.54 (d, J=8, 1H), 5.48 (t, J=4.8, 1H), 4.92 (dd, J=53.0, 3.9, 1H), 4.27-4.08 (m, 1H), 3.95-3.81 (m, 3H), 3.68 (s, 3H), 3.63 (ddd, J=7.2, 4.9, 1.9, 1H). $^{19}$F-NMR: m, −204.

3-(2-Fluoro-2-deoxy-β-D-erythro-pentofuranosyl)pyrido[2,3-d]pyrimidine-2,7(8H)-dione (288): A solution of 5-[2-(Methoxycarbonyl)ethenyl]2'-Fluoro-2'-deoxycytidine 287 (0.16 g, 0.5 mmol) in water (200 ml) was irradiated with a 450 W mercury lamp in a photochemical reactor with quartz immersion tube for 30 min. Water was evaporated to give compound 4 which was purified by silica gel column chromatography. $^1$H NMR (400 MHz, DMSO) δ 11.94 (s, 1H), 8.96 (s, 1H), 7.54 (d, J=9.6, 1H), 6.17 (d, J=9.5, 1H), 5.93 (d, J=16.9, 1H), 5.60 (d, J=6.6, 1H), 5.38 (t, J=5.1, 1H), 4.98 (dd, J=52.7, 3.9, 1H), 4.25-4.06 (m, 1H), 4.05-3.86 (m, 2H), 3.67 (ddd, J=12.7, 5.2, 2.5, 1H), 3.12 (dd, J=27.7, 6.1, 1H). $^{19}$F-NMR: m, −204.3.

3-[5-O-(4,4'-Dimethoxytrityl)-(2-fluoro-2-deoxy-β-D-erythro-pentofuranosyl)pyrido[2,3-d]pyrimidine-2,7(8H)- dione 3'-O-(2-cyanoethyl) N,N-diisopropylphosphoramidite (290): 3-(2-Fluoro-2-deoxy-β-D-erythro-pentofuranosyl)pyrido[2,3-d]pyrimidine-2,7(8H)-dione 288 (1 mmol) on reaction with 4,4'-dimethoxytrityl chloride (1.25 mmol) in dry pyridine provides the dimethoxytrityl derivative 289 which on phosphitylation with 2-cyanoethyl-N,N,N',N"-tetraisopropylphosphorodiamidite (1.2 eq.) in dichloromethane in the presence of 3,4-dicyanoimidazole (0.9 eq.), work up of the reaction followed by silica gel column chromatography gives the corresponding 3'-phposphoramidite 290. Alternatively this compound can also be prepared by treating with 2-cyanoethyl-N,N-diisopropylchloro phosphoramidite in dichloromethane in the presence of Hunig's base.

Compounds in Schemes 18-39:
1. Aluminum Alkoxide-Promoted Ring Opening of TBDPS-Protected Anhydro-nucleosides with primary alkohols.
Typical Procedure:
5'-TBDPS-protected 2'-((S)-2-methyl-2-methoxyethyloxy)-5-methyluridine (501b).

(S)-2-Methoxy-1-propanol (18.5 g, 0.206 mol) dried over 4A molecular sieves was placed under Ar atmosphere to a 100 mL two-neck round-bottom flask fitted with addition funnel and reflux condenser connected to a bubbler. 2M solution of trimethylaluminum in heptane (17 mL, 34 mmol) was added dropwise to the alcohol allowing gentle reflux of the mixture due to strong exothermic effect (~15 min). After the addition was completed, the flask was placed in a heated oil bath and the mixture was refluxed for additional 0.5 hour at 110° C. to insure complete conversion of trimethylaluminum to alkoxide (end of methane evolution). The mixture was cooled to room temperature under Ar, and transferred via canula to a 75 mL pressure bottle containing 500b (5.74 g, 12 mmol). The bottle was sealed under Ar, heated at 130° C. for 66 h, cooled, diluted with AcOEt (50 mL) and quenched with 10% $H_3PO_4$ (150 mL). Organic phase was separated, washed consecutively with 5% NaCl, sat. NaCl, dried over $Na_2SO_4$, and concentrated in vacuo to afford 6.71 g of crude material. Chromatography of the residue over a silica gel column with gradient DCM-MeOH (0-2%) gave 4.44 g (65%) of 501b. $^1H$ NMR (400 MHz), DMSO-$d_6$, J (Hz): 1.02 (m, 12H); 1.44 (d, 3H, J=0.7); 3.18 (s, 3H); 3.41 (m, 2H); 3.54 (q, 1H, J=6.3); 3.80 (dd, 1H, J=3.7, $J_2$=11.6); 3.91 (dd, 1H, J=2.8, $J_2$=11.6); 3.95 (q, 1H, J=3.2); 4.02 (t, 1H, J=5.5); 4.21 (q, 1H, J=4.3); 5.17 (d, 1H, J=5.8); 5.92 (d, 1H, J=5.8); 7.43 (m, 7H); 7.64 (m, 4H); 11.40 (s, 1H). $^{13}C$ NMR (100 MHz), MeCN-$d_3$: 12.3; 16.1; 20.0; 27.4; 56.7; 64.8; 70.0; 74.8; 76.6; 83.1; 85.5; 87.4; 111.5; 128.9; 129.0; 131.0; 131.1; 133.6; 134.3; 136.2; 136.4; 136.5; 151.7; 164.9.

(S)-2-Methoxy-1-propanol (60 mL, 0.62 mol) dried over 4A molecular sieves was placed under Ar atmosphere to a 500 mL two-neck round-bottom flask fitted with addition funnel and reflux condenser connected to a bubbler. 2M solution of trimethylaluminum in heptane (50 mL, 0.10 mol) was added dropwise to the alcohol allowing gentle reflux of the mixture due to strong exothermic effect (~15 min). After the addition was completed, the flask was placed in a heated oil bath and the mixture was refluxed for additional 0.5 hour at 110° C. to insure complete conversion of trimethylaluminum to alkoxide (end of methane evolution). The mixture was cooled to room temperature under Ar, and transferred via canula to a 0.5 L pressure bottle containing 500b (17.2 g, 36 mmol). The bottle was sealed under Ar, heated at 130° C. for 66 h, cooled, diluted with AcOEt (250 mL) and quenched with 10% $H_3PO_4$ (600 mL). Organic phase was separated, washed consecutively with 5% NaCl, sat. NaCl, dried over $Na_2SO_4$, and concentrated in vacuo to afford 19.8 g of crude material. Chromatography of the residue over a silica gel column with gradient DCM-MeOH (0-2%) gave 14.5 g (71%) of 501b. $H^1$ NMR (400 MHz), DMSO-$d_6$, J (Hz): 1.02 (m, 12H); 1.44 (d, 3H, J=0.7); 3.18 (s, 3H); 3.41 (m, 2H); 3.54 (q, 1H, J=6.3); 3.80 (dd, 1H, $J_1$=3.7, $J_2$=11.6); 3.91 (dd, 1H, $J_1$=2.8, $J_2$=11.6); 3.95 (q, 1H, J=3.2); 4.02 (t, 1H, J=5.5); 4.21 (q, 1H, J=4.3); 5.17 (d, 1H, J=5.8); 5.92 (d, 1H, J=5.8); 7.43 (m, 7H); 7.64 (m, 4H); 11.40 (s, 1H). $C^{13}$ NMR (100 MHz), MeCN-$d_3$: 12.3; 16.1; 20.0; 27.4; 56.7; 64.8; 70.0; 74.8; 76.6; 83.1; 85.5; 87.4; 111.5; 128.9; 129.0; 131.0; 131.1; 133.6; 134.3; 136.2; 136.4; 136.5; 151.7; 164.9.

502b was synthesized analogously from chiral (R)-2-methoxy-1-propanol (er=94:6, 16.8 g, 0.187 mol), and 500b (5.26 g, 11 mmol). Obtained: 3.60 g (58%), dr=94:6.

552b was prepared analogously from 2-methoxy-2-methylpropanol (14.1 g, 80 mmol), and 500b (2.87 g, 6 mmol). Obtained: 1.90 g (27%).

599b' was prepared analogously from N,N-bis-(2-methoxyethyl)-2-aminoethanol (597b') (24 mL, 0.211 mol), and 500b (5.74 g, 12 mmol). Obtained: 1.09 g (28%).

501a, 502a, 569a-z are prepared accordingly from 5'-TBDPS-anhydro-5-MeU (500b). Compounds 552a, and 599c'-z' are prepared analogously from 500a, 500b, and the corresponding primary alcohols.

2. Aluminum Alkoxide-Promoted Ring Opening of TBDPS-Protected Anhydro-Nucleosides with Secondary Alcohols, Diastereomeric Resolution.
Typical Procedure:
5'-TBDPS-protected (R) and (S) 2'-(1-methyl-2-methoxyethyloxy)-uridine (512a and 513a).

Racemic commercial 2-methoxy-2-propanol (88 mL, 0.9 mol) dried over 4 A molecular sieves was placed under Ar atmosphere to a 500 mL two-neck round-bottom flask fitted with addition funnel and reflux condenser connected to a bubbler. 2M solution of trimethylaluminum in heptane (60 mL, 0.12 mol) was added dropwise to the alcohol allowing gentle reflux of the mixture due to strong exothermic effect (~15 min). After the addition was complete, the flask was placed in a heated oil bath and the mixture was refluxed for additional 1 hour at 115° C. to insure complete conversion of trimethylaluminum to alkoxide (end of methane evolution). The mixture was cooled to room temperature under Ar, and transferred via canula to a 500 mL pressure bottle containing 500a (18.6 g, 0.04 mol). The bottle was sealed under Ar, heated at 150° C. for 72 h, cooled, diluted with AcOEt (300 mL) and quenched with 10% $H_3PO_4$ (600 mL). Organic phase was separated, washed consecutively with 5% NaCl, sat. NaCl, dried over $Na_2SO_4$, and concentrated in vacuo to afford 21.9 g of crude material. Chromatography of the residue over a silica gel column with gradient chloroform—AcOEt=4:1 to 1:1 gave 6.17 g (28%) of 512a (R) and 4.20 g (19%) of 513a (S).

512a:
$^1H$ NMR (400 MHz), DMSO-$d_6$, J (Hz): 1.03 (s, 9H); 1.06 (d, 3H, J=6.3); 3.26 (s, 3H); 3.27 (m, 2H); 3.37 (dd, 2H, $J_1$=6.6, $J_2$=10.0); 3.77 (m, 2H); 3.93 (m, 2H); 4.11 (t, 1H, J=4.6); 4.17 (q, 1H, J=4.6); 4.82 (d, 1H, J=5.9); 5.23 (dd, 1H, $J_1$=2.2, $J_2$=8.0); 5.80 (d, 1H, J=4.4); 7.45 (m, 6H); 7.63 (m, 4H); 7.71 (d, 1H, J=8.1); 11.40 (d, 1H, J=2.0). $^{13}C$ NMR (100 MHz), DMSO-$d_6$: 17.1; 18.8; 26.6; 58.4; 63.2; 68.3; 74.4; 75.7; 79.9; 83.9; 87.0; 101.5; 127.97; 127.99; 132.2; 132.7; 135.0; 135.2; 139.8; 150.4; 162.9.

513a:
$^1H$ NMR (400 MHz), DMSO-$d_6$, J (Hz): 1.02 (s, 9H); 1.08 (d, 3H, J=6.4); 3.18 (s, 3H); 3.26 (m, 2H); 3.80 (m, 2H); 3.92 (m, 2H); 4.12 (t, 1H, J=4.3); 4.16 (m, 1H); 5.06 (d, 1H, J=5.7); 5.24 (dd, 1H, $J_1$=2.2, $J_2$=8.1); 5.81 (d, 1H, J=4.2); 7.45 (m, 6H); 7.63 (m, 4H); 7.72 (d, 1H, J=8.1); 11.38 (d, 1H, J=2.1).

$^{13}$C NMR (100 MHz), DMSO-d$_6$: 17.2; 18.8; 26.6; 58.3; 63.5; 68.0; 74.0; 76.0; 79.8; 83.9; 87.1; 101.3; 127.9; 129.97; 130.02; 132.2; 132.7; 135.0; 135.2; 140.0; 150.4; 163.0.

512b And 513b were prepared accordingly from 500b (19.1 g, 0.04 mol), obtained: 6.18 g (27%) of 512b (R) and 5.20 g (23%) of 513b (S).

522b And 523b were prepared accordingly from racemic threo-3-methoxy-2-butanol (26.6 g, 0.256 mol) and 500b (6.69 g, 14 mmol). Obtained: 1.50 g (18%) of 522b (RR) and 0.42 g (5.2%) of 523b (SS).

532b And 533b were prepared accordingly from erythro-3-methoxy-2-butanol (21.0 g, 0.202 mol), 500b (5.26 g, 11 mmol). Obtained: 1.10 g (18%) of 532b (RS) and 0.97 g (15%) of 533b (SR).

557b was prepared accordingly from 1,3-dimethoxy-2-propanol (50 mL, 0.41 mol) and 500b (8.60 g, 18 mmol). Obtained: 3.90 g (36%).

Compounds 522a, 523a, 532a, 533a, 542a-b, 543a-b, 557a, 563a-b, 573a-b, and 599a' are synthesized analogously from the corresponding racemic secondary alcohols and 3,2'-unhydro-U (500a) and 3,2'-anhydro-5-MeU (500b).

3. 4,4,5,5-Tetramethyl-1,3,2-dioxaborolane-Promoted Ring Opening of TBDPS-Protected Anhydro-Nucleosides with Pyrimidine Desoxynucleosides, Synthesis of Nucleoside (O)-Dimers.

Typical Procedure:

TBDPS-Protected 5',2'-T-(O)-MeU Dimer (552b).

Thymidine (7.3 g, 30 mmol), sodium carbonate (0.11 g, 1 mmol), and anhydrous diglyme (20 mL) were placed in a 150 mL pressure bottle under Ar atmosphere. 4,4,5,5-Tetramethyl-1,3,2-dioxaborolane (8.7 mL, 60 mmol) was added, the pressure bottle was closed with a cap containing low-pressure gas valve, and heated in an oil bath to 110° C. for 15 min. The bottle was cooled to rt, and anhydro-nucleoside 500b (4.78 g, 10 mmol) was added. The bottle was tightly closed with a regular cap, heated at 150° C. for 64 h, cooled to rt and quenched with sat. NaHCO$_3$ (50 mL) and ethyl acetate (30 mL). The mixture was diluted with water (100 mL), extracted with ethyl acetate (50 mL), the organic phase was separated, washed with 5% NaCl, and dried over anhyd. Na$_2$SO$_4$. Crude material (9.70 g) was chromatographed over a silica gel column with AcOEt-MeOH gradient (0-5%) to afford 2.20 g (31%) of the dimer 552b as white foam. The product was further purified by crystallization from acetone (10 mL) to afford 1.68 g of white crystals (76% yield on crystallization). $^1$H NMR (400 MHz), DMSO-d$_6$, J (Hz), δ=11.42 (s, 1H), 11.29 (s, 1H), 7.71 (d, J=0.6, 1H), 7.63 (dd, J=10.0, 3.9, 4H), 7.54-7.30 (m, 7H), 6.22 (dd, J=8.2, 6.1, 1H), 5.96 (d, J=5.4, 1H), 5.51 (d, J=5.5, 1H), 5.28 (d, J=3.9, 1H), 4.25 (dd, J=9.8, 5.0, 1H), 4.20 (s, 1H), 4.05-3.97 (m, 2H), 3.97-3.75 (m, 4H), 3.59 (dd, J=10.4, 2.6, 1H), 3.34 (s, 1H), 2.11-1.92 (m, 2H), 1.80 (s, 3H), 1.46 (s, 3H), 1.02 (s, 9H). $^{13}$C NMR (100 MHz), acetone-d$_6$: 12.3; 12.4; 20.0; 27.4; 40.7; 64.7; 69.9; 71.6; 72.8; 83.6; 85.4; 86.0; 86.8; 87.6; 111.1; 111.2; 128.8; 128.9; 130.9; 140.0; 133.5; 134.1; 135.8; 136.2; 136.4; 137.2; 151.4; 151.5; 164.2; 164.4.

552a, and 583a,b are synthesized analogously from desoxyuridine and 500a.

4. TBDPS Deprotedtion from Condensation Products.

Typical Procedure:

2'-(R)-(1-methyl-2-methoxyethyloxy)-uridine (514a).

To a solution of 512a (5.83 g, 10.5 mmol) in anhyd. THF (30 mL) under Ar atmosphere was added triethylammoniun trihydrofluoride (6.8 mL; 42 mmol) and the mixture was stirred at rt for 72 h. The mixture was concentrated in vacuo and chromatographed over a column of silica gel with chloroform-methanol (20:1) eluent. Subsequent crystallization of the residue from 250 mL of ether gave 2.56 g (77%) of pure 514a as a white crystalline solid:

$^1$H NMR (400 MHz), DMSO-d$_6$, J (Hz): 1.04 (d, 3H, J=6.3); 3.25 (m, 1H); 3.26 (s, 3H); 3.36 (dd, 1H, J$_1$=6.7, J$_2$=10.0); 3.59 (tt, 1H, J$_1$=3.6, J$_2$=11.9); 3.63 (tt, 1H, J$_1$=3.6, J$_2$=11.9); 3.74 (sextet, 1H, J=6.3); 3.84 (d, 3H, J=3.1); 4.06 (quintet, 1H, J=4.8); 4.68 (d, 1H, J=4.7); 5.13 (t, 1H, J=5.0); 5.65 (d, 1H, J=8.1); 5.79 (d, 1H, J=4.4); 7.94 (d, 1H, J=8.1); 11.3 (s, 1H).

503b (dr~94:6): was synthesized analogously from 3.48 g (6.1 mmol) of 501b (dr=94:6). White foam after column purification, yield: 2.00 g (99%).

504b: was synthesized analogously from 4.21 g (7.4 mmol) of 2e. White foam after column purification, yield: 2.36 g (97%).

514b: from 5.68 g (10 mmol) of 512b. White foam after column purification, yield: 3.07 g (93%).

515a: from 3.74 g (6.8 mmol) of 513a. Yield after column purification and crystallization from ether: 1.70 g (79%), white crystals.

515b: from 4.93 g (8.7 mmol) of 513b. White foam after column purification, yield: 2.07 g (72%).

524b: from 1.44 g (2.5 mmol) of 522b. White foam after column purification, yield: 0.83 g (97%).

525b: from 0.39 g (0.67 mmol) of 523b. White foam after column purification, yield: 0.20 g (87%).

534b: from 1.01 g (1.7 mmol) of 532b. White foam after column purification, yield: 0.56 g (97%).

535b: from 0.86 g (1.5 mmol) of 533b. White foam after column purification, yield: 0.52 g (quant.).

553b: from 1.89 g (2.6 mmol) of 552b. White crystals after column purification, yield: 1.28 g (91%).

553b: from 1.54 g (2.6 mmol) of 552b. White foam after column purification, yield: 0.83 g (93%).

558b: from 3.82 g (6.4 mmol) of 557b. White foam after column purification, yield: 2.35 g (quant.).

584b: from 1.89 g (2.6 mmol) of 583b. White crystals after column purification, yield: 1.28 g (91%).

600b': from 1.00 g (1.5 mmol) of 599b'. Colorless oil after column purification, yield: 0.67 g (quant.).

Compounds 503a, 504a, 524a, 525a, 534a, 535a, 544a-b, 545a-b, 553a, 570a-z, 558a, 565a-b, 566a-b, 575a-b, 576a-b, 584a, and 600a'-z' are prepared analogously.

5. DMTr-Protection of Condensation Products.

Typical Procedure:

5'-DMTr-protected 2'-(R)-(1-methyl-2-methoxyethyloxy)-5-methyluridine (516b).

To a mixture of 514b (2.90 g; 8.8 mmol) and DMTrCl (3.29 g, 9.7 mmol) at 0° C. under argon atmosphere were added consecutively anhyd. pyridine (40 mL) and triethylamine (1.4 mL; 9.7 mmol). The cooling bath was removed and the mixture was stirred at rt for 4 h. The mixture was concentrated under the reduced pressure at 30° C. and partitioned between ethyl acetate (75 mL) and sat. NaHCO$_3$ (75 mL). The organic phase was separated, dried over anhyd. Na$_2$CO$_3$, concentrated and chromatographed over a CombiFlash silica gel column (120 g) with gradient of 50% DCM in hexane to 100% DCM in the presence of 2% Et$_3$N. Pulled fractions were concentrated, diluted with ethyl acetate (50 mL), filtered and evaporated to afford 4.98 g (89%) of 516b as white foam.

$^1$H NMR (400 MHz), DMSO-d$_6$, J (Hz): 1.08 (d, 3H, J=6.4); 1.36 (d, 3H, J=1.0); 3.17 (dd, 1H, J$_1$=2.6, J$_2$=10.7); 3.26 (s, 3H); 3.30 (m, 1H); 3.40 (dd, 1H, J$_1$=6.8, J$_2$=10.1); 3.74 (s, 6H); 3.81 (tt, 1H, J$_1$=4.2, J$_2$=6.5); 3.97 (dd, 1H, J$_1$=3.8, J$_2$=6.5); 4.24 (m, 2H); 4.83 (d, 1H, J=5.2); 5.83 (d, 1H, J=4.9); 6.91 (d split, 4H, J=9.0); 7.27 (m, 5H); 7.32 (t, 2H, J=7.2); 7.40 (d split, 2H, J=7.2); 7.52 (d, 1H, J=1.2); 11.39 (s, 1H). $^{13}$C NMR (100 MHz), MeCN-d$_3$: 12.2; 17.3; 55.9; 59.3; 64.1; 70.5; 76.8; 77.3; 82.0; 84.5; 87.6; 88.2; 111.4; 114.2; 128.0; 128.94; 129.01; 131.0; 136.4; 136.5; 136.7; 145.8; 151.8; 159.76; 159.79; 165.0.

505b (dr~94:6): was prepared analogously from 503b (dr=94:6) (1.95 g, 5.9 mmol). White foam after chromatography, yield: 3.29 g, (88%).

506b: from 504b (2.30 g, 7.0 mmol). White foam after chromatography, yield: 3.77 g, (85%).

516a: from 514a (2.50 g, 7.9 mmol). White foam, yield: 4.76 g, (98%).

517a: from 515a (1.60 g, 5.1 mmol). White foam, yield: 3.00 g, (95%).

517b: from 515b (1.95 g, 5.9 mmol). White foam, yield: 2.94 g, (79%).

526b: from 524b (0.77 g, 2.2 mmol). White foam, yield: 1.33 g, (94%)

527b: from 523b (0.19 g, 0.55 mmol). White foam, yield: 0.34 g, (94%)

536b: from 534b (0.54 g, 1.6 mmol). White foam, yield: 0.90 g, (87%)

537b: from 535b (0.34 g, 1.0 mmol). White foam, yield: 0.62 g, (95%)

554b: from 553b (1.24 g, 2.6 mmol). White foam, yield: 1.73 g, (85%)

554b: from 553b (0.76 g, 2.2 mmol). White foam, yield: 1.22 g, (87%)

559b: from 558b (2.30 g, 6.4 mmol). White foam, yield: 3.86 g, (91%)

585b: from 584b (1.24 g, 2.6 mmol). White foam, yield: 1.73 g, (85%)

592b: from 591b (3.35 g, 9.0 mmol). Yellowish oil, yield: 4.21 g, (69%)

601b': from 600b' (0.65 g, 1.4 mmol). White foam, yield: 0.83 g, (82%)

Compounds 505a, 506a, 516a, 517a, 526a, 527a, 536a, 537a, 546a-b, 547a-b, 554a, 571a-z and 559a, 567a-b, 568a-b, 577a-b, 578a-b, 585a and 592a are prepared analogously.

6. Sodium Hydride-Promoted Alkylation of Protected Nucleosides with Primary Mesylates.
Typical Procedure:
5'-DMTr-2'-(S)-(2-methyl-2-methoxyethyloxy)-adenosine-N-benzoyl (506d).

Sodium hydride (1.84 g, 46 mmol) was added to a stirred and cooled (0° C.) mixture of 507d (14.2 g, 21 mmol), anhyd. DMSO (70 mL), and anhyd. THF (50 mL) under Ar atmosphere, the mixture was stirred at 0° C. for 0.5 h, and (S)-2-methoxypropylmethanesulfonate (8.9 g, 53 mmol) in THF (20 mL) was added. The mixture was allowed to warm up to rt, and then heated in an oil bath at 50° C. for 24 h. The mixture was cooled to 0° C. and quenched by consecutive addition of sat. NH$_4$Cl (200 mL), ethyl acetate (150 mL), and water (30 mL). The organic phase was separated, washed with sat. NaCl and dried over anhyd. Na$_2$SO$_4$. Crude residue (22.2 g) was chromatographed over a column of silica gel with ethyl acetate-hexane (2:1)-methanol gradient (0-5%) to afford 3.96 g (25%) of 506d as white foam.

$^1$H NMR (400 MHz), DMSO-d$_6$, J (Hz): 11.25 (1H, s), 8.70 (1H, s), 8.62 (1H, s), 8.05 (2H, m), 7.65 (1H, t, J 7.4), 7.56 (2H, t, J 7.6), 7.37 (1H, m), 7.23 (7H, m), 6.84 (4H, m), 6.18 (1H, d, J 4.8), 5.26 (1H, d, J 6.0), 4.73 (1H, t, J 4.9), 4.46 (1H, dd, J 10.7, 5.2), 4.13 (1H, dd, J 9.1, 4.8), 3.72 (3H, s), 3.72 (3H, s), 3.60 (1H, dd, J 10.4, 4.1), 3.47 (1H, m), 3.41 (1H, m), 3.25 (2H, m), 3.13 (3H, s), 0.99 (3H, d, J 6.2). $^{13}$C NMR (100 MHz), acetone-d$_6$: 16.1; 55.4; 56.5; 64.4; 70.8; 74.9; 76.5; 82.7; 84.9; 87.0; 87.8; 113.8; 126.0; 127.5; 128.5; 128.9; 129.1; 129.3; 130.8; 133.1; 134.9; 135.6; 136.7; 143.5; 145.9; 151.1; 152.6; 152.9; 159.5; 165.9.

Compounds 546d-e are prepared analogously by alkylation of 507d-e with 2-bromopropionylmethylamide. Compounds 558d-e, 563a-b, 566d-e are prepared analogously by alkylation of the corresponding protected nucleosides 507d-e, 561a-b, and 556d-e with protected nucleoside 5'-mesylates 557d-e, and 562a-b. Compounds 573a-z are prepared by alkylation of 507d applying 3 eq of NaH and HCl salts of the corresponding mesylates 568a-z. Compounds Compounds 505d-e, 506e, and 554d-e are prepared analogously by alkylation of 507d-e with the corresponding mesylates.

Compound 603b' was synthesized similarly from 507d (2.70 g, 4 mmol) using 3.5 eq of NaH (0.56 g, 14 mmol) and mesylate 598b' prepared preliminarily "in situ" form N,N-bis-(2-methoxyethyl)-2-aminoethanol (597b') (0.89 mL, 5 mmol) and mesyl chloride (0.37 mL, 4.8 mmol). Yield of 603b': 0.33 g, (10%).

Compounds 589d-e, 594a-b, 595d-e are prepared analogously by alkylation of the corresponding protected nucleosides 507d-e, 592a-b, and 587d-e with protected nucleoside 5'-mesylates 588d-e, and 593a-b.

7. Synthesis of 5'-DMTr-N-pivaloyl pyrimidine nucleosides.
Typical Procedure:
5'-DMTr-N-pivaloylthymidine (561b).

TMSCl (2.7 ml, 21 mmol) was added to a solution of thymidine (2.42 g, 10 mmol) in anhyd. pyridine (20 mL) under Ar atmosphere. The mixture was stirred at rt for 4 h, and pivaloyl chloride (1.3 mL, 10.5 mmol) was added. The mixture was stirred at rt for 72 h, and water (0.19 mL, 10.5 mmol) was added. After stirring at rt for 16 h, DMTrCl (3.73 g, 11 mmol) was added, and the stirring was continued for an additional 3.5 h. The mixture was diluted with AcOEt (40 mL) and quenched with 10% aq. H$_3$PO$_4$ (150 mL), washed with 5% NaCl and dried over anhyd. Na$_2$SO$_4$. The crude mixture (7.51 g) was chromatographed over a column of silica gel with ethyl acetate:hexane (1:1)-methanol gradient (0-3%) to afford 561b, 3.35 g, 53%. $^1$H NMR (400 MHz), MeCN-d$_3$, J (Hz): 7.66 (1H, s), 7.40 (2H, m), 7.32 (2H, t, J 7.6), 7.26 (5H, t, J 6.5), 6.90 (4H, dd, J 8.9, 1.0), 6.18 (1H, t, J 6.6), 5.37 (1H, s), 4.36 (1H, s), 3.92 (1H, dd, J 7.3, 3.9), 3.74 (6H, s), 3.21 (2H, s), 2.28 (2H, m), 1.51 (3H, d, J 0.9), 1.23 (9H, s).

Compound 561a is synthesized analogously.
8. Conversion of U to C.
Typical Procedure:
5'-DMTr-2'-(R)-(1-methyl-2-methoxyethyloxy)-cytosine-N-acetyl (516c').

To a solution of uridine 516a (2.37 g, 3.8 mmol) and NMP (3.3 mL, 32 mmol) in anhyd. MeCN (20 mL) was added TMSCl (1.06 mL, 8.4 mmol) under argon atmosphere. The mixture was stirred at rt for 1 h and cooled to 0° C. followed by dropwise addition of TFAA (1.3 mL, 9.5 mmol). The mixture was stirred at 0° C. for 30 min and p-nitrophenol (1.53 g, 11 mmol) was added. After stirring at 0° C. for 3 h, the mixture was quenched with sat. NaHCO$_3$ (80 mL) and diluted with AcOEt, the cooling bath was removed and water (40 mL) was added. The organic phase was separated, washed with sat. NaCl and dried over anhyd. Na$_2$SO$_4$. After evaporation of the solvent, the residue was dissolved in dioxane (40 mL), the solution was placed in 150 mL pressure bottle, and saturated NH$_4$OH (6 mL) was added. The bottle was sealed, and the mixture was heated at 55° C. overnight, cooled, evaporated in vacuum, and the residue was chromatographed over a column of silica gel with DCM-methanol gradient (0-10%) to afford 2.18 g, (93%) of NH-cytosine. The latter (1.85 g, 3.0 mmol) was acetylated by dissolving in anhyd. DMF (10 mL) followed by addition of Ac$_2$O (0.34 mL, 3.6 mmol) under argon atmosphere. The mixture was stirred overnight, cooled to 0° C., and quenched by addition of 5% aq. NaCl (40 mL) and AcOEt (30 mL). The organic phase was separated, washed consecutively with 5% NaCl (40 mL×2), sat. NaHCO$_3$, and sat. NaCl, dried over anhyd. Na$_2$SO$_4$, and evaporated followed by coevaporation with anhyd. MeCN (20 mL) to afford 516c' of over 98% purity (H$_1$NMR). Yield: 1.76 g, 89%. H$^1$ NMR (400 MHz), DMSO-d$_6$, J (Hz): 10.92 (1H, s), 8.29 (1H, d, J 7.5), 7.39 (2H, m), 7.32 (2H, t, J 7.2), 5.26 (5H, m), 7.00 (1H, d, J 7.5), 6.90 (4H, d, J 8.9), 5.76 (1H, d, J 1.4), 4.78 (1H, d, J 7.8), 4.23 (1H, tt, J 8.1, 4.8), 4.05 (1H, dd, J 4.8, 1.3), 3.98 (2H, m), 3.74 (6H, s), 3.32 (3H, m), 3.25 (3H, s), 2.09 (3H, s), 1.15 (3H, d, J 6.3). C$^{13}$ NMR (100 MHz), acetone-d$_6$: 17.7; 24.8; 55.5; 59.0; 62.4; 69.3; 77.2; 77.4; 83.3; 83.9; 87.5; 91.2; 96.3; 114.0; 127.7; 128.7; 129.0; 130.8; 130.9; 136.4; 136.7; 145.3; 145.6; 155.5; 159.64; 159.65; 163.6; 171.3.

517c': Was synthesized analogously from 517a (1.87 g, 3.0 mmol). Obtained: 1.55 g, (82%—total). Compounds 505c', 506c', 526c', 527c', 536c', 537c', 546c', 547c', 554c', 559c', 567c', 568c', 577c', 578c', 585c', 595c', and 602a'-z' are prepared analogously.

9. Synthesis of N-SEM pyrimidine nucleosides.
Typical Procedure:
N-SEM-thymidine (591b).

Sodium hydride (60% suspension in oil, 1.32 g, 33 mmol) was added to a solution of diacetylthymidine (9.98 g, 30 mmol) in a mixture of anhyd. DMSO (15 mL) and THF (15 mL) at 0° C. under argon atmosphere. The mixture was stirred at 0° C. for 45 min, and a solution of SEMCl (4.68 g, 28 mmol) in THF was added dropwise for 20 min. The mixture was allowed to warm up to rt in ice bath overnight. 7N Solution of ammonia in MeOH (50 mL) was added and the mixture was stirred overnight followed by evaporation of volatile solvents under the reduced pressure. The residue was partitioned between sat. NaCl (100 mL), 10% H$_3$PO$_4$ (30 mL) and AcOEt. The organic phase was separated, washed with sat. NaCl and dried over anhyd. Na$_2$SO$_4$. Crude residue (10.27 g) was chromatographed over a column of silica gel with DCM-methanol gradient (0-5%) to afford 8.95 g, (86%) of 591b as colorless oil. H$^1$ NMR (400 MHz), DMSO-d$_6$, J (Hz): 7.81 (1H, d, J 1.2), 6.20 (1H, t, J 6.8), 5.25 (1H, d, J 4.2), 5.22 (2H, d, J 1.7), 5.05 (1H, t, J 5.2), 4.25 (1H, m), 3.80 (1H, q, J 3.1), 3.59 (4H, m), 2.11 (2H, dd, J 6.8, 4.6), 1.83 (3H, d, J 1.2), 0.84 (2H, m), −0.03 (9H, s).

Compound 591a is synthesized analogously.

10. Synthesis of Phosphoramidites of Modified Nucleosides.
Typical Procedure:
5'-DMTr-2'-(R)-(1-methyl-2-methoxyethyloxy)-5-methyluridine-3'-phosphoramidite (518b).

To a flask, containing DMTr-protected nucleoside 516b (2.0 g, 3.2 mmol) were added consecutively under argon atmosphere anhyd. DCM (20 mL), DIEA (0.66 mL, 3.8 mmol), and cyanoethylchlorophosphor-N,N-diisopropylamidite (0.85 mL, 3.8 mmol). The mixture was stirred at rt overnight and partitioned between ethyl acetate (20 mL) and sat. NaHCO$_3$ (20 mL). Organic phase was separated, dried over anhyd. Na$_2$SO$_4$, concentrated and chromatographed over a CombiFlash silica gel column (40 g) with ethyl acetate-hexane (1:1) eluent in the presence of 0.25% of Et$_3$N. Obtained 2.06 g (77%) of pure 518b (mixture of diastereomers) as white foam. $^1$H NMR (400 MHz), MeCN-d$_3$, J (Hz): 1.07 (d, 3H, J=6.8); 1.14 (d, 3H, J=6.3); 1.19 (dd, 9H, J$_1$=2.9, J$_2$=6.8); 1.35 (s, 3H); 2.52 (t, 1H, J=6.0); 2.72 (q split, 1H, J=6.2); 3.30 (s, 1.5H); 3.32 (s, 1.5H); 3.34 (m, 1H); 3.37 (s, 1H); 3.48 (m, 1H); 3.63 (m, 2.5H); 3.74 (m, 0.5H); 3.78 (s split, 6H); 3.91 (m, 2H); 4.15 (d, 0.5H, J=2.6); 4.24 (d, 0.5H, J=2.5); 4.52 (m, 2H); 5.94 (t, 1H, J=5.3); 6.90 (dd, 4H, J$_1$=4.7, J$_2$=8.4); 7.27 (m, 1H); 7.35 (m, 6H); 7.49 (dd, 2H, J$_1$=3.3, J$_2$=8.0); 7.53 (s, 0.5H); 7.57 (s, 0.5H); 9.20 (s broad, 1H). $^{31}$P NMR (160 MHz), MeCN-d$_3$: 149.2; 149.6.

508b (dr~94:6): was prepared analogously from 505b (2.0 g, 3.2 mmol). Yield: 1.98 g (74%), white foam.

509b: from 506b (2.0 g, 3.2 mmol). Yield: 2.14 g (80%), white foam.

509d: from 506d (3.26 g, 4.4 mmol). Yield: 3.17 g (76%), white foam.

518c': from 516c' (1.33 g, 2.0 mmol). Yield: 0.91 g (53%), white foam.

519b: from 517b (1.50 g, 2.4 mmol). Yield: 1.52 g (76%), white foam.

519c': from 517c' (1.13 g, 1.7 mmol). Yield: 0.91 g (62%), white foam.

528b: from 526b (0.98 g, 1.5 mmol). Yield: 0.96 g (76%), white foam.

529b: from 527b (0.34 g, 0.5 mmol). Yield: 0.34 g (81%), white foam.

538b: from 536b (0.59 g, 0.9 mmol). Yield: 0.46 g (61%), white foam.

539b: from 537b (0.62 g, 0.96 mmol). Yield: 0.64 g (79%), white foam.

555b: from 554b (0.78 g, 1.2 mmol). Yield: 0.67 g (65%), white foam.

560b: from 559b (1.99 g, 3.0 mmol). Yield: 1.34 g (52%), white foam.

604b': from 601b' (0.62 g, 0.86 mmol). Yield: 0.63 g (80%), white foam.

606b': from 603b' (0.19 g, 0.23 mmol). Yield: 0.19 g (79%), colorless oil.

Compounds 508a,c; 509a,c; 518a,c; 519a,c; 528a,c; 529a,c; 538a,c; 539a,c; 548a-e; 549a-e; 574a-z; 575a-z; and 576a-z are prepared accordingly.

Compounds 508c'; 509c'; 528c'; 529c'; 538c'; 539c'; 548c'; 549c'; 555a,c'; 560a,c'; 569a-c'; 570a-c'; 579a-c'; 580a-c' and 604-606a'-z' are prepared accordingly.

11. Loading of Condensation Products on CPG.
Typical Procedure:
Loading of 5'-DMTr-2'-(R)-(1-methyl-2-methoxyethyloxy)-5-methyluridine (516b) on CPG.

To a mixture of 516b (500 mg, 0.79 mmol) and succinic anhydride (160 mg, 1.6 mmol) were added anhyd. pyridine (3 mL) and triethylamine (0.42 mL, 3 mmol) under argon atmosphere. After stirring at rt for 24 h, the mixture was diluted with toluene (5 mL), evaporated under the reduced pressure, and coevaporated again with 10 mL of toluene. The residue was partitioned between water and toluene-ethyl acetate 1:1. The organic phase was separated, washed with 5% aq. sodium chloride and dried over anhyd. Na$_2$SO$_4$. Evaporation of the solvent gave 589 mg (quantitative) of essentially pure 3'-succinate as free acid containing some toluene that was used in the next step without further purification. $^1$H NMR (400 MHz), MeCN-d$_3$, J (Hz): 1.08 (d, 3H, J=6.4); 1.37 (d, 3H, J=1.3); 2.60 (m, 2H); 2.65 (m, 2H); 3.28 (s, 3H); 3.30 (m, 3H); 3.40 (m, 2H); 3.78 (m, 1H); 3.79 (s split, 6H); 4.15 (q, 1H, J=2.7); 4.54 (dd, 1H, J=5.6, J$_2$=6.8); 5.45 (dd, 1H, J=3.0, J$_2$=5.5); 5.94 (d, 1H, J=6.8); 6.91 (dd, 4H, J=1.1, J$_2$=9.0); 7.34 (m, 6H); 7.47 (m, 3H); 9.14 (s broad, 1H).

To a mixture of the succinate (0.79 mmol) and HBTU (330 mg, 0.87 mmol) were added anhyd. DMF (30 mL) and DIEA (0.42 mL, 2.4 mmol) under argon atmosphere. After standing for 5 min, CPG-500 (maximum loading 140 µmol/g) (6.0 g, 0.87 mmol) was added and the mixture was placed on a shaker for 3 h. The mixture was filtered, the residue was washed consecutively with DCM, 20% methanol in DCM, DCM twice, and dried in vacuum to afford 6.13 g of precapped support (loading 90.7 µmol/g).

Precapped product was treated under argon atmosphere with anhyd. pyridine (30 mL), triethylamine (2.8 mL, 20 mmol), and acetic anhydride (1.9 mL, 20 mmol). After shaking for 1 h, the solids were filtered, washed twice with DCM, once with 20% MeOH in DCM, and once again twice with DCM, and dried under high vacuum for 1 h to afford support 520b. Loading after cupping: 87.3 µmol/g.

510b: was prepared analogously from 505b (630 mg, 1 mmol). Obtained: 10.3 g, loading 74 µmol/g.

511b: from 506b (630 mg, 1 mmol). Obtained: 10.2 g, loading 66 µmol/g.

511d: from 506d (500 mg, 0.67 mmol). Obtained: 5.2 g, loading 79 µmol/g.

520c': from 516c' (360 mg, 0.47 mmol). Obtained: 4.7 g, loading 73 µmol/g.

521b: from 517b (500 mg, 0.79 mmol). Obtained: 6.3 g, loading 91 µmol/g.

521c': from 517c' (360 mg, 0.47 mmol). Obtained: 4.7 g, loading 74 µmol/g.

530b: from 526b (340 mg, 0.53 mmol). Obtained: 4.9 g, loading 61 µmol/g.

540b: from 536b (320 mg, 0.5 mmol). Obtained: 4.1 g, loading 80 µmol/g.

607b': from 601b' (110 mg, 0.15 mmol). Obtained: 1.2 g, loading 65 µmol/g.

609b': from 603b' (100 mg, 0.12 mmol). Obtained: 0.8 g, loading 63 µmol/g.

Supports 510a,c-e,c'; 511a,c-e,c'; 512a,c,c'; 520a,c; 521a; 530a,c,c'; 531a-c,c'; 540a,c,c'; 541a-c,c'; 550a-e,c'; 551a,e,c'; 559d-e; 565a-c; 565d-e; 577a-z; 578a-z; 579a-z; and 556a-c', d-e; 561a-c', 571a-c', 572a-c', 581a-c', 582a-c', 590d-e, 596a-c',d-e, and 607-609a'-z' are prepared analogously.

12. Loading of Bivalent Nucleosides (554a-c) on CPG.
Typical Procedure:
Loading of DMTr-protected 5',2'-T-(O)-MeU dimer (554b) on CPG.

Succinic anhydride (0.15 g, 1.5 mmol) was added to a stirred and cooled (0° C.) solution of the dimer 554b (0.82 g, 0.96 mmol), DMAP (0.18 g, 1.5 mmol) in anhyd. pyridine (5 mL) under Ar atmosphere. The mixture was allowed to warm up to rt and stirred for 48 h. The mixture was diluted with AcOEt (10 mL) and quenched with 5% aq. $H_3PO_4$ (30 mL), washed with 10% NaCl and dried over anhyd. $Na_2SO_4$. Evaporation of the solvent followed by double coevaporation with a mixture of toluene (20 mL) and acetonitrile (10 mL) gave succinates of the dimer as a mixture of isomeric monoacids and diacid in ~1:1 ratio. Yield: 0.67 g, 74%. This mixture (0.95 g, 1.01 mmol based on DMTr) was dissolved in anhyd. DMF (50 mL) under Ar atmosphere, and HBTU (0.65 g, 1.71 mmol), and DIEA (0.82 mL, 4.7 mmol) were consecutively added. The mixture was shaken for 5 min, and CPG-500 (maximum loading 147 µmol/g) (12.0 g, 1.74 mmol) was added. The mixture was shaken for 3 h, and methanol (1 mL, 30 mmol) was added. After shaking for additional 0.5 h, the mixture was filtered, the residue was washed consecutively with DCM, 20% methanol in DCM, DCM twice, and dried in vacuum to afford 12.5 g of precapped support (loading 60.0 µmol/g).

The support was capped by consecutive addition of anhyd. pyridine (50 mL), triethylamine (5.6 mL, 40 mmol), and acetic anhydride (3.8 mL, 40 mmol). After shaking for 1 h, the mixture was filtered, the residue was washed consecutively with DCM, 20% methanol in DCM, DCM twice, and dried in vacuum to afford 12.4 g of capped support 555b (loading 56 µmol/g).

Supports 555a,c and 586a-c' are prepared analogously.
Synthesis of Compounds in Scheme 42
Compound 464:

To a solution of compound 452 (5.00 g, 15.1 mmol) in THF (100 mL) and $H_2O$ (20 mL), lithium hydroxide monohydrate (1.03 g, 25.5 mmol) was added. The reaction mixture was stirred overnight. Additional lithium hydroxide monohydrate (500 mg, 11.9 mmol) was added. After 2 hours, the reaction mixture was treated with Amberlite IR-120 (plus) ion exchange resin. The resin was filtered off and washed with THF/$H_2O$. The filtrate was evaporated to give compound 464 as a white solid (4.78 g, quantitatively).

$^1$H NMR (DMSO-$d_6$, 400 MHz) δ 11.34 (s, 1H), 7.75 (s, 1H), 4.92-4.93 (m, 1H), 4.70-4.72 (m, 1H), 4.45 (d, J=4.0 Hz, 1H), 3.80-3.93 (m, 4H), 3.68-3.72 (m, 1H), 3.61 (dd, J=12.0 Hz, 3.2 Hz, 1H), 3.47 (dd, J=12.0 Hz, 4.0 Hz, 1H), 3.17 (d, J=3.2 Hz, 1H), 2.59 (t, J=7.0 Hz, 2H). $^{13}$C NMR (DMSO-$d_6$, 100 MHz) δ 172.1, 163.0, 150.4, 143.6, 111.4, 83.2, 79.0, 73.7, 70.4, 61.3, 44.1, 32.7. Molecular weight for $C_{12}H_{15}N_2O_8$ (M–H)$^-$ Calc. 315.08. Found 315.1.

Compound 466:

To a solution of compound 464 (4.78 g, 15.1 mmol), 465 (8.81 g, 16.65 mmol), $iPr_2NEt$ (13.19 mL, 75.7 mmol) in DMF (320 mL) and $CH_2Cl_2$ (80 mL), HBTU (6.89 g, 18.17 mmol) was added. The reaction mixture was stirred for 22 hours. TLC showed a coupled product ($R_f$=0.31 developed by 10% MeOH in $CH_2Cl_2$; Molecular weight for $C_{46}H_{74}N_4NaO_9$ (M+Na)$^+$ Calc. 849.54. Found 849.3.) and the solvent was evaporated in vacuo. To a solution of the crude in pyridine (100 mL), DMTrCl (5.90 g, 17.4 mmol) in pyridine (50 mL) was dropwisely added at 0° C. The reaction mixture was stirred overnight. After evaporation, the crude was washed with EtOAc and saturated $NaHCO_3$ aq., dried over anhydrous $Na_2SO_4$, and filtered. Silica gel column chromatography (5% MeOH in $CH_2Cl_2$ with 1% $Et_3N$, $R_f$=0.16) gave compound 466 (12.4 g, 10.98 mmol, 73%).

$^1$H NMR (DMSO-$d_6$, 400 MHz) δ 11.31 (s, 1H), 7.81 (t, J=5.5 Hz, 1H), 7.40-7.43 (m, 3H), 7.27-7.31 (m, 6H), 7.18-7.22 (m, 1H), 6.97 (t, J=5.7 Hz, 1H), 6.86-6.88 (m, 4H), 5.30-5.32 (m, 1H), 5.01 (d, J=4.7 Hz, 1H), 4.73 (J=6.7 Hz, 1H), 4.51 (d, J=2.8 Hz, 1H), 4.26-4.32 (m, 1H), 3.79-3.90 (m, 3H), 3.73 (s, 6H), 3.55-3.67 (m, 2H), 3.09-3.22 (m, 3H), 2.89-2.98 (m, 6H), 2.34 (t, J=6.4 Hz, 2H), 2.14-2.30 (m, 2H), 0.83-1.97 (m, 43H), 0.65 (s, 3H). $^{13}$C NMR (DMSO-$d_6$, 100 MHz) δ 168.9, 162.6, 157.9, 155.5, 150.3, 144.9, 143.1, 139.7, 135.8, 135.6, 129.7, 127.7, 126.5, 121.7, 113.0, 111.3, 85.2, 80.7, 79.8, 73.6, 72.6, 70.8, 64.2, 56.0, 55.5, 51.9, 49.4, 44.9, 41.8, 38.3, 38.2, 36.5, 36.0, 35.6, 35.1, 33.9, 31.3, 31.2, 29.3, 28.9, 27.8, 27.7, 27.3, 26.0, 25.9, 23.8, 23.1, 22.6, 22.3, 20.5, 18.9, 18.5, 11.6, 7.1. Molecular weight for $C_{67}H_{92}N_4NaO_{11}$ (M+Na)$^+$ Calc. 1151.67. Found 1151.4.

Compound 467 and Compound 468:

Selective silylation at 2'-hydroxyl group was carried out according to Ogilvie's method (Hakimelahi, G. H.; Proba, Z. A.; Ogilvie, K. K. *Tetrahedron Lett.*, 1981, 22, 4775-4778). To a solution of 466 (2.31 g, 2.05 mmol) in THF (23 mL), pyridine (0.613 mL, 7.59 mmol), and $AgNO_3$ (418 mg, 2.46 mmol) was added. After 15 min, TBDMSCl (402 mg, 2.67 mmol) was added and the reaction mixture was stirred overnight under Ar gas. Additional pyridine (0.184 mL, 2.28 mmol), $AgNO_3$ (125 mg, 0.736 mmol) and TBDMSCl (121 mg, 0.804 mmol) were added. The reaction mixture was filtered through Celite, then extracted with $CH_2Cl_2$ and saturated $NaHCO_3$ aq., and dried over anhydrous $Na_2SO_4$. The crude was purified by silica gel column chromatography (eluted with Hexane:EtOAc=1:1 to 1:8 with 1% $Et_3N$) to give 467 (620 mg, 0.499 mmol, 24%, $R_f$=0.74 developed by EtOAc) and 468 (440 mg, 0.354 mmol, 17%, $R_f$=0.53 developed by EtOAc).

467: $^1$H NMR (DMSO-d$_6$, 400 MHz) δ 11.31 (brs, 1H), 7.81 (t, J=5.6 Hz, 1H), 7.40-7.45 (m, 3H), 7.28-7.33 (m, 6H), 7.21 (t, J=7.4 Hz, 1H), 6.97 (t, J=5.6 Hz, 1H), 6.87-6.89 (m, 4H), 5.31 (d, J=5.2 Hz, 1H), 4.57 (d, J=6.8 Hz, 1H), 4.53 (d, J=2.0 Hz, 1H), 4.29-4.32 (m, 1H), 4.04-4.05 (m, 1H), 3.88-3.92 (m, 1H), 3.79-3.83 (m, 1H), 3.73 (s, 6H), 3.51-3.63 (m, 2H), 3.23-3.27 (m, 2H), 3.12-3.15 (m, 1H), 2.90-2.96 (m, 6H), 2.18-2.34 (m, 4H), 0.83-1.98 (m, 52H), 0.65 (s, 3H), 0.069 (s, 3H), 0.044 (s, 3H). $^{13}$C NMR (DMSO-d$_6$, 100 MHz) δ 168.8, 162.5, 157.9, 155.5, 150.3, 144.9, 143.2, 139.7, 135.7, 135.5, 129.7, 127.7, 127.6, 126.5, 121.7, 113.0, 110.0, 85.2, 80.4, 79.9, 76.0, 72.6, 70.4, 63.9, 63.4, 59.6, 56.0, 55.5, 49.4, 45.0, 41.7, 38.3, 38.2, 36.5, 36.0, 35.6, 35.1, 33.8, 31.3, 31.2, 30.1, 29.3, 28.9, 27.8, 27.7, 27.3, 26.0, 25.9, 25.7, 23.8, 23.1, 22.6, 22.3, 20.6, 20.5, 18.9, 18.5, 18.4, 17.9, 14.0, 13.4, −4.8, −4.9.

Molecular weight for $C_{73}H_{106}N_4NaO_{11}Si$ (M+Na)$^+$ Calc. 1265.75. Found 1265.6.

468: $^1$H NMR (DMSO-d$_6$, 400 MHz) δ 11.31 (s, 1H), 7.80-7.83 (m, 1H), 7.50 (s, 1H), 7.40-7.42 (m, 2H), 7.19-7.31 (m, 7H), 6.97-7.00 (m, 1H), 6.86-6.88 (m, 4H), 5.31-5.32 (m, 1H), 4.70 (d, J=5.6 Hz, 1H), 4.50 (d, J=3.6 Hz, 1H), 4.26-4.32 (m, 1H), 3.85-3.99 (m, 2H), 3.72 (s, 6H), 3.65-3.69 (m, 3H), 3.08-3.18 (m, 2H), 2.89-2.97 (m, 7H), 2.16-2.40 (m, 4H), 0.83-1.99 (m, 43H), 0.73 (s, 9H), 0.65 (s, 3H), −0.036 (s, 3H), −0.12 (s, 3H). $^{13}$C NMR (DMSO-d$_6$, 100 MHz) δ 168.8, 162.5, 157.9, 155.5, 150.3, 144.9, 143.2, 139.7, 135.7, 135.5, 129.7, 127.7, 127.6, 126.5, 121.7, 113.0, 111.0, 85.2, 80.4, 79.9, 76.0, 72.6, 70.4, 63.9, 63.4, 59.6, 56.0, 55.5, 49.4, 45.0, 38.3, 38.2, 36.5, 36.0, 35.6, 35.1, 33.8, 31.3, 31.2, 30.1, 29.3, 28.9, 27.8, 27.7, 27.3, 26.0, 25.9, 25.6, 23.8, 23.1, 22.6, 22.3, 20.6, 20.5, 18.9, 18.5, 18.4, 17.9, 14.0, 13.4, 11.6, −4.8, −4.9.

Molecular weight for $C_{73}H_{106}N_4NaO_{11}Si$ (M+Na)$^+$ Calc. 1265.75. Found 1265.6.

Compound 469:

To a solution of compound 468 (410 g, 0.330 mmol) in CH$_2$Cl$_2$ (30 mL), DMAP (121 mg, 0.989 mmol) and succinic anhydride (66 mg, 0.660 mmol) were added. The reaction mixture was stirred overnight at room temperature. Silica gel column chromatography (7% MeOH in DCM with 7% Et$_3$N, $R_f$=0.35) of the crude mixture without aqueous work-up gave the compound 469 as the corresponding triethylammonium salt (320 mg, 0.221 mmol, 67%).

$^1$H NMR (DMSO-d$_6$, 400 MHz) δ 11.40 (brs, 1H), 7.98 (t, J=5.2 Hz, 1H), 7.66 (s, 1H), 7.49 (d, J=7.6 Hz, 2H), 7.34-7.38 (m, 6H), 7.27 (t, J=7.2 Hz, 1H), 7.05 (t, J=5.4 Hz, 1H), 6.93-6.95 (m, 4H), 5.38-5.39 (m, 1H), 5.26-5.28 (m, 1H), 4.70 (d, J=2.8 Hz, 1H), 4.31-4.39 (m, 2H), 3.90-3.94 (m, 3H), 3.79 (s, 6H), 2.96-3.06 (m, 6H), 2.57-2.69 (m, 5H), 2.23-2.37 (m, 2H), 1.83-2.04 (m, 5H), 0.90-1.58 (m, 42H), 0.75 (s, 9H), 0.72 (s, 3H), −0.027 (s, 3H), −0.12 (s, 3H). $^{13}$C NMR (DMSO-d$_6$, 100 MHz) δ 173.2, 170.9, 169.0, 162.3, 158.0, 155.5, 150.3, 144.7, 144.6, 139.7, 135.5, 135.4, 129.7, 127.7, 127.6, 126.5, 121.7, 113.0, 109.5, 85.4, 80.9, 77.9, 74.9, 72.6, 70.7, 63.5, 62.5, 56.0, 55.5, 51.9, 49.4, 45.4, 41.7, 38.3, 36.5, 36.0, 35.6, 35.1, 33.7, 31.3, 31.2, 29.2, 28.8, 27.8, 27.7, 27.3, 26.0, 25.8, 25.3, 23.8, 23.1, 22.6, 22.3, 20.5, 18.9, 18.4, 17.4, 11.6, 10.1, 7.1, −5.2, −5.6. Molecular weight for $C_{77}H_{109}N_4O_{14}Si$ (M−H)$^−$ Calc. 1341.77. Found 1341.7.

Compound 470:

To a solution of compound 469 (300 mg, 0.208 mmol) in DMF (20 mL), HBTU (87 mg, 0.229 mmol), iPr$_2$NEt (0.181 mL, 1.04 mmol), and CPG-NH$_2$ (Prime Synthesis CPG-500, NH$_2$ loading=140 mmol/g) (1.64 g, 0.229 mmol) were successively added. The mixture was shaken for 2 hours, then filtered, washed with CH$_2$Cl$_2$, and dried in vacuo. The residual amino groups were capped by shaking for 30 minutes with pyridine (15 mL), acetic anhydride (5 mL), and triethylamine (1 mL). After filtering, washing with CH$_2$Cl$_2$ (20 mL×2), then 50% MeOH/CH$_2$Cl$_2$ (20 mL), and drying in vacuo gave compound 470 (1.73 g).

Loading: 68 μmol/g.

Compound 471:

To a solution of compound 467 (100 mg, 0.0885 mmol) in CH$_2$Cl$_2$ (1 mL), DMAP (2 mg, 0.221 mmol), 2-cyanoethyl N,N-diisopropylchlorophosphoramidite (0.049 mL, 0.221 mmol) and N,N-diisopropylethylamine (0.077 mL, 0.443 mmol) were added at 0° C. The reaction mixture was stirred at room temperature for 2 hours under argon atmosphere. The reaction mixture was diluted with CH$_2$Cl$_2$ and washed with saturated NaHCO$_3$ solution. The organic layer was separated and dried over anhydrous Na$_2$SO$_4$. After filtration and evaporation, the crude material was purified by silica gel column chromatography (EtOAc:Hexane=1:1 to 2:1) to give 471 (82 mg, 0.0568 mmol, 64%, $R_f$=0.56 developed by EtOAc:Hexane=4:1). $^{31}$P NMR (DMSO-d$_6$, 162 MHz) δ 148.03, 147.39. Molecular weight for $C_{82}H_{123}N_6NaO_{12}PSi$ (M+Na)$^+$ Calc. 1465.86. Found 1466.8.

Synthesis of Compounds in Scheme 43

Compound 2312.

As suspension of compound 1 (5 mmol) in POCl3 (50 ml) is heated under reflux for 45 min. After cooling to room temperature the solution is poured onto crushed ice and the product is extracted with dichloromethane. Evaporation of the solvent gives compound 2.

Compound 2313.

Compound 2 (5 mmol) is added to a solution of sodium (0.3 g) in benzyl alcohol (20 ml). The mixture is heated at 115 C for 15 min. The resulting solution is cooled to room temperature and neutralized with glacial acetic acid to give compound 3.

Compound 2314.

To a solution of 35% HF/Pyridine (10 ml) is added compound 3 (2 mmol) at −20 C. To this suspension tert. butylnitrite (1 ml) is added and the mixture is stirred at 10 C until the reaction is complete. Workup of the reaction and extraction with ethyl acetate gives compound 4.

Compound 2315.

To a solution of 4 (5 mmol) in absolute ethanol (200 ml) is added 200 mg of 5% Palladium on carbon. The mixture is hydrogenated on a Parr shaker for 6 h. Filtration of the reaction mixture through Celite and evaporation gives compound 5.

Compound 2316.

To a solution of compound 5 (5 mmol)) in dry pyridine (20 ml) is added DMTr-Cl (6.5 mmol) and the reaction mixture is stirred at room temperature for 3 h. The reaction mixture is diluted with dichloromethane (100 ml) and washed with water. Organic layer is dried and evaporated. Purification of the residue using silica gel column chromatography gives compound 6.

Compound 2317.

To a solution of 6 (3 mmol) in dry dichloromethane is added 2-cyanoethyl-N, N,N,N-tetraisopropylphosphoro diamidite (4 mmol) and dicyanoimidazole (2.5 mmol) under an argon atmosphere. The mixture is stirred at room temperature for 4 h, diluted with dichloromethane and washed with saturated sodium bicarbonate solution. Organic layer is dried over sodium sulfate, evaporated and the residue is purified to give compound 7.

Synthesis of Oligonucleotides

Synthesis and purification of unconjugated and ligand conjugated oligonucleotides are performed according to the procedures and protocols described in PCT publication number WO2009/073809, contents of which are herein incorporated in their enerities.

Postsynthetic Purine Modification of Oligonucleotides
Scheme 45

After on column solid phase synthesis of the oligonucleotide, the support bound oligonucleotide 3001 or 3003 is treated with R'—N(R")—H of choice at ambient or at elevated temperature followed by deprotection of the 2'-O-silyl group if present yields the desired $N^2$-alkylated oligonucleotides 3002 or 3004. The modified oligonucleotide is purified by ion-exchange or RP-HPLC, analyzed by LC-EMS.

Compounds from Scheme 46-1
Synthesis of Compound 6002.

A solution of compound 2 (5 mmol, this is prepared as described in the literature, J. shi, J. Du, T. Ma. K. W. Pankiewicz, S. E. Patterson, P. M. Tharnish, T. M. McBrayer, L. J. Stuyver, M. J. Otto, C. K. Chu, R. F. Schinazi, K. a. Watanabe, Bioorg. Med. Chem., 2005, 13, 1641-1652) in DMF (30 mL) is degassed and purged with argon. To this solution allyltrifluoroacetamide (20 mmol), triethyl amine (10 mmol) bis (triphenylphosphine)palladium chloride (0.5 mmol) and copper iodide (1 mmol) are added and the mixture is heated at 80 C for 18 h. The solvent is evaporated and the product is purified by silica gel column chromatography to give pure 3.

Synthesis of Compound 6002.

A solution of compound 6001 in anhydrous pyridine in treated with 1 molar equivalent of DMTr-C1 in the presence of DMAP (20 mol %) to obtain compound 6002.

Compound 6002 is converted to its corresponding phosphoramidite and CPG (solid support) as described previously.

Compounds from Scheme 46-2

AllylaminoFU 6001:A solution of 5-iodo-2'-fluoroU 286 (1.0 g) and allyltrifluoroacetamide (7 ml) in a mixture of anhydrous DMF (15 ml) and triethylamine (1.5 ml) was degassed by bubbling argon. To this solution dichlorobis (triphenylphosphine)palladium (100 mg) and copper iodide (50 mg) were added and the mixture was heated at 80° C. for 23 h under an argon atmosphere. Solvent was evaporated and the residue was purified by silica gel column chromatography to give 0.78 g of pure 6001.

Compound 6002':

A solution of compound 26 (0.7 g) in methanol (100 ml) was added 10% Pd/C (100 mg) and the mixture was hydrogenated at 35 psi on a Parr hydrogenation apparatus for 24 h. The reaction mixture was filtered through a Celite pad and the filtrate was evaporated. The residue was purified by silica gel column chromatography using a gradient of 0-10% methanol in dichloromethane to give 0.52 g of pure 6002'. $^1$H NMR (400 MHz, DMSO) δ 11.39 (s, 1H), 9.39 (t, J=5.3, 1H), 7.76 (s, 1H), 5.87 (dd, J=18.0, 2.0, 1H), 5.59 (d, J=10, 1H), 5.20 (t, J=5.0, 1H), 5.12-4.91 (m, 1H), 4.14 (dd, J=20.7, 4.6, 1H), 3.91-3.69 (m, 3H), 3.65-3.47 (m, 1H), 3.20-3.11 (m, 2H), 2.15 (dd, J=12.1, 7.1, 2H), 1.72-1.50 (m, 2H). $^{19}$F NMR (376 MHz, DMSO) δ −77.17 (s), −204.83 (m). MS: calcd: 399.11. Found: 400.2.

Compound 6003A:

To a solution of 6002' (1.37 g g, 3.4 mmol) in dry pyridine (15 ml) was added 4,4'-DMTr-Cl (1.45 g, 4.28 mmol) and the mixture was stirred at room temperature overnight. The reaction mixture was diluted with dichloromethane (150 ml) and washed with water (50 ml). Organic layer was evaporated and the residue was coevaporated with toluene. The crude product was purified by silica gel column chromatography to give 2.4 g of 6003A. $^1$H NMR (400 MHz, DMSO) δ 11.48 (s, 1H), 9.37 (t, J=5.5, 1H), 7.46 (s, 1H), 7.39 (d, J=7.5, 2H), 7.34-7.18 (m, 8H), 6.88 (dd, J=9.0, 2.3, 4H), 5.88 (d, J=20.9, 1H), 5.63 (d, J=7.1, 1H), 5.14 (dd, J=53.6, 4.7, 1H), 4.42-4.27 (m, 1H), 4.00 (dd, J=8.0, 3.8, 1H), 3.73 (s, 6H), 3.34 (s, 1H), 2.10-1.82 (m, 2H), 1.51 (td, J=13.4, 6.8, 2H). $^{19}$F NMR (376 MHz, DMSO) δ −77.18 (s), −201.60 (m).

Compound 6003B:

To a solution of 6003A (1 mmol) in dichloromethane (10 ml) is added 2-cyanoethyl-tetraisopropylphosphoramidite (1.3 mmol) and dicyanoimidazole (0.9 mmol). The mixture is stirred at room temperature for 6 h, diluted with dichloromethane and washed with sodium bicarbonate solution. Organic layer is dried over sodium sulfate and evaporated. The residue is subjected to column chromatography to give compound 6003B.

Compound 6004'A:

In a similar manner as described for 6003A, dimethoxytritylation of 6001 in dry pyridine and purification gave 6004'A. $^1$H NMR (400 MHz, DMSO) δ 11.54 (d, J=24.4, 1H), 9.59 (t, J=5.4, 1H), 7.70 (s, 1H), 7.45-7.34 (m, 2H), 7.34-7.18 (m, 8H), 6.93-6.79 (m, 4H), 6.37 (tt, J=17.0, 8.4, 1H), 5.83 (t, J=18.3, 2H), 5.73 (s, OH), 5.60 (d, J=7.1, 1H), 5.25-5.05 (m, 1H), 4.33 (ddd, J=22.7, 12.6, 8.0, 1H), 4.00 (dd, J=5.7, 2.8, 1H), 3.79-3.65 (m, 8H), 3.69 (d, J=7.9, 7H), 3.64-3.50 (m, 1H), 3.28-3.17 (m, 2H). $^{19}$F NMR (376 MHz, DMSO) δ −77.19 (s), −202 (m).

Compound 6004'B:

To a solution of 6004'A (1 mmol) in dichloromethane (10 ml) is added 2-cyanoethyl-tetraisopropylphosphoramidite (1.3 mmol) and dicyanoimidazole (0.9 mmol). The mixture is stirred at room temperature for 6 h, diluted with dichloromethane and washed with sodium bicarbonate solution. Organic layer is dried over sodium sulfate and evaporated. The residue is subjected to column chromatography to give compound 6004'B.

Compounds from Scheme 47-1

2'-Deoxy-2'-F-C5-allylamino C nucleoside 6006 is obtained from 2'-deoxy-2'-F C (6004) as shown in the Scheme 35. The nucleoside 6006 is converted to corresponding phosphoramidite and solid support as described previously Compounds from Scheme 47-2

AllylaminoFC 6006': A solution of 5-iodo-2'-fluoroC 6005' (4.7 g, 12.63 mmol) and allyltrifluoroacetamide (14 g, 91.5 mmol) in a mixture of anhydrous DMF (45 ml) and triethylamine (5.6 ml, 40 mmol) was degassed by bubbling argon. To this solution dichlorobis(triphenylphosphine)palladium (440 mg, 0.63 mmol) and copper iodide (240 mg, 1.26 mmol) was added and the mixture was heated at 80° C. for 18 h under an argon atmosphere. Solvent was evaporated and the residue was purified by silica gel column chromatography using a gradient of 0-20% methanol in dichloromethane to give 0.7 g of pure 6006'. $^1$H NMR (400 MHz, DMSO) δ 9.56 (t, J=5.1, 1H), 8.57 (s, 1H), 8.25 (s, 1H), 7.46 (s, 1H), 7.10 (s, 1H), 6.40 (d, J=15.6, 1H), 5.92-5.80 (m, 2H), 5.53 (d, J=6.3, 1H), 5.29 (t, J=4.8, 1H), 4.88 (dd, J=53.3, 3.9, 1H), 4.23-4.10 (m, 1H), 3.91-3.77 (m, 4H), 3.58 (ddd, J=12.3, 4.5, 2.6, 1H), 2.86 (t, J=6.8, 2H). $^{19}$F NMR (376 MHz, DMSO) δ −77.05 (s), −203.75 (m).

Compound 6007:

To a solution of 6006' (0.52 g, 1.3 mmol) in dry DMF (8 ml) was added benzoic anhydride (326 mg, 1.3 mmol) and the mixture was stirred at room temperature for 26 h. DMF was evaporated and the product was purified by silica gel column chromatography using 0-10% methanol in dichloromethane to give 0.31 g of 6007.

Compound 6008A:

To a solution of compound 6007 (1.3 g, 2.6 mmol) in dry pyridine (15 ml) was added 4,4'-DMTr-Cl (1.1 g, 3.25 mmol) and the reaction mixture was stirred at room temperature for 18 h. The reaction mixture was diluted with dichloromethane (100 ml) and the organic layer was washed with water (50 ml). Organic layer was dried over sodium sulfate and evaporated. The residue was co-evaporated with toluene and purified by silica gel column chromatography using a gradient of 0-6% methanol in dichloromethane as the eluent. The appropriate fractions containing the product were collected and evaporated to give pure 6008A.

Compound 6008B:

To a solution of 6008A (1 mmol) in dichloromethane (10 ml) is added 2-cyanoethyl-tetraisopropylphosphoramidite (1.3 mmol) and dicyanoimidazole (0.9 mmol). The mixture is stirred at room temperature for 6 h, diluted with dichloromethane and washed with sodium bicarbonate solution. Organic layer is dried over sodium sulfate and evaporated. The residue is subjected to column chromatography to give compound 6008B.

Serum Stability Assay for Modified Single and Double Stranded Oligonucleotides.

A medium throughput assay for initial sequence-based stability selection is performed by the "stains all" approach. To perform the assay, an siRNA duplex is incubated in 90% human serum at 37° C. Samples of the reaction mix are quenched at various time points (at 0 min., 15, 30, 60, 120, and 240 min.) and subjected to electrophoretic analysis. Cleavage of the oligonucleotide over the time course provided information regarding the susceptibility of the oligonucleotides to serum nuclease degradation.

Exonuclease Stability Assay for Modified Single and Double Stranded Oligonucleotides.

Single or double stranded oligonucleotides is treated snake venom phosphodiesterase enzyme (SVDP, purchased from Sigma) as reported in the literature (Cummins, L. L., Owens, S. R., Risen, L. M., Lesnik, E. A., Freier, S. M., McGee, D., Guinosso, C. J., and Cook, P. D. (1995) Characterization of fully 2¢-modified oligoribonucleotide hetero and homoduplex hybridization and nuclease sensitivity, *Nucleic Acids Res.* 23, 2019-2024 Reference) and analyzed by the "stains all" approach to obtain resistance and half life of the oligonucleotide towards SVDP Stability Assay for Modified Single and Double Stranded Oligonucleotides in Cell Extracts.

Cell extract stability of single and double stranded modified oligonucleotides are determined as reported in the literature (*Nucleic Acids Res.* 1979 February; 6(2): 767-780. *Nucleic Acids Research,* 1991, Vol. 19, No. 20 5743-5748).

FVII In Vivo Evaluation Using the Modified Single and Double Stranded Oligonucleotides In Vivo Rodent Factor VII and ApoB Silencing Experiments.

C57BL/6 mice (Charles River Labs, Mass.) and Sprague-Dawley rats (Charles River Labs, Mass.) receives either saline or siRNA in desired formulations via tail vein injection at a volume of 0.01 mL/g. At various time points post-administration, animals are anesthesized by isofluorane inhalation and blood is collected into serum separator tubes by retro orbital bleed. Serum levels of Factor VII protein are determined in samples using a chromogenic assay (Coaset Factor VII, DiaPharma Group, Ohio or Biophen FVII, Aniara Corporation, Ohio) according to manufacturer protocols. A standard curve is generated using serum collected from saline treated animals. In experiments where liver mRNA levels are assessed, at various time points post-administration, animals are sacrificed and livers are harvested and snap frozen in liquid nitrogen. Frozen liver tissue is ground into powder. Tissue lysates are prepared and liver mRNA levels of Factor VII and apoB are determined using a branched DNA assay (QuantiGene Assay, Panomics, Calif.).

ApoB In Vivo Evaluation Using the Modified Single and Double Stranded Oligonucleotides.

The assay is performed as reported by Soutschek et al., (*Nature,* 2004, 432, 173)

PCSK9 In Vivo Evaluation Using the Modified Single and Double Stranded Oligonucleotides.

The assay is performed as reported by Frank-Kamenetsky et al., (*PNAS,* 2008, 105, 11915-11920)

Luciferase Assay for In Vitro Gene Silencing Using Single and Double Stranded Oligonucleotides.

Dual Luciferase Gene Silencing Assays:

In vitro activity of siRNAs is determined using a high-throughput 96-well plate format luciferase silencing assay. Assays are performed in one of two possible formats. In the first format, HeLa SS6 cells are first transiently transfected with plasmids encoding firefly (target) and *renilla* (control) luciferases. DNA transfections are performed using Lipofectamine 2000 (Invitrogen) and the plasmids gWiz-Luc (Aldevron, Fargo, N. Dak.) (200 ng/well) and pRL-CMV (Promega, Madison, Wis.) (200 ng/well). After 2 h, the plasmid transfection medium is removed, and the firefly luciferase targeting single or double stranded oligonucleotides are added to the cells at various concentrations. In the second format, HeLa Dual-luc cells (stably expressing both firefly and *renilla* luciferase) are directly transfected with firefly luciferase targeting siRNAs. Oligonucleotide transfections are performed using either TransIT-TKO (Minis, Madison, Wis.) or Lipofectamine 2000 according to manufacturer protocols. After 24 h, cells are analyzed for both firefly and *renilla* luciferase expression using a plate luminometer (VICTOR$^2$, PerkinElmer, Boston, Mass.) and the Dual-Glo Luciferase Assay kit (Promega). Firefly/*renilla* luciferase expression ratios are used to determine percent gene silencing relative to mock-treated controls.

PCSK9 siRNA In Vitro Screening in HepG2 Cells and Primary Cynomolgus Monkey Hepatocytes.

For siRNA transfection experiments, HepG2 or primary hepatocyte cells are seeded at 2.5_104 cells per well in 96-well plates. siRNA are transfected by using Lipofectamine 2000 according to the manufacturer's protocols. Cells are lysed 24 h after transfection, and PCSK9 mRNA levels are quantified by using the branched-DNA-technology-based QuantiGene Reagent System (Panomics), according to the manufacturer's protocols. PCSK9 mRNA levels are normalized to GAPDH mRNA.

ApoB In Vitro Evaluation Using the Modified Single and Double Stranded Oligonucleotides.

The assay is performed as reported by Soutschek et al., (*Nature,* 2004, 432, 173)

Tm Measurement

Thermal melting of duplexes were evaluated as previously reported (Xia et al, ACS Chem Biology, 2006, 1, 176-183).

Each sample contained 4 μM each strand in 100 mM NaCl, 10 mM phosphate, 0.1 mM EDTA, pH 7.

The Tm measurement of various MOE substituted containing oligonucleotides are shown in the table below. Surprisingly, the presence of methyl substituent(s) in the MOE moiety increases the thermal melting (Tm) by 3-4° C.

| Tm Comparison of Substituted MOEs | | |
|---|---|---|
| Control | 47 | |
| MOE (Teo, AD-23140) | 50.4 | 3.4 |
| (1R)-$^{1\text{-}Me}$MOE (Teo1) | 50.4 | 3.4 |
| (1S)-$^{1\text{-}Me}$MOE (Teo2) | 50.5 | 3.5 |
| (2R)-$^{2\text{-}Me}$MOE (Teo3) | 51.5 | 4.5 |
| (2S)-$^{2\text{-}Me}$MOE (Teo4) | 51.5 | 4.5 |
| (1R,2R)-$^{1,2\text{-}diMe}$MOE (Teo5) | 51.4 | 4.4 |
| (1S,2S)-$^{1,2\text{-}diMe}$MOE (Teo6) | 49.5 | 2.5 |
| (1R,2S)-$^{1,2\text{-}diMe}$MOE (Teo7) | 51.5 | 4.5 |
| (1S,2R)-$^{1,2\text{-}diMe}$MOE (Teo8) | 49.6 | 2.6 |

Scheme 48: Compounds used in Table 4

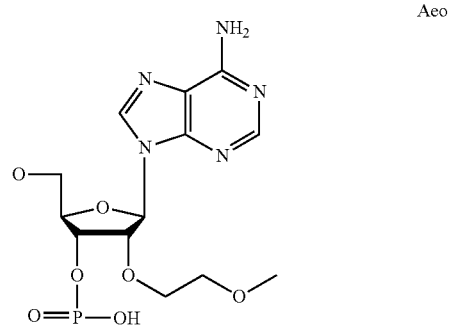

Aeo

TABLE 4

| Target | ID | S/AS | Sequence 5'-3' | SEQ ID NO: |
|---|---|---|---|---|
| PTEN | A-59692.1 | AS | PusUfsgUfscUfscUfsgGfsuCfscUfsusAfscsUfsus(Aeo4s)(Aeo4) | 40 |
| PTEN | A-59693.1 | AS | P(Aeo4s)UfsgUfscUfscUfsgGfsuCfscUfsusAfscsUfsus(Aeo4s)(Aeo4) | 41 |
| PTEN | A-59694.1 | AS | P(Teo4s)UfsgUfscUfscUfsgGfsuCfscUfsusAfscsUfsus(Aeo4s)(Aeo4) | 42 |
| PTEN | A-55156.1 | N/A | UfsGUfsCUfsCUfsGGfsUCfsCUfsUsAfsCsUfsUs(Aeos)(Aeo) | 43 |
| PTEN | A-55311.1 | N/A | UfsgUfscUfscUfsgGfsuCfscUfsusAfscsUfsus(Aeos)(Aeo) | 44 |
| PTEN | A-55330.1 | N/A | usUfsGUfsCUfsCUfsGGfsUCfsCUfsUsAfsCsUfsUs(Aeos)(Aeo) | 45 |
| PTEN | A-55331.1 | N/A | usUfsgUfscUfscUfsgGfsuCfscUfsusAfscsUfsus(Aeos)(Aeo) | 46 |
| PTEN | A-59873.1 | S | AAGUAAGGACCAGAGACAAdTdT | 47 |
| PTEN | A-59876.1 | S | AAGUAAGGACCAGAGACAA | 48 |
| PTEN | A-53611.2 | S | AAGUAAGGACCAGAGACAAdTsdT | 49 |
| PTEN | A-59148.1 | AS | p(Teo4s)UfsgUfscUfscUfsgGfsuCfscUfsusAfscsUfsus (Aeos)(Aeo) | 50 |
| PTEN | A-59149.1 | AS | ps(Teo4s)UfsgUfscUfscUfsgGfsuCfscUfsusAfscsUfsus (Aeos)(Aeo) | 51 |
| PTEN | A-59717.2 | S | UUGUCUCUGGUCCUUACUUAA | 52 |
| PTEN | A-60039.1 | S | uUgUcUcUgGuCcUuAcUuAa | 53 |
| PTEN | A-55495.1 | AS | Q69susUfsgUfscUfscUfsgGfsuCfscUfsusAfscsUfsus(Aeos)(Aeo) | 54 |
| PTEN | A-55496.1 | AS | dTsusUfsgUfscUfscUfsgGfsuCfscUfsusAfscsUfsus(Aeos)(Aeo) | 55 |
| PTEN | A-59427.1 | AS | P(phe)usUfsgUfscUfscUfsgGfsuCfscUfsusAfscsUfsus(Aeos)(Aeo) | 56 |
| PTEN | A-59428.1 | AS | PS(phe)usUfsgUfscUfscUfsgGfsuCfscUfsusAfscsUfsus(Aeos)(Aeo) | 57 |
| PTEN | A-59429.1 | AS | P(pshe)usUfsgUfscUfscUfsgGfsuCfscUfsusAfscsUfsus(Aeos)(Aeo) | 58 |
| PTEN | A-59430.1 | AS | PS(pshe)usUfsgUfscUfscUfsgGfsuCfscUfsusAfscsUfsus(Aeos)(Aeo) | 59 |
| PTEN | A-64228.1 | AS | PusUfsgUfscUfscUfsgGfsuCfscUfsusAfscsUfsus(Aeas)(Aea) | 60 |
| PTEN | A-64229.1 | AS | P(Teas)UfsgUfscUfscUfsgGfsuCfscUfsusAfscsUfsus(Aeas)(Aea) | 61 |
| PTEN | A-64230.1 | AS | P(Teas)UfsgUfscUfscUfsgGfsuCfscUfsusAfscsUfsus(Aeos)(Aeo) | 62 |
| PTEN | A-63828.1 | AS | PY33sUfsgUfscUfscUfsgGfsuCfscUfsusAfscsUfsus(Aeos)(Aeo) | 63 |
| PTEN | A-63829.1 | AS | PY33UfsgUfscUfscUfsgGfsuCfscUfsusAfscsUfsus(Aeos)(Aeo) | 64 |

299
-continued

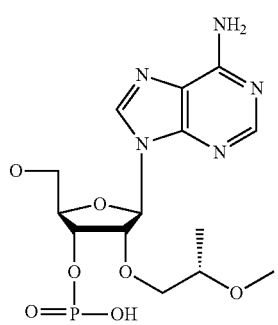

Aeo4

300
-continued

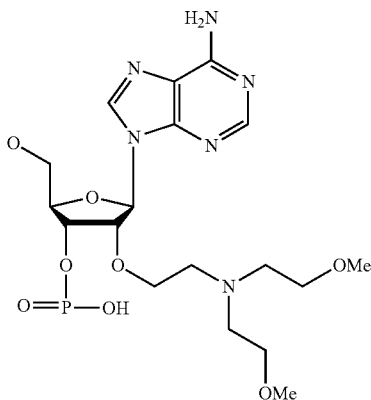

Aea

TABLE 5

Luciferase single and double stranded siRNA sequence for screening

| Target | ID | S/AS | Sequence 5'-3' | SEQ ID NO: |
|---|---|---|---|---|
| Luc | A-53174.1 | AS | UCGAAGuACUcAGCGuAAG(Teo1)(Teo1) | 65 |
| Luc | A-53175.1 | AS | UCGAAGuAC(Teo1)cAGCGuAAGdTdT | 66 |
| Luc | A-53176.1 | AS | (Teo1)CGAAGuACUcAGCGuAAGdTdT | 67 |
| Luc | A-53177.1 | AS | UCGAAG(Teo1)ACUcAGCGuAAGdTdT | 68 |
| Luc | A-53178.1 | AS | UCGAAGuACUcAGCGuAAG(Teo2)(Teo2) | 69 |
| Luc | A-53179.1 | AS | UCGAAGuAC(Teo2)cAGCGuAAGdTdT | 70 |
| Luc | A-53180.1 | AS | (Teo2)CGAAGuACUcAGCGuAAGdTdT | 71 |
| Luc | A-53181.1 | AS | UCGAAG(Teo2)ACUcAGCGuAAGdTdT | 72 |
| Luc | A-53182.1 | AS | UCGAAGuACUcAGCGuAAG(Teo3)(Teo3) | 73 |
| Luc | A-53183.1 | AS | UCGAAGuAC(Teo3)cAGCGuAAGdTdT | 74 |
| Luc | A-53184.1 | AS | (Teo3)CGAAGuACUcAGCGuAAGdTdT | 75 |
| Luc | A-53185.1 | AS | UCGAAG(Teo3)ACUcAGCGuAAGdTdT | 76 |
| Luc | A-53186.1 | AS | UCGAAGuACUcAGCGuAAG(Teo4)(Teo4) | 77 |
| Luc | A-53187.1 | AS | UCGAAGuAC(Teo4)cAGCGuAAGdTdT | 78 |
| Luc | A-53188.1 | AS | (Teo4)CGAAGuACUcAGCGuAAGdTdT | 79 |
| Luc | A-53189.1 | AS | UCGAAG(Teo4)ACUcAGCGuAAGdTdT | 80 |
| Luc | A-53190.1 | AS | UCGAAGuACUcAGCGuAAG(Teo5)(Teo5) | 81 |
| Luc | A-53191.1 | AS | UCGAAGuAC(Teo5)cAGCGuAAGdTdT | 82 |
| Luc | A-53192.1 | AS | (Teo5)CGAAGuACUcAGCGuAAGdTdT | 83 |
| Luc | A-53193.1 | AS | UCGAAG(Teo5)ACUcAGCGuAAGdTdT | 84 |

TABLE 5-continued

Luciferase single and double stranded siRNA sequence for screening

| Target | ID | S/AS | Sequence 5'-3' | SEQ ID NO: |
|---|---|---|---|---|
| Luc | A-53194.1 | AS | UCGAAGuACUcAGCGuAAG(Teo6)(Teo6) | 85 |
| Luc | A-53195.1 | AS | UCGAAGuAC(Teo6)cAGCGuAAGdTdT | 86 |
| Luc | A-53196.1 | AS | (Teo6)CGAAGuACUcAGCGuAAGdTdT | 87 |
| Luc | A-53197.1 | AS | UCGAAG(Teo6)ACUcAGCGuAAGdTdT | 88 |
| Luc | A-53198.1 | AS | UCGAAGuACUcAGCGuAAG(Teo7)(Teo7) | 89 |
| Luc | A-53199.1 | AS | UCGAAGuAC(Teo7)cAGCGuAAGdTdT | 90 |
| Luc | A-53200.1 | AS | (Teo7)CGAAGuACUcAGCGuAAGdTdT | 91 |
| Luc | A-53201.1 | AS | UCGAAG(Teo7)ACUcAGCGuAAGdTdT | 92 |
| Luc | A-53202.1 | AS | UCGAAGuACUcAGCGuAAG(Teo8)(Teo8) | 93 |
| Luc | A-53203.1 | AS | UCGAAGuAC(Teo8)cAGCGuAAGdTdT | 94 |
| Luc | A-53204.1 | AS | (Teo8)CGAAGuACUcAGCGuAAGdTdT | 95 |
| Luc | A-53205.1 | AS | UCGAAG(Teo8)ACUcAGCGuAAGdTdT | 96 |
| Luc | A-53207.1 | AS | UCGAAGuACUcAGCGuAAG(Teo)(Teo) | 97 |
| Luc | A-53208.1 | AS | UCGAAGuAC(Teo)cAGCGuAAGdTdT | 98 |
| Luc | A-53209.1 | AS | (Teo)CGAAGuACUcAGCGuAAGdTdT | 99 |
| Luc | A-53210.1 | AS | UCGAAG(Teo)ACUcAGCGuAAGdTdT | 100 |
| Luc | A-59698.1 | AS | UCGAAGuACUcAGCGuAAG(Teos)(Teo) | 101 |
| Luc | A-59699.1 | AS | UCGAAGuACUcAGCGuAAG(Teo1s)(Teo1) | 102 |
| Luc | A-59700.1 | AS | UCGAAGuACUcAGCGuAAG(Teo2s)(Teo2) | 103 |
| Luc | A-59701.1 | AS | UCGAAGuACUcAGCGuAAG(Teo3s)(Teo3) | 104 |
| Luc | A-59702.1 | AS | UCGAAGuACUcAGCGuAAG(Teo4s)(Teo4) | 105 |
| Luc | A-59703.1 | AS | UCGAAGuACUcAGCGuAAG(Teo5s)(Teo5) | 106 |
| Luc | A-59704.1 | AS | UCGAAGuACUcAGCGuAAG(Teo6s)(Teo6) | 107 |
| Luc | A-59705.1 | AS | UCGAAGuACUcAGCGuAAG(Teo7s)(Teo7) | 108 |
| Luc | A-59706.1 | AS | UCGAAGuACUcAGCGuAAG(Teo8s)(Teo8) | 109 |

Scheme 49: Compounds used in Table 5

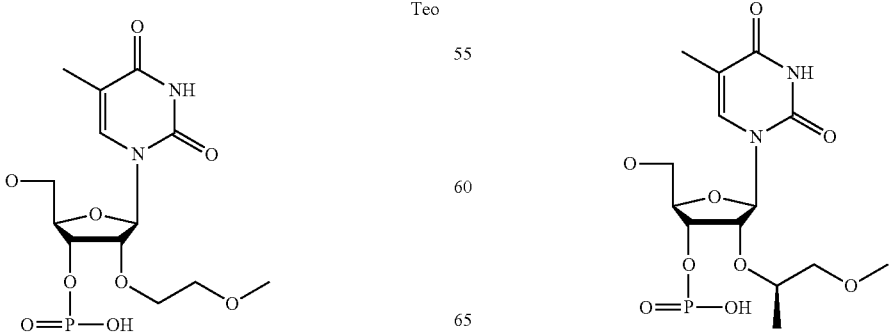

303
-continued

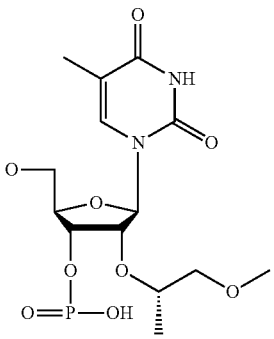
Teo2

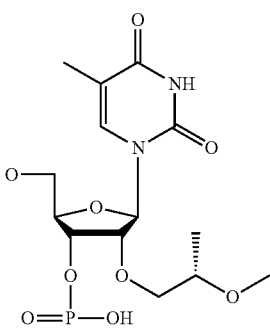
Teo4

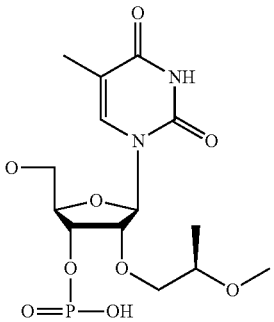
Teo3

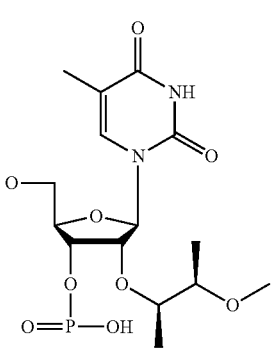
Teo5

304
-continued

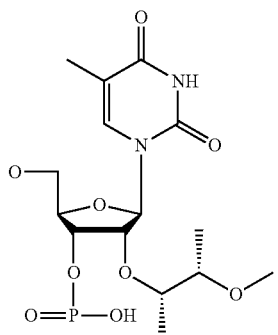
Teo6

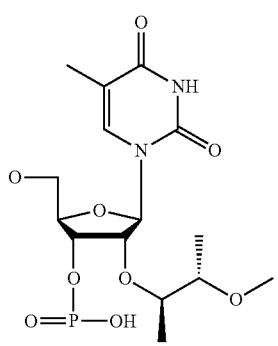
Teo7

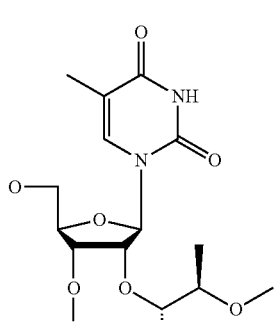
Teo8

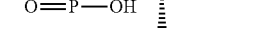

EQUIVALENTS

Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed.

The invention claimed is:

1. A nucleoside represented by formula (3):

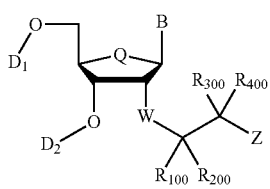

(3)

or isomers thereof, wherein:

one of $D_1$ and $D_2$ is H or a hydroxyl protecting group and the other of $D_1$ and $D_2$ is H, a hydroxyl protecting group, or a reactive phosphorus group; with the proviso that when one of $D_1$ and $D_2$ is H, the other of $D_1$ and $D_2$ is either H or a hydroxyl protecting group;

B is selected from the group consisting of hydrogen, unsubstituted or substituted $C_1$-$C_{24}$ aliphatic, a natural nucleobase, and a universal base;

Q is selected from the group consisting of O, S, $NR_{10}$, and $CH_2$;

W is absent, O, S or NR';

$R_{100}$ and $R_{200}$ are each independently selected from the group consisting of hydrogen, unsubstituted and substituted $C_1$-$C_{24}$ aliphatic, aryl, halogen, 5-14 membered heteroaryl, and 5-14 membered heterocyclic;

$R_{300}$ and $R_{400}$ are each independently selected from the group consisting of hydrogen, unsubstituted or substituted $C_1$-$C_{24}$ aliphatic, aryl, halogen, 5-14 membered heteroaryl, and 5-14 membered heterocyclic; or $R_{300}$ and $R_{400}$ are taken together with the atom to which they are bound to form a carbonyl, thiocarbonyl, $=NR_{20}$, $=N-NR_{20}R_{30}$, or $=N-NR_{20}C(O)R_{10}$;

Z is $OR_{10}$;

$R_{20}$ and $R_{30}$ are each independently selected from the group consisting of hydrogen, acyl, unsubstituted or substituted $C_1$-$C_{24}$ aliphatic, aryl, 5-14 membered heteroaryl, 5-14 membered heterocyclic, $OR_{10}$, $COR_{10}$, $CO_2R_{10}$, and $NR_{10}R_{10}'$; or $R_{20}$ and $R_{30}$ are taken together with the atom to which they are bound to form a 5-14 membered heterocyclic ring; and $R_{10}$ and $R_{10}'$ are each independently hydrogen, unsubstituted or substituted $C_1$-$C_{24}$ aliphatic, aryl, 5-14 membered heteroaryl, or 5-14 membered heterocyclic, wherein, in each occurrence, the substituent group on the substituted $C_1$-$C_{24}$ aliphatic is selected from the group consisting of halo, hydroxy, oxo, nitro, haloalkyl, alkyl, alkaryl, aryl, aralkyl, alkoxy, aryloxy, amino, acylamino, alkylcarbamoyl, arylcarbamoyl, aminoalkyl, alkoxycarbonyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureidos, provided that at least one $R_{100}$, $R_{200}$, $R_{300}$, and $R_{400}$ is methyl.

2. The nucleoside of claim 1, represented by formula (5):

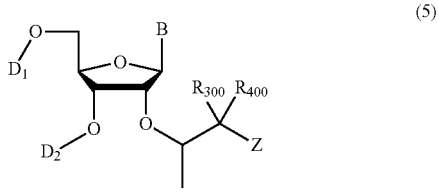

or isomers thereof, wherein:

one of $D_1$ and $D_2$ is H, or a hydroxyl protecting group and the other of $D_1$ and $D_2$ is H, a hydroxyl protecting group, or a reactive phosphorus group; with the proviso that when one of $D_1$ and $D_2$ is H, the other of $D_1$ and $D_2$ is either H or a hydroxyl protecting group;

B is selected from the group consisting of hydrogen, unsubstituted or substituted $C_1$-$C_{24}$ aliphatic, a natural nucleobase, and a universal base;

$R_{300}$ and $R_{400}$ are each independently selected from the group consisting of hydrogen, unsubstituted or substituted $C_1$-$C_{24}$ aliphatic, aryl, halogen, 5-14 membered heteroaryl, and 5-14 membered heterocyclic; or $R_{300}$ and $R_{400}$ are taken together with the atom to which they are bound to form a carbonyl, thiocarbonyl, $=NR_{20}$, $=N-NR_{20}R_{30}$, or $=N-NR_{20}C(O)R_{10}$;

Z is $OR_{10}$;

$R_{20}$ and $R_{30}$ for each occurrence are independently selected from the group consisting of hydrogen, acyl, unsubstituted or substituted $C_1$-$C_{24}$ aliphatic, aryl, 5-14 membered heteroaryl, 5-14 membered heterocyclic, $OR_{10}$, $COR_{10}$, $CO_2R_{10}$, and $NR_{10}R_{10}'$; or $R_{20}$ and $R_{30}$ are taken together with the atom to which they are bound to form a 5-14 membered heterocyclic ring; and $R_{10}$ and $R_{10}'$ are each independently hydrogen, an unsubstituted or substituted $C_1$-$C_{24}$ aliphatic, aryl, 5-14 membered heteroaryl, or 5-14 membered heterocyclic.

3. The nucleoside of claim 1, wherein:

B is a natural nucleobase or a universal base;

Q is O;

W is O;

$R_{100}$ and $R_{200}$ are each independently selected from the group consisting of hydrogen, $C_1$-$C_{10}$ aliphatic, aryl, halogen, 5-8 membered heteroaryl, and 5-8 membered heterocyclic;

$R_{300}$ and $R_{400}$ are each independently selected from the group consisting of hydrogen, $C_1$-$C_{10}$ aliphatic, aryl, halogen, 5-8 membered heteroaryl, and 5-8 membered heterocyclic; or $R_{300}$ and $R_{400}$ are taken together with the atom to which they are bound to form a carbonyl, thiocarbonyl, $=NR_{20}$, $=N-NR_{20}R_{30}$, or $=N-NR_{20}C(O)R_{10}$;

$R_{20}$ and $R_{30}$ for each occurrence are independently selected from the group consisting of hydrogen, acyl, $C_1$-$C_{10}$ aliphatic, aryl, 5-8 membered heteroaryl, 5-8 membered heterocyclic, $OR_{10}$, $COR_{10}$, $CO_2R_{10}$, and $NR_{10}R_{10}'$; or $R_{20}$ and $R_{30}$ are taken together with the atom to which they are bound to form a 5-8 membered heterocyclic ring; and $R_{10}$ and $R_{10}'$ are each independently hydrogen, an $C_1$-$C_{10}$ aliphatic, aryl, 5-8 membered heteroaryl, or 5-8 membered heterocyclic.

4. The nucleoside of claim 3, wherein:

$R_{100}$ and $R_{200}$ are each independently selected from the group consisting of hydrogen, $C_1$-$C_{10}$ alkyl, aryl, and 5-8 membered heteroaryl;

$R_{300}$ and $R_{400}$ are each independently selected from the group consisting of hydrogen, $C_1$-$C_{10}$ alkyl, aryl, and 5-8 membered heteroaryl; or $R_{300}$ and $R_{400}$ are taken together with the atom to which they are bound to form a carbonyl; and $R_{10}$ and $R_{10}'$ are each independently hydrogen or $C_1$-$C_{10}$ alkyl.

5. The nucleoside of claim 1, wherein the nucleoside has the formula of

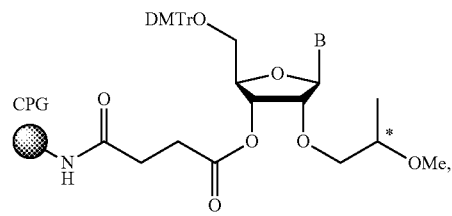

wherein B is U, T, $C^{Ac}$, $A^{Bz}$, or $G^{ibu}$.

6. An oligonucleotide comprising at least one nucleoside of formula (4):

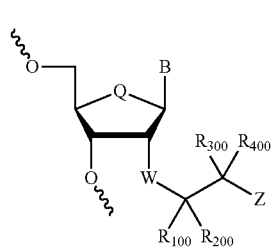

(4)

or isomers thereof, wherein:
B is selected from the group consisting of hydrogen, unsubstituted or substituted $C_1$-$C_{24}$ aliphatic, a natural nucleobase, and a universal base;
Q is selected from the group consisting of O, S, $NR_{10}$, and $CH_2$;
W is absent, O, S or NR';
$R_{100}$ and $R_{200}$ are each independently selected from the group consisting of hydrogen, unsubstituted and substituted $C_1$-$C_{24}$ aliphatic, aryl, halogen, 5-14 membered heteroaryl, and 5-14 membered heterocyclic;
$R_{300}$ and $R_{400}$ are each independently selected from the group consisting of hydrogen, unsubstituted or substituted $C_1$-$C_{24}$ aliphatic, aryl, halogen, 5-14 membered heteroaryl, and 5-14 membered heterocyclic; or $R_{300}$ and $R_{400}$ are taken together with the atom to which they are bound to form a carbonyl, thiocarbonyl, $=NR_{20}$, $=N-NR_{20}R_{30}$, or $=N-NR_{20}C(O)R_{10}$;
Z is $OR_{10}$;
$R_{20}$ and $R_{30}$ are independently selected from the group consisting of hydrogen, acyl, unsubstituted or substituted $C_1$-$C_{24}$ aliphatic, aryl, 5-14 membered heteroaryl, 5-14 membered heterocyclic, $OR_{10}$, $COR_{10}$, $CO_2R_{10}$, and $NR_{10}R_{10}'$; or $R_{20}$ and $R_{30}$ are taken together with the atom to which they are bound to form a 5-14 membered heterocyclic ring; and
$R_{10}$ and $R_{10}'$ are each independently hydrogen, unsubstituted or substituted $C_1$-$C_{24}$ aliphatic, aryl, 5-14 membered heteroaryl, or 5-14 membered heterocyclic,
wherein, in each occurrence, the substituent group on the substituted $C_1$-$C_{24}$ aliphatic is selected from the group consisting of halo, hydroxy, oxo, nitro, haloalkyl, alkyl, alkaryl, aryl, aralkyl, alkoxy, aryloxy, amino, acylamino, alkylcarbamoyl, arylcarbamoyl, aminoalkyl, alkoxycarbonyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureidos,
provided that at least one of $R_{100}$, $R_{200}$, $R_{300}$ and $R_{400}$ is methyl.

7. The oligonucleotide of claim 6, wherein the nucleoside of formula (4) is represented by a nucleoside of formula (6):

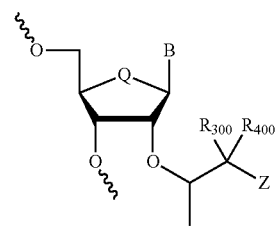

(6)

or isomers thereof, wherein:
B is selected from the group consisting of hydrogen, unsubstituted or substituted $C_1$-$C_{24}$ aliphatic, a natural nucleobase, and a universal base;
$R_{300}$ and $R_{400}$ are each independently selected from the group consisting of hydrogen, unsubstituted or substituted $C_1$-$C_{24}$ aliphatic, aryl, halogen, 5-14 membered heteroaryl, and 5-14 membered heterocyclic; or $R_{300}$ and $R_{400}$ are taken together with the atom to which they are bound to form a carbonyl, thiocarbonyl, $=NR_{20}$, $=N-NR_{20}R_{30}$, or $=N-NR_{20}C(O)R_{10}$;
Z is $OR_{10}$;
$R_{20}$ and $R_{30}$ for each occurrence are independently selected from the group consisting of hydrogen, acyl, unsubstituted or substituted $C_1$-$C_{24}$ aliphatic, aryl, 5-14 membered heteroaryl, 5-14 membered heterocyclic, $OR_{10}$, $COR_{10}$, $CO_2R_{10}$, and $NR_{10}R_{10}'$; or $R_{20}$ and $R_{30}$ are taken together with the atom to which they are bound to form a 5-14 membered heterocyclic ring; and
$R_{10}$ and $R_{10}'$ are each independently hydrogen, an unsubstituted or substituted $C_1$-$C_{24}$ aliphatic, aryl, 5-14 membered heteroaryl, or 5-14 membered heterocyclic.

8. The oligonucleotide of 6, wherein the nucleoside of formula (2) is selected from the group consisting of:

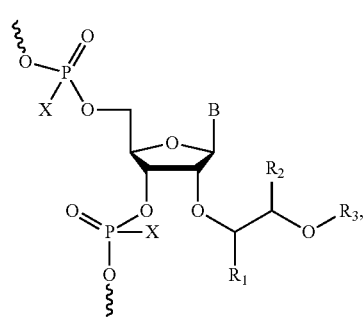

I

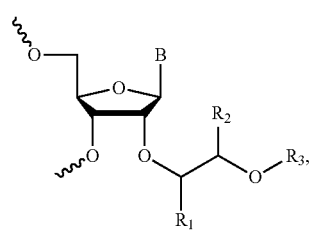

IA

361
-continued

II

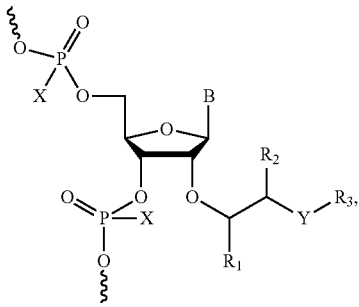

IIA

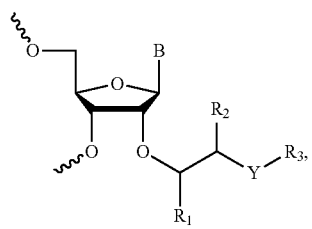

III

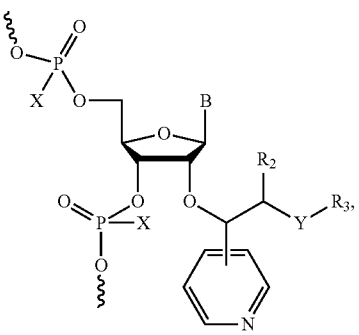

IV

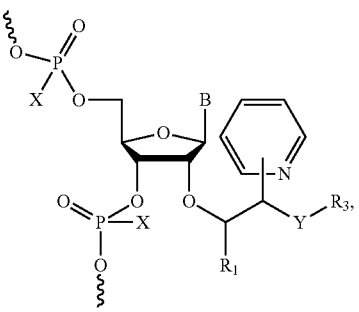

IIIA

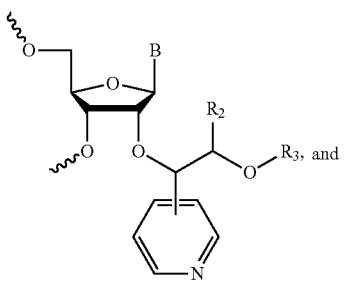

362
-continued

IVA

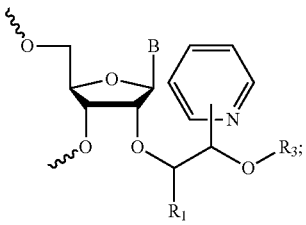

and isomers thereof, wherein:
$R_1$, $R_2$, and $R_3$ are each independently selected form the group consisting of $C_1$-$C_{10}$ alkyl, aryl, $C_3$-$C_{12}$cycloalkyl, 5-14 membered heteroaryl, heterocycloalkyl and acyl;
B is an optionally substituted natural or non-natural nucleobase or a universal nucleobase;
X is O, S, or $BH_3$;
Y is O; and
m, n and p are each independently an integer from 1 to 10.

9. The oligonucleotide of 6, wherein said oligonucleotide further comprises at least one non-phosphodiester backbone linkage.

10. The oligonucleotide of claim 9, wherein the non-phosphodiester of said non-phosphodiester backbone linkage is selected from the group consisting of phosphorothioate, phosphorodithioate, alkyl-phosphonate and phosphoramidate.

11. The oligonucleotide of claim 9, the non-phosphodiester backbone linkage is placed (a) between nucleosides of positions 1 and 2, and/or (b) between the 3'-terminal nucleosides.

12. The oligonucleotide of 6, wherein said oligonucleotide further comprises at least one ligand bonded to a nucleobase, a sugar moiety, an internucleosidic linkage, or a 3' or 5' end of the oligonucleotide.

13. The oligonucleotide of 6, wherein said oligonucleotide is a double-stranded oligonucleotide comprising a first strand and a second strand.

14. The oligonucleotide of claim 13, wherein the nucleoside of formula (4) is present in either the first strand or the second strand.

15. The oligonucleotide of claim 14, wherein said first strand is the sense strand.

16. The oligonucleotide of claim 14, wherein said second strand is the antisense strand.

17. The oligonucleotide of claim 14, wherein the nucleoside of formula (4) is present in both strands.

18. The oligonucleotide of 6, wherein said oligonucleotide has a hairpin structure.

19. The oligonucleotide of 6, wherein said oligonucleotide is an antisense, an antagomir, a microRNA, a siRNA, a pre-microRNA, an antimir, a ribozyme, RNA activator, U1 adaptor, immune stimulator or an aptamer.

20. The oligonucleotide of claim 19, wherein said oligonucleotide is a single-stranded siRNA.

21. The oligonucleotide of claim 6, wherein:
B is a natural nucleobase or a universal base;
Q is O;
W is O;
$R_{100}$ and $R_{200}$ are each independently selected from the group consisting of hydrogen, $C_1$-$C_{10}$ aliphatic, aryl, halogen, 5-8 membered heteroaryl, and 5-8 membered heterocyclic;

$R_{300}$ and $R_{400}$ are each independently selected from the group consisting of hydrogen, $C_1$-$C_{10}$ aliphatic, aryl, halogen, 5-8 membered heteroaryl, and 5-8 membered heterocyclic; or $R_{300}$ and $R_{400}$ are taken together with the atom to which they are bound to form a carbonyl, thiocarbonyl, =$NR_{20}$, =N—$NR_{20}R_{30}$, or =N—$NR_{20}C(O)R_{10}$;

$R_{20}$ and $R_{30}$ for each occurrence are independently selected from the group consisting of hydrogen, acyl, $C_1$-$C_{10}$ aliphatic, aryl, 5-8 membered heteroaryl, 5-8 membered heterocyclic, $OR_{10}$, $COR_{10}$, $CO_2R_{10}$, and $NR_{10}R_{10}'$; or $R_{20}$ and $R_{30}$ are taken together with the atom to which they are bound to form a 5-8 membered heterocyclic ring; and $R_{10}$ and $R_{10}'$ are each independently hydrogen, $C_1$-$C_{10}$ aliphatic, aryl, 5-8 membered heteroaryl, or 5-8 membered heterocyclic.

22. The oligonucleotide of claim 21, wherein:

$R_{100}$ and $R_{200}$ are each independently selected from the group consisting of hydrogen, $C_1$-$C_{10}$ alkyl, aryl, and 5-8 membered heteroaryl;

$R_{300}$ and $R_{400}$ are each independently selected from the group consisting of hydrogen, $C_1$-$C_{10}$ alkyl, aryl, and 5-8 membered heteroaryl; or $R_{300}$ and $R_{400}$ are taken together with the atom to which they are bound to form a carbonyl; and $R_{10}$ and $R_{10}'$ are each independently hydrogen or $C_1$-$C_{10}$ alkyl.

23. The oligonucleotide of claim 6, wherein the nucleoside has the formula of

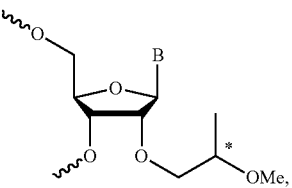

wherein B is U, T, $C^{Ac}$, $A^{Bz}$, or $G^{ibu}$.

* * * * *